US008415319B2

(12) United States Patent
Kaemmerer

(10) Patent No.: US 8,415,319 B2
(45) Date of Patent: *Apr. 9, 2013

(54) DEVICES, SYSTEMS AND METHODS FOR IMPROVING MEMORY AND/OR COGNITIVE FUNCTION THROUGH BRAIN DELIVERY OF SIRNA

(75) Inventor: William F. Kaemmerer, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,458

(22) Filed: Sep. 23, 2011

(65) Prior Publication Data

US 2012/0093916 A1    Apr. 19, 2012

Related U.S. Application Data

(63) Continuation of application No. 11/930,939, filed on Oct. 31, 2007, now Pat. No. 8,058,251, which is a continuation-in-part of application No. 11/253,393, filed on Oct. 19, 2005, now Pat. No. 7,618,948, which is a continuation-in-part of application No. 10/852,997, filed on May 25, 2004, now Pat. No. 7,829,694, which is a continuation-in-part of application No. 10/721,693, filed on Nov. 25, 2003, now Pat. No. 7,605,249, said application No. 11/253,393 is a continuation-in-part of application No. 11/157,608, filed on Jun. 21, 2005, and a continuation-in-part of application No. PCT/US2005/022156, filed on Jun. 21, 2005.

(60) Provisional application No. 60/444,614, filed on Feb. 3, 2003, provisional application No. 60/429,387, filed on Nov. 26, 2002, provisional application No. 60/581,730, filed on Jun. 21, 2004.

(51) Int. Cl.
C12N 15/11 (2006.01)
C07H 21/02 (2006.01)
A01N 63/00 (2006.01)
A61K 9/127 (2006.01)
A61M 31/00 (2006.01)

(52) U.S. Cl. .................. 514/44 A; 536/24.5; 424/93.6; 424/450; 604/508

(58) Field of Classification Search .................. None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,888,829 A | 12/1989 | Kleinerman et al. |
| 4,965,188 A | 10/1990 | Mullis et al. |
| 5,236,908 A | 8/1993 | Gruber et al. |
| 5,354,326 A | 10/1994 | Comben et al. |
| 5,534,350 A | 7/1996 | Liou |
| 5,624,803 A | 4/1997 | Noonberg et al. |
| 5,639,275 A | 6/1997 | Baetge et al. |
| 5,702,716 A | 12/1997 | Dunn et al. |
| 5,720,720 A | 2/1998 | Laske et al. |
| 5,735,814 A | 4/1998 | Elsberry et al. |
| 5,782,892 A | 7/1998 | Castle et al. |
| 5,795,715 A | 8/1998 | Livache et al. |
| 5,800,390 A | 9/1998 | Hayakawa et al. |
| 5,814,014 A | 9/1998 | Elsberry et al. |
| 5,840,059 A | 11/1998 | March et al. |
| 5,882,561 A | 3/1999 | Barsoum et al. |
| 5,911,969 A | 6/1999 | Axworthy et al. |
| 5,925,310 A | 7/1999 | Nakayama et al. |
| 5,942,455 A | 8/1999 | Barsoum et al. |
| 5,968,059 A | 10/1999 | Ellis et al. |
| 5,997,525 A | 12/1999 | March et al. |
| 6,042,579 A | 3/2000 | Elsberry et al. |
| 6,093,180 A | 7/2000 | Elsberry |
| 6,110,459 A | 8/2000 | Mickle et al. |
| 6,151,525 A | 11/2000 | Soykan et al. |
| 6,180,613 B1 | 1/2001 | Kaplitt et al. |
| 6,187,906 B1 | 2/2001 | Gluckman et al. |
| 6,231,969 B1 | 5/2001 | Knight et al. |
| 6,245,884 B1 | 6/2001 | Hook |
| 6,281,009 B1 | 8/2001 | Boyce |
| 6,291,243 B1 | 9/2001 | Fogarty et al. |
| 6,294,202 B1 | 9/2001 | Burns et al. |
| 6,300,539 B1 | 10/2001 | Morris |
| 6,309,634 B1 | 10/2001 | Bankiewicz et al. |
| 6,310,048 B1 | 10/2001 | Kumar |
| 6,310,058 B1 | 10/2001 | Miller et al. |
| 6,313,268 B1 | 11/2001 | Hook |
| 6,319,905 B1 | 11/2001 | Mandel et al. |
| 6,331,427 B1 | 12/2001 | Robison |

(Continued)

FOREIGN PATENT DOCUMENTS

| | | |
|---|---|---|
| DE | 19910340 A1 | 9/2000 |
| DE | 19938960 A1 | 2/2001 |

(Continued)

OTHER PUBLICATIONS

Xia, et al., sIRNA-mediated gene silencing in vitro and in vivo, Nature Biotechnology 20:1006-1010, 2002.

(Continued)

*Primary Examiner* — Richard Schnizer
(74) *Attorney, Agent, or Firm* — Mary P. Bauman; Gerard P. Norton; Fox Rothschild LLP

(57) ABSTRACT

The present invention relates to devices, systems, and methods for improving memory and/or cognitive function by brain delivery of compositions of small interfering RNA or vectors containing the DNA encoding for small interfering RNA. Such compositions can be administered using devices, systems and methods for direct delivery of the compositions to the brain, or using devices, systems, methods of delivery, and compositions that deliver small interfering RNA or vectors containing the DNA encoding the small interfering RNA across the blood-brain barrier. The present invention also provides valuable small interfering RNA vectors, and methods for reduction of BACE1 levels in the hippocampus, cerebral cortex, or other regions of the brain that have beneficial effects on improving memory and/or cognitive function in a subject.

26 Claims, 8 Drawing Sheets

U.S. PATENT DOCUMENTS

| | | | |
|---|---|---|---|
| 6,343,233 B1 | 1/2002 | Werner et al. | |
| 6,372,250 B1 * | 4/2002 | Pardridge | 424/450 |
| 6,372,721 B1 | 4/2002 | Neuman et al. | |
| 6,376,471 B1 | 4/2002 | Lawrence, III et al. | |
| 6,436,392 B1 | 8/2002 | Engelhardt et al. | |
| 6,436,708 B1 | 8/2002 | Leone et al. | |
| 6,461,989 B1 | 10/2002 | El-Raghy et al. | |
| 6,468,524 B1 | 10/2002 | Chiorini et al. | |
| 6,551,290 B1 | 4/2003 | Elsberry et al. | |
| 6,594,880 B2 | 7/2003 | Elsberry | |
| 6,609,020 B2 | 8/2003 | Gill | |
| 6,632,671 B2 | 10/2003 | Unger | |
| 6,659,995 B1 | 12/2003 | Taheri | |
| 6,870,030 B2 | 3/2005 | Powell et al. | |
| 6,945,969 B1 | 9/2005 | Morris et al. | |
| 7,189,222 B2 | 3/2007 | Elsberry | |
| 7,320,965 B2 | 1/2008 | Sah et al. | |
| 7,605,249 B2 | 10/2009 | Kaemmerer | |
| 7,618,948 B2 | 11/2009 | Kaemmerer | |
| 7,829,694 B2 | 11/2010 | Kaemmerer | |
| 8,058,251 B2 | 11/2011 | Kaemmerer | |
| 2001/0027309 A1 | 10/2001 | Elsberry | |
| 2001/0031947 A1 | 10/2001 | Heruth | |
| 2002/0004038 A1 | 1/2002 | Baugh et al. | |
| 2002/0068093 A1 | 6/2002 | Trogolo et al. | |
| 2002/0076394 A1 | 6/2002 | Leone et al. | |
| 2002/0114780 A1 | 8/2002 | Bankiewicz et al. | |
| 2002/0141980 A1 | 10/2002 | Bankiewicz et al. | |
| 2002/0187127 A1 | 12/2002 | Bankiewicz | |
| 2003/0078229 A1 | 4/2003 | Cooper et al. | |
| 2003/0088236 A1 | 5/2003 | Johnson et al. | |
| 2003/0092003 A1 | 5/2003 | Blatt et al. | |
| 2003/0095958 A1 | 5/2003 | Bhisetti et al. | |
| 2003/0109476 A1 | 6/2003 | Kmiec et al. | |
| 2003/0120282 A1 | 6/2003 | Scouten et al. | |
| 2003/0143732 A1 | 7/2003 | Fosnaugh et al. | |
| 2003/0152947 A1 | 8/2003 | Crossman et al. | |
| 2003/0175772 A1 | 9/2003 | Wang | |
| 2003/0190635 A1 | 10/2003 | McSwiggen | |
| 2003/0224512 A1 | 12/2003 | Dobie | |
| 2004/0018520 A1 | 1/2004 | Thompson | |
| 2004/0023390 A1 | 2/2004 | Davidson et al. | |
| 2004/0023855 A1 | 2/2004 | John et al. | |
| 2004/0186422 A1 | 9/2004 | Rioux et al. | |
| 2004/0215164 A1 | 10/2004 | Abbott et al. | |
| 2004/0220132 A1 * | 11/2004 | Kaemmerer | 514/44 |
| 2004/0258666 A1 | 12/2004 | Passini et al. | |
| 2004/0259247 A1 | 12/2004 | Tuschl et al. | |
| 2004/0265849 A1 | 12/2004 | Cargill et al. | |
| 2004/0266707 A1 | 12/2004 | Leake et al. | |
| 2005/0032733 A1 | 2/2005 | McSwiggen et al. | |
| 2005/0042646 A1 | 2/2005 | Davidson et al. | |
| 2005/0048641 A1 | 3/2005 | Hildebrand et al. | |
| 2005/0096284 A1 | 5/2005 | McSwiggen | |
| 2005/0137134 A1 | 6/2005 | Gill et al. | |
| 2005/0153353 A1 | 7/2005 | Meibohm et al. | |
| 2005/0180955 A1 | 8/2005 | Bankiewicz et al. | |
| 2005/0202075 A1 | 9/2005 | Pardridge et al. | |
| 2005/0209179 A1 | 9/2005 | McSwiggen et al. | |
| 2005/0255086 A1 | 11/2005 | Davidson et al. | |
| 2005/0255487 A1 | 11/2005 | Khvorova et al. | |
| 2005/0282198 A1 | 12/2005 | Duff et al. | |
| 2006/0009408 A1 | 1/2006 | Davidson et al. | |
| 2006/0014165 A1 | 1/2006 | Hakonarson et al. | |
| 2006/0041242 A1 | 2/2006 | Stypulkowski | |
| 2006/0150747 A1 | 7/2006 | Mallett | |
| 2006/0178328 A1 * | 8/2006 | Kaemmerer | 514/44 |
| 2006/0210538 A1 | 9/2006 | Kaplitt et al. | |
| 2006/0224411 A1 | 10/2006 | Chang et al. | |
| 2006/0257912 A1 | 11/2006 | Kaemmerer et al. | |
| 2007/0031844 A1 | 2/2007 | Khvorova et al. | |
| 2007/0184029 A1 | 8/2007 | Mishra | |
| 2008/0113351 A1 | 5/2008 | Naito et al. | |
| 2008/0113371 A1 | 5/2008 | Khvorova et al. | |
| 2009/0022864 A1 | 1/2009 | Steenhof et al. | |

FOREIGN PATENT DOCUMENTS

| | | |
|---|---|---|
| JP | 2004232811 A | 8/2004 |
| WO | 9220400 A1 | 11/1992 |
| WO | 93/23569 A1 | 11/1993 |
| WO | 94/02595 A1 | 2/1994 |
| WO | 9618736 A2 | 6/1996 |
| WO | 97/40874 A1 | 11/1997 |
| WO | 9740847 A1 | 11/1997 |
| WO | 9846740 A1 | 10/1998 |
| WO | 9856361 A1 | 12/1998 |
| WO | 9939744 A1 | 8/1999 |
| WO | 99/50300 A1 | 10/1999 |
| WO | 0004505 A1 | 1/2000 |
| WO | 00/30567 A2 | 6/2000 |
| WO | 00/64505 A1 | 11/2000 |
| WO | 01/16312 A2 | 3/2001 |
| WO | 01/49844 A1 | 7/2001 |
| WO | 01/60794 A2 | 8/2001 |
| WO | 0170276 A2 | 9/2001 |
| WO | 0180840 A2 | 11/2001 |
| WO | 01/91801 A2 | 12/2001 |
| WO | 02/07810 A2 | 1/2002 |
| WO | 0205804 A1 | 1/2002 |
| WO | 0222177 A2 | 3/2002 |
| WO | 02063959 A1 | 8/2002 |
| WO | 03042385 A2 | 5/2003 |
| WO | 03/047676 A1 | 6/2003 |
| WO | 03/053516 A1 | 7/2003 |
| WO | 03/070895 A2 | 8/2003 |
| WO | 03/099298 A1 | 12/2003 |
| WO | 03102131 A2 | 12/2003 |
| WO | 2004007718 A2 | 1/2004 |
| WO | 2004/013280 A2 | 2/2004 |
| WO | 2004010787 A1 | 2/2004 |
| WO | 2004013355 A1 | 2/2004 |
| WO | 2004/041101 A2 | 5/2004 |
| WO | 2004/047872 A2 | 6/2004 |
| WO | 2004/058940 A2 | 7/2004 |
| WO | 2004/084955 A1 | 10/2004 |
| WO | 2004/101063 A1 | 11/2004 |
| WO | 2004/101787 A1 | 11/2004 |
| WO | 2004098648 A1 | 11/2004 |
| WO | 2005027980 A1 | 3/2005 |
| WO | 2005/045034 A2 | 5/2005 |
| WO | 2005116204 A1 | 12/2005 |
| WO | 2005120581 A2 | 12/2005 |
| WO | 2006006948 A2 | 1/2006 |
| WO | 2006022639 A1 | 3/2006 |
| WO | 2007039721 A1 | 4/2007 |
| WO | 2007087451 A2 | 8/2007 |
| WO | 2007139811 A1 | 12/2007 |
| WO | 2008004260 A2 | 1/2008 |
| WO | 2008005562 A2 | 1/2008 |
| WO | 2008021157 A1 | 2/2008 |
| WO | 2008046273 A1 | 4/2008 |
| WO | 2008054544 A2 | 5/2008 |
| WO | 2008143774 A2 | 11/2008 |

OTHER PUBLICATIONS

Yamamoto, A, et al., Reversal of neuropathology and motor dysfunction in a conditional model of Huntington's Disease, Cell, 101:57-66, 2000.

Yu, Jenn-Yah et al., RNA interference by expression of short-interfering RNAs and hairpin RNAs in mammalian cells, PNAS, 99(9):6047-6052, 2002.

Erzin-Walters et al., Can. J. Neurol. Sci. 13, 8-14 (1986).

Glorioso, Curr. Opinion in Drug Discovery and Dev't 5(2) Pharma Press ISSN 1367-6733 (2002).

Good et al., Gene Ther. 4:45-54 (1997).

Invitrogen, pShooter.TM. Vector (pCMV/myc.COPYRGT. vectors), for the intracellular targeting of recombinant proteins and antibodies, Catalog Nos. V820-20, V821-20, V822-20, V823-20, Version E, copyright 1998-2001, 35 pgs.

Invitrogen, pTRACER.TM.-CMV2, Catalog Nos. V885-01, V885-20, Version C, copyright 1998-2001, 21 pgs.

National Center for Biotechnology Information, National Library of Medicine, National Institutes of Health, GenBank Locus AF163864, Accession No. AF163864, "*Homo sapiens* SNCA isoform (SNCA) gene, complete cds, alternatively spliced," [online].Bethesda, MD [retrieved on Jun. 21, 2004]. Retrieved from the Internet: <URL:http://www.ncbi.nlm.nih.gov/entrez/viewer. fcgi?db=nucleotide&val=-11118351>; 43 pgs.

National Center for Biotechnology Information, National Library of Medicine, National Institutes of Health, GenBank Locus AF163865, Accession No. AF163865, "*Mus musculus* alpha-synuclein (SNCA) gene, complete cds," [online]. Bethesda, MD [retrievedon Jun. 21, 2004]. Retrieved from the Internet<URL:http://www.ncbi.nlm.nih. gov/entrez/viewer.fcgi?db=nucleot-ide&val=11118354>; 33 pgs.

National Center for Biotechnology Information, National Library of Medicine, National Institutes of Health, GenBank Locus AH003045, Accession No. AH003045, "*Homo sapiens* huntingtin (HD) gene, exon 1," [online]. Bethesda, MD [retrieved on Mar. 5, 2009]. Retrieved from the Internet<URL:http://www.ncbi.nlm.nih.gov/ entrez/viewer.fcgi?db=nucleot-ide&val=663286>; 42 pgs.

National Center for Biotechnology Information, National Library of Medicine, National Institutes of Health, GenBank Locus NM.sub.-000027, Accession No. NM.sub.-000027, "*Homo sapiens* aspartylglucosaminidase (AGA), mRNA," [online]. Bethesda, MD[retrieved on Mar. 5, 2009]. Retrieved from the Internet<URL:http://www.ncbi.nlm.nih.gov/entrez/viewer. fcgi?db=nucleot-ide&val=32313568>; 4 pgs.

National Center for Biotechnology Information, National Library of Medicine, National Institutes of Health, GenBank Locus NM.sub.-000046, Accession No. NM.sub.-000046, "*Homo sapiens* arylsulfatase B (ARSB), transcript variant 1, mRNA," [online]. Bethesda, MD [retrieved on Mar. 5, 2009]. Retrieved from the Internet<URL:http://www.ncbi.nlm.nih.gov/entrez/viewer. fcgi?db=nucleoti-de&val=38569404>; 4 pgs.

National Center for Biotechnology Information, National Library of Medicine, National Institutes of Health, GenBank Locus NM.sub.-000049, Accession No. NM.sub.-000049, "*Homo sapiens* aspartoacylase (aminoacylase 1, Canavan disease) (ASPA), mRNA,"[online]. Bethesda, MD [retrieved on Mar. 5, 2009]. Retrieved from the Internet<URL:http://www.ncbi.nlm.nih.gov/ entrez/viewer.fcgi?db=nucleot-ide&val=4557334>; 4 pgs.

National Center for Biotechnology Information, National Library of Medicine, National Institutes of Health, GenBank Locus NM.sub.-000152, Accession No. NM.sub.-000152, "*Homo sapiens* glucosidase, alpha; acid (Pompe disease, glycogen storage diseasetype II) (GAA), mRNA," [online]. Bethesda, MD [retrieved on Mar. 5, 2009]. Retrieved from the Internet: <URL:http://www. ncbi.nlm.nih.gov/entrez/viewer.fcgi?db=nucleotide&val=-11496988>; 4 pgs.

National Center for Biotechnology Information, National Library of Medicine, National Institutes of Health, GenBank Locus NM.sub.-000153, Accession No. NM.sub.-000153, "*Homo sapiens* galactosylceramidase (Krabbe disease) (GALC), mRNA," [online]. Bethesda, MD [retrieved on Mar. 5, 2009]. Retrieved from the Internet<URL:http://www.ncbi.nlm.nih.gov/entrez/viewer. fcgi?db=nucleot-ide&val=4557612>; 5 pgs.

National Center for Biotechnology Information, National Library of Medicine, National Institutes of Health, GenBank Locus NM.sub.-000181, Accession No. NM.sub.-000181, "*Homo sapiens* glucuronidase, beta (GUSB), mRNA," [online]. Bethesda, MD[retrieved on Mar. 5, 2009]. Retrieved from the Internet<URL:http://www.ncbi.nlm.nih.gov/entrez/viewer. fcgi?db=nuc-leotide&val=4504222>; 4 pgs.

National Center for Biotechnology Information, National Library of Medicine, National Institutes of Health, GenBank Locus NM.sub.-000199, Accession No. NM.sub.-000199, "*Homo sapiens* N-sulfoglucosamine sulfohydrolase (sulfamidase) (SGSH), mRNA,"[online]. Bethesda, MD [retrieved on Mar. 5, 2009]. Retrieved from the Internet<URL:http://www.ncbi.nlm.nih.gov/ entrez/viewer.fcgi?db=nucleot-ide&val=31543619>; 3 pgs.

National Center for Biotechnology Information, National Library of Medicine, National Institutes of Health, GenBank Locus NM.sub.-000202, Accession No. NM.sub.-000202, "*Homo sapiens* iduronate 2-sulfatase (Hunter syndrome) (ID), transcript variant1, mRNA," [online]. Bethesda, MD [retrieved on Mar. 5, 2009]. Retrieved from the Internet<URL:http:// www.ncbi.nlm.nih.gov/entrez/viewer.fcgi?db=nucleotide&val=5360215>; 8 pgs.

National Center for Biotechnology Information, National Library of Medicine, National Institutes of Health, GenBank Locus NM.sub.-000203, Accession No. NM.sub.-000203, "*Homo sapiens* iduronidase, alpha-L-(IDUA), mRNA," [online]. Bethesda, MD[retrieved on Mar. 5, 2009]. Retrieved from the Internet<URL:http://www.ncbi.nlm.nih.gov/entrez/viewer. fcgi?db=nuc-leotide&val=40354208>: 6 pgs.

National Center for Biotechnology Information, National Library of Medicine, National Institutes of Health, GenBank Locus NM.sub.-000235, Accession No. NM.sub.-000235, "*Homo sapiens* lipase A, lysosomal acid, cholesterol esterase (Wolman disease)(LIPA), mRNA," [online]. Bethesda, MD [retrieved on Mar. 5, 2009]. Retrieved from the Internet: <URL:http://www.ncbi.nlm.nih.gov/ entrez/viewer.fcgi?db=nucleotide&val=-4557720>: 4 pgs.

National Center for Biotechnology Information, National Library of Medicine, National Institutes of Health, GenBank Locus NM.sub.-000262, Accession No. NM.sub.-000262, "*Homo sapiens* N-acetylgalactosaminidase, alpha-(NAGA), mRNA," [online]. Bethesda, MD [retrieved on Mar. 5, 2009]. Retrieved from the Internet<URL:http://www.ncbi.nlm.nih.gov/entrez/viewer. fcgi?db=nucleot-ide&val=4557780>; 4 pgs.

National Center for Biotechnology Information, National Library of Medicine, National Institutes of Health, GenBank Locus NM.sub.-000263, Accession No. NM.sub.-000263, "*Homo sapiens* N-acetylglucosaminidase, alpha-(Sanfilippo disease)(IIIB)(NAGLU), mRNA," [online]. Bethesda, MD [retrieved on Mar. 5, 2009]. Retrieved from the Internet<URL:http:// www. ncbi.nlm.nih.gov/entrez/viewer.fcgi?db=nucleotide &val=40548380>: 4 pgs.

National Center for Biotechnology Information, National Library of Medicine, National Institutes of Health, GenBank Locus NM.sub.-000310, Accession No. NM.sub.-000310, "*Homo sapiens* palmitoyl-protein thioesterase 1 (ceroid-lipofuscinosis, neuronal1, infantile) (PPT1), mRNA," [online]. Bethesda, MD [retrieved on Mar. 5, 2009]. Retrieved from the Internet: <URL:http://www.ncbi.nlm.nih.gov/ entrez/viewer.fcgi?db=nucleotide&val=-4506030>; 4 pgs.

National Center for Biotechnology Information, National Library of Medicine, National Institutes of Health, GenBank Locus NM.sub.-000332, Accession No. NM.sub.-000332, "*Homo sapiens* spinocerebellar ataxia 1 (olivopontocerebellar ataxia 1,autosomal dominant, ataxin 1) (SCA1), mRNA," [online]. Bethesda, MD [retrieved on Mar. 5, 2009]. Retrieved from the Internet<URL:http:// www.ncbi.nlm.nih.gov/entrez/viewer.fcgi?db=nuc-leotide &val=4506792>; 7 pgs.

National Center for Biotechnology Information, National Library of Medicine, National Institutes of Health, GenBank Locus NM.sub.-000345, Accession No. NM.sub.-000345, "*Homo sapiens* synuclein, alpha (nonA4 component of amyloid precursor) (SNCA),transcript variant NACP140, mRNA," [online]. Bethesda, MD [retrieved on Mar. 5, 2009]. Retrieved from the Internet<URL:http://www.ncbi. nlm.nih.gov/entrez/viewer.fcgi?db=nuc-leotide&val=6806896>; 6 pgs.

National Center for Biotechnology Information, National Library of Medicine, National Institutes of Health, GenBank Locus NM.sub.-000404, Accession No. NM.sub.-000404, "*Homo sapiens* glactosidase, beta 1 (GLB1), transcript variant 179423, mRNA,"[online]. Bethesda, MD [retrieved on Mar. 5, 2009]. Retrieved from the Internet<URL:http://www.ncbi.nlm.nih.gov/ entrez/viewer.fcgi?db=nucleo-tide&val=10834965>: 5 pgs.

National Center for Biotechnology Information, National Library of Medicine, National Institutes of Health, GenBank Locus NM.sub.-000434, Accession No. NM.sub.-000434, "*Homo sapiens* sialidase 1 (lysosomal sialidase)(NEU1), mRNA," [online].Bethesda, MD [retrieved on Mar. 5, 2009]. Retrieved from the Internet<URL:http:// www.ncbi.nlm.nih.gov/entrez/viewer.fcgi?db=nucleot-ide &val=40806202>: 5 pgs.

National Center for Biotechnology Information, National Library of Medicine, National Institutes of Health, GenBank Locus NM.sub.-000487, Accession No. NM.sub.-000487, "*Homo sapiens* arysulfatase A (ARSA), mRNA," [online]. Bethesda, MD

[retrieved on Mar. 5, 2009]. Retrieved from the Internet:<URL:http://www.ncbi.nlm.nih.gov/entrez/viewer.fcgi?-db=nucleotide&val=7262293>; 4 pgs.

National Center for Biotechnology Information, National Library of Medicine, National Institutes of Health, GenBank Locus NM.sub.-000512, Accession No. NM.sub.-000512, "*Homo sapiens* galactosamine (N-acetyl)-6-sulfate sulfatase (Morquio syndrome,mucopolysaccharidosis type IVA), (GALNS), mRNA," [online]. Bethesda, MD [retrieved on Mar. 5, 2009]. Retrieved from the Internet<URL:http://www.ncbi.nlm.nih.gov/entrez/viewer.fcgi?db=nucleot-ide&val=9945384>: 4 pgs.

National Center for Biotechnology Information, National Library of Medicine, National Institutes of Health, GenBank Locus NM.sub.-000520, Accession No. NM.sub.-000520, "*Homo sapiens* hexosaminidase A (alpha polypeptide) (HEXA), mRNA," [online]. Bethesda, MD [retrieved on Mar. 5, 2009]. Retrieved from the Internet<URL:http://www.ncbi.nlm.nih.gov/entrez/viewer.fcgi?db=nucleot-ide&val=13128865>; 5 pgs.

National Center for Biotechnology Information, National Library of Medicine, National Institutes of Health, GenBank Locus NM.sub.-000521, Accession No. NM.sub.-000521, "*Homo sapiens* hexosaminidase B (beta polypeptide) (HEXB), mRNA," [online]. Bethesda, MD [retrieved on Mar. 5, 2009]. Retrieved from the Internet<URL:http://www.ncbi.nlm.nih.gov/entrez/viewer.fcgi?db=nucleo-tide&val=13128866>; 6 pgs.

National Center for Biotechnology Information, National Library of Medicine, National Institutes of Health, GenBank Locus NM.sub.-000528, Accession No. NM.sub.-000528, "*Homo sapiens* mannosidase, alpha, class 2B, member 1 (MAN2B1), mRNA," [online]. Bethesda, MD [retrieved on Mar. 5, 2009]. Retrieved from the Internet<URL:http://www.ncbi.nlm.nih.gov/entrez/viewer.fcgi?db=nucleo-tide&val=10834967>; 4 pgs.

National Center for Biotechnology Information, National Library of Medicine, National Institutes of Health, GenBank Locus NM.sub.-000543, Accession No. NM.sub.-000543, "*Homo sapiens* sphingomyelin phosphodiesterase 1 acid lysosomal (acidsphingomyelinase) (SMPD1), mRNA," [online]. Bethesda, MD [retrieved on Mar. 5, 2009]. Retrieved from the Internet<URL:http://www.ncbi.nlm.nih.gov/entrez/viewer.fcgi?d-b=nucleotide&val=40254417>; 5 pgs.

National Center for Biotechnology Information, National Library of Medicine, National Institutes of Health, GenBank Locus NM.sub.-002076, Accession No. NM.sub.-002076, "*Homo sapiens* glucosamine (N-acetyl)-6-sulfatase (Sanfilippodisease)(IIID)(GNS), mRNA," [online]. Bethesda, Md [retrieved on Mar. 5, 2009]. Retrieved from the Internet<URL: http://www.ncbi.nlm.nih.gov/entrez/viewer.fcgi?db=nucleotide&val=42490755->; 7 pgs.

National Center for Biotechnology Information, National Library of Medicine, National Institutes of Health, GenBank Locus NM.sub.-002778, Accession No. NM.sub.-0002778, Accession No. NM.sub.—000169, "*Homo sapiens* glactosidase, alpha (GLA), mRNA,"[online]. Bethesda, MD [retrieved on Mar. 5, 2009]. Retrieved from the Internet<URL:http://www.ncbi.nlm.nih.gov/entrez/viewer.fcgi?db=nucleot-ide&val=4504008>; 4 pgs.

National Center for Biotechnology Information, National Library of Medicine, National Institutes of Health, GenBank Locus NM.sub.-002778, Accession No. NM.sub.-002778, "*Homo sapiens* prosaposin (variant Gaucher disease and variant metachromaticleukodystrophy) (PSAP), mRNA," [online]. Bethesda, MD [retrieved on Mar. 5, 2009]. Retrieved from the Internet: <URL:http://www.ncbi.nlm.nih.gov/entrez/viewer.fcgi?db=nucle-otide&val=11386146>; 8 pgs.

National Center for Biotechnology Information, National Library of Medicine, National Institutes of Health, GenBank Locus NM.sub.-004315, Accession No. NM.sub.-004315, "*Homo sapiens* N-acylsphingosine amidohydrolase (acid ceramidase) 1 (ASAH1),transcript variant 2, mRNA," [online]. Bethesda, MD [retrieved on Mar. 5, 2009]. Retrieved from the Internet: <URL:http://www.ncbi.nlm.nih.gov/entrez/viewer.fcgi?db=nucle-otide&val=30089929>; 5 pgs.

National Center for Biotechnology Information, National Library of Medicine, National Institutes of Health, GenBank Locus NM.sub.-004993, Accession No. NM.sub.-004993, "*Homo sapiens* Machado-Joseph disease (spinocerebellar ataxia 3,olivopontocerebellar ataxia 3, autosomal dominant, ataxin 3) (MJD), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=13518018>; 9 pgs.

National Center for Biotechnology Information, National Library of Medicine, National Institutes of Health, GenBank Locus NM.sub.-005908, Accession No. NM.sub.-005908, "*Homo sapiens* mannosidase, beta A, lysosomal (MANBA), mRNA," [online]. Bethesda,MD [retrieved on Mar. 5, 2009]. Retrieved from the Internet<URL:http://www.ncbi.nlm.nih.gov/entrez/viewer.fcgi?db=nucleo-tide&val=24797157>; 4 pgs.

National Center for Biotechnology Information, National Library of Medicine, National Institutes of Health, GenBank Locus NM.sub.-007308, Accession No. NM.sub.-007308, "*Homo sapiens* synuclein, alpha (nonA4 component of amyloid precursor) (SNCA),transcript variant NACP112, mRNA," [online]. Bethesda, MD [retrieved on Mar. 5, 2009]. Retrieved from the Internet<URL:http://www.ncbi.nlm.nih.gov/entrez/viewer.fcgi?-db=nucleotide&val=6806897>; 5 pgs.

National Center for Biotechnology Information, National Library of Medicine, National Institutes of Health, GenBank Locus NM.sub.-009124, Accession No. NM.sub.-009124, "Definition," [online]. Bethesda, MD [retrieved on Mar. 5, 2009]. Retrievedfrom the Internet: <URL:http://www.ncbi.nlm.nih.gov/entrez/viewer.fcgi?db=nucleotide&val=-33636695>; 5 pgs.

National Center for Biotechnology Information, National Library of Medicine, National Institutes of Health, GenBank Locus NM.sub.-011792.2, Accession No. NM.sub.-011792, "*Mus musculus* beta-site APP cleaving enzyme (Bace), mRNA," [online].Bethesda, MD [retrieved on Mar. 5, 2009]. Retrieved from the Internet<URL:http://www.ncbi.nlm.nih.gov/entrez/viewer.fcgi?db=nucleo-tide&val=6857758>; 4 pgs.

National Center for Biotechnology Information, National Library of Medicine, National Institutes of Health, GenBank Locus NM.sub.-012104, Accession No. NM.sub.-012104, "*Homo sapiens* beta-site APP-cleaving enzyme 1 (BACE1), transcript variant a,mRNA," [online]. Bethesda, MD [retrieved on Mar. 5, 2009]. Retrieved from the Internet<URL:http://www.ncbi.nim.nih.gov/entrez/viewer.fcgi?db=nucleo-tide&val=46255011>; 8 pgs.

National Center for Biotechnology Information, National Library of Medicine, National Institutes of Health, GenBank Locus NM.sub.-012104, Accession No. NM.sub.-012104, Version NM.sub.—012104.2, "*Homo sapiens* beta-site APP-cleaving enzyme (BACE),transcript variant a, mRNA," [online]. Bethesda, MD [retrieved on Mar. 5, 2009]. Retrieved from the Internet<URL:http://www.ncbi.nlm.nih.gov/entrez/viewer.fcgi?db=nucleo-tide&val=21040369>; 10 pgs.

National Center for Biotechnology Information, National Library of Medicine, National Institutes of Health, GenBank Locus NM.sub.-013995, Accession No. NM.sub.-013995, "*Homo sapiens* lysosomal-associated membrane protein 2 (LAMP2), transcriptvariant LAMP2B, mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=-7669502>; 6 pgs.

National Center for Biotechnology Information, National Library of Medicine, National Institutes of Health, GenBank Locus NM.sub.-030660, Accession No. NM.sub.-030660, "*Homo sapiens* Machado-Joseph disease (spinocerebellar ataxia 3,olivopontocerebellar ataxia 3, autosomal dominant, ataxin 3) (MJD), transcript variant 2, mRNA," [online]. Bethesda, MD [retrieved on Mar. 5, 2009]. Retrieved from the Internet<URL:http://www.ncbi.nlm.nih.gov/entrez/viewer.fcgi?db=nucleot-ide&val=13518012>; 8 pgs.

National Center for Biotechnology Information, National Library of Medicine, National Institutes of Health, GenBank Locus NM.sub.-032520, Accession No. NM.sub.-032520, "*Homo sapiens* N-acetylglucosamine-1-phosphotransferase, gamma subunit (GNPTAG),mRNA," [online]. Bethesda, MD [retrieved on Mar. 5, 2009]. Retrieved from the Internet<URL:http://www.ncbi.nlm.nih.gov/entrez/viewer.fcgi?db=nucleo-tide&val=42476109>; 5 pgs.

National Center for Biotechnology Information, National Library of Medicine, National Institutes of Health, GenBank Locus NM.sub.-138971, Accession No. NM.sub.-138971, "*Homo sapiens* beta-site APP-cleaving enzyme 1 (BACE1), transcript variant c,mRNA," [online]. Bethesda, MD [retrieved on Mar. 5, 2009 ]. Retrieved from the Internet<URL:http://www.ncbi.nlm.nih.gov/entrez/viewer.fcgi?db=nucleo- tide&val=46255012>; 8 pgs.

National Center for Biotechnology Information, National Library of Medicine, National Institutues of Health, GenBank Locus NM.sub.-138971, Accession No. NM.sub.-138971, Version NM.sub.—138971.1, "*Homo sapiens* beta-site APP-cleaving enzyme (BACE),transcript variant c, mRNA," [online]. Bethesda, MD [retrieved on Mar. 5, 2009]. Retrieved from the Internet: <URL:http://www.ncbi.nlm.nih.gov/entrez/viewer.fcgi?db=nucle-otide&val=21040363 >; 10 pgs.

National Center for Biotechnology Information, National Library of Medicine, National Institutues of Health, GenBank Locus NM.sub.-138972, Accession No. NM.sub.-138972, "*Homo sapiens* beta-site APP-cleaving enzyme 1 (BACE1), transcript variant b,mRNA, " [online]. Bethesda, MD [retrieved on Mar. 5, 2009]. Retrieved from the Internet: <URL: http://www.ncbi.nlm.nih.gov/entrez/viewer.fcgi?db=nucleotide&val=- 46255013 >; 8 pgs.

National Center for Biotechnology Information, National Library of Medicine, National Institutues of Health, GenBank Locus NM.sub.-138972, Accession No. NM.sub.-138972, Version NM.sub.-138972.1, "*Homo sapiens* beta-site APP-cleaving enzyme (BACE),transcript variant b, mRNA," [online]. Bethesda, MD [retrieved on Mar. 5, 2009]. Retrieved from the Internet: <URL:http://www.ncbi.nlm.nih.gov/entrez/viewer.fcgi?db=nucle- otide&val=21040365 >; 10 pgs.

National Center for Biotechnology Information, National Library of Medicine, National Institutues of Health, GenBank Locus NM.sub.-138973, Accession No. NM.sub.-138973, "*Homo sapiens* beta-site APP-cleaving enzyme 1 (BACE1), transcript variant d,mRNA, " [online]. Bethesda, MD [retrieved on Mar. 5, 2009]. Retrieved from the Internet: <URL:http://www.ncbi.nlm.nih.gov/entrez/viewer.fcgi?db=nucleotide&val=- 46255014 >; 8 pgs.

National Center for Biotechnology Information, National Library of Medicine, National Institutues of Health, GenBank Locus NM.sub.-138973, Accession No. NM.sub.-138973, Version NM.sub.-138973.1, "*Homo sapiens* beta-site APP-cleaving enzyme (BACE),transcript variant d, mRNA," [online]. Bethesda, MD [retrieved on Mar. 5, 2009]. Retrieved from the Internet: <URL:http://www.ncbi.nlm.nih.gov/entrez/viewer.fcgi?db=nucle- otide&val=21040367 >; 10 pgs.

National Center for Biotechnology Information, National Library of Medicine, National Institutues of Health, GenBank Locus U24233, Accession No. U24233 "*Mus musculus* huntingtin (Hd) mRNA, complete cds," [online]. Bethesda, MD [retrieved on Mar. 5, 2009]. Retrieved from the Internet: <URL:http://www.ncbi.nlm.nih.gov/entrez/viewer.fcgi?db=nucleotide&val=- 902003 >; 5 pgs.

National Center for Biotechnology Information, National Library of Medicine, National Institutues of Health, GenBank Locus XM.sub.-032588, Accession No. XM.sub.-032588, "*homo sapiens* dentatorubral-pallidoluysian atrophy (atrophin-1) (DRAPLA),mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=- 20555988 >; 3 pgs.

National Center for Biotechnology Information, National Library of Medicine, National Institutues of Health, GenBank Locus XM.sub.—132846, Accession No. XM.sub.—132846, "*Mus musculus* dentatorubral pallidoluysian atrophy (Drpla), mRNA," [online].Bethesda, MD [retrieved on Mar. 5, 2009]. Retrieved from the Internet: <URL:http://www.ncbi.nlm.nih.gov/entrez/viewer.fcgi?db=nucleotide&val=- 20832263 >; 3 pgs.

Ohno et al., "BACEI Deficiency Rescues Memory Deficits and Cholinergic Dysfunction in a Mouse Model of Alzheimer's Disease," Neuron, Jan. 2004; 41: 37-33.

Promega Corporation, T4 DNA Ligase Blue/White Cloning Qualified, Part #9PIM180, Revised Apr. 2005, 2 pgs.

Promega Corporation, T4 DNA Polymerase(a) , Part#9PIM421, Revised May 2004, 2 pgs.

Schenk, "Amyloid-.beta. immunotherapy for Alzheimer's disease: the end of the beginning," Nature Reviews—Neuroscience, Oct. 2002; 3: 824-828.

Zhang et al., "In vivo knockdown of gene expression in brain cancer with intravenous RNAi in adult rats, " J. Gene Med., 2003; 5:1039-1045; published online Aug. 4, 2003.

Aebischer, Patrick, Recombinant proteins for neurodegenerative diseases: the delivery issue, Trends in Neurosciences, 24(9):533-540, 2001.

Caplen, Natasha J., et al.,, Rescue of polyglutamine-mediaed cytotoxicity by double-stranded RNA-mediated RNA interference, Human Molecular Genetics 11(2):175-184, 2002.

Chen et al., Multitasrget-ribozyme directed to cleave at up to nine highly conserved HIV-1 env RNA regions inhibits HIV-1 replication-potential effectiveness against most presently sequened HIV-1 isolates, Nucleic Acids Res., 20:4581-4589, 1992.

Chowrira et al., In vitro and in vivo comparison of Hammerhead, Hairpin and Hepatitis delta Virus Self-Processing Ribozyme Cassettes, Journal Biol. Chemistry, 269:25856-25863, 1994.

Clark, H., et al., Purkinji Cell Expression of a Mutant Allele of SCA1 in transgenic mice leads to disparate effects on motor behaviorsk, followed by a proigressive cerebellar dysfunction and histological alternations, Journal of Neuroscience,17(19):7385-7395, 1997.

Couture, Larry A., et al, Anti-gene Therapy: The Use of Ribozymes to Inhibit Gene Function, Trends in Genetics, 12 (12):510-515, 1996.

Davidson, Beverly L., Molecular medicine for the brain: silencing of disease genes with RNA interference, The Lancet Neurology, 3:145-149, 2004.

Dineley, Kelly T., et al, Accelerated Plaque Accumulation, Associative Learning Deficits, and Up-regulation of .alpha.7 Nicotinic Receptor Protein in Transgenic Mice Co-expressing Mutant Human Presentilin 1 and Amyloid Precursor Proteins, Journal ofBiological Chemistry, 277(25):22768-22780, 2002.

Dropulic et al., Functional characterization of a U5 Ribozyme: Intracellular Suppression of Human Immunodeficiency virus Type I Expression, Journal Virology., 66(1):1432-1441, 1992.

Glorioso, Joseph C., Use of HSV vectors to modify the nervous system, Current Opinion in Drug Discovery & Development, PharmaPress Ltd ISSN, 5(2):1367-6733, 2002.

Good, et al., Expression of small, therapeutic RNAs in human cell nuclei, Gene Therapy, 4:45-54, 1997.

Goto, J., et al., Suppression of Huntingtin Gene Expression by sIRNA: A Possible therapeutic Tool for Huntington's Disease, Neurology, Lippincoll Williams & Wilkins, Philadelphia, US, 60(5) Suppl 1, Mar. 11, 2003 p. A286.

Izant, Jonathan G., et al., Constitutive and Conditional Suppression of Exogenous and Endogenous Genes by Anti-Sense RNA, Science, 229:345, 1985.

Kawarabayashi, T., et al, Age-Dependent Changes in Brain, CSF, and Plasma Amyloid .beta.Protein in the Tg2576 Transgenic Mouse Model of Alzheimer's Disease, Journal of Neuroscience, 21(2):372-381, 2001.

Liu, et al., Specific inhibition of Huntington's disease gene expression by siRNAs in cultures cells., Proceedings of the Japan Academy, Series B, Physical and Biological Sciences, 79:10(pp. 293-298) Dec. 2003.

Sapru, et al., Small interfering RNA (siRNA)-Mediated silencing of alpha-synuclein gene expression., Annual Meeting of the Society of Neuroscience, Abstract 297.9, XP001204566, 2003.

Neurosciences, 24(9):533-540, 2001.

Chen et al., Multitasrget-ribozyme directed to cleave at up to nine highly conserved HIV-1 env RNA regions inhibits HIV-1 replication—potential effectiveness against most presently sequened HIV-1 isolates, Nucleic Acids Res., 20:4581-4589, 1992.

Clark, H., et al., Purkinji Cell Expression of a Mutant Allele of SCA1 in transgenic mice leads to disparate effects on motor behaviorsk, followed by a proigressive cerebellar dysfunction and histological alternations, Journal of Neuroscience,17(19):7385-7395, 1997.

Dineley, Kelly T., et al, Accelerated Plaque Accumulation, Associative Learning Deficits, and Up-regulation of .alpha.7 Nicotinic Receptor Protein in Transgenic Mice Co-expressing Mutant Human Presenilin 1 and Amyloid Precursor Proteins, Journal ofBiological Chemistry, 277(25):22768-22780, 2002.

Isacson, et al., Lack of Efficacy of "Naked" Small Interfering RNA Applied Directly to Rat Brain, Scandinavian Physiiological Society, 179:173-177, 2003.

Gramlich et al., "Postsynthetic DNA Modification through the Copper-Catalyzed Azide-Alkyne Cycloaddition Reaction," Angewandte Chemie, International Edition (Oct. 20, 2008); 47(44): 8350-8358.

National Center for Biotechnology Information, National Library of Medicine, National Institutes of Health, GenBank Locus NM.sub.-000263, Accession No. NM.sub.-000263, "*Homo sapiens* N-acetylglucosaminidase, alpha-(Sanfilippo disease)(IIIB)(NAGLU),mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=40548380>; 4 pgs.

National Center for Biotechnology Information, National Library of Medicine, National Institutes of Health, GenBank Locus NM.sub.-000310, Accession No. NM.sub.-000310, "*Homo sapiens* palmitoyl-protein thioesterase 1 (ceroid-lipofuscinosis, neuronal1, infantile)(PPT1), mRNA," [online]. Bethesda, MD [retrieved on Mar. 5, 2009]. Retrieved from the Internet<URL:http://www.ncbi.nlm.nih.gov/entrez/viewer.fcgi?db=nu- cleotide&val=4506030>; 4 pgs.

National Center for Biotechnology Information, National Library of Medicine, National Institutes of Health, GenBank Locus NM.sub.-000332, Accession No. NM.sub.-000332, "*Homo sapiens* spinocerebellar ataxia 1 (olivopontocerebellar ataxia 1,autosomal dominant, ataxin 1)(SCA1), mRNA," [online]. Bethesda, MD [retrieved on Mar. 5, 2009]. Retrieved from the Internet<URL:http://www.ncbi.nlm.nih.gov/entrez/viewer.fcgi?db=nu- cleotide &val=4506792>; 7 pgs.

National Center for Biotechnology Information, National Library of Medicine, National Institutes of Health, GenBank Locus NM.sub.-000345, Accession No. NM.sub.-000345, "*Homo sapiens* synuclein, alpha (nonA4 component of amyloid precursor)(SNCA),transcript variant NACP140, mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=6806896>; 6 pgs.

National Center for Biotechnology Information, National Library of Medicine, National Institutes of Health, GenBank Locus NM.sub.-000487, Accession No. NM.sub.-000487, "*Homo sapiens* arysulfatase A (ARSA), mRNA," [online]. Bethesda, MD [retrievedon Mar. 5, 2009]. Retrieved from the Internet:<URL:http://www.ncbi.nlm.nih.gov/entrez/viewer.fcgi? db=nucleotide &val=7262293>; 4 pgs.

National Center for Biotechnology Information, National Library of Medicine, National Institutes of Health, GenBank Locus NM.sub.-000520, Accession No. NM.sub.-000520, "*Homo sapiens* hexosaminidase A (alpha polypeptide) (HEXA), mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=13128865>; 5 pgs.

National Center for Biotechnology Information, National Library of Medicine, National Institutes of Health, GenBank Locus NM.sub.-000521, Accession No. NM.sub.-000521, "*Homo sapiens* hexosaminidase B (beta polypeptide) (HEXB), mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=13128866>; 6 pgs.

National Center for Biotechnology Information, National Library of Medicine, National Institutes of Health, GenBank Locus NM.sub.-000543, Accession No. NM.sub.-000543, "*Homo sapiens* sphingomyelin phosphodiesterase 1 acid lysosomal (acidsphingomyelinase)(SMPD1), mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=40254417>; 5 pgs.

National Center for Biotechnology Information, National Library of Medicine, National Institutes of Health, GenBank Locus NM.sub.-002076, Accession No. NM.sub.-002076, "*Homo sapiens* glucosamine (N-acetyl)-6-sulfatase (Sanfilip-podisease)(IIID)(GNS), mRNA," [online]. Bethesda, MD [retrieved on Mar. 5, 2009]. Retrieved from the Internet<URL: http://www.ncbi.nlm.nih.gov/entrez/viewer.fcgi?db=nucleotide &val=42490755- >; 7 pgs.

National Center for Biotechnology Information, National Library of Medicine, National Institutes of Health, GenBank Locus NM.sub.-002778, Accession No. NM.sub.-002778, "*Homo sapiens* prosaposin (variant Gaucher disease and variant metachromaticleukodystrophy) (PSAP), mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=11386146>; 8 pgs.

National Center for Biotechnology Information, National Library of Medicine, National Institutes of Health, GenBank Locus NM.sub.-004993, Accession No. NM.sub.-004993, "*Homo sapiens* Machado-Joseph disease (spinocerebellar ataxia 3,olivopontocerebellar ataxia 3, autosomal dominant, ataxin 3)(MJD), transcript variant 1, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=13518018>; 9 pgs.

National Center for Biotechnology Information, National Library of Medicine, National Institutes of Health, GenBank Locus NM.sub.-007308, Accession No. NM.sub.-007308, "*Homo sapiens* synuclein, alpha (nonA4 component of amyloid precursor)(SNCA),transcript variant NACP112, mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=6806897>; 5 pgs.

National Center for Biotechnology Information, National Library of Medicine, National Institutes of Health, GenBank Locus NM.sub.-030660, Accession No. NM.sub.-030660, "*Homo sapiens* Machado-Joseph disease (spinocerebellar ataxia 3,olivopontocerebellar ataxia 3, autosomal dominant, ataxin 3)(MJD), transcript variant 2, mRNA," [online]. Bethesda, MD [retrieved on Mar. 5, 2009]. Retrieved from the Internet<URL:http://www.ncbi.nlm.nih.gov/entrez/viewer.fcgi?db=nucleo-tide&val=13518012>; 8 pgs.

National Center for Biotechnology Information, National Library of Medicine, National Institutes of Health, GenBank Locus NM.sub.-032520, Accession No. NM.sub.-032520, "*Homo sapiens* N-acetylglucosamine-1-phosphotransferase, gamma subunit (GNPTAG),mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=42476109>; 5 pgs.

National Center for Biotechnology Information, National Library of Medicine, National Institutes of Health, GenBank Locus NM.sub.-138973, Accession No. NM.sub.-138973, "*Homo sapiens* beta-site APP-cleaving enzyme 1 (BACE1), transcript variant d,mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=46255014>; 8 pgs.

National Center for Biotechnology Information, National Library of Medicine, National Institutes of Health, GenBank Locus NM.sub.-138973, Accession No. NM.sub.-138973, Version NM.sub.—138973.1, "*Homo sapiens* beta-site APP-cleaving enzyme (BACE),transcript variant d, mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide &val=21040367>; 10 pgs.

National Center for Biotechnology Information, National Library of Medicine, National Institutes of Health, GenBank Locus U24233, Accession No. U24233, "*Mus musculus* huntingtin (Hd) mRNA, complete cds," [online]. Bethesda, MD [retrieved on Mar. 5, 2009]. Retrieved from the Internet<URL:http://www.ncbi.nlm.nih.gov/entrez/viewer.fcgi?db=nucleotide&val=902003>; 5 pgs.

National Center for Biotechnology Information, National Library of Medicine, National Institutes of Health, GenBank Locus XM.sub.-032588, Accession No. XM.sub.-032588, "*Homo sapiens* dentatorubral-pallidoluysian atrophy (artrophin-1)(DRPLA), mRNA,"[online]. Bethesda, MD [retrieved on Mar. 5, 2009]. Retrieved from the Internet<URL:http://www.ncbi.nlm.nih.gov/entrez/viewer.fcgi?db=nucleo- tide&val=20555988>; 3 pgs.

Ohno et al., "BACEI Deficiency Rescues Memory Deficits and Cholinergic Dysfunction in a Mouse Model of Alzheimer's Disease," Neuron, Jan. 2004; 4I: 27-33.

Tuscjl Lab, "The siRNA user guide," Revised May 2004, [online]. Retrieved on Nov. 29, 2005. Retrieved from the Internet:<URL:rockefeller.edu/labheads/tuschl/sirna.html>; 6 pgs.

Vickers, Journal of Bio. Chemistry, vol. 278, No. 9 7108-7118(2003).

Chen, et al., "Multitarget-ribozyme directed to cleave at up to nine highly conserved HIV-1 env RNA regions inhibits HIV-1 replication-potential effectiveness against most presently sequenced HIV-1 isolates," Nucleic Acids Research, vol. 20, No. 17pp. 4581-4589, (1992).

Dorri et al., "Douwn-regulation of mglur5 by antisense deoxynucleotides alters pharmacological responses to applications of ACPD in the rat hippocampus," Experimental Neurology vol. 147, Article No. EN976567, pp. 48-54, (1997).

Heale et al., "siRNA target site secondary structure predictions using local stable substructures," Nucleic Acids Research (2005), vol. 33 No. 3 pp. 1-10.

Hommel et al., "Local gene knockdown in the brain using viral-mediated RNA interference," Society for Neuroscience Abstract (2003), Abstract 325.14.

Naldini et al., "Efficient transfer, integration, and sustained long-term expression of the transgene in adult rat brains injected with a lentiviral vector," Proc. Natl. Acad. Sci. (Oct. 1996) vol. 93, pp. 11382-11388.

Noonberg et al., "In vivo generation of highly abundant sequence-specific oligonucleotides for antisense and triplex gene regulation," Nucleic Acids Research (1994) vol. 22, No. 14 pp. 2830-2836.

Whitesell et al., "Stability, clearance, and disposition of intraventricularly administered oligodeoxynucleotides: implications for therapeutic application within the central nervous system," Proc. Natl. Acad. Sci. (May 1993) vol. 90, pp. 4665-4669.

Paxinos et al. (2001) The Mouse Brain in Stereotaxic Coordinates. Academic Press, 2nd Ed, (selected pages).

Cahill et al. (1995) Atlas of Human Cross-sectional Anatomy, Wiley-Liss, 3rd ed. (selected pages).

Xia et al. (2002) Nature 20:1006-1010.

Whitesell et al. (1993) Proc. Natl. Acad. Sci. 90:4665-4669.

Matilla et al. (1998) J. Neuroscience 18:5508-5516.

Dorri et al. (1997) Exp. Neurology 147:48-54.

Zhang et al. (1996) J. Mol. Neuroscience 7:13-28.

Serra et al. (1996) Medical Image Analysis 1(4):317-329.

Morel et al. (1997) J. Comparative Neurology 387:588-630.

Clark et al. (1997) J. Neuroscience 17:7385-7395.

Salehi et al. (1999) J. Neural Transm. 106:955-986.

Caplen et al. (2002) Human Molecular Genetics 11:175-184.

Cummings et al. (1999) Phil. Trans. R. Soc. Lond. B 354:1079-1081.

Aebischer, Patrick, Recombinant proteins for neurodegenerative diseases: the delivery issue, TRENDS in Neurosciences, vol. 24, No. 9, Sep. 2001 pp. 533-540.

Caplen, Natasha J., et al.,, Rescue of polyglutamine-mediaed cytotoxicity by double-stranded RNA-mediated RNA interference, Human Molecular Genetics 11(2): 175-184 (2002).

Chen et al., Multitasrget-ribozyme directed to cleave at up to nine highly conserved HIV-1 env RNA regions inhibits HIV-1 replication—potential effectiveness against most presently sequenced HIV-1 isolates, Nucleic Acids Res., 20, 4581-4589, (1992).

Chowrira et al., In vitro and in vivo comparison of Hammerhead, Hairpin and Hepatitis delta Virus Self-Processing Ribozyme Cassettes, Journal Biol. Chemistry, 269, pp. 25856-25863 (1994).

Clark, H., et al., Purkinji Cell Expression of a Mutant Allele of SCA1 in transgenic mice leads to disparate effects on motor behaviorsk, followed by a prolgressive cerebellar dysfunction and histological alterations, Journal of Neuroscience vol. 17No. 19: pp. 7385-7395 (1997).

Couture et al., Anti-gene therapy; the use of ribozymes to inhibit gene function, Trends in Genetics, 12(12); 510-515 (Dec. 1996).

Davidson, Beverly L., Molecular medicine for the brain: silencing of disease genes with RNA interference, The Lancet Neurology, vol. 3, Mar. 2004, pp. 145-149.

Holen et al., Nucl. Acid Res. 30:1757-1766 (2002).

Hommel et al., "Local gene knockdown in the brain using viral-mediated RNA interference," Nature Medicine, Dec. 2003; 9(12); 1539-1544.

Hommel et al., Society for Neuroscience Abstract, 2003, Abstract 325.14 (2003).

Hooper et al., Neuroscience 63, 917-924 (1995).

Hsiao et al, Science 274 99-102(1996).

Huwyler et al., "Brain drug delivery of small molecules using immunoliposomes," Proc. Natl. Acad., USA, Nov. 1996;93:14164-14169.

Invitrogen, pShooter.TM. Vector (pCMV/myc .COPYRGT. vectors), For the intracellular targeting of recombinant proteins and antibodies, Catalog Nos. V820-20, V821-20, V822-20, V823-20, Version E, copyright 1998-2001, 35 pgs.

Isacson et al., Scandinavian Physiol. Society 179 173-177 (2003).

Izant et al., Science 299 345 (1985).

Kaemmerer et al., Soc. Neurosci. Meeting (Oct. 26, 2004).

Kao et al., "BACE1 Suppression by RNA Interference in Primary Cortical Neurons," J. Bio. Chem., Published, JBC Papers in Press, Nov. 2003, 2004; 279(3): 1942-1949.

Kashani-Sabet et al., Antisense Res. Dev. 2: 3-15 (1992).

Katz et al., Bioessays 11(6): 181-185 (Dec. 1989).

Kawarabayashi et al., J. Neurosci. 372-381 (2001).

Kenderell et al., (2000) Nat. Biotech. 17, 896-898 (2000).

King et al., Physiology & Behavior, 75: 627-642, 2002.

Kitabwala et al., New England J. Med. 347(17) 1364-1367 (Oct. 24, 2002).

Kitazume J. Biol. Chem. 280(9) 8589-8595 (Mar. 4, 2005).

Klement et al., Cell 95 41-53 (1998).

L'Huillier et al., EMBO J. 11(12), 4411-4418 (1992).

Laird et al., J. Neurosci. 25, 11693-11709 (Dec. 14, 2005).

Le Gal La Salle et al, Science 259, 988-990 (1993).

Li et al., Mol. Cell Bio. 22 (5) 1277-1287 (2002).

Liszewicz et al., Proc. Nat. Acad. Sci 90 8000-8004 (Sep. 1993).

Liu et al., Proc. Japan Academy, Series B, Physical and Biol. Sciences 79(10) 293-298 (Dec. 1993).

Luo et al., Neurobiol. Dis. 14(1), 81-88 (Oct. 2003).

Luo, Nat. Neurosci. 4, 231-232 (2001).

MacDonald, M. et al., "A novel gene containing a trinucleotide repeat that is expanded and unstable on huntington's disease chromosomes," Cell, vol. 72, 971-983 (1993).

Mas-Monteys, A. et al., "Allele-Specific silencing of mutant huntingtin for huntington's disease therapy", Molecular Therapy 13: S274-S275 (2006).

Matilla et al., J. Neurosci 18, 5508-5516 (1998).

McGarry et al., Proc. Natl Acad. Sci. 83, 399-403 (1986).

McManus et al., Nature Reviews/Genetics 3, 737-747 (Oct. 2002).

Menei et al Neurosurgery 34: 1058-1064 (1994).

Messier et al., Pharm. Biochem Behavior 63 313-318 (1999).

Miller et al Proc. Nat. Acad. Sci. 100(12) 7195-7200 (Jun. 10, 2003).

Mirus, TransIT-Neural.RTM. Transfection Reagent, Product Nos. MIR 2144, MIR 2140, MIR 2145, MIR 2146, Lit. #ML022, Rev. Mar. 2, 2005, 5 pgs.

Mirus, TransIT-TKO.RTM. Transfection Reagent, Product Nos. MIR 2154, MIR 2150, MIR 2155, MIR 2156, Lit. #ML015, Rev. Jul. 2004, 6 pgs.

Mogan et al., JECT 36: 191-196 (2004).

Morel et al., J. Comparative Neurology 387, 588-630 (1997).

Mucke et al., J. Neurosci. 20(11) 4050-4058 (Jun. 1, 2000).

Naldini et al., Proc. Nat. Acad. Sci. 93, 11382-11388 (Oct. 1996).

National Center for Biotechnology Information, National Library of Medicine, National Institutes of Health, GenBank Locus AH003045, Accession No. AH003045, "*Homo sapiens* huntingtin (HD) gene, exon 1," [online]. Bethesda, MD [retrieved on Mar. 5, 2009]. Retrieved from the Internet:<URL:http://www.ncbi.nlm.nih.gov/entrez/viewer.fcgi?db=nucleo- tide&val=663286>; 42 pgs.

National Center for Biotechnology Information, National Library of Medicine, National Institutes of Health, GenBank Locus NM.sub.-000027, Accession No. NM.sub.-000027, "*Homo sapiens* aspartylglucosaminidase (AGA), mRNA," [online]. Bethesda, MD[retrieved on Mar. 5, 2009]. Retrieved from the Internet<URL:http://www.ncbi.nlm.nih.gov/entrez/viewer.fcgi?db=nucleo- tide&val=32313568>; 4 pgs.

National Center for Biotechnology Information, National Library of Medicine, National Institutes of Health, GenBank Locus NM.sub.-000046, Accession No. NM.sub.-000046, "*Homo sapiens* arylsulfatase B (ARSB), transcript variant 1, mRNA," [online]. Bethesda, MD [retrieved on Mar. 5, 2009]. Retrieved from the Internet<URL:http://www.ncbi.nlm.nih.gov/entrez/viewer.fcgi?db=nucleo- tide&val=38569404>; 4 pgs.

National Center for Biotechnology Information, National Library of Medicine, National Institutes of Health, GenBank Locus NM.sub.-000147, Accession No. NM.sub.-000147, "*Homo sapiens* fucosidase, alpha-L1, tissue (FUCA1), mRNA," [online]. Bethesda,MD [retrieved on Mar. 5, 2009]. Retrieved from the Internet:<URL:http://www.ncbi.nlm.nih.gov/entrez/viewer.fcgi?db=nucleo-tide&val=24475878>; 3 pgs.

Paxinos et al The Mouse Brain in Stereotactic Coordinates, Acad. Press 2nd Ed. (2001).

Potter, N. T. et al., "Technical standards and guidelines for huntington disease testing," Genetics in Medicine 6:61-65 (2004).

Promega Corporation, T4 DNA Ligase Blue/White Cloning Qualified, Part# 9PIM180, Revised Apr. 2005, 2 pgs.

Promega Corporation, T4 DNA Polymerase(a), Part# 9PIM421, Revised May 2004, 2 pgs.

Qiagen, Qiaex II Handbook, Feb. 1999, 24 pgs.

Qiagen, Rneasy Mini Handbook, 3rd Edition, Jun. 2001, 116 pgs.

R&D Systems, .beta.-Secretase Activity Kit, Catalog No. FP002, Aug. 2002, 2 pgs.

Roberds et al., "BACE knockout mice are healthy despite lacking the primary .beta.-secretase activity in brain: implications for Alzheimer's disease therapeutics," Human Molecular Genetics, Jun. 2001; 10(12): 1317-1324.

Ryu, Biomaterials 26: 319-326 (2005).

Salehi et al., J. Neural Transm. 106 955-986 (1999).

Sapru et al., Annual Meeting Soc. Neurosci. Abstract 297.9, XP001204566 (2003).

Sarver et al., Science 247, 1222-1225 (1990).

Scanlon et al., Proc. Nat. Acad. Sci. 88, 10591-10595 (1995).

Scherr et al., Cell Cycle 2(3) 251-257 (2003).

Serra et al., Medical Image Analysis 1(4) 317-329 (1996).

Singer et al., Nat. Neurosci. 8(10) 1343-1349 (ePub Aug. 28, 2005).

Stackman et al., Experimental Neurology 184, 510-520 (2003).

Strategene, AAV Helper-Free System, Instruction Manual, Catalog #240071, #240074, #240075, Revision #084007i, Aug. 2004, 50 pgs.

Strategene, pBluescript.RTM. II Phagemid Vectors, Instruction Manual, Catalog #212205, #212206, #212207, #212208, Revision #083001m, Aug. 2003, 35 pgs.

Sullenger, Science 262, p. 1566 (Dec. 3, 1993).

Taira et al., Nucl. Acid. Res. 19(19) 5125-5130 (1991).

Thompson et al., Nucl. Acid. Res. 23(12), 2259 (1995).

Timson et al., Biochem J 363:515-520 (2002).

Tuscjl Lab, "The siRNA user guide," Revised May 2004, [online]. Retrieved on Nov. 29, 2005. Retrieved from the Internet<URL:rockefeller.edu/labheads/tuschl/sirna.html>; 6 pgs.

Valbonesi et al., Ttransf. And Apheresis Sci. 30: 153-156 (2004).

Van Bilsen et al., "Identification and allele-specific silencing of the mutant huntingtin allele in Huntington's disease patient-derived fibroblasts," Human Gene Therapy, vol. 19, pp. 710-718 (2008).

Vassar et al., Science 286 735-741 (1999).

Ventura et al., Nucl. Acid. Res. 21(14) 3249-3255 (1993).

Vickers, Journal of Bio. Chemistry, vol. 278, No. 9 7108-7118 (2003).

Watanabe et al., J. Mol. Cel. Card. 37 (3) 691-698 (2004).

Weerasinghe et al., J. Virol. 65(10), 5531-3334 (1991).

Whitesell et al., Proc. Nat. Acad. Sci. 90: 4665-4669 (1993).

Xia et al., Nat. Biotech. 20, 1006-1010 (2002).

Xia et al., Nat. Med. 10(8) 816-820 (2004).

Yamamoto et al., Cell 101, 57-66 (2000).

Yu et al., Proc. Nat. Acad. Sci. 90 6340-6344 (1993).

Yu et al., Proc. Nat. Acad. Sci. 99 6047-6052 (2002).

Zhang et al., "Global Non-Viral Gene Transfer to the Primate Brain Following Intravenous Administration," Molecular Therapy, Jan. 2003; 7(1): 11-18.

Zhang et al., "In vivo knockdown of gene expression in brain cancer with intravenous RNAi in adult rats," J. Gene Med., 2003; 5:1039-1045; published online Aug. 4, 2003.

Zhang et al., "Intravenous RNA Interference Gene Therapy Targeting the Human Epidermal Growth Factor Receptor Prolongs Survival in Intracranial Brain Cancer," Clinical Cancer Research, Jun. 1, 2004; 10:3667-3677.

Zhang et al., 1996 J. Mol. Neurosci. 7: 13-28 (1996).

Zhao et al., J. Biol. Chem. 271(49), 31407-31411 (Dec. 1996).

Zlokovic et al., Neurosurgery 40 805-813 (1997).

Aebischer, et al., "Recombinanat proteins for neurodegenerative disease: the delivery issue,"; Trends in Neurosciences (2001): vol. 24, No. 9; pp. 533-540.

Bass, Brenda L. "The Short Answer," Nature (May 2001), vol. 411 pp. 428-429.

Cahill et al., Atlas of Human Cross-Sectional Anatomy, Wiley-Liss, 3rd Ed. (1995).

Callahan, et al., "Augmented senile plaque load in aged female .beta.-amyloid precursor protein-transgenic mice," American Journal of Pathology (Mar. 2001); vol. 158, No. 3 pp. 1173-1177.

Caplen, et al., "Rescue of polyglutamine-mediated cytotoxicity by double-stranded RNA-mediated RNA interference," Human Molecular Genetics (2002), vol. 11, No. 2, pp. 175-184.

Xia et al., "siRNA-mediated gene silencing in vitro and in vivo," Nature Biotechnology (Oct. 2002) vol. 20 pp. 1006-1010.

Yamamoto et al., "Reversal of neuropathology and motor dysfunction in a conditional model of huntington's disease," Cell (Mar. 31, 2000) vol. 101 pp. 57-66.

Yu et al., "A hairpin ribozyme inhibits expression of diverse strains of human immunodeficiency virus type 1," Proc. Natl. Acad. Sci. (Jul. 1993) vol. 90 pp. 6340-6344.

Yu et al., "RNA intereference by expression of short-interfering RNAs and hairpin RNAs in mammalian cells," PNAS (Apr. 30, 2002) vol. 99, No. 9 pp. 6047-6052.

Zhang et al., "Uptake and distribution of fluorescein-labeled D2, dopamine receptor antisense oligodeoxynucleotide in mouse brain," Journal of Molecular Neuroscience (1996) vol. 7 pp. 13-28.

Mucke et al., High-Level Neuronal Expression of A.beta.1-42 in Wild-Type Human Amyloid Protein Precursor Transgenic Mice: Synaptotoxicity without Plaque Formation, The Journal of Neuroscience, Jun. 1, 2000, 20(11), pp. 4050-4058.

Vassar et al. (1999) Science 286:735-741.

Messier et al. (1999) Pharmacology Biochemistry and Behavior 63:313-318.

Menei et al. (1994) Neurosurgery 34:1058-1064.

Zlokovic et al. (1997) Neurosurgery 40:805-813.

Le Gal La Salle et al. (1993) Science 259:988-990.

Noordmans et al. (2001) "Adeno-associated viral gene expression in the lateral nucleus of the rat hypothalamus" Soc. Neurosci. Abstr. 27:Program No. 572.14.

Luo et al. (2001) Nature Neuroscience 4:231-232.

Bass (2001) Nature 411:428-9.

Kennerdell et al. (2000) Nature Biotechnology 17:896-898.

Gerlai (1998) Behavioral Brain Res. 95:191-203.

Clark et al. (2003) Annals Internal Medicine 138:400-411.

Demetriades (2002) J. Neurological Sciences 203-204:247-251.

Ambion Technical Bulletin #506 (as published on Nov. 16, 2002) downloaded from www.archive.org.

Brummelkamp et al. (2002) Science 296:550-553.

Katahira et al. (2003) "Gene silencing in chick embryos with a vector-based small interfering system" Develop. Growth Differ. 45:361-367.

Bodendorf, U, et al., "Expression of human beta-secretase in the mouse brain increases the steady-state level of beta-amyloid.", J. Neurochem., 80(5), (Mar. 2002),799-806.

Burger, Corinna, et al., "Recombinant AAV viral vectors pseudotyped with viral capsids from serotypes 1, 2, and 5 display differential efficiency and cell tropism after delivery to different regions of the central nervous system.", MolecularTherapy, 10(2), (Aug. 2004),302-317.

Cai, H, et al., "BACE1 is the major beta-secretase for generation of Abeta peptides by neurons.", Nat. Neurosci. 4(3), (Mar. 2001),233-234.

Cleary, J P., et al., "Natural oligomers of the amyloid-beta protein specifically disrupt cognitive function.", Nat. Neurosci., 8(1), Epub Dec. 19, 2004,(Jan. 2005),79-84.

Fu, Haiyan, et al., "Self-complementary adeno-associated virus serotype 2 vector: global distribution and broad dispersion of AAV-mediated transgene expression in mouse brain", Molecular Therapy 8(6), (Dec. 2003),911-917.

Harrison, S M., et al., "BACE1 (beta-secretase) transgenic and knockout mice: identification of neurochemical deficits and behavioral changes.", Mol Cell Neurosci., 24(3), (Nov. 2003),646-655.

Hartlage-Rubsamen, Maike, et al., "Astrocytic expression of the Alzheimer's disease beta-secretase (BACE1) is stimulus-dependent", Glia, 41(2), (Dec. 28, 2002),169-179.

Kaemmerer, W F., et al., "Adeno-associated virus-mediated delivery of siRNA silencing BACE1 in wildtype littermates of the Tg2576 model of Alzheimer's disease", Presented at the 34th Annual Meeting of the Society for Neuroscience in San Diego,CA,(Oct. 26, 2004).

Katz, J D., et al., "A spontaneous sarcoma dependent on host tumor-specific immune lymphocytes.", Bioessays, 11(6), (Dec. 1989),181-185.

Kitazume, Shinobu, et al., "In vivo cleavage of alpha2,6-sialyltransferase by Alzheimer beta-secretase.", J. Biol. Chem., 280(9), (Mar. 4, 2005),8589-8595.

Laird, Fiona M., et al., "BACE1, a major determinant of selective vulnerability of the brain to amyloid-beta amyloidogenesis, is essential for cognitive, emotional, and synaptic functions.", J. Neurosci., 25, (Dec. 14, 2005),11693-11709.

Luo, Y, et al., "BACE1 (beta-secretase) knockout mice do not acquire compensatory gene expression changes or develop neural lesions over time.", Neurobiol. Dis., 14(1), (Oct. 2003),81-88.

Mucke, L, et al., "High-level neuronal expression of abeta 1-42 in wild-type human amyloid protein precursor transgenic mice: synaptotoxicity without plaque formation.", J. Neurosci., 20(11), (Jun. 1, 2000),4050-4058.

Singer, Oded, et al., "Targeting BACE1 with siRNAs ameliorates Alzheimer disease neuropathology in a transgenic model", Nat Neurosci., 8(10), Epub Aug. 28, 2005.,(Oct. 2005),1343-9.

Zhao, Jun, et al., "Beta-secretase processing of the beta-amyloid precursor protein in transgenic mice is efficient in neurons but inefficient in astrocytes.", J. Biol. Chem., 271(49), (Dec. 1996),31407-31411.

Boill e et al., "Gene therapy for ALS deliver," Trends in Neurosciences, May 2004; 27(5): 235-238.

Cal et al., Nat. Neurosci. 4(3) 233-234 (2004).

Gerlai Behav. Brain Res. 95 191-203 (1998).

National Center for Biotechnology Information, National Library of Medicine, National Institutes of Health, "What does NCBI do?" [online]. Bethesda, MD [retrieved on Dec. 5, 2005], Revised Dec. 2005. Retrieved from the Internet:<URL:http://www.ncbi.nlm.nih.gov>; 2 pgs.

National Center for Biotechnology Information, National Library of Medicine, National Institutes of Health, GenBank Locus AF163865, Accession No. AF163865, "*Mus musculus* alpha-synuclein (Snca) gene, complete cds," [online]. Bethesda, MD [retrievedon Jun. 21, 2004]. Retrieved from the Internet:<URL:http://www.ncbi.nlm.nih.gov/entrez/viewer.fcgi?db=nucleo- tide&val=11118354>; 33 pgs.

National Center for Biotechnology Information, National Library of Medicine, National Institutes of Health, GenBank Locus NM.sub.-000049, Accession No. NM.sub.-000049, "*Homo sapiens* aspartoacylase (aminoacylase 1, Canavan disease)(ASPA), mRNA,"[online]. Bethesda, MD [retrieved on Mar. 5, 2009]. Retrieved from the Internet:<URL:http://www.ncbi.nlm.nih.gov/entrez/viewer.fcgi?db=nucleo- tide&val=4557334>; 4 pgs.

National Center for Biotechnology Information, National Library of Medicine, National Institutes of Health, GenBank Locus NM.sub.-000152, Accession No. NM.sub.-000152, "*Homo sapiens* glucosidase, alpha; acid (Pompe disease, glycogen storage diseasetype II)(GAA), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=-11496988>; 4 pgs.

National Center for Biotechnology Information, National Library of Medicine, National Institutes of Health, GenBank Locus NM.sub.-000153, Accession No. NM.sub.-000153, "*Homo sapiens* galactosylceramidase (Krabbe disease) (GALC), mRNA," [online]. Bethesda, MD [retrieved on Mar. 5, 2009]. Retrieved from the Internet:<URL:http://www.ncbi.nlm.nih.gov/entrez/viewer. fcgi?db=nucleo- tide&val=4557612>; 5 pgs.

National Center for Biotechnology Information, National Library of Medicine, National Institutes of Health, GenBank Locus NM.sub.-000157, Accession No. NM.sub.-000157, "*Homo sapiens* glucosidase, beta; acid (includes glucosylceramidase)(GBA),mRNA," [online]. Bethesda, MD [retrieved on Mar. 5, 2009]. Retrieved from the Internet: <URL:http://www.ncbi.nlm.nih.gov/entrez/viewer.fcgi?db=nucleo-tide&val=4503934>; 7 pgs.

National Center for Biotechnology Information, National Library of Medicine, National Institutes of Health, GenBank Locus NM.sub.-000158, Accession No. NM.sub.-000158, "*Homo sapiens* glucan (1, 4-alpha-), branching enzyme 1 (glucogen branchingenzyme, Andersen disease, glycogen storage disease trype (IV)(GBE1), mRNA," [online]. Bethesda, MD [retrieved on Mar. 5, 2009]. Retrieved from the Internet:<URL:http://www.ncbi.nlm.nih.gov/entrez/viewer.fcgi? db=nucleotide&val=4557618>; 2 pgs.

National Center for Biotechnology Information, National Library of Medicine, National Institutes of Health, GenBank Locus NM.sub.-000199, Accession No. NM.sub.-000199, "*Homo sapiens* N-sulfoglucosamine sulfohydrolase (sulfamidase)(SGSH), mRNA,"[online]. Bethesda, MD [retrieved on Mar. 5, 2009]. Retrieved from the Internet:<URL:http://www.ncbi.nlm.nih.gov/entrez/viewer.fcgi?db=nucle- otide&val=31543619>; 3 pgs.

National Center for Biotechnology Information, National Library of Medicine, National Institutes of Health, GenBank Locus NM.sub.-000202, Accession No. NM.sub.-000202, "*Homo sapiens* iduronate 2-sulfatase (Hunter syndrome) (ID), transcript variant1, mRNA," [online]. Bethesda, MD [retrieved on Mar. 5, 2009]. Retrieved from the Internet:<URL:http:// www.ncbi.nlm.nih.gov/entrez/viewer. fcgi?db=nucleotide&val=5360215>; 8 pgs.

National Center for Biotechnology Information, National Library of Medicine, National Institutes of Health, GenBank Locus NM.sub.-000235, Accession No. NM.sub.-000235, "*Homo sapiens* lipase A, lysosomal acid, cholesterol esterase (Wolmandisease)(LIPA), mRNA," [online]. Bethesda, MD [retrieved on Mar. 5, 2009]. Retrieved from the Internet:<URL:http://www.ncbi.nlm.nih.gov/entrez/viewer.fcgi?db=nucleo- tide&val=4557720>; 4 pgs.

Chowrira, et al., "In vitro and in vivo comparison of hammerhead, hairpin, and hepatitis delta virus self-processign ribozyme cassettes," The Journal of Biological Chemistry (1994), vol. 269, No. 41 pp. 25856-25864.

Clark et al., "Purkinje cell expression of a mutant allele of SCA1 in transgenic mice leads to disparate effects on motor behaviors, followed by a progressive cerebellar dysfunction and hitological alterations," The Journal of Neuroscience, (Oct. 1, 1997), vol. 17, No. 19 pp. 7385-7395.

Coutoure et al., "Anti-gene therapy: the use of ribozymes to inhibit gene function," TIG (Dec. 1996): vol. 12, No. 12 pp. 510-515.

Davidson, et al., "Molecular medicine for the brain: silencing of disease genes with RNA interference," The Lancet (2004) pp. 145-149.

Dineley et al., "Accelerated plaque accumulation, associative learning deficits, and up-regulation of .alpha.7 nicotinic receptor protein in transgenic mice co-expressing mutant human presenilin 1 and amyloid precursor proteins," The Journal ofBiological Chemistry (Jun. 21, 2002), vol. 277, No. 25 pp. 22768-22780.

Dropulic, et al., "Functional characterization of a U5 ribozyme: intracellular suppression of human immunodeficiency virus type 1 expression," Journal of Virology (Mar. 1992) vol. 66, No. 3 pp. 1432-1441.

Ezrin-Waters, et al., "The nucleus basalis of meynert," The Canadian Journal of Neurological Sciences (Feb. 1986), vol. 13, No. 1 pp. 8-14.

Gau et al., "Stable .beta.-secretase activity and presynaptic cholinergic markers durign progressive central nervous system amyloidogenesis in Tg2576 mice," American Journal of Pathology (Feb. 2002), vol. 160, No. 2 pp. 731-738.

Glorioso et al., "Use of hsv vectors to moidfy the nervous system," Current Opinion in Drug Discovery & Development (2002), PharmaPress Ltd. ISSN 1367-6733.

Good et al., "Expression of small, therapeutic RNAs in human cell nuclei," Gene Therapy (1997) vol. 4, pp. 45-54.

Goto et al., "Suppression of huntingtin gene expression by sirna: a possible therapeutic tool for huntington's disease," Neurology (Mar. 2003).

Hooper et al., "Infusion into the brain of an antisense oligonucleotide to the immediate-early gnee c-fos suppresses production of fos and produces a behavioral effect," Neuroscience (1994) vol. 63, No. 4 pp. 917-924.

Hsiao et al., "Correlative memory deficits, A.beta. elevation, and amyloid plaques in transgenic mice," Science (Oct. 4, 1996) vol. 274 pp. 99-102.

Isacson et al., "Lack of efficacy of 'naked' small interfering RNA applied directly to rat brain," Acta Phsyiol. Scand. (2003) vol. 179, pp. 173-177.

Izant et al., "Constitutive and conditional suppression of exogenous and endogenous genes by anti-sense ma," Science (1985) 299-345.

Kashani-Sabet et al., "Reversal of the malignant phenotype by an anti-ras ribozyme," Antisense Research and Development 2:3-15 (1992).

Kawarabayashi et al., "Age-dependent changes in brain, csf, and plasma amyloid .beta. protein in the Tg2576 transgenic mouse model of alzheimer's disease," The Journal of Neuroscience (Jan. 15, 2001), 21(2): 372-381.

King et al., "Behavioral characterization of the Tg2576 transgenic model of alzheimer's disease through 19 months," Physiology & Behavior 75 (2002) 627-642.

Kitabwalla et al., "RNA interference—a new weapon against HIV and beyond," The New England Journal of Medicine (Oct. 24, 2002) vol. 347, No. 17.

Klement et al., "Ataxin-1 nuclear localization and aggregation: role in polyglutamine-induced disease in SCA1 Transgenic Mice," Cell (Oct. 2, 1998) vol. 95 p. 41-53.

L'Huillier et al., "Cytoplasmic delivery of ribozymes leads to efficient reduction in .alpha.-lactalbumin mRNA levels in C271 mouse cells,") The EMBO Journal (1992), vol. 11, No. 12 pp. 4411-4418.

Lisziewicz et al., "Inhibition of human immunodeficiency virus type 1 replication by regulated expression of a polymeric tat activation response RNA decoy as a strategy for gene therapy in AIDS," Proc. Natl. Acad. Sci (Sep. 1993) Vo. 90, pp. 8000-8004.

Liu et al., "Specific inhibition of huntington's disease gene expression by siRNAs in cultured cells," Proc. Japan Acad. 79, Ser. B (2003).

Matilla et al., "Mice lacking ataxin-1 display learning deficits and decreased hippocampal paired-pulse facilitation," The Journal of Neuroscience (Jul. 15, 1998) vol. 18, No. 14, pp. 5508-5516.

McGarry et al., "Inhibition of heat shock protein synthesis by heat-inducible antisense RNA," Proc. Natl., Acad. Sci. (Jan. 1986) Vo. 83 pp. 399-403.

McManus et al., "Gene silencing in mammals by interfering RNAs," Nature Reviews (Oct. 2002) vol. 3, pp. 737-747.

Miller et al., "Allele-specific silencing of dominant disease genes," PNAS (Jun. 10, 2003) vol. 100, No. 12 pp. 7195-7200.

Morel et al., "Multiarchitectonic and stereotactic atlas of human thalamus," The Journal of Comparative Neurology 387:588-630 (1997).

Noonberg et al., "In vivo generation of highly abundant sequence-specific oligonucleotides for antisense and triplex gene regulation-,"Nucleic Acids Research (1994) vol. 22, No. 14 pp. 2830-2836.

Ohkawa et al., "Activities of HIV-RNA targeted ribozymes transcribed from a 'shot-gun' type ribozyme-trimming plasmid," Proc. Natl. Acad. Sci 89 (1992).

Ojwang et al., "Inhibition of human immunodeficiency virus type 1 expression by a hairpin ribozyme," Proc. Natl. Acad. Sci. (Nov. 1992) vol. 89 pp. 10802-10806.

Paxinos et al, "The Mouse Brain in Sterotaxic Coordinates," Acad. Press 2nd Edition (2001).

Salehi et al., "Diminished neuronal metabolic activity in alzheimer's disease," J. Neural Transm (1999) 106: 955-986.

Sapru et al., "Small interfering RNA (sirna)-mediated silencing OF.alpha.-synuclein gene expression," Annual Meetign Soc. Neurosci. Abstract 297.9 (2003).

Sarver et al., "Ribozymes as potential anti-HIV-1 therapeutic agents," Science (Mar. 1990) vol. 247 pp. 1222-1225.

Scanlon et al., "Ribozyme-mediated cleavage of c-fos mRNA reduces gene expression of DNA synthesis enzymes and metallothionein," Proc. Natl. Acad. Sci. (Dec. 1991) vol. 88, pp. 10591-10595.

Serra et al., "The brain bench: virtual tools for stereotactic frame neurosurgery," Medical Image Analysis (Jul. 1996) vol. 1, No. 4 pp. 317-329.

Stackman et al., "Prevention of age-related spatial memory deficits in a transgenic mouse model of alzheimer's disease by chronic ginkgo biloba treatment," Experimental Neurology 184 (2003) 510-520.

Sullenger et al., "Tethering ribozymes to a retroviral packaging signal for destruction of viral RNA," Science (Dec. 3, 1993) vol. 262 pp. 15661569.

Taira et al., "Construction of a novel RNA-transcript-trimming plasmid which can be used both in vitro in place of run-off and (g)-free transcriptions and in vivo as multi-sequences transcription vectors," Nucleic Acids Research (1991) vol. 19, No. 19 pp. 5125-5130.

Thompson et al., "Improved accumulation and activity of ribozymes expressed from a tRNA-based RNA polymerase III promoter," Nucleic Acids Research (1995) vol. 23, No. 12 pp. 2259-2268.

Ventura et al., "Activitation of HIV-specific ribozyme activity by self-cleavage," Nucleic Acids Research (1993) vo. 21, No. 14 pp. 3249-3255.

Vickers et al., "Efficient reduction of target RNAs by small interfering RNA and RNase H-dependent antisense agents," The Journal of Biological Chemistry (Feb. 28, 2003) vol. 278, No. 9 pp. 7108-7118.

Weerasinghe et al., "Resistance to human immunodeficiency virus type 1 (HIV-1) infection in human CD4+ lymphocyte-derived cell lines conferred by using retroviral vectors expressing an HIV-1 RNA-specific ribozyme," Journal of Virology (Oct. 1991)vol. 65, No. 10, pp. 5531-5534.

Whitesell et al., "Stability, clearance, and disposition of intraventricularly administered oligodeoxynucleotides therapeutic application within the central nervous system," Proc. Natl. Acad. Sci. (May 1993) vol. 90, pp. 4665-4669.

Basi et al., "Antagonistic Effects of .beta.-site Amyloid Precursor Protein-cleaving Enzymes 1 and 2 on .beta.-Amyloid Peptide Production in Cells," J. Bio. Chem., Published, JBC Papers in Press, Jun. 2003; 278(34): 31512-31520.

Goto et al., Neurology, 60(5) Suppl. 1 p. A286 (Mar. 11, 2003).

Invitrogen, pShooter.TM. Vector (pCMV/myc .COPYRGT. vectors), For the intracellular targeting of recombinant proteins and antibodies, Catalog Nos. V820-20, V821-20, V822-20, V823-20, Version E, copyright 1998-2001,35 pgs.

National Center for Biotechnology Information, National Library of Medicine, National Institutes of Health, GenBank Locus AF163864, Accession No. AF163864, "Homo sapiens SNCA isoform (SNCA) gene, complete cds, alternatively spliced,"[online].Bethesda, MD [retrieved on Jun. 21, 2004]. Retrieved from the Internet: <URL:http://www.ncbi.nlm.nih.gov/entrez/viewer. fcgi?db=nucleotide&val=- 11118351>; 43 pgs.

National Center for Biotechnology Information, National Library of Medicine, National Institutes of Health, GenBank Locus AF163865, Accession No. AF163865, "Mus musculus alpha-synuclein (Snca) gene, complete cds," [online]. Bethesda, MD [retrievedon Jun. 21, 2004]. Retrieved from the Internet:<URL:http://www.ncbi.nlm.nih.gov/entrez/viewer. fcgi?db=nucleotide&val=11118354>; 33 pgs.

National Center for Biotechnology Information, National Library of Medicine, National Institutes of Health, GenBank Locus NM.sub.-000152, Accession No. NM.sub.-000152, "Homo sapiens glucosidase, alpha; acid (Pompe disease, glycogen storage diseasetype II) (GAA), mRNA," [online]. Bethesda, MD [retrieved on Mar. 5, 2009]. Retrieved from the Internet:<URL:http://www.ncbi.nlm.nih.gov/entrez/viewer.fcgi?db=nucleo- tide &val=11496988>: 4 pgs.

National Center for Biotechnology Information, National Library of Medicine, National Institutes of Health, GenBank Locus NM.sub.-000157, Accession No. NM.sub.-000157, "Homo sapiens glucosidase, beta; acid (includes glucosylceramidase) (GBA),mRNA," [online]. Bethesda, MD [retrieved on Mar. 5, 2009]. Retrieved from the Internet<URL:http://www.ncbi.nlm.nih.gov/entrez/viewer.fcgi?db=nucleot- ide&val=4503934>; 7 pgs.

National Center for Biotechnology Information, National Library of Medicine, National Institutes of Health, GenBank Locus NM.sub.-000158, Accession No. NM.sub.-000158, "Homo sapiens glucan (1, 4-alpha-), branching enzyme 1 (glucogen branchingenzyme, Andersen disease, glycogen storage disease trype (IV)(GBE1), mRNA," [online]. Bethesda, MD [retrieved on Mar. 5, 2009].

Retrieved from the Internet:<URL:http://www.ncbi.nlm.nih.gov/entrez/viewer.fcgi?db=nucleo- tide&val=4557618>; 2 pgs.
National Center for Biotechnology Information, National Library of Medicine, National Institutes of Health, GenBank Locus NM.sub.-000263, Accession No. NM.sub.-000263, "*Homo sapiens* N-acetylglucosaminidase, alpha-(Sanfilippo disease)(IIIB)(NAGLU), mRNA," [online]. Bethesda, MD [retrieved on Mar. 5, 2009]. Retrieved from the Internet:<URL:http:// www.ncbi.nlm.nih.gov/entrez/viewer.fcgi?db=nucleotide&val=40548380>; 4 pgs.
National Center for Biotechnology Information, National Library of Medicine, National Institutes of Health, GenBank Locus NM.sub.-000332, Accession No. NM.sub.-000332, "*Homo sapiens* spinocerebellar ataxia 1 (olivopontocerebellar ataxia 1,autosomal dominant, ataxin 1) (SCA1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4506792>; 7 pgs.
National Center for Biotechnology Information, National Library of Medicine, National Institutes of Health, GenBank Locus NM.sub.-000487, Accession No. NM.sub.-000487, "*Homo sapiens* arysulfatase A (ARSA), mRNA," [online]. Bethesda, MD [retrievedon Mar. 5, 2009]. Retrieved from the Internet:<URL:http://www.ncbi.nlm.nih.gov/entrez/viewer.fcgi?db=nu- cleotide&val=7262293>; 4 pgs.
National Center for Biotechnology Information, National Library of Medicine, National Institutes of Health, GenBank Locus NM.sub.-002076, Accession No. NM.sub.-002076, "*Homo sapiens* glucosamine (N-acetyl)-6-sulfatase (Sanfilippodisease)(IIID)(GND), mRNA," [online]. Bethesda, MD [retrieved on Mar. 5, 2009]. Retrieved from the Internet:<URL:http://www.ncbi.nlm.nih.gov/entrez/viewer.fcgi?db=nucleo- tide&val=42490755>; 7 pgs.
National Center for Biotechnology Information, National Library of Medicine, National Institutes of Health, GenBank Locus NM.sub.-011792, Accession No. NM.sub.-011792, Version NM.sub.—011792.2, "*Mus musculus* beta-site APP cleaving enzyme 1 (Bace1), mRNA," [online]. Bethesda, MD [retrieved on Mar. 5, 2009]. Retrieved from the Internet:<URL:http:// www.ncbi.nlm.nih.gov/entrez/viewer.fcgi?db=nucleotide&val=31981411>; 5 pgs.
Tuscjl Lab, "The siRNA user guide," Revised May 2004, [online]. Retrieved on Nov. 29, 2005. Retrieved from the Internet: <URL:rockefeller.edu/labheads/tuschl/sirna.html>; 6 pgs.
Zhang et al., "In vivo knockdown of gene expression in brain cancer with intravenous RNAi in adult rats," J. Gene Med.. 2003; 5:1039-1045; published online Aug. 4, 2003.
Paxinos et al. (2001) The Mouse Brain in Stereotaxic Coordinates. Academic Press, 2nd Ed. (selected pages).
Caplen et al. (2001) Proc. Natl. Acad. Sci. 98:9742-9747.
Hooper et al. (1995) Neuroscience 63:917-924.
Ezrin-Waters et al. (1986) Can J. Neurol. Sci. 13:8-14.
Vickers et al. (2003) J. Biol. Chem. 278:7108-7118.
Holen et al. (2002) Nucleic Acids Res. 30:1757-1766.
Elbashir et al. (2002) Methods 26:199-213.
Katahira et al. (2003) "Gene silencing in chick embryos with a vector-based small interfering RNA system" Develop. Growth Differ. 45: 361-367.
Li et al, Predicting siRNA efficiency, Cellular and Molecular Life Sciences, 2007, pp. 1785-1792, vol. 64, Birkhauser Verlag, Basel, Switzerland.
Schwarz, Dianne S. et al, Designing siRNA that Distinguishes between Genes that Differ by a Single Nucleotide, PLoS Genetics, www.plosgenetics.org, Sep. 2006, pp. 1307-1318, vol. 2, Issue 9, e140.
Senn, Claudia et al, Central administration of small interfering RNAs in rats: A comparison with antisense oligonucleotides, European Journal of Pharmacology, 2005, pp. 30-37, vol. 522, Elsevier B.V.
Xu, Yunhe et al., Effective small interfering RNAs and phosphorothioate antisense DNAs have different preferences for target sites in the luciferase mRNAs, Biochemical and Biophysical Research Communications, 2003, pp. 712-717, vol. 306, ElsevierScience (USA).

Kashani-Sabet et al., Reversal of the Malignant Phenotype by an Anti-ras Ribozyme, Antisense Res. Dev., 2:3-15, 1992.
Kitabwalla, Moiz, Ph.D., et al., RNA interfence—a new weapon against HIV and beyond, New England Journal of Medicine, 347(17):1364-1367, 2002.
Klement, Ivan, et al., Ataxin-1 nuclear localization and aggregation: Role in polyglutamine-induced disease in SCA1 transgenic mice, Cell vol. 95:41-53, 1998.
L'Huillier, Phillip J., et al., Cytoplasmic delivery of ribozymes leads to efficient reduction in x-lactalbumin mRNA levels in C1271 mouse cells, EMBO Journal, 11(12):4411-4418, 1992.
Lisziewicz et al., Inhibition of human immunodeficiency virus type 1 replication by regulated expression of a polymeric Tat activation response RNA decoy as a strategy for gene therapy in AIDS, Proc. National Acad Sci USA, 90:8000-8004, 1993.
Matila, A., et al., Mice lacking ataxin-1 display learning deficits and decreased hippocampal paired-pulse facilitation, Journal of Neuroscience, 18(14):5508-5516, 1998.
McGarry, Thomas J., et al., Inhibition of heat shock protein synthesis by heat-inducible antisense RNA, Proc. National Academy Science, USA, 83:399, 1986.
McManus, Michael T., Gene Silencing in Mammals by Small Interfering RNAs, Nature Reviews / Genetics, 3:737-747, 2002.
Miller, Victor M., Allele-specific silencing of dominant disease genes, PNAS, 100(12):7195-7200, 2003.
Naldini, Luigi, Efficient transfer, integration and sustained long-term expression of the transgene in adult rat brains injected with a lentiviral vector, Proc. National Academy Science, 93:11382-11388, 1996.
Noonberg, et al., In vivo generation of highly abundant sequence-specific oligonucleotides for antisense and triplex gene regulation, Nucleic Acid Research, 22(14):2830-2836, 1994.
Ohkawa, et al., Activities of HIV-RNA targeted riboyzmes transcribed from a shot-gun type riboyzme-trimming plasmid, Nucleic Acids Symp. Ser., 27:15-16, 1992.
Ojwang, Joshua O., et al., Inhibition of human immunodeficiency virus type-1 expressoin by a hairpin ribozyme, Proc. National Academy Science USA, 89:10802-10806, 1992.
Sarver, Nava et al., Ribozymes as potential anti-HIV-1 therapeutic agents, Science, 247:1222-1225, 1990.
Scanlon, K.J., et al., Ribozyme-mediated cleavage of c-fos mRNA rduces gene expression of DNA synthesis enzymes and metallothionein, Proc. National Academy Science USA, 88:10591-10595, 1991.
Stackman, Robert W., et al, Prevention of Age-Related Spatial Memory Deficits in a Transgenic Mouse Model of Alzheimer's Disease by Chronic Ginkgo biloba Treatment, Experimental Neurology, 184:510-520, 2003.
Sullenger, Bruce and Cech, Thomas R., Tethering Ribozymes to a Retroviral Packaging Signal for Destruction of Viral RNA, Science, 262:1566, 1993.
Thompson, James D., et al., Improved accumulation and activity of ribozymes expressed from a tRNA-based RNA polymerase III promoter, Nucleic Acids Res., 23(12):2259, 1995.
Weerasinghe, Migara et al., Resistance to human immunodeficiency virus type 1 (HIV-1) infection in human CD4 lymphocyte-derived cell lines conferred by using retroviral vectors expressing an HIG-1 RNA-specific ribozyme, Journal of Virology,65(10):5531-5534, 1991.
Cai et al. (2001) Nature Neuroscience 4:233-234.
Ashe et al. (2001) "Learning and Memory in Transgenic Mice Modeling Alzheimer's Disease" Learning & Memory 8:301-308.
Aebisher, Trends in Neurosci. 24(9) 553-540 (Sep. 2001).
Altschul et al., "Gapped Blast and PSO-BLAST: a new generation of protein database search prorams," Nucl. Acids Res., 25(17): 3389-3402 (1997).
Ambion Inc., pSilencer.TM. 1.0-U6 siRNA Expression Vector, Catalog # 7207-20 .mu.g, Nov. 2004, Austin, TX, 6 pgs.
Ambion, Inc., Silencer siRNA.RTM. Construction Kit, Cat. #1620, Instruction Manual, Aug. 2005, 36 pgs.
Ausubel et al., Eds., Current Protocols in Molecular Biology, vols. 1-3, John Wiley & Sons, Inc., New York, NY, 1994; title page, publisher's page and table of contents only, 14 pgs.

Bass et al., Nature 411: 428-429 (2001).
Bertrand et al., Biochem Biophys Res Comm 296: 1000-1004 (2002).
Bodendorf et al., J. Neurochem. 80(5), 799-806 (Mar. 2002).
Boillee et al., "Gene therapy for ALS deliver," Trends in Neurosciences, May 2004; 27(5): 235-238.
Bortolin, Susan et al., "Analytical validation of the tag-it high-throughout microsphere-based universal array genotyping platform. Application to the multiplex detection of a panel of thrombophilia-associates single-nucleotide polymorphisms."American Association for Clinical Chemistry vol. 50(11) 2028-2036 (2004).
Brentano et al., P.N.A.S. 89:4099-4103 (1992).
Brummelkamp et al., Science 296: 550-553 (2002).
Burger et al., Mol. Ther. 10(2) 302-317 (Aug. 2004).
Cahill et al Atlas of Human Cross-Sectional Anatomy Wiley-Liss, 3rd Ed. (1995).
Cai et al., Nat. Neurosci. 4(3) 233-234 (2004).
Callahan Am. J. Pathol. 158(3) 1173-1177 (2001).
Caplen et al, Human Mol. Genet. 11(2) 175-184 (2002).
Chen et al., Nucl. Acid. Res. 20, 4581-4589 (1992).
Chi et al., "Genomewide view of gene silencing by small interfering RNAs," Proc. Natl. Acad. Sci. USA, May 2003; 100 (11): 6343-6346.
Chowhira et al., J. Biol. Chem. 269, 25856-25863 (1994).
Christman, Tissue Engineering (10) 403-409 (2004).
Cioffi et al., Biochem J. 365: 833-840 (2002).
Clark et al., Annals Int. Med. 138 400-411 (2003).
Clark et al., J. Neurosci. 17(19) 7385-7395 (1997).
Cleary et al., Nat. Neurosci. 8(1) 79-84 (ePub Dec. 19, 2004).
Couture et al., Trends in Genetics, 12(12) 510-515 (Dec. 1996).
Dai et al., Developmental Biology 285:80-90 (2005).
Davidson et al., The Lancet, Neurology 3, 145-149 (2004).
Demetriades J. Neurolog. Sci. 203-204, 247-251 (2002).
Dineley, J, Biol. Chem. 277 (25) 22768-22780 (2002).
Dorri et al., Exp. Neurology 147 48-54 (1997).
Dropulic et al., J. Virol. 66(1) 1432-1441 (1992).
During et al., "Subthalamic GAD GeneTransfer in Parkinson's Disease Patients Who Are Candidates for Deep Brain Stimulation," Human Gene Therapy, Aug. 2001; I2(12): 1587-1598.
ElBashir, EMBOJ 20(23) 6877-6888 (2001).
Ezrin-Waters et al., Can. J. Neurol. Sci. 13, 8-14 (1986).
Fu et al., Mo. Ther. 8(6) 911-917 (Dec. 2003).
Gau, Am. J. Pathol., 160(2) 731-738 (2002).
GeneDetect.com Limited, Code GD100X-RV, (GeneDetect rAVE. TM. gene delivery reagent), copyright 2000-2002, Auckland, New Zealand, 2 pgs.
Geraerts et al., Concise Review: Therapeutic Strategies for Parkinson Disease Based on Modulation of Adult Neurogenesis. Stem Cells, Nov. 2, 2006, vol. 25, No. 2, pp. 263-270.
Gerlai Behay. Brain Res. 95 191-203 (1998).
Glorioso, Curr. Opinion in Drug Discovery & Dev't 5(2) Pharma Press ISSN 1367-6733 (2002).
Good et al., Gene Ther. 4: 45-54 (1997).
Harrison et al., Mol. Cel. Neurosci. 24(3) 646-655 (2003).
Hartlage-Rubsamen et al., Glia 41(2) 169-179 (Dec. 28, 2002).
Heale et al., Nucl. Acid. Res. 22(3), 2005.
National Center for Biotechnology Information, National Library of Medicine, National Institutes of Health, GenBank Locus NM.sub.-000157, Accession No. NM.sub.-000157, "Homo sapiens glucosidase, beta; acid (includes glucosylceramidase) (GBA),mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=4503934>; 7 pgs.
National Center for Biotechnology Information, National Library of Medicine, National Institutes of Health, GenBank Locus NM.sub.-000158, Accession No. NM.sub.-000158, "Homo sapiens glucan (1, 4-alpha-), branching enzyme 1 (glucogen branchingenzyme, Andersen disease, glycogen storage disease trype (IV)(GBE1), mRNA," [online]. Bethesda, MD [retrieved on Mar. 5, 2009]. Retrieved from the Internet:<URL:http://www.ncbi.nlm.nih.gov/entrez/viewer.fcgi? db=nucleotide&val=4557618>: 2 pgs.
National Center for Biotechnology Information, National Library of Medicine, National Institutes of Health, GenBank Locus NM.sub.-000181, Accession No. NM.sub.-000181, "Homo sapiens glucuronidase, beta (GUSB), mRNA," [online]. Bethesda, MD[retrieved on Mar. 5, 2009]. Retrieved from the Internet:<URL:http://www.ncbi.nlm.nih.gov/entrez/viewer.fcgi?db=nu-cleotide&val=4504222>; 4 pgs.
National Center for Biotechnology Information, National Library of Medicine, National Institutes of Health, GenBank Locus NM.sub.-000199, Accession No. NM.sub.-000199, "Homo sapiens N-sulfoglucosamine sulfohydrolase (sulfamidase) (SGSH), mRNA,"[online]. Bethesda, MD [retrieved on Mar. 5, 2009]. Retrieved from the Internet:<URL:http://www.ncbi.nlm.nih.gov/entrez/viewer.fcgi?db=nucleo-tide&val=31543619>; 3 pgs.
National Center for Biotechnology Information, National Library of Medicine, National Institutes of Health, GenBank Locus NM.sub.-000202, Accession No. NM.sub.-000202, "Homo sapiens iduronate 2-sulfatase (Hunter syndrome) (ID), transcript variant1, mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=5360215>; 8 pgs.
National Center for Biotechnology Information, National Library of Medicine, National Institutes of Health, GenBank Locus NM.sub.-000203, Accession No. NM.sub.-000203, "Homo sapiens iduronidase, alpha-L-(IDUA), mRNA," [online]. Bethesda, MD[retrieved on Mar. 5, 2009]. Retrieved from the Internet:<URL:http://www.ncbi.nlm.nih.gov/entrez/viewer.fcgi?db=nu-cleotide&val=40354208>; 6 pgs.
National Center for Biotechnology Information, National Library of Medicine, National Institutes of Health, GenBank Locus NM.sub.-000235, Accession No. NM.sub.-000235, "Homo sapiens lipase A, lysosomal acid, cholesterol esterase (Wolman disease)(LIPA), mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=4557720>; 4 pgs.
National Center for Biotechnology Information, National Library of Medicine, National Institutes of Health, GenBank Locus NM.sub.-000262, Accession No. NM.sub.-000262, "Homo sapiens N-acetylgalactosaminidase, alpha-(NAGA), mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=4557780>; 4 pgs.
National Center for Biotechnology Information, National Library of Medicine, National Institutes of Health, GenBank Locus NM.sub.-000404, Accession No. NM.sub.-000404, "Homo sapiens glactosidase, beta 1 (GLB1), transcript variant 179423, mRNA,"[online]. Bethesda, MD [retrieved on Mar. 5, 2009]. Retrieved from the Internet:<URL:http://www.ncbi.nlm.nih.gov/entrez/viewer.fcgi?db=nucleo-tide&val=10834965>; 5 pgs.
National Center for Biotechnology Information, National Library of Medicine, National Institutes of Health, GenBank Locus NM.sub.-000434, Accession No. NM.sub.-000434, "Homo sapiens sialidase 1 (lysosomal sialidase)(NEU1), mRNA," [online].Bethesda, MD [retrieved on Mar. 5, 2009]. Retrieved from the Internet:<URL:http://www.ncbi.nlm.nih.gov/entrez/viewer.fcgi?db=nucleo-tide&val=40806202>; 5 pgs.
National Center for Biotechnology Information, National Library of Medicine, National Institutes of Health, GenBank Locus NM.sub.-000512, Accession No. NM.sub.-000512, "Homo sapiens galactosamine (N-acetyl)-6-sulfate sulfatase (Morquio syndrome,mucopolysaccharidosis type IVA), (GALNS), mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=9945384>; 4 pgs.
National Center for Biotechnology Information, National Library of Medicine, National Institutes of Health, GenBank Locus NM.sub.-000528, Accession No. NM.sub.-000528, "Homo sapiens mannosidase, alpha, class 2B, member 1 (MAN2B1), mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=10834967>; 4 pgs.
National Center for Biotechnology Information, National Library of Medicine, National Institutes of Health, GenBank Locus NM.sub.-002778, Accession No. NM.sub.-0002778, Accession No. NM.sub.-000169, "Homo sapiens glactosidase, alpha (GLA), mRNA,"[online]. Bethesda, MD [retrieved on Mar. 5, 2009].

Retrieved from the Internet:<URL:http://www.ncbi.nlm.nih.gov/entrez/viewer.fcgi?db=nucleo-tide&val=4504008>; 4 pgs.

National Center for Biotechnology Information, National Library of Medicine, National Institutes of Health, GenBank Locus NM.sub.-002778, Accession No. NM.sub.-002778, "*Homo sapiens*prosaposin (variant Gaucher disease and variant metachromaticleukodystrophy) (PSAP), mRNA," [online]. Bethesda, MD [retrieved on Mar. 5, 2009]. Retrieved from the Internet:<URL:http//www.ncbi.nlm.nih.gov/entrez/viewer.fcgi?db=nucleot-ide&val=11386146>; 8 pgs.

National Center for Biotechnology Information, National Library of Medicine, National Institutes of Health, GenBank Locus NM.sub.-004315, Accession No. NM.sub.-004315, "*Homo sapiens* N-acylsphingosine amidohydrolase (acid ceramidase) 1 (ASAHI),transcript variant 2, mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=30089929>; 5 pgs.

National Center for Biotechnology Information, National Library of Medicine, National Institutes of Health, GenBank Locus NM.sub.-005908, Accession No. NM.sub.-005908, "*Homo sapiens* mannosidase, beta A, lyosomal (MANBA), mRNA," [online]. Bethesda,MD [retrieved on Mar. 5, 2009]. Retrieved from the Internet:<URL:http://www.ncbi.nlm.nih.gov/entrez/viewer.fcgi?db=nucleo-tide&val=24797157>; 4 pgs.

National Center for Biotechnology Information, National Library of Medicine, National Institutes of Health, GenBank Locus NM.sub.-009124, Accession No. NM.sub.-009124, "Definition," [online]. Bethesda, MD [retrieved on Mar. 5, 2009]. Retrievedfrom the Internet:<URL:http://www.ncbi.nlm.nih.gov/entrez/viewer.fcgi?db=nucleo-tide&val=33636695>; 5 pgs.

National Center for Biotechnology Information, National Library of Medicine, National Institutes of Health, GenBank Locus NM.sub.-011792, Accession No. NM.sub.-011792, Version NM.sub.-011792.2, "*Mus musculus* beta-site APP cleaving enzyme 1 (BACE1), mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=31981411>; 5 pgs.

National Center for Biotechnology Information, National Library of Medicine, National Institutes of Health, GenBank Locus NM.sub.-011792.2, Accession No. NM.sub.-011792, "*Mus musculus* beta-site APP cleaving enzyme (BACE), mRNA," [online].Bethesda, MD [retrieved on Mar. 5, 2009]. Retrieved from the Internet:<URL:http://www.ncbi.nlm.nih.gov/entrez/viewer.fcgi?db=nucleo-tide&val=6857758>; 4 pgs.

National Center for Biotechnology Information, National Library of Medicine, National Institutes of Health, GenBank Locus NM.sub.-012104, Accession No. NM.sub.-012104, "*Homo sapiens* beta-site APP-cleaving enzyme 1 (BACE1), transcript variant a,mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=46255011>; 8 pgs.

National Center for Biotechnology Information, National Library of Medicine, National Institutes of Health, GenBank Locus NM.sub.-012104, Accession No. NM.sub.-012104, Version NM.sub.-012104.2, "*Homo sapiens* beta-site APP-cleaving enzyme (BACE),transcript variant a, mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=21040369>; 10 pgs.

National Center for Biotechnology Information, National Library of Medicine, National Institutes of Health, GenBank Locus NM.sub.-013995, Accession No. NM.sub.-013995, "*Homo sapiens* lysosomal-associated membrane protein 2 (LAMP2), transcriptvariant LAMP2B, mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=7669502>; 6 pgs.

National Center for Biotechnology Information, National Library of Medicine, National Institutes of Health, GenBank Locus NM.sub.-138971, Accession No. NM.sub.-138971, "*Homo sapiens* beta-site APP-cleaving enzyme 1 (BACE1), transcript variant c,mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=46255012>; 8 pgs.

National Center for Biotechnology Information, National Library of Medicine, National Institutes of Health, GenBank Locus NM.sub.-138971, Accession No. NM.sub.-138971, Version NM.sub.—138971.1, "*Homo sapiens* beta-site APP-cleaving enzyme (BACE),transcript variant c, mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=21040363>; 10 pgs.

National Center for Biotechnology Information, National Library of Medicine, National Institutes of Health, GenBank Locus NM.sub.-138972, Accession No. NM.sub.-138972, "*Homo sapiens* beta-site APP-cleaving enzyme 1 (BACE1), transcript variant b,mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=46255013>; 8 pgs.

National Center for Biotechnology Information, National Library of Medicine, National Institutes of Health, GenBank Locus NM.sub.-138972, Accession No. NM.sub.-138972, Version NM.sub.-138972.1, "*Homo sapiens* beta-site APP-cleaving enzyme (BACE),transcript variant b, mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=21040365>; 10 pgs.

National Center for Biotechnology Information, National Library of Medicine, National Institutes of Health, GenBank Locus NM.sub.-138973, Accession No. NM.sub.-138973, "*Homo sapiens* beta-site APP-cleaving enzyme 1 (BACE1), transcript variant d,mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=46255014>; 8 pgs.

National Center for Biotechnology Information, National Library of Medicine, National Institutes of Health, GenBank Locus NM.sub.-138973, Accession No. NM.sub.-138973, Version NM.sub.-138973.1, "*Homo sapiens* beta-site APP-cleaving enzyme (BACE),transcript variant d, mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=21040367>: 10 pgs.

National Center for Biotechnology Information, National Library of Medicine, National Institutes of Health, GenBank Locus U24233, Accession No. 024233, "*Mus musculus* huntingtin (Hd) mRNA, complete cds," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=902003>; 5 pgs.

National Center for Biotechnology Information, National Library of Medicine, National Institutes of Health, GenBank Locus XM.sub.-032588, Accession No. XM.sub.-032588, "*Homo sapiens* dentatorubral-pallidoluysian atrophy (artrophin-1) (DRPLA),mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=20555988>; 3 pgs.

National Center for Biotechnology Information, National Library of Medicine, National Institutes of Health, GenBank Locus XM.sub.-132846, Accession No. XM.sub.-132846, "*Mus musculus* dentatorubral pallidoluysian atrophy (DRPLA) mRNA," [online]. Bethesda, MD [retrieved on Mar. 5, 2009]. Retrieved from the Internet:<URL:http://www.ncbi.nlm.nih.gov/entrez/viewer.fcgi?db=nucleo-tide&val=20832263>; 3 pgs.

Noonberg et al., Nucl. Acid Res. 22(14) 2830-2836 (1994).

Noordmans et al., Soc. Neurosci. Abstr. 27, Program 572.14 (2001).

Ohkawa Nucl. Acid. Symp. Ser. 27, 15-16 (1992).

Ohno et al., "BACEI Deficiency Rescues Memory Deficits and Cholinergic Dysfunction in a Mouse Model of Alzheimer's Disease," Neuron, Jan. 2004; 41: 27-33.

\* cited by examiner

SEQUENCE LISTING

```
<160> NUMBER OF SEQ ID NOS: 85

<210> SEQ ID NO 1
<211> LENGTH: 21
<212> TYPE: DNA
<213> ORGANISM: Homo sapiens

<400> SEQUENCE: 1
aaccaagagc ggagcaacga a                                              21

<210> SEQ ID NO 2
<211> LENGTH: 21
<212> TYPE: DNA
<213> ORGANISM: Homo sapiens

<400> SEQUENCE: 2
aattcgttgc tccgctcttg g                                              21

<210> SEQ ID NO 3
<211> LENGTH: 21
<212> TYPE: DNA
<213> ORGANISM: Homo sapiens

<400> SEQUENCE: 3
aaccaagagc ggagcaacga a                                              21

<210> SEQ ID NO 4
<211> LENGTH: 21
<212> TYPE: DNA
<213> ORGANISM: Homo sapiens

<400> SEQUENCE: 4
aattcgttgc tccgctcttg g                                              21

<210> SEQ ID NO 5
<211> LENGTH: 21
<212> TYPE: DNA
<213> ORGANISM: Homo sapiens

<400> SEQUENCE: 5
aaccagtacg tccacatttc c                                              21

<210> SEQ ID NO 6
<211> LENGTH: 21
<212> TYPE: DNA
<213> ORGANISM: Homo sapiens

<400> SEQUENCE: 6
aaggaaatgt ggacgtactg g                                              21

<210> SEQ ID NO 7
<211> LENGTH: 145606
<212> TYPE: DNA
<213> ORGANISM: Homo sapiens
<220> FEATURE:
<221> NAME/KEY: misc_feature
<222> LOCATION: (1)..(145606)
<223> OTHER INFORMATION: LOCUS       AF163864           145606 bp
      DNA       linear     P
      RI 24-JAN-2001 DEFINITION  Homo sapiens SNCA isoform (SNCA) gene,
```

... ACCESSION AF163864
<300> PUBLICATION INFORMATION:
<308> DATABASE ACCESSION NUMBER: AF163864
<309> DATABASE ENTRY DATE: 2001-01-24
<313> RELEVANT RESIDUES IN SEQ ID NO: (1)..(145606)

<400> SEQUENCE: 7

| | | | | | |
|---|---|---|---|---|---|
| aattttcctt | gaaaaacata | gatgtccagt | tctatctctc | atatttttc | ttttcataga | 60 |
| gatatggcac | tttaggatta | atttaagctg | caaacagcag | aaaaatgcaa | ataacagtg | 120 |
| gcttaaatga | aatagaaata | ttttatctct | tgaaaagtt | ctgataaaga | cagtcaaatg | 180 |
| ctagaagggc | aactgtgttc | cagaaggttc | tcaaggagcc | aggctacctc | taacccactg | 240 |
| ctctgccatc | tctaattcat | gtcgtatgtc | ctcagggtcc | acaatggcag | taagaacgct | 300 |
| cctcatcata | tctgtgtttc | aaatagtaga | atggagagaa | agagaagaaa | aggaggcatt | 360 |
| aaggaaggtt | ccagaagctg | ccatttgaca | cttctgttaa | catttaattg | gccaaaattt | 420 |
| aatctcatat | cgcataagct | gtaagagatg | ctggaaaact | tatttgtctc | cactctacat | 480 |
| ggacattatc | agagtatttc | tcaacagaga | ggtctatgta | ataatagtaa | aaagtaagag | 540 |
| tggacacaaa | cctagtcctt | tacctttcag | tagaagtaaa | aatgctatat | taatatttac | 600 |
| tctctctctc | tctctctctc | tctctctctc | tcattttgg | ttttgacaat | caaattcagc | 660 |
| taaatatgat | tgaaactaaa | atcaaggaaa | atgcattata | ctctgttgtt | atggtaactg | 720 |
| gaatggtgaa | atgtgtggat | tattttcaca | ccttcaataa | tatgtttcta | accatatatt | 780 |
| ttttaaaaat | tgctgcaggg | tttgcttaat | gaccagagta | taaaggcaca | ttttttctc | 840 |
| agttggcaaa | aacacagttt | tgacaaattt | gacaagtttt | tgtagatctg | taattttattt | 900 |
| gatttaatta | aattttcatc | ttgttttcac | aatgagttat | tgaaaataaa | atctaaagct | 960 |
| ttaaacagga | aaattttaaa | tttgaatttt | cttggttgaa | ctacttatac | ttttcactt | 1020 |
| caattcacta | acagaataaa | tacatcattc | cactgaatat | gagccatcca | tacaaagagt | 1080 |
| ccatgaccaa | atgcaatgtc | actaggtatt | taaagtaacc | tataaattat | gttctgtctc | 1140 |
| attgtccaca | aaatattaca | acctgcatat | ttggaaaaac | attttgttca | tgatatgtac | 1200 |
| atatatgagg | catgcatatg | gataaataca | tataagttg | tgaaaattag | gcaaatttta | 1260 |
| tattttcgtc | cactcttgaa | actttcattt | ttcaaaaaca | aaatttaaaa | tgctaacttt | 1320 |
| taaaataaat | gtgccatagt | agcacaatat | gttaatattg | gggaaaactg | catggaaaat | 1380 |
| atacagaaat | gcttcatact | ttacaattct | tttgtacatc | ccatattatt | tcaaaagtta | 1440 |
| aaagttttaa | atatgttcag | tcttgaaatg | tatcagaaat | gtttatctaa | agttttgttg | 1500 |
| gtgttaagat | taatatatta | gtaatattac | acacagaaag | acagaaggta | aaagtaaagt | 1560 |
| tagtttgaat | atgactgtca | ttttaagtca | ttaacattta | actttaccaa | cttcatctca | 1620 |
| agttggccca | tatcactgcc | caacttaaac | acatggctac | atgcagcagg | taaagtacat | 1680 |
| ggcaggacta | ttgagatatc | aaggagtcac | tgtgtgtcag | gaaatgataa | agttccccag | 1740 |
| cgtctcctca | cctgtgtcag | gccgacttag | ggaaaccaca | ttctacgttc | ataaagagtg | 1800 |
| atctgcgggc | ttgaaaggca | agtaagcaga | aagaagtgtt | tatcccagca | attcatgaaa | 1860 |
| atgttgaaaa | aaagaaaaa | ctaagtcagc | tttccttaga | acccaagttt | cggcctgcct | 1920 |
| tttaaaattt | tctctatcaa | agctgccacc | ttttttccag | atgctcaaga | taaacactc | 1980 |
| aacacagaaa | tgcatgattt | tgttgctgag | ataccggttt | gttgtttaca | ctctgccctc | 2040 |
| ctatccattg | caccttccag | ttccgcttgc | tctcagtctc | cacctctgat | tgctacttac | 2100 |
| acaatttatc | ccatgaaaca | ccatcagatt | attccagcac | acaccagtat | ctctgggcct | 2160 |

-continued

```
tccctggtgc actgcactct ctcctttcca cagagcctgt ggaaagagtg gcacagtagc    2220
tggaggggca cacagggtac agagcacctt tccccaccca actcttgcgg tgctgtagac    2280
ctgaggtggt accatgaagg aaacatggac agttgagacc acatgcaaga gcccagacac    2340
acggctcaag ctcccagggt cagtgatagt gtatagctag ctgggaaccc tgcactggcc    2400
ctgtgttcaa catgagtggg tcaccctaaa agacatttca gcgtggttct gcctaccaaa    2460
tcttgcaaag aaatacctct ccactcagtg agaagtgatc cactagccag gctgccctcc    2520
tagacctgaa ttaaccatag agtcccagaa ttattctata ggcttgagcc ccagcattct    2580
gtggggcatc tggttgaccc cacaggcagc agggctagga agtctgagag tagcatctca    2640
aaagggtgaa gaggctggcc cacaggggtc ctgttcaggc tgagagtgca gctcctgaaa    2700
agcactgcaa accctgaagt tcccagcgtg ggagggaggg cgatttggag aattgtgagg    2760
aaggcattcc aaagtgctac ggtgcccaag tgaagactta cgtcgagaag aaatagaaaa    2820
atgacagctt ttccccaagt ggtaacaaga attagctaaa ccaagcctaa ttgtatattc    2880
ttcccaattt taacccattt attaaatcac tgaagctctc ctgagcagaa taaggggtag    2940
ggaaagaatt cagaataatt cagggaaaat gcctcctcat gaaaactcta aaatttggaa    3000
aacggttggt tcctagtaat cgagatagct atattttcct tcacttacca aaatgaaact    3060
taggaagttc attctctttt actcctaatc tgcaaatacc ttagtccagt gaacaaatgt    3120
gaaccgaaag agccaatctt tcaaaataca acctgagtgg ctaaatgggg ctatgtttta    3180
aatagaggca agtggccatt tgctgactaa agatcacaca tgtatactct gagttccctg    3240
aaaacctaca gctctgctca actttgggac ttccagagct cacctgatct accaatcagg    3300
cctggactgc ttcaaccaat cagggctcag ctgtatcaaa caatgggaac tgagcatttg    3360
cataaacaaa cctgactgga aacttgggtg ggaacttttg ccataataac tgaaccctct    3420
cttggttctc tggatcacac cttcatttta caccaaaagc tttgaatcac ggtttgcaaa    3480
ctgttcactg gaataaagtc tctttcttcc aaattccttt tcagagaact tttgttcaca    3540
gtccctatta tccgagataa atctgtaagc aatatgtatg tgatggaaaa tgtttcttcc    3600
ttcctcccca actttcaatc cttgttcttt tctaatcatc ttatagataa tgtctaagaa    3660
attggcttat ttaagttaaa agttttgact tccttactac tcatttgaaa gtacaaaata    3720
cctcagttgc acatgcctac ctactacgtc aacagtgtgc tgctgcatat taaagagat    3780 ccaatttcaa atcacctaga aaaggctaaa tcttactttt tcttgcttta gatgacctct    3840
ctctatatat aaggctgata tcagccacaa acctcccctt ccttgtgaga ggagggcagc    3900
cttcaaactg aagttcagag cattgttgta caatattcct gaggtatatt gctccccata    3960
ggattgggat ctgtgccata gaacctataa atgggattta cacaagtttc tgttattgtc    4020
cagggaataa attttggacc acaaaagtga atatataat tcccaatgcc ttttaaatgt     4080
ataaatatgg acagcagctc agtgcacttt tcactggatt aacagcatgc tgctatattg    4140
cgatactgcc aaaaaagacc ttatatttca agcagaata cattagtcct agaaaaggag     4200
aagagcagct ctagggtatg tccatgatcc ctctgtgaat ctattgtctg cttcattgcc    4260
tgaggcagaa caaaagagca cgtggccaag aatgaggctc tggatcagcc cagcttgggt    4320
cctcggcctc aaactatggc ctcagcgaca gtttcctgat ttgcggagta atactactg     4380 tgagtatcca acacaattca gaggattgaa tgaggttaat taacttaatt aacaagtatt    4440
aattaattaa ttaaaacac taggtcacag cctgggccat aataagctat caataaacac     4500
ttactattgg tgttagcaat cttttacttt atttaagtga tgtaattact ccaatgtact    4560
```

```
ttatttgagt gatggaatta tagatatata tttataactt atataagtgt aagtagttac   4620
acttttggaa tatacttata caagtactta tataggttat attaaagtat atatttataa   4680
catatttata ggattaatgt aagaatattt tttataaaat gatctaacat gctaaaatat   4740
agaaattaat tagtaaaatt ataatttact ttagcttgtg tttatttgac accaactacc   4800
tggacattta gtccatttac tgcagtactt ctccaggtat gattcttggg ccagcaccat   4860
cagcattacc tgggaaatga gttagaaatg cacattctca ggccccacca caggcccata   4920
taaaaaccat ggatttagtg tatctagaag gacaaaaatc aaaacactta gcttcattca   4980
ggaaaaaaat aattctgata ttgatagata cctctcttca cttttaaaag tttcttctta   5040
tagaaaccag atctgattgt attgttaaaa ttaaacttgt aaatttttc acaacgaatt    5100 tcctgtatgg tggtctatgt ttggggaaat actcatcccg gaactcaact gtacagggtt   5160
gggcatgttt tacatacaag tgtatgtctc tcttcttgtc ttccttctcc cttgaaccct   5220
agtctccctc cctgccttt cagaagtttc cccctggagt tctcagccta ttctctttta    5280
tctttccatc caaacgtagt caccaatata gtcctctttt ctctctcaat ctacacagca   5340
gaagcctcca ctgctgcttt agaatccaga gatatttcca atcccattat ccccaaagat   5400
gaagtctctc ttaaaaatcg agattctcta ttttagtagt ggtggctctg tgttcatgct   5460
gttccctctg cctagaacag catttcttca tattttcaca tattttaca gcacatggca    5520 cataaaaagc acacaataaa caccaacatt ctgagttaaa aatgtgaaat gtcttttcct   5580
gcaaaaataa tatatgcctg gtgtttgtcc cagttcaata cacatttatt gactgcctaa   5640
tactttgcag gcattgaaca aagcatgggg tagaaataat aacagtattt tctccccaca   5700
ctgaagtagt gtgcactcta caaatagggga agatatatat atcttcctta tattatatat   5760
atttatatat ataaatatat atttatatta tttatatata tataaacata tatatataaa   5820
tagattactt tcacataatg tcacaggtgt agcaatagga gagtacacac agtggcttgt   5880
gaatactgag gccaacttga gagatcagaa aaggtttta ggagaaggtg atgaagggct    5940
gaatatattt taaaactgtt aaatgtgttt tcaaagggca ataaacaccc atatgttcca   6000
taaatattat aaacagcatg cttattcaag ttagttcaga ttatgttttc aaaagcaaaa   6060
tagatttaag tcacacttat tcttttccttt aaataaaatg ttcttcaagt taaaagtatt   6120
atgaagtatg tctgggaacc attttcttgt tggaggccct taacatcttc acatattccc   6180
aaatcagaaa ttagcaaacc attttgacat ctccctcttc ctcaattctc tcatacaagc   6240
atccctaagt catatccatt gcattccaa tgttttttcaa attattttt cctttaacat    6300 ttgtattgtc agtgccttat ttttgcatct cctaatttct ttctagataa catcctaatt   6360
ttttccccca aatctagttt tcatcccctc caaatatctg caagatatca cagtgctctt   6420
taagcaaaac aaatcggatc acattttct cttatttaaa tcttttatta ttatgctcct    6480
ctaactagga tgaatatgca tcccagtttg tccaaatgta gatattccag ttttatactt   6540
gctgactagc ataattgtca ggagtgtctc ctttcactct cagaagtgcc tgttctgaat   6600
tcaaaattat atagttagcc ttctcattgc cttcattatt ttgttttaat tcaataatct   6660
tacattaaaa tcttcattta taatgtgagt cctgccatta agagatgcaa gattgctctt   6720
acacccggct ttaccttttt acaatttgag ttcatcaaaa tcatggatta tgtcttaaaa   6780
acaactagta tttaacacca tgcctgccat tgaataggca tgtaatgatg tttattaaat   6840
tttaaatagc tacattttaaa attgaaggtt tgttattaa tcatattcta tgtgaaacat   6900
ccttagatta ttgaaagcat ccatatgctt ttcgacattc ttttatatat atatttttat   6960
```

```
tatactttaa gttctaatgt acatgtgcac aatgtgcagg tttgttacat atgtatacat    7020
gtgccatgtt ggtgtgctgc acccactaac tcgtcattta cattaggtag atctcctaat    7080
gctatccctg ccccatcccc caccccaca acaggcccct gcatgtgata ttccccttcc    7140
tgtgtccaag tgttctcatt gctcaatttc cacctatgag tgagaacatg tggtgtttgg    7200
tattttgtcc ttgcgatagt ttgctgagaa tgatggtttc cagcttcatc catgtctcta    7260
caaaggacac gaactcatca tttgttatgg ctgcatagta ttccatggtg tatatgtgcc    7320
acattttctt aatccagtct atcattgttg aacatttggg ttggttccaa gtctttgcta    7380
ttgtgaatag tgccgcaata aacatacatg tgcatgtgtc tttatagcaa catgatttat    7440
attcctttgg gtatataccc agtaatggga tggctggatc aaatggcatt tctagctcta    7500
gatccctgag gaattgccac actgtcttcc acaatggttg aactagttta cagtcccatc    7560
agcagcataa gagtgttcct atttctccac atcctctcca gcacctgttg tttcctgaat    7620
ttttaagatc accattctaa ttggtgtgag ataatatctc gttgtggttt tgatttgcat    7680
ttctctgatg ggcagtgatg atgaccccttt tttcatgtgt ctgttggctg cataaatgtc    7740
ttcttttgag aagtgtctgt tcatatcctt tgcccacttt ttgatggggt tgtttgtttt    7800
tttcttgtaa atttgtttga gttctttgta gattctggat attagccctt tgtcagatga    7860
gtagattgca aaaattttct cccattctgt aggttacctg ttcactctga tggtagtttc    7920
ttttgctgtg cagaagctct ttagtttaat tagatcctat ttgtcaattt tggctttcgt    7980
tgccattgct tttggtgttt tagacatgaa gtccttgacc atgcctatgt cctgaatggt    8040
gttgcctagg ttttctccta gggtttttat ggttttagat ctaacattga agtctttaat    8100
ccatcttgaa ttaattttc tataaggtgt aaggaaggga tccagtttca gctttctaca    8160
tatggctagc cagttttccc agcaccattt gttaaatagg gactcctttc ccaatttctt    8220
gttttttgtca ggtttgtcag agatcagatc attgtgatg tgtggtatta tctgagggct    8280
ctgttctgtt ccattggtct atctctctgt tttggtacca gtaccgtgcc attttggtta    8340
ctgtagcctt gtagttttgg tgtggatgtc cttctgtttt gttagttatc cttttgacag    8400
tcaggatcct cagctgcagg tctgttggag tttgctggag gtccactcca gaatctgttt    8460
gcctgggtac cagcagagcc tgcagaacag cgaaaattgc tgaacagcaa atgttgctgt    8520
ctgatcgctc ttctggaggt ttcatctcag aggggtacct ggctgtgcga ggtgtcagtc    8580
tgcccctact tgggggtgcc tcccagatag gctactcggg ggtgaaggac caacttgagg    8640
aggcagtctt tccattctca gatcccaaac tccatgctgg gagaaccact actctcttca    8700
aagctcttcg acagggacat ttaagtctgc agaggtttct gctgcctttt gtttggctat    8760
gccctgcccc cagaggtgga gtctacagag gcaggcaggc ctccttgaac tgcggtgggc    8820
tccccccagt ttgggcttcc tggccacttt gtttacctac tcaagcctca gcaatggcga    8880
gcgcccttcc cccagcctcg ctgccacctt acagttcaat ctcagactgc tgtgctagca    8940
atgagcaagg ctccgtgggc atgggaccct ctgagccagg cgcaggatat aatttcctgg    9000
tgtgccgctt gctaagacca ttggaaaagc gcagtatttg ggtgggagtg acccgatttt    9060
tcaggtgccg tctgtcacag ctttgcttgg ctatgaaagg gaattccctc accccttgca    9120
cttcctgggt gaggcaatgg ctccctgttc ttcgggtcat gctcgatgtg ctgcacccac    9180
tgtcctgcac ccactgtcca ataagccaca gtgagataaa cccagtacct cagttggaaa    9240
tgcagaaatc accagtattc tgcgttgctc acactgcaag ctgtagactg gagctgttcc    9300
tattcggcca tcttggaact gccctcactg actcaacatt attttaaca tgtttattta    9360
```

```
cacatttata aaatgatcac tgagtactta atacataatc tagttgagca atgtcctggt    9420
gatgcttgga tatgagaaaa tgaaaaaaca aacatctaat tacagatgct cctcaattta    9480
cagtgatgtt atttctcgat taacctatca taaattaaaa atattgcaaa tcaaaaatac    9540
acttaaacac ctaacttatc aaacactata gcttaagctt ttcctaactt aaaatgctca    9600
gaacactcac attaacctac aaatttggac tcctacattt gggtaggcta atgtaagtat    9660
tctgagccct ttaaggcagg ctaggctaag ctatgtttgt gcatgacaca aagcccattt    9720
tacaataaag tgttgaatat ctcaggtaat agtattatat cacatatcaa tagcccagga    9780
aaagatcaaa atttaaaatt ttaagtacaa tttctactaa atgggcatca ctttgacacc    9840
attgtaaagt caaaaaatca taagtttggg atcatctgta aatgagggca caattcccac    9900
aagaagattt cagaatcaga ttcaagatat tgtgaggaca caaaagagga agttatcaac    9960
tctcagggag tggaggggaa aaaacggctt tatgaaagaa atgacttttg ggcagtcttg   10020
gaagataagc aattgtaaat aatcagtaga actgcagtag gacataagac gagccatgga   10080
ttagcctaga caggttacat agaggtcaga gctcagagga gattattggc cagtccttgt   10140
aaacaacgat gagtgtctaa agagtgtcat gtaagagaaa gagagaaaca gtataaaaat   10200
tcataaaagt cagcctggta gcagtgtgac aagcgtactt aaagaaaaag acacttgccc   10260
taagtcaaca aagtttattt cagaataaga attatattaa tatataggca tctgaattca   10320
atagtatttt tgccaaaatc aaggcataat gtgtaaaaat gtattcattt atatcccacg   10380
ttgattgaag tcatttcttc taattttcag gttttagctc tgcctatgca cgtggatgag   10440
acctaggtct caatcaaggt ctggcagttc agaaggtcaa gtcagaccat caaccatggt   10500
agctacttca ttgaccagcc tcacctagaa tgagtataac tgtgaagctt ttcaattttc   10560
tttattattt tagccatact gctatcatta ggatatttga cctctccaaa cttcacgttg   10620
aaatttgatc cccaatgttg aacatggggc ttcatggaag gtgtttgggt aatggggggca   10680 gatccctcat gaatagatta atcccctcct taggcatggt gatggtaagc gaattctcac   10740
tctattagtt accaagagag ctggttgtta aaaagggctg ggcctggtac ctctctcccc   10800
tctccctctt gcttcctttc tcaccatgca atctctgcac attccagctc cccttcacct   10860
tctgccatga gtggaagcag cctgagacac tcaccagatg cagatggcca attttaaact   10920
tttttcgaaa tcagaattgt gagccaaata aatatttttt ctttataaat tatcagtgtt   10980
ctttactagc aacacaagtg aactaagaca catactgtgt ttgctttctc tttcccatcc   11040
cttaatctga gtagaaatta aactttgac aaattcaatc attaaattta ctccaaaagg   11100
tggtaaacta attcaaaact ttctcctccc tcacattagg ccagaattgt atgatatctc   11160
tggcaacatc ttctccttc cactcctttt agagtaaaca gagatgaatt tatgcattgg   11220
ttgcctgtac gtggtatgag aacatccttg gcctcagttt acttcgttca gatttcatca   11280
gttgctagta gcttttgctg atatgtgaat gttctgtgct tattaagaaa ggttattatt   11340
gtggtaacaa atctacctt taaatctagc gttataaatt caattatttt actgttgatc   11400 ccttaaatt caccatattc catgaataga aagtgtctag gacttggtcc tgtgggaatt   11460
tcttatttta agtaaacact gagtgctaat gcatgtcagc tctcctcttg ccattttgag   11520
attttcaaga tcttgctagc tttgaaagtt gaattgggtg aaataaaaat gctgcaatat   11580
taaaaaaatt taaatctcaa agacctcaag acatagttca gacttttaa aagttcaagg   11640 gtttgtcaat aaataataaa gaatcatttg ttgctttaac aaagaacagc aaaggatgtg   11700
taacataact ggaacattca ataatggctc tatcaaattc ctaaaataag cttaaagaaa   11760
```

```
cataagatct acatattaat atttatgact gtttctgaaa aggatatgag ttaaaatctt   11820
tcccaacagt tgatattaaa caaaatgttt gtccaaacaa aaaaacagaa atttaattgt   11880
atttttaatt aaaatgatgt aactcatatt atatgccaat taaaaaataa agggaaccac   11940
tgggggattg gtcatttaaa aaactgatat aggggctggg cgaggtggct catgcctgta   12000
atcccagcac tttgggaggc cgaagtgggc ggatcacctg aaggcaggag tttgagacca   12060
gcctgaccaa catggagaaa ccctgtcttc tactataaat acaaaattag ctgggcgtgg   12120
tggtgcatgc ctataatccc agctactcag gaagactaag gcaggagaat cgcttgaacc   12180
tgggaggcag aggttgtggt gagccgagat tgcaccattg cactccagct tgggcaagaa   12240
gagtgaaatt ctgcctcaaa acaaaacaaa aaactaatat aggtgatgaa aattgtggct   12300
gttgttataa attgttactg gtcaatgagt ttactacaga aacgtgtaca cacacgtata   12360
caataaatgc tatatattac atgaatttga aaaataatat gcattatggg acagcaactt   12420
caacttttca cagattttaa atgcaaacat ttgaaaaatg aaggaagaag agaatataga   12480
agtggagaag gagctgggga aaaaggaaag gaaggaaatg agaaatacac cttggataaa   12540
caaactgata agttggtgca ttttgaaaag agagttggat agagaactga accatattgg   12600
taactggaga tatgactcat tatttcatgt aatgatggta ttaagcacca actgggctaa   12660
gaatgcatta aaggaaaaaa cataggcatt ggaaacagga gagctgcgtt caaatcctgg   12720
acctatagtt aaagctccct aaggactcac tttccttatg tttcaagtaa gagggagaga   12780
ggtactcatt attcttacct taaaggttaa tgtgggggt taaatgctaa gaggcaagaa   12840
acatattgct tgctacaatt agtgctaaaa aatattaccc cttttcttac tcaatttgag   12900
aggtgctagg ttcttaacat ttgtgcattt tcttgttttgt tttacatata ggcagaggaa   12960
aggcaagata ccatctttag tcatttaaat ctatgatttg gagaaaagat gttttcaaag   13020
tatccttgct cattgacttt gctatactag acagtatgag tattagcttg cagactttat   13080
gagtgtaata ataaaacaga attctatgca tctagaagta taagcagaat ttttactgag   13140
taattttaaa acttttttttg ctattgttca gatcagctta gtccaaattt tttaattagt   13200
tattgaggta gagactaaaa tgtactttct cttacattac atactgaaaa tattattgca   13260
tgtttgatta gttaatatgc atattattaa ttattgtagg tagtaagaaa actgatctaa   13320
aatctttgtt tactcaacct gtttatcatg gtcttaagga acttttttgta aactgcttta   13380 taattttact gtcatatatt cagaatagtc ttattcaaat acatccaaaa cactgagtat   13440
atcaataaag tctttcaaaa accaggaaaa aatagtgggg ttttccaaag atagaactta   13500
atataagaat ttctgtaact gtactgaagg actgccaaag gacataatgg agtaacagaa   13560
agattaataa attcagaaag cagggatctc ccataaaaga agagcaatga aagatagagg   13620
ttggggttat taaaaccaaa aagcttaaag ccatacctct gtagagttgg cacttatact   13680
tctgaggtga ggtgctggca cctcagggg catgaggtga agccttgagg agcttcagtc   13740
agatgcatga ggaaggggca ctgcatggat ggctggtgct ggttactcag atgctcaggg   13800
gaggagtccc acattgttgg gcctcagaga tctgaggaga ggatgctgca ttcgaggtcc   13860
cggaatccct gagggagct tatatggttt ggctctgtgt ccccacccaa atctcatctt   13920
gtagctccca tagttccac gtgttgtggg agggacctgg tgggagatag ttgaatcatg   13980
gggtcgggtc tttcttgtgc tgctctcatg atagagagta agtctcatga tatctgattg   14040
ttttaaaaat gggagtttcc ctgcaaaagc tctctcccct tgcctgctgc catccacata   14100
agacgtgact tgctcctcct tgccttctgc catgattgtg aggcctcccc agccatgtgg   14160
```

```
aactgtaaat ccattaaacc tctttctttt gtaaattgcc cagtctcagg tatgtcttta    14220
tcagcagcat gaaaatggac taatacagta tattggtacc aggagagtga ggcactgttg    14280
aaaagatacc ccaaaatgtg gaaatgactt tggaactggg taacaggcca gggttgtaac    14340
actttggagg gctcagaaga agacaggaaa atgtggaaaa gtttgaattt agtagagatt    14400
tgttgaatgg ctttgcccaa atcctgata gtaatgtgga caataaagtg caggctgagg     14460
tggtctcaga tgaaaatgag gaacttgctg ggaactgaag caaaggtaac tcttgttata    14520
ttttatcaaa gagactggtg gcattttgcc ccgccctcga gatctgtgga actgggaact    14580
tgagagagat aattcagggt atctggcaga agaagctcct aagcagcaag gcattcaaga    14640
tgtgacttgg gtgctgttaa aagctttgaa ttttaaaagg gaagcagatc ataaaagttc    14700
agaaaatttg cagcctgaca atgtgataga aacaaaaatc ccattttctg agaaaattcaa   14760
gctggctgca gaaagttgca taagtaacaa gaaaccgaat gttaatgccc aagacaatgg    14820
ggaaagtgtc tccaggacat gtcagaggtc ttcacaacag tcccttccat cataggtctg    14880
gaagcctagg agggaaaaat ggttttgtcg gccaggccca gagtccctgt gctgttgtag    14940
gctagggaca tagtgcccta catcccagct gctccagcca tggctgaaag aggccaatgt    15000
agagcttggg tcatggcttc agagggtgca agccccaagc cttggcagct tccacatggt    15060
gttgagattg caagtgcaca gaagtcagga agattgaggt ttaggaacct ctgccaagat    15120
ttcagaggat gtaaggaaag gcctggatgc ccaggcagaa gttttctgca ggggtggggc    15180
cctcatggag aacctctgct agggcagtgc agaagagaaa tgtggggtgg gagccccata   15240
cagagtccct actggggcac ctcctagtgg aactgtgaga agaggaccac tgtcctccag    15300
aacccagaat ggtaggtcca ccgacggctt gcaccatgtg cctggaaaag ctgcagacac    15360
tcagtgccag cccatgaaag cagccaggaa ggaggctgta ccctgcaaag ccacagggc    15420
gaagctgccc aagactgtgg gaacctacct tgtgtgtcag agttacctag atgtgagaca    15480
tggagtcaaa ggagatcatt ttggagcttt aagatttgac tgccccactg gatttcagac    15540
ttgcatgggg cctgtagctc ctttgttttg gccaatttgt cccatttgga atggctatat    15600
ttactcaatg cctgtacctc cattgtatct aggaagtaac taacttgctt ttgattttat   15660
cataggtggt atcataggtg gaagggactt gccttatttc agatgatact ttagactgtg    15720
gacttttgaa ttaatgctga aatgagttaa gactttgggg gactgagaaa acatggttgg    15780
ttttgaaatg tgaagacatg agatttggga ggggccaggg gtagaatgat atggtttgtc    15840
gctgtgtccc cacccaaatt ttatcttgta tctcccataa ttcccacgtg ttgtgggagg    15900
gacctgatgg gagataattc aatcatggga gtgggtcttt cctgtgctgt ctctcatgat    15960
attgaataag tttcatgaga tctgatggtt ttaaaaatgg gagtttccct gcacaagctc    16020
tctcttcttg cctgttgcca tccatgacat gctcctcctt gccttccacc atgattgtgt    16080
ggcctcccca gccatgtgga actgtaagtc cattaaactt cttgcttttg taaattgccc    16140
tatctcagct atgtctttat cagcagcatt agaaaagatt aacacaagag caataagaat    16200
gtttctggac atgtagaaag aagttaaagg ctggaaccaa ttgctgtcac tggaacaaag    16260
gaagatggct ggagtgcggg tgccactaac agtaacaatt atcaaataag aaggatcaaa    16320
cgccttttct cccgcctttt actgtcttct aaagtcatta attggcagaa tatcatagaa    16380
agccagatgg tacaggaaca taatttgtag accttagccc cagtgccaga gagaaagggg    16440
aaaaaaatag acttaaagag caatggcttt gtaactagca tactgacatt ttgtaagttt    16500
agaaaactct tattttatca gttttgttct gcaaattcac ttatttagtt attaacatgt    16560
```

```
gttgtttttg tgataatcca tcaaaaagaa ctgagtatct ggtgtttatg gaaagcaaac  16620
taatatctga gtataatttt catttcaatg ttaaatgtct ttatttaaat acagagaaca  16680
gtcgactatc atcatcattt caactgatta tccaactatg acatctagtt gtaaaacaga  16740
aattaattct cagaagttat tactttctat caaaccttaa atattcatca ataagataca  16800
tcttttctag gaccctataa aatgattaat aaatttatta ttattattta ctgtacaaat  16860
attctgctgt tatttattaa aacagaagta ttccatatcc tgaatcagta caatgttaat  16920
ctcctctgtt tactatgtcc atggaaaaat gtgccagtga tttgattagg accataaata  16980
tttgtttttg tattcagagt cccttcatgt tgtcaaaatc cttactgcct gtataatcat  17040
gtttattcct tgtgattttg ttcgtttttt tttgtttttg agacagaacc ttgcgctgtc  17100
acccaagctc ctggagtgca gcggcatgat cactactcac tgcagcctcg acctcacatg  17160
ttcaagtgat cttcccccct cagaccccca agtagctggt actacaggtg catgccacca  17220
agcccagcta attttttaaat tttttgtaga tacaggatct cccttttgttg cccagacagg  17280
tctcaaattc ctaggcccaa gaattcctcc cacctcagcc ttccaaagtg ctgagattac  17340
aggcatgaga caacatgccc agccctggca ttcaatttca gcatctataa aactgtatttt 17400
atttttaaggt tcctcttgaa tcacaattta tccactgagt atacatatca ggacacaaaa  17460
cacactctat cacaactgga aggacaggaa atttggagaa tatagtataa aactaatgta  17520
gtaacaagag tagcctaatt tttcccaaag ggtccatgaa ttcacaccct actggacagc  17580
tgctctcaag ttttcatttt tttcacagag tgttcaataa ttctgtcatt gaaaagtgtt  17640
tctgccagga ttgatggtgt gaaataaaat ttatgggagc cattgctttg gactgagatc  17700
ttgcactagg cccaagggac cagacaaaaa tagtgactca tgttacagtc ccacattatc  17760
aagccaaaac taagttgttt gtctgacctt cctagaaatc aagagagtaa gagacaatag  17820
ccaaatccct agaggagcca gttttagcta gcatgataag gaagtcccct ctgctttaac  17880
ttttataagg aaagaacctt tgaaataaga aatctacttt ttgctctctg tttctgcttt  17940
ccttggcctt ttactgtata taaaaccaaa ctccctctgct cagcttatca aaaaactcat  18000
tatattatat agaatgaagt gtagcctgat tctagaatta cagataaaag ccaattaaga  18060
cctttaaata agttgtaatt ttgtctttttg gcaacagttt ctgaactgag tctgggaaat  18120
aaataatcca acaaccaggt aaaaggaata gagaaagatg agtgaattcc ttaaagctgt  18180
cttttctcat tctggtaagt tccttcactc tactaaaata aataattcta ccacctggat  18240
aaatttggtt ccttaatgga aaaataatat catcagtaaa agtggaaact ctgggtaaga  18300
aaacggaaat aattaaaatg cctaaaccaa ctttattgtc attaaaatat caaacagatg  18360
aactagaatt attcaataag atttcaaatc aactgttagc agtcttttca tgtagaaaga  18420
agtctgcatt taggaagccg ttgaaagaaa ttgctaagct ctaaggacag gtcctgtcca  18480
gaccaaagca ggcccctagc cctaacaggg atcccttggg taaggagacc atttgctgca  18540
ataagaaaaa atgacatcaa aggagaggct gagtgctatg atctgaagat cagcaggtga  18600
ggaatctctt gggaatctcc tggatgcttg ctctggacac aaggcaggca ctggagatgt  18660
aaagaaatgt gtggccctca attgttcaac aaatagccat cagttcaaac tgaatatgta  18720
ataacgcatc ggtctgcaat cagaatttca aagcccagag aaatacattt aaaagatcaa  18780
tcctttagaa tatagcaata ttctttattg tctatgccct gtttagcaat caaccttcca  18840
cattttctac tgagttttct agacagctta gaatgaaagt cctacagggt aagaagttca  18900
agagttaatg gatgcttttg ttcttccagt tggttctaat aagagtggta aaatacaaca  18960
```

```
gcatattctt tataatttga ttttaatcca attttgtaca ttctcagacc taaacattgt  19020
ttaccacact aattattttt gaagttaacc tcccctcaat acccttttta aagagtgagt  19080
gctgaaatta taacagccat atgatattga tgaggctgct tttagagcct caaattcaac  19140
tccagaaatt tatttttagt tgtgcatatt tattgtaaaa tatttgtagt gccagcttat  19200
gttttctatg tccagatttt gttctccacc ttctgaagcc cacagagtgt gaaacaagca  19260
tttacaatgg agatgatggt gctaattta tgtattttat tccctggcat atttgattgc  19320
aatagagtag acaaaaggat ggattagtag ctatgatctc tctctctctc tctctctctt  19380
tctctctctc tctctctctc tatatatata tatatacaca cacacacaca cacacacgga  19440
aggcatcaga tatctcatgt gtgtatacac atacatatat ataggatata atgatttatg  19500
tgatatatat gtgaggtaag tcttcatgtc ttccataggt atagtaccag ttggttaatc  19560
ttgggccagt catgtagctt ctacaaactt taggctttct ggacaaagca gtatataatg  19620
ttcattatgt agctatgcca aaacaaaggt caaaataaag aaagattcta cctagagcaa  19680
aagagaattt atatatataa attttatatg caaattatat acagctttat atacaaatat  19740
aaatatcacc ctgatgtagt agtttgctag gattgccata acaaaatgct acagactgtg  19800
tggttaaaca acagaaattt attttctacc aattctgaaa gctagaagtc tgagatcaat  19860
gtatcagcgg ggttggtttc ttctaaggcc tctctccttg gcttgcagat ggctgtcttc  19920
ttccagtgtc tttatattgt cttctgtgtg tgtgtgtcag tgttctaatc tgctcttctt  19980
ataaaaatat cagtcagatt agggttcact ccaaggtaag aactgaagag catgctcttt  20040
tctttgatgg ggacaagtga ctctatctag acataagtct ttggagagca gtctctcaga  20100
tgctgaccct ctctacaatg gagagagcgc atggcatggc ctgctaagct acttctctgc  20160
cattctgcta ggcaggtttc aggccctgac aatataagac gtgagcctct actcatcttt  20220
ggataagtct ctctgcatta ttgcaaatac aagaagcatt ttgtagctgt gtagtaaaga  20280
gaggagaaca cttgcaatat tctcagtcaa gattctcaac tccctgaaga aaaacagtgt  20340
attttacata aattcatgct gttataatta cattatataa aaagattatt aaccaaatat  20400
tgtacatatg aaaacagagt tgaaagctct tcaactattt caactgatga ctcccaagat  20460
ggacctgact gtactgatat aatctgatgg atttttattt gaagctattc taacagaact  20520
atattttatg gtatggaaac gaagagaatt gttttaggga agagcatgtt taatgttttc  20580
aaatattttt gtctctgact taaattttgg cttttctagt ttgtttcaaa ttttcacact  20640
tgggtcaatt ctcttttgct ctaggtagtt ttttttttta tcttgacttt gttttggtgt  20700
atttctgcct gactggaaaa gttttgtaa ccccactttc ttttcatccg attagtagct  20760
cttctgtgtc catagataaa tatatccttt acttctgtga gcattatttt ggtatatgta  20820
tttttgttcc agttaggaaa agagcagcaa aatgattttc tttcttgttt tcttcctaaa  20880
acttgattta gaagctaagt gggagcagcc ctttcacaca ccatcatggt agttatttac  20940
gtgcattagc gcgattcatt ttcacaaatt tatgagatgg ttaaagttaa ctttcatttc  21000
ttaaagagag agaacaagtg gagaaaaagt tcaactgcag aggcttgaga ttgtattgtg  21060
tgttgcttaa gaagaaatat ggagtcaaag tgcctcatca tttaccagtt gtgtgacata  21120
tcacaaaaag agggagtgta accagccaaa aatttaactt ggacaattgg attggtaaaa  21180 acttttatg ggatatgcag gaatacagtt cttaaaattt tataagatgg cataaaattt  21240
atttctttga taaatgatat tttcttaaga tatctttcta gaaatggaat tgctgagtca  21300
agatgcatat tgagggattt tgatacatat ttttaaatta ccttttagaa aaggtaattt  21360
```

```
ttagtaggaa agtagaagtt tatctcctat tgctaggcat actgattttt ttcttttcct    21420
tatctgcatt taatcacttt tctttaatga gcatatacta cttgtataac agaaaataaa    21480
ggatgattat atttgggaag tgtcatgtca gattgtcctg tccagtttga aatccacttt    21540
gactttaat ctaccttgag atgttatttt agctccctac aggttaaggg cataatccaa     21600
gatgattaag gagattgaat tctcatttaa ttgattgttg ccacagacac ttacacagag    21660
ataaagtcat taaacacatg tctcttttac atttgaaaag acatggcaaa taattttact    21720
gctttcttta gtatacataa tgtcataata ttgtgagtgt gcatgtgtat accattctgt    21780
ctatatctta atgatctaga atgtatatgc tactttctta catgcaaatg agctgtacat    21840
atttgagtaa tattggtgac tttttatat aaatcaattt ttcctttga tgattacatt      21900
atacgaagat gtttgaatgc tgttttttct ttgttatgtg tatgcttata tctgtgaaac    21960
atctagctag atgtcctgca ggaatcagtt ttacatatgt aaacaggcat atttctgcac    22020
tctaaattt gataattaaa ataattcgta actttattat tcaactctca agtgtttaat     22080
agccattact aacaaaaatt tctctttgtg gctaatctga ttacttggaa tcttttttat    22140
tgtgaccaaa aaaagcaacc ctgcacatac aactttaact tcaatatttt aatgacgaaa    22200
tttaaggata atttaaatag aaatggactc agaaaagaat cagtaagact tagtgaagga    22260
tcattgtcta ttatagagaa gttgatttaa gattaactta ttagtaatat ttaacatata    22320
taaagaatta ttagactggg tatatagaca agcgttttat tcttggaaga caaaaagaag    22380
aaaaattgaa ttcaaccgat gtatacgaaa ataaaaagta acagtaaatt aaaaaatagat   22440
aattaaataa atatatgata cagtataacg ttttatagcc aagatgatgt tacaaatcca    22500
tatttattga catggatatg tttttatact aaagtgttta tcaaatagcc attaagagat    22560
aacttctttg aataatttgc tttctaaatt tcttaactac ataaatttcc agctttatat    22620
ggaacaccaa gttttcaaac cattagtgat gtgctttta tatggtgtta aaagtttct      22680
ttctttcttt tttcttttc ccccaagatg gagtcttgct ctgtcgccca ggctggagcg     22740
cagtagtgcg atctcggctc agtgcaacaa ccacctcctg gtacaagca attctcctgc     22800
ctcagccccc caagtagctg ggattacagg cacctgccac cacgtccagc tgattttgt     22860
atttttagta gagacggggt tttaccatct tggccaggct ggtctctaac tcctgacctc    22920
aggtaatctg cccacctcag cctcccaaag tgctgagatt acaggcgtga gccaccatgc    22980
ccgacctaaa aagtttctta aacgtcactt tatactctca aattatctag aaaggaaaac    23040
gtattagatt cctggatatt ttggatattg taaggaacat acttatttgc tgtatatact    23100
ctgtttgtaa cagtattgta acttcagttc aaaacaatac acaaaacatt acaagttccc    23160
gtgatatttt aaaaattcat ttattttctt cctttctgaa tacaaatgct gttcagtctg    23220
ttgattcttc actaatctga aatattaggg actgatttct gaattggata ttcattctga    23280
agcctttcag agccactggc acaaagggtc tgtcaaactt ggaacaccat tgttgtatc     23340
attttatttc tttctcttgg caaatccaca taattcatac aggactatgc cagtgtcttt    23400
tgaaagaaac aaggtttaag aaagtaaaaa tgttaataaa gatagtgaat gttaattctg    23460
tcattgttac tgtatttctt caagctgtgg ctgcaaactg ctttgagtga tgttattgta    23520
actcgcacat tagggagaga aagagatgtt tggtagattt ttaattaatg atccctatca    23580
atgctccttg agctttccca ctctatctct ccacaacttc catccctggt tggaaatttt    23640
ttgcttaccc atactaagtg agagttattg atgggaaggc atcagatatc tcacgtgtgt    23700
tgctggtggg atgggagact gtggaggatg ggaacaggtg gaaatctact gcaatggaaa    23760
```

```
aaaaaaaaag catgtcctag gacacccaaa acatggaggc tagataataa caatagctac    23820
ttgtactgag agcttccact ctgcctggct ctttgctatg agccacatta ttcattcctt    23880
acaacaatca aacaagacaa gtaaaatatc atgcccattt tttaatgaga aaactagaga    23940
ttagagaggt tatagatact tgctctgagt cactagtaat gagtagtaga gctttaataa    24000
gtccctgaat ttaggttgta tctagtacat ttactcttag aagtctatca tgctcaccag    24060
agttgcagag ttgcgtgtat ttcttgggct cattaatgtg ttttttttctt tctaaaacta    24120 aagtcatttg aacttgttag attttgaaat atttaaatat cttttctatc tggctttaac    24180
atctttaatc ttggaatctt gcatgccttc atattcttag gaccacgaaa ccacaggaat    24240
atttaaaatg atatctagtg gaaacaatat gaagttggcc atggggtcaa attagagaat    24300
ctgaatacta tgcttctcct tgattgctct tcccatttct tcagagtaac cctattcccc    24360
catctcatgc tcaccccctt tccaaaatca tacataatga tctcccaaca ggatgcatta    24420
ggctttctct actctaccca ctatgaaatt acacaagaag cctatcgcaa tctcactacc    24480
tcgtctctct cacaggttta cagaaggtga gaggaaggtg cagatagaga ataagaagca    24540
ggtggctcca gcatcaacat tacatcaccc cttgtgttca caacaaatat ggaatattat    24600
ccaaagataa taaacgttgt attttcttaa cttaaacaca ttaaatcagt cctctcttta    24660
atcacttgtt aatgggcagc atctttattt tcatgccatt ctactctgct gtctttgcta    24720
tagcacaagt ttaccacata ccatacctaa aaattcagtt gttctatggg ggtaaacaaa    24780
gtctaggtta agcatatatt tcatagaatg ttaatctata gcaaaattaa tgaattaaat    24840
ccagataaaa gaatcctatt atggtctggt aaaatattta tatttcactt agcaaagaga    24900
aaacaaaaca tgaatattgt agttatgaac agaatatgca tgttagtaat gcttccaaat    24960
atgttattac ttcataactt catatttctt atgaggtaca agccattcaa ttagtttaac    25020
gttatattca gagaggctaa agatttactg aagaccatgc tgtccatcaa taatgaaaag    25080
aaaaattaaa aaaactttat tttaacttct agttcccttc tttgtacttg agcagctttc    25140
cctccttaag aatacagacc tagaacatat gcaatatcac tatcaatatt atgtgtaatt    25200
aaaagttcat tggatgttta ctgtgttcaa ggcatttaa ggagtgacaa gagttaaaca    25260
tatagttgta attcaaaatg acaacgaaat tagtttacag ttttcttttt ttgtaggtag    25320
taagaaatca tctcccccta ttgaggaata ccaatataga aaaggcaaaa ctttaaatat    25380
gaatgaactg tttcataata acataagttc ttcttgattt ccattgtcac atccaaattt    25440
gaaggctatt tctaacacag ctgggttcta ccttttttcct tctcactctt taccacaccc    25500
aatctgtgag gcttcagaca caaactgcta attcaggaga caattgtgcc ttctgtaaca    25560
gtttctgcta aattgtctca gctctgccac ttaaaatagc taggtgatct cagcatatca    25620
ccaaaactct tggagctcag tttctctgtc tataaaagtt acataaaatg taattgatct    25680
gcttgttatg actaaataac atagtacatt agtccttttgc caaaggacta acaaattacc    25740
aaataaaagt ttggaatcat gttaaacgtt tataagaagt acaactgtcc agaaataatt    25800
ctctcacatt ggtctgttgt aatgagacct aaaaatatctc attttattta cctctttgac    25860
ttaaagcact aggtctcaag gaggtcatgg ttatactata aatatgtcat gtgaaataat    25920
atattaaata attgttgtaa tactctattg agatactagt tgtaaagagg cacaatggaa    25980
aacttatact attaacagta gtaaaaagaa acaacaaaaa gcaataaaaa acaaaacacc    26040
cattcatgca acgacatgaa cgaacctcac aaatattata ctgagtaaaa gaagtcagac    26100
aaatataaaa caaagtttat actacgtgat tagatcttta tgacattcta gaatatgcac    26160
```

-continued

```
atgaaggtac aaggtaactg tctggaatga tgaaaatgtc ctgtgtcttc aaaatagtgt   26220
gggttacact aatgcatggc tttttcaaaa ctgatttaaa gggacacaac atctgagcat   26280
ttccctaggt gtaaattaca ctgcaatttt aaagaatcat ctaatgatat tgtggttatt   26340
tttaaacagt ccttaaattt tgtggatgca tactgaatgt ttacagcgga aaagatatat   26400
ataaagcttg aatttggtaa aaaaaaaaaa aagagggagg attggtagtg ataaagtgag   26460
tggacttatg gatgagacat gatcagccat gcattgaaaa aatgtaaaag ttggatgatc   26520
ttcacatgag agtcctttat tctgtctact tttgcatatg tttgaatatt tcccataaca   26580
aaaagttgaa aatagagtga tcacatgagt taatctccta atttacaaaa aagaaaactg   26640
gaaacagaag gagaacaaaa cttgttcaag gtctcaaagc cagacagcaa actagctccc   26700
aagtccaacc ttcttgctcc ggtcctaagc aaacaaaaaa tattaatatg agctactgca   26760
ttaaggaaag tctgcttttc caagggcag accaatagtt caaggaagag tttaaataat   26820
aaatatttgt gatcttactt tcatgctttt ctattttcca ctgaacacat atgcattatc   26880
ttctatatgt cttttatgta taatcatttg cttcctgttc cttgtggttt taaagttgtt   26940
ttgtatgttt aaatttgatt ttactcaaat ttcagaaccc aaattagcgc aagaatcaga   27000
caaagcataa ctttctataa atataaaaac aattaaaaaa aaaacataca gcaaaaacga   27060
gttgttgttt ccccctcct cttccagtgc ttaactaatc ttccgaatcc aggcacagaa   27120
agcaaaggct ttctgctagt gggaggagct tgcttctcca ttctggtgtg atccaggaac   27180
agctgtcttc cagctctgaa agaggtgaaa atgtgttaag cgatgcaaaa attgtcttga   27240
agttcgcgtg tgtatgtctg tgtgcatgtg cgtgtggtgg gtgggggag agaaaagggg   27300
gtgtcaattc tgagggcaac gagaatcaga agtcagaaag gtgagtggtg tgtagcatct   27360
cccttttcaga aggggctgaa gaagaaattg gatatgatgg tccggtaggc taaatcacgc   27420
tggatttgtc tcccagataa agggaggtct gcaaagtaag tcccatttct agagcgaaaa   27480
gccttaggac cgcttgtttt agacggctgg ggaatattta ttccttgttc cactgatggg   27540
aaaatcagcg tctggcagga gctgattggt ggaaaggaaa atggtgatag tggcgtggaa   27600
agaggatttg ctgagccttc tcctgcctcc tcaacctgtg actcttcctt agtagtctcc   27660
ctttcaccct caggacccctt tccggctctt cctagattaa gagcaaacga aaaccttgaa   27720
gatatttgaa ctaaagcgac ccctaacgtt gtaacctgtg accgtgatta aatttcagcg   27780
atgcgagggc aaagcgctct cggcggtgcg gtgtgagcca cctcccggcg ctgcctgtct   27840
cctccagcag ctccccaagg gataggctct gcccttggtg gtcgaccctc aggccctcgg   27900
ctctcccagg gcgactctga cgaggggtag ggggtggtcc ccgggaggac ccagaggaaa   27960
ggcgggggaca agaagggagg ggaagggggaa agaggaagag gcatcatccc tagcccaacc   28020
gctcccgatc tccacaagag tgctcgtgac cctaaactta acgtgaggcg caaaagcgcc   28080
cccactttcc cgccttgcgc ggccaggcag gcggctggag ttgatggctc accccgcgcc   28140
ccctgcccca tccccatccg agatagggac gaggagcacg ctgcagggaa agcagcgagc   28200
gccgggagag gggcgggcag aagcgctgac aaatcagcgg tggggcgga gagccgagga   28260
gaaggagaag gaggaggact aggaggagga ggacggcgac gaccagaagg ggcccaagag   28320
aggggggcgag cgaccgagcg ccgcgacgcg gaagtgaggt gcgtgcgggc tgcagcgcag   28380
accccggccc ggcccctccg agagcgtcct gggcgctccc tcacgccttg ccttcaagcc   28440
ttctgccttt ccaccctcgt gagcggagaa ctgggagtgg ccattcgacg acaggttagc   28500
gggtttgcct cccactcccc cagcctcgcg tcgccggctc acagcggcct cctctgggga   28560
```

```
cagtcccccc cgggtgccgc ctccgcccct cctgtgcgct ccttttcctt cttctttcct   28620
attaaatatt atttgggaat tgtttaaatt tttttttttt aaaaagagag aggcggggag   28680
gagtcggagt tgtggagaag cagagggact caggtaagta cctgtggatc taaacgggcg   28740
tctttggaaa tcctggagaa caccgggtgg gagacgaatg gtcgtgggca ccggagggg    28800 gtggtgctgc catgaggacc cgctgggcca ggtctctggg aggtgagtac ttgtcccttt   28860
ggggagccta atgaaagaga cttgacctgg ctttcgtcct gcttctgata ttcccttctc   28920
cacaagggct gagagattag gctgcttctc cgggatccgc ttttccccgg gaaacgcgag   28980
gatgctccat ggagcgtgag catccaactt ttctctcaca taaatctgt ctgcccgctc    29040 tcttggtttt tctctgtaaa gtaagcaagc tgcgtttggc aaataatgaa atggaagtgc   29100
agggaggcca agtcaacagg tggtaacggg ttaacaagtg ctggcgcggg gtccgctagg   29160
gtggaggctg agaacgcccc ctcgggtggc tggcgcgggg ttggagacgg cccgcgagtg   29220
tgagcggcgc ctgctcaggg tagatagctg agggcggggg tggatgttgg atggattaga   29280
accatcacac ttgggcccgc tgtttgcctg aggttgaacc acaccccgag tgagcagtta   29340
gttctgttgc ctacgccttt ccaccatcaa cctgttagcc ttcttctggg attcatgtta   29400 aggataccc tgaccctaag cctccagctt ccatgcttct aactcatact gttacccttt    29460
agaccccggg aatttaaaaa aggggttaat cttttcatgc aactccactt ctgaaatgca   29520
gtaataacaa ctcagaggat tcatcctaat ccgtggttag gtggctagac ttttactagc   29580
caagatggat gggagatgct aaatttttaa tgccagagct aaaaatgtct gctttgtcca   29640
atggttaaat gagtgtacac ttaaaagagt ctcacacttt ggagggtttc tcatgatttt   29700
tcagtgtttt ttgtttattt ttccccgaaa gttctcattc aaagtgtatt ttatgttttc   29760
cagtgtggtg taaaggaatt cattagccat ggatgtattc atgaaaggac tttcaaaggc   29820
caaggaggga gttgtggctg ctgctgagaa aaccaaacag ggtgtggcag aagcagcagg   29880
aaagacaaaa gagggtgttc tctatgtagg taggtaaacc ccaaatgtca gtttggtgct   29940
tgttcatgag tgatgggtta ggataatcaa tactctaaat gctggtagtt ctctctcttg   30000
attcattttt gcatcattgc ttgtcaaaaa ggtggactga gtcagaggta tgtgtaggta   30060
ggtgaatgtg aacgtgtgta tttgagctaa tagtaaaaaa tgcgactgtt gcttttcca    30120 gatttttaat tttgccctaa tatttatgac ttttaaaaa tgaatgtttc tgtacctaca    30180
taattgtatt tcagagaaca gttttaaaaa ctcatagtct tttaaaaaat aatcaagaat   30240
attcttaaga atcaaaatca ttgatggatc tgtgatttct tttaccatca tgaaaaatgt   30300
ttgtcaattt taatccattc tgattttaa aatatgactt tgatatgccc ctgtgatgtg    30360
tataaagaga cctatttgtg gccctaaaat ggaaagaaca gattagtctt tgataaagtt   30420
acttcatgtg atcatttggt ctctgtgaac actgaggaca gagaaaagtg cttgagggct   30480
gctactaatc tctcagaaac atttgtatag ttcatccatc aaatgacaca catactaaaa   30540
gaataaagaa attgatgctt attacctact tgttcctaaa gttccacctt ggggtataca   30600
cccaaactct gactctcttt tctgtaactt gaactgtatt caattgagtg ttattttaca   30660
aaccactctg aattccttgg aaaagaatag acacacactc tcatccacag gcatagacac   30720
acacactcaa cacagacaca ttgcccattc ttcctctctt ctttctcctc tgagcttttt   30780
cacattctct ggtggcaact atagcagtaa gagtcacagg atgaacagtc aggtggagga   30840
tgaccacatt gagttgccta gctgaaacat gtgctctgtc tatgtctgca aagtgaaaga   30900
aagctacact atctcttcaa catagatcag tgggggaaat tttatacttg ggatgattta   30960
```

```
tatgaatgca tctcatcaaa gttcacaaca cattttttt ttcagttttt tattttcagt   31020
ttttagagtc agggccttgc tctgtcgccc aggctggact gcagtgatgc tatcatagct   31080
cactgcatcc ttgaattcct gggctcaagt catgcccca cctcagcctc ctgagtagcc    31140
aggattatag gcatgtgcca ctgcctcatt atttagactt tcttatgtt gacttaatct    31200 tcccacaaat cttcaattaa attacttttt ttctacctta aaacatattt tcagaaagtc   31260
attgaaatag ggtgttacaa gaggaaaaaa ttgatgagtt aatttaaat attttatgaa    31320 gtgtgaatta tacctttta gatggaattt ggaatactga atcagtgaca tgcagtttat    31380
cagtatcttt ccgtttgtcc tcagatttcc aagttctgca agcacaagtt gctttgactt   31440
agttaccttt taactgttca ttgaaatcat tttcaatgtc tctcatggca tttaacacat    31500
agcacattct ataaattatt tattggttac attctgagtt ctaattgaga gttgaactta   31560
cacacagaat ttaagataaa aaatgaccat gtgaagacac aatagtatag tccagggatt   31620
ggcaaaattt tgggtaagga atcagatagc acgtatttta agccatgaga tctatgtctt   31680
ggccaggtgc cgtggctcag gtctttaatc ccagcacttt gagagcccga ggctggtgga   31740
tcacttgagc ccagggggtt gagaccagcc tgggccacag ggtgaaaccc tgtgtctaca   31800
aacaacgcaa aaattagccg ggtatggtag catgcacgtg tattgccagc tacccaggag   31860
gctgaggtag gaggatggct tgagccatac agctcactgc agaggttgca gtgagccgag   31920
atcgagccac tgcactccag cctgggtggc agagtgatac cctgtctaaa aaaaaaaaa   31980 aaaaaaaat ctatgtctca attctgctgt tgaagtgtga aggtagtcat aaacaataac    32040
tagtgtggct gtgttccaat aaaacttcat ttatcaaaac aggtggtggg ctggaattgt    32100
cttgtatgtt gtagcttgct gactactgat agagtggaaa gaacatgcac taatcacaca   32160
aaccaaagtt ttagttgaga ctacatcact tatcacccttt agggtcttgg ggaagcgtac   32220
ttaacatctc tgagcatcac ttccctgatt agtaaaaaat atgatttaga aaacttcaac    32280
taccttgcag tttttgtgag aatgtcataa taagacagga catatgaata attgagcaca    32340
cttttatata taggaaccat ggttattatt atcaaataaa ctctccaacg gaataattac    32400
tttgccaaca cgttttccat ttattctttt atccttcatt acataactag tttgaaaggt   32460
tggaggcgac caaagaccat tttataattt cacttatggc cgaagatgtt tggtagaagc   32520
ctcataagaa aagtaatctc attcctttat aagaatatac ttttaacaac tacttttttaa  32580 ctcattgaat aactaccta atgatcagtg ttattttat gggttttgtt ccctccattt      32640
ttgttatctg catacaccaa ttttcaatca acatacttca attaataga caaaaatttc    32700 ttcaaatgac tcagaaatta attagatcta aatccaaaag cagaaagatt taattatctt   32760
tatataatgc tcagtaatat aaatgcaata aatacaagaa aatgatgatc tttgagtgtc   32820
ttccaatgcc actctgctca ataagcagca gtggccatca gtgaaattga tagcaaattc   32880
tcaagtcaaa atgtgcttca cctcactaag ctgacaaagt caacataaca tgcacaacag   32940
ggataactga gttctcaaaa ctctcaggta ttacttctga ccttcttctc cactctgtgc    33000
tcttttgagg ttgggaagac aagatagggt gtgtgtggga cacctccgct cagggaagcc   33060
atcagctctg gtgtccctac agcatttata ccttgctagt cacataacca cttggcacct   33120
attttgtagg tgtatgttat caattacaga ttactcataa attaaaggct aaccatcaat    33180
tacagattat tagtaaataa ttatgacctc aaagaacaac tgattggttt gatacatggt    33240
aaccttatga ggactctcat ttatctcgtt tttttaagtt atatacctat ctctttgggg   33300
ttgcactaca aaaatataaa atatgttgca taagatattt ataaaaaata attaattata   33360
```

```
agttctagtg gtgtggttta gtggcattct tttttttttc ttttttttctg agatagggtc   33420 tcaatctgtc acttcactcc aggctgaagt gcagtggtgt gatctcggct cactgcaacc   33480
tccgcctcct gggttcaagt tattctcctg actcagcctc ctgagtagct gaaattacag   33540
gcacgcacca ccatgcccgg ctaattttg tattttagt agagatgggg tttcaccatg    33600
ttagccagga tggtctcgaa ctcctgatct catcatcctc cgacctcggc ctcccaaaat   33660
gctgggatta caggcgtgag ccattgcacc cggcctagtg gcattctttt ttaaaaataa   33720
atttaattgt gtatatttag ggtatgcaac atgatgctat cagatacatt agacactaaa   33780
aaattactat attgaagcaa attaatatat tcataatctc tcatagttac cttttttgtt   33840 gttttttgtgg caagggcagc taaaatccac ttatttatca tgaatctcaa atatagtaca   33900
attttatcac ctacagtcct catacattag atctgtacac ttgttcatct tacacatctg   33960
ctacttgctt ggatcctatg gcctatatgt ccctattttc tacctacttt tccaccccta   34020
ttaaccctgt attttacgta gtctctgtat atttgaattt tgtttcaagc ttccacatat   34080
atgtgagata atgtaatatt tttctttctg tgtttggctt atttcactta gcataatttt   34140
gtctgggttc atccatgttg taaatggtag gatcttgttt tttagggct gactgatatt    34200 ccattgtatc tatgtaccac aatcttttta tctacctatc tatcagtaga cactttagtt   34260
gtggctatta tgttttcttt tttttcttttt ttggagacag ggtcttgctg tcacccaggc   34320
tgcaatggag tggtgttatc atagctcact gtaacctcaa acttctgggc tcaagagatc   34380
ctcctgcctt ggcctcccaa gtagctggga ctacaggcat acattaccat gcctggctaa   34440 ttttaatat tttttgtaga tatagcatct cactctgttg cccagactgg tctcaaactc    34500
ctaattcaaa tttagaatag agtatgacaa ttctgtaaaa tataaaaaac atgtccactc   34560
cgtataggaa gttatacaat gagaagaaga caaacactat ttacattact cttgataagt   34620 ttttacaaa gaataaaaac actttaattt ctaatgtttt aaattctggt ttgctaaata    34680
aataaatatt agttttagtg tttttaaaat tccttatata gttataagtg atcttcctgc   34740
ctcagcctcc caaagcactg ggattccaag caagagccac tgtgttgggg cccttggaaa   34800
cagatatgct gaaatctttt cttgtggatc tacacccaga agagggattg ctgggtcata   34860
tgctactcta tttttaattt ttcttttatt tttagtgaat atgtaataat tgtatataat   34920
tgtgggatcc agaattatat ttccatacat gtatacagtg tgtgataatc aaattagggt   34980
aattaacata tccattaccct gaaacattta tcattccttt gtggtgggaa cagtaaaaat   35040
taaaaattct ctcttctaga ttttttgaaca tatgcaataa actattgtta agtatatcac   35100
cctacagtac tacagaatgc tagaactcat tcctcatatt tggctccaat ttcatattct   35160
ttaaccaacc tctccatatc ctccccctccc tcttacccctt gtcagcctct aataatcata   35220
attctactct ctacttctat ctcattgtct ttgatttaga atatgtttca taatttaacc   35280
aaaggtcaaa ttcttaggta ctgctaaggc aaagaacaaa gatcgcattc cagctgttag   35340
acatttctta ctactagtca ttttttaagac aacatggggt gcaggtggtg aggatgagag   35400
atagagattg aaacatattc tcttaaatat cagctgttct cactctgcat agttccagca   35460
caaacaaatt ccaggtacta tggttagtta aataacacca gccccctaaca acacaattca   35520 aatttctgtt accacagtat accgaaagtc attgcataaa gtacaaactt tgctgctaac   35580
tcttcagcct tcaaatcatt acataaataa cagaaaccca ttataatcag tgacaaaacc   35640
acagcacttc tttcaaagct ttttggagat tggttgcttc acatctgtta tgcagttcat   35700
acagacagca atgcccggac ttgtgtggcc acattgtctc ccagtggtga gcccatgtga   35760
```

```
tgtttcacaa aaatgcgcaa tcaaaagagg aaactggcca gcaaagatga aagagtagca   35820
aacaaaggaa gtgaaacatt ctggaagtaa aatttgaatc aaacataagt tgatgtatac   35880
aggaagtagc caccctgagg atgttgtcac tgctgcaatt caggagactc taaatatgca   35940
gtcagaggaa cgtagtgagg tgaaggtatc cgtataatgg ggaaagaggt tgtgataaag   36000
agtgaaggtg tcccagagga agcgatgctg aaaaatacac cttatgttaa atacactgtc   36060
agtatatcat gacattaaag tgcaaatgat aacattttgt aaactgatcc aaacttaaaa   36120
aggagtatga taattctgta aaacataaaa atcatgccga ttccataaat tatacagtgt   36180
gaattacact gaaaaatcca acattagaga ggatatgaat acaattttt acaagcataa    36240 ttttaataat acacataata attatttgta ttcaagttta gtaatggtca aggtttggaa   36300
gaaattctga tcctgtgtag agaccctagt ttgaatgtgc ttatagccta ttattacatg   36360
tgtaatgtta cataaattac ttaactcaga tttttaattt catcagctat ttaaaatggg   36420
cataatataa ctatattaag tggatgttat gaagattaaa taagatgata tgtaaaatgt   36480 gtttttttgtt tgtttgtttg tttgtctgtt tgttttttg agacagagtc ttgctctgtt   36540
acccaggctg gagtgcagtg gcacaatctc ggctcactgc aagttctgcc tcccgagttc   36600
atgccattct cctgcctcag cccctcccaa gtagctggga ctacaggcac ccgccaccac   36660
gcctggctaa ttttttgtat ttttggtaga gatggggttt caccatatta gccaggatgg   36720
tctcgatctc ctgacctcgt gatctgccca cctcggcctc ccaaattgct gggattacag   36780
gcatgagcca ctgcgcccag cctaaaattt ttttacata atgggtgttc agcacatgtt    36840
aaagccttct ctccatcctt cttccctttt gtttcatggg ttgactgatc tgtctctagt   36900
gctgtacttt taaagcttct acagctctga attcaaaatt atcttctcac tgggccccgg   36960
tgttatctca ttcttttttc tcctctgtaa gttgacatgt gatgtgggaa caaaggggat   37020
aaagtcatta ttttgtgcta aaatcgtaat tggagaggac ctcctgttag ctgggctttc   37080
ttctatttat tgtggtggtt actggagttc cttcttctag ttttaggata tatatatata   37140
tttttttttt ttcttttccct gaagatataa taatatatat acttctgaag attgagattt   37200
ttaaattagt tgtattgaaa actagctaat cagcaattta aggctagctt gagacttatg   37260
tcttgaattt gttttttgtag gctccaaaac caaggaggga gtggtgcatg gtgtggcaac   37320
aggtaagctc cattgtgctt atatccaaag atgatattta aagtatctag tgattagtgt   37380
ggcccagtat tcaagattcc tatgaaattg taaaacaatc actgagcatt ctaagaacat   37440
atcagtctta ttgaaactga attctttata aagtattttt aaaaaggtaa atattgatta   37500
taaataaaaa atatacttgc caagaataat gagggctttg aattgataag ctatgtttaa   37560
tttatagtaa gtgggcattt aaatattctg accaaaaatg tattgacaaa ctgctgacaa   37620
aaataaaatg tgaatattgc cataatttta aaaaagagt aaaatttctg ttgattacag    37680
taaaatattt tgaccttaaa ttatgttgat tacaatattc ctttgataat tcagagtgca   37740
tttcaggaaa cacccttgga cagtcagtaa attgtttatt gtatttatct ttgtattgtt   37800
atggtatagc tatttgtaca aatattattg tgcaattatt acatttctga ttatattatt   37860
catttggcct aaatttacca agaatttgaa caagtcaatt aggtttacaa tcaagaaata   37920
tcaaaaatga tgaaaaggat gataatcatc atcagatgtt gaggaagatg acgatgagag   37980
tgccagaaat agagaaatca aaggagaacc aaaatttaac aaattaaaag cccacagact   38040
tgctgtaatt aagttttctg ttgtaagtac tccacgtttc ctggcagatg tggtgaagca   38100
aaagatataa tcagaaatat aatttatatg atcggaaagc attaaacaca atagtgccta   38160
```

```
tacaaataaa atgttcctat cactgacttc taaaatggaa atgaggacaa tgatatggga    38220
atcttaatac agtgttgtgg ataggactaa aaacacagga gtcagatctt cttggttcaa    38280
cttcctgctt actccttacc agctgtgtgt tttttgcaag gttcttcacc tctatgtgat    38340
ttagcttcct catctataaa ataattcagt gaattaatgt acacaaaaca tctggaaaac    38400
aaaagcaaac aatatgtatt ttataagtgt tacttatagt tttatagtga actttcttgt    38460
gcaacatttt tacaactagt ggagaaaaat atttctttaa atgaatactt ttgatttaaa    38520
aatcagagtg taaaaataaa acagactcct ttgaaactag ttctgttaga agttaattgt    38580
gcacctttaa tgggctctgt tgcaatccaa cagagaagta gttaagtaag tggactatga    38640
tggcttctag ggacctccta taaatatgat attgtgaagc atgattataa taagaactag    38700
ataacagaca ggtggagact ccactatctg aagagggtca acctagatga atggtgttcc    38760
atttagtagt tgaggaagaa cccatgaggt ttagaaagca gacaagcatg tggcaagttc    38820
tggagtcagt ggtaaaaatt aaagaaccca actattactg tcacctaatg atctaatgga    38880
gactgtggag atgggctgca ttttttttaat cttctccaga atgccaaaat gtaaacacat    38940
atctgtgtgt gtgtgtgtgt gtgtgtgtgt gtgtgagaga gagagagaga gagagagaga    39000
ctgaagtttg tacaattaga cattttataa aatgttttct gaaggacagt ggctcacaat    39060
cttaagtttc taacattgta caatgttggg agactttgta tactttatttt tctctttagc    39120 atattaagga atctgagatg tcctacagta aagaaatttg cattacatag ttaaaatcag    39180
ggttattcaa acttttttgat tattgaaacc tttcttcatt agttactagg ttgaatgaa    39240 actagtgttc cacagaaaac tatgggaaat gttgctaggc agtaaggaca tggtgatttc    39300
agcatgtgca atatttacag cgattgcacc catggaccac cctggcagta gtgaaataac    39360
caaaaatgct gtcataacta gtatggctat gagaaacaca ttgggataaa tcagctgcta    39420
tcataatcat tcctcttcca catcagataa atgaattaac ttttttgaata gggttattta    39480 atataaagtg cttaagtcta attatgagaa gaaataagat aattacactt caatggttaa    39540
agagagggag aataatttgc atattatgcc tgatgtaaaa tgtttattat gggtacatat    39600
taagtgctaa ctaatcgtta attgttcttg ctacaagtct taatgcaggg aaacaagaaa    39660
ttattacata gtacctaata ttatcttcta atattaaaga aacaatttcc cctaaattca    39720
tcccattagc ttttttttttt cggtggggca ggggagaaat acagacttca gtaaacttgg    39780
gccgggaact ttctacctac aaagttcaaa taaaataaat tatcctagtt agataatatc    39840
aatgaaaaat ccaccaactt aaatcctggc tgtttgatct caggaaatta tttcagttat    39900
caacttaatg catcatatta tagaaatata tgaaaatgtg tttaattaaa cttactgaat    39960
gatatgtttt ttaaggtact ttaaaaataa acctatgata taaagttact tattttttcat    40020 gcaagtatag tataaagaaa tttctaacac tggagatttt ctgaaggttt tgattcttat    40080
aaatttatta catcataatg aacaaaacta attttcaaca tattatgatt taaatttcct    40140
tagtaaattg ttttaaattt attttctttta aatccatatt tacatatgta tatttaaata    40200
tacatattta cttgtataac aattcaaaac catatattaa ttttataatt ttgtttaatg    40260
tcaaaggtta gatttggcta tatctattct aaaagttgct atcacatttc ctttttggaa    40320
ttttattttt aaagtagcta aagtcaaata taaacctatt atttatatta atgcagacat    40380
tagaggtaga cactaaattc gttttagtat attctaaatt atttattatc tactatgaaa    40440
taatataaag aaaaataaag cagaatccct gatttcaaag aactcagttg ccgaaaaaca    40500
gttaccattt attagaccca aaatgtacta atatgagtgt gtctcttttc cttttgtttt    40560
```

```
gtcacccgtc atttggaatg tcagtgagta gagagatagt gtgaaaggcc ctcaagggga    40620
aaaatagagg ttaaaggtca gcagagaccc tactagagaa atcagttcta cagaaatgtt    40680
tttaaatgtg tcgattattg ctacatgtac actctgtcat tttgtaatgt agccatttta    40740
tttatgatta aataataaa acaacaaaat tataataatg tgtagagtac attttactgt    40800
gcagtgtatt gcattaaaac tagattaaaa tttatacata tataaaggt tatctagata    40860 ttataaaatt tatggctgga tctgtaaaaa attcaaaacc tattttaat cttgctttga    40920 gattttataa caagaaaatg ttcgtttcaa gcaaaatttt caattcacgt ccttgaaaag    40980 gaaaaaatg acaacttgaa acacataatt gactatttt aaaggatcaa catttcagaa    41040
atgttttaaa acataagatt ttcagtacag cttttcgctg gcatttaaat cgaactttga    41100
attgtaaata gctcttactc ttaaggagac atcagccata tccttagaag tggcacggag    41160
ttggtaggta gttgtacaaa attctagcct aaaagacaaa tagggagcaa cactactgtg    41220 gacccttct ggtcttgggc tgtgtggcta tgtcaggctt gcccacattg cctgaactaa    41280
ggagaaagcc tcttgtcctt acagacccc ttagcttaca tagtctattt gaaaacgaat    41340
tgctttgtcc acaccattta aatattggct tcaggccggg cacggtggct cacgcctgtt    41400
atcccagcac tttgggaggc tgaggcgggc agatcacgag gtcaggagat cgagaccatc    41460
ctggctaaca cggtgaaacc ctgtctctac taaaaatata aaaaattag ccgggcgtgg    41520 tggcgcgcgc ctgtagtccc agctgctggg gaggctgagg caggagaatg gcctgaaccc    41580
gggagtcgga gtttgcagtg agccgacatc gtgccactgc actccatcca gcctgggtga    41640
cagagcaaga ctccgtctca aaataaataa ataaataaat aaataaata ataagtaaat    41700 attggcttct tcaactggtg agatgaaaac tatacaatag tcatgtgaat agcactaaac    41760
agctgacatg gtgtaactcc tctcagactg aggcttatct ggggagtaca aagcatgtca    41820
agaaaatgtg ccttcatttc cttagatgag tgtccccatc ctccactctc ctccactgtt    41880
ctcctctctg cttctatgat atcaactttt ttttttttct ttagattcca catgagtgag    41940
atcatgtggt tgtttgcctt tctgtttctg gcttatttaa ctgaacaaga aagttttga    42000 catgaaatta aacttctgct tgtaaactca attcaaacta tttacactgt cttctcaaaa    42060
atgttaactt attttaataa atctactgaa tgaccgtatc tcattttgtt ttatgaaaag    42120
aaattgtaag ggtgctcaat agcctcttca ttttcatact gtctagctcc tgtgctccta    42180
ttaaaattac tgcaaattta gcttttaag aacccctttgt ttcactacct gaagttctat    42240
aaaaagatcc aagttccttc acaaccgttt cttatgctgt tattcgtaca tatgtgataa    42300
taccacgtct gaacacgtag ataataagta gggctgggt gcggtggatc atgcctataa    42360
tcccagcact ttgggaggct aaggcaggtg gatcacctga ggttaggagt tcaagaccgg    42420
cctggccaac atgatgaaac cctgtttcta ctaaaaatac aaaaaataat aataataata    42480
attagccagg tgtggttgtg ggcacctgta atcccagcta ctcgggagac tgaagcagga    42540
gaatagcttg aactcaggag gcggaggttg ctgtgagctg agattgtgcc attgcattcc    42600
agcctgaaca acaagaatga aactccatct caaataaata aataaataga agtatgtatt    42660
gtgttgctta gaaggtgtgg tggaaattaa cttgctgagt gagatcaaag gattggcact    42720
gaattgaaat aaagaaatat tcatgctgag tctggttcaa atataactgc acctgtaaga    42780
attgctttct gtaaactttc catagtataa accaaatcca aatcactcat ggctttacat    42840
tcctgatcgt taaacttgaa gcactttta atactgcatg actttagcca aaatatctta    42900
gccaagattc aatgtttggt tgaaccacac tcacttggac atcttggtgg cttttgtttc    42960
```

```
ttctgaccac tcagttatct atggcatgtg tagatacagg tgtatggaag ccgatggcta    43020
gtggaagtgg aatgatttta agtcactgtt attctaccac cctttaatct gttgttgctc    43080
tttatttgta ccagtggctg agaagaccaa agagcaagtg acaaatgttg gaggagcagt    43140
ggtgacgggt gtgacagcag tagcccagaa gacagtggag ggagcaggga gcattgcagc    43200
agccactggc tttgtcaaaa aggaccagtt gggcaaggta tggctgtgta cgttttgtgt    43260
tacatttata agctggtgag attacggttc attttcatgt gaggcctgga ggcaggagca    43320
agatacttac tgtggggaac ggctacctga ccctcccctt gtgaaaaagt gctacctta    43380 tattggtctt gcttgtttca ggcattaacc cagataaatg ccatgcaaat tttataatta    43440
ttatgattgt ttcaatttct ggaagaaagt taatgaaaca aaaaatgtag taaaatgcca    43500
aaggaacagt gacatttcag aaagaatgag ggctttcatg ttaattgtaa gtcttggaat    43560
ttctcttcct tggagtaaca aatccctttg tgcctaattt cctaatttcc aaaataaagt    43620
tcttttactt atttctttat agtgacatca tctcttatta aatggcatat ctgcatatta    43680
cataacagtt cattgccaaa tacatatttg tgggaaatga gagacttaaa atacatacca    43740
accagagata tagttttgag gtagatttta aaattctgag aagaatttg actgaatttt    43800 tttgacaaac atgggacacg aataagatta taccaaagat attataactt tcattttaaa    43860
tatgaaacta atacagtatg aggtgtcaac aacgttgaag tttcacaaac atcaccacaa    43920
cagcaaaata attttgctt tttccctgcc acaatgacct ccttgctatt tcttgaataa    43980
atcaagcata cccttgccct gacacgttct tggggaggcc tgccctaatc tatataaaat    44040
tggagccatt cttctcacct ctggtattcc cagtctccct actttttttc cttctttctt    44100 tcttttctt tttctttctt tctttccttc tttctctctt ttctttcttt ctttactttc    44160
tttcctttct ttcttttccc ttccttcctt ccttcttccc ttccttcctt tctccctttc    44220
tttctttctc ttttttcttt cttgcttcct tccttccttc tttcctttc tttcttttcc    44280 cttccttcct ccctctctcc ctcccttcct tcctcccttt cttctttct cttttttcttc    44340 tcttgcttcc ttccttcctt cttttccttt ctttctttt cctttctttg ccaaagtgtt    44400
attcaccttt aaatataata cataatgtgc ttactttaat gtatgatttt tattttattt    44460
ctcccttcta gaatgtaggc accatgagag tgaaatatat ttattttgtt cattgatatt    44520
tcacaagtgt ctgggagagt ttccaactta cagtagacaa ttaacaaaca tttattaaat    44580
taaggaggga aggaagtgag taagcacaac aactttcatt tctgggtctt ttataatcat    44640
atgcttagta taagaacagt gctattcagc tatccaaaag ttacaatcaa aatgattttg    44700
gatgaatatc ttgaaaattg tgagaagaa gttttatttg ctggcaaact attctgggtt    44760
gtttccactt catgtaatcc taagtagcag ccttaccttg atagcccatt aaaactctga    44820
taataaaaag gcagaacaaa aatatctgtg atatatttag atttactaca tgtacttaca    44880
tgtctagtgt ctggtgcaat ggatgctaat gatggcaaat ccttactggg cttctagtga    44940
agttcttcag ctaatgcttg aatgcatggt tggtcatggt ggtaccccct tgtacaaaat    45000
atgcttttca aataatctta ttagggataa taattatatt aattcctggt ttccatctaa    45060
aattttaatt ctatttatag cttcgtaaga tttcacaagt taagagggac ctcagattaa    45120
attagtacac aggcaattaa tcagttttgt gtctccgacc cttttcacgg gctaatagaa    45180
gctatagacc ctcttagctt cagaaaaatg tgcactcaca tacgcacatc aaagagctta    45240
atgggaagtc cattgacaga ccctctgttc agatcaatct tctgattgta gagatgagga    45300
aacagaaatc tacagaggaa gtgggtagtc caagattgca cagtcatttg gaatagactg    45360
```

```
gacaccagta gtactttcc agccactata tcacttcccc aagcacttcc tcaaaactta    45420
ccttcctttg ggtctttata cattcagtta tggacaacta gatttaacta gaggatttta    45480
ttgcttcaga atattaagca acagggaaac atgtaccgtc ttttattcac ctgcatttaa    45540
ggcatacaat ataaattgca aatggagcat gaaagtgctt aatcttttac aaaactgggt    45600
ttgctttcca cccatctaaa aatacttcta tttattttaa tatttaaagc agaaatctaa    45660
gtgatgtgac aaaattaatc atttggagat atttccctta taggtagtat agttccttac    45720
tgatttctaa tatgaaaatg aagccataga acctagaaat tgcagcatag ttgtggaaat    45780
aaacattgga ctgagagtga aaatggctag tcttcctctc tgctcataca ccacctgact    45840
ggataacctt ttgcagatct cctaaaagtc tttctcataa aatgaggaag ctctactaga    45900
aaattgttga agtctaattt agcaataaag ttctgagttt ctataataat tcaaagaata    45960
ctctaataaa tgtctgcaat tgtggtcaca tctatgggat gctaaaaaat ctggatggtt    46020
tcaatgaaag tatttaattt gttcattatg aactttgaaa taatttattt cattttttaa    46080
actttgatca aaatgaccct ggtaaataga aataagcaaa ctcttttttgc ttgaaatgct    46140 tattaatgac tgcattgaga cactcattca tcattcaaga aagaatgttt gctcacactg    46200
tgccagaaac ttggaggaag agggatgtga caagtagggg tactggatgt ctagcttgta    46260
gaagtggatt aatggctctg cttttaagat caggaacact gaaagggagt aatggcaccg    46320
gttttcacct ttcatgccct ttgagggtat ctggtccatc accctctagt tgatgaggga    46380
gggaaagttc cctctccctt cacaaatagg tggaaattaa atgacataat tctgaacaac    46440
caataaatcg agagtaaatc aaagcagata cctgttttgt taatttgatc atatgaatgt    46500 agctgcccctt agtaataatt tctaagtata agactagtta aaggacaaat gagttatctt    46560
gaattataag attttgtttt acagaacaat attaactctt gtgtttagta cattagaata    46620
atagatattt tgatccatat ttttactcat gtgcacataa gaagttatca gtcatacaat    46680
tcatttcttg aagttcatac ctttcattgg cagagtagaa acaggttaaa agtgcactgg    46740
cagaaatttt aagtgcaaag caacagtgat gttatataga gaaaatttat atttcctact    46800
tctattgaag aagaaagatc tgcttgttct aagaatattg tacaaagaaa gtgacttgaa    46860
tcagcgttat tctgtaatgc tactatgcgt gcagtgtgga gtagccacta gaacacttgg    46920
tctatcccag ctcctcaaca gtgtcttgct tgtggctggt gctcaaataa atccttgctg    46980
aactaatgag catctctttc atgccacatg gaatgctcta aaagagttgg atcctgaagt    47040
ttttatattt ttgtaatttt ctggagtgtt agagagcaaa agtcctgaat aaactgtgaa    47100
gccactgcct gacaaataat acagcagtca gcttcgttat catatcccat tgagacacga    47160
cttatctaca tgatgattaa tagttttcac gcaagaaata agcttgaaat gtctgttgcc    47220
ttgggtactt aaaacatcca ggttcagcga tgttatttat tgttgttcaa aatcagaatg    47280
aagttcctaa gcaatgccat tttggaaaaa ttacatcaat atattatgaa caactttttt    47340
taaatcttga tttcaaatgg attgacacgt gtatattctg taataatcct gacttaattc    47400
ataaaaggat agctagccag ttgtgtgcta gatgaataaa aaaaaagcag ttttaaaat    47460 gtcaggtttg acatcgtgaa tataatatct aagtatcctt ttactcattt cctttgactt    47520 actatgctg tcatgttggg cttcatgaaa atttatttt aaacacttga gtgttatgga    47580
ccctctgatt aaatgattaa tcagatgatg tatgttgcca tcagctgaat catttaatgt    47640
tgatttcaca aacaagcaca ggtcacaggc aacatttcag atttctttga agaagcacac    47700
acaggtcaca ggcataatct taaaataatt ttataacaag gtagtaataa gagatgtcag    47760
```

```
gactggagaa atattttaat ttatagtaag ctttcccctt aagtgtctaa taattgttaa    47820
tataatacat tgcctcaaat aattaaaagt ttggttcttg tccttgtgct tgacttcaga    47880
agataaccag atgactatta ggtatattta gacctaaatt aaaagctttg agacacaatg    47940
aattgcctga tttgtatttg tgtttcgagt ggcatatact attactggca ctataatctt    48000
agattaaagc atactgtgat tattaaagaa aaatttaaga ttgatttgtt tctaaaggta    48060
tgtaacagtg acattttgca atgtggtatg taaaagttgg tatttctcac tcatatgaga    48120
gcccactaat ggtacataaa ctgtccccac ttagaaacac aattattatg gcctttcttt    48180
gtatctgaca aaatttcact gggttcaaga tggatgaata gtgaattcta atgaccctta    48240
atcctgtaag gttctaggtg ggaaagtact ctgtaattat gtataaaatt ataaggaaaa    48300
taggcttact gctatgtttt cattaaaaat cattaactga gtacttaata tgtgccagac    48360
actcagctgg gcaccatgag aaatacaaaa ctgagtaaca tatgggtggc tcctgccttc    48420
aagaaatggg cagttcaggc cgggagactg acatatttac cctgggaaaa agggagcagc    48480
tgtggtctct gagaacaata tggtttgtta caagtatata tccatcatgg aaaaaaagag    48540
atttatctta gaaatgagag aggctgatgc tctcaataaa tatcatacat taaattgtgt    48600
ttttgtcagt agactgaaat tacctcacat acacgcacag atagtagcca tgatatttta    48660
gctgcttaga tatagagaca aatacttcca cccaaatctt aggatcagtg gttaatagtc    48720
tgtaagcatt acaatcccac aacatatgca tgactataca tccaattttta atattcaaag    48780 aactgattgc gatgatagtt ttgtttgtca aagaaatgta ttataggatg agtgggatag    48840
aactgcatca cgttacacca acaaataggt ttaaatcata tttgtgcact tcccttgttc    48900
cttcataaat gtttaacata gcttaaaatt ctgtggactg caacgtgaga gcaatgacca    48960
cacttctgtg aacccatttt tactgtgcat gtgctaacgt ctattgttag tattccttca    49020
cttgcaaaga tggcatgata attttgctgg tttcattaat gagatactgt taaatgtagg    49080
atgacttcaa acttagttgt attgtaaaat tattttttaat tgtatacatt taagttgtac    49140
agcatgatgt tttgagatac ttatctttat ttatatatat atataatata cacacgtata    49200
taaaagtgat tcctacattg aagcaaatta acatacccat catcatatgg ttatctttgc    49260
ttttttacta tcagtgccta aaatctactt tcttgaaaaa ttaccagtat gcactacaat    49320
attattaaca ataatcttca tgttgtacat tagatcttta gacttactca tcttacatga    49380
cttaggtttg tttttacctc tactaccatc tgagccatat ttccactttg taatttgata    49440
ataaacttgg aaaaatagca cttatatgtt taggtgacgg gcataaatag gataagatgt    49500
gtttatatat tattccatat atcttgtctc caactacaat gataaacaac ctgtttgtcc    49560
ctaaaaagta agaaataact tgactttctt gcccccttcaa gcataggctg ttagcttttta    49620 agtttagg agacattgat gatgctattt gctttatcaa gaggaaattg tcaaaagagg    49680
tcttttggtt ctcaaactat tcaaagtatt taaaaatcag acaaaatat gtttacgtga    49740 tattcaaggg tacagaaatg aggtaaatga gatgccaatt gtatttgtca tgcaaatata    49800
taattatgtg tatgagagtt agatgataca tctcatcaat ttaattgttc ttctacaagg    49860
agaaaatgaa caatttgtca actcgtatat gaagtaattt ttataagaaa ttttattaaa    49920
acttttaaca acatttggat ttttaagttg caatttaaat atccccttct accaggtgat    49980
tctggaatca ctaagcagtt acctgtgaaa attccaaagt agcatttaat tcttattaat    50040
gtcatagtga acactaatgc aaagaatact gagccagaaa ttatgcttgt tgaataaata    50100
gattatttat tgaacaagta agtgaaaaaa tggaaataaa gaacagatat atattttatc    50160
```

```
ttcctgctta gatgtgggac tgtcctactt ttctctggtg ttcacaacaa caatatgata    50220
aatctaattg gaattcagtt cataggaatg aattcagtta cattatggat tgtgatgaat    50280
aatgtacact tttaatttaa tgaaatcaaa tagattttaa ctatctatgc ttacaatggg    50340
gtgacataag tctgacaatc cttaatatca agtcatctcc aattcacatg tatacacact    50400 tttttctat ttggctattg ggaatcctca caaaaatcga aaattgccct ttcagtgtac    50460
gttacggtat ttcatgccac acagattttc tgaggttgta catacagctt tgccttgagg    50520
ttccaatttt tgctcagtgg attgagtata tattatttgc tatatatcag aagaggcatg    50580
tgcttcctac ttatgtcacg taactttggg attaatgtaa ttgtcctaca aagcatagat    50640
agatagaaat acttcatcct taatttctaa tattatgaca tatctaaagt aggcaccttt    50700
aaaagataat ctccactaaa tacgaatgac tgcttatagt ggcaattcat ctttcatggt    50760
agtcctccta caaaggtata ctaacattta tgagtttgaa acaaaggcaa ttcacaagtg    50820
ttctgctaga gatggtctat atctgctgtt tgatccagca tgatggccag ctggccctcc    50880
tgtgcatgac ggctcgtggt ttaactgcac cattttgttt ggtcatatac agggaaaaca    50940
tggcatggtg tggagggcat gggcttgaat tcagggaaca gagagttggt cttctctctc    51000
tcactctact ggatgatgtc atctcccctc tctaagcatg agttttctta tctgtgaaat    51060
aaaaatgttg aattaaatga gttcaaaatg ctttcagtct gtgtttaata gcttgaatct    51120
taagacaatg tattcaatta tgcgttgcca gatccctggc aactcatgta accttttctaa    51180 accatagcta ctcatctgta actggccagc caactgccca gggttggagt gtgaatgaaa    51240
taagataatg cagacaaaag atttttaaaa attgtagtgc attatacagt tgtaatattt    51300
tgccaagaac ttacattttc tctaagaagt gtgtcgatac atgatcacag aaaatctttt    51360
ccatattcct ttgtagtttg atgatattaa gtaagtaaat tgtataacac aaagagggaa    51420
aagcatcact gaacatgccg ttttatttag ctaaataaaa tgtaatcact attagtttc     51480 ctctgatttc cccaaagtca tgtgattcca ttgagtatta tgcacatggt ataattagaa    51540
tggattctct gctcaaataa ttttgggaaa catttaaatt aacaaagttt aaaagtatct    51600
ctgttaagct gaagcaaatc tcaaaggcct taatattgta tgtaagagga atagttacca    51660
tctttcctaa tgcctctttg acgccaaacc catggagaat agttctaggt gttcagtaaa    51720
acacagattt gggatgccac aggttaattg gaactgtccc ctgcaatctt tttctctttt    51780
tcttaataat ggctgattgc aggtcctaga tgaaagacat ttagagagat tatcaggact    51840
cagcatccca tatcagaatc cattcttta tagtcatttt ctgttacatt tcttgggaca    51900
acaccaaaga aatgaccatc ttcattcaca taggctttgt accaaatgct gacaaagatc    51960
cttggtgacc tagatgggg caggtctaag tagattgcag ctgtaaaatt ggctgatgaa    52020
tgatctcagc ccctttact cacactcaaa ggcaggacag tccattaagg ggaaggaggg    52080
cagagttttt ccttaggcca attccctatg ccagaacttt ttagaatgga agcatttcca    52140
gaggagaaac aaccccaagc acagttcaaa gccccctcct cccaagttca tttgaaagtg    52200
ggatggttta tctgcaaagg gggaaaagat gagggatagg gacgggaata tccctaccct    52260
tcagagagtc tggtttcatc ctgcactttt actgcacagc cacaaatgcc ttggggtgaa    52320
tctacaatat gatacatcat atggtctaaa cgtgcctggc tgatcctctc taatacttca    52380
ggggtctaaa agggataaca tgctctcctg ttactcaccg actctgtccg ccatatttca    52440
cccagccagc cactgccttc acttccgtcc gaggcctaat ctgagcccat gggaaaccta    52500 agaacccta ccacaactgc ctcaactctt gggaatcagg gtgtatgggg gtgacaggaa    52560
```

```
gtgagcatac attctccaac ttgatatgtc agcccccacg tctgtatgaa tgtttgctca   52620
cactgtgact gccggccttg ctcctcaggc tgcatcctac cagggagtaa gacccaagtc   52680
cttcctgctt tcagacaaca ccaagcctca tgagtcccca ctcagaggaa ggaccagaga   52740
caaactctaa tgttccacta atacttccct tcttattact ttccttgaaa atcccttctc   52800
cctctttctt tttatacttc gctaatgaaa ggtaatgaaa gggtctggca cttggaattt   52860
agaattgata catggttttt aacccgcgga cgtattccac aataaccctt gcatcttcta   52920
ctaagatgtg ggctaggaag ggaccagcca gttcccaggg tcacagtgcc tcagctgatg   52980
tttcatattt tcagcaactt tatgttagag atgtccatca atcagaacaa tatggttaga   53040
gaataaacta ataaaagtca cttttgagga catgttggaa gtctatcaaa agcattgaaa   53100
ttatgcatgc tctgaccagt cgcatgtcta agaatttaaa tatgatcata agtttaaata   53160
tgaagatgtt tatcacagaa ttgattataa acaaaattg aaaaaaatag tgctagaagt   53220
ttgatcatag ggacctcatt aaatgcatta tggttgatcc atgcagtggt ttgctgaaca   53280
gccattaaaa tgttgtagaa taattattaa tggtgtggaa ggatgctatt gttgcagtat   53340
gtgaaaagaa caaattacaa agcagtttgt gcagcataat attttattt tttaaaaacc   53400 tgtatgtggc ttatgtacat ataaagacgt ggaataaatg cacaaggtac tcagttttc   53460 tcagtgaagc ccatttttgca ttttgggctg ggtaattctt cgctgtggag aactctcatt   53520
cattgtagga tgtttacaag ccctgggcct tacctcttta acgccagtag gcaccccag   53580 catggcaaca agcacaaaat ggtctctctc atattgccct tgaggaaatt ttgcaactaa   53640
gtaactatta ctgggtccta gattacagtc tggattattg cgttcctttc ttatttttat   53700
tttctccaat tccctttaat aagcatgtac tggattcata aaaaaacaac ataaatggta   53760
attacaatat tccgcactgg ttaaaactta tgtaaataag cattctgctg ctttagccac   53820
aattgcaatt tatgctcctt ctcttttctta agttcccagt tcccacgtac attcattcga   53880
ctgattcaaa agtcatttta gcttgataga ctcttaaaag ttagagttat catttctgct   53940
atttattctt tcaattatcc atttgtccac ccatccatct gatccatttt gttgatgcat   54000
gctgtgtata aaatactaca ccagcctggt gcggtggctc acgcctgtaa ttccaggact   54060
ttgggaggcc aaggcgggtg gatcacctga agtcaggtgt tgagaccag cctggccaac   54120 gtggaaaaac cctgtctcta ctaaaaatac aaaaattagc caggcatggt ggcagacgac   54180
tctaatccca gctacttagg aggctgaacc aggagaatcg ctcgaaccca ggagatggag   54240
tttgcagtga gctgagatca tgccaataca ctccagcctg ggtgacagag caagactccg   54300
tctcaaaaac aaacaaaaaa aatacaatgc caagcatcat aaaaaatata gtgatatata   54360
agacctattt gttgtgctct aggcattgac atctagctgt caaccattaa tatgtgtagg   54420
agtctatcta tcaatattat ggactgtgct tgaagacttc ttccccaatc tttttctctt   54480
cccattaagt ttgaagtgag gttttctgag tgaagtatca tagtacatac agtctcatta   54540
tttttcaaaa atctctggtt atagtacatt tctttccttt atcccctttg ttcccaacta   54600
tcaaaccatt ttggatatcc agtattggta tccagtatta ttaaaaagca aaacagaaga   54660
ctattaacaa aaaaatttgt aggagtaatt ggttgtatgg tatccagtac tattagatag   54720
taaatcagaa aattattaac aaaaattta gacgaataat ggattgtctt gcccaagtga   54780
attgagtgat ttagttgttc tttcatttttt agcaagtaca gctgatcatt tgaggcctta   54840
ctcattgttt gattttgcaa attcttacta ttataaatgt tttgggctct gagaaagctg   54900
ttgtcttaat ctgtttgtgc tgttataaca aaatacatga gactgggtaa tttacaaaca   54960
```

```
acagaaattt atttctcata gctctggagg ctgggaactc caagatcaag gcatttgtct    55020
tcaggttcag tatctggcga gggccggttc tctactccca agatggtgtc ttgtcactgt    55080
atcctccaga gggccaaatg ctgtgttctc acatggtaga gagatagaaa gggccaactc    55140
actccctcaa ggcctttcat aatgttacca attccacttg tcagggctct gccccgtga     55200
ctttattacc tctgcaaggc cccaccactt aatactatca cgttggttat tacgatttat    55260
cacatgaatt tcgaccatac tagttgccat cctttcattt tcatatatcc ttaaaacttt    55320
gcctttctca ttttaatgta ctttatccac agtatgccaa cttttcgata cttttgttaa    55380
cctgtctgac gatatatagg aaactgtaaa agtgcagttt ttgatacact ctttagctgc    55440
ccgtttactt ctactgtcgt tagagaaccc catccatagt gcatgtgttt attttgtgta    55500
tgaacaaaga cttatatat agtttgggtc attttattc attagtgctt cccttataat      55560
ctctgaatac cattttatta gtacatactg ctattcttaa tagtaactag catgcctgat    55620
catcccaaat gtctaggttc acattttaaa ataagttata tctttgggct taacagttta    55680
ttgaaaggta acaaggattg agtcatagtt gtatgttttt ggaagtagaa ttcaactgta    55740
aatagaaatt ggttgtttag atctcactat atatgaaaaa atgaaggctt taggagaaaa    55800
tctccccaaa gtacccattt ttcatgtgat aaatatcatg aaatgatttg agaaaaaaat    55860
gtatatttgt tacagctaac aaatatttgt gttttttatt cttcatggag agaatgaaat    55920
ttcttctctt ctttacacat ttctttttct tattagaaac taattggtgc ctttataaaa    55980
attaactgca gagcactaac gtgtatatat aagtattatg tagggtgtag ggtatgttca    56040
gggtatggtg tgtgtgtgtg tgtgtgtgtg tgtgtgtgtg tgtagctgtg tgtgtatata    56100
atgaaatata tggtagtgtt gtttcagaaa tctgcttggt cttcccagag ttcattcatc    56160
ttataaattc atctacattg atctctattt ttggaatcca tgaaatgttt tttggcagta    56220
cttcctttaa tatagtgtgc tggaaatctg gaaatttcta gccagattag ttacaaaaaa    56280
ttagccagtg gttttgcact ctctatagaa tcaaggccca aggcctactc ttgttactca    56340
gggccttgtt ttatctggcc tcttttctttt cagccatata gctctcaaat actcaacaaa    56400
attcttcatt ctaggtagac aagtatcttc aaaatacttc ccaattatct ataactgtc    56460
ttaccactaa gaaggctttt atgtctcctg tctgaatttt atccatgcaa aaaagtccag    56520
cccaagcctc cagaactcca aaaagttatc cctaactgct gaaacacagt aatttcacta    56580
tgtgaaattt cactttggtc tcctagcatt tgcagatata ccatacatat ccttgatcct    56640
tttcctttca tacctttttat atctaaccct taagctaata attttaccta cactgtaatt    56700
caaaatgtat ccccagtctt accatgtctc ccttctctac tgttaccacc ctaggctagg    56760
ccttcatcat ttctcacctg gactccttcc ctaacctctg aactgatctg cctgcttcca    56820
cttagacacc caacctagtc cattcttgag cagtcggaat aattctttta agaaagaaac    56880
cagatcacat cccctctgc tcccaaccat ccagtgacct cttatcatac atagaatgaa     56940
atgcaaatct ttactgtgtt ttaaaggccc tacattatct ggccctcagt aacttcttac    57000
ttcctatccc ttttctcctt gtatgccacc ctccaactac actctaacta cactgtcttt    57060
ttccctgttc ttcagacctg ccaaccatat tttcactgct caattaatat gtagaaaatg    57120
aattgttcgt taaatgtaga ctgtttcctt cttaaagcaa agataaatga cattgtcttc    57180
aaaaacaact aactgcccag aattcctgat tttaatttta aaaagacaaa ctgcaagaat    57240
gtgttaaaca gtaaggaaac aattcactac ttcagaattc tatatgattt cactgcacgt    57300
tagtaatttt gtatattata gaatatgagg gtattctaat aaacttaact ctatgctgta    57360
```

```
tacttatcat gatagctcat tttcttatat gtttataaca gcactactta ttgtacatgg   57420
atacgtggga aataaattaa ttttctcctt aagaacaaag caaccatttc actcatgaga   57480
taaatcttga agatttaaaa actacttata attaattata cattattcat ataatgttaa   57540
gtattttctt agtaaaccac ataatttaga atggcaattg gacagatggg cagaaccaca   57600
tgcatccact attaggcagt tggtgagcat aagatgccag aaagaagatt aggaatatca   57660
aggcagggag cttccgatcg ctcttgaaaa cattgaccct tcactcctca ctctccacga   57720
tgcatttcct ttgaaaagta atgccttcca aaacaaagtt ctctgtttta tatctaaact   57780 tactcaaatag tttctcatgg ttattgatat ataaaaaata aagtaaaatg tttaggcaga   57840
ccaaaagaag aatttccccc tccctctgcc ttttatgcca aggtgacagc tatgaaatgt   57900
acagtacgtt tcctctgcaa ggaatgtagc agtgttccat tgcaagaaga tgagagggag   57960
agaaaggttg cacgctgagg aatatagtgt catttgtcac tgcctagact catcagctgt   58020
gtggaactct gagaggcacc aggcttcttt atttatttct tcagaaactt cagcaaaaaa   58080
gatttcatta ggagcagaga aaaatgtgaa aaacgaatta gcttttgtga tggggagtag   58140
tcatctctga atattgatca agattaagag ggttgtcttc gtaacttctt ttatccatag   58200
tctatactga tttaactaga aaactaattt caggtggtat ttcgggtgtg gcagatcttt   58260
atagtaaatg aagaatctag tcaaatctac tgaaaaactc tgcttacttt aatgtttgat   58320
ctggttgaaa ccatttagc ttaacaatcc ttcctctgaa acagggaatc aattgatatc   58380
ctacagcaaa attatgtgga agggccatta gcttcacatc caatgcaaat tttgcctgtg   58440
tttactcttc cccaatccaa aatatatcag atcctagatg ccagtgaaat cgtttgagct   58500
agatggcttg agggtcatag ctttttttcat ttcctgttct cagacctctt ataattgata   58560
gaataaaatc agaagagccc tagagctgtc ccacctattc tgcctcacaa aagtagaagt   58620
aatggcaacc actatcatag ggatcatgct cacctttttc ttaccagaca aatttggata   58680
ttagcttgaa attaatacct tccttaaaat gttggaattt ggttatatgc gaaattttgc   58740
tctatttatt cattatattt tgtatggaat tattttttgcc ctatattttc acttaagtgt   58800
tctctaccca agatttaat tgaacccaaa tcagccagac acacagacat ggattttgct   58860
gccaccaagg ttaattcttc ttttaaagtt aacttttaaa atttggtaaa atatagcttt   58920 gaaaattgc attcgtctag tgtttgttat gtatttcccc cttttgtttg attatatgtc   58980 tatattttc ttgtagaaat tgattttaa cctgcttttt atgttagctt ttatgagctt   59040
ctgtctgaat tctgaatatg tctttcttaa tgtcttctaa atgtttcttt ctggattatt   59100
aaaagattta ttaggctttt aataattata tttgttacct tagggaatgt gtttgaaaat   59160 atttttaaatg gaattgccag ttaacacagc attgaacttt ttcttgttag agatacattg   59220 tttttctaggc attttattgg gagagaagtt agtatgatat aatgtctttg gctgatatta   59280
actcttctaa gatgcattgt ttctgagaac accattgtct gatttcattc agggaaattt   59340
cacacaagcc agtagagtca atactttttt caagacctgt taattgatat atataaaaac   59400
ttgccattgt ttacatgccc atttcagatc ctttatgtga cctaagctag aaatgcattt   59460
taacagcatt tgttttcca aaaatattta tttatttatt tattatagag acagcgtctc   59520
tctatgttgc ccaggctggc ctcgaactcc tgggctcaag caattctcct gcctcggcct   59580
cccaacagtg ctgggataca ggtgtgagcc attgtgccag gccttgtttt ttatttttt   59640 taaacattgt attttgaaag gggttttgaag gtgatcccta gatagcaacc agtaatgatt   59700
cgagcagcaa acaatctaa aaagtaattt tataagaaaa tgcagaacat aaatgagccc   59760
```

```
ataaaaaatt atattaggtt ctatttacat tactaccttc tttcacatgt aatatttcac   59820
taacatttaa tgaatttctg tgcagtgcca tataccatta tgaattctag gatagaagaa   59880
tgagtgagaa atgttcttag gccttaggaa gaaggaacaa gcatctctgt gtaatagtta   59940
tttcaactct tcttttacac ctcattccca tattaaatct cagaaaagct aaagtaatag   60000
ctatcccaga tctattttag actccagaca cttacttcaa tgtcttgttc tccttatcag   60060
actggaatca ttccaaacct cttaacttct gggcaaccat gataatgcga cagaaaggac   60120
actaaatctg tcgcaaattt atcttgatat tctatccagt cttacttggt actgaaggtc   60180
acaagtaaaa taaggtggtt gttttttgtt tgttttttt ttttttttga cagaagagaa   60240
aagaacactg tgagcacaga gtgaatgtct aacattgatt cttgagtagc aggaattctc   60300
tatgcgagag gatctctatg caaaaagatc tcatattcta gcacaattta aggatctcta   60360
tgcaaagata tcccatattt tagcattatc aataagctat ggggtaatat attgtatgtg   60420
gtgtggcttg aattctagaa atttgatttc tagaaatggt ccctgtagtt aaggatatat   60480
aatgtggccg tctccagttt tctatgagga ataggaaaat actatcatta ttagctgtgt   60540
gaccatggac aacttgcttc gttcttcagt tgcatcatct gtataaaata agaataagaa   60600
aatttacatc tgcaaggtgt gatggagatc acatgggata attgtggtcc cagagcctgg   60660
cacaaaaggg cttaatattt ataatcctcc ccatttctcc gtatactcta aaggaagttt   60720
attgcttatc aaattgtgcc gtggttagtt gtacagcttc cctgccaaat tgtaaactcc   60780
aacactaatg tgacgttaca ttttatatag tgctatgatt ttcaaattgt ttgcataatt   60840
tcaaatacac agtaaattgc ttttttattag tataattatt gctattgtca atattattat   60900
tacaacagct tcacagtaag atgggcagaa aaaatttaa ttttccatttt acaaatgcac   60960 ttttgaggct cacagaagtc aaatagacca aagtcacagg gctagtgagg gacccagaag   61020
aaacaaattg taattcactg attccaagtt cagtggttgc cttactgcat cataaaggct   61080
attacacaat ccaggtgtat catatgattc ttgtctatat attcatacat atcagaaaaa   61140
gtgttctact caaaattgct agcaatcaac agatactgat agtcattagt acttaaatct   61200
ttatcaaatg aaatattaat acccatgaaa gagaggacaa tgaaaggttt gtatcatttg   61260
tatgtcacaa gtcaacttttt ttcaatcact cattattagt ttaactgtaa aaaattattt   61320
acatttagcg tgaaactttc ctgtattctc aacatatttc cttcggtaga aaagcaaacc   61380
tccagttctc tgttctttgc ttggatactt gccagtttgt aactcagcta tcaaacagta   61440
aagctcacaa aacacttatt aaaatgacta aaatccaaaa caccaagagc acagcatgct   61500
ggtgagatgt ggagcaacaa gaactttcat tcattcacta atgctggcaa tacaaaatgg   61560
tacagtaact ttggaagata ggttgacaat ttccttacgaa gctaaactat acttaacata   61620
tatatttgtc cattttcaca gtgctaaaaa gaagttcccg agactgggaa atttataaag   61680
gaaagaggtt tatttaattg actcacagct cagcatggct gaggaggcct cagaaagctt   61740
ataatcatgg tggaaggaga agggaagca aggcacctac ttcacaaggt gacaggaagg   61800
agaatgaatg caggaggaac taccaaacac ataaaaccat tagctctcgt gagaactcac   61860
tcgttatcat gagaacagca tggggaaac agctctcatg atctagttac ctccacctgg   61920
tctctccctt gacatgtggg gattatgggg attataattc aagatgagat ttgggtgggg   61980
acacaaagcc taaccatatc accatatgat ccaaaatcat gctacatgat attcacccaa   62040
aggaaatgta aactgtgtcc acaccaaaac ctgcacatgc acgtttatag cagctttatt   62100
cataattgcc aaaacttgga agcaaccaag atgttcctca ataggtgaat gaacaaaaag   62160
```

```
actggcacat gtactcaatg gaatattatt cagtgataaa aagaaatgag ctatcaagcc    62220
acaaaaacac atggagaaaa cttaggtacg taagccagtt tgaaaggttg cattctatat    62280
gattccaata tatgcattc tgaaagagac aaaattctgg agacagtaaa aagatcagtg    62340
attgcctggg gctctgagaa agtgcagagg gatgaatggg tgaagcacat ggcatgttta    62400
ggacagtgaa actattctct atgatactgt catggtggat acatgacctt atacctttgt    62460
taaaactcag aattttacaa tacagagtga attctaatat aaactatgga ctttagttgt    62520
aataaggtat caatgttatt tcataagttt taataatgta ccacactaat gcaaaattat    62580
aataataggg gaattggggg aagggtaatg gagtatatgg gaatgcactg taatctcagt    62640
acaattattc cacaaaccta aaacttcttt caaaaataca agctattggt caggtgtgat    62700
ggcttatacc agtaatctca gcactttggg aagtcaagac cctcagatca cttgaggcca    62760
ggagttcgag accagcctgg ccaacatggt gaaatcctgt ctctactaaa aatacaaaaa    62820 aaaaaaaga aagaaagaaa agaaagaaag aacagaagaa atgaaagaaa ggaaagaaag    62880 aagaagaaa agaaagaaag agaaagagag aaagaaagaa ggaaagaaag aaacagaaag    62940
agagaaagaa agaaagaaaa agaaagaaag aagaaagaa agaaaagaaa gatgcggttg    63000
ctcatgcttg taatcacaac tactcgggag actgaggcat gagaatcgcc tgaactcaga    63060
aggtggaggt tgcagtaggg tgagattacg ccactgcact ccagcctggg tgacagagca    63120
aggctctgtc tcaaaaaaaa aaaaaaaaag ctattaaaaa tatgtaaagc tcagtctaga    63180
tacagtacca gaatagtagg aactttattt cacctgtcct acaaattatg gttgtgtgcc    63240
acttgggtaa aactcagaat ccaaatatgt gaatgtaaga tttatgggga aattatttgt    63300
atttcaaaat aatccttaat gaatgcactc cttctaaagt agccattaat aaagcagtta    63360
atgtttcatt taattataga ttaatgtaca taagatatgc caggaatgca attaggaact    63420 gggaagggggg tgttattcta ataacttcca catagcattg tgagacattt tctgctttct    63480
tcaaatttca tttaattaca ttttaaacaa atatttttgt gagcctatta tatagtcctt    63540
cgctagcact gaggagacat gctttgtgac cttggtgatt tcacattcaa atttcccttt    63600
cacctacact cttccttgtt ttttcatgcc tgtgtagatt gtaaattctt cctcagatta    63660
agacatttta ttcacctttg taacatccac agtatctagc acaatcagtg ccttcaaaaa    63720
caattggcct caagaattga ttgactcaat gagtgactga aagactaaat taataagtac    63780
acatctattt gtacttccct gcttacttat aaggtatgac aatgaaatac tgagacagtt    63840
atacattact tacggactca atctcatttc tttacaatct ctattcttct tttttgagta    63900
taatgttatt ttacaattcc actaacttgt cactcttat tataaattca tatctccatt    63960
tcacctgaga ataataaagg caaggaagta ttttaaatga tcttgttttt tataactagc    64020
attcattgag caaatcaaag tatgaaaata atataggtgt cagtgattat tataaagttg    64080
tatgcacaaa acattccaat gattgggggcc aatacagaga aaacatctca atatttggaa    64140
ttttgctttt ctgtaaatac tttgatatgt acttacatca tatcaattat aactcctgct    64200 gaaacaaac agtgcacaca aatttggtag ttggaggaga cttttataag ggactaatta    64260
cgaaggttta gaccgggtta ggaaaaacac atggaatagt gcaatacttt aggatggcaa    64320
cagcgagcac cgttataacc actaggccaa aatgaactaa atgaacaggg agattaccat    64380
ttatcagaaa aagagggaga aaggaaggag agatgaccaa gcaagtccta tgtgaagacg    64440
gctgcctgac ttgagctgtg tgatcttttgg actgatacca cctgcctgca ctggcctagc    64500
agggcgagaa tagtcaatat ctggaaaatg gatcacctga ccttactttc ctccctccct    64560
```

```
gtttcctctt tgtggtgttt ccactggcca aactcacagc gtagacaaaa ggagtgcatt   64620
gatgtagcag tggttctaat ccagggccaa ttgtgctccc agggaacatt agtggttatc   64680
acagctcagg ggaggaaggg agaggagtgg agtgctacta tgattcactg agggattttt   64740
ttaaacatct acaatgcaca ggacatcctt ccacaacaaa gtatccagtt aaaaaatgtc   64800
attactgcca aggttgaaaa accgtggtgt agtcagtaca attcatcttc tccaggcaca   64860
gtgcaggagt ggggtggagt gtctgaaggg gaagaaggaa gaaaccagca cccccacaa    64920 aagtaaccaa tgcaaatacc aaataggaaa agacagcact taaaatacaa aagtctcagg  64980
aatatatctg atagtgtttt atggaattta ttaaaattta gcctggagtg agtaatattt   65040
agcaagccag gtttgtcttt agagaaatcc ttgtggggtt tatacaacga tttattaaca  65100
aagggcacac acaatactca tattacagtc agtctggtta tgtaaaacat gggcaagaat  65160
gtaacaggac aatgtgatgt attcacaaag gattttagga ctacacagat aatcctctaa  65220
tgctttcact tacgtactat gaaaggctat agtttgcata gtgatatagc cacgtaagat  65280
agtaaacttg acattcatgc agctatacat gtttgcacac accaggatgc atgccctttc  65340
tacctggttg attttttatt cttttattaa tctctaattt attccccaga acactctcca  65400
taaaaacttt ctcacaactt aaatctttaa tctattgtgt ggatttctga ctcattctcc  65460
aagcttttcc tcttccctcc gcaatgcctt atagtcttat gactatttat ccctttgcct  65520
acatttctag ccagatctct tgcctgatac acactctcat atttctcttt gcacgctaca  65580
cattttattt tagatatcac actactactt tgatttcaac aggtctcagt ttaacttaat  65640
ttttccttca agcaaggagt cccttcatat cagttatcac cattggcacc agaatttttc  65700
ttatgacttc ccatgaccta caatataaac catataaatc actgatgcct ccatagttcc  65760
ctccctctca aatttagcca taagatgatt ttaggatcct tgttttttcc aatctctctt  65820
tcattctctc ccccatctct tccattatga aggtttggat aggacacaac tcatgcctag  65880
attagtgcaa tagatgctga gcctgtgcag cggtagttta gctttctctc ctggttaact  65940
ttaactgcca catatatcac ttcacacgtc attttttcatt caaacgtatt taactggctc  66000
ttcattcata agaagctgga atttgtcgtt tgactgatat tttaaagatt ttatatttttt  66060 tctccatcct cgttctaatg ttgtatcttg tgtcatttgt tcattcataa acttaagact  66120
tagctaacca ctgagcatcc aggaaaattca gtatctatca tgtgaattct ctaatactgg  66180
ttgatccatt gtcaccagag catagcaggc ttctcctgcc tttatgtatg tttgtcatat  66240
agttcatgcc taaaattctt tcttaaatct taaattccta agatacacac ttttgcccaa  66300
gatcacagta atctctgcca taatctctgc tggaatctgt tcactgtgtt gctcctgctg  66360
aacttcttac agatgacttt ttttcttttt ggtttccctg gtatctagta taatttctta  66420
tataggtact caataaatgt ttcctgttga tctctacacc tactctgtac aataccatag  66480
tgactagaca catgttgcta tcaagcattt caaaagtagc tagcctgagt tgagatatag  66540
gggtaaaata cacaacagat ttcaagacat attatgaaaa aaacccataa aatttctcag  66600
taattttttt atagattaca tgtagaaact ataacatttt gaataagttg tatcaaataa  66660
aatataaaat tcacccggtt cttttttaatt tgttaaatgt ggtggctaga aaatttaaaa  66720
ttacataatt ggctcacaga ataattataa tggatggtat tgctttagat caagtttgtc  66780
taacccgtgg cccatgggcc acaagcggcc caggatggtt ttgaatgaga tccaacacaa  66840
atgtgtgaac ttccttaaaa cattatgaat ttttgtttg ttttgttttt gtttttttct   66900
catcagctat catgagtgtt agtgtatttt atgcatggct caagacaatt aattcttctt   66960
```

```
caaatatggc ccagggaagc caaaagactg gacaaccctg ctttagatag taaagcatat    67020
gagtagttaa tgtgtactat aagcagtgtg atctgataga ctatttaatg ttgtttgatg    67080
gtacattatt caagtcgatt attatgtcta cctatgcagt ttaacgacgg taatgagaga    67140
gggcagcttg attacaggtc ttatcttttg actaacttgc taggccacct gagaaggacc    67200
caaattatct gaatgcttaa ctcaactaat ttgtattcac ttgaagaatt tcaaggatgt    67260
ttatatgcca tcaacttgct ttaaatttt tctctcagtg aaaatttttc ttaaaatgag    67320
tatgtggtat tcaaatttat ccttgttttc tatgattatc ttttcatagc actgtggttt    67380
ccaggaacct tttttttttt gagatgcatt ctacatgtaa ctattgcaca gtttgcatgt    67440
agtaaggttc attattcttc tacttttcca acacctggc atgtttactt gaggttggta    67500
caccttgtat cccagatttt gctgttttta acctaaatat tgaatatttt gattaaacat    67560
tatggaaagt ttaaatgggt caagaaaaat agcttttctt cccatgaaga acaatacggc    67620
ataggagtta agagcataga tttaaagtca gaaaacctgt gctgcctact tgtgcaaagt    67680
cacttacatg ctgtacttct gtttcttcat ctgtaagttc taccctagg tatttactta    67740
agattaatgg aagcatatgt tcatacaatg acttgtacag aattattcac gatagcatta    67800
ctcttaatag ctctaactgg taacaacaca ataatcaatc aacaattgtg ctgtattcat    67860
acagcagaat actacttagc aacaaaaatg gaatggacta ctgataacct caacaacatg    67920
gatgaatctc aaaactatca tgctgtgtga tgccaggcac aaatcagtac atactataat    67980
tccagaaaag acaaatgtca tccatagtaa caacaagatc catgcttgct ggaggtagag    68040
gcatcagttc agtcattcag gaagctgatt ccaagatggt gttagaatta caaccatcca    68100
caagagattt attgcaggca atagctatga aaggtagaaa gagaacagga gaaaaaccag    68160
gcaaggaaaa accacaatgt agttgtgata tcacttcaaa gggaggcaga aggaaggaga    68220
attgggtagg aatagccaca gattacagtg cagttacaag aaagtcttgg cttccaacaa    68280
aggttacttg ttgaggagtc atgcattagg cagacatgtc tgggctgtag tttccttgct    68340
gctcccagtc attggctgga ggccagtctg ggttcctgtg ctgtggtgga tcccattgct    68400
gctgcagcag gaggccaata gcactcctgg cagctaattg gagagaaaag atccaagagg    68460
tgtaccttca tggctacccc catggggctg gggtggaggt ggaggagaag gagaaggaat    68520
taactagaaa aaggcacaaa ggaaaattgg ggaaaataat gaagatatat gatttctcaa    68580
ttgtggtggt cgttacatgg gtttattaat gcatcaaaac tcaagaaatg tacatttaaa    68640
atgagtgcat atgattgtaa gtgaattata cctcaatata gttaatttt taaaaatcat    68700
agatttcttt atatttaatg catgaacata aacctaagac actcctccac tccaaaactt    68760
aattccttg tgatcagcag agcagaaggt actttgtgat atataggtag agaagatgaa    68820
gtcttgtgac atttaacaag ggacaggaaa atggaccttg tcctaagtta ccaaactgca    68880
aaaatatcac ctacaaaggc tattcataac atacattttc aaggggtta caatatttgc    68940
ctactataaa attttggatc tgtaaagggg ttaaattatt tgtgcagggg aataaacatc    69000
aaagaaacat taagaggtcc agagaagtaa aataggaagg gtcttttggc tagaggagat    69060
atttaacttt cagaacatgt ggaattaagt tgtattgatt atgatctgat cttcttcccc    69120
ctaaatttga tcctcttcct gtaatctatt gtttccatca tcttcaactc ttcccttttcc    69180
ctctcccttg tccctcagtt ctagtcaatc acaaagtcct acagtttcac tttctgtata    69240
ccttatttct ggaattcatc tctagacttc aaaatatata tatatatatt ttttttttgag    69300
atggagtctc gctctgttgc ccaggctgga gtgccgtggt gcaatctcag ctcacagcag    69360
```

```
cctctgccac ccaggttcaa gcgattctcc tagttcagcc tcctgagtag ctgggattac    69420
aggcatctgc caccacgcct ggttaatttt tgtattttca gtagagatgg ggtttcgcca    69480
tgttggccag gctgatctcg aactcctgac ctcaggtgat ccacccgcgt cagcctccca    69540
aagtgctgga attacaggtg tgagccactg cttccagccc aaaatatctt aagtagataa    69600
ttgcacgact aatctctgct tttctctccc agcagccttc caaattcatg tctcacagct    69660
gacagagttg ttcctgcctt cagattcatg acctggctct gtgttccagc tcaggctttc    69720
tctctcatat cacctcttgc ctctctgttg cccccatatt ttcccctctg gttggttggt    69780
gctcctttgg aaccctctgc atatcttttc aagaatatta tgacttatta tgcctataaa    69840
ctttgtttaa ttatttattt ctaaaatttg acagggaact ttccgaaggc aggtattgtg    69900
tctttctcat ttaaaagcaa attctcgcct ggcatggtgg ctcatgcctg taatcccaca    69960
ctttgggagg ctaaggtgga cagatcactt gagcctagga gttcatgacc agcctgggca    70020
acacagttag accaaaaaaa aaatatatac gaaaattagc ctggcatggt ggcacacccc    70080
cgtagtctca gctagtctgg tagctgaggt gagaggatca cttgagcctg gatggttgag    70140
gttgcagtga gctgtgattg tatcactgca ctccagcctg ggcaaaaaag taagatcctg    70200
tctcaaaaaa aaaaaaaaa aaaattagtg aatcctcagt gtttaaaaag tccataaaca    70260
tactaaacat agaagacctc caaatgaaat taatcaatta ttatttagtg ggttgcttct    70320
cttttgtttt aatatagttt taacaaagag taaaagttat gatctttta tatgtaaaat    70380 aaataatgcc gggtttgaca taaattttag gaaaactaga gacgctactt cctaaaaatt    70440
ttctttctat aatcttccta aatatttttc cataaagtac aaaataatag aaaaaaatta    70500
agagattgag tatcctttca ggaagtgata tgacaaatag ggttcgagaa ctatttgaat    70560
tctcaccact tttcataagg gcagatctca agttaaattt ttctattcga atttaaatga    70620
ctttcactgg aataccatta cagaaaagct tctgtgttta gatggcaata tggagtttct    70680
tttcttggaa tattaattga aggagaagtc ttaattttt aagtctatat ctccgtatat    70740
atttgaacct attttatatg ttagtccttc tctttagtaa ccttcatcca cagtgaacaa    70800
gatttaccct tacctttaag cagtagcggc tactttatgt gaagtgaaca gctgcttttt    70860
ttatctgcat ctagacatca agtagtccag agtccttcct aacaccctag caatagaagt    70920
aagaatattt tgaccattcc atgacttgat gatacttcta gtaataatac tgtattatta    70980
aaaacaaaca aacctttgtg cagtggtaat tgaagcagtt ccttgggaac atgtattaag    71040 tacttttag cagttaagtc cactctctgt aggttaagga atatttaaat aaaataatgt    71100
ggcaaatgag ttcaagatga taaatgcgat gagaactaaa acagctttaa ttttatgtgg    71160
gaaataaata gaggaaaagt acattacagg gctcctggac ttatttcttt cttcaaagtg    71220
tttctcctag cgaatattat tactattttt tctcttaagt aaaaaataca caagtatga    71280 atctacacag gataataata ttgaagttaa ggatgatgtc tcctccttca ctctccaaaa    71340
tactatttac ttggcttcat ggaaatctct ctcactccaa ttccaccgtg tcaactgagg    71400
tcttctgttc tttctctccc tatagcatat tcctgttaca taaatcctaa actgtgtcgt    71460
gttagtcaca cactgtaacc tctagataag cgcctgtcca gaggttctca atcagagcct    71520
tgcaaatatg tattaaatca atgggtcatc ttcagtgtct cagtgggccc ttggatatgt    71580
tttgcagact gctgtgagta tgtagggatg tccagtatcg agggaagtgt ggatggcttt    71640
cattggttct tatagggctg aagaacacat agagcagtaa gcacttctac tgtagggaga    71700
gatcgagctt ctcccatccc cactgctggc accaccacca ccctacaccc cattttgagt    71760
```

```
tctgaaagtg aatccttgag aaagaacaca caaaacaacc atcataatag tgggcacagc    71820
tgtgggtggt agaataacat tcccaagctt cttttcctac acatgattaa tattaattca    71880
gcaaacattt attcagctcc tacttttaaa caggcactat tctaggtact aaagacatag    71940
aggcaaagca tacaagactc tgcctttgtg aaacaattaa gaaataagta aaagaaaag     72000
aaacagaaaa ggcaatttgg atagtgtcag gtgctataaa gaaaacaaaa tgccattta     72060
ataaataata ataatacaat gttttcatac tatgtgctag acactatgct agtaggtatt    72120
tatagacata acctcaatta atcctcaaaa tggcatgttg atatcaatac cccaagttta    72180
catatgagac ttaagatgtc tgagtatatt cccccaggta acaattaata tgcacaataa    72240
aacttttgc tcattcattt attaacctat gttgattgag tacctatttt gtgtcaggca     72300
tcatttaag gcacctggat atagttatga acaaacaaat aaaaatctct gccctcaaat     72360
aattaatatc tcacagaggt taggcaaaat ataatcagaa aataagtata acgtatagga    72420
tgccagatca tgaaagaagc tatgaatggc atcaagaagc tggaaaaggc aaggagacag    72480
attttctcct agagtctcca aaacagaaca cagtcctgcc gacaccttaa ctttaggcta    72540
gtgagacccc tattggactt cagacttaca atcccacaat gtaataaatt tgtggtaatt    72600
cagtagggga acaatagaaa actaatacga tatcaaaaca aattatatca tagaacaaga    72660
aaatgtaatt gtgacaaata ataccctacaa aaatgttgta aatgctaggc aaataatgtg    72720
tttaaagcac ttaggccaat gttcaacgta aagtaattca tgctataata tcatcatcat    72780
cattaccaat atttaggggc tctaacaaat gatgtacgtg taagcagatg taagaaaatt    72840
tccttgctga agaggaggta ttaatagagt atataacaat agataacaaa ttccaaataa    72900
aggcaaacta aatgttttat tggattaaat ttaattttaa aaactacaag aggccgggcg    72960
cggtggctca cgcctgtaat cccagcactt tggaaggctg aggtgggtgg atcacgaggt    73020
caggagatcg agaccatcct ggccaacatg gtgaaacgct gtctctacta aaaatacaaa    73080
aattagctgg gcctggtggc gcgtgcctgt aatctcagct atttgggagg ctgaggcaag    73140
agaatcactt gaacaaccaa ggagtcggag gttgcagtga gccaagattg tgccactgca    73200
ctccagcctg gcaacagagt gagatcccgt ctcaacaaca acaacaacaa caacaacaac    73260
aacaacaaaa ctgtgagatc catggtgggc ttttaagagg aaaatgcaag ctaaggtttg    73320
tttagactct gagtactgca tgtgtaaaaa taaaggcatg atgaaagat caagagatta     73380
gagtgatact ttttatctac tagtgtcaga gtcatgacca ggggattggc tatgagaata    73440
cataagctgt gccaggagta atccaaggag attgtttcaa tttggaagag tgtccacaga    73500
atgattctca tactagacgt tgggctattg taaagaaagt tggtaggtac tccatcgcta    73560
ggatcatatc agggagaaat tgaacaggat ggccctaatg accctgttgt accccctagct   73620
tatggattag gcaagtcact tctactcgta taccctgttt ccccatttgt aaataagagg    73680
atgtgttact ctaaggatct ctaagattct ttgcagttgt taaattgcat agctctccac    73740
tgattccatg gtggaaattt gctattctat tacaaatatt ctaaatgtat gagatatcag    73800
acatactcat ttaaaaaaca aaatacaaaa aataagtatt ctacaaataa acacagataa    73860
tgtttaaatt ctatatgtct ttgtttctct tcagaagcat ccaaaataca aaccatctaa    73920
gaggcaagaa aatgtcgtga tgttcctagt gcaagttaaa aagatttgct ttcctcaagt    73980
cggaaagccc ttctcatttt tgaggttttt ttcttctttt ttttttcaag tgaaagcatt    74040
ttggaggagt caatatccat cttttaaaggt agccaggtca catgtataca tatgtaacta    74100
acctgcacaa tgtgcacatg taccctaaaa cttaaagtat aatttaaaaa aaaaagaatt    74160
```

```
taaataaaaa aagaaaatca gagagaaaaa aaaaaaagat gcatgtgcac cctgatacta    74220
ccatccatag tgatacggtt tggctttgtg tccccaccca aatctcatct tgaattgtaa    74280
cccccatgtg ttgagggagg gaccttatgg gaggtgattg gatcatgggg gtagtttctc    74340
catgctgttc tcatgatagt gaatgagttc tcataagatc taatggttta aaatcatggc    74400
acttcctttt gctctctctt tctcctgcca tgtgaggtgt gccttgcttc cccttcccct    74460
tctgctatga ttgtaagttt cctgaggcct cctcagctat gcagaactgt gagtcaatta    74520
aacttctttc tttataaaaa aaaaaaaaa aaaaaaagg tagccaggta aaaattactt     74580
gtttccagga cattttcacc tgaaagaagc attgtcatat aacatagaag caagaaatcc    74640
agtagtgggg gttatttaaa aatagctgga aaatttcaat cagcatgagt ttgaagcaac    74700
aatttatcat caccttttat ggtgggtggg gttaagaaca tttcagcggg caaagtggtg    74760
gtgatgggga agagacacca ggggaggtga ttcccattgc attgctttgt aaacagaggc    74820
acaggttctt cattttgtc acacaaaatc acagctatgc agaatttatt aatttattct     74880
tctgagacaa gaaaaagcc accaaggaa accaacagct tgctcctctc acactggggg     74940
aaccgtatga gagacttatc tatccctgac tttaattttg acctgaggag agctcctctt    75000
aaggaaaaca aattaattca atgactatac tacttaatca ttgacccttta tttaataaga   75060
gattttttcca taggatatgc tgagctgtct cacttacatc agttgtgtct cctgaggtgg   75120
gtgacaggag accacaaata ttgcatagca cacaaatcgt taatagcagc tgtataccaa    75180
accattacct aaatatgtag agtacaattc attctcacta atgtcagaga gcatgctata   75240
aaatggtgaa tccggacagc tgaagatact gaataataac ctctatttg aacaagttta    75300
cagtgttcca atcagtaatt aaattgatac ctgatgaata tatgtgtgtg tatgtattca   75360
tagcagagat ggttttcctg agataaggat tttgttattc ggataggctg ctgctggaat   75420
tgtccttcta cccttgtttc tttgtcctta gtcatcactc ataccctcttt ccactcttct  75480
gccatcactt ttgtcaccaa agtcatggtc cttttccccgc cgattgctgc tgcaggtcta  75540
gggcaccaag acttaggcag cactcaccat gtgccaagaa ctggaccaca ggtaccatcc   75600
agcattgctc atggagactc tgtccctttc tgtaggacac cctcctttta gctagcaacc   75660
cctccaccac ctagagcctc tggacctctc atttaatat taagaactag gaaaacttac    75720
cgctgagaat aactagtaca actagaactg gtagagaaat ctgggtctct tgggaatgga   75780
ttttttaggct ttattgatta gaggtgtatt aataatgcag tgttatagtt tcatgacata  75840
acgaataaaa aagttcattt tggacttgcc tttcagctcc ctaggagcta aaagacgtat   75900
ttaatgtaac ttgtgtggtg gaaataagtt ctttttcag gcaaaagatg tgcaaaccca    75960
tctggggaag aaacattaaa aactaaggag acagtgtcct agataactat gttctttcc    76020
tgttttagtc taaaataatg attagttttc ttatatatct tcatttgtct tggttccttt   76080
tagcccaatt taataatatt attgcagata ttgatgaaaa cctttacctt cctcttaatt   76140
catcaaagta cttgataaaa tttatacata gtacattaat tgggaggttt ttatgagatt   76200
aattaatata atgaactgat gttgaaatta tttaaaacct gaattattat tgtattaagt   76260
aggacactta atacagttaa tcagttctgt ctttattcat ttgtgagaat ttttggcaag   76320
ctattgtgaa tattcaggga agggaatgta ttttagcag gaatcttata cctcctacat    76380
agaaatgaag catttactga aacatccatg aaacaaaatg tttctgaatg tgtactatac   76440
acttgttata agcccctttt cttctgtagc tatattttgg agaaaatct ttgctttgac    76500
aaaaaaaatt atgttgactt acacatatat tttataacta agcagtgttt ggtttgtgat   76560
```

```
aaaggataca aaaatataaa aatgttcagc acacgtaagt aaggccttgt tgacaatgtg   76620
agttatgcta ctggatactc aaaaggaaca ttcagtgttc tcaggtggtc tctagactgt   76680
ctcaagccta ggaagatatt ttataagcaa aggaataaga gaaggaagat tcagatttaa   76740
tccaagtgaa gaattcagtt ttgtgtgcct tatcctgtta ttttgagagg cagccaaaag   76800
atgctggtca gcaaggagaa ttgtaagttg ggcagccaac tctgatttct caacctctta   76860
gctgttttct taaactcaga attttttaatg aatttaaatg tccatatcag gtagactttg   76920
gggatgcttt taccagtgat tttcagaatg ttactttctg gcatttcttt tcacgtagca   76980
ttatattaaa aatgaattca ttcatccacc ttcccttgtc cttactaatt ttccctccta   77040
ctcccttccc ccttgttctt gccatgggga catgcaaaca ctggtggttg atgtctgagc   77100
aaggctgctg acaggggggag gaaggagatg tcaagcagag gtcaatggca gtgtgcccag   77160
cagcctagga agtaggaggg aaaagagaga gagacagaga tggtggatga aagagaaagc   77220
caggatgatt atggtggtta tgatacttgt catgctgaac acccaattga gcacccaata   77280
agcacataat aatttaatca tcctctggct tggatggcag tgttctatca gtgttgactt   77340
cctggttgtg acagttttac agtgttagtg tagaagagaa tccttgcttt agagaggtac   77400
ttactgaagt acttagggtt aatgcaccat tgtgctggaa aaagatacgc acacacacgc   77460
acacacacac acacacacac tcacacacac gcacaaatac atccatgtgt taggcagagg   77520
gagcaaatga ggtaaaatgt taataattag gaattctggg tgaagtggat agagggactc   77580
tttgactgtt cttgaaactt ctctatacat ttgatctgtt tcaaattctt cagaaaatca   77640
aactacaaaa acttaattca tttagtgaac atctactgaa catctgtata ttaaatagtg   77700
ttaaatgaat gtcaattaaa atgctcaaac acagtagagg ttgattctca ttcacataag   77760
tccatggtag gtgttttttgg caggtgggtg agtttctccc ttagggagat tgaggaaccc   77820
agactcctcc caagttgcag ccccaccgtc ttctgagggg atgcatccat acccacttcg   77880
aagtagcata cattattttcc tttctcattc ctttggatac cagccacaat ttattcaagg   77940
tagacagaaa attgtagtat atagccatat gccctgacaa agaagggaga acagattttg   78000
gtggacaact agcaaactct gatacaatct gttattaagc actgtgtgtg gatagatgct   78060
aactagaagg agattatctt cccttcagca aatataaact gaatgccgtt tatttggttg   78120
aaactaagct agatcatggg agtatagaaa ttttataaga agacatagtc acttctgtca   78180
gtgagctcaa gaagaattag tatgcggaat gtaatcatac ctacaggggg cttgtgccac   78240
ttaagtaaaa tgaaacatta ttttgagtac aatttagcaa taaatgtact acgagatcat   78300
taaaaatcat gtttgaatgt tattgtgtca aggatgggaa aaagactttt gggttgtaga   78360
cttgataatt atagttaaaa acagttttta ttccttgttta gtcttatttt ttatgtttaa   78420
acatatttat acttgctaac atttatactt gctaagtaaa gactgttttt acaaccatga   78480
caagaacaaa acatattagt aatgcaaatg ccacatttcc tacaatcaac taatcacact   78540
aacatatttg catggaagaa tcactgggat tgatctggcc acgtgtgtag tcatgcccaa   78600
aatgtgaagt ccatctgttt tgcaatttttt tttaaccact gttatccaaa tgctccttgg   78660 attttttttta ttagtggata tattttggag gtcagacacc ctcttggcta gatcatcacc   78720
tttataacaa atatatatac tattctcatg gaaatatatt tagacgttgc cctactggga   78780 attttttttca agtaattaat gtacagcttg tgcaacagct tgatcttggc ttcatggaaa   78840
taattcactc ttagcagcat ctaatgccac aaagcattta tggatgtcag ctcagaactt   78900
acttttattt atctctgagt tactttttttt tttttttttt ttttgagaca gagtctcact   78960
```

```
ctgtctttgg cttgtcccta acctcttaac agacttaata ttaagctcca tttcactcag   79020
tcgttctgtt gtcatataaa tgagacattc tacaagcata gttttagtt tctgccagag    79080
catcatacaa cattgtgagc tatgatgaag ataaagacct agagaagata tttaatatga   79140
agttcattat ctaatatttg gtatgtgtgg caaaatagca atctactgct tggttctgct   79200
gtaatctatt tacccaccca tcccatcttt cttcaattt aaaaggataa tgattttagt    79260
cacgattata cataaaccca ttaccatagg caataaacaa tggggcaaac cattggtccc   79320
atagttggag tgtggtctga agtgtgtttt ggtggagaga gatctatgtc tggagatagc   79380
taacatggat ttggatccca gatctgctcc tacctgttgc tgtgcctgtg accaaatcat   79440
gtgatctctc tggtttcagt ttacttgtga ataaagtaaa taccttcatc aacacctgtt   79500
tttgaataca atgttttct gtaattttg cttcttataa tgttataatg atcatcctta     79560
catctaaatc ttggtttaca ttttcatcaa ttcttttgga aagattggag aagtaaattt   79620
tggagatgta tgtcggctat taaaaatgtt taatttttta attaaaaatt aaaacgttga   79680
aaaatcctga tgcaaaataa atgcattatg cttagtgaac tcttctcatt tcgaagttta   79740
ttcaccttct tgtttttgca gtttcctga aaaatgcata taaagtcact aagttagcag     79800
aactttataa aattatataa ctatatataa tcttttgata tcagtgaagc cagctgatcc   79860
tatagaaata atgtaggaat tataatcact agcacataat ttaagagtcc tgtggtctta   79920
ttcatgttat ttaccctctc tgaatcttac atatagtaag agggttatta tacataatat   79980
gtgtacatgt atacaggtaa gtaagtatat atgcttatgt gtaaaagcag agttattgtg   80040
agagtcaaat ggaaatgtga agtactttg tagttttta ttactattat taattttaa     80100
taaaatggta acattcattt aataatcatt agttttaact tcagattgta ctggatttcc   80160
tctagtattt cttaagatta gtgaataaag tatttctcct aataaatata ttgactactg   80220
tctttcgatc aaacatatta ggtatatttt tacagtagca tcaggcagtg aaaatttgaa   80280
gctctttata gaggactgat ttatgatgaa aaggaataac atgaacaaat ggaattatat   80340
gaagcttccc cagaaatatc taagaggggc caattttaag aaatatctga cttcttttc    80400
atggacattt caaaataaac ctaactcata tggtacagtt tttaagaggg aaaagaaaaa   80460
accatctgag aatctctgga attctgccga aagtatcact tggcatttta ttctaccttc   80520
tggatgcagt tgattgacag tagtgttatg atgccagggg tatagtgact agaaaaagaa   80580
aaccagggaa ttcagtgttc ttgctcatga agaacagctt ggttctttaa aaacaatgag   80640
attttgccac cccatctcac aaacctatga tttgtgagaa caatcccttt tgtgttgcaa   80700
gacttttaca tttctcttcc cacactatat tagaagaata aacattgctt cataagtacc   80760
gattgatagt ctcatttcat attttaaaa tagagttact ttaaggttaa atttttcatg    80820
tagattaaaa tgactaagta accattcaca tatttcaaat aaaatatatt tttactacaa   80880
aaggaaaata actagattct taagtgttat agtcaagtgt aattgagtaa tatgaattct   80940
aaatgaattt ctaagatctg ctcagctttc actactttag gaaggaacaa cttaagaaaa   81000
atttttaataa agatatctct tcacacacat ggcagtgttg tacttagaga acatgaccca  81060
aaatttttta tgactgcata ttgaattcct gatactcttg ggaagctcca aaagcaccag   81120
tggagtttcc agatgtaact gtggctgcag acccgccagt cccggtgttg gaagggatca   81180
ttataggctc ttgtgtgcag actcatcttc agacccagag gaattaaata acttgcccaa   81240
agtcgcacaa ctttctcatg gtaggttggg cactagaata aatattgctt tttcttaaga   81300
gttttagcct ccgtattatg aaatcttcta tgttctgctg atgatatctc ccttcttcat   81360
```

```
ctgttttcta tttttaagca atggaaatac aaacttgcaa ctccccattt ccaacacaac    81420
ttagaaaaaa caatatttaa agaaaaaatt acaggcatct catctccttt acctgacaga    81480
tgcttgatag taatggcctc tagataggga tgacatctaa tataaatgtg tcctttcaag    81540
tcaagctttc tctgttcatt agtagaaata ttgtatatca agtgtgcaaa aattttcttc    81600
aacagggagc tttgtttccc tccttttatt ataacaatct gagctttgtg gtcccagggt    81660
ctcctagtgc ctgtctttag gtctgtttat tcacatgaag aaagcatgtc atatagtatt    81720
atctaagact caggctgctt atgcatgatg acagaagggt tcccaggcac aaacattcat    81780
ccatgcattc atccatccac ctattcatcc attgatttgg ctgataatta ttgactactg    81840
ttgagttgcc ctcagattta gtttctgtcc ttctgccatg gggaaatatg gggttaagcc    81900
acaacatact cttctcttct ttttctgcac cttcttagta tatttagttc cattttgtct    81960
agccctgcct ctgacttctt tgttgtactt caggtttttt atcattgaaa gttatttctg    82020
gatcatagat cattctcttg gtcactttgc ttgttcactt ataaaattaa ttcagaaaaa    82080
atgacccaca gtaattactg taaatcacag accataaact ataatactgt atattgtatt    82140
atagtacaga aatatttata ctttaaaatg ttttaaatat agatattata aaagatatg     82200 tctcatataa gtaatataaa tactttttta ttacctcttc tctccctatt ctccaggcca    82260
gtgttttaaa aatccatctt tatatgtcca tcctggaaaa aactcatgat cataaatgag    82320
tttctcaata gagtttataa gcccacagtt gaaacacaat tgtcttagca tccatttagt    82380
tgtcatactt ttaagattta atggcaaata ttatgttttg tttcttcaaa agaaatattt    82440
taaaatttta gtaaaggcag ttagagaagg tagagataat ggactgttta atcctactt     82500 tcatcccaca agtgaacaaa aaatgataa aacatttttc ccaaaatgta gctttaacta    82560
tacttaaatt tggactaaaa tgggagatat cttttctact attgaaaagc cgtgtctgta    82620
gattaatgct aaaatcgggt gtaaaagcaa aatttgtttg gcttgattgc caatggccca    82680
ttcatttggc tacagaaaca atagcacata gcaacagata atgatgtgag atcacctagc    82740
tcaagtaaga gtgtctgatc cgtcaaaaat atatacatca agattcaaaa gaatgtgtg     82800 ttttctcaag tcatctctgt aaaaatacat taaatagagg aatagaagtt tgactttgaa    82860
aatacattgc agacccaatc cgtctttcct attttctggt gaaaagtatc aaatatgtgg    82920
aacctggaac tgctattctc cttcttaaaa atctttctta atattctatt gataactggt    82980
gcaagcctaa cttttttgtct tacccgattc ttctcacacc aaagtgatag gaccttcagg    83040
tagcctttgg atagaagata aataataatt taactattga tggaagttag tattagaatt    83100
agacttggaa gtctatggaa taaaatgatt ctacaacaat ttgtacttca gacattagta    83160
taacaaaaca tgtttgcccg tgcatgcgga acaaccaat ttcatgtgga tgcttatatt     83220
cacaaaggag taaccacctg gggtttccca ctgttgctcc agagaaaact agcagcagga    83280
gaacttctct gaaggtatca agacatcttt aaaaaacact tgttaagtgt tggttcagct    83340
aaagcaggga gttttcagtt agtaatggct tttaaaaatt aaaacaagtt tagcatgtag    83400
gtcattaacc ttgaatcact gtcatgatta ttattaacca tctgttctca aatcgaaaga    83460 tattttctt ttctagatca catttattct cacattgctc aatttcacta tatatcaaga    83520
catgaaaact gtaaaatca caccttctac attattattt ttattgaaaa attcctaatg    83580
aaacagtgcg ctctgggata gagaaaggaa ctaactgaca ttttgcttct taacttgttt    83640
ttatgcaagt tctaagtggt ttctggccat gtacataaaa gacaaatatc tggaaaaaaa    83700
actagcagaa gtcagttatt tggctctatc tactttgaga attatgttat ataaatgtta    83760
```

```
ggaaattttt tgtaatattc ttatttagaa atgaaatata aaagttttta aaatatcta    83820
aggacagtat acagtcctaa agtaaagctg ttaggtaaat gctacacaat cctcttatta    83880
cagagtcact tacctgagaa tataagaaga gggcctcttg tttaagagta aatgtgagct    83940
gcaatcagga ttctgcactc atttggacac ttagttttgt ttttccatga ctggtgttgc    84000
ctgttactga gacacctacc tgtcatgtga ccacagctta tgttacaatg tgtctagtca    84060
gacttagaga tgtgtgaaag agcagtacct agacgggaaa ctatgggtct ataaaggttt    84120
tgccttcttg ggcggagttc aaactaggaa gccacaaaac ttccagttgc attttcacag    84180
attaatgaaa tatattttac acttttcctg aaagatattt tatttgtgca aaccttgtta    84240
caaagtacag ccagttgatt aatcgatgaa gtgatttgta gtggattctt atattttgtg    84300
taagggtata tgtgaggccc tatatatgag gctttctata taatgaagta taattcagtt    84360
cagcatttca attcagcaat cacttattgg gcctctactc agttgccttc agggctttat    84420
aatttaattg ataaagggag gttaattaat taattataac aacagatcgc ttaatagtgt    84480
aactactaat ttaattaatg acaaataaca atacattaaa agaaatgcat taataaaaat    84540
aatatattgg tgttatagac aataattttc tgattaactt tattattatt atttcaatag    84600
cttttgggga gcaggtggtt tttggttata tggagaagtt gtttaggtat gatttctgag    84660
attttggtac actcataacc tgagcagcat acactgcacc caatgtgtag tctttcattc    84720
ctcaccttcc tcccacccct cccctcaagt ctccagagtc cattatatca ttcttatgcc    84780
tttgcatcct ttagtttagg tggcagttat aaatgagaac atgtaatgtt tggttttcca    84840
ctcctgagtt acttcactta gaataatggt ctccaactct atctacgtag ctacaaatgc    84900
cattattttg ttccttttta tggctgagta gtattccata gcatccacac acaccccct    84960
atgctttata tatatatgta aatatatcac attttcttta tccactcatt ggttgatggg    85020
tatttaggct ggttccatat ttttgcaatt gtgaattgtg cagctataaa catgcatgtg    85080
caagtgtctt tttcatataa tgacttcttt tcctctgggt agatacctag gagtgggatc    85140
gctggaacaa atgattgttc tactttagt tcttttaagga atctccataa cttttccatg     85200
gtggttgtac tagtttacat tcctaccagc agtgtaaaaa aatgttccct ttttaccact    85260
tccatgccaa cgtttatttt tttattttt aattatggca attcttgcag gagtaaggtg     85320
gtatcacatt gtggttttga tttgcatttc cctggtcatt aaagatgttg agcatttttt    85380
catatgtttg ttggctgttt gtctatcttc ttttgagaat tgtctattca tgtccttagc    85440
ccactttttg ataggattat ttgttttttc ttactgattt gtttgagttc cttgtagatt    85500
ctggatatta gtcctttgtc agatggatag tttgcagata ttttctccca tctgtgggtt    85560
gtctgtttac tctgatgatt attctttttg ctgtgcagaa gctttatagt tttaggtccc    85620
atctatttat cttttttgtt gttgttgcat ttgcttttgg tttcttggtc atgaactctt    85680
tgcttaagcc agtgtctaga agagttttac caatgttatc ttctataatt tttaaggttt    85740
tgggtcttag atttaagtct ttgatccatc ttgagtggat ttttgtataa gttgagagat    85800
gaggatccag cttcattctt ctacatgtgg cttgccaatt atcccaacac catttgttga    85860
ataggatgtc cttttcccac cttatgtttt tgtttgcttt gttgaagatc agttggctgt    85920
aagtatttag ctttatttct ggattttcta ttctgctcca ttgatctaca tgtctatttt    85980
tatagtagta ccatgctgtt ttcctaacta tagtcttgta gtatagtttg aagttgggta    86040
atctagtgcc tccagatttg ttattttttg cttagtcttg ctttggctgt atgggctgtt    86100
gttttgttcc atgtgaattt taagattttt tttcttgttc tttgaagaat gatggtggca    86160
```

```
ttttgatggg agtcgcattg aatttataga ttgttttttgg cagtgtgctc attttcacaa  86220
tattgattct gccaatccat gaataaggga tgtgttttca ttagtttctg ttgtctgtga  86280
tttctttcag caatattttg tagttttcct gtagagatct tccacctctt tggttaggta  86340
tattcctaag cattttttt ttttgcagct gttgtaaaaa ggctcaggtt cttaatttga  86400
ttctcagttt tgttgctgtt ggtgtatagc actggtactg atttgtgtac attgattttg  86460
tatctggaaa ctttactgaa ttaacttatc agatctagga gcttttttgga tgagtcttta  86520
ggttttctag gtatacaaac atatcatcgg caaagagcaa cagtttgact tcctctttag  86580
cagtttggat gctctttatt tctttctctt gtctgattgc tctggctagg atttccagta  86640
ctatgttgaa tagaagtggt gaaagcaggc attcttgtct tattccagtt ctcggggaa   86700
atgctttcaa attttccccc gttcaatata atgttggctg tgggtttgtc ataagtggct  86760
tttattacct taaggtgtgt atcttatatg ccagttttgc tgagggtttt aatcataaag  86820
caatactgaa ttttgtcaaa tgcttttttct gcatctattg agtttatcat atgatttttg  86880
ttttttactcc tgcttatatg gtgtatcaca tttattgact tgcatatgtt aaagcaaccc  86940
tgcatccccg gtatgaaacc cacctgatca tggtggatta tcttttgat atgctgctgg   87000
attcatttag ctagtatttt attgaggatt tttacatctc tgttcatcag ggatattggt  87060
ctgtagtttt cttttttttgt tatgtccttt tctggttttg atattagggt aatactggct  87120
tcatagaatg atttagggag gattccctct gtctctatct tttggaacag tttcaataga  87180
atttgtacca attttctttt gaatttctga tagcattcac ctgtgaatcc atctggtcct  87240
agactttttt tgtttcctga cattttttct attattgttt cactctcact atgcattatt  87300
ggtctgttaa taatttctat ttcttcctgt tttaatctag gaggtttgta tatatgcagg  87360
aatttgtcca tctcttcttg gttttctagt ttgtgtacgt aaatgtgttc acagtagtct  87420
tgaataatct ttttttattc tgtggtatca gttgtagtat ctcccatttc atttctaatt  87480
gagcttgttt agatctttt tcttgttttc ttggttaatc ttgccaatgg tctattgatt   87540
ttgtttatct tttcaaagaa gcaggttttt gtttcattta tcttttgtat tgtattttgt  87600
gtttcaattt tatttattta tttatttatt tttatttta ttttttgaga tggagtctca   87660
ctcttgttac ccaggctgga atgcaacagt atgatcttgg ctcactgcaa catctgcctt  87720
ccaggttcaa gtgattctct tgcctcagct gcccgagtag ctgggactac aggtgcctgc  87780
caccacacct ggctaatttt tgtatttta gtagagacgg ggtttcacca tgttggccag   87840
gcaggtctca aactcctgac ttatggtgat ccgcctgcct tggcctccca aagtgctgcg  87900
attacaggtg tgagccacca cactaagact caattttatt tatttctatt ctgatctttg  87960
ttattttcttt tcttctgctg ggtttgggtt tgctttgtct tgttttttcca gttcctagag  88020
gtgtaagctc agattgtcta tttgtgctct ttcagacttt ttgatgtaga tatttaatgc  88080
tatgaacttt gctcttaaca tggcttttgc tgtatcccag aggttgtgat aggttttgtc  88140
attattattg ttgaattcaa atattttaa aatttttcatc tttcttgatt tcattgttga  88200
cccaaagatc attcaggagc agattattcg atttccatgt atttgtatag ttttgagggt  88260
ttctttggga gttaattttt aatttttattc cactgtggtc tgagagaata cttgatataa  88320
ttttgatttt cttaaattta ttgagacttg ttcatatggt ctgtcttgga gaatattcca  88380
tgtgttgatg aaaaggatgt agttgttggg taggattttt tgtaaatatc tgttaagtcc  88440
atttgttcta gggtatagtt taagtccatg tttcttttgtt gactttctgt cttgatgacc  88500
tgtctagtgc tgtcagtgga gtactgaagt cccccactat tattgtgttg ctgtctatct  88560
```

```
catgtcttag gtctagtagt gattgcttta taaatttggg agcccaagtg ttagatgcat    88620
atacacttaa gattgtaaat ttttcctgtt gaactaatta ttttatcatt atataatgtc    88680
tctctttgtc ttttttaatt gttgttgctt taaaatcttt tttgtctgat ataagaattg    88740
ctattctttc tcactttgag tttccatttg catggaatat cttttccac cccctttacct    88800
taagtttatg tgagtcctta cgtgttaggt gagtctcttg aagacagcag atacttggtt    88860
gatggatttt tatccattct gccattctgt atcttttaag tggagcattt aggccattta    88920
cattcaacat tagtattgag gtatgaggta ctgttctatt catcatgata gttgttgcct    88980
caataccttc ttgttgttgc tgttgttaat tgtgttatta ttttatgggt cctgttaaat    89040
ttatgcttta aggaggttct attttgatgt attcaagtta ctgtttcaag atttagagct    89100
ccttttagca tttctcagtg ctggcttggt agtggcaaat tcagcatttg tttgtctgaa    89160
aaagacttta tctctctttc atttatgaag cttagtttca ctggatacaa aattcttggc    89220
tgataattat tttgtttaag aggctaaata tagggcccaa tctcttctgg ctagcagggt    89280
ttatgctgag aaatctgcta ttaatctgct atgttttctt ttataggata cctgatgctt    89340
ttgcctcaca gctcttaaga ttctttcctt catcttgact ttagacaacc tgatggctgt    89400
gtgcccaggt ggtaatcttt ttgcattgaa tttcccaggt gttctttgtg cttcttatat    89460
ttggatatct agatctctag caagactagg aagttttttct tgattattcc ctcaaataag    89520
tccttaatga ccccactata taacatgaaa tatctgttat tggtactgag gtgctggcca    89580
caaacaattc tgtgtgtcct gaaaactctt cagaatattc gtcatcttta gcacttgtta    89640
tcttagtgtt tgggcttggc ttagagtgat acatctcata acagggcaac agaaagaacc    89700
aggaaccaag atttatataa cataagtcag taaaactaga ggcaccagag gtttacattt    89760
acattaggtt acattttcta acaggtagca aagcacatga atgaagttca gtggaaggcc    89820
ttcctcagga atccagtaaa aaccaaacat acacacacac acacggacat ccgtgaggca    89880
ggaagggatg tccactatag tacagacaag catcctggaa ggccatcaag gagtaggtgg    89940
gtttcagttg cctcaggaat gtggcatgga cccaaactaa gtgagtacag atacttgtca    90000
ttgaggagaa gattcaaaat agcatcctag gtgtaaaaac tgaggcacct ggggcagggg    90060
aactaggtct ctggaatgtt ggcttaaaag caccctctc aggaaaggcc tcatatgcca    90120
tgcaggggt tatatatgtg ttgtgggaca cagatggcaa ggagataatt ctatgcacca    90180
ggctccacta ctaacaggta aacagaccaa cattaacaga gacttaggta aaaaggtagg    90240
tgcccagtgg tcagttctca ggcacttcca agatgcacct aacagaaatg taacttggtg    90300
tctattgtgt cctaggtcta acaactgaag agaagtgaat tagtacctct tgtggacaga    90360
gaaacagggg cagagaccca ttacaaagct gtctcagata ggcatttgaa gctgtttaag    90420
tatgtagagg cttaagtcag gctggttctg aaatgtgaga gagggttaag cttcatggga    90480
aatcagcagg gtagtttgct atttttttatt ataaccaatc tcacaatagt ttgggacatc    90540
aaatatcaaa ttgttgggaa tatttatcca tattagtctt tttgccacta atatttaaaa    90600
atagtttaca atatacaaca aaagttgta aaatttccat ctccacttaa tcgatcttat    90660
gtaacccata caatacatca aatgtccttt ccccactttta tgttttatt tgctttgtca    90720
aagatcactt ggctgttagc atttgggttt atttctaggt tctctattct gttttattgg    90780
tctgtgtgcc tattttata ccagtgccat gctgtttgg tgactatggc cttatagtat    90840
agtttgaaag caggtaatgt gatgcctcca gattttctt tttgcttaat cttgctttgg    90900
ctatgtgggc tcttttttgg ttccatatga attttaggat tgtttttttct agttctgtga    90960
```

```
agaatgatgg tggtattttg atgggaattg catttaattg tagatttctc ttggcagtat    91020
tacccaggct tttcttattt tggcaccctg tgctgctgtc tccttttcct tctttctgct    91080
tctcttaacc aactgttacc tacacttcaa tactttctga gggcaattca tcctccagta    91140
agtctccctg aatcttctct tccttccctg gcttattata tatccttcct cttggttccc    91200
atagcaccta tgcacacttc tgtcattgca cttgccaatt tgttttataa tgatctgctc    91260
atctgtctcc tcacttagac tatgagctca ctgagagcaa tggctgttgc attcaccttta    91320 tatcctcaac accattctga aggcaagaga aagaataccc agaggtggag ctgggaagct    91380
ggttgtccaa gtagtgaatg actctagttt gaattgaact ctatagccag tgggcaatgt    91440
ggatgtgttg acagttttt aacaggggac tagtgaaaac acattttggg tttagaaaaa    91500
attgcaagtc tgatgacata cataggagaa gagattagag ataggaattt cacttcagaa    91560
atttaaccac aagagcaagt gacagatcac ggaagtctga accagactat aaatgtgaga    91620
atagagaaaa aagttaacaa tttgggtgtg aaagggcgag ggagagaggt gtgaagaatg    91680
actaagtgtg gatctgtttt taaggattga atggaaattt gagcattta gctaatcagg    91740 cctaatattg agcaaagcaa aactcttgca aattgttatt tcaagtgtgg gctgagaaaa    91800
tgaaaaaata taaattctca cgttataacc tcttccgtgt gtctgatttg atagaatcca    91860
gccccattgc ctccaaattc cattgcatct tagaccagca aacacaagtg aattctactt    91920
aaccccagaa ttctgtatga aaatcttact gccttttttt ttctaatcat gtgtcaaagt    91980
gtgggaagaa cttttattta tgttttaata aattgtcagt ataaccattt ttacttgaaa    92040
atattataat ttttcaagta aacaaattgt ttctctaagt tgaaaatttt atgatggaat    92100
aaaagtattt ttcctcaaaa cacatagaaa tttacaaca atatttaga gttaactaaa    92160 tgtttcttta gtagtttagt cacttaaaaa gtgatatgat tatgaaaata cttaaacttt    92220
gtcttttaac tatttctaat aatgctattg gtataatttc atattttat actgatcttt    92280 tctccaaact ttagtaaaac atacttctgt aaaccccctgc ccacaaaact gaagtccaca    92340
tttacttctg aatgactgat aagtttgtaa aagtatgcat gaatttcgtt attaaattaa    92400 agttttatt atattttatg cacaatggta taaattatta aattaattt caagcttata    92460 gaacattgat aaagattgtc attagaaaac cctgagttga ttgttataca ttacataacc    92520
tttcattggt ggattagtga atatgttata gggtgaccat gaatccaaag aatcaaagct    92580
ggctacagca aacagagggt caaaaggata tggaactatg catgatccag caaaacactc    92640
aatatctgtt ttcctggaat gttaaaagac aagaagaaa acttggggaa cactagatgc    92700
atatagttct ggttctttaa gaataaaaat atgggccggg cccggtggct catgcctgta    92760
atcccagcac tttgtgggag gccaaggcgg gtggatcaca aggttaggag ttcaagacca    92820
gccaggccaa catagtgaaa ccctgtctct actaaaaata caaaaaaaa ttacaaaaaa    92880 aatacaaaaa aaaaaatagc caggtgtggt gacaggcacc tgtattccca gctacttggg    92940
aggctgaggc aggagaatca cttgaacccg ggaggcagag gttgcagtga gccaagatag    93000
tgccactgtg ctccagcctg ggtgacatag tgagactctg tctcaaaaaa aaaaaaaga    93060 ataaaaacaa gaatggtcag agtcctagta ccttgtccag tgtagtgctg ccttgagatt    93120
gcattgcaat ctgtctgaga gatagtaaaa gaaagtgata ccttccttag ccctgttcct    93180
ctttagacta tgctttcccc tctccaagtt aatatctctc agtctaaagc ctgggaaaag    93240
gtgccaattt tgttttcctt tcttcctcac acctcctaga agttacactg ggacactatt    93300
acttttttcc aggctttggc catgtgtatt gttttggaga gtcaacttcc ttttttcttt    93360
```

```
cattctgcaa atagttttga gctgtcactc tgtactaggt gctataaaac ttacaggtgc   93420
attttacatg cctatttcct ataggccacg atttaacaaa atgttcataa atgagaatta   93480
ggagtgcatg tattgaatca ccacacatta actgaacagc tttcattggc cagagactat   93540
attgacagtg gagattcaaa gataaactag agaaatctca tgcttaaata actttctata   93600
ataaattata taagagaagt aggttcaggg atcttgggag ctcagaagca ggatgagtta   93660
aacaaaagtt ggattttgcc tttagcttgg tttcattatc ctgaaggaag agcctgaaat   93720
atagtgtagg gtgcaagtag tatatgtggg tggcaatctc gggaacagg agcatgtgat    93780 gaataaggag aaaaagccaa tataaaggta ctgcattgag ggcaatgagg gctctaattc   93840
tctgcacctt ctcaagcatt gtgcagattg gttttctgga ttatcagcct gaaggacaaa   93900
acgaagaaac agccattagc tcctgtctcc cattgtctga gagctgccac taggatatta   93960
acttcctgaa attctgcaga aatctcctct tactttggca ctggagatgc ccatacgcag   94020
aaagcaaaaa ggcacagcat atttaaggaa gctcataaga aacagtgcat ccagaagtgg   94080
cgagaattgg aggaatggac atgagactct aagaaccagc gcctttgatg ttccttttga   94140
tctgttatgt agctcttctt gtacacaggt gagcaaaggc atgctggaca aatggattca   94200
catgtgctaa agcatggggc aaaaaccaca tattaattca ggaaaagaca agatgcgtgg   94260
ccctctctgt ctctgtctaa gggtgaatta aagaggggat atatgtacag agtggcaggg   94320
caggacttga gataagaagg ctaggtgggt gctctcatgc tagtagcatt atagtacagg   94380
tgatgagaag ctcctgaaga atcatcttaa catttgtatt ttagagcaac agtattgagt   94440
tctgacttag agacagcaaa actaaagaca gaaagactat tttgattatt aatgatgtag   94500
atataagaat atcgtcaatg tgaactaaag catgaagcta cttatgatat atcattaaaa   94560
ggatttaact gattggagac aaacgagagg gatggggaaa agaattcatt tgttttagt    94620 tgctctttt ttcctactta ttcctttgtt ccgagtgtga ataaactttg taaacttta     94680 tactaaaaca ttctgctcat tcatacttat ttctttgatg aaacaaggaa acccttgtat   94740
agttataaac gtgtgaatca atttaaatat taggaaattt ttttaaataa agctagtttt   94800
ctgaagggga aaaacttggt tcaattttt gctggcaatc tgctttgtga tttttgaaca    94860
tgatatctac atctagactc atgttttgct agctggaatt ttttttcaaa ttaacgctac   94920
cattattata tgctttacta tttagctttt gcagccttgg aaatctatga ttaatacaaa   94980
taattctcta tggcaatttt aaaaatacat gtaaaagcct tcaatctaca ttgctactgt   95040
gtcgtagcac aaaaaaagaa aatgtgatca aatttttaata aaatctacaa tttattccct   95100
tctaaataca gtcctagctc aggagaaagg aagctatttg tattttcag aatcaaattt    95160 ccctaaatga atatagagaa agaattataa ctgaaatatt gttgaaacag tggtcatctc   95220
aaatctgaag gtcattccaa aaagtttct gagtttcat tgcctcaatc taaaagttgg     95280
cctttttggt aatagatgaa agtaaaataa ttgaaagggt ctgttgcagt tttgaatat    95340 cttgaaaata tagtagagtg aagccttctt cccttaaata aaagacaagt tgctgattgt   95400
tttctttcta gccagataag aataatgcct tctttctctt gttagtctta cacctcact    95460 tgttactatg tgtcagaaag gcgagacacc ataaatggag atactactga tggaggtcat   95520
ctgacatggg gctggtaggc agtgggaaga ctggtatgga cacaggtggc ttaggggttg   95580
gggaatgata tggaactaag gaaatgataa ttagcagaac ccagtgtgca tgtgtgtgca   95640
ttcgtgtgtc cgtgtatgtg tgtactgtag cacaatgcaa gaaagaaaaa acaaggcaga   95700
cttttcataa tttcagggat aaataaatcc tttatcactt catgtagaat attggctact   95760
```

```
tggaggtata tctaaacgta aatatataac tatataacta catgctaatt aaaaacatac   95820
aaagaagaag tgcctaaaga attacaacag aaagtggcat agtgattatt agagttaata   95880
taatataaat aaggccaggc atggtggctc atgcctataa tcccagcact tttggaggtc   95940
aagttgcagg gatcacttga ggacagggga tagagacaag cctagccaac atggtgaaac   96000
ccatctctac taaaaataca gaaattagct gggtgtggtg atgggcgctg gtaatcccag   96060
ctactcaaga aactgaagca ggagaattgc ttgaacccgg aagctgggc tgcagtgagc   96120 caagatcgcg cactgcactc cagactgggt gacagagaaa gacccggtct caaaaaatta   96180
aaaaatagta taaataatat ttcaaaacac aagtctgtta agataaaagg tacagaggaa   96240
tggtgagatg acttttttat ttgtgtgata agggactgtt ttctgtgatt gtgagaaaga   96300
ccaggagtta agaaaaagtg gccatcaata aatcagccac ttatggggaa gaaccataaa   96360
ccactctcag atgaaataca aatgcagtca ttatttaata ttattggaat atttgtatta   96420
gtttttggta tgtgctgcta gtgctggtac attttagtag tcaattaata ttttgttaat   96480
cttaatttct aactaaattc cagagtgaaa tggaaataat aatgaaaaaa ttttatttac   96540
aaaacagatt ttgttttttt ctgttaagaa tgatacacag ttgtccttca gtagccatag   96600
gggattggtt tcaggacctc ccttgggtac taaaatctgc agatgcctaa gccctgtta   96660 taaaatggct tagtatttgt atataaccta tgcacatcct ctcatatact ttcaatcagg   96720
ggtccccaac cccagggcca tgaccagtac tggtccatag cctgttaggc tgttcgatac   96780
caggctgcac agcaagagct gagctcctcc tcctgtcagc tcagtggtgg cattagattg   96840
ccataggagc acgaacccta ttgtgaactg cacatgtgag ggatctaggt tgtgcgctcc   96900
ttatgagaat ctaatgataa atgtaatgtg cttgaatcat cccaaaacca ttccccttcc   96960
cctcaccatc cctgtccgtg gaaacatttc ttccagaaaa ccagtccctg gtgccagaaa   97020
ggttggggac tgctgcttta aataatctct agattactga taatgcccaa tacaatgtaa   97080
attctatgta aatagttttt atactatatt gtttagagaa taatgaaaag aaaaagtcta   97140
catgttcagt ttaagtgttg ataagtgtgt agagaaaagg gaaccttgt acattgttgg   97200 tggaaatata gattggtgca gtcattatgg acaatagtac ggaggttcct aaagaaatta   97260
aaattagaat tacctaagac ccagcaatcc ctcctctgga tgtacccaaa ggaaataaaa   97320
tcatcacctc ataagatat ctgcactgct atattcattg cagcattatt tacagtagcc   97380
aagatatgga aaccacctag gtatgtgttg gtgcatgaat ggataaaaga aactgtggta   97440
tatgtatata caatggaata ttattcagcc ttaaaaaagg agaagaccct gtcatttgcc   97500
acaacatgca tggacctgga ggatattaag ctgtgggaaa taagtccaac acacatccac   97560
acacaaaatt gcataatctc acttatatgt ggaatctaaa aagaaaaagt tcaaatataa   97620
agttagaata aaacagtggt taccggccgg atgtggtagc tcacgcctgt aatcctagcc   97680
ctttgggaag ccgaggtggg tgaatcacct gaggtcagga gttcaagacc agcctgacca   97740
acatggtgaa atcctgtttc tactaaaagt acaaaaatta gccgggcata gtggcaggtg   97800
cctgtaatcc cagctactca ggcagttgag aaaggagaat cacttgaact caggaggcat   97860
aggttgcagt gagccgagat ggcgccactt cactccagcc tgggcaaaag agcaaaactc   97920
tgtctcaaaa taaaaaaaca aaaaacacag tccacacact ggttaccatg agtgaggtgg   97980
cagggaggag attgggagat gtagatctaa ggatacaaag tagcagatat gtaggaggaa   98040
ctaaaaagct gacatgcagg atgacaacta tagttagtaa tagtgtattg tattcaggat   98100
ttttgctaat tgagtagatt atagctgctc ttgccacagg ggaaaaagtg ggtaactacg   98160
```

```
tgagatagac aatggatgtg ttaattttg tcactataat aaccttttca ccatatacat   98220
tcatcttata acagcatgtt gtttactgta aatatataca ataaaattta tttttaaata   98280
tctgagtatg atttgatgat ttgtgaaaat agagtgaatt ataataattt taaatgtaag   98340
ttaatgttat tagaaaagaa acagaaagaa cataccacac agaaagtctg tctgaaggat   98400
ctttgttttc tccaccaata caagtgttca ttgattcaga ggtggattat gagatatgac   98460
cataaaacaa aaatttcaag ggaaatatat tttattcaat gaaaaattct caacacaact   98520
gttatatgcc agtaaacact atatctttta aataacaggt catatctatt atatttaaaa   98580
ttcaaggaga gactacatta gagatgctat tagatcaact tctaatttca aagatttcta   98640
agatatggaa cagttactcc ttatacaaat taaaaaagca aatgctgaag aaattcagct   98700
acatggatac accatgaggt ggaaagatgc tccataactc ttagttaaac tgcactaatt   98760
acacataaaa ggaaaatgtt tcatttcact gtaatttgga aaccaaagaa agaaaagact   98820
gaatttttac atactgttaa agagattgcg tatctgttct aagtttaaga cagaggcaaa   98880
atgtatttta ttcatttgtc ctgcaccgtt tagaaataaa attcaacttc cttttaattt   98940
tttttaagaa taaaaactc agtctaagga aagtcttaaa gttttcattt taagtgatcc   99000
actgttctag aagtttaata ttttgtttaa aatgtttatg ttctgtattc caccaagtct   99060
agttttaaaa caaacaaac aacaacaaaa tacttctcta acttggagtt taaggtgaaa   99120
gaaaccaatt acgtggtttg gaaatgtcac acttttcatc tctttttaa aaaaatttt    99180
aattcaggac agaaattgta tggatttagt gtaagtcttg ggatctcaca agtgtcagta   99240
tttcactctc ctccatatct tgatagcaat aacttgaaat aggatctcag tagctcaagc   99300
aatactgggc tctgagagtt ggttaaaaat tatttgcctg agcgcctgtt gctgagggaa   99360
gaactaatct cgagcatatt tttggagcca aataccaaat tgtttgtgct agcaacaca    99420
gcaccaggct tgcccttcag aatgattcta gaccaaatgc cagaaatgct ctggttctga   99480
ctacagagtt ctattcacaa atgacaggag gcaagaggtc ctcctcactt tcagaagaaa   99540
ggtcctttgc tttcttagtc aatggtagga aaaccattgt ggttttcatt gcattacata   99600
attttttaagg tgattacttc aataagaagt gctctgtgta tatgtgtgtt tatagacgca   99660
tttttttaaac actggagaat ttctgaaagt agtacaaacc ttgtaatgtc aagtagatgt   99720
gggaaaaagg gagtttacaa cattctctcc tgacattgct ctccttttggc atctgcattt   99780
ttaaaatgtt aaaaatgttt aaaaacgtgt gcttaacact taatttggtg atagttgctg   99840
ttaccaaggc aactctgtaa ctccacccag ataaaaataa atcttgaaga tgagtttctg   99900
tgtctctgag caaatatttt tgtgaatagt agaagcagag aaagttaaag atacctgagc   99960
ttttgatctt tactagtttt atagatatgt ttatagttat acatttttat tcatacattt  100020
tagataaata actttgtaaa gcaattgatt cttcttgtaa aaatcaagta tattcttaat  100080
agactgataa actttctttt tttgagacag agtcttgctc tattgcccag gctgaatac   100140
agtgccatga tcttggctca ctgcaaccta cctctgcctc ctgggttcaa gcaattctcc  100200
tgcctcagcc tcttgagtag ctgagattac aggtgcatgg taccacaccc cactaatttt  100260
tgtattctta gtagagatgg ggttttgcca ttttggccag gctctgagaa acttttaag    100320
gtctcttttg cagccagcta tttgtctacc ttatttcatt cttaatctca ctagccaata  100380
ttttttctgt ttaagtgctt tcagcaaata ttaaatgctt gtgccttcag tcttatcctg  100440
tggaaacact ggtaatgaca aaacacata tttcaaccta atatacaata gaaacagaat   100500
gccagttatt catggaggag aagaatagac ttctgtattt aaaataacat tttgctctgt  100560
```

```
gttttaaaat cattcttcct tcatcaattg taagcatctt gactataatt tatacaccta   100620
aagataaata attcagtagc aatgataact gaaaacagga cacatacaat gaactagcta   100680
aattaccata cattctcatc catttcaaaa atagctctgt acttttttca gatttgtta    100740 gaagaatatt caatacaaat ttttattcaa tgaacacttc agatgtcaag attgttaccc   100800
acatggacaa cagtaaccta ggtaaagatt ctgcagccag gcgtggtggc tcacacctgt   100860
aatcccagca ctttgggagg ctgaggcggg cagatcatga ggtcaggaga tcgagactat   100920
cctggctaac atggtgaaac cccatctcta ctaaaaatac aaaaaattag ccaggtgtgg   100980
tgtcatgtgc ttgtagtccc agctgctcgg gaggctaagg caggagaatc gcttgaaccc   101040
gggaggtgga ggttgcggtg agccgagatt gcaccactgc actccagcct gggtgacaga   101100
gcgagactct gtctcaaaaa aaaaaaaaaa aaattttata cctgggctct gtgctcacca   101160
gcagaagggg taacatggct tcttaggaca accttacttg accatttact tctttgacac   101220 tagggggtatt cttagatcag caggtccttc cctccactta tgcacatgag gctcacagag   101280
agtctgggag gcagggaatt tatgattgga aacagtatac tttttatcta agaaattatt   101340
aatgtcactg cattcaagtg attaacacca tcaatatctt caagactaag gggattacat   101400
gatgtgtaaa attagaaaac tgtcatctac tagtggctag gcactttaat tatattaagc   101460
atgcaacaag agaactcttc aaatgaatcc atctctcctc tgtattattt ccaacccttg   101520
gatccccatc tgtttctgca gacaacagct atgctgctga atgtcttaat ggtttgctgc   101580
cccaactagc ttcaagatac tgcaggtcaa gcatagcatc ttactcttcc ctgcatctcc   101640
agcacctctc agaatgttgg tcacatagaa gatgtttgct gaggagttga ataagaatat   101700
gtacaaggga cacaattagc attgttttaaa aaagatgtaa caagatagggg taaggaaag   101760 cttttggagga taaatctttta gaacaatcaa taatatcttc tcctctgttg gttagttgcc   101820
cttcaatctc agccactgaa tcaaatacaa cataattact attctgatat gttcttgaat   101880
cgaatatcca ataataagat attcggatgc atagccatgt ctaatatcaa agcccatgct   101940
tttcgctatt attgtactcc atacattagc ttccaaattt atttgcaatc caaatattaa   102000
aagcaagtca taagcttagt atcgccaatg tgatactaag tatccactta ctaaactttα   102060 ttttcaaaat gtggttttat ctcagtttaa tgaacacggc atgttttaat ttacactttc   102120
atattatata gtaagggcgt ggttacagat atgttaattt cctgtgctgc ttcacaatga   102180
tggaacataa tagcaaatga aactgttaat ttgcagatac ccataggcct ttggtgtctg   102240
aatagaaata aacacaccta caactgagag aggaagcatg tgaagcattc cagtgaacag   102300
aggccattta ttcagtcaca gacacaggag aaaaacaaca attaaaaaaa aatctctgat   102360
gaaaagttca taaaaagttc actcagttta agcatatgtc ctataactac ttaaaataga   102420
gttcttctta aatatcattc tttgctgttt ttagatttct tctgcctgta tcaaattaat   102480
agaacacagc atactttaa tttgctctgg tttcttagtg gggcatttat taaacacatt   102540
aaaacaatag tctcagggtt ttactgctga tgttaaagtt ctgctttcct acttaccaac   102600
tgtgtcatct taaggcacat actttgcctc tctctcaaat ctcccaaatg gagaatgata   102660
agaatacgta cctcaattaa agaagctata acaagtagaa tgtttggaaa agtgccgggt   102720
acaccataag cccactatga gtattggatt gtattacctc tgaaagctgc agaatggaat   102780
tctcaaagtt atatgtccct aaaatcctct taagtgacag aaatggagaa attagcagtc   102840
tgtctaagag agcttttcta gagtctgggc atatgttttt aggacaagac agttcagctt   102900
cagcttaaaa tgagagagca cgtctgtgtc cttactcctg ggtgccaggt ttcttgtccc   102960
```

```
catcttaaga caaataattt tggtggagaa gaggcagtct ctttgatttc gctctaaaaa   103020 cctttctgg aggaggtaga cactctccac ccccgttttg agactcatgc agctgaggat   103080
gactggctga gtacaagcaa ttgttccttc taagcagttt caattcttat aacttgtgga   103140
gatattctta agtccagggg attttgtgta tggtggattt ttattacaaa gtcctgtact   103200
tcataggaac aaaataattc aaagtcagga accagatcaa agccacaact cagatatggc   103260
accttgagaa gttcatttgt atttcacttg cataaaaacc ctcaccactg ctatctgatt   103320
ttcacaaatc attcaacagc tatccatgaa gcacccactg tgtgtctggt ctctgtgtca   103380
gtccctggct tcatgtgtct ttccttctgt accctgactc cccaactcat gaacacatga   103440
agtaaaaaaa tgaaaatctt tttctgacct ctcttcaaaa tcactttttt caaaacaaac   103500
acctctcacc tgctcatcct ccagccagta aatcacaggg gcctagaaat gtcacttaca   103560
aatattttct gattctgtcc ctcccttcaa gcttgccaac attatcacag tttagggcct   103620
gctcatcttt cccccaatct ccaattagat ctctccacaa tgcaattctg cacattccct   103680
gttacaaccc ttcaattatt tcccagccca tccaaaataa aatctaagcc tcttactaac   103740
acattcagga actctgtggc ctacggtttt ctacagacta attttccagc agttgacttc   103800
cagtgcaagt gaaaacctag tgtcatgcct gcatgataga taaatttgaa gctgaagagc   103860
ccaaatgtat agaccatgcc atgaaaggtt tatagtcatg acacagtggc cctatagtac   103920
agtgcttgaa gctggctctc tactgtcaga cagaccactt gccagccatg agacctgggg   103980
caaaatgcct taattttat gtgcctcaag ttctcatgtg agatgagaat aaaaattacc   104040
cctatttcat aagatttgat aaagtgttta gcataatacc tcataacaat tgcaattcag   104100
tggtggttat tattataaag aaaagatgat taactttatc ttaatgttta acttgttctg   104160
atagttattg atctatagct ttgatatgga ggtttgagaa tgacctggaa agaattggcc   104220
acaatgattg aagatagtga tacaagaata aaagatgact gcaaaatgta aacctgcaat   104280
aacagaaaga atgaagtcac tggtctcatg ggaactgata tgggagaaaa aaacagatca   104340
aaaggctatt catgttttgg gcctctttgt caaaatggaa atgagaaact ggggaataaa   104400
aattaaagca attctagcat ctggttttaa cataattctt atccctaaaa agaatctata   104460
agaaactccc aaaatgacag gcagccgtgg gtagcattgc atttcaagta atcttttaat   104520
tgttaaaatt taagtttcca acatgaacat aaaattttca acctaaaaga aatgagttcc   104580
aaatctgaga caagtgaaaa aggataaagc ctactagggg gtaaattcca tctctttaga   104640
gatctagtac ccaatttagc aatgtccaat caagccttta actactacat ttgaacaccct   104700 catcatttca aaatgttact taatgatgcc aattaactgt acaatgtctc tgcatagcac   104760
atagccctaa aatgatttgt gcaatgttac tgtcagtaaa actgaactac agggaatgct   104820
catattctat gtcattatat acagaaatgc aatatcaata aagtgatatc tgttggtatt   104880
agaaaaaagt gaaatttttc atatctttct attttctttt ttcctcaatg ggatgctctt   104940
gttaaagata gctctgcata gtaaggtttg tataaacatt atttagctaa agttaaaagg   105000
ggtaacatac tggttctagc acagatatta aaacaaatta gtttgtaggt agggcagcaa   105060
tcaattatat tactaaccat agctttggtc cttttatcct ttcccatttg attttacaca   105120
gtgggatgtt aaaggttgaa tgtctttggt atctataaac ttaattgaaa gctgttattt   105180
gtttgtttaa gtctgttgat ttttataatc ataatttac tcctatagat ttcttgtagg   105240
agtactatat gaatttatgt tgcactgaat tttgttatgt tatacaaatt aataggcttt   105300
tatttatgga aagctactat tgatctgtca tttcttaaaa aattactaaa aagtgttaaa   105360
```

```
actttaaatg ttggagagtt tatatttaa aagttacatg ctagaaaaac atgatgtctg 105420
agtatattag aagttataga taattcatct gtcaactata aaactctcca acactgcctt 105480
tctttaatga ataatatgaa atttagcagt gaaaatgtga caatgtacaa tcctaaataa 105540
atcaacaaat ttagagatgt acctctaaaa ccattgtaaa ttcaacagtg taattttcca 105600
ttggactttc acttattcat tcattaaaca aatgtttgtg agtgcctgca atgtatgaga 105660
cattgtactg aagctaggca gtgtgagtta tcatatggga ttatccttta aatacttctg 105720
agggcaaaaa aaaaaaaaa aagaagagaa aaggtgtgag gaaagataaa gggttaattc 105780
attaaaaaat aacacttgag gactgttttc tttgcaaggc ataaagttat caccctttca 105840
aacagtagat atttcacatt taggatgcga gactccagtt ccaacaaagc tcattgcaca 105900
gctgctaccc tgattaaact gctacatgaa ctctgagcaa tgtagcatgg tagccgcatg 105960
cttctgcttg catgatggtt aattccttcc attctcatta gtgattttct gagctttgaa 106020
attctgatgg tacctaggat ataaagcata tttatctaac tgaaaaacag ataattagat 106080
gtaacataaa atatgaatgg cttgtcact ttattgtagc agagaatgaa tgtgggataa 106140
attaaagctg atgctagaac atatgcctat ttttagctg gaaaatttca agatttatgt 106200
actttgggct tgagaaagaa atggagttta tttttatgc actgacatct ctttttttt 106260 tttttggaa gagctctctt aggaatgaat ggtatgtaaa tacagtagga atgtaattat 106320
agattttcct gacccagttc ctaaataata gatatcattt cagaagtgcc ccaatacctg 106380
accttttgct ccaagccata tcaaagcaca catctagtct actttcact ctcattccta 106440 gccactatga caatactatt cagataaaac ttctagtcct ctacttatgt gactcatacc 106500
aacttgacct tacgatagtg actgggggtg catatctagg ttcatgctgt ttgtccatta 106560
ttatggtttt gtgagaaaag gcaaaatttc taggtaaagt gttatgagga cgaataatcc 106620
accaggcaac caactgaccc tttcatttgc catcttgtca cttcaaacag ctctccagaa 106680
cctgcagcca gcacagacca aagtcaggtt tgtctcctct tctgttgatg aacaaaggtt 106740
gattccatat cgtggctatt gtgaatagtg gcagtaaaca tggcagtatt gtatgaaaat 106800
atcacagata gcccttaaat atgtgcaact atgatgatct atcaaaatta aaattaaaa 106860 tttatttta aaagttcagt tagaaagctt gtagttcctg gcaaactact accttctcg 106920 gcaaagaat ttgatatctc ttaaatattt tctgcctaat gctgatagat tgtatttaca 106980
tattccatta atgcaataaa taaaattaca ccaaaacatc agcattattt atttccaggg 107040
gcatctctca aaataaattc ctccaaaatt cacaaaacca aaaccaatgt gaaattgtac 107100
tcagggatgc aaatgtagcc cagtgaagca tttgcccact tgtttggtat tattgaagca 107160
caattagaaa aatgtgcaat gtatgcccaa aaattctata ataagggcca ggcgcggtgg 107220
ctcacacctg taatctcagc attttgggag gccaaggtgg gcaaatcatg aggtcaggag 107280
atcgagacca tcctagctaa caccatgaaa cccagtcttt actaaaaata caaaaaattg 107340
gcccagacgt ggtggcggga tcctgtagtc ccagctactc gggaggctga ggcaggagaa 107400
tggcatgaac ccaggaggca gagtttgcac tgagcctact ctccagcctg aacgacagag 107460
cgagacccca tctcaaaaaa aaaaaccata ataagaactt tttaatatac tatattataa 107520
tgtaaaaaga ctagatgtca aacaaattag gtgatgggaa ggaattgagg gagaattta 107580 gactaagcaa ttgagcagca cctgttttc accacaaatc tgttacatgt attgctcaat 107640
tgtgctgaat ccatattggg tcctggtggc tatgtaatag tctctttctt ggataaatgt 107700
ttgtcctctc ttatggttta ctaatggtgt acagaacagc attgaatagt ggttatttcc 107760
```

```
tatgacttcc tagatatctc tctcataatc ctgaatgttt taaagatcat tcttagatag   107820
agtacagcta gacacgaacc atagtggaaa tcaggtagac aaaatttaaa aggagtctta   107880
attgaaggtc attttattgt cctcagtatt aatcttactt aaaacaaacc tgtcactgag   107940
cagaactcaa aacaccagag ccctttgcca aatgtgattt tttacaacag gagcgctggc   108000
agttgagagg agtattctgt cacacttgag agaattcgag tccctgaaga tttatatgaa   108060
tgcttagcta ttatcgaacc atctcttcac agatgactta gtaaatgtct gcctttgcat   108120
cagataatgg cttacaagtt aatctcctct tgctccctgt tacacacata tacaccttct   108180
tcctaaacag ctcataaggt gaaagaaaga ctcagatttc tgactatgta attgataata   108240
tcacacggac tgcctgctca tcatctgcta gtcacattgg cagagttgac agttttggag   108300
acactgaaga cagtgcatat attaggaaat aagcagtttc ctgatataaa ttttcttgta   108360
gtttataaat tacatagcat ttattattcc ctcatatttt ataacattta ataatagaac   108420
tgacacatat attcatttta aactcaattg tgtataataa ctatcatagc aacccttcag   108480
tgcctaaata tcaaatcttc cattcctccc atgaacatct tgaatatata ggtactgtgg   108540
ttagctccaa caagcttttg gttagaattc attgcactga tacatagaca ttgttttaaa   108600
ggcaatttca aatcaaagct gtcagctgtg aatcaagcac accttaaaaa gtgacacatt   108660
tgtcactaga ttccagcctc tcaaattact gacacgcatc cttttatgt aaagatgaca    108720 ttgttctttc ctgatatatt gcattcctca tgaatttctt atagtcatag aattttata    108780 aaccatttca gaatcgctga aataaacatc aatattttta acttttcat tctgtcaaaa    108840 atattgtatg cagagatatt gctgtaagtg tgtatacctg tgcttaagag actagggctg   108900
aagagaagta atcaaccgaa ccactggtgt aaatgtgcgt cacatttta gtgactagaa    108960 attgaaataa ttccaacaaa tttatgtgct ttgggcttga gaattcagac tgccttaggc   109020
taagataaaa atcttttcct ggtactatat accttctttt attgaatgac tacctggctc   109080
tttctattat atatgcagat tttgtacctc tggtcatctt tgtaaatggt gcctaaaaga   109140
tatttgaaga ataagtgacc agcaataaga acaaatgtct atacaaaagc ccctttagt    109200 tggatgtaat tcactacttt gagttgttaa taacctctaa ggatgacagt agctattagt   109260
tgaataaacc attatgtcta ttattagaac actagatagt ttataagtcc aaacaatgca   109320
taaaatacct atctcatgtt accattgttt aggttaccag ataattgttc tgtccaatta   109380
ttccacttaa ttttttgctt gcccattagc taaatggcaa gataaaattt gtcaaacggg   109440
ggggaatgta ttgaaaatgc tagacaacta cacttaaaat gaaaacaggc caggcgcggt   109500
ggctcaggcc tgtaatccca gcactttggg aggccaaggc gggtggatca cctgaggtcg   109560
ggagttcaag accagcttga ccaacatgga gaaactccat ctctactaaa aatacaaaat   109620
tagccgggca tggtggcaca tacctgtaat cccaactact ggggaggctg aggcagaaga   109680
atcgtttgaa cccaggaggc ggtggttgca gtgagccgag attgtgccac tgtattctag   109740
cctaggcaac atgagcgaaa ctccatctca aaaaaaaaa aaaaagaaa gaaaagaaaa     109800 caaatgcata atttgcaaat attatttta tattgtatgt tatctagggc ttctaaatgc    109860
attcttctta taagcctagg tttgcaataa cattcattta gaattgagta attttaaata   109920
taatatttta taaaataaaa tataataatt tctcttaatt ctttgaaaat attaaattaa   109980 aaggggggttg caaactctgc attccacatt tccatcccaa catttaattt tagcaatttt   110040
gtagtctgcc taaaatgcaa tccatcattt actgttagga aatagggaa tgtacacaaa    110100 ggcctttcag cttccctga actccataaa aatctttttg cttctttact gccccccttt    110160
```

```
gtcaggagtt ctgaggaact gttttttatc ttaagtctca caaagcattt aggagaatat    110220
ttaaacttaa attcttttaa aacttatgtt caggacaaag taacattgta tgcattggtg    110280
tcatatgtat ttaaattttg aaattttaa tactggcaaa atgaggtttc aattttaata    110340
taaattattt aacaatctta aatcattaaa tatattactt aatatattta atatatctaa    110400
acagtcacaa ttttcccata ctaataatca taaaaaatct tacccaatgg tcatatagat    110460
atacttaatg gagttttggg ggggtatttt tgtatattaa aaaattcata tatttgcctt    110520
acttagaaga actgattaaa tgaaagtata atattaacaa acatattgtt attttatatt    110580
tgcatttgtg ataattatat ttgaaacgtt caagattttc caatgaattt cttttgcatt    110640
tgcgtatttg tgccttttta ttataaaaat aggtggcttt ttagttccac tgcataagtt    110700
tcaacatagg tctacaaata gtgcatcttt ttgaagttaa tcattataat cacaaattga    110760
agttgcctga gctccaattg gagtctaaat ggatgactga atcttattat tcgaaaccca    110820
ctgttgctac acaatatggc cacacaagag agtacacaag acccgtctga ttcagcctca    110880
gtgccataaa tattttaatg gtttcgttgg aatctggaaa tggagctcac cacaggagat    110940
gcttcttcct ttgactctca ttattatttc ctttacaaat taattaataa aaacttagat    111000
gctaaattag cacttgatga aaacttatat agccttgaca ttttgattct gtgagtgaat    111060
aaaaatactt ggagaaataa aaatcctaat catgttcagg aatacccaca aggtaacaag    111120 tacatttta aactttaaaa acatttatta ttcatgataa aacatgttgt gtgatttaaa    111180
tataaatttt tattatttgc tttaacttat tccggatta aaaagtaaat gtttacctag    111240
ctgttctaaa tggtaatcct catgattaaa acagcaattt gtcatatttc agttacaaat    111300
gatcttttat tattagttat agaacataag tttcttcatt gactgaggcg atgtttcaag    111360
tagataaatc tgttaaaaaa attgtggtca tattctgtta aattctcata ccaggcaatt    111420
tgtttgatat tcaggaaaaa cctagccact gaccaaaaac tctacctgcc ttctcagttg    111480
tatcctcttg gacttaaagg ggactgggaa agttataaga tggttcatga tagtccatca    111540
acatcccaag aacaaaaaca gatgttgtac tgacagcatc atatgatcat atgcatgtaa    111600
gagcacattc atattgccaa atcagttgga attttttcacg gttgaaagtt aaatgaaatg    111660
cttagatgta tgagtcatcg gagttaaaga caattacagc cagatttatg gctgtgctaa    111720
aataaagcta gttagaaaac agaccaaatt ccatgacgat accaagtctg actaatgatt    111780
caccttaaat ttcggagcaa catttatcct cacttgtttg tttatttgac aatgtgccct    111840
tatccattaa gtaactagga ggaagggaaa agcactacgt gggtgagtga caagacactg    111900
acactgattt gtgactttgg ataattcctg gatgctgtta tctgttttgg catagagatg    111960
gatctgtaac tgctaataat tgccgactgt gaccatccca gaggccattt acttaaccca    112020
ggtatttcag acctgacagc ccgaggataa acacgatttc cctccatcac taacttcatc    112080
tgcagggcct aagcctcctt cacagtctct ccagtgattt attggcatct ccaagggtat    112140
ctcacatgtg ctgaagaaca aatctgctca cttcatctg cttggttttc ccttttgaaa    112200
tctgctgctt taaaattact aagggaggaa tcatgcctgc tgctacccctt gccagtgacc    112260 ttgcagtttg tgccctgatt gttccaatta ccacaatcaa aacagaagcg tttgcagtta    112320
ctgcagtgct ctctctgtgg atgtcaggtc tgactcagag agccaggctg gggaacagcc    112380
atttccactc ttgtacctct gcaaaaggac ttccatgttc cgtaaacaga ctcccacctc    112440 tcatttt ccc cccaagcaaa gcatcataaa ttagagagca tgtaacggga aagaaaatcc    112500
attagccatt tgggttcagt cagacaagcc agctcatgga aagtttatac aggaaggtca    112560
```

```
catttcaatt gagatcagga gggtgaaagg gtccagctgt gtgatgagag agagaatgtt    112620
cgggaatgtg gaacagaggt atccaaggca gaacaaactc gtatatgaag gctttaaggg    112680
tgtgcaaatc tagcatattt tatgacataa aagagtcctg attagctaga atatgatgaa    112740
tgtgagaaga ggtgaaggct ggagatagga aaaattattc cagatcttat aagctatagt    112800
aagaaatttg catattatat atagacttgt gggaagccat tggattttgt aagaaggaga    112860
ttaacattat cttatttatg ttatttgtga tttataaccc caaatgtgcc agatacaaac    112920
aaaccaaaaa taataataat aataataaga agaagaacaa caacagcaat ggaactgtgg    112980
tgatggtttt ggtcacaaaa tgcatatata tctattttc acaatgcaaa atatttcat    113040 tatttcaaat tttaacataa atgtgggtat gcatgagctt acaaatcttg aagtttattg    113100
gggaatattg gtgagcatgg ttttttattgc atggtcacaa cttactaatg ggaaacatct    113160
gaatacctat tgagttaatg catgcacatt tttattttcc tggaatactg agaaaaaggt    113220
tgctacataa tgtcttgata gcttctaagt catggctcaa aagtgaatgt ggaatctgct    113280
aatcggaatg gactcagatt cagccaagtt ctcaaaaaca tttgctttca tagatgtctt    113340
caagaaacaa ggagtcttga atttaaattg tgaagtgtct atcttagaat agagagattt    113400
aaaatctgac tgtattttgt ttaaaaaagc ctatataact gtattatata aaattattta    113460
tactacagtt aaaaaaagaa tcccatccta tttgtgccta aataagtgcc tgcttgtagc    113520
atgaaaacta tttgttgagg gtccttagat cctcagagca tgctgtgaaa gtaggtacaa    113580
ttgttctttc tatataagcc tcttaagata acagataatt gccagaaata cagcacacag    113640
tacaaaatta ccttgtttta cttttgccac aaaaaacaat ttcttttggc tttgagcaat    113700
aaagtccaat gatttttttc ctttcaaaat atcttcctcc ctctccataa gtttatatt    113760 tattcacgaa ggaatattcc aatatcggat gttttttgtct gtgtctcttc ctggaacaaa    113820
tgttaattaa tctctttggg tttgtatgtc aagtggaggg gtggggattg gggacaggtg    113880
atagttgtct agggagttaa cttcatctct ataggagagt ggatagacgc tgtatacgaa    113940
aagctcttga aaagggaaat acagcagcca cttcctcagg gcttccatgg tggtcagact    114000
ccttgattgc tttagattaa ctctggcttt tgtccttcgg aggccaccag attgggtgga    114060
tagacattgt ccttgctgtt cttttgacct acctacttgt actttagggg aaaaaaatgc    114120
ctgtaatagg ttaaatgctt tctcaaagat caccaaagta tataacacat ggcaaataga    114180
cagagaaatg agacagtata atcagtataa tttataaaag taccttacag caggatccca    114240
tgggatatgg gttttttta aaaaaatct acctaatctt ttcattgaac tcctattcag    114300
gattcattat attgaatatg gctcagagac ctggaaaatt gtttccacct ttttaattta    114360
ttcaccatca tttatggaag ttttcaagga cgtttactta cctacctcag ttaacagatt    114420
gtactacttg ggaagtctat aaatatgagc ttaaagcatt ttctgagttt taaaataatt    114480
tagattgtgt agaatgttaa aactaaaaga ggaaaaaatt attcagttcc tcagttgaac    114540
ctagcaattt atcttttcac agtgtgctca agtatagttt ttgaaaagta aagaagatgg    114600 ttttttataca aacataaaca catttcaaag atttttattca actaattaat tagtagtgga    114660
gccaataagc tggtaagact ggtttaaagg aatatctgag gaataaagat ttatagaaac    114720
agtcaaagaa attctaaaga gaattgacta atagatataa atctagtaaa tatttgatta    114780
ataatagcag taacctatgg aattatgttt tctactgagc ataaatgagc atgaatctct    114840
ttgggtttgt atgtcaagtg gaagggtggg gattggggac aagtgatagt tgtcaaggga    114900
gttaacttca tctctatagg agagtggata gatgctgtat aagaaaagct cttgaaaagg    114960
```

```
gaaataaagc agccactgca catctgcaca tataacctgt agatctgggg gctctaataa    115020
aaaagttaat ggcaatgtca aaatctggtg ttttatctta gataacttca tagtcattga    115080
ttgagcccct taaaaataac atttaaagga catgtagtca ttctgtttct ttattgccaa    115140
gttttcagca attttctca tgagaatgag tgctaagaaa cttttggtgg agcgtggtgg    115200
ctcaagcctg cagtcttgca ctttgggacg ccaaggctgg ccaattactt gagatcagta    115260
gtttgagacc accctggcca acatggtgaa accttgtctc tactaaaaat acaaaaaaaa    115320
aaaaaagtgg gatgtggtgc atgcgcctgt aatcctggct actctggagg ctgaggcacg    115380
agagtcactt gaacccggga ggcagaggtt gcagtgagcc gagatcctgc cactgcactc    115440
cagcctgggc tacagaggga gactccatct caaacaaaca aacaaacaaa aagaaacttt    115500
ttaaaatata acaatagaga cattacatag gcccacaaaa ccacctccaa aaaagcattc    115560
tatcacctgc aagaaagcat atatatatat ctgcttttgt gtatatatat atatatatat    115620
atatctgctt ttgtgtatat atatatacac acacacacac acatatgtgt gatatcagca    115680
tgtgtattta cacatatatt ttgtgcatgt atattttaa ctaaaaatgt gctaggagtt    115740
agatatgaac tgattttgga ggaggtgata tgctgtagag agagagaatg ggagaatagc    115800
agtattataa tctctctcca ttgtattcag tttttttctt tgtctgaatt tttaatagaa    115860
gtcagccaga agatgttagt ttctgggaaa tgtgttgaga tttacagtca aatccagaga    115920
gaactagagg cttatgagta aataagtaaa ggttatgcag agaaagtatt cttttcctg     115980
tgtaaacttg aatattggcc aggcgcggtg gacacctgta atccagcact tgggaggcc     116040
aaggcgggtg gatcgactga ggtcaggagt tcatgaccag cctgtccaac atggtgaaac    116100
ccattctcta ccaaaaatac aaaaattagt gggtgtggtg gcaggatcct gtaatcccag    116160
ctactacgga ggctgaggca ggagaattgc tttaacctag gaggcggagg ttgcagtgag    116220
ctgagacagc gccattgcac tatagctacg gcgataagag tgagacttca tctaaaaaaa    116280
aaaagaaaa gaaaaccttg aatatttctt gtacttgtgt tcaaatcata cagttatgaa     116340
agtttacccc tagctgttac acttaaaatg tacttctgaa atatacagag agatgataca    116400
gactattaat gagttccact aaactttta tggtttagaa aatacaaata ttttcttatt     116460
tttctggaat tccagccatt aatgtaaaac attggtttca acataaataa cacactggca    116520
tgcacatatg cctaagcatg ggcccccaca catacagaca ttctgaaaga ccactttta     116580
aaaatattca gtaccgtata ttgtgcattc cttctttatc cacatactta agctgctgca    116640
agcatcccat tgataacacc agtaataaaa gatgggacca tcagtaatga gatttgaaag    116700
cccctttgc aagaaagtaa ggactagaag gtggaaatca ctctgtctta gagtcatatg     116760
gattggggct ttgctagaag tgtgtgctct cagggaaagc tgccttttta ttttctccag    116820
agaaaagcct ttttgtcagt aaaagaagat gtatcatcca atgcatatgt aaaattctaa    116880
acagcagata aaacaacatt cactattaat ctctgcaaaa gaagatatat tgaaaaaatc    116940
ctcaagtgtc cctctttggg tttctttgtt atatattaaa gcagttatct ttagatgcat    117000
gagaatcacc tgaagacctt atttttaaaa ttcagattcc tgtcagttca ctcccaagaa    117060
ttccgattca gtagttaaga gacaaagcct aggaatgtga atttacaatc aacacctcag    117120
gtgatagcca tgcatgttct taatgctcta ctactatcta tgcataaaag gaagataaag    117180
ttttaaaaac ttgaaatgtg gtataacagt ttagtattga ataatataca tttttactta    117240
ttgtaacaaa ttatgatatc tacttggggc aacagtatct tttatttgg atctgaatcc      117300
taattttggc taggtatcac tgagggattc ttagtctaaa acaattaaat ggagttagtg    117360
```

```
gttttttttta gtaactcttg attttctgtt tttttccatt ggcatcttac aaaatttatt   117420
cattcatttt tccctttttc acttggcatt atttgttaga cagtggacaa agaactata   117480 gaaagtagag aagcatgtga tgttgtcctg ctcttagatt ctcgcaactc aggagaggac   117540
attcgcttac accaatcatc tcaaaacatg gcagtttatg ctgaactcag tccaatggga   117600
gagcatttga ctgagcacat agggagagaa gttagctctg ttgaaggata atcaacgaag   117660
aattcttagg aaaggtacag tcattcattg aatatttgct cggcacttac taggtgcata   117720
tgtgcactaa gatctaagga tgggctgatg aagaacccag gtcccttttc ttctagtgga   117780
catgcagact ggcctaaaaa aaaaaaggta actggaaaat ggataaggaa actgagtcac   117840
tcggtttatt tattatcact cggtttattt gcttttgttt gtattttcat tttgacacag   117900
cacagtgtca tcttaacgca tcctccaaag tgaaggatgg ggtggataac actttagttg   117960
gcatttctgt agccaggagc caggatcttt ctcccataat tgcattaacc tgggaaggca   118020
ccctctaggt agatttgtat agcaccctgg ttaatcaatt atcagtttac ttcttgtctc   118080
actaagcttt aacaccttac atttatgaag cagtgtaaat ataactttag catcttgatc   118140
acagcaagca cctgatttgt attttttttat tagctcaagt gaaatcagat cagagaagta   118200
cattacaggt cataaaatat gtgcaaattt cataatgacc tcctttaaa atgtgcaaaa   118260 ataagattgt taaggcacat tccagagcct tgggggtgt gtgtgtgtgt gtgtgtgtgt   118320
gtgtgtgcgt gtgtgtgtgt gcttgtcttt tgagaatatc tgtatatcag aaaatttggc   118380
tgagaagcaa tcttcttctt agtggttctt tttctctttt gaaataaag tactaaaaat   118440 acttaaagat gcagaacagc aacctgttcc cagtgagact ctcgtttaat taatgtggtg   118500
atctatatag agaaaaggga caattgcaaa agtccctcaa taattatcta accacagtct   118560
ttaggtaatt acagcagaaa gattttcaag acacaaaaca ccctgaaaaa tttgacctct   118620
tattttgatt caggccttc atttcttaaa tattttcttt aatgttgatg tttatgcttg   118680
acaaggtcag cctaatgcca gatgaatccc tggaactcaa acattgctg aattcacagt   118740 tgaaggattt taatataata taccagcttt taaaaatcct acagtgagaa taacaggact   118800
gaataaaaaa attaagaaat gctcaggtag aaataaatag agaaatttag aaaaaaaata   118860
aaacgtattc aaaataagta ttaagcattg gcaaagaaaa aatagtagca gacaattaca   118920
tgttccattt gtaaagatga ttattaatta gtggtcttgc aaaacattgg agaaaatttg   118980
ctgaaccatc acattcataa atattaaaac cacccattag tgaaaatctt tttactaaac   119040
ttcacaactg atagtcaaat aatgttcagt ttttctccat tgcaataaaa aataaaggct   119100
tttgccttca gatcagtctc tgggccttat taattcagtc agccagaagc cacatggaaa   119160
tattttgttt tgttaaaagc cagcttgccc tcatgatctt ttaaaatctt ttaaaatct   119220 tccatcagcc ctctccctga cttgaattat ggcagtgctt tctaaactgg taaactcaat   119280
ctccttggtg tgcctcaaga tagagtacat aaaccctcct tagaaattga gctctcaatt   119340
ctaaattgca ctctccatga gagcaagcaa gaatgctttg ctttgtatta agtggtcaca   119400
atattaaata taaccataga cagcactgta ttttctaaac accttatttt ctttaatga   119460 ctgacataaa ttagatcata agtatacaaa tgcatatctg ttgtatttt cagcaccatg   119520 tgttttttt tcttttttct gagttatttt cctgctttcg gcagccttt ctctcaggtg   119580 ccttgtgatc cacagtggtg tgtgttcaca ctaaccaaag caatagtctt acctgccaga   119640
aatagctgtg acatttaaag agaggtccag gggaaggcac agtgcttaac atccaagtct   119700
gaagagctaa tagtgaaatt ggggcatcag ctacagagag atttaggga agtaacaggc   119760
```

```
aggttaaata ttttatggaa atgatttctg ttctgtatat gattgcaatt aacacatgtc   119820
aatctgtttc attaatttgt taactcatct attatgctat gccatgaaga aaataaaatt   119880
ggagttcttt attttttttga gatggagtct cactctcttg cccaggctgg agtgcagtgg  119940
caggatctca gctcactgca atctccacca cccaggttca agcgattctt ctgcctcagc   120000
cacctgagta actgggacta caggtgcgtg caaccatgcc tggctaattt ttgtattttt   120060
agtagagatg gggtttcacc atgtgggcca ggctggtccc aaactcctga cctcaagtga   120120
tccgcctgtc ttggcctccc aaggtgctgg gattacaggc gtgagccacc gcgcccgcc    120180
acaaaactga agttctaagc ttcagtttag atgctcacta aatgcttgtt ttgcaatacc   120240
tgactgtaac tggcaggaat atgttttgaa agtcctcatt ttccaggtat gcagatgaaa   120300
tataggggca ttatctacta tgtcaaatta taatgattta tcagtggcac atgaaagtcg   120360
cctcacattt cttaatcagt gatataccat tatgtcatgc cacctttttaa tgtaatatgt  120420
ttacatcttt ctttagatgt aagcattcat ttagttcatc acggtggctt tcacacttac   120480
tccaagaacg ctatgagttc ctttgatgtg ctcaagtctc ctgccccagg gagaaaggga   120540
gtggtgagca ggaatcgctt taatctattt acacagatat tttcttttcc atttatttta   120600
aaggaatttt ttttaactta atgagtatgc agtgacggtg gtgatgatga tgatactaag   120660
gtttaaatga ttagatagtc aaatctgggc tggaattgta atactgtttt gactttttaat 120720
cttagagaag ctccagtctg cttatttttct gggcataaac acatgagaac aataacacag  120780
ttctgttatc tgaatgttgt tatattttgt ttgaaacatt cagtgacttt caaatattgt   120840
atttgcctaa gaaaattcaa cagagtcaga cattctcttc caggttaaat ttggtgagtc   120900
tgctaggaaa ataaattttg tgcactggtc attctgatct agtggacgtt ctaataaaag   120960
caccttttgtg ctgcctacgt cttcactttta aagataagat acctgggtac tcgacaccaa 121020
attatagttt gagatctcaa aaatgggata gggaaaccac agctcaaaaa caaaaatact   121080
agcactggaa aagatagaac tagtgaagat gaatcattct ctagacttta aattcagaga   121140
tatcaaaatt aagaaaaagt aggaggaata aaaaagagg gtaagcaaaa caatataagt    121200
ttgtatagca agagggtata aagcaaatac aatatttttc agaaaaatta ataaaaata    121260
gatttacata acattgtttt taatctcaaa gatcaaattt caattttcat ctcatttaa    121320
aacccatatg cacagtctcc tttatataca tcagttgggt gtcaaagtga cttttttctt   121380
gtttccaaat acagttattt ttaaaattta attgtatgat ttaggaattt gaaagcaagc   121440
cagtttgcac acacatatgt tattatatgt gtgctttaga cttggttttt agttaatgta   121500
acatgacagg gccacctgag ttatttgttt acaaactagc tggaaagcca ccctggagga   121560
gaaacctggc aacaaaatgg tctgcagctt tgttattgtt atctatagga ttggatgcca   121620
ttattgctgt aaaatagttc acaagaactc agtctatggg aaagactcaa aaattctttg   121680
cctgttaaag aaaaatcagg atattggact ggttagttta actaaaaagt gatgatactc   121740
agattctgct tggattcact gcttctcagc agttgttttg tttctttcta attgatattt   121800
tattttttcag agaacccatt ataaaactct tcttcttccc ttaaaatcac aaccacacaa  121860
cagcaattaa aacatgcttt gacgtaagac tgatatggtt ttaaacccag cttgactatc   121920
gaatttttta ctttaggcaa aacacctctg acatttatgt cttatcgtca gtaaaaaggg   121980
gtgattaaca gttttacaag attattcaat aaataaatat aaattcctcc ttttccttcc   122040
tttcctttct tcatcttcag catctgcatg ccataagctc attttagttc tctggactca   122100
tgttaacatg tcccacccttt cccaaattaa acatcatctc tgttattggc tccattcttt   122160
```

```
tcctctcatt tgagacaatt ctttatcaac caacaccctc tctgctctgt attgtgaaac   122220
tctgctccta ctacattaac agtctcttgg tttctttaaa aagaagacaa aacaattaaa   122280
gaacagaagc aaaaaatcta ctcaaatccc caattgttac cctcaaaatt aattgtccca   122340
cccctagctt tctcattgca caactctttg tcaaaatgtt ttctaccatc acagccttca   122400
atgatctttc tggttccttt atctcctgaa gtctgacttc tacctccatc tttttctgga   122460
ctattcaaca cactttgaga aaaaacatac ttttgttaaa caggtatgca tccctgaagc   122520
ataaaataca tagtactgaa agtgcacatg tgtggttctt cccattttt ttacagcact    122580
tgaaactgac aagtagtagt accaattact tagtaaaaga ccttttcat ttcatttctg    122640
aaatattgtt attttccttt ttcatcttcc atctctgact acacctccaa ttttacctct   122700
ttgctgcctt ccttcctaag aaagttcttc atgcaatgcc atcttgtttt tcttcacttg   122760
cctctttttc tcactttaat tttatgaact ctgatgactt acctctgtag tgtaactact   122820
caaaatatgt atttctgaag tctcaactcc aatctcatat tttcaactta tatttatgga   122880
ggcatctcag actcaaccta cctaaaaaat ggcttatctg ccctaaaatc tactttgttc   122940
tttttttctc tactgctaat aattatcttc ctagttggtc aagctcaaaa cctaatcatt   123000
tttactcctt gtccctgtgt cagctgtcca cattcaagca gcgtatcatt tctgcacatt   123060
tttcaagcaa gtcagtaact gccttttgtt tgggactgtc ttttcatata gtgaacagcc   123120
ttggaagata gaaatcattt ctccttctaa aacaaaaggc aggtgtgctt gcagccttgg   123180
atagaggtag tgcctctttc taaagcaaag ggacatcttt actggccatt ataaatatc    123240
catgtttcct gagctctgcg ttcctcttt ctaatgcaac ccactgagca tgtaggtgtc    123300
acctgagctt ttctgtggga attgcggctt gaggaatcag tgcaagaaaa tcatgatact   123360
cttgctaatg ctattaatgt gagtagtaaa gttaattgtc tctgacccag cactattgtg   123420
tctttgccca gcactcaaaa gactggcagg cttgcaagta ggacaaaatg ttagattttt   123480
cacagttctt ctgcttataa gtacttgtta aaaccaatta aaacacaact tgtagtttgc   123540
acctataatt ttgtagcatt tgcttcttat ctatgtcact aggatgtgct tagtgacaga   123600
cccatctatc atctattact caagttttg gctgtattcc taggcaacag agagaagggg   123660
aacaaacaag aggacctgtg cacagtttga gaaaggcaaa acaccgagct taattgcaga   123720
cttgaatgta gctagcaaac gaagtaaggc aaaaggttcc ttttttttt tttagatgg    123780
agtctcactc tgtcgccagt ctggagtgca gtggtgctgt ctcggctcac tgcaacctcc   123840
gcctcctggg ttcagcgat  tcttctgcct cagcctcccg agtagctggg actacaggca   123900
tgtgccacca tgcccagcta acttttgtat ttttagtaga cggagtttt caccacgttg    123960
gccaggatgg tctcaatctc ttgaccttgt gatccgccca ttcggcctcc caaagtgctg   124020
agattatagg tgtgagcctc cgttcccggc caaaagtttc cattttttaa atagttgggt   124080
ttttagtttc gattctttcc aaaaaaaggt tttcttaaaa aaataaaatt agcaataaga   124140
tgaaatataa caacaatata atcttattaa gacaatatat gatatacatt tatcaaaata   124200
cttatatttt caaaagtgct taaaataatc tagcacatag tagatgctca gtaaatattt   124260
gatattatga ctgtgcatgg gtcattatag gctactttat gtatatcatt tcatttagta   124320
caacatcact ctgaaaaatg ttttattgtt accgtttttc agttgaaaca tttacgttgc   124380
tcaagatctc actggtacca tctactatta ggtcagtctg ccaccaaatc tcatgctctt   124440
aaatgccctt tttctcctga gcttccaaca aatagtgtac tgtatataat tgttgaaggg   124500
aggggactgt gagacaaaat atttagagtg aatgtgtagc cacaatttca gttcctcaac   124560
```

```
aaagtgataa aattaggaat catcctcaat atatattctt ccaacacaca cacacacata  124620
cacacacaca cacacacaaa taccacaagc ccacttgaat gcaccccacc tacacattgc  124680
aaccatagag acaattgcag cattaaatac agaatattct gtgtgttgtt tgtttgttct  124740
cccctttgcta caaaaatcag aatttctact caataaacag caaagggaga tacaaatgaa  124800
ccaaattaaa gaaggaaaaa atgttgaaaa aattatatac agaactatgt attgatttat  124860
tgagagttca gtaatgtaat ccagaaataa tggatgcctt aaaagtaatt aaaagaatgc  124920
aaataaacat ttagtgccaa ttaaagaaaa agaaatacaa cattagacaa aataaaagat  124980
attcatttga tgcaatgagg aaataatctt ttattcctct ttaaattctc tgtggaataa  125040
ggcatggtta taaataaata aacatctgcc ccatggactt aatggatcgt tatattttat  125100
tgcgataatc ataatgaaat tgttgggagg gattagtatc tctagtgtaa tgctaagaaa  125160
gataaagcct gtgcccaggc aaaagctttc ttggttggtc aaaaggtttg aagacatttc  125220
aaactattct aaaacaaaca aacaagcaaa caaacaaaaa acatacaatg tctttgccac  125280
atatttagga aacaaaatga acaatttatt tctgacaacc tcatagtctt tgttctgtca  125340
gaacaataat ggaaaggtct aaaccagaaa atgctatgca ttgaatttat aataaactat  125400
tttttcctgt aacaaaaaat tgataaactt gatatttgca gatttaatga ttatgtgttt  125460
aaaaaaaatc tggttttttgc ccttgcaaaa aatcatatat atacacatag atatgtatgt  125520
gtgtgtgtgc atagtatata tatatgtata tacatatata tacacacatt tatatatata  125580
aacatttcct ttaacctcct attttattcc aataaaaata ttggtattag agatagttct  125640
gatatttcat catgaatagt taacattgca tttggaaagg attaattttt ttgaaacgta  125700
attttacctt aataagtagc ccagcgtaat attttagtaa ttacacagat ttttttttca  125760
agacatttga caactaatat tgcataatag ttaagagtgt gggctttgga gccagacttc  125820
ctatctctgt tcattcactg ataaaatgga gacagtagta acttcctcaa agagttgttt  125880
tttaagatca aataatgcat ataaaactct tgaaatggta ccaaatacag agtaagcacc  125940
aaataaacat taactgttat tgttattcca tgtccgaata acacagaaaa gtaagaattt  126000
taatatttca tttgaatgac cttttaagga tacacctagc ccattatctt tcttgataat  126060
cttgtaagat gattcctttt ttatctccga tctgttgagg catggataga ggttttcaga  126120
gaaacattt tctaggtaac tgaaagaaag tagcaacaac aaactgtgac aaaacttaac  126180
aatgagagaa tttacaagat agaataattg caactccttt tgaaatcaac cactatggtc  126240
ctctggctgg gatagctaag caaagatatt ccagcctgaa ggttgagatc tacttgaaga  126300
gttttctatc cagattgtga gggcccctca aacttcactt agtatctgtt tctattagta  126360
tggaaacttc tggaaccttg tggtatcaca ttcacttgac tactttattc ctgctctagc  126420
tatcttaaag ccttttcttaa tcttttatct tttagagaag atacttctag gttttaaatc  126480
caccgatctt gaagctattg ccttcactct ctgcttcaga gcccatcctt ttgtatatga  126540
gtagtttgtt ttgcctaaag tactttctcc cagtcagatt ttaagtccag tttctcatct  126600
gttttttgaga gcaaactcct gggccttggc tcactaacat cttgacagca tatttcttct  126660
ttcctatggg cttttcagca ttccctgggt ttttctaaaa tatgaaagca gactctttat  126720
ctcttacttt gtcaaagcct accctcccca ctgatttctc acccagttgc tagttttaag  126780
acctgcctct ggccgggcgc agtggctcac gcctgtaatc ccagcacttt gggaggccaa  126840
ggtaggtgga tcacgaggtc aggagatcga gaccatcctg gctaacacag tgaaaccctg  126900
tctctactaa aattacaaaa aaattagcca ggcgtggtgg tgagcgcctg tagtcccagc  126960
```

```
tactcgggag gctgaagcag gagaatggcg tgatcccgtg aggcagagct tgcagtgagc   127020
tgagatcgcg ccactgcact ccagcctggg cgacagagcg agactctgtc tcaaaaaaaa   127080 aaaaaaaaa aaaaaaaaaa aaagacctgc ctccaaatat cattgtattt gcaaacatga   127140
aatgacttat tgattctgag ctcagcacaa gagcaaacct ttctcagctt gacccatctt   127200
cacatcgtta atgtcttatt cagtcactac ccaaggggct gaccttcaag attctaatcc   127260
atgaaagctt aaaatagtaa acaaatttga atatagttta acatacataa taaattttat   127320
ttctagaaga ggaggatcag cccttagaca tgaaaagtaa aaatagttta ttcccagatt   127380
tccctttgtg cattagtata ttcaaccgag tctatccaag taacaggaca aaaaagctg   127440 gcagttgttg ctgcgctgtg aagtcttatt aggtgagtca gctaattata tggcactacc   127500
ataaatacag caggcactgc cctgcttgtt aggcttgcca aggaaaataa ggatttaaag   127560
cagcatacta cctctttgct atataatgac atttcttct taaaaatgat tttgcaccaa   127620
ttcctgattt atccaccaat tattttttaa tttatggttg aatgtattta aacctgaatt   127680
cagagataaa actagtaaat agctccccaa aataacccca aatatattta atatattagc   127740
tttactctct cctccactgc caaaccttta aaaactgaaa taaattgttt ttatttcatc   127800
ttttctcttt ttctctctct ctaaggtgat tgccaagact aaagaaacag ctagaagggc   127860
aaaagacaag aaaatcagta agatagtaac agattatcca aagtagagca cggctcaggt   127920
gcagtggctc atgcctgtaa tcccagcact ttcggaggct gacgcaggag gatcacttga   127980
gtccaggagt ttgagaccag cctgggcaac ataatgaaac ttcatctcta taaaaaaaaa   128040
aaatttaaat agccgagcat ggtggtgtaa gcctatagtc ccagctattt gggaggctga   128100
ggctggagga tcacttgggc ccaggagttg gagactacag tgagctatga ttgtatcact   128160
gcattacagc ctgggcaata gggcaagacc ctgcctctaa acaaaagata aacaaagtag   128220
agcataaatg gcttctaaat atatgttatt tatgtgtaag actgggttct ctaaaggtat   128280
catttaatta aaatagattt gcattctcaa tctgtaggta tggattatgt ataatgtatt   128340
taagatatga cttacagcgt tcaccaatgt gactattccc aagtgatcca gatggctgat   128400
gacatagtaa tttgtacatt tgctgagacc tgatctgagt aggtatgtaa cataactgag   128460
ggagagcaag tccatttgcc gaaagaaagc ctagcatatg acccaggagc cacatcttca   128520
ctcagccttg ttgctaggtt tggcttagca tatataatag catagcatgt ataatttatg   128580
acaaaaaatt atactttgca cttttttaatt agaacattca aaatgatctc aggaagtggc   128640
accagagatc atcagtggtc tactgtactt cgtgtgtatt tgtctgtgag tatgtatgtg   128700
tttgtgtgtg ttcccacatt ctaaggcatg tcttttacag gttagtagaa aatgttgata   128760
gaaaattata gatttcaaca tctaaaacac agtaggtcac tacattgtta aaacttggaa   128820
ttttttatct tgttgtaaag tcaggccaac caaacctaaa atactgctac attgaaatag   128880
tgcaaaatat tcaaaatact atagttatag atttggtagt aggactgtac cagacctgtc   128940
actctataca agacttatgc cttgcccttt cacttacctg ttcccttta catctatctt   129000 actagatgta atgctataaa ttatatttct aatatattat aatttatcat gtattataat   129060
gtatcaaata ttacaaatta tgttgcaact ccccttacct ttcgtctgca tattgcctca   129120
gaaagaacag atggatccaa cagacttcaa ccacaggccc ttagtgacaa atagctctta   129180
atgctgggct tgccactttg atgcatttct aaagttatag aatgttaaat gcaccaagtc   129240
ctttggtcat tttatttcta ccttagatct aagccataac tatactttcc caaaaattaa   129300
agtttgaatt ttaacttaac catatataat tggaaaagga ggttgggttc gttaagtgta   129360
```

```
attttatcat gctttattat cctttgggca ttggatacag cagaacatgc caatttctat   129420
ggcttctcat gtgacagaat atacttacta ggatgcaatt aaatactcct cagagtatgt   129480
aaacaataaa tgtaatcatt acattatttt tatattgttc tttcttatgc ataatagtaa   129540
gactgaaaat atagtgttat ttctgaaata tgcatattgt tttgcttttg atgattaaat   129600
aacattgtcc aaagttttag gttttttgaa atcttatatt ttttaacaaa atatctagcc   129660
tttccaaaac aagacctcaa taattcgttt aagacccaga gttgttcctc tccacataga   129720
tctcttaaaa aggcagagga tttatgacct caagagaaat cagagtatcc aaagtttgct   129780
ttaattcaat gttttaaaaa taaaattcct tagattttat caaaaattga gattagtttg   129840
attttgaatc agatgcccct tgctccccac cccaaaatgg cattatgagc agactaggaa   129900
ttgataatag aaaattgaac atatgaaata tatctttacc ttgcttttta acaaggtatt   129960
catgtctatc gccttcattt ttaagtgcat caataaaata catggtaatt ctcttagtga   130020
aatatactat ctacactatg tacacactcc cctgtctgag gtagagaagt agagaatatt   130080
cacatttttg aaacgtctat gctattttta tttaaatacg agttctgggc ttgatttcat   130140
tttggaacac gggtgtgtgc ttaagttgaa ccttttttttc ctcttaagtc aaagttcttt   130200
tttagtttct tcttttatct ttttggctac tatctctctc cttcatcctc ctggtgtgag   130260
ttgttgagtg aaggtattaa ttccattatt tgaggctaag tgacattgtt caataatgca   130320
gcaaaacaat ggttctaccc aaaatatctt caagtgtaaa agcagtgggc aaaagagaaa   130380
gtgcgcttct gctgctttga atgtttaagg ctgtgaaagt tgatcacaca aattgggtca   130440
ttcttgttat acccaactaa aacaatcaag aagcctggga ggaaaagcat tcaagaaaca   130500
tcacattgct ccaaaagtgt aattttctac aagtccgcat gctgaggctg cctgttgtaa   130560
cctgggacca atttttttctg taactgctga aaaaacttgc tgcagctcta ggactaattt   130620
tgcccaccac tgtcactcac caattgaagc ttactagctc cccagaacct ttctagtgcc   130680
aatgaacttt ctcaaagagc agcgtgtatc atttctcttt ttcagaacac ctccaacctc   130740
ctctttgttc tttgggtata ccaaagacca accagccttg aatttcaatt tttcttccca   130800
cataaaagtt ttaatttaga aatgtatctc tacatttcta actttgacaa agcatagata   130860
ccagataatt gatgaaacct tgctatttta acgatcacca tggattactt cccagtgtct   130920
tcagataacc ctcaacattt gccaacattt gatggacttc aaaatgagca tatctttttt   130980
aaaaaaaatt attcacactg acagcaagta cattggtata ctctatatta aattatacca   131040
cagggtttac aaacaattgg tgatgtcggg cagtggtttc caaggaacat acttaacaag   131100
acactcacaa ggccctacaa acctgcattt ttaacaaggg ccctagatga ttctagaaga   131160
gtgtggtttg gaaagcaatt tttgcccttta ttatgtgtca ttttaaatat atttaaaatt   131220
aaagttataa gtcatagaat tgaataaaga taatttcctt acagaaagta ttactaggta   131280
tctaaataca atatggttca aaacaggaaa tttaaaaaga ttatgtaaat tctgtagttg   131340
tattcctaaa gacagtagct gaaattttttt cctacttctc cttgtatcac ttcccttttc   131400
cttcactttc acttccctgg aattgtactt cccaataagc tattagcagt gaaggaagct   131460
tcgtctcatg atctgtttta tagagcactt cagctgggac gagtacgaaa tgataatcag   131520
ttatatcagc tattcaaccc tacaggttta tttaaaaaga acttgaataa gcttttttagg   131580
gagaaagagg tcagtctcag ccatttctgt ttcctaatat agctttttaag tctttcctta   131640
ttagcaatga gggtcattcc attgtaattt tttgataacc attttttcttt ctgtgtgtca   131700
aatgcagata taagatactg aactgagtct atttcactgt tcgtaaaaca atcccatttg   131760
```

```
aaaaaaaaaa gtctacagct attccaggga tagggcctag tagagagaga ataaaaggta   131820
ttttcttact atgtctctat atcctaccct gtaggttctc ttattaagca tacaggcata   131880
taccaaaatc cagacgtttt tctcatttat tttattgccc taacatattc tgggttaata   131940
taatatcata atgaaaattt gagaaaaaat tgattttttc aaaagtgttt aacatttgtt   132000
atattggtag ttttttttct tgtttgtggt aaaaataaat agaaggtgca cttcacacct   132060
tcaagtatga ttatattttg aaaacaagtc atgaatactc ataaaatgca aattttaatg   132120
ttcttttttt gttacagcca aactatatta ggcacagttg taaattggag ttgaaattta   132180
atatttcttt atagataaca atgtttttag aaataggttt atgaaacagt aaatatacag   132240
gtatagggat aaaattgtgt ctgatggtca tatgaagtgt ttgttgttat attctccttg   132300
gaatagctgc caaatatttt agtatgctta aaatctacga atgtgataga gtcaacaaat   132360
ttagatcaca tattcagaaa aacatagtta gagaactaac tattgaaatg agcatacagc   132420
agtcttcctt tatctacagg gatacattct gaaaccccca ctaggacacc tgaaattgcg   132480
gatagtagca aaccctacat atactgtttt ttccaatgct tatgtaccta tgaaaaagtt   132540
taatttataa actaggcaca gtaagagatt aacaacaata actaataaca aaagagaaca   132600
attataataa tatactgtaa taaaagttat gtgggtatgg tctcgctttc tctttccctc   132660
tctctctgtc tctaaatatc ttagtatttt ggggttgcaa ttggtggtgg gcaactgaaa   132720
ccatggaaaa caaaaccacg gataaaagga gactactgta tatactttt aaaactgatg   132780 aaatattaaa ctcatgtttc ttctatatcc cacccatttc ccccacccaa acctagatag   132840
atatcttatt tgatctgtaa acatttaatt aatttgtaaa agttaagaac tttttgaagt   132900
aaaactgcaa tatatcatca cacctaaaga aataaacaat aattcttaaa tatcaagtca   132960
gtgttcaaat ttccccaact acctcatatg tgttttccat ttgcttatgt agggttccca   133020
atgagaatga aataaagttc ttaggttgca attggctaat gctctctcac ttctacttta   133080
agcggcaggt tcccactaac ttcttttag ttgcaattta cttattgaaa ttagacgtat   133140
tctttgtctt gtgtagtttc tcacagtgca aaatttgctg attgtagcca ctgttgtaag   133200
caatgaacat gtttttcacc accttatatt tgctgtaagt tgtcagtgat agttaaatgt   133260
taatcaaatt caaattcgga tcacgtaggg cttttctttt tttgttttct ttttctattt   133320
atatatttat ttatttattt tgagacggag tctcactccg tcaccaggct ggagtgcaat   133380
ggtgtgatct gggctcactg caatctccac ctcccgggtt caagtgattc ccctggctca   133440
gtctcccgag tagctgggac tataggaaaa ccaccacgcc cggctaactt tttgtatttt   133500
agtagagatg gggtttcacc atgttggcca ggatgctata gatctcctga cctcaccgat   133560
catgtaggac ttcaattgtc gaacaaacga acctttaata gcagttacac cattaggatg   133620
acctgatcca acatcgaggt cgtaaaccct attgtcgatt tggactctag aataggattg   133680
tgctgtcatc cctagtgtag cttgttccca cttgatgaag ttattggatc agtgaacaat   133740
agcccactta aactagtaca gtcttagttt aagatggtga tgtgtatgta cttccatcag   133800
agggcacata atacagtaaa tcctcactta acttcatcaa tagtttctgg aaactgtgac   133860
ttgaagcaaa acaacatata acaaaaccag ttttaccatt ggctaattga tataagcaag   133920
aattaagtcc tatggcaaat ttctggacac aaaaacacca tcaaactcct aaataaagat   133980
aaatcacttc tgacattaaa cattgaaatt aatgtgagct atatatacgt ttaagaaaga   134040
ttaatacaaa caagtcaaat aacttaccta attatttcgg tggaggccgc aggtggttgg   134100
agcctatcct ggcagctcag ggagcaatat gggaacccac cccggacagg acgctgttcc   134160
```

```
attactgcag ggtgctcttg tacacaccca ctcacccagg ctggaaccat gcagacacac  134220
acactcacct aacctacaca tctgtgtaca tccttcaaag ttcagccaaa taacatataa  134280
acaaatccag taatatccat cagtcttagt tccgtcataa caactccttt ttgatcatca  134340
aacaacaaac agggtaggtc tgccatattt acttgtctgg tccatatcaa aattttctaa  134400
caaattatat tagaaaatca aatctctgtc agtttcaaaa tcatggaaaa aaatttgcct  134460
tatttccctt atacttggat atcctaacag taatctaaat attaatgaga aagttaatga  134520
tgtcgtttcc ttctccctgt tgtaaagaag gttttgctgt cccgtttgat cactaagact  134580
aattgacact cagaaaaagc ataggaaact tctcagcatc acaaaagctc tgtcatctag  134640
agaagctagg acttgagctc aagtcctgtg acatggaagg ccttgtgcct agccatcctg  134700
cagcagaggc gtatctacca agaagtgaaa cactacgaaa acagtatgtt tactccacat  134760
tttaaagtga ggtagtttgg ggtggttcat attttattta atttatatat tatttggatt  134820
tttttttagtt tataaaaagg gcattggcaa gggcagaatg atctgtaagc ttctctgccc  134880
acctaccata agcatgatct ttagtgtgac cttttcttac tgttagccat tttcttatac  134940
ttctgcgtcc ctgtcagtca cttccatgtg aagacatggg gaagcttttt tacatcagac  135000
atgttgttga aaatcagccg cgttggctga gggattattt gatctctttc tccaagtccc  135060
tttaggctca cattgcctct ctgttctttg aattttcact tacctttatc ttcttataat  135120
tactttgctg aaataaatgc aaagcaacaa aaggtattta gtgaagaata ccaacaaagc  135180
catgaccatt tcaggctgag ttttgtagta ttctttgtct aggaagagat acctagaaaa  135240
attttctgac catgtatttg attattttcc ttcaatatgt atagtctcag tcttcaaatt  135300
tcagaaaaga atttgtttct tcattgtcat taaaattaa tgtgttaaat atgtatgctt  135360
ttacattata agtggttata aaagttaaac acttagaaaa aaagtcaaaa taacatacat  135420
actatccaac aaaataactt tcatatttta ttgtgttttc ttccaaactt tttacctttg  135480
cgtctgaatt ctgtgtaggt tgtatctata atatagacaa cacttatag cctgctaaat  135540
attataccat aaataggtag ttgttacata attctcaggt aatagtaata caggtcttta  135600
tcataatcta ctgagtagtt gaatgataat ttttttttaag acaaggtctc cctctgtcac  135660
ccaggctaga atgcagtggc atgcacatgg ctcactgtag cctctacctc ccaggctcaa  135720
gtgatcctcc tgcctcagcc tcccaagtgg ctgggactgt aggcatgtgc caccatgccc  135780
agctatttat ttgtattttt agtagagatg gggtttcatt gtaacagccc aggctggtct  135840
tgaactcctg gactcaaatg atccacctgc ctcagcctcc caaagtgctg aaatcacagg  135900
agtgaaccac tgcacccagc aataattttt taactcttca ttattcattg aacatttagt  135960
taacaattct aaaaattttg tttcctgctg tcattgatct tgtgaaaaat atctttggac  136020
tatagctgtg gattatttcc taaatagtaa attacttgag caaaaagttt acatactttg  136080
agggttgata acccatgttg ccgcaatgtt tccccggagg cattgtggag tttagaatgc  136140
cagtagtaat attaaggtgt gccatttttca agatccgtgg ccaacatccc tatatgtaag  136200
attttttccaa aacatggttc tgattttttaa aagtgaaaaa tgctacttca tcatgttctt  136260
tttgtgcttc ttactttaaa tattagaatg aagaaggagc cccacaggaa ggaattctgg  136320
aagatatgcc tgtggatcct gacaatgagg cttatgaaat gccttctgag gtaggagtcc  136380
aagctgaatc tttctaacaa gacagtacca aaaacctgtc attgtcacat ttctctttca  136440
ttagtgctta gtgagaatca tttgctctct acatgctcat tacgtggaca acttgcaagt  136500
taagaatagt ttttacattt ttaaagggtc cttaaaaaaa aagaggagga ggaagatgaa  136560
```

```
gaagaggaag aaaggatgta aaagaaatca tatgtagtcc acatagctta atatacttac   136620
tacttgaccc tttacaggaa aagtttacta accccctgcat tagagaatat attttttagaa  136680 actttacatt ctaaaataaa tttctaaatg gaaagttagg gaaatcaatg gaatgccaaa   136740
ggaaggttat tattttttgc catacatgtc caatgggatg acgcatagta aaataaaagt   136800
tacccacaca agttatagaa taaaaagata aatgcatgat ttgcgacaat tgatatattc   136860
cagtataatg ttttaaacaa cacaatatga ttgttaattt tattttgatt gaaaatgaaa   136920
gtatctttaa tagaaaatgt atcaaaaggg aaattagaaa atactgttag atgaataaaa   136980
ctggcccaag aagaaacagt aaatctgaat agatttgtaa cacagcgaat agattaaatt   137040
agtaataaaa aaaaaaacct acctgcaaag aaaatcccag gccgagatgg catcactggt   137100
aaattctacc aaacatttaa agaggaatta atactaatta gttaacacca attaatatct   137160
cttacaaaac agaagaggag acatttccca actaattttg tgagaccaat attaccctga   137220
taatcaaaac caaacgaaga tatcacaaga aaagaaacta tataatggct ccattaaaaa   137280
ttgagttcaa gtatgttgta gtttggttat gtattattcc tcacggcatt attaaaaggc   137340
atgtcgagga tggcacagc agttcacacc tgtaatcccg cactttgtga gccaaagtgg   137400
ccaggttact tgaggccagg agttggagac cagtctggcc aacatggtga aaccccatct   137460
ctactaaaaa tacaaaaatt agccgggcat ggtggtacac gcctatggtt ccagctactt   137520
gggaggctga ggcatgagag tcacttgaac ccaggaggca gaggttgcag tgagctgaga   137580 tggcaccct gcactccaat cttggtaaca gagcaagact gtctcacaca gacacacgaa   137640
aggcatattg ataataattc aacttataga aattgagatt aaattgtttg tttgcctaat   137700
aagaatttcc aatattttgg ggtcttttat gcaagacaca gtactaaaca caatggaaaa   137760
ctatagagta attgacatta ccaggacata aggagtttac agtctggtag gtttgatgaa   137820
aaaaaataga aattcattca ttcatttctt cattatgatt cctttaacaa acataattga   137880
ttgtcttcga tgtaccaggc atcacaggag caaaaatata taagacatac taaaaagtaa   137940
aacattttaa agatctgttt caatcaatca ggagaagttt tattgaggag gtaatgttga   138000
tctgggtggg aaaaggtaag agatatagta ggtcaaaaca aacagaggac attctggcac   138060
aagggaatat cagaagcaaa ggcatgtatg tctgagcatg caaatggata tgtctgagaa   138120
cagtgaataa ttatgactca agcttaggaa caaggaaaat ggtgatagat tgaatttgca   138180
gctatgggtc aaagacaagt tatagagtat taggataatc ttgtcatttc agcttgtatt   138240
ctattcagaa acaacttga gttattgaag ttatgcttat ttgtttgttt ttaagcagaa   138300
tcctgatatt attagagttg ctcttttagga ggaataatct gatcccttta attaaatcca   138360
ttaatatttg tgttgtggat gctatccaga tactgtatgg agagcttgag gtttgaaata   138420
caagtaataa ttgaagccat agatgaagac gaaattttca actgggagag tgaaagtagg   138480
gaaaatgtat cttgccttca aacatcttaa tttccttctg agaattagag catcttagtc   138540
tggaaaaggc tttatagaca gcttgatttt gttctcacat tttacaggtg aagaaactga   138600
gaaccagaca gtccaactta tttgtcctac caaactaggt atatgatcat taaatggtgc   138660
atccggatca gaacctagat atttaactc tgactactac tgtaattcac ttttatatca   138720
gacaagaaag acacaactat taaaaataag ataatatttg ctgcagaata tttgcaaaaa   138780
cattgattgt aaatttttagt gtaagtgggg agccattcc tatctcattg gctgtcagtg   138840
ctgatgcgta attgaaactt atactaacag tgtgtgctgt ctttttgatt tttctaatat   138900
taggaagggt atcaagacta cgaacctgaa gcctaagaaa tatctttgct cccagtttct   138960
```

```
tgagatctgc tgacagatgt tccatcctgt acaagtgctc agttccaatg tgcccagtca   139020
tgacatttct caaagttttt acagtgtatc tcgaagtctt ccatcagcag tgattgaagt   139080
atctgtacct gcccccactc agcatttcgg tgcttccctt tcactgaagt gaatacatgg   139140
tagcagggtc tttgtgtgct gtggattttg tggcttcaat ctacgatgtt aaaacaaatt   139200
aaaaacacct aagtgactac cacttatttc taaatcctca ctatttttt gttgctgttg    139260 ttcagaagtt gttagtgatt tgctatcata tattataaga tttttaggtg tcttttaatg   139320
atactgtcta agaataatga cgtattgtga aatttgttaa tatatataat acttaaaaat   139380
atgtgagcat gaaactatgc acctataaat actaaatatg aaattttacc attttgcgat   139440
gtgttttatt cacttgtgtt tgtatataaa tggtgagaat taaaataaaa cgttatctca   139500
ttgcaaaaat atttatttt tatcccatct cactttaata ataaaaatca tgcttataag    139560
caacatgaat taagaactga cacaaaggac aaaaatataa agttattaat agccatttga   139620
agaaggagga attttagaag aggtagagaa aatggaacat taaccctaca ctcggaattc   139680
cctgaagcaa cactgccaga agtgtgtttt ggtatgcact ggttccttaa gtggctgtga   139740
ttaattattg aaagtggggt gttgaagacc ccaactacta ttgtagagtg gtctatttct   139800
cccttcaatc ctgtcaatgt ttgctttacg tattttgggg aactgttgtt tgatgtgtat   139860
gtgtttataa ttgttataca ttttaattg agccttttat taacatatat tgttatttt    139920 gtctcgaaat aattttttag ttaaaatcta ttttgtctga tattggtgtg aatgctgtac   139980
ctttctgaca ataaataata ttcgaccatg aataaaaaa aaaaaaagt gggttcccgg     140040 gaactaagca gtgtagaaga tgattttgac tacaccctcc ttagagagcc ataagacaca   140100
ttagcacata ttagcacatt caaggctctg agagaatgtg gttaactttg tttaactcag   140160
cattcctcac tttttttt taatcatcag aaattctctc tctctctctc tcttttctc     140220 tcgctctctt tttttttt tttttttta caggaaatgc cttttaaacat cgttggaact    140280 accagagtca ccttaaagga gatcaattct ctagactgat aaaaatttca tggcctcctt   140340
taaatgttgc caaatatatg aattctagga tttttcctta ggaaaggttt ttctctttca   140400
gggaagatct attaactccc catgggtgct gaaaataaac ttgatggtga aaaactctgt   140460
ataaattaat ttaaaaatta tttggtttct ctttttaatt attctggggc atagtcattt   140520
ctaaaagtca ctagtagaaa gtataatttc aagcacgaat attctagaca tgctagcagt   140580
ttatatgtat tcatgagtaa tgtgatatat attgggcgct ggtgaggaag gaaggaggaa   140640
tgagtgacta aaggatggt taccatagaa acttcctttt ttacctaatt gaagagagac     140700
tactacagag tgctaagctg catgtgtcat cttacactag agagaaatgg taagtttctt   140760
gttttattta agttatgttt aagcaaggaa aggatttgtt attgaacagt atatttcagg   140820
aaggttagaa agtggcggtt aggatatatt ttaaatctac ctaaagcagc atattttaaa   140880
aatttaaaag tattggtatt aaattaagaa atagaggaca gaactagact gatagcagtg   140940
acctagaaca atttgagatt aggaaagttg tgaccatgaa tttaaggatt tatgtggata   141000
caaattctcc tttaaagtgt ttcttccctt aatatttatc tgacggtaat ttttgagcag   141060
tgaattactt tatatatctt aatagtttat ttgggaccaa acacttaaac aaaaagttct   141120
ttaagtcata taagcctttt caggaagctt gtctcatatt cactcccgag acattcacct   141180
gccaagtggc ctgaggatca atccagtcct aggtttattt tgcagactta cattctccca   141240
agttattcag cctcatatga ctccacggtc ggctttacca aaacagttca gagtgcactt   141300
tggcacacaa ttgggaacag aacaatctaa tgtgtggttt ggtattccaa gtggggtctt   141360
```

```
tttcagaatc tctgcactag tgtgagatgc aaacatgttt cctcatcttt ctggcttatc   141420
cagtatgtag ctatttgtga cataataaat atatacatat atgaaaatat gtatttggtt   141480
tctgcctcca gttcttacaa agagctccta aaacccttgt aatttcctga gtagtagggg   141540
tgctagggtc atcttttgtt ctaatatttg gtctttgact ctgctttctg acagagctcc   141600
ttagtccctg ggtgagagta gcatcttctc ttctaatgaa gtgactcttg ctgggttcct   141660 ggatggggc tggtcaccag aaaggtcaag ccatgataag aagcttgaag cttttggccc    141720
cattcacatc ttctggggac gggagagaag aggagctgga gattgagtta ataagcaaca   141780
atgcttccat gatgaagact ccataaaaat ccctaaaaga caggattcag agtgctttga   141840
aataggtgaa catgcagagg tgctgggaat tgtggtgtgt ccagagaagg catgcaagct   141900 cccacgcct cccccatacc tttccctgtg catctcttcc atctggctgt tcctgagttg    141960
tatcctttta taacaaactg gtaatctagt aagcaaactg ttttcctgaa gtctgtgaat   142020
cacactagca aattatcaaa cctgaggaga gggccgtgga gaccttggat ttgtagacaa   142080
gtcaaacaga agctatgagt aacatgagga ctcattgctt gtgattgtca tcttcagtgg   142140
gaaggggaaa atcttgtaa aactgagtcc ttaacctgtg ggtcaatgct aactccaggt    142200
agatagtgtc cgatttgaat tacgggacac ccagttggta gccacaaaga atgggagaat   142260
tgcttggtgt agaaaacaca ccccacacac acatgtggtg tcagaaatga accggaaata   142320
ttgtgttccg gaaatattga gtgttgtgag tgagtgtata gaaagaaaaa cagcgtttcc   142380
ttttcactac tagattaaaa caaacacact catgcattca cacatctcaa agacaactat   142440
taattctcaa agacagtgct gtctaaatcc atactgagga agaaaacaca ttttcttttc   142500
aaatctgtaa acctgacaga ctgcctctgt ccacacacta atggaactct gtgtttcatc   142560
tgaaatgtgt tcatcccact ttgttctttc tgtcttgggc agggcaagag tgcaacaggg   142620
ctgacatttt catatgagct ctgtccctgt tattggctat actttagaca aattattatg   142680
tgtcaaatat agatgtaagt gatttatcaa tattaagtca tttaattctc aaaacaacct   142740
taataggttc cattatgatt ctaattttac acataagcca aaggaggcac ccacaggcta   142800
gataactttc ccacggccac acagctagta agcggcagag ccaagaggcc caacattaca   142860
gcaccacagt ctgtgctctc agccccttgg ccacatagtg tcagagtgag gacacacagc   142920
tatttaagaa aacttccaga agtctaggaa atggggtgat agccccactt ttctaggtat   142980
aataattaga tatttgtttt tcttcaggta cctaaagaaa atttactaga gtttgagcct   143040
ttagtaagtt ttgctagtac atctgttttt cttcaggtgc ctgaagacaa acatatacac   143100
acacacacac acacaaacac acacaaaatg tgtatctata tatatgtgta cacatatctc   143160
tcatctctat atatatgtct ctgtatatct atatatctat aaacatatct atatctatag   143220
atacatatag agagatttct ttttttttt ttttgagatg gagtcttgct cttgccacct    143280
aggctggagt gcaatggcac aatctcagtt cactgcaacc tccgcctccc aggttcaagc   143340
gattctcctg cctcagcctc tcgagtaggt gggattacag gaacacacca ccttagcccg   143400 actaatttt gtattttag tagagacagg gttcaccacg ttggccaggc tggtctcaaa     143460
ctcctgacct caggtaatcc acctacctcg gcctcccaaa gtgctgggat tacaggtgtg   143520
agccaccatg cctggccaag atttctaatt ctaagagaaa ttagcacctg ataggtattt   143580
ccttgtaaat aaaccgggca tatcctgatt atagaactaa gttaattatt ttccgtggaa   143640
gatacgaatt ttgatgcaat aagagcagca gtctacagta aggtgggctt tgtaattttc   143700
tgtgttgaat catggcatgg gtacttggct tatgtcaaat agacaaaaaa atataaatta   143760
```

-continued

```
aggtataact gggattgtca attatacata tttagtaatg gaatgaatga atttataaat 143820
agatagtaaa gggcatgaat taagaatcta taggtataaa taatattagc aacttaatat 143880
tgtataataa agtttgattt tctaggtgta gttgattgat gcagtaatgt tcgttttatc 143940
ctttgagtaa gcctagaatt gaagaaccca aaatgcaata gaatagatat aacattgaaa 144000
ctattcctaa atatgatttt agttccaatg ttctttgtgt aattacctaa gcttttcttt 144060 aatgttttg ctgctactac agtatcctta attatttgaa atcttatatt ggaagcagtt 144120
aaaccacatt ccttcaaaga gcccttagtt tgagcctcta gtaagttttg ctagtataat 144180
ttggttttaa aattggctag aattgcatag ggaatttcca taacgtatag ttgatctgca 144240
actataggtt aacatactag gatggcttct cttatgaacc ttatgaaaat acatcctcag 144300
attccctgga aggtcagtga ccagaaatcc tcgttgtttc tatggcaaca cagcaagata 144360
tggtgccttg gaaatgtgct gcattttaat taggttcctc tagggcttcc taactgcctt 144420
ttgcaggtaa actaaatatc agattgcctt ttatcttgca acaaaatgaa acctaaccca 144480
tgtctgtaaa tgtcaaagct aagctgtgtt ccagtaaagc tgaatccaaa caaatatagt 144540
agcaagtcat gttttttatct tagaaaagaa tacaatactc tttacctaga atagtcaagg 144600
atgctgctta atgaggtagg ttagagtaat agagactatc ctgaactcca aaactattaa 144660
tagactatgg aacttcgact cccatttatg tctcttacta cttaatatta gtgtctctgt 144720
ttccttatat gtaaatatgc aaatgataaa aatagtgcct catagcattg ttgcatgcat 144780
taagtgagtt aatgtaagtg gaatacttag gactgcctgg ctgatagtaa gtgatctatg 144840
agtcaatgat gctatttatt agtagtagta ctagtacagc acactgtatt tttaaaggta 144900
aataagaaat aacaattttt ttaaatgttc atatacattc acatgtcttc ttttaatata 144960
aaatagcaat caagatcagg ataatggtag agatattttg gagacacaag gcagaagcta 145020
tttactaata gctaggggag catttttacta gttactaac caatattact atacttatgt 145080
gtacttagca gaatatcacc tagcaccaaa aagaaattaa gaaagtgtaa cttactgaga 145140
agtgaatatg caccaactcc ataaacacta tgtttatgga acacatctaa ctttagactt 145200
agctatactc atcgactcac atatcttctc atccaagtgg gatgtgttta atatttacca 145260
tatattcata agttcactga gtattgttct ggtaactaga aaaaaaaag gacaagcata 145320 tataagtaaa actcactgat ttaaaacaga gtattatcaa ctacaaaaga aaaaaaaac 145380 cacttgaacc tccactgatt tctcaaatct catttatttc ccattatctt ccctcatacc 145440
tcttgcattt atttggttaa atttcttttt gatccaaaag gaagcaatgt ttacctgaca 145500
atttctactt tatgccagaa caacaaatgt accagcaatt acaatatttc caagaaaagt 145560
attgtttgtt ttctcttcat gtctttggtg agtctctcgg aattag            145606
```

```
<210> SEQ ID NO 8
<211> LENGTH: 4349
<212> TYPE: DNA
<213> ORGANISM: Homo sapiens
<220> FEATURE:
<221> NAME/KEY: misc_feature
<222> LOCATION: (1)..(4349)
<223> OTHER INFORMATION: LOCUS      DRPLA                 4349 bp
      mRNA      linear    P
      RI 13-MAY-2002 DEFINITION  Homo sapiens
      dentatorubral-pallidoluysian atrophy (at rophin-1) (DRPLA), mRNA.
      ACCESSION   XM_032588
<300> PUBLICATION INFORMATION:
<308> DATABASE ACCESSION NUMBER: XM_032588
<309> DATABASE ENTRY DATE: 2002-05-13
<313> RELEVANT RESIDUES IN SEQ ID NO: (1)..(4349)
```

<400> SEQUENCE: 8

```
acgccatact ggacgccaag tgggaggaac ttcaaggctg tccectgcgg gcctcccgct      60
ctgcttctgc gaaggtttca ttgaaaacag atcctgcaaa agttccaggt gcccacactg     120
gaaacttgga gatcctgctt cccagaccac agctgtgggg aacttggggt ggagcagaga     180
agtttctgta ttcagctgcc caggcagagg agaatggggt ctccacagcc tgaagaatga     240
agacacgaca gaataaagac tcgatgtcaa tgaggagtgg acggaagaaa gaggcccctg     300
ggccccggga agaactgaga tcgagggcc gggcctcccc tggagggtc agcacgtcca       360
gcagtgatgg caaagctgag aagtccaggc agacagccaa gaaggcccga gtagaggaag     420
cctccacccc aaaggtcaac aagcagggtc ggagtgagga gatctcagag agtgaaagtg     480
aggagaccaa tgcaccaaaa aagaccaaaa ctgagcagga actccctcgg ccacagtctc     540
cctccgatct ggatagcttg gacgggcgga gccttaatga tgatggcagc agcgacccta     600
gggatatcga ccaggacaac cgaagcacgt cccccagtat ctacagccct ggaagtgtgg     660
agaatgactc tgactcatct tctggcctgt cccagggccc agcccgcccc taccacccac     720
ctccactctt tcctccttcc cctcaaccgc cagacagcac ccctcgacag ccagaggcta     780
gctttgaacc ccatccttct gtgacaccca ctggatatca tgctcccatg gagccccca     840
catctcgaat gttccaggct cctcctgggg ccctcccccc tcacccacag ctctatcctg     900
ggggcactgg tggagttttg tctggacccc caatgggtcc caaggggga ggggctgcct     960
catcagtggg gggccctaat gggggtaagc agcaccccccc acccactact cccatttcag    1020
tatcaagctc tggggctagt ggtgctcccc caacaaagcc gcctaccact ccagtgggtg    1080
gtgggaacct accttctgct ccaccaccag ccaacttccc ccatgtgaca ccgaacctgc    1140
ctcccccacc tgccctgaga cccctcaaca atgcatcagc ctctcccct ggcctggggg    1200
cccaaccact acctggtcat ctgccctctc cccacgccat gggacagggt atgggtggac    1260
ttcctcctgg cccagagaag ggcccaactc tggctccttc accccactct ctgcctcctg    1320
cttcctcttc tgctccagcg ccccccatga ggtttccta ttcatcctct agtagtagct    1380
ctgcagcagc ctcctcttcc agttcttcct cctcttcctc tgcctccccc ttcccagctt    1440
cccaggcatt gcccagctac ccccactctt tccctccccc aacaagcctc tctgtctcca    1500
atcagccccc caagtatact cagccttctc tcccatccca ggctgtgtgg agccagggtc    1560
ccccaccacc tcctccctat ggccgcctct tagccaacag caatgcccat ccaggcccct    1620
tccctccctc tactggggcc cagtccaccg cccacccacc agtctcaaca catcaccatc    1680
accaccagca acagcaacag cagcagcagc agcagcagca gcagcagcag cagcagcagc    1740
agcatcacga aaactctggg ccccctcctc ctggagcatt tccccaccca ctggagggcg    1800
gtagctccca ccacgcacac ccttacgcca tgtctccctc cctgggtct ctgaggccct    1860
acccaccagg gccagcacac ctgccccac ctcacagcca ggtgtcctac agccaagcag    1920
gccccaatgg ccctccagtc tcttcctctt ccaactcttc ctcttccact tctcaagggt    1980
cctacccatg ttcacacccc tccccttccc agggccctca aggggcgccc tacccttcc    2040
caccggtgcc tacggtcacc acctcttcgg ctaccctttc cacggtcatt gccaccgtgg    2100
cttcctcgcc agcaggctac aaaacggcct cccaccctgg gccccaccg tacgaaaga    2160
gagcccgtc cccgggggcc tacaagacag ccaccccacc cggatacaaa cccgggtcgc    2220
ctccctcctt ccgaacgggg accccaccgg gctatcgagg aacctcgcca ctgcaggcc    2280
cagggacctt caagccgggc tcgcccaccg tgggacctgg gccctgcca cctgcggggc    2340
```

```
cctcaggcct gccatcgctg ccaccaccac ctgcggcccc tgcctcaggg ccgcccctga   2400
gcgccacgca gatcaaacag gagccggctg aggagtatga accccccgag agcccggtgc   2460
ccccagcccg cagccccctcg ccccctccca aggtggtaga tgtacccagc catgccagtc   2520
agtctgccag gttcaacaaa cacctggatc gcggcttcaa ctcgtgcgcg cgcagcgacc   2580
tgtacttcgt gccactggag ggctccaagc tggccaagaa gcgggccgac ctggtggaga   2640
aggtgcggcg cgaggccgag cagcgcgcgc gcaagaaaaa ggagcgcgag cgcgagcggg   2700
aacgcgagaa agagcgcgag cgcgagaagg agcgcgagct gaacgcagc gtgaagttgg   2760 ctcaggaggg ccgtgctccg gtggaatgcc catctctggg cccagtgccc catcgccctc   2820
catttgaacc gggcagtgcg gtggctacag tgccccccta cctgggtcct gacactccag   2880
ccttgcgcac tctcagtgaa tatgcccggc ctcatgtcat gtctcctggc aatcgcaacc   2940
atccattcta cgtgcccctg ggggcagtgg acccggggct cctgggttac aatgtcccgg   3000
ccctgtacag cagtgatcca gctgcccggg agagggaacg ggaagcccgt gaacgagacc   3060
tccgtgaccg cctcaagcct ggctttgagg tgaagcctag tgagctggaa cccctacatg   3120
gggtccctgg gccgggcttg gatccctttc ccgacatgg gggcctggct ctgcagcctg   3180
gcccacctgg cctgcaccct ttccccttttc atccgagcct ggggcccctg gagcgagaac   3240
gtctagcgct ggcagctggg ccagcccgc ggcctgacat gtcctatgct gagcggctgg   3300
cagctgagag gcagcacgca gaaagggtgg cggccctggg caatgaccca ctggccggc   3360 tgcagatgct caatgtgact ccccatcacc accagcactc ccacatccac tcgcacctgc   3420
acctgcacca gcaagatgct atccatgcag cctctgcctc ggtgcaccct ctcattgacc   3480
ccctggcctc agggtctcac cttacccgga tccctaccc agctggaact ctccctaacc   3540
ccctgcttcc tcaccctctg cacgagaacg aagttcttcg tcaccagctc tttgctgccc   3600
cttaccggga cctgccggcc tcccttttctg ccccgatgtc agcagctcat cagctgcagg   3660
ccatgcacgc acagtcagct gagctgcagc gcttggcgct ggaacagcag cagtggctgc   3720
atgcccatca cccgctgcac agtgtgccgc tgcctgccca ggaggactac tacagtcacc   3780
tgaagaagga aagcgacaag ccactgtaga acctgcgatc aagagagcac catggctcct   3840
acattggacc ttggagcacc cccaccctcc ccccaccgtg cccttggcct gccacccaga   3900
gccaagaggg tgctgctcag ttgcagggcc tccgcagctg gacagagagt gggggaggga   3960
gggacagaca gaaggccaag gcccgatgtg gtgtgcagag gtggggaggt ggcgaggatg   4020
gggacagaaa gcgcacagaa tcttggacca ggtctctctt ccttgtcccc cctgcttttc   4080
tcctccccca tgcccaaccc ctgtggccgc cgcccctccc ctgccccgtt ggtgtgatta   4140
tttcatctgt tagatgtggc tgttttgcgt agcatcgtgt gccacccctg cccctcccccg   4200 atccctgtgt gcgcgccccc tctgcaatgt atgccccttg ccccttcccc acactaataa   4260
tttatatata taaatatcta tatgacgctc ttaaaaaaac atcccaacca aaaccaacca   4320
aacaaaaaca tcctcacaac tccccagga                                    4349

<210> SEQ ID NO 9
<211> LENGTH: 13994
<212> TYPE: DNA
<213> ORGANISM: Homo sapiens
<220> FEATURE:
<221> NAME/KEY: misc_feature
<222> LOCATION: (1)..(13994)
<223> OTHER INFORMATION: LOCUS       SEG_HUMHD            13994 bp
      DNA         linear    P
      RI 12-FEB-2001 DEFINITION  Homo sapiens huntingtin (HD) gene.
      ACCESSION   AH003045 REGION: 316..14309 VERSION       AH003045.1
```

GI:663286
<300> PUBLICATION INFORMATION:
<308> DATABASE ACCESSION NUMBER: L27350
<309> DATABASE ENTRY DATE: 2001-02-12
<313> RELEVANT RESIDUES IN SEQ ID NO: (1)..(614)

<400> SEQUENCE: 9

| | | | | | | |
|---|---|---|---|---|---|---|
| atggcgaccc | tggaaaagct | gatgaaggcc | ttcgagtccc | tcaagtcctt | ccagcagcag | 60 |
| cagcagcagc | agcagcagca | gcagcagcag | cagcagcagc | agcagcagca | gcagcaacag | 120 |
| ccgccaccgc | cgccgccgcc | gccgccgcct | cctcagcttc | ctcagccgcc | gccgcaggca | 180 |
| cagccgctgc | tgcctcagcc | gcagccgccc | cgccgccgc | ccccgccgcc | acccggcccg | 240 |
| gctgtggctg | aggagccgct | gcaccgaccg | tgagtttggg | cccgctgcag | ctccctgtct | 300 |
| attaatttcc | ttcttttttt | tattttttaga | aagaaagaac | tttcagctac | caagaaagac | 360 |
| cgtgtgaatc | attgtctgac | aatatgtgaa | acatagtgg | cacagtctgt | caggtaattg | 420 |
| cactttgaac | tgtctagaga | aaacttgaca | gtttctcttc | ttttttttgct | tagaaattct | 480 |
| ccagaatttc | agaaacttct | gggcatcgct | atggaacttt | ttctgctgtg | cagtgatgac | 540 |
| gcagagtcag | atgtcaggat | ggtggctgac | gaatgcctca | acaaagttat | caaagtaaga | 600 |
| accgtgtgga | tgatgttctc | ctcacttcca | taaatctctt | gtgatttgtt | gtaggctttg | 660 |
| atggattcta | atcttccaag | gttacagctc | gagctctata | aggaaattaa | aaaggtgggc | 720 |
| cttgcttttc | tttttttaaaa | atgtcttaat | gcaaccctca | ttgcaccccc | tcagaatggt | 780 |
| gccctcgga | gtttgcgtgc | tgccctgtgg | aggtttgctg | agctggctca | cctggttcgg | 840 |
| cctcagaaat | gcaggtaagt | tgtacactct | ggatgttggt | ttttagaatg | acttgcgttc | 900 |
| ttttgcatac | acaggcctta | cctggtgaac | cttctgccgt | gcctgactcg | aacaagcaag | 960 |
| agacccgaag | aatcagtcca | ggagaccttg | gctgcagctg | ttcccaaaat | tatggcttct | 1020 |
| tttggcaatt | ttgcaaatga | caatgaaatt | aaggtatgat | tgttgcctca | ggtcacaaac | 1080 |
| atgttttatc | tacttggact | tttgcttccg | taggttttgt | taaaggcctt | catagcgaac | 1140 |
| ctgaagtcaa | gctcccccac | cattcggcgg | acagcggctg | gatcagcagt | gagcatctgc | 1200 |
| cagcactcaa | gaaggacaca | atatttctat | agttggctac | taaatgtgct | cttaggtaag | 1260 |
| gtggaggcat | atgagtggaa | gagtctgtta | agatgtcttg | cttccacccc | cacaggctta | 1320 |
| ctcgttcctg | tcgaggatga | acactccact | ctgctgattc | ttggcgtgct | gctcaccctg | 1380 |
| aggtatttgg | tgcccttgct | gcagcagcag | gtcaaggaca | caagcctgaa | aggcagcttc | 1440 |
| ggagtgacaa | ggaaagaaat | ggaagtctct | ccttctgcag | agcagcttgt | ccaggtagga | 1500 |
| gcacagggtt | tactctagga | actgaccaga | acacctgtgt | ttctctgttt | ctaggtttat | 1560 |
| gaactgacgt | tacatcatac | acagcaccaa | gaccacaatg | ttgtgaccgg | agccctggag | 1620 |
| ctgttgcagc | agctcttcag | aacgcctcca | cccgagcttc | tgcaaaccct | gaccgcagtc | 1680 |
| ggggcattg | gcagctcac | cgctgctaag | gaggagtctg | tggccgaag | ccgtagtggg | 1740 |
| agtattgtgg | aacttatagg | caagttatta | gcaaggtcta | cacttacaaa | ctttatctgt | 1800 |
| cactttctgt | gatttgcagc | tggaggggt | tcctcatgca | gccctgtcct | ttcaagaaaa | 1860 |
| caaaaaggtg | attatttcag | aaatcagagt | cttgtgttaa | aaggaatgtt | ggtacattat | 1920 |
| ttactaggca | aagtgctctt | aggagaagaa | gaagccttgg | aggatgactc | tgaatcgaga | 1980 |
| tcggatgtca | gcagctctgc | cttaacaggt | agttctcact | agttagccgc | tggtgtggtt | 2040 |
| tgacaaatga | gtgtttctct | gtcttcagcc | tcagtgaagg | atgagatcag | tggagagctg | 2100 |
| gctgcttctt | caggggtttc | cactccaggg | tcagcaggtc | atgacatcat | cacagaacag | 2160 |

```
ccacggtcac agcacacact gcaggcggac tcagtggatc tggccagctg tgacttgaca    2220
agctctgcca ctgatgggga tgaggaggat atcttgagcc acagctccag ccaggtcagc    2280
gccgtcccat ctgaccctgc catggacctg aatgatggga cccaggcctc gtcgcccatc    2340
agcgacagct cccagaccac caccgaaggg cctgattcag ctgttacccc ttcagacagt    2400
tctgaaattg taagtgggca gaggggcctg acatctttta attctcacag ccccccttga    2460
accgtttagg tgttagacgg taccgacaac cagtatttgg gcctgcagat tggacagccc    2520
caggatgaag atgaggaagc cacaggtatt cttcctgatg aagcctcgga ggccttcagg    2580
aactcttcca tgggtatgtg gactacaggt gatgcgctac aaacacttaa tcttgatttc    2640
tctgttttta aagcccttca acaggcacat ttattgaaaa acatgagtca ctgcaggcag    2700
ccttctgaca gcagtgttga taaatttgtg ttgagagatg aagctactga accgggtgat    2760
caagaaaaca aggtgaggga cataggcttg agacgacttg gtgacaaaca agtgtcattg    2820
tctcctttct agccttgccg catcaaaggt gacattggac agtccactga tgatgactct    2880
gcacctcttg tccattgtgt ccgcctttta tctgcttcgt ttttgctaac agggggaaaa    2940
aatggtgagt acaaaagggg atgtgcacag ttgactgaag gtggcttggg tgatttcttg    3000
gcagtgctgg ttccggacag ggatgtgagg gtcagcgtga aggccctggc cctcagctgt    3060
gtgggagcag ctgtggccct ccacccggaa tctttcttca gcaaactcta taagttcct     3120 cttgacacca cggaataccc tggtatgtta aaagttcaca tctgatgtgc tcgttccatg    3180
gctgagcaat ttatctccac agaggaacag tatgtctcag acatcttgaa ctacatcgat    3240
catggagacc cacaggttcg aggagccact gccattctct gtgggaccct catctgctcc    3300
atcctcagca ggtcccgctt ccacgtggga gattggatgg gcaccattag aaccctcaca    3360
ggtaacggcc agttttttcag ctgtgttttt tatgatgttt gttgcttgtt cttctggtta    3420
ggaaatacat tttctttggc ggattgcatt cctttgctgc ggaaaacact gaaggatgag    3480
tcttctgtta cttgcaagtt agcttgtaca gctgtgaggg tgagcataat cttctgtgga    3540
accatttctt gtcctcttgc cttggacctt gtgttccaga actgtgtcat gagtctctgc    3600
agcagcagct acagtgagtt aggactgcag ctgatcatcg atgtgctgac tctgaggaac    3660
agttcctatt ggctggtgag gacagagctt ctggaaaccc ttgcagagat tgacttcagg    3720
taagtgagtc acatccatta gatttcatga tttcattgtt aaatgtgctc ttttgttagg    3780
ctggtgagct ttttggaggc aaaagcagaa aacttacaca gaggggctca tcattataca    3840
ggggtaagca gtttattttt gtgagatgct gtttgtttat ttttattatc cttctctcta    3900
aagcttttaa aactgcaaga acgagtgctc aataatgttg tcatccattt gcttggagat    3960
gaagacccca gggtgcgaca tgttgccgca gcatcactaa ttaggtattt accaatattt    4020
tatctctttt cctttaagc aaattaacct tactttgtg ttaggcttgt cccaaagctg      4080
ttttataaat gtgaccaagg acaagctgat ccagtagtgg ccgtggcaag agatcaaagc    4140
agtgtttacc tgaaacttct catgcatgag acgcagcctc catctcattt ctccgtcagc    4200
acaataacca ggtatgctga cccagtggca tcttcacatt gtattttaag tctctatatt    4260
tttgttatta gaatatatag aggctataac ctactaccaa gcataacaga cgtcactatg    4320
gaaaataacc tttcaagagt tattgcagca gtttctcatg aactaatcac atcaaccacc    4380
agagcactca cagtaagtct ctttcttgat gcctcttact gaggtgtgat tttattgttt    4440
ctttcttctg agtttggatg ctgtgaagct ttgtgtcttc tttccactgc cttcccagtt    4500
tgcatttgga gtttaggttg gcactgtggg tatgtatttt cctcagtata tattaatagt    4560
```

```
aatttgactt tgcaaatgtc tgcttccaga ggtgcctcca ctgagtgcct cagatgagtc    4620
taggaagagc tgtaccgttg ggatggccac aatgattctg accctgctct cgtcagcttg    4680
gttcccattg gatctctcag cccatcaaga tgctttgatt ttggccggaa acttgcttgc    4740
aggtactggt actgagttga aacagggact ccggagaggt nntgtctgtg cccatatcac    4800
agccagtgct cccaaatctc tgagaagttc atgggcctct gaagaagaag ccaacccagc    4860
agccaccaag caagaggagg tctggccagc cctgggggac cgggccctgg tgcccatggt    4920
ggagcagctc ttctctcacc tgctgaaggt gattaacatt tgtgcccacg tcctggatga    4980
cgtggctcct ggacccgcaa taaaggtaat gtcccacttg ggtgctggat tcatattgtt    5040
ttttgttttt gttttctat tttaggcagc cttgccttct ctaacaaacc cccttctct    5100 aagtcccatc cgacgaaagg ggaaggagaa agaaccagga gaacaagcat ctgtaccgtt    5160
gagtcccaag aaaggcagtg aggccagtgc aggtaggaaa cagcgtgggg aagggaggga    5220
caagtttatc ttttgtgtgc atattttaa agcttctaga caatctgata cctcaggtcc    5280
tgttacaaca agtaaatcct catcactggg gagtttctat catcttcctt catacctcaa    5340
actgcatgat gtcctgaaag ctacacacgc taactacaag gtatgggcct ctgcatcttt    5400
taaaaatata accgtgtgtt ctctccttca ccttcccaag gtcacgctgg atcttcagaa    5460
cagcacggaa aagtttggag ggtttctccg ctcagccttg gatgttcttt ctcagatact    5520
agagctggcc acactgcagg acattgggaa ggtttgtgtc ttgttttttc tccttgggtt    5580
gtcgcttaat gtctgacttg tcttctaca gtgtgttgaa gagatcctag gatacctgaa    5640
atcctgcttt agtcgagaac caatgatggc aactgtttgt gttcaacaag taagagcttc    5700 attctttttcc tcttctgtta ttgttgatgc ctcattttt tcactgtagt tgttgaagac    5760
tctctttggc acaaacttgg cctcccagtt tgatggctta tcttccaacc ccagcaagtc    5820
acaaggccga gcacagcgcc ttggctcctc cagtgtgagg ccaggcttgt accactactg    5880
cttcatggcc ccgtacaccc acttcaccca ggccctcgct gacgccagcc tgaggaacat    5940
ggtgcaggcg gagcaggaga acgacacctc ggggtaacag ttgtggcaag aatgctgtcg    6000
ttgctctgct tccctttat tcccatttgg cagatggttt gatgtcctcc agaaagtgtc    6060
tacccagttg aagacaaacc tcacgagtgt cacaaagaac cgtgcagata aggtaaatgg    6120
tgttgtttgt ggatgtgaac tcattctttc tttcttttt tctttttat agaatgctat    6180 tcataatcac attcgtttgt ttgaacctct tgttataaaa gctttaaaac agtacacgac    6240
tacaacatgt gtgcagttac agaagcaggt tttagatttg ctggcgcagc tggttcagtt    6300
acgggttaat tactgtcttc tggattcaga tcaggtttgt cacttttatc tttcatccat    6360
catattgatg taaattttat tttccttcct gtaggtgttt attggctttg tattgaaaca    6420
gtttgaatac attgaagtgg gccagttcag gtaatagcat tttattattt tagatttttt    6480
aaggatctaa atgatgtttt tgtttctag ggaatcagag gcaatcattc caaacatctt    6540
tttcttcttg gtattactat cttatgaacg ctatcattca aaacagatca ttggaattcc    6600
taaaatcatt cagctctgtg atggcatcat ggccagtgga aggaaggctg tgacacatgg    6660
taacnggaca cacctttcac tgtcgtcttc ctgataaggg tacccttttg tccccacagc    6720
cataccggct ctgcagccca tagtccacga cctctttgta ttaagaggaa caaataaagc    6780
tgatgcagga aaagagcttg aaacccaaaa agaggtggtg gtgtcaatgt tactgagact    6840
catccagtac catcaggtaa gaggaatgta tgttggaact gtcgtgcaga cttctctaatt    6900 gtgcacgctc ttataggtgt tggagatgtt cattcttgtc ctgcagcagt gccacaagga    6960
```

-continued

| | |
|---|---|
| gaatgaagac aagtggaagc gactgtctcg acagatagct gacatcatcc tcccaatgtt | 7020 |
| agccaaacag caggtttgtc cccgcagcct tggcttgttg ttgtagaaat gtttgtggtg | 7080 |
| tctaattcca cagatgcaca ttgactctca tgaagccctt ggagtgttaa atacattatt | 7140 |
| tgagattttg gccccttcct ccctccgtcc ggtagacatg cttttacgga gtatgttcgt | 7200 |
| cactccaaac acaatggtga gtctctcgcc tggctcagca gatgaagctg tgacttatgt | 7260 |
| attatgttta ttttaggcgt ccgtgagcac tgttcaactg tggatatcgg gaattctggc | 7320 |
| cattttgagg gttctgattt cccagtcaac tgaagatatt gttctttctc gtattcagga | 7380 |
| gctctccttc tctccgtatt taatctcctg tacagtaatt aataggttaa gagatggggga | 7440 |
| cagtacttca acgctagaag aacacagtga agggaaacaa ataaagaatt tgccagaaga | 7500 |
| aacatttttca aggtatgctt tctatctgag cctataacta acttcactgt catctttttt | 7560 |
| ctttcttgga aggtttctat tacaactggt tggtattctt ttagaagaca ttgttacaaa | 7620 |
| acagctgaag gtggaaatga gtgagcagca acatactttc tattgccagg aactaggcac | 7680 |
| actgctaatg tgtctgatcc acatcttcaa gtctggtagg tgaatcacat tagtcttcct | 7740 |
| ggagtaaaga catttctcct taactttgtt tctaggaatg ttccggagaa tcacagcagc | 7800 |
| tgccactagg ctgttccgca gtgatggctg tggcggcagt ttctacaccc tggacagctt | 7860 |
| gaacttgcgg gctcgttcca tgatcaccac ccacccggcc ctggtgctgc tctggtgtca | 7920 |
| gatactgctg cttgtcaacc acaccgacta ccgctggtgg gcagaagtgc agcagacccc | 7980 |
| gaagtaggtt cataatgccc cacagcccag ggccattgtc aatgcatctg ttgctccttc | 8040 |
| tagaagacac agtctgtcca gcacaaagtt acttagtccc cagatgtctg gagaagagga | 8100 |
| ggattctgac ttggcagcca aacttggaat gtgcaataga gaaatagtac gaagaggggc | 8160 |
| tctcattctc ttctgtgatt atgtcgtaag tttgaaatgc ctgtaaacgg ggttgaaatg | 8220 |
| aatctctcat catatttttc cttagtgtca gaacctccat gactccgagc acttaacgtg | 8280 |
| gctcattgta aatcacattc aagatctgat cagccttttcc cacgagcctc cagtacagga | 8340 |
| cttcatcagt gccgttcatc ggaactctgc tgccagcggc ctgttcatcc aggcaattca | 8400 |
| gtctcgttgt gaaaaccttt caactgtacg tcttcatcct gccgactatt gccagatctt | 8460 |
| ttcttcttttt ccttcttgct gttagccaac catgctgaag aaaactcttc agtgcttgga | 8520 |
| ggggatccat ctcagccagt cgggagctgt gctcacgctg tatgtggaca ggcttctgtg | 8580 |
| caccccttttc cgtgtgctgg ctcgcatggt cgacatcctt gcttgtcgcc gggtagaaat | 8640 |
| gcttctggct gcaaatttac aggtattggg aagagaaacc ctgatattga ttcaaacaca | 8700 |
| ctaatgtgtt tttgtctatt agagcagcat ggcccagttg ccaatggaag aactcaacag | 8760 |
| aatccaggaa taccttcaga gcagcgggct cgctcagagg taatgctgga aacacaggtc | 8820 |
| gtccttgtga ctgtaatttc atttttattt gtattttaga caccaaaggc tctattccct | 8880 |
| gctggacagg tttcgtctct ccaccatgca agactcactt agtccctctc ctccagtctc | 8940 |
| ttcccacccg ctgacggggg atgggcacgt gtcactggaa acagtgagtc cggacaaagt | 9000 |
| aagtgtccag cgtgtctgca tgggaggctg ttccccttat ccatttttttt cttcccagga | 9060 |
| ctggtacgtt catcttgtca aatcccagtg ttggaccagg tcagattctg cactgctgga | 9120 |
| aggtgcagag ctggtgaatc ggattcctgc tgaagatatg aatgccttca tgatgaactc | 9180 |
| ggtacggggg gagcagtgga ggcaaggaat cgtttgttaa cctttaatgc tctgatttca | 9240 |
| ggagttcaac ctaagcctgc tagctccatg cttaagccta gggatgagtg aaatttctgg | 9300 |
| tggccagaag agtgcccttt ttgaagcagc ccgtgaggtg actctggccc gtgtgagcgg | 9360 |

```
caccgtgcag cagctccctg ctgtccatca tgtcttccag cccgagctgc ctgcagagcc   9420
ggcggcctac tggagcaagt tgaatgatct gtttggtaat taaaattaaa atttatctta   9480
ttttagcacc cacccacgag gtccttctgt ttcaggggat gctgcactgt atcagtccct   9540
gcccactctg gcccgggccc tggcacagta cctggtggtg gtctccaaac tgcccagtca   9600
tttgcacctt cctcctgaga aagagaagga cattgtgaaa ttcgtggtgg caaccctt ga  9660 ggtaagaggc agctcgggag ctcagtgttg cggcattctg tgactcggta cttcccttta   9720
ggccctgtcc tggcatttga tccatgagca gatcccgctg agtctggatc tccaggcagg   9780
gctggactgc tgctgcctgg ccctgcagct gcctggcctc tggagcgtgg tctcctccac   9840
agagtttgtg acccacgcct gctccctcat ctactgtgtg cacttcatcc tggaggccgg   9900
tgagtccccg tccatgaacg gtgggttcca ttcttctctt tgttctgttg taattttagt   9960
tgcagtgcag cctggagagc agcttcttag tccagaaaga aggacaaata ccccaaaagc  10020
catcagcgag gaggaggagg aagtagatcc aaacacacag agtaagtctc aggacccatt  10080
tttttcttac aaaagtcctc tcttaaccgt tgcttgttta gatcctaagt atatcactgc  10140
agcctgtgag atggtggcag aaatggtgga gtctctgcag tcggtgttgg ccttgggtca  10200
taaaaggaat agcggcgtgc cggcgtttct cacgccattg ctcaggaaca tcatcatcag  10260
cctggcccgc ctgccccttg tcaacagcta cacacgtgtg cccccactgg tgagtctgct  10320
cgttccttgc agaagaccag atgatgtcac ttccttttca tcttctcagg tgtggaagct  10380
tggatggtca cccaaaccgg gaggggattt tggcacagca ttccctgaga tccccgtgga  10440
gttcctccag gaaaaggaag tctttaagga gttcatctac cgcatcaaca cactaggtac  10500
tcttggggcc tctccttcag gtcacccact ctctcatgta agatttatat ttgtaggctg  10560
gaccagtcgt actcagtttg aagaaacttg ggccaccctc cttggtgtcc tggtgacgca  10620
gcccctcgtg atggagcagg aggagagccc accagaagta aggccacacc ctgtgctggt  10680
tggcacagct cttgttacat gtgggctctc cttccaggaa gacacagaga ggacccagat  10740
caacgtcctg gccgtgcagg ccatcacctc actggtgctc agtgcaatga ctgtgcctgt  10800
ggccggcaac ccagctgtaa gctgcttgga gcagcagccc cggaacaagc ctctgaaagc  10860
tctcgacacc aggtttgctt gagttcccac gtgtctctgg gaaacactct ttacctttt t  10920 tctaaaatgt aggtttggga ggaagctgag cattatcaga gggattgtgg agcaagagat  10980
tcaagcaatg gtttcaaaga gagagaatat tgccacccat catttatatc aggcatggga  11040
tcctgtccct tctctgtctc cggctactac aggtacctga gggaaaggga gcggggcagc  11100
gggatcaaga ctcagggtgc tggtgttcac aggtgccctc atcagccacg agaagctgct  11160
gctacagatc aaccccgagc gggagctggg gagcatgagc tacaaactcg gccaggtcag  11220
tctcgcgnnc ccgccgcctg gcctcacact gagcagtgcc ccgtttctgt ggcaggtgtc  11280
catacactcc gtgtggctgg ggaacagcat cacacccctg agggaggagg aatgggacga  11340
ggaagaggag gaggaggccg acgcccctgc accttcgtca ccacccacgt ctccagtcaa  11400
ctccaggttt gcagatggcc tttttatttt taacagtgga aaataccccat ctcgcatatt  11460 ccacaggaaa caccgggctg gagttgacat ccactcctgt tcgcagtttt tgcttgagtt  11520
gtacagccgc tggatcctgc cgtccagctc agccaggagg accccggcca tcctgatcag  11580
tgaggtggtc agatccgtaa gtgagccttc ccattcccct cacacccctt gccctcctgg  11640
ttttccacat ctccagcttc tagtggtctc agacttgttc accgagcgca accagtttga  11700
gctgatgtat gtgacgctga cagaactgcg aagggtgcac ccttcagaag acgagatcct  11760
```

```
cgctcagtac ctggtgcctg ccacctgcaa ggcagctgcc gtccttggga tggtaagtga    11820
caggtggcac agaggtttct gtatgcagca gcttttgtct gtgtgtgcct aggacaaggc    11880
cgtggcggag cctgtcagcc gcctgctgga gagcacgctc aggagcagcc acctgcccag    11940
cagggttgga gccctgcacg gcgtcctcta tgtgctggag tgcgacctgc tggacgacac    12000
tgccaagcag ctcatcccgg tcatcagcga ctatctcctc tccaacctga agggatcgc    12060
ccagtgagtg ggagcctggc tggggctggg gcgctgagcc tggatgctgt ctcccgtttt    12120
gagctgcgtg aacattcaca gccagcagca cgtactggtc atgtgtgcca ctgcgtttta    12180
cctcattgag aactatcctc tggacgtagg gccggaattt tcagcatcaa taatacaggt    12240
gagtgggccc tggctgtctt cctctgcatt tgacacagag gcctttgtcc ctgtgcagat    12300
gtgtggggtg atgctgtctg gaagtgagga gtccacccccc tccatcattt accactgtgc    12360
cctcagaggc ctggagcgcc tcctgctctc tgagcagctc tcccgcctgg atgcagaatc    12420
gctggtcaag ctgagtgtgg acagagtgaa cgtgcacagc ccgcaccggg ccatggcggc    12480
tctgggcctg atgctcacct gcatgtacac aggtgagcat gtacacggtg cccataaggc    12540
cataaccttc gtactgaaca cttttgttac aggaaaggag aaagtcagtc cgggtagaac    12600
ttcagaccct aatcctgcag cccccgacag cgagtcagtg attgttgcta tggagcgggt    12660
atctgttctt tttgataggt aagaagcgaa ncccatccct cagcccgttc agtctctgac    12720
ctgcgtccct cctcccagga tcaggaaagg cttttccttgt gaagccagag tggtggccag    12780
gatcctgccc cagtttctag acgacttctt cccacccccag gacatcatga acaaagtcat    12840
cggagagttt ctgtccaacc agcagccata cccccagttc atggccaccg tggtgtataa    12900
ggtgaggttg catgtgggat gggggatggag ttgacactca ggcgcctgct tgctcttgca    12960
ggtgtttcag actctgcaca gcaccgggca gtcgtccatg gtccgggact gggtcatgct    13020
gtccctctcc aacttcacgc agagggcccc ggtcgccatg gccacgtgga gcctctcctg    13080
cttctttgtc agcgcgtcca ccagcccgtg ggtcgcggcg atgtatcctc tctggntccc    13140
tggtnctggc ccgccggcct tttttccttaa ctcctgcacc agcctccac atgtcatcag    13200
caggatgggc aagctggagc aggtggacgt gaacccttttc tgcctggtcg ccacagactt    13260
ctacagacac cagatagagg aggagctcga ccgcagggcc ttccagtctg tgcttgaggt    13320
ggttgcagcc ccaggaagcc catatcaccg gctgctgact tgtttacgaa atgtccacaa    13380
ggtcaccacc tgctgagcgc catggtggga gagactgtga ggcggcagct ggggccggag    13440
cctttggaag tctgtgccct tgtgccctgc ctccaccgag ccagcttggt ccctatgggc    13500
ttccgcacat gccgcgggcg gccaggcaac gtgcgtgtct ctgccatgtg gcagaagtgc    13560
tctttgtggc agtggccagg cagggagtgt ctgcagtcct ggtggggctg agcctgaggc    13620
cttccagaaa gcaggagcag ctgtgctgca ccccatgtgg gtgaccaggt cctttctcct    13680
gatagtcacc tgctggttgt tgccaggttg cagctgctct tgcatctggg ccagaagtcc    13740
tccctcctgc aggctggctg ttggcccctc tgctgtcctg cagtagaagg tgccgtgagc    13800
aggctttggg aacactggcc tgggtctccc tggtggggtg tgcatgccac gccccgtgtc    13860
tggatgcaca gatgccatgg cctgtgctgg gccagtggct gggggtgcta gacacccggc    13920
accattctcc cttctctctt ttcttctcag gatttaaaat ttaattatat cagtaaagag    13980
attaattta acgt                                                       13994
```

<210> SEQ ID NO 10
<211> LENGTH: 118777
<212> TYPE: DNA

| | |
|---|---|
| <213> ORGANISM: Mus musculus | |
| <220> FEATURE: | |
| <221> NAME/KEY: misc_feature | |
| <222> LOCATION: (1)..(118777) | |
| <223> OTHER INFORMATION: LOCUS AF163865 118777 bp DNA linear ROD 24-JAN-2001 DEFINITION Mus musculus alpha-synuclein (Snca) gene, complete cds. ACCESSION AF163865 | |
| <300> PUBLICATION INFORMATION: | |
| <308> DATABASE ACCESSION NUMBER: AF163865 | |
| <309> DATABASE ENTRY DATE: 2001-01-24 | |
| <313> RELEVANT RESIDUES IN SEQ ID NO: (1)..(118777) | |

<400> SEQUENCE: 10

```
gaacctcaga cagctgacag aaagtcctcc aattctgagc tacaggagtg aatctgctac      60
tgaaaacaca ggcagagcag acacgctgct gtagacacag aggaagatga cagggacagg     120
aagatgtaga cactgatagc aattagctaa ggagattcat ttcttttttc cctaaccagg     180
caaggaccct gactagaaga cattttgttg ttgaaacatg ttgttgaaga tacagttttg     240
gggatgtatg tgagaaaatg aagagtaaac ctgaattaaa caagccatgg ctttgggtct     300
ggtaccatga cgaagcataa gttacagaat actttctcgt tgccgttttt tggtttgtaa     360
attcagtcct tcaaatatcc atacatactg ggctcttgag aacccatgaa gaaggatgg      420
aatacttggt gtttatgcaa acttatttaa tacctactgc aaagttcaag tcaaggctta     480
atgccttgac tactttcaca atcagccact acttattgga ttgggtggtg aaaacatggc     540
tgagacatct tgtagtcata atttttttt aaagaaaagt acctgatcct tcttagaagg     600
gggaacaaaa tacccatgtg gggagataca gagacaaagt ggaacagaga tgaaaggaaa     660
gaccatctag agactaccct acctggggat tcatcctata tagagacaac aaatccagac     720
actatagtgg ataccaacaa gtacttgctg acaggagcct gttgcagttg tctcctgaga     780
ggctttgcca gtgtctgaca aatacagagg tggatgcttt cagccaacca ttggactgag     840
cacagaggcc ctaatggagg ggctagagaa aggacccaag aagacgatga ggtttgcaat     900
cccataagag gagcaacaat atgaaccaac cagtaacccc agagttccta gggactaaac     960
caccaaccaa agagtataca cggagggact catggctcca gttgcatatg tagcagagga    1020
tggccttgtt aatcatcaat ggaaggagag gcctttggtc ctgtgaatgc ttgatggccc    1080
cagtgtagtg ggatgccagg accaggaagc aggagtgagt gggttggtga gctgtggggg    1140
atcaggaaaa gggataacat ttgaaatgta aataaagaaa atatctatta aagaaatta     1200
cccttcatgc tgtcaaacac cttttagttc ctgtaatcag gcttcctggt tcttcttct     1260
tccccttttg acacagactc tatgtccaca aggctagcct gactgttgca gtaattctct    1320
gaccaaatct ctcaagtgct gaaatcatag gcactaacta ctaggcctgg ctctaacact    1380
ggatttttaa gatcctataa atcctggaca ctttaaactt ctattttact cagaattttg    1440
ttggagaacg tactgtgtgg gacacaaatc actgctatag tgtttccaga aatttgaaga    1500
atactgagtc ctgttatgtg gtgactgaat ggagctgtga cctcctacaa agtagagctc    1560
aaggttctac attctctgtg gggtctccag taattccatc attgcaatgg actcctgcca    1620
ggaccatagt ttcagaatgg agtgtagaaa ataaatagta caacatctgg gtaagaaatt    1680
tggagaaaca tgatggagcg cttcaaagct gtctacacac acacacacac acacacacac    1740
acacacacac acacacgtga tcatgatgca ttgagagtaa gaataacaac attgctaaag    1800
agagtttgtg ggtacagaag agaaagagaa aatgcttaa attaaacatg caaataaaac    1860
ttcatttaag aagtttgcag aatgaatctc caagctctaa agacaaatat tatccaaaac    1920
tactatgctg gaatgccagt caacacaggg gccactgggc aagttttctc taatttaaac    1980
```

```
aaaaccaaaa accaaaccaa accaactaat taaccaaacc aaaatcccaa ccaaccaact    2040
aaccaaacaa gcaaacaaaa atcctggaac aacatgagag cccaaggact gtgaatagaa    2100
tctcaatatt caaggtgtat ttgggaagct ccagcaagtg agctaagacc acaaggcaga    2160
ccagggaggg ataaagagac agtctctcta gatcaatctc taaacagtca tagatacaaa    2220
ctacacaggg gcttactagg ccacagttta aatttcacac aaaaaacaaa attcattgaa    2280
aagctgatcc cttagagtat gtaaaaattc cttgtttctg ctctagttgg cagtgtcatg    2340
agccttatca actggatggt gcagggactc catgttacac aatgtttttc ttcttctatt    2400
tgtttctaaa atcagtggtg agatcaggca catttttaaa aacatgacca tactcttgtt    2460
cattaccttc tcaagtaaaa aaaaaaaaaa acctatgatt tggcgggttc tgattatgga    2520
gggctgaaat agtaatatca gtcatgaaca gctgagagca ctggtttctg agcctctgat    2580
tgaagcttta gaatcctgtg tttggatgta taatattaaa gaaacaatag tcataagcct    2640
cagcctgtac tcaagatagt tttaaatgtg tggttatttg ctggtatgta tgtccgtgca    2700
gcatttctgt gcctgatacc tgtggaggtc agaaaagtgt gttggatttc ctgggattgg    2760
agttacagac aattttgagc tgccatgttg gtactgggac tcaaatccca gtcctctgca    2820
agagcagcct gtgcccttat ctgctgagcc acctctctag ccccattata acaagaattt    2880
ataaagctga tgacctattc catgtatccc ctagttcatt gcattgtgag agtgaataat    2940
ggtatttgta gataggttga aattataaat gtatttccta ttggttcatc atgagccaga    3000
catacagctt ttccaagatt taggttccct ggataaagcc ctcagtcata ttatcagcta    3060
tcaatgtaat gttatgttgt aaatataaat attagcccta gtacactaag gtagccacga    3120
gaagacttgc tgtgtcttaa acaagagaaa tttgttttct cacagttctg gaggttagaa    3180
gtctaatatc agatgtcagc agggttgatt tattctagtg ctgctgtcct tggctcacag    3240
gccactgcct tcacagtgca gcctctatgt ctacttctaa tgtattctag cctactcttc    3300
ttgtaaatac atcaatcatg gtagatttgg gcactcttca atgacacatt ttaaccttta    3360
tgtcctcata ctgagggtaa gaacttcaac acacagttgt aaaaatttat ttgtaagtca    3420
tttacttaaa aagttttttaa taacaaaatt tttcgtgtga atataacgca ttcagattac    3480
tctcatcttc cactgtcttt tatttaccct ttactcttat caaatctcac tgtcatcccc    3540
ccccaaaaaa aactctttc cacatttatg tcttttttgtt ttgtgaccca ttgagtttaa    3600
atatgtccat ttatgtgaca atgaaatatgt gaccattgga tcctggtgag cttactagtg    3660
ggtacacagc taaagacaat gactttatgt ctttcaccat ctatcaatag caaacaatta    3720
atcatggaga ggtaggggca catacaccct tctactggtg gtacataatt aacaggcaca    3780
gtcttgaata gatccagtgc caagaacttc agctgctgta agctcatgat taaaatggct    3840
gtattatggc ctgaagatta tgttttgtac tcttttctcca taacatttag catattatat    3900
tcttcccctc ttcagcttttc attccataaa ctttagatgt actggttcaa atgtcctgtt    3960
tagggatgaa atatggagac aaagtgtgga gcagaaactg taggaaaggc catccagaga    4020
ctatctcacc tgaggatcca tcttgtatat agacaccaaa cccagatact attgctgatg    4080
cccagaagtg cttgctgaaa ggtgcctgat atagctgtct actgagaggc tctgacagag    4140
cctgacaaat acaaatgtag acgctcacag acaaccgttg ggctgagcac gtaggtccct    4200
gataaaggag ttagagaaag tagggttagc aaccccatag gaagaacaac aatatcaacc    4260
aaccagaccc cccagagctt ccagggacta agccacctac caaggagtac acatagaggg    4320
acacatagct caggctgcat atatatgttt ttcaggcatc aatgggagga gaggccctcg    4380
```

```
gtcctatgaa ggctggctgg atgcccggt  gtaggggaat tggagggcag ggaagcagaa  4440
gggtgtggat gggttgggga gctccctcat agaagcagag gaggggatg  ggatagggg   4500
tttcaggtgg ggatcaggaa agcagataac atttgaaatg taaataaaga acatattccc  4560
cccaaaaaga caaatatcac atcacacaca cacacatgtg cacacacaca cacacacaca  4620
cacacacaca cactcagaga gattgagaga gagagagaga gagagggaga gagagagaga  4680
gagagagagg tgcagagagt ggaagaggca gtttaaccag gacagttgaa cagagacagg  4740
ttgcacaaag agaacaagct agacacagaa gacagaataa accaagggat gagaaagagg  4800
cagagtagaa catattgcca aagttagtat caggtcaagc agagcaattt agaagaggcc  4860
gagagagaga agccagaatg aatcaatcag tgtggagagg attttgagcc ataacagctg  4920
agttgaacca tgtagagtta aaaagaaca  agagagggtg agcttattca tcattaagtc  4980
ttagaggctg aaaatattct agacctagat aatactgtat ggagggtaga agcttccagg  5040
actaggccta tgttagcaga gagaggcagt aagcctctga tatgacaatt acattaggtc  5100
aaaaatagtt acaattacat ttaggtagca tgttttcatt attcatcagc tgacagacat  5160
ttagaccgtt tctatttcat ggctattatg aatagagaag aaattaacat ggatgagcaa  5220
gcctctctga agtggaatat agagttcttt gggaatatgc ccaggagtta tacagcgtga  5280
tgatatggaa gacctacttc ttctcttttg tagaaactct acattgattt tcatagtgaa  5340
tgcttcccct tttctccaac catcattaaa ttaatgtttg cctttcccaa gtctgtacta  5400
gaatttgtta tttgtccatt tgtcttagac atcctgagtg gggtaagact ggggcctcca  5460
gtctcttgag ggttaggtgc atcatctctg tatgaacaca gccttggcag tcctctactg  5520
taagtgtttt gggggcctca tatcagctga tatatgctct cggtttggtg gtccagtttt  5580
tgagagatct tgggggtcca gattaattga gactgctggt cctcctacag aatcaccccc  5640
tttctcagct tctttcagtc ttccctaact cggaaacagg ggtcagctgt ttctgtccat  5700
tggttggttg caagtatctg catctgacac tttcagctgc ttgttgggtc ttctggtctg  5760
tggtcatgat aggttggtcc ctttgtgtga gcgctccata gtctcagtaa tagtgtcaag  5820
ccttgggacc tccctttgag ctggaatcca ttttggacct gtcaagggat cttcttcagg  5880
ctcctctcta tcttttctca aatgtatagc taataaatat tttgaaaatt tccctcagtt  5940
ttcagaatgt ctcttcacac aaaggatggt gttcttttaa gcttcacagc cctatttgtg  6000
agttattctt aatatctgtt caactgtgtc ctgttccaca acctataagt tgaggtatat  6060
tttctttctc ctctgaggaa tcatgttatc agatttgtgt tgaggtgctt ggagttggat  6120
tttgtacaag gtgaagtaga agaatctagt ttcacttttc tacacattgc tattcagttt  6180
gaggaacata attgaactat tctgaactga gattctctaa actgaacaga actgaattga  6240
actgaattga aatctctatc cttccctgat gtttaagtag cctctttttc ctgtctgttc  6300
ttgtgagagt taggcatatc ttatttgtgt ctcattctgt aaaatctttg tctgtacctc  6360
aattagatat cactgtttgg gattaaaggt atgtacaaaa gatatgtcta aatcccagcc  6420
agggaaatta aatgtatgtc tactctgcat tccagtagaa ttatatcttt gtatgtgatt  6480
ccttgcccaa gcacccatgt tgcttgatta aacctctac  aacatttatt ccaagatatt  6540
ttatttttc  tgtggttatt gtcaccactt aatttgatga cataattatt aaaataatta  6600
ctctccccct gaggaagact gagctacacc atctctatgc tagctcaaga catacttcct  6660
actggcatga ggattctaat tgactcccta tcttctgaat tcagagtgag ttatatatga  6720
cacacgatat tcattaacac aattaaagga taagtatgaa tatttggtag tttttaatgt  6780
```

```
ggtcaacagc atccaacaat gacaggagag tttgaaaaaa tttcatagga aaattgtcac   6840
tggtttttaa ttaacactta aaaggtgtaa catttttttt atgctattaa gctctattcc   6900
aaaaagtgtt aagttcattt tgtctatttg ggaaaaagaa gaggtagaaa atatcttgag   6960
aagaaggaat attgtgatca caaggctaca gtgaaatggg ccatgtccac tagagtagta   7020
gaggaaaagt aatagaggaa attatcatgt attgtaaaaa tgacacttta ttatcagcaa   7080
ggtggagcag tagaatgttt gtatgctgcc tagataggaa tgaaagagca tgcttctttc   7140
tttgatggga acaaatgact tgtacagaa acattttcct ggagataggt ctctgagatg   7200
tggaaccttc cctagtgaaa aggaccatgt ttcctgctgt gctgccatga atatttttag   7260
tcttgctcat ctttggctaa gcctcagtgt ttgtggatac cagatgcatt gtgcaggtgt   7320
gatgtggaaa caggaaatct gactacttgc catattctca aacatatttc ttatctccct   7380
gaagcaaaag tagaacataa aacatttctg ctatcaccta ttctaattaa atgcatatat   7440
aggattattt attaaaaata gtatttatga aaaaggctga agctctgtg attttttcagt   7500 taactccttt atgcacatgg ctatactgct gatatctgat gaatatgtgt ctgatgctat   7560
ttgtgttcat cacttttctg ttgccgtgac aatataccac aaccaaagca tcttatagaa   7620
ggaagagttt atttggctta tggtttctta tgaagatcct gaaagtaaag gaagccctga   7680
aaaaccattg tgtgaggctt tgaaaatgaa gcctgggtta cagtagatcc caaggctt   7740 agagattcca aagccttaca cagtggtctc tcagggcttc ttttcctttc agtatcttca   7800
ttcaggatga acttgccaca tatagcatgg cctcagaaac tctctcaaac aatggagaaa   7860
actccatgag cccttaactc ttaaaaaaca aacttccaca atattcatgg aaattatgat   7920
attcttggac attaatctat ctctgaagat gcatcttcca ttagagtcta taaaaaggta   7980
aacaagagaa aacaaggcag agaaaaaaaa tagataaagg taagtggcca aaggtttgta   8040
aacaacactg agccaaaaat tcctggcctg gaaatgagta gagtaaccag atcataagga   8100
tggtcagaat ctcagatgtt taagtgaaac tgtattctcc tacataacaa aatcattccg   8160
tgtcagcgcc aacatggctc caaagagtca gatctggtca acagccaaat ccttaagaaa   8220
tctagctcca agttcatttc caactgacta gaggtaaatg ttatgctttc ttctgagtaa   8280
ttttctctaa atgatttaaa gaaagggtga agataattta gaactcaaat taaaggttac   8340
taaacaaaat tcaaacttca ttttccagtt ctttttcagt ttgtttttta aaaatataat   8400
tatatcattt ccacttttct tttttctttc tccaaactct cccatatagc caatttgctc   8460
gcaaattaat tgcttcctct ttataaaact gttattacaa ttttgcatat tatcattttt   8520
aatactttat agtatctgca ataacaataa ttaatataaa cataatacta atatataata   8580
tatattttcc tatacataaa accaccacct ccttggactg tataatgtta ctgtgtgtac   8640
atgttttgag ggttggtcat ttggtattgg aaagatcttc cttggggagc attatttcta   8700
ccattctcat cactccttag gaacctacaa ttctttgtgt agggtttgag gcctcttcag   8760
cccccattca cattagcatg cgtattggtg tgttccttgg ttgggtcatg tttaggcacc   8820
catgaggatg agactttggg tatagtttct tacatttctg ggagacacag ttttacagca   8880
cactctgtgc tcctctggct cttatagtgt ttctgctccc tttccagaag ggccttcaag   8940
cctaaaggaa ggaccgtgt tgtagttaca tcagttgggg tgtggctcta caactctgaa   9000
ttttaattgg ttctggtttt ctgctatagt ctctgtctgt tgcaaagtga agtttcctca   9060
atgagggagg aatgagaatt atacttatct ataaatataa tgcatacat ttcaaatgta   9120 gttagagatt ataattgttt gtaggctctc caatgttcat gactttgcaa gtcctgggta   9180
```

```
gttggctagg tttcaatgac cagacatgtt ttctcccttg ctgtgcaggt cataaattca   9240
atgagagcta ttggttgtca cgaaggtatg catgccactt atacacccca agggttatca   9300
ctccatgctg gtcacttgtg tttcacaggc atatatctgg gtagaacaag gggttgcttc   9360
tcacctttgc tagtgtacat ggcaccttct ggtactgaaa gctactcctt agggaggagg   9420
cttttaggtc agttccagct tagggcctct gtgctccgtg tttgaagtac atattgtcat   9480
cagcaataac aatttacctt ctacttctga aggacaacca aaagaaataa tatcagtaac   9540
gtataatgta ttctgtgtct cttctataat cctgaccaat aactcaaaag aggatttctc   9600
actcatcaac ccctgtaagt atcgttgttg ttttgttttg atataattgc aatatttcac   9660
ctctcttttc ctctcttcaa gttttccagt atacctctcc caggtctcct tcacattgaa   9720
tgttctcttt ttctttaact gttattgcat aatatatgta tatacatatt tattcttcag   9780
tataacctac tcagcctgag agtgaataat gctacttgaa tgtatgtttt cagggctgac   9840
cacttggcac tggacaagca atttgtatgc tcttctctac agagatcata tctcctgcac   9900
ccagcttttc tcagttacct attgtccttc atgtagcatt gaggtctcat ggacttttcc   9960
ctgtccactt tgacatttcc ccttgtgcta accttgttca gttcaggttt gagtagtcat  10020
gaatgtgaga cttcatgggt atagcttctg acattattag cagacataat ctcatgcaaa  10080 cttttcttgat cctctggctc ttacaatctt tctgttccct cattcataaa tgtttctatt  10140
gggactgggc tctaaaactt tgtattttga ctggttgtag cttttctgta gtggtctcta  10200
tttgtttcaa agaaaagatc ccttataagg agcaaagtct atacttatct gtgggtataa  10260
caacaaatgt ttgtagattg tagttaggga ttattctggt ttagtaaatt agtggttgta  10320
gtttctcctc caacatccat gacttcacta gcactgacta gttcactagg ttttcaggta  10380
ccaggcatgg tttctctctt gctgaatgac tcatacccac aattagaggg ctgttggtta  10440
atactcacaa gtatgcatgt gactcctgca tgcttttggt tatcatggac cctgatgcca  10500
ctgaaacaca ctaacatcac ctttttttat tttatcgctt tcaagaaaca gaaaataggg  10560 tctcttttagg gagcttgaaa ccttggtttg tggagtattg tttgaggaca cccttccctt  10620
catttcaatg caaagtagac ctgtccttaa tggtgtaaaa cttttaaata attacagcct  10680
tccttctgtt gctttggcag taacataaac atactgttgg tcttttttctc tctaaactat  10740 acattttgta tttctgcccc agttgctctt tctttcatta tagatctgca taagtgttat  10800
agtacaacca ttccacagat tcatcattat gttgtcttac aatcacttcc actaaagaaa  10860
ttcatccttt acttttcaat tgagtctcag gcaagtattc tgctcaggac atgagcagaa  10920
ggtggccaca aaccatgatg aaaaaatgaa tagcctccaa cacacttgct gttaacgtcc  10980
ttcattcctt ctgaaacctc ttggtccagg cttctacagt atttatccct ctcagccctg  11040
ctgtcttcca atcttctacg agaaggacct tttcatctct gctcatagca ttcatctgcc  11100
tttcgctttc aatgtttaca ttcctccaaa ccccaaaatg attgggttct tcacagaaat  11160
agccaacttt ttttggtacca acttctgttc tcatttcttt tctattgctg tgaaagacac  11220
cacagccaga aagcaacttt ggaggcgaac ctttatttca gcttgaaggt tatagtttat  11280
catcaaagga agtcttggca gaaactgagc cagaggccat ggaggagtgc tacttgctgg  11340
cttacttcca gaatcacatt cagctacctt tctttcttac atgtcccaac ttcattgttc  11400
acagtagact aaactctttt acatcaatca tgaagcaaga aaaccactac atatacaccc  11460
acaggccaat ctcacaggta tcagttaagg ttctcccctt ctcagacata tctcaattca  11520
taacacgttg taagcacaac cagcacacta ttcaaacaga tttgcttagt gatgggggaa  11580
```

```
gcaaaaggaa ctgtcttaga ctgatatgct tgcaatgttt tcaaatagct tcatctctgg   11640
actaaatttt gggttttttt tttgtttgtt tatttcaaat gtttatattt ctttaatttt   11700
gtaatgtaaa tatgctgaga aatagtatat agtatttgtt gaagagcttt aattcaatct   11760
ccttgaactt catatccaga tatcaatcac tttttataaa attatatttt cttttgccct   11820
aaatacgtga cctaggaatc agtataaata taataaaatg taagtataaa tgcaagcatt   11880
tatgtgtcaa tagtctttgg cctcttagtc aattcttcct ttctttcttt tttgtttgtt   11940
ttcttcaaga cagggtttct cagtatagcc ctggctgtcc tggaactcac tctgtagacc   12000
aggctggcct tgaactcaga tatctgcctg cctctgcctc ccaagtgctg ggattaaagg   12060
catgtgccac caaagcccac tttcttagtt agttcttgtg gctgcttaaa catggtttca   12120
tcgctagttg gaaataactt acttgccaga gtaagattaa tggagagttt gtataatttt   12180
tcttcttttt cgccaattag tatcactctg gaaacatatg cagatctgct tattaactgg   12240
gcaaatttca attgggcaga catattttat tatatatatt ggtttcacct aagaaaagca   12300
cagcaatgtg aatactctct tttttctttt gtttgtttgt ttcctgatat atattgcata   12360
agctaagtgg gtcacccatc atcacaacac ttgtttgtat gctttaggtt gctatatgct   12420
ttaaaaaact ctgggaccag aatggttggt catgtcctaa tggatgaaac accttttcac   12480
ataaagagtg ggtgacttag atagatacct gagcaaaaat tttacatgga caattgcttt   12540
ggcaaaaaaa ttatggaaag tgcaggatca ttatcaacag tttataaaat ggtaaaacat   12600
gtttcttgga catatgtcaa cattctgagg atgtatattt tataatcatc aaggaaagat   12660
tgtcttttaa tataaaattt tagtcaaatt taaaaatttg tttgtgagga agactgatac   12720
catattgagt ttaattttttc tatcatcatt gatctaattt ttttcaacta acagtaaaaa   12780
tgaaccattc tatatgtatt gtatgaagtc tgttcatttg tcacagaaac tcatgttgat   12840
ttcccatctg tctttagtgt tatttttaact acttaaataa tctctataca taagaccaca   12900
gcacaagata attaaggagc tagaatgctc attcacttaa ttattgccca acacacttac   12960
agagctccat tttacatttg aaaaatttgt caaattgttt tactctctct ctctctcttt   13020
atatatatat atatatataa aaggtgtgtg taatagtatg tgtgtagtat atgtatgtgt   13080
gcaaatgtgt tttaatatgt atagtctatc actctctatt ttcagtatca ttaaaaattt   13140
tatgctattt ctttgcttga gaagaaactg cacatttgag taaaataagt tggatttttt   13200
ctttggataa ttcacattgtg tgaagatgtt taaataagtg ttttttttcat atgcacatat   13260 taaagatcat ctgtgaaaca tctatatttg ttatgaatta aaaagacaaa tatttagaaa   13320
gccatatttc tatagtctag gctttgacaa gtaaagtgag aatccatagc tctgttctttt  13380 ccatcttgag catgacacac acacagtctc tttgtaaatt actcaggctt tcttattctg   13440
atataaatac aaacacaaaa taacttgtat tttgatgaga aaactgaagt ggaacttaaa   13500
tataaatgga cttgaagatg ctatatttag aagctaaagt attactttgc ccctaatttc   13560
attttctaat ttgtttaatc acttgttcca tatttgatat ggaataacaa gctttcacaa   13620
tactgatgat gcattttata taatgttgta ggcaatcgtt tcaatgctac tccatacttt   13680
caaattgtct aaacaggtaa aaagtattag aatctctgag cgcctgctgg acatgctcct   13740
tttattgact ttctgttatt tatttccttg aaaggcataa taaccaaatc aatactgtca   13800
gaaaaatata aatcctcttg gtatgctatt ttatccactt attttttccct ctgaaaataa   13860 atattactga aaaatatatc tgtcttatta atctgcccag ttttgctcac aaaagatatt   13920
ataagttgga tttcataact tttctatctg gttggaaata ttttacatcc tatagtaaga   13980
```

```
taaagctatt gatggcagtc acagacatct caggtatctt gtgaatgaac taagaaatga   14040
ttcaaggctg caaataagac ctgaccaaat taaaagaaat gcttcctagt tcaccctaaa   14100
catcagttta cataaaaatc tccactcatc gtactaaaga dacagtttag taattaagag   14160
ctcaaattgc tcttgagatc tgagttcagt tttgagcacc tacatcagga ggctcaaaca   14220
tcctgtatct cctgcttcag gtgacccttat acctctaggc tccttgagca ctggattcat   14280
atttatacac actaaagtaa acattaaaaa catgcagtca tttttaagaa tgcactcagt   14340
tgaattattt ctaagaacac tcttatttct gtcattacac aatacacata aaatacctgc   14400
cctattttac agagattaga gaggtgaggt gctagctcta actcactgct agttcatagc   14460
agcacacagg tccatctagc ctctgagttg tatgtggaca ccctgtctca gatttatgtc   14520
ctgctttctg gagttgagtg catttctggg gttcatcagt atgatctttt tcctcatttt   14580
gaaataaata aatttcttat attccaaaat atcaaatgta ttttctattt ggttttatag   14640
tctttaagtc ttgaaatcat ggacatcttc attttcatag gactacagca atggttgtga   14700
tgtttagaaa gacatccaac tgaattattc acatatgcca tgctattttc ctgtggccaa   14760
agttaacacc tgttcttcat tgttgttcat taccctctga gcgtgtggaa taatagaata   14820
aactgcacaa gaggtcaaat taaagatttt cttcagacac tacattccct cttcattgat   14880
tcttttttct ttttaaattt agtgtcccat tattgttctg tctcaagttt aaatctttga   14940
aaatgaaata tgattatcat cttaaagcca tatattggca gcttctctgc tgcatatccc   15000
atataagatt gtaagataca tatatgcaga tttcagcagc acatgtctca tgtaattaca   15060
gaagatgaag gagggacagg cagatactaa gaagcacata atactaagca tattatgtct   15120
gtactcagtt aagcccatta aatcaacgct ttccacccct ttaatcactt tgcgaccatc   15180
agcttccttc tcaccatgac atttcactct gctttctttg taatagtgta ctgttaaact   15240
caggacaaac ctcaaaactc acttgtctca tgggaaatca aagagagtgc aggtcaagta   15300
tatatttgcc tagaacatta atctacagca taattacgtg attaagctca gttaaatcaa   15360
tgctattagc atggcaaaat attagatttc actcgtggga gagcacctgc acacatcact   15420
cacatgtccc attaagttgc tctgccttac actacaggct ttgagtttaa actttaagtt   15480
ttaaagtgat tttcagaaca aggctttgat actaatggag gtgcgggaca gaaaggagaa   15540
aacaacagga atgtccagtt cctctctttc ttacagaggg ctgcagctcc attataaatg   15600
cagagacaag aacccacagg ttgatcttag aaaccgtcag catagtttga aaagctgctt   15660
actgtgctca gagtgctttg aagtgtgtat agaataaagc agaaatataa taataaatca   15720
aaatggtgaa aattattttta caattttatt gtagtctttt tgtaatctgt gcatgtgtgt   15780
gcgtgcatgt gtgtgttcat gcatatgtgc aagcatgaat gtgtgtgtgt gtgtgtgtgt   15840
gtgcatagaa agaatttccc aacaccaaag aacgctgata cagatactcc aaatataact   15900
gatatgtgtc ttcatgtgta cctcagctcc cgattttcca tgttcatatt cacatttgag   15960
ggcgatttgt aacacagctg ggtcctacct tgttactttc catccctgct ctgggagact   16020
tcacagactg gtttacagtg atagaggatt gtgccttctg gaaaagccta ctggattatc   16080
tcatatctga ctctgatgtg atctgagtcc aatgcactct cagagctcca gtttccctgt   16140
ctagaaaagt gacacaaaac taaacttatc cccttgtgat gattaaacgg ttcagcacct   16200
ctgttctttg ccagacataa agcacagtgc acagatgtgg agttatggag ccattgtagg   16260
aagcacaact atcccagtga gtccttcgtt gctcggcagt tgggccttaa agtatctgac   16320
attttatttc tcttttaact gaaatcccaa ggcttaagag gagatccctg tgaatttata   16380
```

```
aatatgtcat atcgggaaat atattaggta gttgtcactg cagtctatcc aactaactga   16440
attttatggg tcactgtgaa aatgcattat tggcagtaat aaaagaagaa aagaaactaa   16500
taaactagtg atttatgcaa cagcataggt gaactaacac atcatgctga ctggtataaa   16560
caaaggccat atactccatg gatatgtaca gaatcaaata gaattataaa catagttcaa   16620
agggatgaaa catttccttt tatcttttga gatttcactc aggtcagata actggccaga   16680
ctgtgtgact gaagataata gaaaccagac agtgctgatg ttaggagcaa caccctgacc   16740
agtaccgctt agttttgcat gcaatgagtg ttctagatat tgaaatagtc tctctttaaa   16800
atggtatgct atcacttgga cttttttcaaa atctgcagac acaaaatcag agcagttcac   16860
tctataaact ataattcaat gtagaatatc atttgatgcc atcctgggta tttcagtcat   16920
tctcacattt attaatgtgt gctagaatgt tcccagatgg aaaaacatga aaagcttaaa   16980
tctctagaag gagagaagtc gatagtgaca gagtagccat gctgaaggca cagaatgatg   17040
cttgtggaag ctggtgatat ttatgtagga atcttagtct cacaactgta aatatgttta   17100
aatgttttac attctaaaat tttagaggag aggtgtcatc tcaattcact ttctcttcta   17160
taatagaaaa aaaaaaaacc tggctaaata gaacataact tggtaaagtt ctgagaggca   17220
gaaaaccaac gcccagacgc aaccaaaaca ggcctggcaa acattatcc cgaggaaacg   17280 tttgtgtcct ctcatctggc tttagactat tgacaaatag accccaagaa attggaagtc   17340
ctccaggaat ttgctgaggg aaggaaaagg ctgaagcctt gtgtcaatta cagggtgagc   17400
atgtctccca ggaagaaata tcagatatca gatacttagt cagacctcct tgcagaagag   17460
actggagcgg agacagagac agtagctgga agcacacttt gacctactgc ttagtcatac   17520
atacatcctg acctctatct aaacaagatg aacttggggc actaaacctc tgttcctctt   17580
cttaacgtgg ccacattgaa ttactcccat ttctagtatt tcactattta tatgtcactt   17640
tacctggctg gttgaggaca ggtgtcctaa cttggcagga tggggatgct agagcccagg   17700
atctaaccct atctactgca gaggtgccac cttttccttt aatttcaagt aaacatggta   17760
tgtgccacta gtgtgtagga aggttgattt ttaaagggaa taagaattga aggcgttgct   17820
taaacagtta atttctgtca cattacttgt actctgcatt tgtggtttta tctgcctcct   17880
tcctttatag catgccaaac aagctgcttg tcccttgttt caaatgcttt tttagacttc   17940 aatttatttta tttatttatt tatttatttta tttatttttc aggattcaga agtcaactga   18000
cttcaaggat cagagaaagc attccctcct acgaccccc ccccctttta atacagtaaa   18060 cgcttgatt agcttccagt gcccaacaca agttcagaat acaagaaagg aaaagcaagg   18120
cactctgctg ggggaggagc ttggcactca aatccactct gctataaaac agtggtattc   18180
tgctcatctc agagagaagt gggaacgtgt taagtaacac agaaattgtc tcaaagcctg   18240
tgcatctatc tgcgcgtgtg cttggattgg aagaagagtc tgttcgctgg agctccacgc   18300
agccagaagt cggaaaggta agaggtgtgc aaaatctgcc attaagtagg gactaaggaa   18360
gaaactgcct gtgatggtcc cagagggtga atcccacagc cgctaccttc ctatcctgta   18420
actctatagt aagccacttt ctcaagtgca aaaaagcctt gaggcagctg gttttcgacg   18480 gttggggat atttattcct tgctccacag atggggaaaa aaaaatcagc gtctggcagc   18540
cgctgattgg tggaaaagaa aatggtgata gtggagtggg aatgaggatt tgctgagcct   18600 cccctgctt cttcgacctg taactcttcc ttagtcggct ccccctttgca cccagaaccc   18660 ttttagactc ctccggggta aaaacaaatg gaaatcttaa gctgtgtgaa caaaagcaac   18720
cccaagggtg tgtgctccct ctccattgcc tggctccgca cacagaccat tcaggcggt   18780
```

```
ccagctctct ggtgtggcat ctgggctcgt cctggaggag ggggtcgcct agaggaactg   18840
ggaacagact gaggcaggga aggaggggggg tggggcagga gaggcgccag ctcaagttca   18900
gccacgataa aactgagggc cctctgaact cgagggagg ctcaggccgt cctctcttcc   18960
ttccatccgg gggaatgtgc tccagatacc cacagccctc acgcaccgca cctccaacca   19020
acccgtcccc tccctaggaa gaggagcgaa ggcacgaggc aggcgagggg cggggagagg   19080
cgctgacaaa tcagctgcgg gggcgacgtg aaggagccag ggagccagag cgcccggcag   19140
caggcagcag acggcaggag accagcaggt gttcccctg cccctgcctg cccttgcctc   19200
tttcattgaa attagattgg ggaaaacagg aagaatcgga gttcttcaga agcctaggga   19260
gccggtaagt acctgtagat gggggcagctc tggggatctt agctagccgg agcaaagagc   19320
cgggacgcct agagaagacc aactacagct gctttggcgg tggggactgg gccagtgcgt   19380
ggaaagtaca tcactcggct ttcctttcgc tggagacatg cccttccatc ctgtcaaagc   19440
ccgagggaaa ggccaggttg cctgtggcat ctgcttttc aagcggaaac gctagggtgt   19500
ttcatgttga gtgctggatg gtggaagctt agtgctgggc attgggtgga atttgagcat   19560
ccaactttca tgctccaacc ccaggcattt cagcttcttt ctgtagagga agaagggtgc   19620
ctttggccca tgattaatag aagtgcagag gacagtaggc aacaggtgat aaagggttaa   19680
tgagcatggg gtgcagggtc ttctagagga ttccagctga ggacagagct tcttggttgg   19740
gtggtgctca agtgagactg ctcaagtgta tggacagcgc ctgctctggg cagatagcag   19800
gcaaagagct agtggtgggc agaaggtctt gcaagattag aaaggctggg cttcaagcag   19860
ttccctactt ctagattaaa cagttcccct cccttccttc tccaaagact gactcctctc   19920
tgggtctttt atcctcttgc ccccactcca tctctgtacg cccacctccc atgttccttt   19980
tctagatagt cttttactt tgaatgtaac ctttgggccc tgggaacttg atggggtaga   20040
ggatgcccac ctccccttct gcaactcttc ttctgaaata tgtatgtaag agcagtcgaa   20100
tgatcaaact agatccatcc catccttaag tgacatgact ttttcctagt attgagtgac   20160
ataactcaac aatcaatcaa cactgtgccc agcaccccca catcccccca cccaagaaat   20220
cacacttaca ccaggacttg ggggaaggca tactgatttt tcccccctcaa tttcctttct   20280 ttctctagct gttttaaacc ttattattat tatttttta cccaaattt ctaattcaaa   20340 atgtattctg tattctctag tgtggagcaa aaatacatct ttagccatgg atgtgttcat   20400
gaaaggactt tcaaaggcca aggagggagt tgtggctgct gctgagaaaa ccaagcaggg   20460
tgtggcagag gcagctggaa agacaaaaga gggagtcctc tatgtaggta ggtagtgaca   20520
ctgtgactaa tgaattgggg tggctggtgt gtggtgtctg attcgtgtgc atcacagctt   20580
ctcagaagag tgacagctgt gtggaggtga gagaatatga acctgcatat tagctctcag   20640
aaacaaacag ggacaatgtt ttctgtcctt agattcatta atcttgttat ttatgtaggt   20700
tttttatttg gttttctgtt tctgtgtatg aatacactga attttaaaaa ttggcaaccc   20760
atgaaaaata accaagaata tgcttatgaa tcaaagacat gtatggcagt aagcctggtg   20820
gcatttggga agtggaggcc caaggaccag gagttgatgg tcatcttcag ctacacagag   20880
aatttgatgc cagcctgaac tatgtgagaa cacacacaca cacacacaca cacacacaca   20940
cacactcaca ctctctctct ctctctctct ctctctctct ctctctctct cacacacaca   21000
cacactcaca cacacacaca atacacacac acacactctc tcttacacac acacatacac   21060
acatacacac atacacacac acacatacac acacacacac actcacacac acacacaaag   21120
aaataaagaa ataaaggaag gaaggaagga aggaagaaag aaagaaagaa agagaaagaa   21180
```

```
agaaagaaag aaagaaagaa agaaagaaag aaagaaagaa agaaagtgag ccacaagtac   21240
tcatgggact ttgatttctt tcatcatcac tataggtaat acctgctaag tttaataaat   21300
tataaagctt taaacaatag ttttgcataa ttttatttta caactgtgaa aatacaactc   21360
ctttgacccT caaatagaag aaagaaagca agtcttcttt ggtggatctc cttttaggga   21420
tcacttggtc agtgggaaca gcgggactta aggaacttca gaaatgtttg tttagttcac   21480
ctgtcagaga tcatacatgc tgaacagtaa gaggttgata tttagtgcca ttttctgcct   21540
gactgtacac attgaaagga aggccaacac tcccttctc tgtctttccc tgtgttaaat    21600
tggctgtaac tttacaaatc ccttctagta ctttcatgga aggaatagac acccatgcac   21660
acatgcttat ccccagcaga gacacaggtg cacatgggag cacagttgca gggttcatct   21720
acctctcttt cctcctgtga acactgtttc caccttctta ggagggcatc tctcttggtg   21780
gaagactcag ggtaaacatt caggctgaaa aggagcagaa caggtggcaa aagtgatgca   21840
gatgctaccc agagtaccaa tcgggggaag ccatgctgac cctccaaacg atcagtgagg   21900
aattgatact tgtaaacatt ttcatgaatg tgtcttttca ttgaagtttc tagcagatca   21960
cctttcctaa ttcttcacag aataatttta cattgaatta attctctttt tctacttaaa   22020
acatcctttc agaaagtctt gtaatgagta ttgtaagaga agggtgtcaa tgagctaatt   22080
ttagagtgtt tttttttaa tgaattgtga agtataatgt tttagataga attcagaata   22140
taaaagcagt aatttgtaga tttggggaaa aactcaattc ttccacaact acaggcttgt   22200
gactgatttt tttttttttt acttcagttg cttaagaaac atatctgtag atcactaatt   22260
taaagcaaat ttagaagttg ttgaatatta atttagtata ttactctttc tggataataa   22320
atggattttg tcaagcagaa cacttctttg tttttattgt taattttgag tttgggcaaa   22380
taaagtgatt atattttca aagattaatt ttgttggtct ctgtgaggcc attatattga    22440
aagtgtaatt ttaatatgtc taatattatt aaaattatca atgtctgtta ttatatttaa   22500
aacatgttta attaatcaat tgcttattat gttctggaat ctaattaaaa gctgaacaca   22560
tgcatagagt ttgggatgaa gagtaatgtg tgaagataag aatgatagct cagatatttg   22620
tcaacttctg ttaatgttcc aacacatatt agaaaatctg tcatagataa tcagctgtac   22680
tgttggctat actgattatt gcttagataa tcaactgtgc tgttaaagta tgaaaacaac   22740
cataggcaaa aaacagtgtg actctgcctc tgtctttatt gactcagaga ctatagagaa   22800
atgaaaggaa tgtagactct ggacttgact tgatacagac agaaatttaa ttcaagccac   22860
atgatttctg cctttagcat ctgcaggagg taacttgata tctttgagtc tcctcccctt   22920
tttcacatac acatagttca taaaaatgca actgctttgt aaagttacta aagttatgta   22980
gttaaggtag taactgagtg cactttcata tttaggaaac ttgaatcttg tcagagaagt   23040
tgttcaatct atctgttact cagtcaacct aatttcttac ttttttatcca agatatgaaa   23100 ctattattaa tacctaacct gaaggattag aaataatctg gactttggac atagctcccg   23160
tggcacagtg cttgtctgcc agcatgcagc cctgggttct attcccgtac cagaaaaaca   23220
aaagattaaa aataaaaggt tagaagtaat caaagaaaaa caatgtaaac ttcagcactt   23280
atggctgaaa aggcttggca gaagtctcat ctcatctcta ataacaaatg ccttggacaa   23340
ctgcctttca atgaattgaa gacctgccat actaatcagt gtgctgattg tctctgtgat   23400
atttgcacaa aaaattcaat taacatattt tagcttcata atcaacagtc tcaatggcgt   23460
gatgtataat tataaattga atttaaagtc aaaaagtttt cttcacttca tgttagtttt   23520
attaatacta taaagaaaat caccttcaag ttctgtttca ctgcctggtg aagagctgtg   23580
```

```
gtcacacatc taactcctaa gtctcacatg tgagacttaa ctacatgttg ctaagtagtc    23640
agcatataaa ccaatgatat gactcatttc tcacattcct cttaggtccg tatccttgta    23700
atattccaaa taaacaagac agggtggggt ggaaggcagg gtacatttct aggctcagag    23760
aagccattat tatattgttc cccagcttcc atatcttact tcttatttgc tacttgatga    23820 ctaattttt  tttgctatat cttatcagtt agatctcacc tgtaaactga agataaacta    23880
tcatttataa cttagctgat aattaggata acaaggtga  gaggtatggt ttgagataca    23940
gggccttcaa gactcatttg tctttcatta aagaggcatt ccatgatttt accaaacgtc    24000
aaattctctg ttactgctga ggcaaagaag acagacaaga gaccagccag tgagcattag    24060
ttttccttgg tcatgctttt tttttaattg ggtatttat  gtatttacat tttaaacgtt    24120 atccctatt  ctattctaaa ccccttccct ggcttctatg agaatgctcc cctgccaccc    24180
atatactttc acctcacggc cctggcattc cctacacta  gcgaatccag ccttcacagg    24240
tccaagggct cttcttctat tgatgccaga caatgccatc ctctactaca tatgcagctg    24300
gagctatggg ttcctctatg tgtacttttt ggttggtggt ttatgggagc tctggagggt    24360
cttgttgatt gatattccta tggggtttca aaatggttgg cttccagcat ccgaatctgt    24420
attgatcagg ctctagccga gcctctcagg agacagctgt atcaggctcc tttcagcaag    24480
cagttcttgg tattagcagt agtgtctggg tttggtgtct gcaaataaaa tgaagccttt    24540
ccttcagtct ctgctccact ctttgtccct gtgtctcctc tagacaggag ctcttaaagc    24600
ttgttgtagt gaagatgata cagaagagtt gagttctctc acgcaagctg ttctactact    24660
tgtgcagggt gccctgccca ccaccatttc cagttgtgat gtgaatagca cctgtctcat    24720
aaagcacaac ttaaacacct gtgattgcag tgcataaatt aatagtaatt attcgaggta    24780
caaactttac tgctagcact tcaccctaaa aattatcgca aaaataatga agcccaatg    24840 taattggtga ctacattaaa ctacttcttt cagaatttgt ccatgagctg ccactttcca    24900
tctgttacaa gatttgcaca aaaagcagca cctgtgggtg tgctgtcttt tgtaacctgc    24960
taataaatcc gtgtgatatt tttacagaca cacatctcag aaaggggaaa ctgaccagct    25020
gaggtgaagt cacatcaagg caataaagtg caaaatcctg ggagcaattt gtttatagaa    25080
aaataacagc tgaatattca gattgcagaa atgtaaattg aatatttaat aattttggaa    25140
atagcaattg gttcataccc gggttagtgt atatcaactt gaaagaaagt agagctagca    25200
tatgtggtct ctagtgtagt cctagatagt atgtacacac ttcagggtca ggaggtaaat    25260
gtacaagctt acactgagga ttgtgacata tcagaagcca ttgtctcaga ggaagtaatg    25320
ccttcttaac cccatgctaa aagaactatc agagtcagat cgcggcatga agagttgtgg    25380
tggtttgaat aggaatgcca cccagagtct catgaacctg gtaccagcca gtggtactgt    25440
ttgggaagga atatgcagtg tagccttggt agccgaggta tgtcacaggg agaggcagtg    25500
aaggtttaat agccacccat cattcccagt gtactcttgg tccctgctt  ttggatcaat    25560 atgcaagctc tccattgttc ctgctgccct tcccttccta ctccactgtg gattctaaca    25620
cacccaatgt tttaggacat gaaaaagata cccacaccgt aaaggcatat gcaatgagaa    25680
gaaggcaagc tttgttgaaa ctacttaata agcacattgt ttttgcaaaa attaaaaatt    25740
ctaaactaca aaatataaaa taatattag  ctttaacatt ttatcatttc ccaacatact    25800
tgtgtttaat aatttgactc atagccccct caccatccac tgcttataca gtttccccat    25860
tcattgttag gttctgtaca ctgatcagct cagcttgtcc tcacagctct acagtccctt    25920
gcaaaatgag cagtgcctat gaaatgcatg cagacagcac ccatgcagaa cacatatccg    25980
```

```
ttcctgctaa caagtgtgcc tttctctctg cgctgcttct agtgcggtga tctttcctgt    26040
gctttcagct tcagcttctc cttcagaggc atttgtatgg gtaagaacaa gagtttgcac    26100
catgtctgta tcatgcattc aacagtactg agggctttac ttcaacgatt tccttttatt    26160
cttttgccaa gatcatgatg cagatttcgt taacctttag tgaagtgaag agttaaatct    26220
ggactctgta tcggggtggg ggtggtggt tctttatttt caaaataaaa gttcctacat    26280 atgcttttt aattaatgag ggtttaattg actcctttct aaaatattat tttaaataaa    26340
atagacaaaa attctcttaa ggctatatgt atatatcttc aaaactattt actaaataat    26400
ttaacatact tttgtacatg tacttaggtt atcttattga tcatattatt cagcttgtag    26460
aaatgcacat ctgaatttta agcaattttg gaattagaaa ttacctcata gttagtgttt    26520
gtcaacttga caggaagtag agatatgtgg gaagaggaca taacatttga ggaaatgtct    26580
acctctgatt tacccatagt aatgtttgtg aggatatttt cctgattgac aactgatgga    26640
ggagcaccca gcccactgtg ggtggcacca cccctaggca ggtattttg agtgttataa    26700 gaaagcaggc tgagcaagat atggagagca aaccagtgag cagcattttc ccgaggtctc    26760
cacatcagag cctgcctcca ggttcctgcc atgcttggag tttctacttt tggttccctc    26820
gataatgaac ttccaaactg gaagctgaga atctccttt tccacacttt gtgtttggtc    26880
acagtgttca tcaccaaaca gaagactttg attggcaagt tagttatgta cagggaatgt    26940
ttactctaaa tgttggtatc tgtactttat gactgagcag ttggcttcta ggaagctatg    27000
tatatgatat agttttgta ctagtttttt ttcctcttct tgttttctgt ccatgtagca    27060
agacattttt tttcttctca aatagtgcat ttttaaaatc cactatttta agttttaaa    27120 attcccccc cccacatgc tggcctaagt cttttcagc ttatatgtcc tcatgtcctt    27180
tttatccttt gcattcttct gtgtctagat aagattattt tagttaatgt tcctctctcc    27240
atctctttag tccttcttc cttggttct tggtaatatt ggggatcaaa tttaggtcct    27300
taaacatcag aaaacagtgc tgcactaaga actatgtctt tatccctata ggatagcttt    27360
cacttaaaaa tgtgtatttt tatatgtatg tatatataat atgcatgtat attgtatata    27420
tatacagata tataaaaatt ttatgcatgc agataaaatt atcagtattg attgtacaaa    27480
gtgagaggcc tcattatgat gtgtgggtct ccccttcctt ggaggtaatt ggcaactggc    27540
ctaataggct gaggggagca gaggcggttc aggcttcaga ctaccataag tatgatggat    27600
tgacttctgg gatcagcttt agtgagacat aacaacttag acagtgctag ggatttctgg    27660
gtgggtgtag attattggct aggttcgagg tgctgaggat gtgtcattta agaaagagg    27720 aattccagga attattggga gagaggttgt tgaatctgta atctggccat tgacaacatg    27780
attgtcttta taggtgaggg acatagaggc ctgatgccac agcaagtaga ctaagaatag    27840
ggagagagtg atcctaactc ctgcctgtct aaggatgaga tttgtcagca tcttgatccc    27900
gtctcactct tgctccaggc tagctctgct ggctgcacat tctcacaatg atcttccac    27960 agatgcattt aatatacaag gttatagcca cccttctatt actagttttt tattattatt    28020
tgtagagata atgctttta tatttttatt tgctttgtta ttcctgcgct ttcattttg    28080 ttgtgtatac tcattgttca tggttccatt ccataaggac attttatat aagtatatag    28140 aacacgattt ttcacaattc atgaatgtat tttgatcata actcctctcc tttattcttt    28200
ctcccccttg ctcttcctct ccacttcttt agtaaagccc agctgctttt gcgtacttt    28260 tatcactcta tgcatatctg ggagaaaaaa tgatgctatg tttttctctg tgagctgggt    28320
catttcattg aacatgatga tctgactttt tccctacaca tatcataatt tccttctttt    28380
```

```
ttatttccga ctacaagtca attatgaaac ccagtgtgtg gagaattctt aaaaagtaag    28440
aaataaaatt tccagccatg ccacttctgt gcaaccacca gagccaccat acaagaatga    28500
tgtactgcat accatgcata tttgactatt caaccataga gtgttatgga agcaacccag    28560
atactcacca gtggatgact ggaagaagag actctggtat aaatcaaaac cagagttttt    28620
caaatgaacc ttaaatctcc aaactattta atcaaatggt ggtcattata ctgaaatttt    28680
aagcattaga aagattattt ttaaaatgat taacaaactt acttttaata atatgtgcaa    28740
tagctatttc tttgtttagt aatggctcaa ggcataggtg aaattcttat cttacataca    28800
gtcctagttt gaaagtaaca tgctgttact taataattat gcaaatcact taattatgat    28860
ttttagtttc cttatgtatg aaatgggtat tgaatggctg catcagagat gatgtgaggt    28920
caatctgtac caggggttgg gcagacgctg atatcttctt tcctctccct tttttgttgt    28980
ggattgtgca gtctctgctc tgttgtgctt ttacagcatt ctcaggtctg cacagagaat    29040
cttactatgc ctgtgttatc ttccctttcc ttctctctgt aaattgatga agaaagcatc    29100
aagcaagggt tatgtaaaga gtcgttatgt tttgtgcatt gtgttttatg ttttatctga    29160
taaataaagg cacaaaactt ttaccagtgt tgcctctggt gcagttccca tccatgttca    29220
cattgtgtgg tcaagctaca catatctgtt gcctctaaca tatgtcagat ctttatgata    29280
ttaaccactg aagcttgtag cctttttgaga tccacagtgc ccagttgctg tctattatct    29340
cccaggtgga acagcacagg agcttcatac tgctgactaa ctcaactggc tacccactaa    29400
accctctcca ggcttccctc ctgaactcaa cctggatagg ctggtggtag cttcctctg    29460 gggtggtggc cagatccccc ccactttagt gatttctgag tgtgattggt ggttgttagt    29520
cttctgaagt tatctttgta cattcccttc tgaatattga aattttttaa ttggctgctg    29580
taaattgaag gacagtttaa tatttatgcg ttcaatttct ttgttctttta ggttccaaaa    29640 ctaaggaagg agtggttcat ggagtgacaa caggtaagct ctgttgtctt ttatccaggg    29700
gtgatatgcc gaatgccttc taggctaaat taacttgatg cttatacttc aagatataag    29760
tgtaagagcc attgtctaca gaggaacatg ggtcaattta ttttttttatg tatctaatt    29820 ttaattttgg tatggtgaga tggagtttag ctacacaagc cagaacagct tctgcttcaa    29880
tcttctaaga actgggagta caggtatcac caatggacct tgcatattgg ctttgtttaa    29940
agtttaatgt ttatgcaatg aaatatttt aagtagacaa atatggatta aaaatgtata    30000
gcccaatatt ctaatggcta agaatgacgg atttagattt gtcaatggta tttaattcta    30060
ataatttggt atttgggtag taggctaaat aaataaaata taatgatgct attattaatt    30120
taaatatttg atgtaaacat ttctttagta tttagtattt ataccatcag ttatactgat    30180
tagatatttc ctctgtgatt aacaatcctt tttagaaaat atacttagta gtgtgttatt    30240
tttaaaaagc tgtatatttt tattttattt gtatccactt gtcatatctt caaaaagatt    30300
ttcaataaga ctaaaataat aaatattgaa ctaatatgac taaaattata atgatcaaaa    30360
atgacaaaga caatgaattt actgtgggag gaaaagcaac aggagaacaa taagaaggga    30420
aaaaccaaag agaaaatgat aaacataacc aagctgccaa agcttggtgg tagctaaagt    30480
tccttatgtc catttgccat gcatcagact accttaagtg ggaaaagacc tgtcaggaat    30540
gaacttgata tgatcaggaa ccttggccat gacaccacat aacaaagcaa atgcactgca    30600
taagatagca tcacacagtg gcaacctgtg tcttccagtg gctctttccc aagaatcatt    30660
tgctggccat ggaggaaaag aactcattct ttttagcaca ctgataaaga ataatgatgc    30720
taaagcaaca ctgaagccca ggaacaagac ccttttggaa gttcacaatg gtgaggactt    30780
```

```
ctttcagttg ctgtcccaca aaaagtgcag atagcaagag agtaagcaga ctgattggtt   30840
cctggaagct gaaacttagg cttgactctc ataagacaga taagacaggt acagagtgct   30900
ggaggcccac atccagagcc acgatgttcc agcttccata gttgagggag aaggaactgg   30960
tgagattcag agtctattgt ggatgcattg ttctctattg acaactttgg aaattttttaa  31020
tattccctga atgacaagga tataaagcat gagtttttat actgtgtgga aaagagagtg   31080
ggggctggag gagcaagaga ggtcagaggg gtgtggaaag tttctgcagt aggcaacatt   31140
ttagaaatat tttctagaaa ataattgtca gcaagcttgc atttccatag tttttataatg  31200
ttgacaattt acatgccttt tatatatcct tttagtctat taaggaactt gaaatgctcc   31260
acagtaggta aagacacatt ataatata  acccaggatt cttgaatatt tactactgaa   31320
agttcccttc catatttaac tgtatcaaat ctagtgttaa caaaacacta taagagacac   31380
gttttttgttt gtttgttttt tgttttgttt ttgttttttgc ttttttgggac agggtttctc  31440
tgtatagccc tggctgtcct ggaactcact ttgtagacca ggttggcctc aagctcgaaa   31500
atctgtcttt gcctcccaag tgttgggatt aaaggcatgc acctcccggc tataagagac   31560
actgttaagc agcaaggaca cagtggtgtg gttgtggcac cttgtaccac cattctacca   31620
gtttagaaac ctgacagtaa tatataatat caaatatact gtcacaatta gtcagactat   31680
gaagaaatgc attgtcaaga aaggccacag taagtgctat ctctcccccat cacatataaa   31740
taaattgcgt aatttattga gtagtatttg tgctgctcaa aagttaagaa tttaggaaca   31800
ttttgaattc tggactttca aagaagtgcc actacatatg tttgaaatgt tacttagaag   31860
ggataataga agtgactttg ggaagtgagg tcacagagct agctggcttt gatactgaaa   31920
ttgtatagca atgctcagac ttgacactgc acctggctgc aatgttttgt gtccactcac   31980
ctcaatgcaa accaaatcca attcacttgt tgctatgtgt tataattaaa ctcccaatat   32040
tttctaattt ctgcactaaa ttcatattca gtgtttggct gaaacatgtc tcttctacct   32100
tgctgtcttg tttcttcaga ctcctgttac ctatgatata tgtgtctata aagttgaca   32160
gctgctagaa gtggaattat taaagtctct gtcacaccat catcttttac tctgttgtca   32220
ctcttgattt tcttaagtgg ctgagaagac caaagagcaa gtgacaaatg ttggaggagc   32280
agtggtgact ggtgtgacag cagtcgctca gaagacagtg gagggagctg ggaatatagc   32340
tgctgccact ggctttgtca agaaggacca gatgggcaag gtatggctgc ctgttttatg   32400
ctcagtaata accctggaca ccatgtcctt gcatgcatca tagagcatgc acatgatgca   32460
cactgtgggg aacactgcct ttaaagggct cttattttga tgcactgatg tccttgggaa   32520
atgtcatgca cacaataacc ctgattgttt tagtttctgg aagaaagata tagaactaaa   32580
aaaacgtagt aaacactaag agaccagtga catttcagaa agaataaccg ctttcatgta   32640
aatggtaggt ctggaattcc tctttatagc aatagcaagc attttcatga gtaattttta   32700
cactgaactt agccaaaagg ttgagaagca atcatgagta atttctaaat tttcagaaag   32760
aagatctttc atttgattta tttggaatga catcatctct tattaaatga catatttgca   32820
tatcatgtaa caactcattt ccaaatatga ttttgccaac tgggagactt aaagttcata   32880
ccaaacacag atcatggttt catatggtga ttcttacatt ttcagaattt taaatttgct   32940
tctggataaa tatgaggctg cagtgacata ttctaggtat aatttcccta tcaaatgtta   33000
aaggaacaga aaatgaggac ccctggaaga tgacgtttca caaacctcat gatcttacag   33060
taggatgagt tttgcatttt tatgtcacat gtacttttat actttttttg agagattcca   33120
gcttcccccc aaaaaagccc atctcagttt ctcttgctct gggtctttgt taaatgacat   33180
```

```
cttccttgca atgcctaatt tatttaaagt tggaaccatt ctcacccatg aaaaccataa   33240
cctttctatt ctaatttctt cttgtttgat aaagtgtcat tgcatttaaa ataaattaaa   33300
taatctactt gttttgagta tgttattttt ctttgtctat gtaggcacta tcataatgta   33360
aatatttatt ttgcttgttg atacttcatg tgtctaggca agttcctaac tacaaattca   33420
gtaatgaata agagcttatt aaggatcgaa agaatggata aatgacaatt ttctaaggat   33480
taataatcat atacatggtg taaaacettt ggctattgac tgatccaaaa gttgtaatca   33540
aatgggttct gaagtagaca tcctgaaaca caaaagaaag atactttcac ctgtgggcag   33600
actactatgg gtcttctcta tttcactcat cctaggtggc agaacaaacc atggatagtg   33660
gattgggaaa ctgaggatgt acatttcata gacagttcta ttgttaggga aattaaatgt   33720
aacccaagat aatctaggaa gtgttcagag aagtgctcag ctgatgtcaa catggactga   33780
tcaattcagc tctgctctga gtgcaatatg cttttgtggt aacgtcattt ttgtggtaat   33840
aactatatca atgcctattt tccatttgac attgtaatca tatgtttatc tttatcatac   33900 ttaaatttt aagagacttc agattagtat caaggagtct agaattacag gttctttgac   33960
aatctagtga aaacaaggga acctcttgtc agaaaaacac atgatcacac atatacaaca   34020
aagcaccaaa ggaaggccat caacagaccc tcaatttaaa accaactcct gatgaggaat   34080
gtggaatttg tagaggggaa gtgagtgtca agttcctgca gtgactggag ttacccgatg   34140
accctcacac acatctatct gagttggcaa gatgtgaagt gttttaataa accgtttgtg   34200
acttataatg catgttttaa gtgcagacaa agtgacatca cttgcccagc tgtgtcacca   34260
atacatacct tcctttgtct actgattgaa ttgtgcaata ctagagttag tggaaaacct   34320
tagtgctttg gaatgtataa aggctgggaa gcatgtctca ttccatttcc cactttgtct   34380
gcacctaaaa catgcattat aagtcacaaa cggtttatta aaacacttca catcttgcca   34440
actcagactt atttttctacc ttttataata acaatccata ttttagtatt ctaaagcgga   34500
aatctaccag tgttacaaaa tgaaacattt gcagatattt ctcctagagg aattaactct   34560
gggctcctaa aattttctaa tataaaaatg aaaccataaa cagaaattgc agtaaaaaaa   34620
attgggataa aaccctgttg gtttggggtt agatggttga tcttcatagt atactggtca   34680
tttggtagct atgaaagctt gtgctaagcg cccaagacct atccttatgt aatgggagc   34740 tctgagtttt gctaccttac caaaaagctg gtaaagccca atttagaaat gaattctgaa   34800
tatctacaat aactcaagga atacacaaat aaatgccagt aattgtggcc atattacttg   34860
attcaaaaca tatccacagt ttaaataaaa ttggatttat ttctaaagaa atttgaaata   34920
ttttatttca tctttcagat tctaattaaa attatcttgg tgaaaagaaa caagcatata   34980
tttgttaaat tttttaattg attgttagtg accccaattg gcccatttgt aacaaataat   35040
gattgtgtct cgtgtgtgag aaacttggaa gaacagggat ttgaccaata gctctcatat   35100
actaataaaa ggctaataga agggattagt cacactatct tggtggttgg gtctcaagga   35160 ctagctttt ttttttttgt aaagttttat tcatttattt tatgtatatg agtacagcat   35220
tgctttcttc agacacacca gaagagggcg tcagacccca ttatagatgg ttgtgagcca   35280
ccatgtggtt gctcagaatt gaacgcagga tctctggaag agcagtcagt gcccttaact   35340
gctgagccat ctctccagtc ctgttcccag ctttaataag acaattaatt atatttatgt   35400
tatttatctt tatctatttt tctgaataac taactatgtc tgcctagcac tgagaaggag   35460
ttcaatgatg attaattata tctatctttt attatttatt ttaatttaaa ataacaataa   35520
aatttaaaat gattactcta caaaaaagta gaatatgtca taacacatgt taacagtaga   35580
```

```
atgttatatt aagtatacat acaaccacaa actgttatag caatcaaggt aattaacata   35640
atcaatgact tcaatgactg tggtggcagt caggtattat taactgcaag aactgtgtca   35700
catgttaagt ttcaagggca ttccctccct cccagttcct tacccctgat aacttatgag   35760
caacatcttg ccatttcttc caccttctag ccctggtag ccacaaatct aacctgtttc     35820
tatggacttg atgttttctt agaatatatt ctacatagat gagagatacc aaagtatata   35880
gctttgttcc tctggtttac tttgcattgt ataatgtcct caaggcttat ccatgctgtg   35940
gcaaatgtaa ggatttccct gtctgtatag accttttgaa ggcttaataa tattgcattt   36000
gtacacatat gcacacatct ttacccattt agctgctaat tactctttgg catgtttgca   36060
catcttaact attctgcggg tttctttctt tatatctacc aattcgagtt tcagactata   36120
tggtagctgt gattttagtg tttgaggact tgcactcagt cttagtagtg actcagttat   36180 attttagca gaggtgctaa agcttccctg tcctctacac cctcaattct gccgtgggt      36240 tgtcctttg atgaccagtc taatggcgat aggtgataat agatcattgt ggctttgaat    36300
tgtttttact tacgggttag tgaagaattg ttttcataca gccttggct atttgtatgt     36360 cttctgtgat aagtgtcttt ccagccaatt agttcagtgt gtgtgcatgt gtgtgtgtgt   36420 tgttttggt gtgtttatat gtgatatgtg tctgttgtgt gtctgtggta tgtagagtat    36480
atgtgtatgt gcattttatg tgtagtttgc atgtgtatat gtatgtaaca tgtgcatgtg   36540
agtttgtgtg tgttatgcaa attcacttgt ctgaacaggc atgtatagag tccatagatt   36600
gacattggga tatttttca gtcatttgtt tcaggatcca tttcctagtg ttgaatttac    36660
aggtgtgcac tgtcacgtgg cttttcacgt ggatcttggg gatccaaatc aaggacatgt   36720
gtttacacag caagcatgtt actcagagag ccaactctaa agcttctttc gtcgattttt   36780
ttctcttaac caaaatagat ttttttatac agaatattct gaatatagtt tccctcctcc   36840
aactcctccc agttctcccc catctcccct ctcatttgta tccataccct ttctgtgtct   36900
cttagaaaac aaacaggtat ctaagggata ataataaaat tagataaaac gaaacaaac    36960 agaagaaaag cagtgaaaga aaagcacaca agaacacaaa tgaatgcaga gacatacgtt   37020
tacacacaca ggaatcccat attaaccaca agaatggaag cggtgataca tgcataaaga   37080
cctgtaagtt aaatacagtg ctctgacaaa atattgaaag agaaagaacc tccaaagatg   37140
ccactgacgt aattttctct ttggcatcta ctgctgggca tgcagcccat ggcttgttac   37200
tccagtgagt cttgcttgga gaaccaagt tttatttgc aagtggttat ggattggagc     37260
aagcttctag tgagggctga aggcatgtgt ccacttctcc tttcatctct aggactccat   37320
ctggtgcagc tgtgcaggct ctgtgcatgc tgcctcaggc tgtgtgagtt cctctgtggc   37380
catgtttaga ggccttgttt ccctggtgtc ttccattccc tttggctctg atactatttt   37440
tcacttactt tcttttttgtt gagcactgaa caaatacata gtttgcaaat tgtttctcct  37500
ctttacaggt tactcctgta tcttgatagt agtctaattt acagtggaga agctgtcagt   37560
ctgatgcagc ttctatgtat tcccactcta gccagtagat tttgagtttt accaccaccc   37620
ccaaatattg ttcagaccaa tgttgataca ttttcctttg cactttatta taatagttt     37680 caagtgttga atgttgtgtt tgagcttttg gctgttcagt tttcccagca atgtctattg    37740
atgatgtcct agagctgctt tccccattgt gtgattttga cacttttgac atagcttgcc    37800
tgctgttgag tctgtgggtc tacagttctc tgttccagtg cacacattat gccagtacaa   37860
tgctgttttg gttactcaag tcttgttacg gattttaaa tctggcattc tgatgcctcc     37920
aggttgaatc tgaaattttg atattattgc ttgtttctta aggtggcttg gatatttaaa   37980
```

```
gtcctctgat ttgactcttg tgggtttagg gttttgact atgtctgtaa aatgtttcat    38040
tttagtttgg ggaagaggca catcccatct ctaagtcatt ttggcgacgt tggtaattct    38100
tcagatccat gaatacaggt tttctttcca tttacctctg tctcacttt taaaaaatca    38160 atgttttata atttttagtt atttaggctt taaaacctac gttcgattta tttctatgta    38220 cttttattg acactcttaa tgctcttgac actatttaag tggaattact ggtttctttc    38280
ttagttagat atctgtgtaa aactgattct taatttgcc tattgacttc atatcttgaa    38340
actactttat ttattaattc tatttggtgt aatatttaga ttcttacat gtacatatca    38400 atttaccat ataaaacata tgtatatatt attactgtac tataaacaat caggcataaa    38460
cacttaatga tataaaacat ggaagatttt agaagtgact cagtacttgg tagatctgat    38520
ctacaatgtg ctatgtgtaa aagcttatca gttgttacaa actcattcag ttgattgtta    38580
cagtggaaac tgactaatat gagttgacag aaatataagc tagtagtggt tttatgtaca    38640
gcatataaaa ctagtcccca ttttcacaga gagaacgatc tgcttgtacc aagaatgttg    38700
aacttaggaa gttactggcc tccatgctgt tgagtaatgg cacagtgttt acaatgcaaa    38760
gctagtcact gagcatctgt ctgggacatc tggcctgtct gtctgcttaa tggtgttctg    38820
tttgggccta ctatttaaac caaccattgc taaataaatg gacatcttt tagttccatc    38880 tagagtgctc tgaaaagttg tagctaaata tttaaaaaat gttttgaaaa tgagtgaagg    38940
actgagtcaa ttgtggagtg tgctgccttg catatatgac attgctctgc ctcttatcct    39000
gtgcttttag gtatcaatct attcacatga taactcatag ttttcacaca ggtaagcttg    39060
aagcaccaaa gatcaggagt gttaattatt tttctccaga gtcagaagaa agtgctgaag    39120
cattgataat cgtgaaacat tcatcattag attataaata atttttttaaa tttatctgtc    39180 tggtcaactt tattttttt tggattgcat tttattttat ttagttattt ttttacactc    39240
cagattttat tccccccacc ctgtccaccc tccgactgtt ccatatccca tacctctact    39300
ttacccactt gtcttcacaa ggatgtcccc cgccctcacc caaccagacc tctaaattcc    39360
ctgaataaaa ataatgtttg aaaaccttaa tttcaagaca gaataaaaca catgcagtct    39420
ataatcattt cttgattgat aagaagagag ctaaccaaat gcagaaagaa cagtgtcatg    39480
tttggcatgg tctttaatga tcatgacatt cttctccctg cttcctgttg gcacgattga    39540
tgagcgcagt gttgtgcaca ttaagtccta aacactgaaa ctgactttga tcagatgata    39600
tatgctgcct ctaggtgagt gatttgatca caatctcaca aagaatccac aggtcatagg    39660
caacattttg catttctcta aggaaataca tatattacag gtggaatcaa aggtgaggat    39720
tagtgaaaca ttttccttta ttttaagatg ttttccttca gtgtttaata atgaccaatg    39780
caataagttg tgtgaaagca ttagaactcc aagttctgtc tgttcagtcg aagatagtca    39840
ggacagtatt caaacctaaa tgaaagcttt gtgatacagt gagtgatctg ctctgttgtg    39900
gtagtggagt ctgtgagcag cattggaatc ttaaagtatg ataataccccc tcaaaggaat    39960 aaacacaatg ggcttacttg atctgtttca aaatcagtga tgttccatat catcagtagc    40020
atttttgcaa tgtgatccat ctaagatagt attttttcact aaaaggagaa catgctaatt    40080
gtgtacatta tccttgctta gaaacaacag gggaatgcca gggccaagaa gtgggagtag    40140
gtgggtgggg gagcatgtgg gggacttttg ggatagcatt ggaaatgtaa atgaaataaa    40200
tacccaatta aaaaaaaaga aacacacatg ttgagtggtt gtattgtaca taaatgtttc    40260
actgctctta tatgtatgga gaggaattgt gaatcttagt gatttctaat cagggaaatt    40320
tctaaaagga aagaattct gtaattgtaa ggaaaaatag ccttactgga cttttgtttg    40380
```

```
ttgtaattcc aaagcactga gtcatttgct aatatgtgat tggtatccag atggatcagc   40440
aagaaatgca tgaatcatga atgcatgttc cctgtgttat gtatgtagac cactgagggc   40500
aacagacatt atccctagtg aaaaacagtg agtatagtat gtatattccc taagcttata   40560
tctattatag aaagagttaa gtggcttttg ttagaaatga aagagaattt gtattattcg   40620
aaataaatac taactctgat gagtgttaac ctgggttttt gtgaatagca aatgaagtag   40680
cttcagacaa ataataacca taatatttca cctgcttgac acaagaacac aaactttttc   40740
cactcaagtt ctatgttcag tggttttataa tctgtcagca tgaaaccttc agcaacatag   40800
acatgaataa aaatgtttaa aggccagact atggatgatg ctctttacaa aagaaattgt   40860
aaggccagca tggtagtatg actttaagca taccagtgga caaatacaag ctatactatg   40920
caaatctgtt tattttctca caagtgctgg cagaggttaa tattctaaca agtgctaata   40980
cagtttcatg aattgatttt taaatttttt attggttatt ttatttattt acatttcaca   41040
tgttatcccc cttcctggtt tccctgcata aaacctctac tccatttcct ttccccatta   41100
cttatatgag ggtgtccccc ccccactccc accttactcc actatcattc tcctacactg   41160
gggcattgat ccttctcagg accaagggcc tcccctacca ttgatgccag acatggccat   41220
cctctgctac atatgaagct ggagccaagg gtccctccat gtgtactctt ggattggttg   41280
tttaatcctt ggaaactctg ggggatctgg ttggtggatt tgttgttcta attggtctta   41340
gttgtataca tgtgaacatt tattgctact gtcctttcac ataaaaccat tgtataatat   41400
tttatagggt ttcatttgag ctgctactat tatgtttaag atgatttcaa acttacatga   41460
ttttatggaa tttatttatt aaagggatta aaaatgatac atatgcgcgc gcgcacacac   41520
acacacacac ataccacatt tctacaatcg aacaagttaa catgcctgct atctcacaga   41580
gtacttctct ttgttttttta gtaacagaag ctaaagtta ctctttgga aaattgcttg   41640 catacactct atattaggta ttgtctttac attcctgagc tcgccagact tgctcacaca   41700
gttgactgta ttcttttaa tatctttgca catctaactt gtatttttac tttgtaatga   41760
aatggcaaac tcttcatatg gaggcagaat ctgattataa tgtgcttatg tgacagtcac   41820
tagtcttatc ccaaattcaa agagtaagaa ataattgat tagttccttt tttggatgta   41880
ggctttgact agaaacatag cttgtattgc tacttatcaa aataaaatga cagaaaatgt   41940
cctatagttt tccaaatatt cacaatacac aacaattcag gacataagtc aattactgat   42000
atttccctcg acaatttcag gaataggaat aaataagacc agttgtgttt gcattgggaa   42060
tatatgatta tgaaagtggg aattagatgc tatcatgaat ctgattattc tattaggtga   42120
aaatgaatta tcaattccta tataaggtaa ttgctccata agaaacttta ttaaaatttc   42180
taattacact ttaattttta ggtatacttt aagaatccac cctactccct ggtgtagtgg   42240
aattattaaa catatttgta atattttcat ggtagtattt aatttccttt agagctataa   42300
tacatagtaa aacaaacagt gtagtctgaa atgagtgaat agataatgat gaaataagtg   42360
aaaaatgcga aaaattatgt acatttcaat ttccttttta aaaaaatttt attaggtatt   42420
ttcctcattt acatttccaa tgttatccca aaagtccccc atcccaccc ccctactccc   42480 ctacccaccc actcccccctt tttggccctg gcatttccct gtactgaggc atataaagtt   42540
tgcaagacca atgggcctct cttttccaatg atggctgact aggccatctt ctgatacata   42600
tgcagctaga gacaagagct ctggggtact gattagttca taatgttgtt ccacctatag   42660
ggttgcagtt ccctttagct ccttggttac tttctctagc tcctccttcc tttctgcctc   42720
atctttcatt cgtatttttct tattcaaaca ataggactaa tttgtttgga actcagttca   42780
```

```
acaaatgaat acagttgcag gtctgtgtat gcaaggagta aaatgaaatt tacattttaa    42840
ctacacttgt gagggatgt gtttgaaaat tcacatctct atttgattat tgggtgtcca    42900
cacacacaaa tgagaaacaa tttaaatatg ttatatgatt tcctgtcatg caaccttatg    42960
gagtgcgtac tcagcttagc ttggacactt taagctttgt tcagtaattg tatgttatct    43020
gataagtctc tgggggtagg catgtgcttc ctacttatgc tacctagctt ggaattaatc    43080
tatctgttat acaaagtcta aaatttacta gaatatttca tctttaatct aattttataa    43140
caaatgtaag gcagatacct ttcaaaatat ctctgctcaa actaacagaa ttgcttatag    43200
tagcaatcat ctgtccatgg aggacagcca ctgtaagatt gacagagagg tagttcttac    43260
atgttctgtt agagctactt catacctgct actcaatcca ctttgatagc ctgatctta    43320 tccccagggt ctggtttata tgccctattt gctcaagcat atagaaagtg tggctgggta    43380
agagggcagc tctgtacttc atggagtgtg gcattatctc tttcaccatg ctgtatgagg    43440
tcaccacact gctttgagca ctgacatttt tatccatgaa atagaattgc tgaatgaaat    43500
gagctcaaaa tgttttgtat ctcgattcag tggcttgaaa tttaggacag ttgttttca    43560 attatgcact gccagacccc tggcaactca tttaaccttt ctgaagaagc gtttatcctc    43620
tgtaattggc cagccaactg cagagttgga atgagaagga aatgtagcag caaaggcaaa    43680
caatcaaatg gactgtggca taattgtgat attttctat aaagaatctg atgtttctat    43740 ttatatctttt ggtttagaca tgtgattatt gagatgactt ttttttttt tggtgtggtt    43800 tggctttatt aagtggttta acaccaaaag gaatacactt gagagagggg atctctttat    43860
tgggcttaat aaattgagtc acattctttg tcttagtttt tttttttcca tgttgatctg    43920
attaaaatcc tctgacttaa gcaacttgaa gtagaacagt tttctttcac acacagatca    43980
tggatacagt acatcatggc agggaagcag aggcagcaga acatgaagc gtcaagtcac    44040 ttacaaaaaa aaaaaaccta gtcaagtaca gagagtgacg attgctagca attcagtcat    44100 ggccttttt atatataatt caagatccta gtctaggaca tggtgttact cacagtggac    44160
tggttttccc aattcagtta tctaatcaac ataacctctc acaggcattc ccagaggcta    44220
atctcctagg tgatcctaga ttccatcaaa tttacaattg aagttagcaa taacacctct    44280
gttacattga attaaatttc tcaaaaccaa ttttattaaa ggttttatta aatgttatct    44340 tcatgttta attagaaagc atcctgttca aaggattttg agaacactgg tataaacaaa    44400
gttttaaaat ttatctttta aattgaaaat gccaagtact tagcattata ttgcaagggc    44460
ataattatct ttcttagtgt ctcttcacac cagatgcata gagaataatt ctaagtactc    44520
atggagcaca tatacaagat ggcctgagta atgaccgttc tcactctgtt ttccttgtct    44580
tagtaatagt cttttagat cccagataaa aggacactca gaacaagtga atgatctctc    44640
agcatttcat atcacaatct atttttga gacactttt aaaacattct tgaaagaagg    44700
acaaagacat aattcctgtg ttccatgtaa ggttttccat caaatcatgg aaaagattct    44760
gatagcctag atgatgagag tccagctaga ccagctatga aattctcctt gctctcttct    44820
ctctttgtgg tgagccagcc tacacttcct ttcaacacct aatttggacc cagataacct    44880
aggaatctgc cattgcagtg ttgaatctca tgaactgagg ttagtgtggg aagggcacaa    44940
tgctctctgc tgatgctcac atgttgagca tgtctgtgtc acaggttaaa aatgcagtga    45000
tagaagcatc cctgagtaca cacggtacac tggcggaaaa gcactgcaag tatgcctctc    45060
cactcagtgt attttgtgtc taagagttta acagctctag atttacatat aaggttattt    45120
atcaaagcat tggtaatgat acatttctta aatgctggaa acttggcaat agccactagg    45180
```

```
ctaaatacat gatggcttat cccctgtaat aattatttca acagaaaggt acagaagagc   45240
aatgggtgac ataataggtt gttcttgctg cattaagtga aaatatgagg ttatagaaca   45300
tattaaagtt tgtaaacact tttgttatta aaaacaaaca tgtcatgtga tgtctgtgtg   45360
tatttctaag cagtcttttc atttaattac aattagaaat taaggtaca acattttatt    45420 ttacttgttt gtccaaatcc aactttaat tgatttataa aataatttta cctatgtagg    45480
acattaatgc agttattaat atgactgtga ccattgctgt ttattcattt acttagccac   45540
acatatatgt gttggcctac ctaattcata ctatgtgttc tactttgcac caagtattat   45600
aactgtaggg atgtagaagg ttgatttcca ggacccagtt cattgacatc aatcatcttg   45660
tctcctccta gtatgaaata agacttgttt tgttttcttt gttttgtttt gttttgtttt   45720
ttcgaagcag ggtttctctg tgtagccctg gctgtcctgg aactcactct gtagaccagg   45780
ctggcctcaa actcagcaat ccacctgcct ctgccttcca agtgttggga ttaaagatgt   45840
gtgccaccac tgcctggcga aatcagattt cttttgtgaa gttctgaagc ttttaatcat   45900
taaaaattcc aacctggaat agttctttta tatattatta ttattgataa taattatcaa   45960
atcaatatga ataccatttt cagcaattct cttttcttgtt ggcttatgat aattgcatgg   46020
cttatccaaa taccagaaca cacttgaaca aaaaatttct aagagcaaag aattgtatta   46080
cctgagtggt taatttaatg gctcatgtat atttgacaag aatttctgat cttctgagcc   46140
ctgataatta actggctttg ctgattctta tctttggact ctgagagaga gctatcctca   46200
tagtcagtat atgctagggt aacaaaacac atgcaattga gtaattcttg aaaaacagaa   46260
tttacttatc acattgtaaa gctgggaact cagagatcta gacgagtttt gtgtcctgga   46320
gaatctcatc tttgttctga gatgacatct tgttactgtg tcctggagga gagcattttc   46380
aaggtgaata gaactgaagg ggtaaaactg tccccttgta cagcacaaac cccacatggt   46440
accattacct gtaaagagcc ctacctcaca attgggacat tagtgacgac atttcaagta   46500
atgggttttg gggatattca ggtcataata gctattatct ttattttcat gtaccattag   46560
aatgttagct tcttcttttt attaatatca ttcacagtag ggagaaatcc ctgtattaaa   46620
taccattccc tgtgtgcttg ttatccactt tggtaagaca cagaaagcca caaagcaca    46680 ctctggaact ttgctttcgt catttcactc ccagtagtta gacacatcca tagtgtatgg   46740
gtttatttta caactgaaca ggaatctcac atgtcatgtg ggagtttttt taactataca   46800
tgcttgtatt tgaaagcaac atttaactgt gcattttcct ttggaaataa caccttccaa   46860 aacaatttc cccagctcaa atcgaaacat acacaatgtt tcctgtagta attagaatat    46920
aagcaagaaa atgaaactct gaggtaggca cagaaaaggt ttcatgttcc ttctgccttt   46980 attgcctta actagtcata caggatgcca gtaaaaaaaa aaagtaaat tccttgaaaa     47040 ggaatacttt agtttactta atgacaagga tgagagagac agagacagaa agagaacaca   47100
tatacacaca actctctagc tctctctctc tctctctccc tctctctctc tctctctctc   47160
tctcacacac acacacacac acacacacac acacacacac acacactcag aggatgtgta   47220
ttaaggacta caaatgagat tgtgctgctg tgatgaatgg gacagtgtga ttttatcact   47280
ggactctgca gttcagtgga accctgtagg tcctgctgaa accctaggct gcttaaattc   47340
ttcagcaatg atactttcat tgtacaaaga gacatgtcaa aacacatttg cttttgtgat   47400
tctgagtatt cacttctgaa attaatcaat gttccacaag gaaaactgtg atttccttta   47460
tttatagctt gtaataatct agctagatat ttctcatttg gaggcatatc ttcaatttta   47520
acaaatcatt gtattacaaa agcatattca aaattcccaa gaaatttacc ctactgcact   47580
```

```
gtttgttctg gttgaaaaca ctgtaggtag gtgtcttagt cagtgttcta ttactgtgaa    47640
gagtcattat gaccatggca agtgttataa tgaaactctt aaaactgggg cttacttaca    47700
gattcagagg cttagtccag tgtcgttatg gcagggtcca tggcagcatg cagatagcca    47760
tggtgatgga aaatagctga gagttctgta tccaggtctg cagccagtag gaagagagaa    47820
agccactgga cctcgcttgg gttactaaaa cttcaaagct ctctactagt aacacttcct    47880
ccaataatgc cacacctcct aattctgtta agtagtgtca cttcctgatg agtaaatatt    47940
caaatataaa tatctataga gctattctta ttcaaaacat agttagcaat ttctcttttgg    48000 tgggagagaa tcaactgata cgctatagca caaccatgtt caatgctgtt acctgtatgt    48060
ccaaggcata ttttgtgtgc acttattcct tcattcaaaa cacacctgtg gtatctggag    48120
gccagtgaga attatgtgag caagatgttt gagagacaca gtctttcacg tctgtacttg    48180
cttgaccctc atctaagtga cgttgttaga gaagtccaaa gctggcgttg tagcattctg    48240
ctgccacagg tcatcatcca caccttatcc tactctattg ggataattac ttggaattaa    48300
aaccaatcta atttgtaggg gaattggtta tgcaaataat cagcttagat ttttctggat    48360
ttattcacag tatttaatgt gtaattattt ctgccctcac ttttacatgt tctttaccca    48420
gcattttaac caaacctaag acaggctgca tgtgcacatg ggcaggtttt ttttgtgttt    48480
tgttttttgt ttttgttttt tttttctgca atcagaacca ttttttcttg gaaaattaat    48540
ttcaaaatac attcagtcag aaaaaaaagt gcttataatg tttgtctggt gtttcacaag    48600
agctgccctc atgtcctact gcttacatat ctatagtttc catataaagt ttcattttct    48660
acgggctttt catgttagtt cctctaagtt ttctctcaat ttgaaatttg ttttcctcaa    48720
tttctttcct atgtgtttct ttttggataa ttgaaagaag atgcacaatt tcttaattct    48780
tatatttgaa ataattgaaa tgtgttttaa aagtcatcac tgttactata acacagtttt    48840
ccacaagagt tctatctttg gttttttgtgc atttcagtgt gcctggctga tgttcagtgt    48900
cctaggatgc gctgaaatgc tatggcatca tttcatccag ttatatttca catgagctgg    48960
tagagataat cctttagtcg ggacctattg atgcctagat ttttaacagt gtcatacttt    49020
acctgtctta gcatgttgtc ctaagataca agaatgatta agatgtattc ttagatccag    49080
gataatgagc atagcatctc catggaatac ctctttctct tattttctgt tgaattccca    49140
tactaaattc aaaaattaac cgaaaggtag agtttcctca gtctgtctta acacacgaca    49200
ttctgtgcag tgctggtttc tcctgtccac agtggaatca tctcaaactt cttaactctt    49260
gggcagccat gaagatgaag gctaagacac taaatcttcc acaaatttat cttgctcttc    49320
tgtctactct cacttttact ggcagtggca aatagaattg aggttgttaa gagtctgttg    49380
ttacttattt aatagaagga aaaagtaaaa cagtattatt gctacagagc cttgatcaaa    49440
accaagactc aaggaagtac aaatccttgt acttccagta agagcatctg gcaaagagac    49500
ccaagatttt ggcaccatcc atatgctatg tgataatgta tgcatatggt gtggttttaa    49560
gaaattagaa ttctaaaata gtttgtatag tcaggctatg taatgtcgct ttctctagtg    49620
tcctgcagaa agtgagagtg ctctcattag gtacctggtc aggaacaaat tgcttcattc    49680
ttcagttatt taataatgga aacttaaaaa aacaaaaacc caaaacatg ttttagaggt    49740 gtggtgataa atgtcctagt gcctgccata taagagctta gagattatag acttggtatt    49800
ctttcgaggg ctagatattt taatgcttta tcctgacatt tatcaaattg cacttcggtt    49860
ggtgagtgtc acattaccct gacaaattat taacattata aagaaaggac tgtcaccaat    49920
gagtcaatat aatttttata gtgttttata aatttcatat tttgtataac ttaaggtgca    49980
```

-continued

```
tgggatattt attaatttct atttgttgtc aacactaatg ctacataaaa tgtaatgtaa    50040 tttattttg  caaatacatt ttaaagtctg taaaaaggac ccaaatatac tccaaatctc    50100
ataaatggta agtgaccctg aaagacaacc tactgagatt tagtgacttg aaagtccatg    50160
tttgcatgac tcatcagaag tactgtacct caaagaattt catcttaagt catagaagtc    50220
tcatgaatat agtcatatgt atcgcaacat gcggccttt  actcaaaaat cctaacagtt    50280
aacaaatcta tatcctatga aatatttaaa ccagtagaaa atgggtagtg aaagatttat    50340
atcttgtcta cgtagaagtc aaattttaaa agtcacccat taaaaatctt agtttagcct    50400
ggcgtggctg tgcacacctc taatcccatag cactcgggag gcagaggcag gtggatttct    50460
gagttcgagg ccagcctggt cttcagagtg agttccagga cagccagggc tatacagaga    50520
aaccttgtct caaacaaac  aaacaaacca aaaaaaaaa  aaagaaaac  aaaacaaaaa    50580 tcttagttta actactttga tattccctgt atttaacatt ttgcctatca gtagtatcta    50640
ttcatttctt tagtgcttga ttggaacagc aaagaaagtc tatatgacag ctagccacct    50700
gaaaagctca ctatataact gctggatgac caaatctata tcagagaggg gtggttagga    50760
agagaaaccc aagcattgca tctgtataca cagagcatgt tttgtcattt tggaatacag    50820
tttggatgtt tcttttcgtg tttgtttgtt tgtttgtttt tacaaagcta actctgtata    50880
tgatccaaga gtcaaaatca ttggtatttg cttgcttgag ttgaataacct atgtttacat    50940 gtgaacctgc aaataattgg taccagcttt atctgcagtc caccaaacat ggaagaagtc    51000
aagaactttt ttaataagga aacacaatgc atccattttg tggaattta  ttcagtgatg    51060 attaaaattt gagccatgat agcacaaagg cacatggagg aaattaaaat atatatgcca    51120
aatgaaataa gacactcttt agactatgaa ccaaggatgt gatgatatat aaaaatgtga    51180
tcgttttgga atgccaaaat tctgaggaca gtaagaaagc aaagcaatag ttgcagggggc    51240 ctctggagag gtggaagact gtgtggtcaa acaacaggat gggagtgggg tacaactagg    51300
cagggaagtt attatgacag catggttttc tatggtaggc atttgctgac tcatataaaa    51360
caaggaggtg ccaactgtga tcttcagtga tgttatctca attctcatta acaataggaa    51420 cttttcaagtt cgtaactcag taaggcaaga taataacgtg ggattgtaac atctggaaat    51480
cctctttatt gctgtgtgat tattctgccc aaagtgtcta taaaaacaat gtatcagaag    51540
ggtgtaaaca catgaaactc aagaagaaca aagaccaaag tgtggacact ttgcccctta    51600
aaattgggaa caaaacaacc atggaaggag ttacagagac aaagtttgga gctgaggcaa    51660
aaggatggac catctagaga ctgccatacc cggggatcca tcccataatc agcctccaaa    51720
cactgtcgcc attacataca ctagcaagat tttgctgaaa ggaccctgat atagctgtct    51780
cttgtgagac tatgccgggg cctagcaaac acagaagtga atgctcacag tcagctattg    51840
gatggatcac agggccccca atggaggagc tagagaaagt acccaaggag ctaaagggtc    51900 tgcaaccta  taggtggaac agcaatatga actaaccagt accccacaga gttcatgtct    51960
ctagctgcat atgtatcaga agatctagtc ggccatcatt ggaaagagag gcccattggt    52020
cttgcaaact ttatatgcct cagtacaggg gaacaccagg gccaagaagt gggagtggct    52080
gggtaggggg gtggaggtga gggtatgggg gacttttggg atagcattgg aaatgtaaat    52140
gaggaaaaca cctaataaaa taaagggtg  taaactcttg agtatcgaaa tttccagagt    52200
gctcagagcc tcatttgtac cctttaccat cctatctcat gctgttggat tcattgtggt    52260
aagagtataa atgtaaatat gtaggtttaa aatgtatggg aaaatatttg tatatcaaaa    52320
ataatctcat tactacacag gctggacgta ggcctcctgc acatatgtag cagaaatgca    52380
```

```
gtttaatctt catatgggtc cctaactatt agagtcaggg ctaccccaaa agctgatgcc   52440
tgtaagtgga atatgttctt ctagctgggc tgtcttgtct ggcttcagtg ggagaggaag   52500
cacctagcca tgaaaagact tgagtgccag ggtgaggagg acatccaacc actcagagga   52560 gaagggggtgg gggaggcttg gacaagtgtt gtgggagggg attgcagtga gcaggataca   52620
aaagtgaaca agtaaataaa taaatacaac tgtaattttg ttactacagc gttcctcaaa   52680
taaagaggag cagaacatgt caaatgagta ccttaaccac ggaagactgg tgggcatcag   52740
ctacatctgt agctggagcc tgagagaagt gtttactctg atagctccac acaaaactga   52800
agcactggga agagattttt gtcttctccc ttcagacttc atgtaacctg gatgcattca   52860 ataagtatt ttgtgtggcat tgttgagtag tcccttata ggcactgtaa aggtttctta   52920
gtgacactga tggtttaata ctcaggttta atgtccagtc cctatatagt cttaattgct   52980
tgtcttgctt tggaggataa cacatcttcc tcaggctcag actgcatctt acttgcactt   53040
gcacttctac agtattgatc tcatttcaca ggcacctata atgcgtggac tcatgaaatg   53100
atcccataac taaaggagta gccagacata tatttctcct tgcttgtttg tttataacat   53160
tagacaggta aatgctacag aaggtatttg ctgcccatgg cctcagggca tggcctcagg   53220
tcatgacctc agggtcgact gccttagggc acctctgggt gcccttgtag cagtgctgtt   53280
ttgcaaagcc catgatgagc cactccttat tataaacacg tatttcacat gagaatgata   53340
aggtgagttt ttaataatct ttctaattaa acaaataaag gtatgaaagg aactgaaatg   53400
tttagtgcat gattactaca aggctgtatg cactaacatc ccagtgtcta gggccaagat   53460
ggagagaact tagtaactat ctacaatttt tcttttctct aaatattgcg atatatactt   53520
tctctgtatt tattataatc cccgtaagaa cagatggcct gcacagatta gacaacttca   53580
ttaagtgaca aattgtggag gttggtaata aaagaacctt acagcaacca gttaatcagg   53640
agaggtcatc ataaagagaa ggaagagagc tagggagagg gatggatttg gagaagggag   53700
gacaacagag aggtcatgag agcaggggaa gcaaatagca agccctgtgt gaaaatggcc   53760
ttctgactgg gcttgccatc tgtgaaatgc ctgcttaccc tgggcctggc aggtagtagc   53820
ctaggactgt ctggaaacag attgcctcac ctcatatgac cttccccatg ccctctttat   53880
ggtgcttcat ttggccaatg tcttataatt gtgtagacat gaagcagcat ttagacatag   53940
agtactttat gtaggacagg tttctccaaa gggactcttc gagtgcacct caatccatga   54000
gagagatgta tttcccaaca ttctctgcat agaagctaag gattctctgt ccaacctcta   54060
gtggtcagaa tacatcctat gattcagtca actgtttaga tgttaatagt gtaagtctca   54120
acaagcccca gtgcagtcca tatggttctt ctctgggcat ggcaggagta ggtggttgcc   54180
agtgtctgaa acataaaaca ggtgaaaaca gacctgcgga gagacagcag gaaaaataga   54240
agacagctcg caagtacatc tggtggtgtt tatgagattt attaaaattc aacaaggagt   54300
gcttaacatt tagcaaatga agtttgtctt taggaaaatc cttgtgggat ttatacaagg   54360
atctgttaat aaagggcaca tacaacactc ataatacagt cagacatgtt atgtaaaaca   54420
ggacaagaaa gtaataggat aacagagtgt ttgcacaagg gattttgtga tataacacat   54480
gattcttcag ccttcgctct gcacttttag aggctgggat ttgcatagtg atgcagccac   54540
acgagacagt aaccttgaca tttttgcagc tgtacatatt tgcacacacc aagacacata   54600
gtcttcctgt ctagttacta tttgattctt ttgttcatct cttatttatt accaaaagta   54660
gtgttcacaa aactgtttct cacaatttaa gcttttaaat catggtgtga attacagaca   54720
ttttatccaa gtttaccttt ttcagcagaa atgccatatg ttctcaaaac catttatcac   54780
```

```
tttatttaca attctagcta ggttgtttgc ttaatatttc ttagcataca ccacatatgt   54840
ttactttgat actccatttc tgcctcaaat ggtcaaaaag ttcaacttaa tcttttttcct  54900 caaataagca tttctacctt atccatcaat aacgttgcaa acagtatttt actgtgatcc   54960
ataacacaaa tcacagatgt atttgaggtt tgtaattctg cttctctctc caatataatg   55020
aacctaggtt ctgtctttac aactctgtct tccatcattt tcattcagaa ggtttggatg   55080
agactttgca tggagagtgt aggagaccat caacttgtct acctgcttgg cctttccttc   55140
cagttaactc ttagctgcct ttgtccctag ccacatcatt tcctgtgaac acagactttc   55200
ccaggtcctc atgataaggc agagtttctc ttaagcttct gcttttctcc atcttcattg   55260
tgtgcattgt gtgaccttct gtcatttgtt tattcacgca tttgaatgag ctaattattg   55320
aagatccaag atagtaccct ttctaacaca gtggctaata agtacttctt gttgatctct   55380
atagttttct gcctaaggca tttgtaattg ggttgatatt gctttctaac ctttagaact   55440
gagatgcagt tgtagcacac acttaactga tagataggtc aaataggttt ctacacacaa   55500
tctcaattgc gacataggtt aaataggctt ctggccacca cattacaaac tacaagaaaa   55560
cctacttaat ctatctacca atggttgtat gtggaatctg tgtaagagta tcaagaaatt   55620
ttatgttatt taaaagacat gtttctatgt cttagacatc cagtacactc tttatatccca  55680 cacctcacaa tttaacattt gacacatttg gagtctatca atgtatcaac tttatatgat   55740
gctgcaagat agtgtaacca tcttcttatg cctattgtca gcactgcaag gtaccctctc   55800
taaatccttt cattattaat cttcttcatt aatactttgg tatatgatga ttatgaaacc   55860
tttgcttggc tattcaaaaa aattaattaa gcaagtagga taaagttttc agaagcagaa   55920
gtctaaaaag aacaacagca attgaggact ggaagaggac tcttgttata caatgtgag   55980 gaatttaact ctgaatcaca cgagctaatg tggactcagg tatagcactg tgtgtctgta   56040
ttcctaggtc tctctcatat gatggacata ccatctttgt tgtggctaga gaaatggctc   56100
agtcttcagc tccttgggta cttttctctag ctccttcttt gggggccct gtgatccatc   56160 caatagctga ctgtgagcat ccacttctgt gtttgccagg cactggaata acctcacaag   56220
agagagctat ttcagggccc tgtcagcaaa atcttgctgg catatgcaat agattctggg   56280
tttggtggtt gtatatggga tgtatccctg gatggggcag tctctggatg gttttttcctt  56340 ctgtcttagc tccaaactttt gtctctgtac ctccttttcgt gggtatttttg ttccccatta  56400 taagaaggac caaaatatca acactttggt cttttcttctt cttgagtttc atgtgttttg   56460
caaattgtat cttgggtatt ttaagtttcc aggctaattt ccacttatca gtgagtgcat   56520
accatgtgtg ttcttttgtg actgggttac ctcactcagg atgatatcct ccagatacat   56580
ccatttgcct aagaatttca taaattcatt gttttttaatt gctgagtagt actccattgt   56640
gtaaatgtac cacatttttt gtatccattc ctctgttgag ggacatctgg gttctttcca   56700
gcttcaggct tttataaata aggctgctat gaacatagta gagcatgtgt ccttattata   56760
agttggaaca tctttgaaat gtaatgaaga aaatatctaa taaaaagtt ttggcaggta   56820 aaagaaaaag gcttaattaa taattcaata atataccatg gtcttaaaac aaaacaaaac   56880
aaaacaaaac caacaaaaaa agaaactag aaagatttcc tttcctaaag ttgggatata   56940 tctttttccct tttatccttt caagtcacag gagttgtagg agtcactcca agtatttgaa   57000
gacagagcaa aattacttgt ccagaggaca tcttcatctg tagattctgt ggccatatag   57060
cacagaaaaa agaaattcag tgatgggtat gtttataaag actgaggtga aagcaatctt   57120
gagaggatag tgtgttgcca ccttgtcaca tgtttgatac taagagcatg tcactgatcc   57180
```

```
aagtggtgac attctaaatc acagtggtgt ttattattaa ttctttctgt gaggaaacaa   57240
aaaagctacc agtggacatc aagttgccct cttcatattc agaggatggt gtgacttcct   57300
atcaatcaga gaccactgtt agaggaatca tgtccaccta atggccaggc tacttgatct   57360
ctatctcagc ttcattagca ggttttttc tctctctttt tgacatgtgg aactgtcata   57420
tgaaacagga atgaagtggt cacagcatta aaggtatac agaccttgag taagagctgt   57480
gtgcttgagc attaaagtag tcctgactcc tgtcagaaga cattctagaa agtactggat   57540
tcaggcaggc tacagacatt gcctagcaac tattttttgg ccagcttgta cttctgttaa   57600
caaatgatta tttcctgagg ccagaatttc gtcccttcga tagactatct ctgaactttt   57660
tgtttttctt tgtttcatag ttcttgagta tcactctgtc ctctgaagtc acttcttccc   57720
tagcagcagg ccatcagcat tgagttcctc tccctgttca ttgccactaa gtaaagttat   57780
gatgaagaac ccgtgtatac tacccatcag gtgtacatgc acactgcttc actttctaaa   57840
agccagctcc cctctgcagt gacacctcct ttacaccatc actaagttct tcccccatac   57900
agggcctcag agcttcttgt aatatgaatt aggaaggctt aatactggca aggatattaa   57960
gttcaactag aggtggtaga gaatgaggg tcttgagagt ggattttgg aatcatgagg   58020 ggcaaggaca cagcattaag tcttataata aatttaaaag gattattttg ggcttttctt   58080
gggaattaaa cacaccctta ataaaaattc tcaggtgaaa aaagaaattt ttttcagatt   58140
aaagacttgg taagtacata ttagggagaa gcacatttct aacttaaaat tcatgctttc   58200
gtcatgttac attaggaaac acgattggtt tgtatatcct tatatctgtg ctttcagttg   58260
aaactaacag cattattgag ggaaacaaag aattttttt cctttactgc tagcctatca   58320
aacctctcaa tgaaatttta tgcatagtac agtaatcaag attttttgt caatatttaa   58380 tacaatggat agatgcagaa attattgaaa atccaaatta ttattttgtg aaccatggta   58440
ccgatgttca ggcctgcctt catgcatttg tgagaaattt tgacaagctg ttgtgagtgt   58500
tcaccaaagg gaacacactt ttggcaggac ccttgcattt cctacatgga cagaaagtgt   58560
ttactgtgaa acaactgttt ctcgatgtgt actgtcctct cctaatttaa gcataaacct   58620
cttttcttcc tgaatgtaga gttcagagaa aggatttgtg atgacccaaa gtcttgactt   58680
aaagagatat tttataaagc agtgctgtgg ctcataataa aaagctgtaa gatgctaaat   58740
gccaagcata cagaaataag acattgccag ccatctgact tttgcaactg gatgatttaa   58800
aagaacattt gttgatctca agttgtcctt agaccatcct agttctaaca agatccaaag   58860
tgaaatgtga atgtctgcgt ttggtttctg atagggatgt tttttaaaa aatattttta   58920 ttaggtattt tcctcattta catttccaat gctatcccaa aagtccccca tactctcccc   58980
ccaactcccc tacccaccca ctcccacttt ttggccctgg tgaaaaactg attttcaaat   59040
cattctggca tgactttgaa agcatacctg ttcaacactt ttccttgtt cttctacctg   59100 cccttttgata tttctaacca cccccatatt ggtatgggga tatgaaaaca ttagtgcctg   59160
gtatctgaac aggcctgctg aacaggaaaa aatgaaatta agtcatgtaa aggtgagtgt   59220
ccagaagcca cagaagtagg aaaggaaaga aagaggtgtc tgaacagtgc tgaaagaagg   59280
tatggcttca gactgtctgt cacaccaaaa attaatggaa caaataataa gtagaataat   59340
tttaacattg tctggctttc atagtggtgt tgtggttggt attggctttc tgactgatga   59400
gaaattttat gttgtttgca tagactagtc ttctttccag gggatacatg ttgaagggt   59460 tacgtcccat catctacctt gctacacaca caacacacac acacacagat agagagagac   59520
agagacagag agagacagag agaaacagag agacagagag agacagagag agacagagag   59580
```

```
agagagacag agagaaagag agagaggaag aggaggagag aggaagaagg agagagatgg   59640
agtgagggag gaagggcaag agagagaagg agagagaggg gaaagggaga gagtgtgtca   59700
atgaatagat aaatgaggta acatgtttat gattagagat tctgagcaat gtgggtataa   59760
tgctccttaa aaatattatt gaaacttttc tgtgggtttg aattttgaat taagtaaaac   59820
ttaaattaca aaataagtat gattcactga atctcctata aaaaagatt aattataata    59880 aagacaaagt gggtgttttg gaaagtggga actttctaag caaagaaatt taggcagcca   59940
atttctctcc tgctactggg tactgcccta tccaagagtg tgtccatcat tctgtcctgt   60000
gcttgtagta gcgcatatca tttgttttc cataccatga gctctgattc ataatctaag    60060
gaggctggaa aaatgtcctg ttgtgtacat gtcagacaga gaaggagaa cagattttg     60120 gcagatcact agaaagccac aataagcccc ctatgaagca caatatgggg tctgatacca   60180
gaacctttcc tcaagaggag agctgatcat cttctttg tttgaaactg ggctaggaat    60240
ttaacaagaa gataccgttc tgtcagtgag atcacaaaag gtgaatgtgt gaaaataat    60300 aatgcctatt caaaactagt acaatttaaa taaaatggaa cattctaaag tacaatttag   60360
caataaattg ctgtaggcag gctgaaactc atcattaaat acatcatgtc aaggagaaaa   60420
agatgagttg cagaaatagt aattgctaaa acagttaccc ccctttttg tttaaagata    60480 tttatacttg tcaacattca agattgtaat tttaaaacca cagtaagaaa acatgttatt   60540
aatgaaagtg ttgcattttt tcacaggcag caatctgatc accttggttg ctctgtacag   60600
aactgacctg gccatgtatc tagccatgac cagaatacaa ggatgcccat ttgtgctgca   60660
gatttccacc cactcacatc caattcctcc tcacatagtt ttactagtgg catattctga   60720
ggccagactt cctcttggct agaacataac ccttttaaaca aatctatatg ctattctaat   60780
ggaaatatct tcaggcattg ccctactggg catagattca agtcagcttg tgggccagct   60840
tgaacttggc ttcttgtatg tggtttgcct ctagaagcat ctactgccag caggacactg   60900
gcagcctttg tgaatgtaag ctcagaactt tcttccaata tacgttatct tttatttgaa   60960 atagttttg gacttatgaa ggaaatcaaa attattatgt gggtaagtaa attatatgaa    61020
gaagactcag ttaagtgtct atggtgactt atcccttact tttcaataaa cttttagat    61080 tccttttcac ccaggccttt tgtcgctacg tcgtgagcca agtgttcata gactagtttt   61140
taatagacta tcaaacacaa ctgtgacatt atgtagaagt aaaggcagga ggacttgggt   61200
tttaggtaaa ctggaatata cagtaagttt aaggccaaca aagactacat ggtgaggtcc   61260
tggaggtcct gtctccagag aacaaaaagc aaaaacaata gcaaaaaaaa aaatcccaaa   61320
aacaacaaaa aatacaagga aagagattta acattatcat atcatctaac ttttggcatg   61380
gtagcaacat aatagtagta gctctactat agtctgttac ccatcactgc ttgtgatttt   61440
acaagatcca caagtatata caagatgaag ttcacagatg caactgcacc aaccacaagc   61500
actttgggta gaatatggca gtatcctagc agggagaatt tatgctcagg cagctaacaa   61560
gtgattaaat ccaagtctgc ttttgctctc ctgcaatgca gtgaggaaat cagatagccc   61620
ctttgccctc tgtttatttt gaattaaact ttatccactc aattttttaaa aatttactag   61680 attaattaat gttttatata ttataaatac agttttgttg gacatctttc ctaatatctt    61740
aactggtcct tgggaaaatt tatagtaaat aatagaagta caaaattgcc actcaaagta   61800
ttgtaaattc ccaatggata aattcatgtt tagtaaacat ttcacattta atatttgttc   61860 acttttttcat tttcacgata tttttttcta aataagtgcc tgtcaggtca tgaaaatgcc   61920
agtaaaatct catgaaatca tttatccata aacaatcttt tgatgttagt gggctagttg   61980
```

```
attctatcaa aggaatttag agattatcag tagcacacag ttttagaatt ctagggtctg   62040
attgtgttac acctcctgtt agagtctagt tatagcagaa tagttgctgt caatatcttg   62100
ttgctgccaa tatcttgtaa ggcagtgtgt ttactggttg gaaacatgta aatctaacca   62160
ctttataagc agtaatagtt tttatagttt gaccgttatt aattttttat taataaaata   62220
tataacactt tcaatttcag ttatatatat atatattcag tcctctttaa tacatcataa   62280
cacttgtcaa tagctatgat ttatttatta tattgtgtgt atgcgagtac cagtatgttc   62340
attacatgtg tgtatgatcc ctgcagaggc cagaagaggg tgtcagatcc cagggaacta   62400
gagttgcaga aggttgtgga ccacagtgta ggttttggga acagaactca gattcttgcc   62460
aggagcatca agtgatttca taactgctta gccatctgtg tagccttgtt ttttctattt   62520
tttggagtat gatgtgtttc aaaatacagt atctaaatct gtagtccagg atagcttgag   62580
attcactata caggcttccc cctagactca agcaaatagt attggtttta actaagctac   62640
atttaaaaaa tccatttgcc agtgtgtttt agttgaacat atagacttac ttgaagcagt   62700
ccctagacac agatcagttc atggctcaat tccaagatgg gtctcatatg gtgtatgata   62760
aaaggaaagc agtacaagaa atccatctga tctttgaggg cttgtagaaa ggttaacttg   62820
acatcttatc ccaccttctg gtgcaggtag gtaactgaca cagtgatatg atgactgggc   62880
atgatggacc cagaaagaga aagctagata atagcatgat gtcccttcag aagagcagct   62940
tgtttcatac aaaacaatga aaaaattatc acctgttgat ggagaaatgg ctcatcattt   63000
acgatgactt gctcttcctg caatgaacct ggcctcagtt cccagcaccc acatggtgat   63060
tcacaactgt ttgtaactac agttctaggg atactacatc ctcttctgat ctctatggtc   63120
attaggcatg tgcatcacac agagacacac aatcagggca aaacatatac atacataaaa   63180
ggaaaataaa ctttttttca cattgaaaaa atatttacct catccccact tgtacaagaa   63240
atatgtgtcc aataccattt gtattgtaga attttatact gtttccctat actgtcttat   63300
acaagtaaaa cctaaactag ataatctgat aatcttattt tatatatttg aaattctttt   63360
tagattgaat ctctgttttc agattaaaat gagtaactac acatatattc caaacaaaat   63420
aatttgtaaa agaagcatga ttatttttaa gttttataat tgagtaaata gcattgactc   63480
tgaatgagtt attaaagttt ttcttaattc tcatttattg ggaaggaacc atcaaagaaa   63540
cgttttactt tacactcatg gcagtttttt gattagaaaa taatttctta ttacatatca   63600
aattcctaat attttgtgca agcttcaaaa gatgccaatg aaatttccag aacaagagtt   63660
cagaaacaac tgtctacatt caggtaggat gcacactgtt ctttatgttc agttttatct   63720
ctagatccag atgaactgaa ttacagtcag tcaactagac agggaaaatg agcatctgca   63780
cagctctagc tttggctgat ggagccaact tactacatag cttcctgtgt tgtggtatca   63840
tcaaatattt aacttctgtg atatttcttt gcctgttgcg taagtttaac caacaaaaac   63900
acatttccca ttgcccatcc caacatgtaa tagcagcaat tatttaaaaa tcatagtcat   63960
ttgctcttta tgtctacaag acaatacttg ttagtacatt caatataaat gtttttctttc   64020 acaccaaggc agtttcctga ttcattagag ggaattttgt atctgagcag aggaactctc   64080
atgttccccg ctttcccttg ttataacatt ctgagctcca tgaccatgta ttattccagc   64140
tccatgtttg gacacgggtg aaggaagcat atcacatgtt cttcctaaga gacttagact   64200
aagtatgcaa aagacccaaa attttcgaag gtccaagtcc ctatctgttc ataagctcat   64260
ccctagtcat tcattgcttc agctgctgtt tttggaccag tattgagtca acttcacatg   64320
cagtttctcc ctttctacca tgaccatttg tacatcctct ttgtttcatg gtttaatcct   64380
```

```
gcaaaagtat atatttactt ttgtttggcc taatcttgac cataacctag attgtacttt    64440
agacttctta ctctttaaaa ttttaaaatg tgcagcataa ataattttct cctactttga    64500
ttaatccaaa aactatttcc aaggtcatta taaaaggtcc caaattatga gttccaatat    64560
tatggtcagt agacctattt gtgctctata acagtgttat ataatatttt aataggaata    64620
ttagaacgga aatgggcctc atgtgaacaa tgtgttttat attactccct tccccattta    64680
tcatgcctgg tatatgtgag tatgtatgta tgtatgtatg tatgtatgta tgtatgtgtg    64740
tatttttat gtattgttat gtatatacaa gtgatatata tatatataat atatatgtgt    64800
gtgtatatat accttatgt atgtatatac acacacacac acatatatat atacatacac    64860
acatatatat atatgtatat atatatgtgt atgtatatat atatactgtg tgtgcattca    64920
ggtgcatttg tgtgtggagg catctatgtc tttggcaatg attctcatag aattttttga    64980
aacattgtct ctcactgaat ttggaattac tgtttcagct agactggctg gcccttgaac    65040
ttcttcaaag ccccctgcac tgggtttata aacacatcta tgccagcttt tggttgtatg    65100
gtaggtatac aagttcattt cctccttctc ttcagcaaac actttaccca ttcttcataa    65160
ttcctatgct ctaagccaag atattttttt cttaatgtgt ccaccatggc aaaggctcag    65220
aattataaat gtgtttctcc aaaaccctca gttaagaata tggctgccta attatgcatt    65280
taactaatag gcttctgaaa ttaataacca atataatatc gtggttcact aagacaaata    65340
tttgtagatt ttaataaagg caggtaatga agctaaagtt aaagaaaacc ttcaatacta    65400
tttatcactg tttgtgaaca aaatatgatg aaaatatttt gcccataaca taacactgcc    65460
ttaactatat ccatcttgac tcaaagagat agaaatccgt tctgtcactc acagtatatg    65520
tttgcagatg aatgctagaa ctgatcacag atgggaaact aggtgtgcat tgcaggggct    65580
caggtatagg tcacaactct atcagtctct gaacatcatg acacaggtag gaagaccagg    65640
aagaaatgtg ttttgtttca ggcctctata atgaaaagtg aatgtgaaaa ctcaaaactt    65700
cacccttgaaa agcctctgta tatcttatat gttttttccca tttcctggtg aataggtaga    65760
atacagggaa caaaaaccac tgctctcatc ccagtatcag cccagactct tttcccagta    65820
cctcatctca cagatattcc tccattcctt cctccccttc tcctctgaga atagggagcc    65880
ccacttctcc ctataacctt acccccaacc cctggcacat caaatcacag caggtccatg    65940
taaatcccat cccactgagg ccagataagg cagctcagct aggggagcag gatccacagg    66000
caggcaacag agtcaggggc agcccctgtt ccaaaccatt ctcattccta gtaatgctgt    66060
cctagcacta tgctgatgac tggaccaaac atacaatttt tgttcttact tgactcttac    66120
aacttcaaaa attaacagtg taaatttcca gttagctttt gattttaaga caagctaatt    66180
agtgaagaat taggcacaga aatctacata ataaaataat tacagaaaaa gaaagtatct    66240
aaggtcagca ttagtatggc atcttatttt ctgtctgtca tggggaaaca agcaattcca    66300
tatggatcgt agaggtcaga aagaggcact gctgatccca cactgctgtt ctatctagca    66360
caagcagcaa gagactctcc aaagcccagt aagcaaaagc gccctgctta tgttggctcc    66420
actaatgcag ggaatttcaa atgatggatg aattaaaaaa tttgaaagag gttccgcctg    66480
acagccactc atctgtgata tatcctttgc tgtcacgatg attagccatc tgttcctttt    66540
ctagatctta cccatccact atcattacca tccaccatca ctatctacta ctaaaaccat    66600
taaagcacat ttaaagatgt gaggtctagg aatggtatct ttaaggtagc atatatgtcc    66660
agtgtggtag cacgtgctca ggataggtcc tgagttctat cctccagcac catcaaacca    66720
caaaagataa aaaatgaaga tgtatgaact atatacttta ttagcttcta tctattacta    66780
```

```
gcaatacaat gtcacactcc atggcagtgg aaggaaggag ataccaggca tgccacttga   66840 caagtttta gacttgtgac tggtttcagg ttatgttcat aaaagacaca tggaaaggaa    66900
aagtagttaa atttgtgtgt ttggatggat ttactttgag gactgtggtt atgaagcact   66960
tgtttctaga ttatttcctt ttatccaaag tagaagggac ttaaaattgt ctacgttagt   67020
agttctcaac ctgtacctgt ggattgcaac ccctttgtgg tcacatatca gatatctaca   67080
ttatgattca taacagtagc aacattacag taatgaagta gcaacaaaag aatcttatgg   67140 ttggggtca tcacagcatg aggaactgta ttaaagagtt gcagcatgag gaaggttgag    67200
aaccagtggt ttaaggtcag tgtacagtcc caatttgaag cagcacagat gcaagtgctc   67260
ttgggtaact tctacatggt tgttttactg tagttactga tctaactgtg aaaagtggtc   67320
agcctgttgc agactgaatc tgaatagaaa tcacaatttt gcatactctt ggtttcataa   67380 ttccttatg cacatccttc tgagaccctg gttgtactac actactacca cttgggccta    67440
gagcccctct cactgtgaaa gaatgattgt atccttgggg agctataaag attatgactt   67500
tgtgaattaa tctcaaatca gggagccaca ggacttccaa ctttattttc aaatatgtgt   67560
gaactcccct gtgagatggt ttatcgaagc ctttgggagg tgcagccatc tgattgacca   67620
gttatcttat ttgcaattga ctcttttatt ttatatgaag ctctgtttgc taagaaggac   67680
aattcaatca gcagtcactc atagaactac tcagttgatg taatgaataa agagacatta   67740
gggtcagtga aatgactcag tgggtaaaga aacattctgc caagtctgct gacccaggtt   67800 tgataccta ggatcgacat agttgaagga aggaacacta ttccaccagt tgtactttga    67860
cctccccatt ctcactttag cacatatgca tgcccatact aaataaatgc aaagtttaag   67920
agaaacacca agacttattc aacaaattta ataacttatt agaatactca agtacacagt   67980
caaagaaaga agttatatta tggattaata gcaaaacaca tactgagtgt taaaaattat   68040
atactggagg agaatgggga agggtagatt gagagctaga catatacaac agagtgaact   68100
ttcatctggc ccttcaaaat tcttagtatg aaaaggaata gggacttgca actgaaaaga   68160
actctaatgg caattcataa aaactttagg gtagaatta gaagagggaa ttaaaatttt    68220
aagtctacaa tcaattcata caacaatctc tttatataac agtgttttt gtacactgaa    68280 tactgtgcaa atattttgta aaaggtatca agaactattc tgttaacagt ggcttgcata   68340
taatcagaca agatggcata catactctac ataacgcaca tttgtataaa acataaataa   68400
attgtaaaaa caatagccta cacactatat ttttaaagta gcattttctt attttgtaa    68460 taaataagat ttttgagatt tagcttattt agccaactaa tcattgacct ttttataagc   68520
agatgtagta attcttaaag ttcccaatta aaataaaatg caagttttt gctattggtt    68580 ttgatacact gactccaaac catatggtag tataaagata tttcttgaaa actctgaaat   68640
cttttcattg tcttctctta gaattgtttt atgactgttc ttctttaaca gtgtagatga   68700
atgaatgaac atccaaaatg aatagaccaa gcagcccgtg ttagaaaatt cattagtttt   68760
actggattcc actgaggact ggacaataag tggcaaaaca tatgaatgca gttctgtgga   68820
agcttcctca ggatttaaat aaattcaagc aacacacaca cacacacaca cacacacaca   68880
cacacacaca cacacacttg tgtacaggga ggagagccat tgtattagaa aatgcaacct   68940
ggatggccat cagggtgtga atgtcagcta ccacaaaata tatcagactc aaagctgaac   69000
aggcaccagt acttttatg gagaagaacc aggatggcct caaactcacg attcccgtc    69060 tcatcctccg gaacactggg attataagta tacgccacca catttggtga aagaaaggac   69120
ttgttttgaa tttctgtatg aatgaagttt caaaagaatg caattaagta cgagatcaaa   69180
```

```
tttagaagaa agatttgatc taaaaaatac aactaaatga gaaaaggtgg ataggaaaaa    69240
gcacagtatg cattctttat tgtgttgctt tcacgatgtc aaaaacaaat taaataggct    69300
agtaaaatgg aaaggccatg aacaaatgtt ccttgtagta tagaatatac tagactatct    69360
cttctatata aattgattta aaattaatga caaacttggt ttcaattcaa ccagctcatt    69420
ctaaaaagtt gaaatataca tatgtgtgtt tgtgtgtgta caaatgaata tataatgtat    69480
ataatgtaca atgtgcatat acattgtata catatatatg ttagaatgat gggtgtaatc    69540
atgtatttat atttttgaat aaattctaaa cataaccaaa ttccagaaca acttagcagt    69600
actaagaatt actgattaca ttaaagttta tttataatca atacacaaag atattaatgc    69660
atgtaattct atcagtattt atgtttctga tgttataatg ccaatgttta tttcacatac    69720
gtttgaatat tgtttaatat tatacatatt ctaaatatag taccaaatga tatttttatt    69780
tacattaatg agaaaatgta agtcctggtg aaattctgtg aaaaaagtta tgtatcagtg    69840
aaaaatggta tggaacaact ttcttttcagc tccaaaaatg gcaatacttt tcccttttatt   69900 caataaagag tatttttaag tagaaaagtt aaaaaaaaaa aacgggattc tagtcagaca    69960
actcgaaata tatgggtcag agtaacagta tctctggaat gcaggcttaa aacctgacta    70020
agatcagaga cttgagtacc atacaggggtt ttatgtgtgt attgtctgat aatggcaaaa    70080
gaagatggtt ttaaaaatga ctgattcata agcaagtcaa cattaagtga aacttgaatg    70140
gaaatttagt tttctagtaa taagcattta gataataagg agtgccttat tattattaga    70200
tattaagctg gtaccccctg tgccttggct atgactctga aatgaataga atgaagttac    70260
agttaacaga gatgcagagg cagacacttc cctgtgctac ctaaacaggt acttagtgta    70320
ctttgaacct tatttctgac aggtctgaga tgtaaaagga gggaaaccag tgagcccagt    70380
gattctagcg ttgccgtgaa ctgctcagag gtagtttgtc attgcacaga gctgttctca    70440
taatagttat gatcccaagc cttaaattgt tgggaactat gttactgttt atttgttgtt    70500 gtttttttttt ttttcctcta ccctctggtt aaaatataat tttgatgcat cagcatagtt    70560 atgaaggggga cttactagca agtgctttt aacactgata tttgggtctc ctggattcta    70620
tgaaagtcat gtctccttaa ctactttatc tcctgcactg cgccctcccc cccatatcca    70680
cagagcatct gaatggtcac tcgtggccat gctccagagg tgagtgatgt acacacgggt    70740
ggagaatcca atttaaaata gcatgagaat gtagaagaga caaaggagca ctgcaggagc    70800
atgtgcagat ataagtgctg gaagtcccca gactgctttc tccagacttt ctcagctcct    70860
ggtgttgctg cccactctgc tgccctggtc cttaccttaa ccagctccct tatatgcttc    70920
catgttttat ccttcactaa gtctctttct ctctggttct ggatgcttag atgttcttcc    70980
atttggttcc atgtcatatg gtcatttctg tttctgcagc agctaaactg ttggataatg    71040
gtttgcaggt ctgactccca agtaccactg tgagctcatt aacaatggct gccatctcct    71100
tgtatcctct gcactatacc agcagatgaa gttggaccat gggctgtatt ccatggtgaa    71160
tgagtgctct gtgctggttg gaaccctata gcaatagaca atgtgaatac attgacagtg    71220
ttttgttgtt gttgctgctg ttgctgttgt tgttgttgtt gttgttgttt ttggcaagat    71280
actcacttca gggttttaag aacatgaccc aacctgttaa aaatcaataa attcagacag    71340
aggatttttt agttaagagt taaggtacaa atgagagatc actgaaggtt ttaagcagac    71400
tgtaaggtaa gaagggaaga aagttcccaa agtatatgct aggagctagg gctccagtgt    71460
aaaggatggc taaacgtggg tctgttttaa ggggtgtaca aacatatttg ggctaagaag    71520
gcccaatatt tactttcgaa tgagggaaaa tgcttgtgac ttaacaggtt gcctgttcaa    71580
```

```
tgaactaaaa aaatgtaaac tcttactcca taatctcttt aatatctcac ttttgccaaa    71640
ggaatctaac cttattgcca ccaaatccca ctgaactcct agacgagcaa aaaaaaaaaa    71700
aaaaaaaaaa aaagggggg gggagttcta ccaatcccca tgacattctg caattttcta    71760
attatagatt gaaaagagg gttgaattca tttcatggga cattcactgt gtgtccctac    71820
aggatgctga gccataattg acccacacat gtggtgtgtg atatttgatc agggatccta    71880
ggctggaaag acagctcagt aggtaccttg caaacacaag gatttggatc cacagaactc    71940
aattttaaaa agctggtcat gataacacac atgagtgatc cccgctctaa agacaagga    72000 tagtaagatg tctgggtttc ttggctaacc agcacaacct acttggcaga ttccaaacct    72060
gctagagata ttgttggaaa gaaagttctc aacagaatct gaggaacaac accagaaaca    72120
gtctacatgt ctacacacac ctatcatccc cccacatcca catatacaca tgtacatgta    72180
tacctataga taaacattac cctcccccac acttgaaaat acacatatac acaacattca    72240
ttttaaagac acaggctaca gttttcactg tcttgggcat tgctcattct tttttgttaa    72300
gaaactgcca atgccattcc ccttgctaat aaatgttata aactgtggtc acattatgct    72360
gcagtagaaa tgccagagac tcttcctttc tactagtatt ctgatgtgtt tattcagctt    72420
cctcccacct cctctatccc tgtttaccct tcatagtgtc tcatgacagc tttctactct    72480
ctatatcttt gaaataaaga ctttaccaac attttaataa ttttttttcat ttgccgtttt   72540 tattttatc tttttaaaat tattattagt tattttcctc gtttacattt tcaatgctat    72600
cccaaaggtc ccccataccc accccccaa tcccctaccc acccactccc cctttttggc    72660
cctggtgttc ccctgtagtg gggcatataa agtttgcaag tccaatgggc ctctctttgc    72720
agtgatggcc gactaggcca tcttttgata catatgcagc taaagacaag agctcccggg    72780
tactggttag ttcatattgt tgttccacct atagggttgc agttcccttt agctccttgg    72840
gtaaattctc tagctcctcc attgggggcc gtgtgaccca tccaatagct gactgtgatc    72900
atccgcttct gtgtttgcta ggccccggca tagtctcaca agagagagct atatctgggt    72960
cctttcagca aaatcttgct agtgtatgca atggtgtcag catttggaag ctgattatgg    73020
gatggatccc tgcatatggc aatcactaga tggtccatcc tttcgtcaca gctccaaatt    73080
ttgtctctgt aactccttcc atgggtgttt tgttcccatt tctaggaagg ggtaaagtgt    73140
ccacactttg gtcttccttc ttcttgaatt tcatgcgttt ggcaagttgt atcttaagtc    73200
ttgggtatcc taagtttctg ggctaatatc cacttatcag tgagtacata ttgtgcgagt    73260
tccgttgtga ttgggttact tcactcagga tgataccctc caggtccatc catttgccta    73320
ggaatttcat aaaattcattc ttttaatag ctgagtagta ttccattgtg taaatgtacc    73380
acattttctg tatccattcc tctgttgagg agcatctggg ctctttccag cttctggcta    73440
ttataaacaa ggctgctatg aacatagtag agcatgtgtt cttattacct gttgggatat    73500
cttctggata tatgcccagg agaggtattg tgggatcctc cggtagtact atgtccaatt    73560
ttctgaggaa ccgccagact gatttccaga gtggttgtac aagcttgcaa tcccaccaac    73620
aatggaggag tgttcccctt tctccacatc ctggccagca tctgctgtca cttgagtttt    73680
tgatcttagc cattctgact ggagtgaagt ggaatctcag tgttgctttg atttgcattt    73740
tcctgatgat taagggtggt gtgactctaa ctaaggaagt gaaagatctg tatgataaga    73800
acttcaagtc tctaaagaaa gaaattaaag aagatctcag aagatggaaa gatcacccat    73860
gctcatggat tggcaggatc aacattgtaa aaacggctat cttgccgaaa gcaatctata    73920
gattcaatgc aatccccatc aaaattccaa ctcaattctt caacgaatta gaaagggcaa    73980
```

```
ttggcagatt catctggaat aacaaaaaac agaggatagc aaaaagtctt ctcaatgata    74040
aaagaacctc tggtggaatc accatgccag acctaaaact gtactacaga gcaattgtga    74100
tcaaaactgc atggtactgg tatagtgaca gacaagtaga ccaatggaac agaattgaag    74160
acccagagat gaatccacac acctatggtc acttgatctt tgacaaggga gctaaaacca    74220
tgcagtggaa aaaagacagc attttcaaca attggtgctg gcacaactgg cggttatcat    74280
gtagaagaat gcgaattgat ccatttctat ctccttgtac taaggtcaaa tctaagtgga    74340
ttaaggaact ccacataaaa ccagagacac tgaaactcat agaggagaaa gtagggaaaa    74400
acctcgaaga tatgggtata ggggaaaaat tcctgaatag aacagcaatg gcttgtgctg    74460
taagatcaag aattgataaa tgggacctca taaaattgca aagcttctgc aaagcaaaag    74520
acaccgtcaa taggacaaaa agaccaccaa cagattggga agggatcttt aaaactgtac    74580
tacagagcaa ttgtgatcaa aactgcatgg tactggtata gtgacagaca agtagaccaa    74640
tggaacagaa ttgaagaccc agagatgaat ccacacacct atggtcactt gatctttgac    74700
aagggagcta aaaccatgca gtggaaaaaa gacagcattt tcaacaaatg gtgatggcac    74760
aactggcggt tatcatgtag aagaatgtga attgatccat ttctgtctcc ttgtactaag    74820
gtcaaatcta agtggattaa tgaactccac ataaaaccag agacactgaa actcatagag    74880
gagaaagtag gtaaaaacct cgaagatatg ggtacagggg aaaaattcct gaatagaaca    74940
gcaatggctt gtgctgtaag atcaagaatt gataaatggg acatcataaa attgcaaagt    75000
ttctgcaaag caaagacac cgtcaatagg acaaaaagac caccaacaga ttgggaaggg    75060
atctttacct atcccaaatt ggatagggga ctaatatcca atatatataa agaactcaag    75120
aaggtggact ccagaaaatc aaataatccc attaaaaatg gggctcagag ctgaacaaag    75180
aattctcacc tgaggaatac cgaatggcag agaagcacct gaaaaaatgt tcaacatttt    75240
aataatttta atacagtcat ttattgtaac aaccatttca aaaacacttg tttccttaga    75300
atgaaaattt taactagata aatgtggtta tccatgaaaa tattaaagaa tatacaatat    75360
acattatatt attgtatata taatatggta tagcacatga tataacacac acacacacac    75420
acacacacac actttacaaa aatgttaaaa aataatacca cacagaatgt tgtgagaaaa    75480
tagcattagt gtctgactca tcttctcata ctttttagaaa taaaattaaa gttcttcaca    75540
ctttgtgtaa agcccaaaag gttcagccct aaggaaaact tgaaatttgg gtgttaaata    75600
agccaccagt ctaaaagttg gacatttctg aattaaggct catgcctcat ttccaccaag    75660
tgctgcttca aaacaaaaca gtgataatgg ccacaaaaaa cctctggcaa ctctaattta    75720
aggtgacgta tactgatgaa tgatttattt atcttagaag tgccaatatt tcactctttt    75780
ccatgtcttt aaagcaactg aaatagtttc atgagcacag gcataactgg attcttggat    75840
ttggggagaa atgatttggc tatgtgcctg ttgctgagga agaaactgc caacactgag    75900 gatgtttcta aagccaagtg ccaaattgtt tgtgcttagc atcatgtatc aggctggccc    75960
tgcaagatga ttccattcca aaggtcagaa atactctgcc ctgtttccag aattttattc    76020
agaaattgga aatagagaca gcttcaaaat agtcacatc ccatcttctt ctcagaatga    76080
gggctttgat ccaagccttg ctatgtaaaa tgcatgggag gaagaggaac ctaatacaaa    76140
ctttgtttat tctatccgcc attgctgttt tcatcttcag aagaattctg cttttggtt    76200 tagtggtaat aacttgtacc aagtcgatgg caactccacc cagataatga tgagtttgtg    76260
agaacatatt tttcacatgt ttgaagaata gagctacata gggttgaatc tgccttgcaa    76320
tttgatcttt atcagtttta tggaggcata tctccatgat taccctgtg tatgtttact    76380
```

```
ttaattagat aaataaccag aaaccaattg ctccctcact tatgattatg tgtattctcc   76440
atggagtgag agacaatagc tagtagccat ttgtttacct tcttactttc ttactctcac   76500
tacccagtat ttcctaatta aagctatcag cagccaccat atgcctgtga catgagtctt   76560
actctgtgga aacaccatga tcaaacaaac aaacaaacaa acaaacaaac aaacaaacaa   76620
caggttgcat tctcagcagt tgcagaaaaa ctcactttct tttgcatttt caacttgttt   76680
ttacattaat cacaaacatt aacagtctaa caacataatg tgttcactta aagataaaca   76740
acacagcagt tgttaactga aactcagatg tcaacactgg gttaagagaa ttatggtggg   76800
tttaccgaaa agttgaaaga gagaattgtc tcagtgaggt gtggccttca actggaagca   76860
ctgaagccag acaattagag ggaagattca aaggaggtgc tctcaggatt taagtcacca   76920
tgtctcagtc ttcagaagaa tgtgcagctg accaaggcca gacctgtgaa gagacccaga   76980
aactacaggt tgcagcagcc tccatcgatg ttgaggagcc atgttcctca cctcatctta   77040
tggctactag tctgaaggac cagaccagtg aggagaccca gtctccaag gatgtggagg   77100 aaccatgttc ctcttctcaa cttcttatgg ctagcgacca ggatgattct gaagatgaga   77160
cagccagtac ttccagtgat cttcagcatc cctatgactc ttcaagcgag tctactgagg   77220
atcttgatga ccaagaagtg cagggtagcc cagtcattcc accagatcag tcagatagca   77280
cagatttacc tgtgatgact gtagatggga aagttgattt cttggtgaat tacatgctgt   77340
acaagtatca ggtgaaagag gtgatgagta tgaatgatat aatgacactc attgtcagag   77400
aggatgaaga tcgttttcat gaaatcctca tgagagcttc tgagcgcatg gagatggtct   77460
ttgggctgga tgtgaaggaa gtagatccta tcaaccattg ctatgctctc tttatcaaat   77520
taggtctcac ctatgatggg atgcgcaatg atgagtacag ctttcctaaa actggtctcc   77580
tgatactcat cctgggtgta gtctttatga agggcaaccg tgccactgaa gaggagattt   77640
gggaagtatt gaatccaatg ggaatctatg ctgggatgac tcatttcatg tttggtgacc   77700
ctagagagct gataactgat gagtttgtga gggagcaata cctggaatac cagccaatag   77760
ccaatagtga tcccatacag tatgaatatg tgtgggggct acgggctaaa gctgaaacta   77820
gtaagatgag agtgttagag tttgtggcca aggttcatgg gtcagaccct actgtgttcc   77880
tttctcagta tgaagaggca ctgattgaag aagaagagag aacccttacc atgctattag   77940
agcatgctga ttcaagttct acttctggtg aaagttctag tgacacaagc agcaacttct   78000
ctcaggtcta gtacagtcag agatcagttc cttctgtata atttacagag aatttttaaa   78060
cttgcgggga aagatgtacg acctagattg tataggagga agggagcgtc ttagctgcat   78120
agttctaatt tgtataagca ccatgccatg ttttttcattg tttgcccttt atatatgaaa   78180
atacttacac ttaaaagcat tgttgtttag tttcaaaatc tcaacttaat accattcaca   78240
aatttaataa gagcgttgtc ataacataaa actaattggg aaataatccc atctatctgt   78300
acagttatct ggaatagtta aacatgcgtt ttctaagctt ctacctttta aacagctttc   78360
ttctaattac tcccttttgta cctttccatt tctcagtaaa attacatgct ctatgtggag   78420
ttgtttactt tatagttgcc aataaaattc aagaaagttt aaaaaaaaaa agagagaatt   78480
atggtaattc ctctcaaaaa aaaagtgtc tcaccattat tttctcacat cttattagaa   78540
gggtatctaa caagatccgt aggtatgtag agccagcaag catctggctt tcatctctg   78600 tggtggaagt aattaaagta ggaagtgccc attttgactc tgctgtcagc agaagagaac   78660
acactagact tgttagtgca gccttagcca ggccatctac ttccatgaca tgggataggt   78720
ataaattagc atggccatcc tttcttgtct ttgtagttca tacagaatcc aggaagcaac   78780
```

```
acatttagga gtaggagttg taccattttt gcataggaaa tgtacagttt cagtgtcaat    78840
gcagggaatt actatattta taaaaatcac agagtccctc tggctggtgc tttttagtca    78900
aatatgaaat gagtagtatt ggaattacaa gctggcatca cttccgtcat tggagacctg    78960
tttctgcagt cacagctgct aaaacagctt catgattcct ttactacgag ctttgtggtc    79020
ctgcagatga aggatatcat agtacatttc ctgcatctct catgacactc gtgatcagca    79080
tataagactt ttcttttgtc gagaattaaa taagaatatg gccaaggaac agaattagta    79140
ttgtgaagaa ggtgtaatga gataagataa agaatgattc agagctgcca atcatgtatc    79200
cctcttgctg ggttcattgt ctctctatct caggcattga atgaaacata ctcttgttcc    79260
tgactataaa atcagtaata taaaacaacc aatttaatag catttagaag agactcaata    79320
gaccggcagg gagaagactg tatccactga tttaaaatat gtattatgat accataaatt    79380
ttaaaaagaa aggaaggata gtcttataaa ttcctaagtt tgatagcaca taagggctga    79440
atggtgatca cttgggtccc ctttaccttc attggttctt tgcatcttca cctcgagcaa    79500
ttgattgtgt ttcgcttgtt tgggttctct gcctttctcc acactccatg attttttttca    79560
aaactgtctt ctgttcccct tcttgcccac attgtaaaca tgtgaagtag aaaagtgaaa    79620
gtgattttgg tgtcttttct tcagaatcat tatgttttcc agcaagaact aacactgaaa    79680
gctacctgaa acacaaataa attaatgaaa ttgagccata cagtcatctg tatataaagg    79740
tgtaacgtaa aagggccact atataggaag gcagagtcag cataaggctt gatttaaaaa    79800
aatggcagaa caattatccc tttgatgaga tagacttaca tcttacaagt gtagtcatgc    79860
tacatcataa gttgacctca ttttctaaat tagtcagagg agcataactt ttttttctgt    79920
ctttcatttt ttttgctttg ttttttgtttt tctagacagg gttctctgt gtatcactgg    79980
ctgtcctgga actcactctg tagaccagac tggcctcaaa ctcagaaatc tgcctgcctc    80040
tgccttccaa gtgctgggat taaaggcatg ggccaccacc attgcccggg tcgtctgtct    80100
tttctaagta tgcttcctcc agtacatgta atgtttctcc ttttttccca tattttcctg    80160
ttctgggcag ctgttaggat ttacagattg cttgcttgcc tttggttatt tcctgttgcg    80220
ctgtaataaa actgccctct tttaataaac ataggctttg cttgacttca gaacctgttt    80280
tagatgtgtg tttccaaaaa ggttcccatc tgtattctta gacccctat gtcttgcatg     80340
agcacattct tccccagttt gtatactaaa gatacttggt tgaacccatg tttgtttgga    80400
acatatttat ttcatttgga ttctgagttg ttcctttgct ttacctagtg gagcagagct    80460
tatgggaccc cagagtcttt tctggataag ctttcttcca tgaagcaagg cttctgggat    80520
tttataagat gttctaagga aaattcagtt taaaatgaga cgttatgttg atgtgataaa    80580
ggtacaaatt tatgacaact actttattgt tgccagttaa gaaccacatt gtaaacatac    80640
cccctagaat acatttaatt ccatagcact taactatatg tccctacaag taaggtatga    80700
cactcttctg tatataaagg catcctcata atctttatca tcagtgtttg gtaaacattt    80760
acctgttcaa attctgcttc atggtgagaa tttttattca gaaatataac aaactaatta    80820
aatccttttt tgcaattttt ctgtattatt taaatacatc atactaaaga ttttagtata    80880
ttaactaaat aaagattata atattattta agtaagccc atcaatgaat aagatatata    80940
cgcacatagg gacccttag tcacagtcta gtagactcag gcttctcatt gtttccttt      81000
ccatcctttc cttttctagt tgataccat gagtttgcag gtttgttgtt gaaggaagtt     81060
gctcctgaaa gactctgtcc aggccaacag tggccacaag agcagggcca gatgcaagtc    81120
tctcttccag ctctacagtg atagttaaga tggctgccat cttaccctcc acagctactg    81180
```

```
tcaaccatct gaactagcag ttccacatac atctccccta agcttgctta cattaagatc   81240
agcatctcct tttccctggt ctctagttag atctttccat attatatttc caactacaac   81300
ttttaaatgc tttctcaaaa ccttcaaaac attgtaaagc atattattaa caaacccagt   81360
ttgtcattgg tctaacttca ttttcttctg ctgctacttt tccagcaact agcttccact   81420
gcaagtaaaa ttttactatc accaacacat gagaggtaaa catgaagcca gaggagtctg   81480
tatgtgtatt ttgtgcaata agttggttca tggccattac accaaatgcc tggttgtact   81540
ggttgacaac tgtctttcta ccagatagac tgtttgccca ctgtgcgatc ttggacaaca   81600
tttaaatttt tgtgtttctt agctttttta catgtgacat gaggataaaa attactccta   81660
cttcatcaga tttaaataaa gtgttttaac ataataccta ccctataaca attcagttca   81720
atgatggtat catgaagaga aaacacatga ctttaattga attttagagt tctgatgtgt   81780
gtgtgtgtgt gtgtgtgtgt gtgtgtgtgt gtgtgtgtgt gcatgtagat ataaaatatg   81840
aaccagagga ttacctggaa ataactggaa acagaatgac agaatgtatg atagattcgg   81900
aatgaccata gaattaatat ttgcaaataa atagtagaat gattccactg atcttttgga   81960
aactaaaaga gagaagaata tttcaaacag cttttcagtgt ggctttctgt gatgctctct   82020
gtctgctgct tctgctgctg caaaataaag cttccctcct cccccttatg agcagtgaga   82080
gtgacacttc cctgtgggtg ttgggataac tatttagaat gcagcgagga attacattgc   82140
ttagaaacgt ggcaatagaa cttctcttct agggtccatt aagtcaccag acacaggtag   82200
tgggctgatc ttacagtaac caagcatgaa tctccccata tttagcaggc catgagccaa   82260
ctaggagacc agtatagaaa tctatagcca gcaagaaggc agagaacaat tgactcttgc   82320
ttgcttgtcc ccatcaattc atttacaaac agcccatata ccaaaggtgc tggagacact   82380
gtggaagagg gggtagaaag acaatgagac cagaggactc agtggtttgt tagcatatgg   82440
ggtcttccta ataaaatgca aaaggggtat ggagaggga gtgtgagtga atatgtgcat   82500
atgaccagat acagtgtatg aaattctcga agaattaaat tctcaatata actcccaact   82560
gcaggctaga gagttattct tagacccaca gataagtgta gcccttacca ttcatcatag   82620
aaagccacag ttaaaagcca tctaaattgc ttttttccctc tatcatgttc cagaagctca   82680
gtgacatcat tattcccccc catttacaaa tataaattct atagtatttc cattttttaa   82740
aatttcctgt tttcggtgtt tattgtttgt ttgcttgtat gggattcttg ttgttgttga   82800
ggcagaatct ctctacgtag ttctaccgtt cttataacta cttgtgtaaa ccaggctgac   82860
ttcaaacaca cagagatctt cctggcctct gcctcctgaa tactgagatt atagatgtgc   82920
agtgccattt ccagctactt atttcaaaa ggctgttcat attttggtgc ctgtttctgt   82980
caaactccaa gtgagaagat ttggattaag aattatagcc cctttccatc tggtttgcac   83040
ctaattctga tcctaaaaca aagtaagctt cttttcaaat tatctttat ttatcaaaac   83100 catggtttaa atttccagca tgaatataca atttgccatt taaaagtaat gtttgaaagt   83160
tgtgacagct gaccagagac aaggcctact gaaggtgagt tccagtgctg tggagggaga   83220
ggtcatgaat ggtcttgatg aagcttattg catgcaagat catcacaact tcagaaaaga   83280
ccttaagatg ccaactaact atgttattgc tggggttcag agagcctaaa atgtggtgtg   83340
gattgtattg gcaatgtaac taagagcaa gaatgttcat attttatgtg attttaaagg   83400
tattaagtat caatgaacta attctttcaa gagcagagat aaatgaaaca ttttatctt   83460 ctgttttcct tcttactctc taggaggctc atgttgaaga caagtctgaa taggaatgct   83520
tgtagaagca ctcattaact aggattaaaa tagctagcat ggattcacca cagaccttac   83580
```

```
agtaattggt ctgcaagcca ttcaatcctg ccaccataac attagtcctt tttaaatttt   83640
ttaaatttta tttatcaatt tcaatctgat tttacatagt gaggttttca aatttcaatg   83700
tctttggtcc ctgcaagctt tattgaaaga tatattcatc tatccagggc taatggtatt   83760
tataagcata actgtactca catggatttc ttaagaggaa caatacataa aatttacatt   83820
acaacaaatt ttgtgaagac tttatataag tgtgcctcag cttatagaaa gtatagatag   83880
aaagtttaat ggctatcaac atcatagact ttatgtttgt aaagttaaca agaaagtcta   83940
cactataaag cgataataga taattataca taaagtatgt aactaatacc aacttccttt   84000
aataaattgt agggaatttg gcagtaaaat tacagcaatg tgctaaccta gtaactcaat   84060
cactgtgtat cacctctaaa attcatttta aattcaacag tataatttct cataagcaat   84120
ggcttactca ctcattgaac aaatgttgag catttgtgga gacatagtac ttattctagc   84180
caggtatgtt gttatgtggg ctcattttgt atatacagaa tataagaaat tatctgagaa   84240
aagacagagt taaagaattc aacagtaatg cttgagagtg gttattgttt ggcaaggcac   84300
ccagctgtcc tttctagaga gtaacaactt cagcattggg atgagaaatt ctcacttctt   84360
tgtacctcac tgaccagggg tgagcagagc tgctcagaag ctctcttggt gcctaatacc   84420
ctccattctt gttagtgatc tgaaactctg aatctcccca cagttcccca ttcatagagc   84480
ctgtttatct aagtgaaaaa ataagaataa aaaagggtgc tgtaacaaat acacaagaaa   84540
tatgaacggc gttctcaccg tgttcttgta gaaatgtaat agaaatttaa gctgatgtta   84600
ggtgacaatt aaaatctggg aggtgttttg tacactatca cctctttggg atgagatctt   84660
atgaatgagt gatgtctagt agaaaagacc tgtaatcata ggttttgttg accctttttcc   84720 tagataatag acgctgtctt agaagcgcca ctaacctctg atattttcct ccaagacctc   84780
tgcaaacctg tattctgctt attgtacatt gccatggcaa tactgtctag tctgcccatc   84840
caggtcccta ttcatatgac tcacttggct gctccacagg agaggagtta gcttcaccta   84900
accagcacca ctgtagcttc caggaaggga catgggaaag aatagcctgc caactagcca   84960
gcaggcctgc tcgtcccctc tttacttcta atagcaactg cagggctata gccagcacag   85020
atcactgtta atattaaaag cttgtgaatc atggcaaatc atcgtctttt atggtcagaa   85080
agaatgatgc ctcttataag tcttttctgc ttaattatgg tagaaggttt ctacatgttc   85140
ctctaattat agcaaatata atcagactaa agcttggtag ctaatgctat acttatagga   85200
agtgtacaga acagtgaata atgtagatgt tgataatata cacatgctaa agtatcctct   85260
aagaaaagaa ggcagtgtcg caaatgaaag taatttaagt gaaagtgttc ctatgaagaa   85320
tcattgtcgt cacaagcctg gcaacatatg aatgtataat ccctgtggtt ccttctgtga   85380
taatatgaac tcgatcttct tacttccata aaggaatgac aagccaagct ataggaacaa   85440
gaaagcaagc aaggcacaca agtattgcct acttttctt ttcttttctt ttttttgtg    85500 attacactgt cagaactcag caaatgccta tatccctgg tagcctttaa caggaacatt    85560
ttcattgtct ctgtcataaa acgactgtat gtcacatgga ttgagtgaaa ggaaggcact   85620
gagtaagaac tgtggattct gaatatcagg atatcctgtt tttacgccaa ggctctttgt   85680
taaccatctt gatcaatgat gccaaactag tctagattta ggctgtgaga taaacatttg   85740
ttcttgtata cagttccccg atcatggcca aaggacagca tgaacagagg tgaaggtctc   85800
ggtttcccag acagtggtct cattatctct tttgcatgtt ttaagggtca ttcttaacta   85860
cagcccaaga ctcttgataa cagggctcac gtagaataat tgcaggacag gtttagtata   85920
gtatcatttt tcatcctcca atgctaatca gattgaaaat aaacctgtca ctgagcagaa   85980
```

-continued

```
gaaacaaggc caaggccatt tgctgcatgt gatcttttca cactggcttg ctgagtttca    86040
gatgattttt ctgtcacact ccaaagaaca tgagtccctg aagactttg tgaaggctta    86100
gctattatca agccattgcc tcatggatga cttcataaat gtttgctttt gcatcaggta    86160
atggcataca acataatttg ttcctgactc cccactatac acacatatat ctcctttgac    86220
attagctaat aaaatgacag agagacgttg atttctgact gataatatca caagagctcc    86280
ccacacactg tctcctacaa atagagtgga atttacagtt ttataatgtc cttaacattt    86340
ttctttcaaa tgattatatt taaacatcta acatttatgc atacatttat agcaaagcat    86400
ttaatttcag caaccttcct gctcctaatt aagcagtcat ttactctata gaataagga    86460
gtatatcaat ctcaaaggcc atctttcaac atgctcacac ttgacactct tgtttcattt    86520
acccatgttt tctgtcacag gttctgatgg attaatttct gatttctctc aaagcctacc    86580
aaaaattttt ttatcataaa atcatttaga gtggttattt ttaggaataa ttaatattgt    86640
atgcttgtga aaatataga tatttaaaat aaaatattag agttaataaa ataaaataaa    86700
ataatcatat aatgtgtttg tttgataaaa ttaagcttaa acaatatttt atttattaaa    86760
tttacatatt ttcttatata tatttaatat atctgttcac agtgttctta taataatcat    86820
caaatacccc tctcagtggt catataaagc aaattttata aatttctcat ttctgttatt    86880
tatccaccaa taatgtatat gtcattgtcc ttctatataa cactcctgcc tagtggttat    86940
ataaagtatg ctttgtaaca ttttctctct tttaaaattt acacatcaat aattcatata    87000
ccgttgttcc tccatatttg taagtgaagg ctccagaccc tcttcagatg ccaatgattg    87060
aggtagcatc gtcatcactc tatatctata ggacatagtt ttagaaccccc cttccaatgc    87120
ccatgagtca aatgttatca tccatttgta cctataagaa atggctccaa cacccccctt    87180
gagaggccag attgaaattg cttgaattca ttaaactgta taataaatac tttcaacttg    87240
tatcttccta caaacttaca ttatagtacc taatacaagg taaatgtcat gtaagtagtt    87300
gttataatgt attttatgg acttttggtc tagcattgat atcaatctat ggcttcacaa    87360
atgaataaga ttctttgctt tgattaatta cagttgcatc tttccttct gtgggtgtgt    87420
ttgctgtttt tggagggtac taggttgtag aacagtttgg taatattttt gtctgttaga    87480
ctggtatctc aagcaccagg ttctatatcc aatctgccct tgtgtactct ctatggcaag    87540
tctttatcca acagcaaacc actctgatat taaagaaagt ggtggctaaa tccacatact    87600
tgttaggtgc ttattagttt gaggagtcaa gtgacttcag aagtactgtt taattagtag    87660
ggttatgatt ggaaagggaa aagagagttc agaaatgatg ggaaacgagt gacacgtatt    87720
agattattag ataggaatta gaggaggagg atatgtgtgt gggaataatt gatgcaaagg    87780
ggagaaatgc catgtatgtg tggaggttag agctaggaga ctaaaaggag taggtaaaaa    87840
tacgtactca gatatcataa accaggtcag ccgctgatct ttgggagatg tggcaataag    87900
tgggaaaggt acagaaagaa ggaaaacacg gaaaagaaag tcggaaaagg aaagacgatg    87960
agggagataa ggaagacaag caggaggaga agaaaaggaa gagagggaga gaaagaatgc    88020
caatcagtaa caggtggaga gtgaaggggc ctgggttgaa ggctacttca tctactagac    88080
tgtaaagaca ggaaatagct gtgcagagag aagagctaag cagaaatagg aaatctctgc    88140
cagatatgtt actggtggag agatatggac aatataagga aatgaggcaa ctggcttgag    88200
tgctgttttt ttttttttt ttttttttt ttatcatcct agtggatctg gggcttaggc    88260
ttccttggtc ctggtctttg ctttatctct gttgagttta actggtccag ccgtcttttg    88320
tactcacatt tctccttgca tttggagttt cttgactatc ttttgtgaac tgtggatagt    88380
```

-continued

```
gtggatgcaa actcttccaa actgagttgc tgtgattttt tgtctttttt tttaattagg   88440
tattttcctc gtttacattt tcaatgctat cccaaaggtc ccccataccc acccccccca   88500
atcccctacc cacccactcc ccctttttgg ccctggcgtt ccctgtact ggggcatata    88560
aagtttgcaa gtccaatggg cctctctttg cagtgatgtc cgactaggcc attttttatg   88620
atcaacagag gagtctggct tgtggtgcc caaatgactg ttttgagctt gcctttcctc    88680
acggggttgc tgatgatggc ctgagcagca gtcacagcaa acttccttt taatatctgt    88740
acaagcacag cttttgtaga ttctttgata ggaacctgca gtccacttt tctggagtgtg   88800
atagaaaagg caactgagtt ggaagctgtg ttgaatttag attcagctgg aaatccaggg   88860
taatggcaaa gaaggtgtgt gcatccaaca attgactttt gttagtatgt tgatcaagtc   88920
aatacagagg ctagagaagc tgagcatcat taaatacttc tatttacttg ttttcctaa    88980
gtaaggatat gttttagcat ggcttctaat caccattctg tcccagttta atatattaa    89040
atatatac ttacttggat ctcattaata tatttaaata tatatactta cttggatctc     89100
attgaattga aaaccacagt tctatatgat aactaattgt ttataattta accagataga   89160
tgaaatgaaa atatatattatt aacatgtgta tataatactc agcttaaaat gaggggggga  89220
tgtctccatc aatgtcctcc cctcagatct tagggaaccc tgtggaataa aaagcagaaa   89280
gaaccagagg agctggagga caccaggaga acatgcattc tgaataaaaa aaccaggctc   89340
atgtgagatt gaataaccaa gcacagggcc aacatgggcc aacactaggt ccccggcata   89400
catatcacag cttccagttt agtgctttta tggttcttca agtgtgagaa tgagtgggtc   89460
ttgtgccttc tcctgggttc ttttcattct attggtttat attgtgcaac attgatatga   89520
tcatttttgt tttatgttat tatatttat ttgctatatt ttattattat ctcttagaag    89580
cctgttcttt tctaatgaaa gacaaaaggt ggctctagat aggaggagta gaggatgggg   89640
aaaatgtaat caggatagat tgtgtgagga aagaatctat tttcaaccttt aaaaaagtgt  89700
gtcctgatat tttgtatta tatcataata atcatgtctg aaacaagcag tcaagttcta    89760
attagttct tgtgctattg tatattttg cttttgggac ccacatagac ttgtaaacag     89820
cgttactatt tttgaaattc accataactg caaactgaag ccgtcttcac tgccctggga   89880
gcctgactgg atgtctgagc cttatctttc caaaccctct actgctgtac aatatggtca   89940
cataggtgca tacacaagcc tgttggactc agtctccaag ccataaatag tctgttgaat   90000
ggcttaattg gagtctagaa atggagctgt tcacatatca tgcctctttc tttgaatccc   90060
attaccttcc ttatgagttg atgaacaaaa actgttaaca gttgaagtct tcaagatctt   90120
tgtatttaga ttcagtcagt gaataaaagt tcccagaaat taaaaaatgc cacccatgat   90180
tggcaactat ctttattttt gtcttaatcg tgtctataat tatctttaac aaatgactga   90240
ctgcatgtgg gcatttgttc ctgtagagga tatcaaacat ggttttgaaa catacaaaga   90300
tttggtgttt attgtgaaac atattaaaca cactttaaaa tcaaactgat tgcttaaatt   90360
taattttaga ttaaaaaatg acaattcttg agatcaaaaa aagcaattca ataactcgat   90420
taaatataaa cttattcct aacagctatt cagctttata taaacttatc actgactgat    90480
gatgttatag caaatatgtt tttaaaatga atagttatgc tgtgttcatt ttctttttt    90540
tttgatgtgc actctgagct tagtgctttg tcttttacta gttattaat ttatataaat    90600
attaatgcaa aataaatcat aataagatca tgtagtaata cattttttca agttattcta   90660
gattttagt tttttttaa attaggtatt ttcctcgttt acattttcaa tgctatccca     90720
aaggtccccc atacccaccc cctcaacccc ctacccaccc actgccccctt tttggccctg  90780
```

```
gcgttcccct gtactggggc atataaagtt tgcaagtcca atgggcctct ctttgcagtg    90840
atgaccgact aggccatctt ttgatacata tgcagctaaa gacaagagct cccgggtact    90900
ggttagttca tattgttgtt ccacctatag ggttgcagtt ccctttagct ccttgggtat    90960
tttctctagc tccttcatta ggggccgtgt gacccatcca atagctgact gtgatcatcc    91020
acttctgtgt ttgctaggcc ccggcatagt ctcacaagag agagctatat ctgggtccta    91080
tcagcaaaat cttgctagtg tatgcaatgg tgtcagcatt tggaagctga ttatgggatg    91140
gatccctgca tatggcaatc actagatggt ccatcctttc atcacagctc caaattttgt    91200
ctctgtaact ccttctatgg gtgttttgtt cccatttcta agaaagggta aaatgtccac    91260
actttggtct tcattcttct tgaatttcat gcgtttggca agttgtatct tatatcatgg    91320
gtatcctaag tttctgggct aatatccact tatcagtgag tacatattgt gtgagttcct    91380
ttgtgattgg gttacttcac tcaggatgat accctccagg tccatctatt tgcctaagaa    91440
tttcataaat tcattctttt taatagctga gtagtattcc attgtgtaaa tgtaccacat    91500
tttctgtatc cattcctctg ttgagggggca tctgggttct ttccagcttc tggctattat    91560
aaataaggct gctatgaaca tagtagagca tgtgttcttc ttaccggttg ggacatcttc    91620
tggatatatg cccaggagag gtattgcggg atcccataac cccattaaaa aatggggctc    91680
agagctgaac aaagaattct cacctgagga ataccgaatg gcagagaagc acttgaaaaa    91740
atgttcaaca tccttaatca tcagggaaat gcaaatcaaa acaacactga gattccactt    91800
cactccagtc agaatggcta agatcaaaaa ctcaggtggc agcagatgct ggcgaggatg    91860
tggagaaaga ggaacactcc tccattgttg gtgggattgc aagcttgtac aaccactctg    91920
gaaatcagtc tgtgttcatt ttctaaaagc ataattaatt tgacattaaa ggaaacatct    91980
agtgaccgaa tatatactcg gccatagcca ctgcctctca aagatttcct attttactta    92040
gagtaggtca atgaagatat aaaatggttc aagttaactg acattgcaag aaaaactatg    92100
accctagaat cctgtgcatt gaaaggatca tgcaatacag agatgagtgc caattcctac    92160
tgtcacatca gttgcaggtt tccattgttg aaagttaaat ggatgcttac atgtactcca    92220
tcatggagtt aaagacaatg acaatggcat gtctgtacta aaagaaagct ggttaggaac    92280
agatgaaatc ccgactgata gagtttcact agttattcag cttatgtgtg tcttcccttg    92340
tctgttcaac agctgaccta tagctgttta gtagtgagta ggggagggct gagcaatgag    92400
tgtgtacctg acaaggcact gaagtaggtt tgtggctttt cataatctta gacactatgt    92460
tggtatagag atggatctgt aactgctaat cattgactct ttccatccca cagctcattt    92520
ccttaccccg aacatcttca aacctagtag cttgagacta acatgttttt tttttttttg    92580
tttttttcat tgtaaatgct atctttgggc aacaagcctg cttcccagac cactagcgat    92640
ttattagcat ctatcagctt atctcataca cttgagaatg aataagtttg ctttgacctg    92700
cttggctgtc cttttgaaa ccagctacct atgagttact cagagaggaa tcatgcaagt    92760
ctgttcccct tgctaatgac ctagtttctt gtgtctggag tattccagct ggagagtcct    92820
ctgtggatag cagtgcaatc cttcatgcca ggctggaaat aagcactgct tccttaatct    92880
ctcccatagt tacttacatc tattgtgatt ttgtgaatgc aggcacatac atatttttca    92940
aattattata aaataacagc atatgagata tgaatgtaat acagcccatt ttatatatag    93000
gttatacaga aagcctgcat ttcaatgtgg aacatacaga caaagaatca aaccatatca    93060
caatagcaga ctgtcaggga tggtcccatt agattgtagg attgacatat tcaaagcaga    93120
aaaattcctg tatgaagttc gaaaagattt gagaatcttg tgtcttaact tcatgaaact    93180
```

```
gcagtctgag ggtagatgga ttaggtcagt tatagcaaga ataaaatttt aattttgtat   93240
atacacttgt taatatttta tgaaaagaat tattattgtc tagcttaaga catattttac   93300
ttataaccag ttctaatcca gaaacaaact tggacaccaa tactgggatg gtagtggcca   93360
gcagggtccc aaaatgcatg tatatgcttt atacagatgt aaagctcttt tactactttc   93420
cttacgaatt tatacatgca tatgtttgtg aatgctaaat tttattggtg atggttgcta   93480
aaatgatttc cacttactaa taagaaacat atcactcttg agctaatgca tgcacttctt   93540
tttttaacct tcttagaata ctggaagaag aaattacttc aaagtgtaca taagggcttt   93600
caagtaattt tgtgactaga gagggtataa atggttggtt tatggcttca aaaccatcac   93660
tgaaagcaga tgtatagtat ggattcccct acctccatcc attctctaga tgatgagtat   93720
ctgggcttgt tccattgcct atgcttgaga agggagatga agggaggaag agagatactg   93780
agagaacaat ggagaaagaa atcaaatagc tcacgttttc tctcatatac agaatctaga   93840
tttaaatata tattgctcta agtatgacag gaaaatacaa gtgaagcatt ggggaagaag   93900
agaggtgtcc gtatgaagga gagaagggtt aaagaggac aatggggaga atatgatcaa   93960
gtacagtgat gtaaacctag ggaaatactg taaggaaatc aatcacttca catgctcact   94020
taaatattta atttaaaagt gaacttggaa tttaccaatt gaaatagact cagaattccc   94080
acattctcaa agcatttgct ttcatgggtt gcttcaagta gcaagacatc ttttttaaagt   94140 gttgaggaca aggctgtaga ttttgctgta taaaagatg ctgaaagaaa gaaagaaaga   94200
aagaaagaaa gaaagaaaga aagaaagaaa gaagaaagaa aggaaggaag gaggaattta   94260
agaaaaaaga agctccgttt acaccagtat tacatgactt tatttacaaa tggatactat   94320
tctgtctttc tgctggcagc tttactgtct gcttgctcaa tcttctactg atctccttgc   94380
tagactttag acactttatc catttgatgt aatcttctca gaagaccaag gctgcagtta   94440
cagtccacat tcaatatctt attcttttcc tttattttga acataagtaa cacttgtctc   94500
taagtaacaa ggtcaaggtt tttgctttat ttctgcctcc ctcaaaacat ttctcttcct   94560
ctctacaagt ttcaaactta ttcacaaagg aatattgcaa tacggatgct attgtccgcg   94620
tttcttcctg gaacaagtgt taattgatct cttttgggtct atgtgtagag aggagttggg   94680
acctaggaaa ggtattatct ggggagttcc cttgtccttg gaacagaaca aagagatgct   94740
gcctacaaag gctttacctc cccagggctt ctctgtggct agactcaatt acagctggag   94800
aagctgtggc ctatgtgctc ccaaggccat ttgacaagat agtcagctgt ttattcttgt   94860
ttcttccctt gtacctgtac tcctcagaaa aacattcttc gaataagtga cacatttaat   94920
ctgcaatctt caaagggcat agtgtgttca aacacaaaaa taaatgagac aatgcaattt   94980
ctgaaatcga cttacagcga tatcccatgg gagtgtactc caaaccatcc acccaggctc   95040
attgctcttc taggcaagag ccattacaga gagcacagct ggaaacctgg aaaacagctt   95100
tccctagcat ttgtggttgt agagcttttc ttacctactt aggtgacatt atagtactta   95160
cagagtctat aaatagacta agatattttt tgaggttaaa acagtttaaa ttgtacagat   95220
tattagaact aaaaaaggaa aatgattcca ttacacttga ccttagttta cgggttgctc   95280
tccttagact agatgaagca tttttcaaaa gctaaaaggc tgtggcgatt gcacagaagc   95340
aaaaacaaca catatcatag acgttatctg attatttaat ggacaggtgg gaagattgaa   95400
acactgcttc ataagacctg aagtgggtta gccagtggga agactgataa gcattatcta   95460
gggttgaacc tgtgctttct actgcagaat actacaagtt acttataaaa ctgtgaggtg   95520
gtagggctct aatcagtcaa atagttatca gggcaatgcc tgagtcagtg aagttcttgc   95580
```

```
cattcacaag acaaatacct ggctcctgta cagccagcct atgctagtca gagtcccagg   95640
ctaaacagac accttgtttc aaaaaacaaa ttgtacatat cctgaaaaaa tgacactcaa   95700
ggttgccctg tggcctgcac ccccaccacc cccagacata catgtgcaca catataaata   95760
aaagagaaaa aaatagtaaa attgagggca tgctttggtt ccctagttct aatgtccatt   95820
ttctcatgaa actgaatgct gacaaaactt gacaaaagcc aagaatcaca cagggtctca   95880
gaacaacctc tcaaaaagca tgcctaactc aagtgtgacc taaataggct tcttaagtac   95940
ctgcatctta cctatatcta acatacaaag ttgcccgttg ataaccactg tggaagaagt   96000
gccagtcttt agagatgcaa tctgagagtg acagtataat gatccattgt gttatctgtt   96060
tttgttcttc taaatatttta atagaagttt gtaagaagat gtattagttt ctgagcaatg   96120
tgaccaaatt taaagccaaa tctagaggac actttcgatt tcagaataag atgtcaaatt   96180
aaaaaaaaat ttcatatgta aagcaatatt tgtgtgtgtg tgtgtctgta tacaatcaat   96240
tataaagttc ccacatgtct gtaatagctt tactgtagta ttagaaagtg tgtaatgcac   96300
actgaatgaa ttcaatggta ctttctatta ttttgaaagt aaaagtattt ccccatcttc   96360
ttgaaatttc agaccataag gtgaagactg gtaagtggtt tctgccatac tggcttgctg   96420
tcccctaagc atgaagccac acatgaatgt gctctgagag ccctggggt ctggtagctc    96480
agaatgaagc cttgcttcct aatcatcctc tgtaatggag agctctgggt taatcatctt   96540
cagagtaagt gtaatccttg atgacaccta ctgagactga gctaaagttc tgtaaaggga   96600
acttaaaaaa aaaggggcca ttccacgcta gtgccggcta ctctctgacc ccggcagtct   96660
cgctacctcc atggctagcc ccatgtagca accttacatc tcgtggttct cttttttgcag  96720
attgtaaccc gataaaataa aaactctaga ggcttgtgat ttattaatca gatttatatt   96780
agtaaattct caacccacaa aatgcctgca caatgaactc aaaactcaat taatataaac   96840
acaagctaca cccctagatg aggcacatga accctactta ttatttaatc acctatgtaa   96900
gaaatcccca atacttaccg ctcccaggac tgtttgcttc tggctcctct tcctctccta   96960
ctggttccat cttatctctt cctctccccc ccctttttt ttctcttggt ctctctgtcc    97020
tcatctctaa aatcctcagc ccactttcct tgtctactgc ccagtcacag gctctcacct   97080
tatcttgtaa ctgtcctcac ctgcatatag acagcagcct tcaaagttct cagtgtgttt   97140
ctgacaagga ctaaatcttc agaaatgtgt caatgtaagt cctctgccct acagccccct   97200
ttattgtcaa gattctgtag atttaaacct tgcccacata actcatcttc tggcaatttc   97260
tgagaaactg tgccttctgg taatgtcaga agctacaccc ataaagtctc atcaatatga   97320
ctgcctaaac atgaactgaa caatgacaat gaaatgctaa actggaagga aaagagccca   97380
tgggatctca actctacaca aagaactata ggcagctaaa gaaatctgat aatgagagaa   97440
atagtcttcc ccagggaaga gcacaacaac tggctatcca ataccagaca gctctgaaaa   97500
tgcacacata agtaacatta taaagactga agaatattat atttagaaat atgtatagta   97560
tatatataca tgtacatatg tgtatgtaac aacaatgaat gaaaaaggtg ccattagttt   97620
gaaaaggagc aagaggggt atatgggagg ggttagaggg aagaaaggga agtgataaat    97680
gatgtaatta tattaaaatc tcaaaacaga aagaacaac tcaatatcaa caatgcgcat    97740
gttttccta tgatataaga aaatcatata tgcttaggac agtagttcct tttaaaattc    97800
agccacaaat cactgagagt ttccagttta aaacagttaa aattgtctca catatttatg   97860
cttttccattt tcaattttca gtttaaaatt gagaaaaact tataaaagtt gcagataatg   97920
gtatgtgatt tccttatttt taagatcttc atcaccatat tggaataaag gcttttatgt   97980
```

```
actccagaac tgtccatcat ggcactctat gtggaagggt acttgcatta gcacataggg    98040
aagaaataat tccattagaa ccaaggttga ctctcatctg tagaatctaa gaatagggaa    98100
caccattggg ttactcttct catatccctt ttcttcttgg ggcatatctc ccagccttag    98160
cacaaaggac ttaggagagt aggtgaggga agggagtcca agtttatcag tcaagtaaca    98220
cattactata acataggcag cctctgaatg tctctgggaa atatgcttta atgctcatct    98280
taccatcaca ttgttatccc aagagaagcc cttgggctag atgtgggcca gtctccagtt    98340
gatcacttca gttctcagct cactcctcat cttgctgtgc tttctcacct gacagtggtg    98400
atacagtgtg aagacaattt tagccacttg atgacagcca gcacctggtt cacatgtcta    98460
tgctagttca aatgaatcag ccagaaagta tattagaatt catcaaagat gtgtgaattt    98520
caaaatgacc tatttcttta aaatgtgtaa agtacaatt gtgaaggctc attctagaag    98580
attctttcct ttgcttctcc cttttccatt aaatctctga gtgagaaaat gtagctgaga    98640
agcaggcttt ttatcttaat atctccccaa ctctgttaag aaataaaaga ctaaaaataa    98700
attactttaa gattcagagc agcaacctgt ccccagtgaa gctctcttaa ttaatgtggt    98760
gacctgtgta gagaaaaggg acaactgcag agtctctcag taattatcca accaaagctt    98820
cagataatta cagtagggag gttttttgaga cacaggacat cctgaaaact tgaacttcct    98880
tgttgactta ggcctttctat tcattcatgt tggggtttgt aattgacaaa gtcagagcat    98940
atcagaaact cacacattac taaagtctct gtgtttgtac ttgacaaaga cagcacatat    99000
cagaaattca aacactacta aagtctctgt gcgagttctc aacagaaaat aaagtgcctc    99060
ataaaatggt ggaaattagg ggattagcta aaggtaaaat tgagaagtgc tcgtgcagta    99120
ctgagtaatg tgggccagat aaaagatata ttttatatag actataagat atattagaca    99180
gcaaattgag aactgttgtc aaagattgat accagacaac aatatgttgt attcataaag    99240
agtattcttc agcactccaa taatgggcag tgttggaaaa tctttccaag gtgctgtatt    99300
tatgaatgtt caaactactc attagctaaa tttccttttg atttaaactc ataattggta    99360
atcaaaataa atttcaattt ccccctttgc ggctttaaaa aagtggaatc tcagtggcct    99420
tcaggtgact cactggactc gtacattcag tcaatctgaa accacataaa tggatttggt    99480
ttcattaaaa ccatttcgcc ccagtggctt tctaagccta taaaaaaacc tgctctcagt    99540
gacccagtct aacttaaatc acagcagtgc tttctcaaaa caataaatgt tatcttttcc    99600
atgggagtca agatgagaag ctaaaatcac cttagagacc aagctatctc atagatgtcc    99660
tgtccttcaa taaagaaaga atatttgctt tgcactgagt ggccacagtg ttcattttag    99720
ccacagacca tgcatgttct ttttggcaca gctatgtagt aggctacaag atggaaggct    99780
tatattgact gttctcagta ctctcctcat gtctcctggg ttgctctcct gctttggtag    99840
ccttttctca caggtgcctt tgctgcacag tactgtgtgt tcattaagca agagagtcat    99900
tgtttcttcc agaaagagaa ggcctttaaa agaaagggtc tgtggcaaca atggcctgta    99960
acatgcaaag cagatgaaat gataagttaa agagtggttt gggagcaatc cgtagcagct   100020
ccatttcaaa tacagtcaca aatggttgca tgtaatgaac aataacgctc ctcaactagt   100080
tgcagcagat tgctgactca tccggtacat attttgatgg tatatgaaga aaataaaggg   100140
aaattctaaa ttttctaggt gtgctgttga tatgcagcat attgggtact cagtcaaatt   100200
gtaatttatc agtgcaatgg acgtggcctc attcattaat cagtagcagt ggattgtatt   100260
atgtatgtct tttggtagaa atatgactta gtttactgct gtggttttca cacttgttcc   100320
agtgaatcgt atagatacat tttatgtgtc taagtcatat aatccagcag aggcaggtgg   100380
```

```
atatctgagt tcaaggccag ccttgtttac agagtgaatt ctaggatagc cagggttaag    100440
cagagaaacc ctgtcttaaa taatcaacca accaacaaac aagatatttc tcccccaact    100500
ctatatatcc tcccaaggag tctttgatgg gggcagcagc tagcacaaga ggtggtatgc    100560
actgcccctc cacactgctg ggctttcaca cccatcacat ttgtgctacc tacatcatga    100620
tcaatctgca cagattgaat gttcaagtac tagacacaaa attatgattt aaggaatgaa    100680
taataagcaa gaagagccac agtttcaggg gaaaatgcca gcattcaaca aatgtcacta    100740
ggaaatagct cagaattgag agttatcaaa agcaagtgat agaaccaata tgcattctat    100800
ctatttgtga aaatctcaag gagtaaaaat gaaatttaat taaaaaatta aagtagcaag    100860
aatgtatcaa attcggtaag tcgaatagta agtttctcta gagagataat acaaaaaaaa    100920
accaatattt gctcagaaca aataaataaa aacagatcca tttgtgtttc atttcaaaaa    100980
gcaactctca atttttaaag ttcattgtgt aaaatcactt ttgtgtaagt caatttatg    101040 ttcaaatgat atttttctt ttagatcttt gttggttttc ttttacatcc aatattttaa    101100
tacaggaatt taattcatga atttgatagg attatatttt gcatatgtgt tacacatgtg    101160
tttaacttgt catttagtag ctgtgacatt gtagggcacc tgactccttt atgtcccacc    101220
tagctgaaca tgctccttgg agaattgttg ctgttacttt ggacagtatt ttttcattat    101280
aaatacaaac agtctgtatg ttattttgtt cttaaaagat taataatttt tactgtcttt    101340
aatttttaga gaaaaatgaa gacatcaggc tgactgacta accctaaat ggcaaggccc     101400 aggttctatt tgttatgctc cacttcttcc tcaacaatgc ccaggtccca ttagttacac    101460
attgcctctc tcagcagttg gctaatttcc ttctaattta ttttttcagac tccattatag    101520 aacttttcca attacagcta catctcagca cttaagaccc atgctttggt ttaacatttg    101580
cacggctgca gactgagctt gaaggccatc actgtcactc cagagataga gatgtactct    101640
caagttttac tactctaaat aagataggtt gaattcctgc ttcacagggt tacttggtga    101700
ataaatgaat cccccttct cttttgcttt cttattctgg atcttatcag tttcaatgag    101760
aaaagaaagg gtgtgtcatc tttggactct cccatcaggg tagaggacta ttgcttatac    101820
attagccaga gatttatgtt tgttggctca gctgcagact tatttctctg aactttaacc    101880
acctgtgacc ctggaactta cttcctattg taaccatcaa tttccagctc caatgaatgc    101940
tctttgcatg caggcagctc ctgccagtga taacagccct ctgtaggaca ccaagactag    102000
gacccatagc taccatggct agtgttgtag ccttctgaaa cagttcttcg ttactattct    102060
cctcatctct aaagcactgt gtcatagttc caggattgtt tgggttgtca gctgttgaca    102120
gcatccagga tacaaggtct aagtcatctt catgcctggg ggcttcctgg aacttgcagt    102180
ggaggtaggt gtgcagctta ttgtatctag ctccttacag ccttcatggt cttcatgacc    102240
tctgctcccc gtcatctctt ctcagctgtt ctctggagct tttcagcctc tctcttcact    102300
gctgtgcagc tgttctcctt tcttttgttg ccatatcagc tactctactg atggctaatt    102360
gactgacagt cggtcactca gacagggtac cagagaaatt ctagcagctg tcagttagcg    102420
aggtacactc cacaccaacc cattccatag tttatttaaa agaaaagcat gcgtcaaaat    102480
agtgttcagg ataaaggctt atcataaata ttactgatgt tttaatggta tttagcaatt    102540
tctaaatctg cccagtgcct cagttacagt ggcctccttc tcttatttgt ctttaaaaca    102600
cacttatagg ggctggggac aaaaaaaccc acacacttat atatctgata tctttaatgc    102660
atcatttatg gtaggtttga agaagcatct ccgacaatgt ataccagaca ggatttatgt    102720
gccctgaaat gtctttttt ctatagctag taacagtccc tgtcttgatg atcaatcaaa     102780
```

```
cacaaattcc aataactggt caatgaaaac atacatataa gtaacattat atggagtcaa 102840
caggctatgt tagaaatgta tatctatata caaatacatg tgtatgtgtg acataatgat 102900
gaaaatatga cctcaaattt gaagtagaac agagggtggt atatggaagg atttagagga 102960
agaaagggag aaatataatt aaattataat ctcaaaaaat attaaaaaat gctaaaaaac 103020
caatcagttc atcccctttc tttctaacac ttatccagat tcacacagtc ttggaatcca 103080
cagatctcac atttctgcat atttttaaaca aggcaccaat tgctttcgct tgggtctgcc 103140
ttcatgagga tattagcaca atgatcagcc ttgaaaggta gaagtagttt ctcctcctga 103200
gtcaaagaca gatgtgagtg tgtagccttta gtcagatgct cggtttatag tcattcctta 103260
taatttaaaa aaaatctgga ttggtgagat ggctcagtgg ttaagaacac tggctgttct 103320
tccagaggac cctgttcagt tcgcagcatt cacatggcag ctgacaactg tctgtaactc 103380
catcccagag ggtttggctc cctcacatag acatttgagc aggcaaaaca tcaatgcaca 103440
tgaaaataaa tcttaaaaga tgctatttcc ttaagttcca aagttctctt ctatcatgaa 103500
cccagtgact gggagttttg gtgtctttaa actttcctgt gagaattggg acgttccctg 103560
tggctttggg atttccatgt gagatctgtg ctctggctcc tgctattttc ataaacagtc 103620
atgtaacttg tctcaaaatt ttgtattttg tttcaacttc tatagtattg atcttgacaa 103680
atgtgataat ttacaagtag tacaaaacca aactgtggac aactttttaag taatcattgc 103740 caattcaaat gaagtaaatt atagctactc catcttcatt tttaatatgc aacctgtcca 103800
acataaggtt tcgctgtcat gtgcacctga tcctcatgtc ctgcagccat tctgcaggtc 103860
actgccagac tgatttacct gaaccaatt ttcaccttat agctgtcagt caaagcatgg 103920
tggttattaa atgtgcaagc cctgttggca agtgttcccg gtactcatct acctccaatt 103980
cccattagcc cagggacagt atcacttttc ttctgccata ttttgtccat gatatatccc 104040
gtgtttagtt ttcccagcta gcctcaaaat attgagattc aatactgatg tttctgggag 104100
taatcgctcc tcattttgaa tgtgttattt ttacgtctca gtgccctaga ccaaggttat 104160
atagtcttct gttttttcag atctcacatt ttatttaatt ttctagaatt gatagtttga 104220
ggtgaaactt atgtttcact atatactttg caattattga cctcattcac agtatataca 104280
aatgtttata ctgctaattc ctccttcttt tgaagaacca atatgctgat attagtagga 104340
acactgtaga tttgttggca ttaagcatag atctcatcaa ggagttagaa tgtagagaaa 104400
caacattttc tattcaattt catgaaagtt ttttagtttt tctgctacat aaaaatacaa 104460
tgttcttatg acttgatcaa ttcttcatat aaaataactt aaagtctaca ttttcagaag 104520
tcttataacc tcttaaccca caaaatatat catggttttc aaatctggct actatgcggc 104580
gagttgctgt cataagcatt aatactgtgt gataattaat tgtcagcttt aagacagtaa 104640
ccttactttc tgtgctgtgc ttatgtcaca gttgtgtctg tccaatataa gcaacataca 104700
gtttcgtaga gagtacatta ggtcttctgg gagtttgaag acagagactc aaagaaaaag 104760
tcatgctttt cagagagttc ttaacctgct ttacttaaag agaaccagtg actgaaatat 104820
taagagctgt tttcttggca gcatcataag aatcaataaa agactactca ttctccagaa 104880
ccaaggctgg aaagtgtcc caccaagtgc tttgttgtca cctcagctct ggctgctgtg 104940
ggtaagcctg caagtgaagg atcctggcag ctgcacttta gtttctgctc tgtgcctttg 105000
tctcacacca ggtgcttcct acccatggct agggcttcag cacctgttcc tacagtctac 105060
acctaaattc ctgggcagct gagaggtggg gatatggaat atgtgtccca cttttgacaaa 105120 gacaaacatt gaggttttgt agagtctcaa atgaaactaa ttggtgaaag cagacaaaaa 105180
```

```
gtttctatta taaaaagata aaaaatgaag cctattctga agaaaaactt agctacaact  105240 tgataaatata aaaataataa gtactcatta attaaataat atgtgtttat taaaatacgt  105300
aaacaaatta gatgctatcc gagtacatag ggtctcagta aatattctgt tatataacta  105360
tgtactggtg attactggct actctatgtc accgtgttta atatctctaa tgtcacaggt  105420
accatttgcc acatggcaag tcagttacca aatattttgt ttagagcagg gaggggtata  105480
ctttatccag agtttccaat caacccgtca tatgtgcagt tttgaggaag ggactctgac  105540
acaaggtgct tggagtggtt ttgtaaggaa gcttttattt gttccataaa gtgataaagc  105600
tggccatttt ttacagatgt acttctctgt cacatacgca tgcactctca ccacagaaga  105660
gtgcctgcag ctactgctca cattcataaa gatgctcaca ttgtcttatt acagatactc  105720
tgtctgtggg aaactgagaa ttcctgttga acattcataa gtagatctaa aggaaccatg  105780
ctgaaggaag atccattgag aatgttgagc agagctgtgg attgacttat tgagagtttt  105840
ataatgtgtg taatccagaa ataatggatg ctttagaagt aattaaaaga ctataaataa  105900
acacttagtg ccttaatata aagaggagaa agacaacatt gagctcatca gctgtgatga  105960
cgaagtaatc tttctcttta aacgctatgt gaataagtaa gcaaactaca cttgatgact  106020
agatacagca tctgcctcat ggacttaatg gatcatgatg ccttattata ataatcaaag  106080
tggacataaa tgcaggggct taagagggat taccaccttc agtgctcagc aaagctttgc  106140
tccttgtcag caggggagaa gaaagcactc aagtgatgat aattcaaact attctagttt  106200
gaagttccta gtggcagaac ctccaataaa atggcttact acaaattcag aagataacat  106260
tgtctgagca gctctcttca ttagaagcaa tgtgttcatt gcccctaaa taaaaggtc  106320 catttttgta cttggcaaaa catcaggcac acacacacac acacacacac acacacacac  106380
acacacacac acactcaact cccttagctg tctgagatta ctcctcttga tgcaaatagt  106440
aacaagcttt aattaatacc agaggtagtt gaggtactca gacattaatt atacctcatt  106500
catggaatct ggcttaatgt tttattatga aaggtttatt tacaagaagt gtcacaaaat  106560
acaacataat aattaggagg gcagactttg gaaccaggtg tagtctgttc tgcagtgggt  106620
aaaatgggaa tcataatggc agccttctct aaggactagt ttgagttcag gtaaagttta  106680
taccgtcttt ggaatgtgtc cagaccccaa taaagcacca aggagagtct ggtttgttgt  106740
tattattgtt gttttttaaac tgtggtttat ttataagtaa gatgggcaag aaatcatttg  106800
gtagcatttg cttttaatta ccttaatttt ttttaaaatt taacttagtg tattaattta  106860
cttagtttta aaatcaagcc tcactctata tttcatcctg acttgaaact tactaggtaa  106920
aaatgggtgg cctcaagtcc ttggcattcc tgcttgagtc tccaagggca gtattacagg  106980
catgaagcac catgacaggt tttgccttgc atatcaggtt tctttataat ctagtttaga  107040
gttccccttt atcactaatt tgtccaaaca gatttgaagt tcccagaaat actctaagtt  107100
tagaaaagtg accactggca cgatgtgaca atatttaact gtgacagtat tttcaaatcc  107160
ttctgaagtg tattgctgtg atctgcgtgg ccctacttcc tcagtgctga tgatcccatg  107220
gagacactga tagcacagtc actttaatag gctgggccc agtgaggaac ttttccttct  107280
agatggtaga cctggtagac ttcacttggc ctcagctcac attcttgctt cagctttctt  107340
aaagcctttt aatcactcag ataagaaaga catagcctcc ttgtgtacta taaagaacat  107400
atctaataaa aaaaagagt tcttggtttc atatctattg atttctaagc cttcagtcta  107460
tgtcagaacc tcacaactct tgtcattttt ttggatacaa gcatcttgtt ttgcctgaag  107520
catttttcat cagtcttata gtaagataga ctatccacca tttctttctt tgtttaaagc  107580
```

```
aagcacccgt gccatggttt gctaaagtgt gaatgttccc tcttttttc cttcaaattc 107640
ttcaccattc cgtaaggtct tctaaaatga aagcatcaat cctgttttat agatggccaa 107700
agtctacctt ttttattcag ttactgattt taggacttcc tttcaaagac cattgcatta 107760
atgaacagga tgcagccttt aaaagtccaa tctatacatg tttaaagtaa tagtaaaaag 107820
aacctcatgt atacatgcaa tcatacaaaa atcatacatt ccctcaacag tcctaaagca 107880
ctggaaatgc aggttattct caggtttcca ttgtgtgtga gtatttccac cagaacatat 107940
tcaaataaca ggaataaaag ctggcagtgg ttgcctcgct gtgtaggctc attagatgag 108000
tcagctaatg acagggttgt gcattcaaaa gggcaggcac tctgccactt accaaagaga 108060
atgaggatta agatagcatg ttacctcctg aaaactagag ttaaaaatgc ttttgcctag 108120
atacctactt agtgtgccaa gtgttttata caactgggtt tttgataatt gattaaaacc 108180
ctcttaaaag attcttcaag tatatttaat atattatctt gcttttttcct tgtctcccaa 108240
aacttttaaa agaatgaggt aaaggagtgt ttatctattc tctgtactgt tctgtccctc 108300
taagagacta aatcactgtg ccagaggggg gagaacctg agcaatcaga ctttcaaagc 108360
agaacacagg cacatgttca atgagaagag gagtacacgt catttccatg taggactaga 108420
ttctccatga atgccactga actgtataaa aatttataca cataaaaatt tattgtattc 108480
acaatctgaa aagtgacccg agaagagtgt gttttcggca ttgcttatca gtgttcccta 108540
actttgctat tccagtgtga cacatgcaat tgatggcata gcaatttcct gttcactgag 108600
gaaatcttgc tagatgtaat gaagctggat gtgccataat aaatgagggc agataagtca 108660
ctctgatcag caagtagcct ttcagatgag ctaggaaact cctatcttca gtcagcttgt 108720
ggctagtcat tttgttgtgg ttgtggttgt taaaatcagg ctgtagttat ggttttgttt 108780
tatggtttta aaaactcaac tactgaaccc tttagttttta atatatatat taatatatat 108840
atactctgta tcaccatgta tatgtatatg aatatagggt gcctggtata gggtttgcct 108900
gttagtagat atatataggt taaagataat ctggaagtag tttttcccag gttccacaca 108960
ggcagagtca tttggagaca tggaactgag agtagattag cttgtctaat cagcaagctc 109020
caaggatcta cttgtcctta atgcccatca ttaacctgcc gcccactctc cgctgccaca 109080
tatatacaca tatcctatcc agagaataca agcacacgct actctacttg gttgctcatg 109140
catagaaagg ggcattttc attttttcaag ggctctctcc ccgcctaatg ttttcatata 109200
gaacaaagcc cctccaagtt gtaaattgtt tatgatggtg aatatctagg ccagggcaaa 109260
aattggcaac agaaaaggct gaatacatgg taaatatctt gtttgtttgt ttgattttttg 109320
agacagggtt tctctgtata gccctggctg ttctggaact cactttgtag accaggctgg 109380
actcgaactc agaaatccgc ctgcctctgc ctcccgagtg ctgggattaa aggcatgcac 109440
caccatgccc ggcatatggt aaatatctta cacttatgtt ctaacaagtg ttttttttt 109500
atttctgcca agttcacttt tttaatgtgt ccatataata catggctatt tctcttagta 109560
aaatgtgctt tgtaatatat atatatgcac ttccctacgt gggaaatgaa gtatatggtg 109620
tgtacacttt ttctattaaa tttacctaac cgttttacac acacaaacac acacacacac 109680
acacacacac acacacacac acacacacat cttctaatta ctctctccct aacaccatta 109740
tttttctttc atccctatta agaccttact cccaccattg ctactagtcc ttccccagaa 109800
ttcatggatt ttggttttgt gactcatttg gtttagtcag acctttttct gtgaactttc 109860
gattgagact gcacatcagt acatgatgtg atcttcagtg ggtataaaac tgaaggcaat 109920
gatttaccct tgccccaaat catcagtagt aagtagtata gcagtgacag ggtcatctga 109980
```

```
gtccttctat ctatttctga catttgacag gctcatattt gtgtatatac aaaatattta    110040
tgcatatatt tgcatatatt aggcatatat ttatgcatat acagagcaag cacctgtagc    110100
ttctataagt tcatgattga aattcctatg atttgccatg gaacactatt tcttcctttt    110160
ggcccttaca atctttctgc tgcccttct tcactaccta ctggtcctta gaagagacag     110220
gataagtgta gtgtttatac ctgagcacta atactctgcc ttttgtaacc tggaaccacg    110280
tgtctctaca tttaccattg ttcactgaaa ggagaggttt atcttattaa ggctgaaagt    110340
agcttttgtt ccatgctact gtgacagaca acaaagagga atggcaagaa cctgtactgg    110400
ttgaggggtt tacttgtgtc tttgtgatga acagtcctgg aatttgggtt ttggtataat    110460
aaaatgactt ccaggacaaa ttttgttcag cctgtacttt tttttttaaa tagatctatg    110520
ttatttttta tttaaaatgg aattctggga tgtattttat attagagata cttaacacag    110580
taagatgtat gcttaaataa accttgccct atcatgtcaa agttctttta aatgtctgcc    110640
tttttcttta tggctgttgt tttctccatc tttatgatct attgagcaaa tgtgttactg    110700
tatttattaa tgggttgatt aatattacct gacattataa caaaatactg gtctcatcca    110760
aaacatatgt ttagcataag agcagtggga tcagatcttg acctgctgct ttcagtgttg    110820
taagtgtaga tatcaggtac ttgtttagcc cttacatttg aaaaaatacc atatactctt    110880
ccagctgtct ttcagaaacc cagttttcct ttagctcctt gtaaattttg aagcagagat    110940
caccttttat tttcctgtat ttatattggt agatagaaca ttgttatttt cttatattaa    111000
atgtcactgt ggaggtgaca aatgattgct gacagtggat agtaattacc agggtcaatt    111060
gtaaattttg gtcagttctg atcttaaatt ctgtttacgt gaataatctt tgttttctgt    111120
attgcaacat tgccaccaag aattatcctt tacaaaatac tttgttgtaa acatcagtga    111180
agattatgat gcaagctatg catggggagg taagatgtat actatacatg ggagccaagt    111240
agcatgcaag ttagggtaca gtctatgcat taggggccag gaagtttcaa gacatttatg    111300
agggttgggt aggatggaaa ctgtacatga aaagaccagg tagcatgaaa gctatatttt    111360
aggaactaga aacatgcaag atatatgtgg aggtggcagg taggatataa actatgcatt    111420
tggagtccag gcagaatgga aacatgttag aaggattcaa gctatgcatt aagaaccaga    111480
cagaattcaa gtgataagga gggggtatgg agggggggt agtgggatac aagctgtgca    111540
ttaaatgcaa tgtgacctgc tggctatgca ttaggggcta ggtaggatgc aggatataca    111600
gtaaggacca agtagcatgc attaaagtcc aggtagtata cgagtataca agctacacaa    111660
aagaagctag gtggtattgc agcacagatc tctctgaaaa agaggagata catatttgat    111720
atccttgata cagaattttg acgatcttct ctgcaggaaa aatggtggat gcgagcctgt    111780
cttttgtatg gccactaaat ctgtaccaac accttgacct gtactagatc ctctatcttt    111840 gcccttttgac aggttttgcc cacatgcagg ttaccagtta gtgttttttt gtttgtttgt   111900
ttgtttggtt ggttttttt tgtttcgttt tataggtcaa gacacttgct tttttattta    111960
gacagcatct ctcttctttt gagtatgtat ttatatttta aatgatacag ttctctgttc    112020
acagataaac ttatggacac atccgtggtt tcacttttat tatagaaatt atggatcctt    112080
tatgatttta tggaacccttt gcctacaaat taagctgtga attttaaaa aaatctttga    112140 taaatttgta gctggagctg tgagtccctc catgtgtact ctttgatgg tggtttagtc     112200 cctgggagct ctgggggtac tggttgcttc atatcgttgt tcctcctata gggctgcaaa    112260
tcctgtctgc tccttgggtc cttttctag ctcctccatt ggggaccctg tgctcagtcc     112320
aatggttgac tgagagcatc cacctctgta tttgtcaggc actggcagag cttctcagga    112380
```

```
gacagctata tcaggctcct gtcagcaagc acttgttggc atccacaata gtgtctggct    112440
ttggtgactg tatgtgggat ggatctccag gtggagcagt ctctggatgg ccttcccttc    112500
tggtcatcaa taggaggaga ggccgttggt cctgtgaggg ctcaatgccc cattgtaggg    112560
gaatgccagg accaggaatt gggagtggat gggttgatga gcagggggga gggagagagg    112620
atatggggtt ttcagcaggg aaaccaagaa agggtagata cttgaaatgt aaataaagaa    112680
aatatctaat aaaatatta agcacacata caaaaaaaac tttgataaag ataactcctc    112740
aagatttgtg gaacacggtg tttcctaaat gaatgccagg agagtacaat ctttagcaca    112800
ggaaaatgta gtactaagaa acacaaacac gtatactatg ttttttaaaaa gaaaccaaca    112860 attattgatt tacaacttgg atgattttat gattaaaatt gacatgaagg gatttttaatt    112920 gattgtattt catggtaaac ccaggaagga atttctaagc aacattcagc attatctgga    112980
tgaactctga agggcaaaca cagttatccc cttatacaca tggacaccca cagcctgtga    113040
catcctcttc tactaatgta ggaatatcag agttaggagc ccccagggtt ggcctttcat    113100
attgtcttat ccagtttata acataaatct cacaagttac attggaaaat gcactgaaga    113160 ggtggttac tatatttcct tcctatgagc tgtataaaaa tcacgtaaac atcagtgaga    113220
ggggtccatt gtgtcacttg ctcctcccag ttatatacaa atgaaaagat ctctttgctg    113280
tcttttctca acacagttag ttgatgctca ggagtggtgg taacatgccc agagtcacaa    113340
aagataactt aggctggaat tgtaatgtgc atcctatgat caagttctgg ggctgaacta    113400
ccacacaacc aaaacctgga ttcttatact accatgtaaa atactgttac tctacatttt    113460
gaagtgaggt gatttgggga cagtttaaga cttatttaac ttataaacaa attggcctct    113520
ctgggtttgt aaccagagat tgttgatatc tatacagcat gataggatga tctgtaaggt    113580
gccctgccaa gctaccgaaa gcatgacctt cagagtctga ccttgcctta gtgtcaactc    113640
ttatttcttc cctctgccca cctgtccatt atgcctatga taaaagcaga gggagatagc    113700
atttacagtg agtatattgc ccacagaagc tgagcatcct ttgatctcat tgaaatagac    113760
catttagcct ctagttgctc tttgagtatt tgctgaactc tgtcattcaa taattacttt    113820
ggtggaacaa atggaaaaga acaaaagatc tttgatgaag gatacaaaaa agctccatca    113880
tgtcaagctg aatgctaggg tgtctgcatt gtggagagat aatctgaaat tttgtccaat    113940
catatctttg ttttggtttt ggttttggtt ttacttcaag tacatataat ttcaaacttc    114000
agctttccaa agagaactat ttcttttggca gcatttaaga atgaattatt ggggctcaaa    114060
atatagctca ctgtttaaga acatatgtat ttttcttcca gaggactcta gtttataatc    114120
tagcacctat atggagaatc acaaggatct atagctccgg ttccagggaa tgtgatgccc    114180
tcattattca ccacacatgc acatagtcca cacacatact cacaaataaa agaaaagaaa    114240
acaatgaatt ataaaacaca tgtactttac cttttaaaat ttaggaaaaa taataataa    114300 tgataatttg tcaatatttg ttttactttt ttggaacatt tttacttttt cattgaaatg    114360
ctatgtgggt tctgtctaca aatgacatcc tgttaaacat tacaccaaaa ataagctatc    114420
cttattagag aattggcaaa tgatttcaga aaagttttga atacattact gttatttgat    114480
tcatcattac ccattgacta caaaccattg ttactatagc attgcgctta tggagagaac    114540
ttatggactt tagctttggc aacttccagt gtagttaatt acctgtgcaa atatttgta    114600 ctctttagat tggtaaccca tgcatgcaca atgttttttc cagtggtttg gtacacttag    114660
aatccatcaa taatacagaa gaatgcactt ctgataacac ttcgtgcagc accttgaaga    114720
taaggtgtct ttttcaagct ggttttcaga agttaaaaca ctctcttatt gtgctttctc    114780
```

```
ttccctctct gtagggtgag gaggggtacc cacaggaagg aatcctggaa gacatgcctg   114840
tggatcctgg cagtgaggct tatgaaatgc cttcagaggt aaatgcctgt ataaagaaaa   114900
ctaagcaaaa cactttaggt gtttaatttg gaacacatac catcaaaacc ctgccactat   114960
cagatctctc tcacattatg gttggcatag ttcaatcaag aaaatatttt agagcaaatg   115020
attttaatct ttgtgggaga gggtaaggga tatagtaggt caaaattaaa acattctaga   115080
acaagagact ggtagtaaca aaggcatatg gaaatgtctg agtaacaacg ggcagttatg   115140
aatcatggtt agaaaacaga aaaatgacag attaaggctg aagacataac taaggtttta   115200
gacaaactgt agagccccaa gttaccatca tttaagttta tttttacatt tggaaaaaga   115260
agagtttgat gataggttta gtttaacagc acaatcctaa ttagagttaa ttttgaggaa   115320
ggctatcaaa ttcagttaca ttgggtcatt actgtcatga atgttatctg gattttgtcc   115380
aggaggcttg ggcttttcatg tgaaagatcc ttcatggaag caattcatga aggtggagtg   115440
ttctaatggg ggagagaaag gcgaaagatg agctctggag gaggcttcat gcagcttacc   115500
taggtgtgca cagctcacac tgcagagcaa aggagagaat ccagagaccc tgccaattca   115560
cactgcagga ggagagcaca gatcaaatga tatacctaga attgggccta ataatctaac   115620
ggtgatgtcc tctataactt acagttgata cgtatgaaaa agccaataaa tgtcaatgac   115680
agataagttc caaacactgc tctgaggatc aattttatct gattgaaatg atgagccctc   115740
ccccactgtg aagcagacag ttgatatctg tcacttcact gacaaggcat gctgttatta   115800
ttttcttttc ctgatattag gaaggctacc aagactatga gcctgaagcc taagaatgtc   115860
attgcaccca atctcctaag atctgccggc tgctcttcca tggcgtacaa gtgctcagtt   115920
ccaatgtgcc cagtcatgac cttttctcaa agctgtacag tgtgtttcaa agtcttccat   115980
cagcagtgat cggcgtcctg tacctgcccc tcagcatccc ggtgctcccc tctcactaca   116040
gtgaaaacct ggtagcaggg tcttgtgtgc tgtggatatt gttgtggctt cacacttaaa   116100
ttgttagaag aaacttaaaa cacctaagtg actaccactt atttctaaat cttcatcgtt   116160 ttcttttttgt tgctgttctt aagaagttgt gatttgctcc aagagtttta ggtgtcctga   116220
atgactcttt ctgtctaaga atgatgtgtt gtgaaatttg ttaatatata ttttaaaatt   116280
atgtgagcat gagactatgc acctataaat attaatttat gaattttaca gttttgtgat   116340
gtgttttatt aacttgtgtt tgtatataaa tggtggaaaa taaaataaaa tattatccat   116400
tgcaaaatct ttcctggttc cttttacttt agtaacaaaa tcatgcatat cgggaacatg   116460
aacatttaat gacaactgac acagtgaact ggaatgaaaa gttgcaacat gtcttaagga   116520
accgagggga tttagagatg gaacagcagg aaggattctc cagtgagatt gaacacagcc   116580
agctttatct acagttctgc tcagagctgt ggctgcactt gaggaaacac ttcattggaa   116640
ctaaaacgtg tgagggatag tgaacttta catattcata agacacatta gcatatcaga   116700
ggcaggccat tgaagaacct taatttggaa tttatggcat gtatatgtgt gtgtgtgtgt   116760
gtgtgtgtgt gtgtgtattt gtgtgtgtgt gtgtgtgtgt gtgtgtgtgt gtgtgtgtgt   116820 ataaagaac ccaggaaata ccttaaaact cctcagggac cccaggcagt gggctatgta   116880
tatgatacct tagcaggtac gcaaaggtaa aagcaaaatg gaacaaaagg caatgtcaat   116940
ttgtgaataa caggaattg ggaatatctt ttaggaaaag gtttctttag ataggcttaa   117000
ttacccatga atgaagacaa aaacttgact gactgagaaa ttactcagtt catcttccta   117060
attattcaga agaaaccag caaagccaca gtgaaaacca cttgcagaga gtacactttc   117120
tgtaacgaat attgttgctc ctgtacggtc atgagtaatt gatgtgtgtt ggacagtgac   117180
```

```
aggaacagaa gaggagtggg agaccatgaa gatagcacca ctggaacttc cttctgccca    117240
gttgagaaaa tactatggag tgttcagttg catgtgtgct ttgaccctgg aaataggtga    117300
taactcctta tctaatttat gtttccttga agctgatgaa ggattcatta ttaaggtagc    117360
ccagatggtg tttagggtac attatatatt taccgaaagt accctcttct taaaaaggaa    117420
agatacaaac agaacacaat caaattgatg acaatgacaa tgagcagtgt aggactggag    117480
gcagactgtg cttgaccttg agaactgcta ttgatgggta tggtattgta aagctcttct    117540
tctcttaagc agtgccacgc tgtcaatgtg cgaacagtta atgagttttt gctgtttagc    117600
tttcttttat cttaagagtg tttcactcac cacctaaagg aagctcctta gttcacacaa    117660
gccctggtag gagtccagcc cttgagaagt gcagtctgag gatgcctctt gactagagct    117720
ttagctttcc agatttaaat cccaagtcag agctgtttga tttgtaatga gtccacgaag    117780
gactttaaag aaagccgtcc acagcaggct tgggccccac aattggcagc actacacaat    117840
caaatgtaca ctttggaatt tcaacttttg ccttctttc aaaagtctct tctccagatt    117900
gtaagatgca agtatacttc ataatttgta tagctatttg tggcataatg gaatttatac    117960 ataggggtgtc atacaactag tacacttata atctattcag agccaggagg cttatggttt    118020
gagacactgt ctcaggaaac atattcagaa tgtttctgcc tctaattcct ggaggagtaa    118080
tttaaaagca ttgtgatttt atgtgccata tgattgctaa gtgtgtctct tattctaata    118140
actgatctat cgatatctat ctatctatct atcatctatc tatctatcta tctatctatc    118200
tatctatcaa tcatctatct atctatctat ctatctatct atctatctat atcatctatc    118260
atctatcgat ctatctctca tccgtggttt gcacatagct cccagtgcta agaatttctt    118320
aactcttgtt ctgatgaaat gcacacaatt tggcttctga agctggctga tgtataagag    118380
agaaaggact atatttacct caatcagcac aaggatggca gtagatatct ctgtaagaaa    118440
gaagagcaaa atgaagagct aacttagcta accaaagttt ggcatgatag atgaggagtt    118500
aggcattaag ggctaaaaat agtagaaaac tatattttta tgtttgaatt ttgtagaaga    118560
ataaacagtt ttatagaact atggttaact tcaaatgtca tatcacctaa tggaaatata    118620
ctgagagggc tgacaaatcc agtttgtatt tttcttgctt ctgttagtat tctttccttc    118680
ggagatgggt gagtattact tgagggtctt cagagatgga aaggtcagag agaaggagga    118740
aggtaggggg gagagagaga gagagaaaga gagagag                             118777

<210> SEQ ID NO 11
<211> LENGTH: 4047
<212> TYPE: DNA
<213> ORGANISM: Mus musculus
<220> FEATURE:
<221> NAME/KEY: misc_feature
<222> LOCATION: (1)..(4047)
<223> OTHER INFORMATION: LOCUS         Drpla                4047 bp
      mRNA      linear    R
      OD 16-MAY-2002 DEFINITION  Mus musculus dentatorubral
      pallidoluysian atrophy (Dr pla), mRNA. ACCESSION   XM_132846
<300> PUBLICATION INFORMATION:
<308> DATABASE ACCESSION NUMBER: XM_132846
<309> DATABASE ENTRY DATE: 2002-05-16
<313> RELEVANT RESIDUES IN SEQ ID NO: (1)..(4047)

<400> SEQUENCE: 11
cacgacagaa taaagactcg atgtcaatga ggagtggacg gaagaaagag gcccccgggc      60
cccgggaaga gctgagatca aggggccggg cctcccctgg aggggtcagc acatccagca     120
gtgatggcaa agctgagaag tccaggcaga cagccaagaa ggcccggata gaggagccct     180
```

```
ctgccccaaa ggccagcaag cagggccgga gcgaggagat ctcagagagt gagagcgagg    240
agaccagtgc gcccaaaaag accaaaaccg agcaggagct ccctcgcccg cagtctccct    300
cggatctgga cagcttggat gggcgcagca ttaacgatga cggcagcagc gaccctagag    360
atatagacca ggacaaccga agcacatccc ccagcatcta cagcccgggc agcgtggaaa    420
atgactcgga ctcatcctct ggcctgtccc agggccccgc ccgcccctac cacccacctc    480
cactcttccc tccttcccct ccaccaccag acagcactcc ccgacagcca gagtctggct    540
ttgaacctca tccttctgtg ccgcctactg gatatcatgc tccgatggag ccccccacat    600
cgagattatt ccagggccca ccacctggag ctcctcccac acacccacag ctctaccctg    660
ggaatgctag tggaggtgtt ttatctggac ccccatggg tcccaaaggg ggagccgctg    720
cctcctcagt gggtgcccct agcggaggca agcaacaccc cccacccact accccaattc    780
caatatcaag ttctggggcc agtggtgctc ctccagcaaa gccacccagt gctccagtgg    840
gtggtgggag cttaccttct gcaccaccac cagcttcttt cccccatgtg acaccaaacc    900
tgcctcctcc acctgccctg agaccctca acaatgcctc agcctctcct cctggcatgg    960
gggctcagcc aatccctggg catctgccct ctccccatgc catggggcag ggcatgagtg    1020
gacttcctcc tggcccagag aagggtccaa ccctggcccc ttctccccac cctttgcccc    1080
cagcttcttc ctctgcccct gggcctccaa tgcgatatcc atattcatcc tccagtagct    1140
ctgccgcagc ctcttctagt tcctcctcct cctctgcctc ccagtaccct gcttcccagg    1200
ccctgcccag ttatcctcat tccttccccc caccaactag tatgtctgtc tctaatcagc    1260
cacccaagta cacccagcct tctctcccat cccaagctgt gtggagccag ggtccacctc    1320
ctcctcctcc ctatgccgc ctcttggcca acaacaacac ccatccaggc cctttccctc    1380
ctactggggg tcaatctaca gcccacccag cagcccctac acatcaccat caccagcagc    1440
agccacagca acaacatcat catggaaact ctgggccccc tccacccgga gcgtatcctc    1500
accctctaga gagcagtaac tcccatcatg cacacccctta caacatgtca ccctccctgg    1560
ggtctttaag gccctacccc ccagggccag cacacctgcc tccacctcat ggccaggtgt    1620
cctataacca agcaggtccc aatggtcccc cagtttcttc ttccaactct tccgggtctt    1680
cctctcaagc ctcctattca tgttcacacc cctcttcatc ccagggcccc caaggagcat    1740
cctaccccctt cccaccagtc cctccagtca ccacctcctc agctacccctt tccactgtca    1800
tcgccaccgt ggcttcctcg ccagcaggct acaaaacagc ttcgccacct gggccccctc    1860
agtacagcaa gagagcccca tccccagggt cctacaagac agccacccg cctggataca    1920
aaccggggtc accaccctcc ttcagaacag ggaccccacc cggctatcga ggcacctctc    1980
cgccagcagg cccagggacc ttcaaaccag gttcaccgac cgtggggccg gggccctgc    2040
cacccgcggg gccttcaagt ttgtcatctc tgcctccgcc acctgcggcc ccgactacag    2100
ggccgcccct gaccgccacg cagatcaaac aggagccggc ggaagagtat gaacctcccg    2160
agagtccggt gcctccggcc cgcagcccct cgccccctcc caaggtggtg acgtgcccca    2220
gccatgccag ccagtcagcc aggttcaata agcacttgga ccgcggcttc aactcgtgcg    2280
cgcgcagcga cctgtacttc gtgccgctgg agggctccaa gctggccaag aagcgcgcgg    2340
acctggtgga gaaagtgcgg cgcgaggcg agcagcgcgc gcgcgaggag aaagagcgcg    2400
agcgcgagcg ggaacgcgaa aaggagcgcg agcgcgagaa agagcgcgag ctggagcgca    2460
gtgtgaaact ggcccaggag ggccgtgctc cagtggagtg cccatctctg ggtccagtgc    2520
cccatcggcc tccctttgag cctggcagcg ctgtggctac agtgccccct tacctgggtc    2580
```

```
ctgatactcc ggccttgcgc actctcagtg aatacgcccg acctcatgtc atgtctcctg    2640
gcaatcgcaa ccacccattc tatgtgccct tgggggcagt ggacccgggg cttctgggtt    2700
acaatgtccc agccctgtac agcagcgacc cagctgcccg agaacgggag cgggaagccc    2760
gtgaacgtga cctccgtgac cggctcaagc ctggctttga ggtgaaacct agtgagctgg    2820 aaccccctaca tggggttccc gggccaggcc tggatccctt ccccgacac ggggggcctgg    2880 ctctacagcc cgggccacct ggctgcatc ctttccctt tcatccgagc ctggggcccc    2940
tggaacgaga acggctagcg ctggcagctg ggccagcctt gcgtcctgac atgtcttatg    3000
ctgagcggtt ggcagctgaa aggcagcatg cagaaagggt ggcagccctg gcaatgatc    3060 cactagcccg gctgcagatg ctcaacgtga ctccccatca ccaccagcac tcccacatcc    3120
actctcacct tcacctgcac cagcaggatg ctatccacgc agcctctgcc tcggtgcacc    3180
ctctcattga cccccctggcc tcagggtctc accttacccg gatccctac ccagctggga    3240 cctcccccaa ccccttctt cctcaccctc tgcacgagaa cgaagttctt cgtcaccagc    3300 ttttgctgc cccttaccgg gacctgccgg cctcccttc tgctccaatg tcagcggctc    3360
atcagctgca ggccatgcac gcgcagtcag ctgagctgca gcgcttggcg ctggaacagc    3420
agcagtggct acatgctcat cacccattgc acagcgtgcc actacctgcc caggaagact    3480
actacagtca cctgaagaag gagagtgaca agcgctgta gagctgcgat ccagacagca    3540
cccactgctc cttcatccag accttggagg accaccccaa ccttttgacc ccaccccacc    3600
cccagccgag gagagggtgc tgcccgcttc cagagctcct gcagctgggt agagggaggg    3660
agggaagaag ggacagacaa ggtcagggcc cggggttgtg tgcagaggtg ggaagtggca    3720 agggtgggg cagaaagtgc acagtatctt ggaccaggtc cctcctccta tccctgctt    3780 ttcttctcct ctatgccgaa tccttggtgg ccactgcccc tccctaacc cattggtgtg    3840 attttttca tctgttagat gtggctgttt tgcgtagcat tgtgtgctgc cccgccccat    3900
ccctgtgtgt gcaccccctc cctcggcgat atgtgccctt accgtccca cattaataat    3960 ttatatatat aaatatctat atgatgctct ttaaaaaaca tcctgaccaa aaccaaccaa    4020
acaaaaacat cctcacagtt ccccagg                                        4047
```

<210> SEQ ID NO 12
<211> LENGTH: 10033
<212> TYPE: DNA
<213> ORGANISM: Mus musculus
<220> FEATURE:
<221> NAME/KEY: misc_feature
<222> LOCATION: (1)..(10033)
<223> OTHER INFORMATION: LOCUS      MMU24233             10033 bp
      mRNA       linear   R
      OD 18-JUL-1995 DEFINITION  Mus musculus huntingtin (Hd) mRNA,
      complete cds. ACCESSION    U24233
<300> PUBLICATION INFORMATION:
<308> DATABASE ACCESSION NUMBER: U24233
<309> DATABASE ENTRY DATE: 1995-07-18
<313> RELEVANT RESIDUES IN SEQ ID NO: (1)..(10033)

<400> SEQUENCE: 12

```
ggctgagcgc cttggttccg cttctgcctg ccgcgcagag ccccattcat tgccttgctg      60
ctaagtggcg ccgcgtagtg ccagtaggct ccaagtcttc agggtctgtc ccatcgggca    120
ggaagccgtc atggcaaccc tggaaaagct gatgaaggct ttcgagtcgc tcaagtcgtt    180
tcagcagcaa cagcagcagc agccaccgcc gcaggcgccg ccgccaccgc gccgcctcc    240 gcctcaaccc cctcagccgc cgcctcaggg gcagccgccg ccgccaccac cgcgctgcc    300 aggtccggca gaggaaccgc tgcaccgacc aaagaaggaa ctctcagcca ccaagaaaga    360
```

-continued

```
ccgtgtgaat cattgtctaa caatatgtga aaacattgtg gcacagtctc tcagaaattc      420
tccagaattt cagaaactct tgggcatcgc tatggaactg tttctgctgt gcagtaacga      480
tgcggagtca gatgtcagaa tggtggctga tgagtgcctc aacaaagtca tcaaagcttt      540
gatggattct aatcttccaa ggctacagtt agaactctat aaggaaatta aaagaatgg       600 tgctcctcga agtttgcgtg ctgccctgtg gaggtttgct gagctggctc acctggttcg      660
acctcagaag tgcaggcctt acctggtgaa tcttcttcca tgcctgaccc gaacaagcaa      720
aagaccggag gaatccgttc aggagacctt ggctgcagct gttcctaaaa ttatggcttc      780
ttttggcaat ttcgcaaatg acaatgaaat taaggttctg ttgaaagctt tcatagcaaa      840
tctgaagtca agctctccca ctgtgcggcg gacagcagcc ggctcagccg tgagcatctg      900
ccaacattct aggaggacac agtacttcta caactggctc cttaatgtcc tcctaggtct      960
gctggttccc atggaagaag agcactccac tctcctgatc ctcggtgtgt tgctcacatt     1020
gaggtgtcta gtgcccttgc tccagcagca ggtcaaggac acaagtctaa aaggcagctt     1080
tggggtgaca cggaaagaaa tggaagtctc tccttctaca gagcagcttg tccaggttta     1140
tgaactgact ttgcatcata ctcagcacca agaccacaat gtggtgacag ggcactgga      1200 gctcctgcag cagctcttcc gtaccctcc acctgaactc ctgcaagcac tgaccacacc      1260
aggagggctt gggcagctca ctctggttca agaagaggcc cggggccgag gccgcagcgg     1320
gagcatcgtg gagcttttag ctggagggg ttcctcgtgc agccctgtcc tctcaagaaa      1380
gcagaaaggc aaagtgctct taggagagga agaagccttg gaagatgact cggagtccag     1440
gtcagatgtc agcagctcag cctttgcagc ctctgtgaag agtgagattg gtggagagct     1500
cgctgcttct tcaggtgttt ccactcctgg ttctgttggt cacgcacatca tcactgagca     1560 gcctagatcc cagcacacac ttcaagcaga ctctgtggat ttgtccggct gtgacctgac     1620
cagtgctgct actgatgggg atgaggagga catcttgagc cacagctcca gccagttcag     1680
tgctgtccca tccgaccctg ccatggacct gaatgatggg acccaggcct cctcacccat     1740
cagtgacagt tctcagacca ccactgaagg acctgattca gctgtgactc cttcggacag     1800
ttctgaaatt gtgttagatg gtgccgatag ccagtattta ggcatgcaga taggacagcc     1860
acaggaggac gatgaggagg gagctgcagg tgttctttct ggtgaagtct cagatgtttt     1920
cagaaactct tctctggccc ttcaacaggc acacttgttg gaaagaatgg gccatagcag     1980
gcagccttcc gacagcagta tagataagta tgtaacaaga gatgaggttg ctgaagccag     2040
tgatccagaa agcaagcctt gccgaatcaa aggtgacata ggacagccta atgatgatga     2100
ttctgctcct ctggtacatt gtgtccgtct tttatctgct tccttttgt taactggtga      2160 aaagaaagca ctggttccag acagagacgt gagagtcagt gtgaaggccc tggccctcag     2220
ctgcattggt gcggctgtgg cccttcatcc agagtcgttc ttcagcagac tgtacaaagt     2280
acctcttaat accacggaaa gtactgagga acagtatgtt tctgacatct tgaactacat     2340
cgatcatgga gacccacagg tccgaggagc tactgccatt ctctgtggga cccttgtcta     2400
ctccatcctc agtaggtccc gtctccgtgt tggtgactgg ctgggcaaca tcagaacccc     2460
gacaggaaat acattttctc tggtggactg cattccttta ctgcagaaaa cgttgaagga     2520
tgaatcttct gttacttgca gttggcttg tacagctgtg aggcactgtg tcctgagtct     2580
ttgcagcagc agctacagtg acttgggatt acaactgctt attgatatgc tgcctctgaa     2640
gaacagctcc tactggctgg tgaggaccga actgctggac actctggcag agattgactt     2700
caggctcgtg agttttttgg aggcaaaagc agaaagttta caccgagggg ctcatcatta     2760
```

```
tacagggttt ctaaaactac aagaacgagt actcaataat gtggtcattt atttgcttgg    2820
agatgaagac cccagggttc gacatgttgc tgcaacatca ttaacaaggc ttgtcccaaa    2880
gctgttttac aagtgtgacc aaggacaagc tgatccagtt gtggctgtag cgagggatca    2940
gagcagtgtc tacctgaagc tcctcatgca tgagacccag ccaccatcac acttttctgt    3000
cagcaccatc accagaatct atagaggcta tagcttactg ccaagtataa cagatgtcac    3060
catggaaaac aatctctcaa gagttgttgc cgcagtttct catgaactca ttacgtcaac    3120
aacacgggca ctcacatttg gatgctgtga agccttgtgt cttctctcag cagccttttcc   3180 agtttgcact tggagtttag gatggcactg tggagtgccc ccactgagtg cctctgatga    3240
gtccaggaag agctgcactg ttgggatggc ctccatgatt ctcaccttgc tttcatcagc    3300
ttggttccca ctggatctct cagcccatca ggatgccttg attttggctg gaaacttgct    3360
agcagcgagt gcccccaagt ctctgagaag ttcatggacc tctgaagaag aagccaactc    3420
agcagccacc agacaggagg aaatctggcc tgctctgggg gatcggactc tagtgcccttt   3480 ggtggagcag cttttctccc acctgctgaa ggtgatcaat atctgtgctc atgtcttgga    3540
cgatgtgact cctggaccag caatcaaggc agccttgcct tctctaacaa accccccttc    3600
tctaagtcct attcgacgga aagggaagga gaaagaacct ggagaacaag cttctactcc    3660
aatgagtccc aagaaagttg gtgaggccag tgcagcctct cgacaatcag acacctcagg    3720
acctgtcaca gcaagtaaat catcctcact ggggagtttc taccatctcc cctcctacct    3780
caaactgcat gatgtcctga agccactcca cgccaactat aaggtcacct agatcttca    3840 gaacagcact gaaaagtttg gggggttcct gcgctctgcc ttggacgtcc tttctcagat    3900
tctagagctg gcgacactgc aggacattgg aaagtgtgtt gaagaggtcc ttggatacct    3960
gaaatcctgc tttagtcgag aaccaatgat ggcaactgtc tgtgtgcagc agctattgaa    4020
gactctcttt gggacaaact tagcctcaca gtttgatggc ttatcttcca accccagcaa    4080
gtctcagtgc cgagctcagc gccttggctc ttcaagtgtg aggcccggct tatatcacta    4140
ctgcttcatg gcaccataca cgcacttcac acaggccttg gctgacgcaa gcctgaggaa    4200
catggtgcag gcggagcagg agcgtgatgc ctcggggtgg tttgatgtac tccagaaagt    4260
gtctgcccaa ttgaagacga acctaacaag cgtcacaaag aaccgtgcag ataagaatgc    4320
tattcataat cacattaggt tatttgagcc tcttgttata aaagcattga agcagtacac    4380
cacgacaaca tctgtacaat tgcagaagca ggttttggat ttgctggcac agctggttca    4440
gctacgggtc aattactgtc tactggattc agaccaggtg ttcatcgggt ttgtgctgaa    4500
gcagtttgag tacattgaag tgggccagtt cagggaatca gaggcaatta ttccaaatat    4560 attttttcttc ctggtattac tgtcttatga gcgctaccat tcaaaacaga tcattggaat    4620
tcctaaaatc atccagctgt gtgatggcat catggccagt ggaaggaagg ccgttacaca    4680
tgctatacct gctctgcagc ccattgtcca tgacctcttt gtgttacgag gaacaaataa    4740
agctgatgca gggaaagagc ttgagacaca gaaggaggtg gtggtctcca tgctgttacg    4800
actcatccag taccatcagg tgctggagat gttcatcctt gtcctacagc agtgccacaa    4860
ggagaatgag gacaagtgga aacggctctc tcggcaggtc gcagacatca tcctgcccat    4920
gttggccaag cagcagatgc atattgactc tcatgaagcc cttggagtgt aaataccttt    4980
gtttgagatt ttggctcctt cctccctacg tcctgtggac atgcttttgc ggagtatgtt    5040
catcactcca agcacaatgg catctgtaag cactgtgcag ctgtggatat ctggaatcct    5100
cgccattctg agggttctca tttcccagtc aaccgaggac attgttcttt gtcgtattca    5160
```

```
ggagctctcc ttctctccac acttgctctc ctgtccagtg attaacaggt taagggdtgg   5220
aggcggtaat gtaacactag gagaatgcag cgaagggaaa caaaagagtt tgccagaaga   5280
tacattctca aggtttcttt tacagctggt tggtattctt ctagaagaca tcgttacaaa   5340
acagctcaaa gtggacatga gtgaacagca gcatacgttc tactgccaag agctaggcac   5400
actgctcatg tgtctgatcc acatattcaa atctggaatg ttccggagaa tcacagcagc   5460
tgccactaga ctcttcacca gtgatggctg tgaaggcagc ttctatactc tagagagcct   5520
gaatgcacgg gtccgatcca tggtgccac gcacccagcc ctggtactgc tctggtgtca   5580
gatcctactt ctcatcaacc acactgacca ccggtggtgg gcagaggtgc agcagacacc   5640
caagagacac agtctgtcct gcacgaagtc acttaacccc cagaagtctg gcgaagagga   5700
ggattctggc tcggcagctc agctgggaat gtgcaataga gaaatagtgc gaagaggggc   5760
ccttattctc ttctgtgatt atgtctgtca gaatctccat gactcagaac acttaacatg   5820
gctcattgtg aatcacattc aagatctgat cagcttgtct catgagcctc cagtacaaga   5880
ctttattagt gccattcatc gtaattctgc agctagtggt ctttttatcc aggcaattca   5940
gtctcgctgt gaaaatcttt caacgccaac cactctgaag aaaacacttc agtgcttgga   6000
aggcatccat ctcagccagt ctggtgctgt gctcacacta tatgtggaca ggctcctggg   6060
cacccccttc cgtgcgctgg ctcgcatggt cgacaccctg gcctgtcgcc gggtagaaat   6120
gcttttggct gcaaatttac agagcagcat ggcccagttg ccagaggagg aactaaacag   6180
aatccaagaa cacctccaga acagtgggct tgcacaaaga caccaaaggc tctattcact   6240
gctggacaga ttccgactct ctactgtgca ggactcactt agccccttgc ccccagtcac   6300
ttccacccca ctgatgggg atgggcacac atctctggaa acagtgagtc cagacaaaga   6360
ctggtacctc cagcttgtca gatcccagtg ttggaccaga tcagattctg cactgctgga   6420
aggtgcagag ctggtcaacc gtatccctgc tgaagatatg aatgacttca tgatgagctc   6480
ggagttcaac ctaagccttt tggctccctg tttaagcctt ggcatgagcg agattgctaa   6540
tggccaaaag agtcccctct ttgaagcagc ccgtggggtg attctgaacc gggtgaccag   6600
tgttgttcag cagcttcctg ctgtccatca agtcttccag cccttcctgc ctatagagcc   6660
cacggcctac tggaacaagt tgaatgatct gcttggtgat accacatcat accagtctct   6720
gaccatactt gcccgtgccc tggcacagta cctggtggtg ctctccaaag tgcctgctca   6780
tttgcacctt cctcctgaga aggaggggga cacggtgaag tttgtggtaa tgacagttga   6840
ggccctgtca tggcatttga tccatgagca gatcccactg agtctggacc tccaagccgg   6900
gctagactgc tgctgcctgg cactacaggt gcctggcctc tgggggggtgc tgtcctcccc   6960 agagtacgtg actcatgcct gctccctcat ccattgtgtg cgattcatcc tggaagccat   7020
tgcagtacaa cctggagacc agcttctcgg tcctgaaagc aggtcacata ctccaagagc   7080
tgtcagaaag gaggaagtag actcagatat acaaaacctc agtcatgtca cttcggcctg   7140
cgagatggtg gcagacatgg tggaatccct gcagtcagtg ctggccttgg gccacaagag   7200
gaacagcacc ctgccttcat ttctcacagc tgtgctgaag acattgttta tcagtctggc   7260
ccgactcccc ctagttaaca gctatactcg tgtgcctcct ctggtatgga aactcgggtg   7320
gtcacccaag cctggagggg attttggcac agtgtttcct gagatccctg tagagttcct   7380
ccaggagaag gagatcctca aggagttcat ctaccgcatc aacaccctag gtgtggaccaa   7440 tcgtacccag ttcgaagaaa cttgggccac cctccttggt gtcctggtga ctcagccccct   7500 ggtgatggaa caggaagaga gcccaccaga ggaagacaca gaaagaaccc agatccatgt   7560
```

```
cctggctgtg caggccatca cctctctagt gctcagtgca atgaccgtgc ctgtggctgg   7620
caatccagct gtaagctgct ggagcaaca gccccggaac aagccactga aggctctcga   7680
taccagattt ggaagaaagc tgagcatgat cagagggatt gtagaacaag aaatccaaga   7740
gatggtttcc cagagagaga atactgccac tcaccattct caccaggcgt gggatcctgt   7800
cccttctctg ttaccagcta ctacaggtgc tcttatcagc catgacaagc tgctgctgca   7860
gatcaaccca gagcgggagc caggcaacat gagctacaag ctgggccagg tgtccataca   7920
ctccgtgtgg ctgggaaata acatcacacc cctgagagag gaggaatggg atgaggaaga   7980
agaggaagaa agtgatgtcc ctgcaccaac gtcaccacct gtgtctccag tcaattccag   8040
aaaacaccgt gccggggttg atattcactc ctgttcgcag tttctgcttg aattgtacag   8100
ccgatggatc ctgccatcca gtgcagccag aaggaccccc gtcatcctga tcagtgaagt   8160
ggttcgatct cttcttgtag tgtcagactt attcaccgaa cgtacccagt ttgaaatgat   8220
gtatctgacg ctgacagaac tacgagagt gcacccttca gaagatgaga tcctcattca   8280
gtacctggtg cctgccacct gtaaggcagc tgctgtcctt ggaatggaca aaactgtggc   8340
agagccagtc agccgcctac tggagagcac actgaggagc agccacctgc ccagccagat   8400
cggagccctg cacggcatcc tctatgtgtt ggagtgtgac ctcttggatg acactgcaaa   8460
gcagctcatt ccagttgtta gtgactatct gctgtccaac ctcaaaggaa tagcccactg   8520
cgtgaacatt cacagccagc agcatgtgct ggtaatgtgt gccactgctt tctacctgat   8580
ggaaaactac cctctggatg tgggaccaga atttttcagca tctgtgatac agatgtgtgg   8640
agtaatgctg tctggaagtg aggagtccac cccctccatc atttaccact gtgccctccg   8700
gggtctggag cggctcctgc tgtctgagca gctatctcgg ctagacacag agtccttggt   8760
caagctaagt gtggacagag tgaatgtaca aagcccacac agggccatgg cagccctagg   8820
cctgatgctc acctgcatgt acacaggaaa ggaaaaagcc agtccaggca gagcttctga   8880
ccccagccct gctacacctg acagcgagtc tgtgattgta gctatggagc gagtgtctgt   8940
tctctttgat aggatccgca agggatttcc ctgtgaagcc agggttgtgg caaggatcct   9000
gcctcagttc ctagatgact tcttttccacc tcaagatgtc atgaacaaag tcattggaga   9060
gttcctgtcc aatcagcagc catacccaca gttcatggcc actgtagttt acaaggtttt   9120
tcagactctg cacagtgctg ggcagtcatc catggtccgg gactgggtca tgctgtccct   9180
gtccaacttc acacaaagaa cttcagttgc catggccatg tggagcctct cctgcttcct   9240
tgttagcgca tctaccagcc catgggtttc tgcgatcctt ccacatgtca tcagcaggat   9300
gggcaaactg gaacaggtgg atgtgaacct tttctgcctg gttgccacag acttctacag   9360
acaccagata gaggaggaat cgaccgcag ggctttccag tctgtgtttg aggtggtggc   9420
ggcaccagga agtccatacc acaggctgct tgcttgtttg caaaatgttc acaaggtcac   9480
cacctgctga gtagtgcctg tgggacaaaa ggctgaaaga aggcagctgc tggggcctga   9540
gcctccagga gcctgctcca agcttctgct ggggctgcct tggccgtgca ggcttccact   9600
tgtgtcaagt ggacagccag gcaatggcag gagtgctttg caatgagggc tatgcaggga   9660
acatgcacta tgttggggtt gagcctgagt cctgggtcct ggcctcgctg cagctggtga   9720
cagtgctagg ttgaccaggt gtttgtcttt ttcctagtgt tccctggcc atagtcgcca   9780 ggttgcagct gccctggtat gtggatcaga agtcctagct cttgccagat ggttctgagc   9840
ccgcctgctc cactggctg gagagctccc tcccacattt acccagtagg catacctgcc   9900
acaccagtgt ctggacacaa aatgaatggt gtgtggggct gggaactggg gctgccaggt   9960
```

```
gtccagcacc attttccttt ctgtgttttc ttctcaggag ttaaaattta attatatcag    10020
taaagagatt aat                                                      10033

<210> SEQ ID NO 13
<211> LENGTH: 3616
<212> TYPE: DNA
<213> ORGANISM: Mus musculus
<220> FEATURE:
<221> NAME/KEY: misc_feature
<222> LOCATION: (1)..(3616)
<223> OTHER INFORMATION: LOCUS       Sca1                 3616 bp
      mRNA       linear    R
      OD 07-JAN-2002 DEFINITION  Mus musculus spinocerebellar ataxia 1
      homolog (human) (Sca1), mRNA. ACCESSION   NM_009124
<300> PUBLICATION INFORMATION:
<308> DATABASE ACCESSION NUMBER: NM_009124
<309> DATABASE ENTRY DATE: 2002-01-07
<313> RELEVANT RESIDUES IN SEQ ID NO: (1)..(3616)

<400> SEQUENCE: 13
ctcttcctcc actccctcca caggaagggc gtcacctgtc agattgcggc atcctggaac      60
agaatgaaag gatctgtgtt gaaacagcta cagtagggtt acagtagacc ctgagaaaac     120
agagtggact tcagcctgca cggatgagct tgaagcagga atggtttggg ttcaggcctc     180
ttacactgaa tttctctact gccacccttt ctactcaagc aacatcttac ggaaaagatc     240
tcccgggaag gaagtggctg cttgtggctt tgcactgtga tgaaggcaaa tggtacagtt     300
ttccaaagaa aatagaccaa aactttcttc ttgagaagaa acaaacctgc tgttggcaga     360
gggtatttct aacctctctg cgaaagaaag aaagacacca ccagaacctg gcatcccag      420 ctgctgaggg aagtttccat ggtgaagtct caggaggct tcctgggagc agagcatagt      480
gaatgctaat ccggagctgc cactgccagc ctaaagaacc cacgggagat gattccccat     540
gaagggcctg gatcccctac agaaatccaa tgtgactctc tgtttatcag actaaaacca     600
gagccggcca gccagtgaaa cagccaccgt ggagggggga cggcgaaaaa tgaaatccaa     660
ccaagagcgg acgaacgaat gcctgcctcc caagaaacgt gagatccccg ccaccagccg     720
gccctcggag gagaaggcca ctgctctgcc cagcgacaac cactgcgtgg agggtgtggc     780
ctggctcccc agcacccctg gcatccgcgg ccatggggt gggcggcacg ggtcagcagg      840
gacttccggg gagcatggtt tacaaggaat gggtttactt aaagcactgt ccgcagggct     900
ggattactcc ccacccagtg cccccaggtc agtccccaca gccaacacgc tgcccaccgt     960
gtaccctcct cctcagtcag ggaccccggt gtctcctgtg cagtacgccc ccttcgca     1020 taccttccag ttcattgggt cctcccaata cagtgggcct tacgcgggct ttatcccttc    1080
ccagctgatc tccccatcag gcaacccggt caccagtgca gtagcctcag ctgcaggggc    1140
caccactcca tcacagcgct cccagctgga ggcttattcc accctgctgg ccaacatggg    1200
cagtctgagc caggcaccag gacataaggt tgagcccct ccgcagcagc acctcagcag     1260
ggctgcagga ttagtcaacc cggggtcccc tcctccaccc acccagcaga accagtacat    1320
ccatatttcc agctctccac agagctccgg gcgggcgaca tctcccccac ccatcccggt    1380
ccacctccat ccccatcaga cgatgatccc gcacacactc accctgggc cttcatccca     1440 ggtggttgtg caatatagtg atgccggagg ccactttgtt cctcgagagt ccaccaaaaa    1500
agccgagagc agcaggttgc agcaggctat gcaagccaag gaagtcctga atggggagat    1560
ggagaaaagc cggaggtatg ggcatcatc ttctgtggag ctgagcctag caaggcaag     1620 cagtaagtca gtgcctcatc cctatgagtc caggcatgtg gtggtccacc caagcccagc    1680
```

```
agactacagc agtcgtgata cctccggggt ccgtggatct gtgatggttc tgcctaatag    1740
cagcacaccc tcagccgacc tggaggccca gcagaccacg catcgagagg cctccccatc    1800
caccctcaat gacaagagcg gcctggcacc taggaagccg ggccacaggt cttatgcgct    1860 gtcccccac acggtcattc agaccacaca cagtgcatca gagcctctcc cggtgggcct     1920
accagccacg gccttctacg ctggcactca acctcctgtc atcggctacc tgagcggcca    1980
gcagcaagca atcacctatg ctggtggtct gccgcagcac ctggtgatcc caggtaacca    2040
gcccctgctc atcccggtgg gcagccctga catggacatg cctggggcag cctcggccat    2100
cgtgacgtca tcaccccagt ttgctgcagt acctcacacg tttgtcacca ccgccctgcc    2160
caagagcgag aacttcaacc agaggctctg gtcacccag gcgtcctacc agccatggt     2220 gcaggcccag atccacctgc cggtggtgca gtccgtggcg tccccacca cggcgtctcc     2280 cacgctgccg ccatatttca tgaaaggctc catcatccag ctggccaacg ggagctgaa    2340 gaaggtggag gacctgaaga cggaggattt catccagagt gcagagatta gcaatgacct    2400
caagatccac tccagtactg tggagagaat cgaggagagc cacagccccg ggtggccgt    2460 gatacagttt gctgttggtg aacaccgagc ccaggtcagt gtcgaagtct tggtagagta    2520
tccttttttt gtatttggac agggctggtc atcctgctgt cctgagcgga ccagccagct    2580
ctttgatctg ccgtgttcca aactctctgt tggggacgtc tgcatctcgc tcaccctcaa    2640
gaacctgaag aatggctctg ttaaaaaggg ccagcctgtg gaccctgcca gcgtcctgct    2700
gaagcaggta aagaccgaca gcctggctgg cagcagacac agatacgcgg agcaggaaaa    2760
cggaatcaac cagggaagcg cccaggtgct ctctgagaat ggcgaactga gtttccaga    2820 aaaaatagga ttgcctgcag caccttcct cagcaaaata gaaccgagca aacccacagc    2880
cacgaggaag aggaggaggt ggtcggcgcc ggagacccgt aaactggaga agtcggagga    2940
cgagccacct ttgactcttc ccaagccttc gctcattcct caggaggtta agatctgcat    3000
cgaaggccga tctaacgtgg gcaagtagag accttgcgag cagcggaggc ccggggctct    3060
tttactgtct gtatccagat tactgtactg taggctaagt aacacagtat ttacatgtta    3120
catcctcttt aggtttgtat tctaaccttg tcattagagt caaacaggtg tgtcgcagga    3180
gactggtgcg tttgcattgt ctgcaagggt ctgttgagga ctggtgggt tggaggatgg    3240 tcagaaccat gtccatggag ctcccgggca tccttagtgg ccctgaatgt ggcttcatca    3300
gcccctgcct tctccggcag tgtgcagagt cgaggggcat cagttccac tggtttcaag    3360 aacaaacaca gtgggaagta tcctgcaagg gagtgtctgg gtgcgtgtcc cttgtgaagg    3420
agtgcgagtg agggtgtctc tttctctgcc tctgtctccc tcacttgctc cctctcagtg    3480
tggggttggg ggacctgggt ttcccacctg caaagtcatc agggaaccca gcttccaggc    3540
attgtaggga gacatcagac aggcggatgg gaaactagtt tcaaagaacg tggttctctc    3600
caacatattt tacaat                                                    3616
```

<210> SEQ ID NO 14
<211> LENGTH: 1543
<212> TYPE: RNA
<213> ORGANISM: Homo sapiens
<220> FEATURE:
<221> NAME/KEY: misc_feature
<222> LOCATION: (1)..(1543)
<223> OTHER INFORMATION: LOCUS       SNCA                  1543 bp
      mRNA     linear      P
      RI 05-NOV-2002 DEFINITION Homo sapiens synuclein, alpha (non A4
      component of am yloid precursor) (SNCA), transcript variant
      NACP140, mRNA. ACCESSION    NM_000345: VERSION       NM_000345.2
<300> PUBLICATION INFORMATION:

<308> DATABASE ACCESSION NUMBER: NM_000345
<309> DATABASE ENTRY DATE: 2002-11-05
<313> RELEVANT RESIDUES IN SEQ ID NO: (1)..(1543)

<400> SEQUENCE: 14

```
ggaguggcca uucgacgaca guguggugua aaggaauuca uuagccaugg auguauucau      60
gaaaggacuu ucaaaggcca aggagggagu guggcugcu gcugagaaaa ccaaacaggg     120
uguggcagaa gcagcaggaa agacaaaaga gggguguucuc uauguaggcu ccaaaaccaa    180
ggagggagug gugcaugguga uggcaacagu ggcugagaag accaaagagc aagugacaaa    240
uguuggagga gcaguggguga cgggugugac agcaguagcc cagaagacag uggagggagc    300
agggagcauu gcagcagcca cuggcuuugu caaaaaggac caguuggggca agaaugaaga    360
aggagcccca caggaaggaa uucuggaaga uaugccugug gauccugaca augaggcuua    420
ugaaaugccu ucugaggaag gguaucaaga cuacgaaccu gaagccuaag aaauaucuuu    480
gcucccaguu ucuugagauc ugcugacaga uguuccaucc uguacaagug cucaguucca    540
augugcccag ucaugacauu ucucaaaguu uuuacagugu aucucgaagu cuuccaucag    600
cagugauuga aguaucugua ccugccccca cucagcauuu cggugcuucc cuuucacuga    660
agugaauaca ugguagcagg gucuuugugu gcuguggauu uguggcuuc aaucuacgau    720
guuaaaacaa auuaaaaaca ccuaagugac uaccacuuau uucuaaaucc ucacuauuuu    780
uuuguugcug uuguucagaa guuguuagug auuugcuauc auauauuaua agauuuuuag    840
gugucuuuua augauacugu cuaagaauaa ugacguauug ugaaauuugu aauauauau     900
aauacuuaaa aauaugugag caugaaacua ugcaccauua aauacaaaau augaaauuuu    960
accauuuugc gaugugucuuu auucacucgu guuuguauau aaauggugag aauuaaaaua   1020
aaacguuauc ucauugcaaa aauauuuuau uuuuauccca ucucacuuua auaauaaaaa    1080
ucaugcuuau aagcaacaug aauuaagaac ugacacaaag gacaaaaaua uaaguauauu    1140
aauagccauu ugaagaagga ggaauuuuag aagagguaga gaaaauggaa cauuaacccu    1200
acacucggaa uucccugaag caacacugcc agaagugugu uugguaugc acugguuccu     1260
uaaguggcug ugauuaauua uugaaagugg ggguguugaag accccaacua cuauuguaga    1320
gugucuauu ucucccuuca auccugucaa uguuugcuuu auguauuuug gggaacuguu     1380
guuugaugug uauguguuua uaauuguauu acauuuuuaa uugagccuuu auuaacaua      1440
uauuguuauu uuugucucga aauaauuuuu uaguuaaaau cuauuuuguc ugauauuggu    1500
gugaaugcug uaccuuucug acaauaaaua auauucgacc aug                      1543
```

<210> SEQ ID NO 15
<211> LENGTH: 10660
<212> TYPE: DNA
<213> ORGANISM: Homo sapiens
<220> FEATURE:
<221> NAME/KEY: misc_feature
<222> LOCATION: (1)..(10660)
<223> OTHER INFORMATION: LOCUS    SCA1    10660 bp
      mRNA    linear    P
      RI 31-OCT-2000 DEFINITION  Homo sapiens spinocerebellar ataxia 1
      (olivopontocere bellar ataxia 1, autosomal dominant, ataxin 1)
      (SCA1), mRNA. ACCESSION    NM_000332
<300> PUBLICATION INFORMATION:
<308> DATABASE ACCESSION NUMBER: NM_000332
<309> DATABASE ENTRY DATE: 2000-10-31
<313> RELEVANT RESIDUES IN SEQ ID NO: (1)..(10660)

<400> SEQUENCE: 15

```
ctactacagt ggcggacgta caggacctgt ttcactgcag ggggatccaa acaagccccc     60
```

```
gtggagcaac agccagagca acagcagctg caagacattg tttctctccc tctgcccccc      120
cttccccacg caaccccaga tccatttaca ctttacagtt ttacctcaca aaaactacta      180
caagcaccaa gctccctgat ggaaaggagc atcgtgcatc aagtcaccag ggtggtccat      240
tcaagctgca gatttgtttg tcatccttgt acagcaatct cctcctccac tgccactaca      300
gggaagtgca tcacatgtca gcatactgga gcatagtgaa agagtctatt ttgaagcttc      360
aaacttagtg ctgctgcaga ccaggaacaa gagagaaaga gtggatttca gcctgcacgg      420
atggtcttga aacacaaatg gttttttggtc taggcgtttt acactgagat tctccactgc     480
caccctttct actcaagcaa aatcttcgtg aaaagatctg ctgcaaggaa ctgatagctt      540
atggttctcc attgtgatga aagcacatgg tacagttttc caaagaaatt agaccatttt      600
cttcgtgaga aagaaatcga cgtgctgttt tcatagggta tttctcactt ctctgtgaaa      660
ggaagaaaga acacgcctga gcccaagagc cctcaggagc cctccagagc ctgtgggaag      720
tctccatggt gaagtatagg ctgaggctac ctgtgaacag tacgcagtga atgttcatcc      780
agagctgctg ttggcggatt gtacccacgg ggagatgatt cctcatgaag agcctggatc      840
ccctacagaa atcaaatgtg actttccgtt tatcagacta aaatcagagc catccagaca      900
gtgaaacagt caccgtggag gggggacggc gaaaaatgaa atccaaccaa gagcggagca      960
acgaatgcct gcctcccaag aagcgcgaga tccccgccac cagccggtcc tccgaggaga     1020
aggcccctac cctgcccagc gacaaccacc gggtggaggg cacagcatgg ctcccgggca     1080
accctggtgg ccggggccac ggggggcgga ggcatgggcc ggcagggacc tcggtggagc     1140
ttggtttaca acagggaata ggtttacaca aagcattgtc cacagggctg gactactccc     1200
cgcccagcgc tcccaggtct gtcccgtgg ccaccacgct gcctgccgcg tacgccaccc      1260
cgcagccagg gaccccggtg tccccgtgc agtacgctca cctgccgcac accttccagt      1320
tcattgggtc ctcccaatac agtggaacct atgccagctt catcccatca cagctgatcc     1380
ccccaaccgc caaccccgtc accagtgcag tggcctcggc cgcaggggcc accactccat     1440
cccagcgctc ccagctggag gcctattcca ctctgctggc caacatgggc agtctgagcc     1500
agacgccggg acacaaggct gagcagcagc agcagcagca gcagcagcag cagcagcagc     1560
atcagcatca gcagcagcag cagcagcagc agcagcagca gcagcagcag cagcacctca     1620
gcagggctcc ggggctcatc accccggggt ccccccacc agcccagcag aaccagtacg       1680
tccacatttc cagttctccg cagaacaccg gccgcaccgc ctctcctccg gccatccccg     1740
tccacctcca cccccaccag acgatgatcc cacacacgct cacccrggg ccccctcc        1800 aggtcgtcat gcaatacgcc gactccggca gccactttgt ccctcgggag gccaccaaga     1860
aagctgagag cagccggctg cagcaggcca tccaggccaa ggaggtcctg aacggtgaga     1920
tggagaagag ccggcggtac ggggcccgt cctcagccga cctgggcctg gcaaggcag       1980 gcggcaagtc ggttcctcac ccgtacgagt ccaggcacgt ggtggtccac ccgagcccct     2040
cagactacag cagtcgtgat ccttcggggg tccgggcctc tgtgatggtc ctgcccaaca     2100
gcaacacgcc cgcagctgac ctggaggtgc aacaggccac tcatcgtgaa gcctcccctt     2160
ctaccctcaa cgacaaaagt ggcctgcatt tagggaagcc tggccaccgg tcctacgcgc     2220 tctcaccccca cacggtcatt cagaccacac acagtgcttc agagccactc ccggtgggac    2280
tgccagccac ggccttctac gcagggactc aacccctgt catcggctac ctgagcggcc     2340
agcagcaaga aatcacctac gccggcagcc tgcccagca cctggtgatc cccggcacac     2400 agccctgct catcccggtc ggcagcactg acatggaagc gtcggggca gccccggcca      2460
```

```
tagtcacgtc atcccccag tttgctgcag tgcctcacac gttcgtcacc accgcccttc   2520
ccaagagcga gaacttcaac cctgaggccc tggtcaccca ggccgcctac ccagccatgg   2580
tgcaggccca gatccacctg cctgtggtgc agtccgtggc ctccccggcg gcggctcccc   2640
ctacgctgcc tccctacttc atgaaaggct ccatcatcca gttggccaac ggggagctaa   2700
agaaggtgga agacttaaaa acagaagatt tcatccagag tgcagagata agcaacgacc   2760
tgaagatcga ctccagcacc gtagagagga ttgaagacag ccatagcccg ggcgtggccg   2820
tgatacagtt cgccgtcggg gagcaccgag cccaggtcag cgttgaagtt ttggtagagt   2880 atccttttt tgtgtttgga cagggctggt catcctgctg tccggagaga accagccagc   2940
tctttgattt gccgtgttcc aaactctcag ttggggatgt ctgcatctcg cttaccctca   3000
agaacctgaa gaacggctct gttaaaaagg ccagcccgt ggatcccgcc agcgtcctgc   3060
tgaagcactc aaaggccgac ggcctggcgg gcagcagaca caggtatgcc gagcaggaaa   3120
acggaatcaa ccaggggagt gcccagatgc tctctgagaa tggcgaactg aagtttccag   3180
agaaaatggg attgcctgca gcgcccttcc tcaccaaaat agaacccagc aagcccgcgg   3240
caacgaggaa gaggaggtgg tcggcgccag agagccgcaa actggagaag tcagaagacg   3300
aaccaccttt gactcttcct aagccttctc taattcctca ggaggttaag atttgcattg   3360
aaggccggtc taatgtaggc aagtagaggc agcgtggggg aaaggaaacg tggctctccc   3420
ttatcatttg tatccagatt actgtactgt aggctaaaat aacacagtat ttacatgtta   3480
tcttcttaat tttaggtttc tgttctaacc ttgtcattag agttacagca ggtgtgtcgc   3540
aggagactgg tgcatatgct ttttccacga gtgtctgtca gtgagcgggc gggaggaagg   3600
gcacagcagg agcggtcagg gctccaggca tccccgggga agaaaggaac ggggcttcac   3660
agtgcctgcc ttctctagcg gcacagaagc agccgggggc gctgactccc gctagtgtca   3720
ggagaaaagt cccgtgggaa gagtcctgca ggggtgcagg gttgcacgca tgtgggggtg   3780
cacaggcgct gtggcggcga gtgagggtct cttttctct gcctccctct gcctcactct   3840
cttgctatcg gcatgggccg gggggttca gagcagtgtc ctcctggggt tcccacgtgc   3900
aaaatcaaca tcaggaaccc agcttcaggg catcgcggag acgcgtcaga tggcagattt   3960
ggaaagttaa ccatttaaaa gaacattttt ctctccaaca tattttacaa taaaagcaac   4020
ttttaattgt atagatatat atttccccct atggggcctg actgcactga tatatatttt   4080
ttttaaagag caactgccac atgcgggatt tcatttctgc ttttactag tgcagcgatg   4140 tcaccagggt gttgtggtgg acaggaagc ccctgctgtc atggcccac atggggtaag   4200 gggggttggg ggtggggag agggagagag cgaacaccca cgctggtttc tgtgcagtgt   4260
taggaaaacc aatcaggtta ttgcattgac ttcactccca agaggtagat gcaaactgcc   4320
cttcagtgag agcaacagaa gctcttcacg ttgagtttgc gaaatctttt tgtctttgaa   4380
ctctagtact gttatagtt catgactatg gacaactcgg gtgccacttt ttttttttc   4440 agattccagt gtgacatgag gaattagatt ttgaagatga gcatatatta ctatctttaa   4500
gcatttaaaa atactgttca cactttatta ccaagcatct tggtctctca ttcaacaagt   4560
actgtatctc actttaaact ctttggggaa aaaacaaaaa caaaaaaaac taagttgctt   4620 tcttttttc aacactgtaa ctacatttca gctctgcaga attgctgaag agcaagatat   4680
tgaaagtttc aatgtggttt aaagggatga atgtgaatta tgaactagta tgtgacaata   4740
aatgaccacc aagtactacc tgacggggagg cactttcac tttgatgtct gagaatcagt   4800
tcaaggcata tgcagagttg gcagagaaac tgagagaaaa gggatggaga agagaatact   4860
```

```
cattttgtc cagtgttttt cttttaaga tgaacttta aagaaccttg cgatttgcac    4920
atattgagtt tataacttgt gtgatattcc tgcagttttt atccaataac attgtgggaa    4980
aggtttgggg gactgaacga gcataaataa atgtagcaaa atttctttct aacctgccta    5040
aactctaggc cattttataa ggttatgttc ctttgaaaat tcattttggt cttttacca     5100 catctgtcac aaaaagccag gtcttagcgg gctcttagaa actctgagaa ttttcttcag    5160
attcattgag agagttttcc ataaagacat ttatatatgt gagcaagatt ttttttaaac    5220 aattactta ttattgttgt tattaatgtt attttcagaa tggcttttt tttctattca      5280 aaatcaaatc gagatttaat gtttggtaca aacccagaaa gggtatttca tagttttta    5340 acctttcatt cccagagatc cgaaatatca tttgtgggtt ttgaatgcat ctttaaagtg    5400
ctttaaaaaa aagttttata agtagggaga aattttaaa tattcttact tggatggctg     5460
caactaaact gaacaaatac ctgactttc tttaccca ttgaaaatag tactttcttc      5520
gtttcacaaa ttaaaaaaa aatctggtat caacccacat tttggctgtc tagtattcat    5580
ttacatttag ggttcaccag gactaatgat ttttataaac cgttttctgg ggtgtaccaa    5640 aaacattga ataggtttag aatagctaga atagttcctt gactttcctc gaatttcatt    5700
accctctcag catgcttgca gagagctggg tgggctcatt cttgcagtca tactgcttat    5760
ttagtgctgt atttttaaa cgtttctgtt cagagaactt gcttaatctt ccatatattc   5820
tgctcagggc acttgcaatt attaggtttt gttttctttt ttgttttta gcctttgatg    5880 gtaagaggaa tacgggctgc cacatagact ttgttctcat taatatcact atttacaact    5940
catgtggact cagaaaaaca cacaccacct tttggcttac ttcgagtatt gaattgactg    6000
gatccactaa accaacacta agatgggaaa acacacatgg tttggagcaa taggaacatc    6060
atcataattt ttgtggttct atttcaggta taggaattat aaaataattg gttctttcta    6120
aacacttgtc ccatttcatt ctcttgcttt tttagcatgt gcaatacttt ctgtgccaat    6180
agagtctgac cagtgtgcta tatagttaaa gctcattccc ttttggcttt ttccttgttt    6240
ggttgatctt cccccattctg gccagagcag ggctggaggg aaggagccag gagggagaga    6300
gcctcccacc tttcccctgc tgcggatgct gagtgctggg gcggggagcc ttcaggagcc    6360
ccgtgcgtct gccgccacgt tgcagaaaga gccagccaag gagacccggg ggaggaaccg    6420
cagtgtcccc tgtcaccaca cggaatagtg aatgtggagt gtggagagga aggaggcaga    6480
ttcatttcta agacgcactc tggagccatg tagcctggag tcaacccatt ttccacggtc    6540
ttttctgcaa gtgggcaggc ccctcctcgg ggtctgtgtc cttgagactt ggagccctgc    6600
ctctgagcct ggacgggaag tgtggcctgt tgtgtgtgtg cgttctgagc gtgttggcca    6660
gtggctgtgg aggggaccac ctgccaccca cggtcaccac tcccttgtgg cagctttctc    6720
ttcaaatagg aagaacgcac agagggcagg agcctcctgt ttgcagacgt tggcgggccc    6780
cgaggctccc agagcagcct ctgtcaccgc ttctgtgtag caaacattaa cgatgacagg    6840
ggtagaaatt cttcggtgcc gttcagctta caaggatcag ccatgtgcct ctgtactatg    6900
tccactttgc aatatttacc gacagccgtc ttttgttctt tctttcctgt tttccatttt    6960
taaactagta acagcaggcc ttttgcgttt acaatggaac acaatcacca agaaattagt    7020
cagggcgaaa agaaaaaaat aatactatta ataagaaacc aacaaacaag aacctctctt    7080
tctagggatt tctaaatata taaaatgact gttccttaga atgtttaact taagaattat    7140
ttcagtttgt ctgggccaca ctggggcaga ggggggaggg agggatacag agatggatgc    7200
cacttacctc agatcttta aagtggaaat ccaaattgaa ttttcatttg gactttcagg     7260
```

```
ataattttct atgttggtca acttttcgtt ttccctaact cacccagttt agtttgggat   7320
gatttgattt ctgttgttgt tgatcccatt tctaacttgg aattgtgagc ctctatgttt   7380
tctgttaggt gagtgtgttg ggttttttcc ccccaccagg aagtggcagc atccctcctt   7440
ctcccctaaa gggactctgc ggaacctttc acacctcttt ctcagggacg ggcaggtgt    7500
gtgtgtggta cactgacgtg tccagaagca gcactttgac tgctctggag tagggttgta   7560
caatttcaag gaatgtttgg atttcctgca tcttgtggat tactccttag ataccgcata   7620
gattgcaata taatgctgca tgttcaagat gaacagtagc tcctagtaat cataaaatcc   7680
actctttgca cagtttgatc tttactgaaa tatgttgcca aaatttattt ttgttgttgt   7740
agctctggat tttgttttgt tttgtttttt aaggaaacga ttgacaatac cctttaacat   7800
ctgtgactac taaggaaacc tatttctttc atagagagaa aaatctccaa tgcttttgaa   7860
gacactaata ccgtgctatt tcagatatgg gtgaggaagc agagctctcg gtaccgaagg   7920
ccgggcttct tgagctgtgt tggttgtcat ggctactgtt tcatgaacca caagcagctc   7980
aacagactgg tctgttgcct tctgaaaccc tttgcacttc aatttgcacc aggtgaaaac   8040
agggccagca gactccatgg cccaattcgg tttcttcggt ggtgatgtga aaggagagaa   8100
ttacactttt ttttttttta agtggcgtgg aggcctttgc ttccacattt gtttttaacc   8160
cagaatttct gaaatagaga atttaagaac acatcaagta ataaatatac agagaatata   8220
cttttttata aagcacatgc atctgctatt gtgttgggtt ggtttcctct cttttccacg   8280
gacagtgttg tgtttctggc atagggaaac tccaaacaac ttgcacacct ctactccgga   8340
gctgagattt cttttacata gatgacctcg cttcaaatac gttaccttac tgatgatagg   8400
atcttttctt gtagcactat accttgtggg aattttttt taaatgtaca cctgatttga   8460
gaagctgaag aaaacaaaat tttgaagcac tcactttgag gagtacaggt aatgttttaa   8520
aaaattgcac aaaagaaaaa tgaatgtcga aatgattcat tcagtgtttg aaagatatgg   8580
ctctgttgaa acaatgagtt tcatactttg tttgtaaaaa aaaaagcag agaagggttg    8640
aaagttacat gtttttttgt atatagaaat ttgtcatgtc taaatgatca gatttgtatg   8700
gttatggcct ggaagaatta ctacgtaaaa ggctcttaaa ctataccat gcttattgtt    8760
attttttgtta catatagccc tcgtctgagg gaggggaact cggtattctg cgatttgaga   8820
atactgttca ttcctatgct gaaagtactt ctctgagctc ccttcttagt ctaaactctt   8880
aagccattgc aacttctttt tcttcagaga tgatgtttga cattttcagc acttcctgtt   8940
cctataaacc caagaatat aatccttgaac acgaagtgtt tgtaacaagg gatccaggct   9000
accaatcaaa caggactcat tatggggaca aaaaaaaaaa aaattatttc accttctttc   9060
ccccacaccc tcatttaaat gggggagta aaaacatgat ttcaatgtaa atgcctcatt    9120
ttatttagt ttatttgta ttttttattta atataaagag gccagaataa atacggagca    9180
tcttctcaga atagtattcc tgtccaaaaa tcaagccgga cagtggaaac tggacagctg   9240
tggggatatt aagcaccccc acttacaatt cttaaattca gaatctcgtc ccctcccttc   9300
tcgttgaagg caactgttct ggtagctaac tttctcctgt gtaatggcgg gagggaacac   9360
cggcttcagt ttttcatgtc cccatgactt gcatacaaat ggttcaactg tattaaaatt   9420
aagtgcattt ggccaatagg tagtatctat acaataacaa caatctctaa gaatttccat   9480
aacttttctt atctgaaagg actcaagtct tccactgcag atacattgga ggcttcaccc   9540
acgttttctt tccctttagt ttgtttgctg tctggatggc caatgagcct gtctcctttt   9600
ctgtggccaa tctgaaggcc ttcgttggaa gtgttgttca cagtaatcct taccaagata   9660
```

| | | | | |
|---|---|---|---|---|
| acatactgtc | ctccagaata | ccaagtatta | ggtgacacta | gctcaagctg | ttgtcttcag | 9720 |
| agcagttacc | aagaagctcg | gtgcacaggt | tttctctggt | tcttacagga | accacctact | 9780 |
| ctttcagttt | tctggcccag | gagtgggta | aatcctttag | ttagtgcatt | tgaacttggt | 9840 |
| acctgtgcat | tcagttctgt | gaatactgcc | cttttggcg | gggtttcctc | atctccccag | 9900 |
| cctgaactgc | tcaactctaa | acccaaatta | gtgtcagccg | aaaggaggtt | tcaagatagt | 9960 |
| cctgtcagta | tttgtggtga | ccttcagatt | agacagtctt | catttccagc | cagtggagtc | 10020 |
| ctggctccag | agccatctct | gagactccgt | actactggat | gttttaatat | cagatcatta | 10080 |
| cccaccatat | gcctcccaca | ggccaaggga | aaacagacac | cagaacttgg | gttgagggca | 10140 |
| ctaccagact | gacatggcca | gtacagagga | gaactaggga | aggaatgatg | ttttgcacct | 10200 |
| tattgaaaag | aaaattttaa | gtgcatacat | aatagttaag | agcttttatt | gtgacaggag | 10260 |
| aacttttttc | catatgcgtg | catactctct | gtaattccag | tgtaaaatat | tgtacttgca | 10320 |
| ctagcttttt | taaacaaata | ttaaaaaatg | gaagaattca | tattctattt | tctaatcgtg | 10380 |
| gtgtgtctat | ttgtaggata | cactcgagtc | tgtttattga | attttatggt | cccttctctt | 10440 |
| gatggtgctt | gcaggttttc | taggtagaaa | ttatttcatt | attataataa | aacaatgttt | 10500 |
| gattcaaaat | ttgaacaaaa | ttgttttaaa | taaattgtct | gtataccagt | acaagtttat | 10560 |
| tgtttcagta | tactcgtact | aataaaataa | cagtgccaat | tgcaaaaaaa | aaaaaaaaaa | 10620 |
| aaaaaaaaaa | aaaaaaaaaa | aaaaaaaaaa | aaaaaaaaa | | | 10660 |

<210> SEQ ID NO 16
<211> LENGTH: 1900
<212> TYPE: DNA
<213> ORGANISM: Homo sapiens
<220> FEATURE:
<221> NAME/KEY: misc_feature
<222> LOCATION: (1)..(1900)
<223> OTHER INFORMATION: LOCUS        MJD                 1900 bp
      mRNA    linear   P
      RI 31-JUL-2002 DEFINITION  Homo sapiens Machado-Joseph disease
      (spinocerebellar ataxia 3, olivopontocerebellar ataxia 3, . . .
      ACCESSION   NM_004993
<300> PUBLICATION INFORMATION:
<308> DATABASE ACCESSION NUMBER: NM_004993
<309> DATABASE ENTRY DATE: 2002-07-31
<313> RELEVANT RESIDUES IN SEQ ID NO: (1)..(1900)

<400> SEQUENCE: 16

| | | | | | | |
|---|---|---|---|---|---|---|
| ggggcggagc | tggaggggt | ggttcggcgt | ggggggccgtt | ggctccagac | aaataaacat | 60 |
| ggagtccatc | ttccacgaga | aacaagaagg | ctcactttgt | gctcaacatt | gcctgaataa | 120 |
| cttattgcaa | ggagaatatt | ttagccctgt | ggaattatcc | tcaattgcac | atcagctgga | 180 |
| tgaggaggag | aggatgagaa | tggcagaagg | aggagttact | agtgaagatt | atcgcacgtt | 240 |
| tttacagcag | ccttctggaa | atatggatga | cagtggtttt | ttctctattc | aggttataag | 300 |
| caatgccttg | aaagtttggg | gtttagaact | aatcctgttc | aacagtccag | agtatcagag | 360 |
| gctcaggatc | gatcctataa | atgaaagatc | atttatatgc | aattataagg | aacactggtt | 420 |
| tacagttaga | aaattaggaa | aacagtggtt | taacttgaat | tctctcttga | cgggtccaga | 480 |
| attaatatca | gatacatatc | ttgcactttt | cttggctcaa | ttacaacagg | aaggttattc | 540 |
| tatatttgtc | gttaagggtg | atctgccaga | ttgcgaagct | gaccaactcc | tgcagatgat | 600 |
| tagggtccaa | cagatgcatc | gaccaaaact | tattggagaa | gaattagcac | aactaaaaga | 660 |
| gcaaagagtc | cataaaacag | acctggaacg | agtgttagaa | gcaaatgatg | gctcaggaat | 720 |
| gttagacgaa | gatgaggagg | atttgcagag | ggctctggca | ctaagtcgcc | aagaaattga | 780 |

```
catggaagat gaggaagcag atctccgcag ggctattcag ctaagtatgc aaggtagttc      840
cagaaacata tctcaagata tgacacagac atcaggtaca aatcttactt cagaagagct      900
tcggaagaga cgagaagcct actttgaaaa acagcagcaa agcagcaac agcagcagca       960 gcagcagcag caggggggacc tatcaggaca gagttcacat ccatgtgaaa ggccagccac     1020
cagttcagga gcacttggga gtgatctagg tgatgctatg agtgaagaag acatgcttca     1080
ggcagctgtg accatgtctt tagaaactgt cagaaatgat ttgaaaacag aaggaaaaaa     1140
ataatacctt taaaaataa tttagatatt catactttcc aacattatcc tgtgtgatta     1200
cagcataggt tccactttgg taatgtgtca aagagatgag gaaataagac ttttagcggt     1260
ttgcaaacaa aatgatggga agtggaaca atgcgtcggt tgtaggacta aataatgatc     1320
ttccaaatat tagccaaaga ggcattcagc aattaaagac atttaaaata gttttctaaa     1380
tgtttctttt tcttttttga gtgtgcaata tgtaacatgt ctaaagttag ggcattttc     1440 ttggatcttt ttgcagacta gctaattagc tctcgcctca ggcttttcc atatagtttg     1500 ttttcttttt ctgtcttgta ggtaagttgg ctcacatcat gtaatagtgg ctttcatttc     1560
ttattaacca aattaacctt tcaggaaagt atctctactt tcctgatgtt gataatagta     1620
atggttctag aaggatgaac agttctccct tcaactgtat accgtgtgct ccagtgtttt     1680
cttgtgttgt tttctctgat cacaacttt ctgctacctg gttttcatta ttttcccaca     1740
attcttttga aagatggtaa tcttttctga ggtttagcgt tttaagccct acgatgggat     1800
cattatttca tgactggtgc gttcctaaac tctgaaatca gccttgcaca agtacttgag     1860
aataaatgag cattttttaa aaaaaaaaa aaaaaaaa                               1900
```

```
<210> SEQ ID NO 17
<211> LENGTH: 1735
<212> TYPE: DNA
<213> ORGANISM: Homo sapiens
<220> FEATURE:
<221> NAME/KEY: misc_feature
<222> LOCATION: (1)..(1735)
<223> OTHER INFORMATION: LOCUS       MJD                  1735 bp
      mRNA      linear    P
      RI 31-JUL-2002 DEFINITION  Homo sapiens Machado-Joseph disease
      (spinocerebellar ataxia 3, olivopontocerebellar ataxia 3,
      autosomal dominant, at axin 3) (MJD) . . . ACCESSION   NM_030660
<300> PUBLICATION INFORMATION:
<308> DATABASE ACCESSION NUMBER: NM_030660
<309> DATABASE ENTRY DATE: 2002-07-31
<313> RELEVANT RESIDUES IN SEQ ID NO: (1)..(1735)

<400> SEQUENCE: 17
```

```
ggggcggagc tggagggggt ggttcggcgt ggggccgtt ggctccagac aaataaacat        60
ggagtccatc ttccacgaga aacagccttc tggaaatatg gatgacagtg gttttttctc      120
tattcaggtt ataagcaatg ccttgaaagt ttggggttta gaactaatcc tgttcaacag      180
tccagagtat cagaggctca ggatcgatcc tataaatgaa agatcattta tatgcaatta     240
taaggaacac tggtttacag ttagaaaatt aggaaaacag tggttaact tgaattctct     300 cttgacgggg ccagaattaa tatcagatac atatcttgca cttttcttgg ctcaattaca     360
acaggaaggt tattctatat ttgtcgttaa gggtgatctg ccagattgcg aagctgacca     420
actcctgcag atgattaggg tccaacagat gcatcgacca aaacttattg gagaagaatt     480
agcacaacta aaagagcaaa gagtccataa acagacctg gaacgagtgt tagaagcaaa     540
tgatggctca ggaatgttag acgaagatga ggaggatttg cagagggctc tggcactaag     600
tcgccaagaa attgacatgg aagatgagga agcagatctc cgcagggcta ttcagctaag     660
```

-continued

```
tatgcaaggt agttccagaa acatatctca agatatgaca cagacatcag gtacaaatct    720
tacttcagaa gagcttcgga agagacgaga agcctacttt gaaaaacagc agcaaaagca    780
gcaacagcag cagcagcagc agcagcaggg ggacctatca ggacagagtt cacatccatg    840
tgaaaggcca gccaccagtt caggagcact tgggagtgat ctaggtgatg ctatgagtga    900
agaagacatg cttcaggcag ctgtgaccat gtctttagaa actgtcagaa atgatttgaa    960
aacagaagga aaaaaataat acctttaaaa aataatttag atattcatac tttccaacat   1020
tatcctgtgt gattacagca tagggtccac tttggtaatg tgtcaaagag atgaggaaat   1080
aagactttta gcggtttgca aacaaaatga tgggaaagtg aacaatgcg tcggttgtag    1140 gactaaataa tgatcttcca aatattagcc aaagaggcat tcagcaatta aagacattta   1200
aaatagtttt ctaaatgttt cttttctctt tttgagtgtg caatatgtaa catgtctaaa   1260
gttagggcat ttttcttgga tctttttgca gactagctaa ttagctctcg cctcaggctt   1320
tttccatata gtttgttttc ttttctgtc ttgtaggtaa gttggctcac atcatgtaat    1380
agtggctttc atttcttatt aaccaaatta acctttcagg aaagtatctc tactttcctg   1440
atgttgataa tagtaatggt tctagaagga tgaacagttc tccctttcaac tgtataccgt   1500 gtgctccagt gttttcttgt gttgtttct ctgatcacaa cttttctgct acctggtttt    1560 cattatttc ccacaattct tttgaaagat ggtaatcttt tctgaggttt agcgttttaa    1620
gccctacgat gggatcatta tttcatgact ggtgcgttcc taaactctga aatcagcctt   1680
gcacaagtac ttgagaataa atgagcattt tttaaaaaaa aaaaaaaaaa aaaaa         1735
```

<210> SEQ ID NO 18
<211> LENGTH: 5832
<212> TYPE: RNA
<213> ORGANISM: Homo sapiens
<220> FEATURE:
<221> NAME/KEY: misc_feature
<222> LOCATION: (1)..(5832)
<223> OTHER INFORMATION: ACCESSION   NM_012104 VERSION    NM_012104.2
      GI:21040369
<220> FEATURE:
<221> NAME/KEY: misc_feature
<222> LOCATION: (1)..(5832)
<223> OTHER INFORMATION: LOCUS       BACE    5832 bp    mRNA    linear
      PRI 05-NOV-2002
      DEFINITION  Homo sapiens beta-site APP-cleaving enzyme (BACE),
      transcript variant a, mRNA.
<300> PUBLICATION INFORMATION:
<308> DATABASE ACCESSION NUMBER: NM_012104
<309> DATABASE ENTRY DATE: 2002-11-05
<313> RELEVANT RESIDUES IN SEQ ID NO: (1)..(5832)

<400> SEQUENCE: 18

```
ucccagccc gccgggagc ucgagccgc gagcuggauu augguggccu gagcagccaa      60
cgcagccgca ggagcccgga gcccuugccc cugcccgcgc cgccgccgc cgggggggacc    120 agggaagccg ccaccggccc gccaugcccg ccucucccag ccccgccggg agcccgcgcc   180
cgcugcccag gcuggccgcc gccgugccga guagcgggc uccggaucccc agccucuccc   240 cugcucccgu gcucugcgga ucucccccuga ccgcucucca cagcccggac ccggggggcug  300 gcccagggcc cugcaggccc uggcguccug augcccccaa gcuccucucu cugagaagcc   360
accagcacca cccagacuug ggggcaggcg ccagggacgg acgugggcca gugcgagccc    420
agagggcccg aaggccgggg cccaccaugg cccaagcccu gccccuggcuc cugcugugga   480 ugggcgcggg agugcugccu gcccacggca cccagcacgg caucccggcug ccccugcgca   540 gcggccugggg gggcgccccc cugggcugc ggcugcccccg ggagaccgac gaagagcccg    600
```

| | |
|---|---|
| aggagcccgg ccggaggggc agcuuugugg agauggugga caaccugagg ggcaagucgg | 660 |
| ggcagggcua cuacguggag augaccgugg gcagcccccc gcagacgcuc aacauccugg | 720 |
| uggauacagg cagcaguaac uuugcagugg gugcugcccc ccaccccuuc cugcaucgcu | 780 |
| acuaccagag gcagcugucc agcacauacc gggaccuccg gaagggugug uaugugcccu | 840 |
| acacccaggg caagugggaa ggggagcugg gcaccgaccu gguaagcauc ccccauggcc | 900 |
| ccaacgucac ugugcgugcc aacauugcug ccaucacuga aucagacaag uucuucauca | 960 |
| acggcuccaa cugggaaggc auccgggggc uggccuaugc ugagauugcc aggccugacg | 1020 |
| acucccugga gccuuucuuu gacucucugg uaaagcagac ccacguuccc aaccucuucu | 1080 |
| cccugcagcu uuguggugcu ggcuuccccc ucaaccaguc ugaagugcug gccucgucg | 1140 |
| gagggagcau gaucauugga gguaucgacc acucgcugua cacaggcagu cucugguaua | 1200 |
| cacccauccg gcgggagugg uauuaugagg ucaucauugu gcggguggag aucaauggac | 1260 |
| aggaucugaa aauggacugc aaggaguaca acuaugacaa gagcauugug gacagguggca | 1320 |
| ccaccaaccu ucguuugccc aagaaagugu uugaagcugc agucaaaucc aucaaggcag | 1380 |
| ccuccuccac ggagaaguuc ccugauggu ucuggcuagg agagcagcug gugugcuggc | 1440 |
| aagcaggcac caccccuugg aacauuuucc cagucaucuc acucuaccua augggugagg | 1500 |
| uuaccaacca guccuuccgc aucaccaucc uuccgcagca auaccugcgg ccaguggaag | 1560 |
| augugggccac gucccaagac gacuguuaca aguuugccau cucacaguca uccacgggca | 1620 |
| cuguuauggg agcuguuauc auggagggcu ucuacguugu cuuugaucgg gcccgaaaac | 1680 |
| gaauuggcuu ugcugucagc gcuugccaug ugcacgauga guucaggacg gcagcggugg | 1740 |
| aaggcccuuu ugucaccuug gacauggaag acugggcua caacauucca cagacagaug | 1800 |
| agucaacccu caugaccaua gccuaugca uggcugccau cugcgcccuc uucaugcugc | 1860 |
| cacucugccu caugguguguu caguggcgcu gccuccgcug ccugcgccag cagcaugaug | 1920 |
| acuuugcuga ugacaucucc cugcugaagu gaggaggccc auggggcagaa gauagagauu | 1980 |
| ccccuggacc acaccuccgu gguucacuuu ggucacaagu aggagacaca gauggcaccu | 2040 |
| guggccagag caccucagga ccccuccccac ccaccaaaug ccucugccuu gauggagaag | 2100 |
| gaaaaggcug gcaagguggg uuccagggac uguaccugua ggaaacagaa aagagaagaa | 2160 |
| agaagcacuc ugcuggcggg aauacucuug gucaccucaa auuuaagucg ggaaauucug | 2220 |
| cugcuugaaa cuucagcccu gaaccuuugu ccaccauucc uuuaaauucu ccaacccaaa | 2280 |
| guauucuucu uuucuuaguu ucagaaguac uggcaucaca cgcagguuac cuggcgugu | 2340 |
| gucccugugg uacccuggca gagaagagac caagcuuguu cccugcugg ccaaagucag | 2400 |
| uaggagagga ugcacaguuu gcuauuugcu uuagagacag ggacuguaua aacaagccua | 2460 |
| acauuggugc aaagauugcc ucuugaauua aaaaaaaaaa cuagauugac uauuuauaca | 2520 |
| aaugggggcg gcuggaaaga ggagaaggag agggaguaca aagacaggga auaguggau | 2580 |
| caaagcuagg aaaggcagaa acacaaccac ucaccagucc uaguuuaga ccucaucucc | 2640 |
| aagauagcau cccaucucag aagaugggug uuguuucaa uguuucuuu ucugugguug | 2700 |
| cagccugacc aaaagugaga ugggaagggc uuaucuagcc aaagagcucu uuuuagcuc | 2760 |
| ucuuaaauga agugcccacu aagaaguucc acuuaacaca ugaauucug ccauauuaau | 2820 |
| uucauugucu cuaucugaac cacccuuuau ucuacauaug auaggcagca cugaaauauc | 2880 |
| cuaaccccu aagcuccagg ugcccugugg gagagcaacu ggacuauagc agggcugggc | 2940 |
| ucugucuucc uggucauagg cucacucuuu ccccaaaauc uuccucugga gcuuugcagc | 3000 |

```
caaggugcua aaaggaauag guaggagacc ucuucuaucu aauccuuaaa agcauaaugu    3060
ugaacauuca uucaacagcu gaugcccuau aaccccugcc uggauuucuu ccauuaggc    3120 uauaagaagu agcaagaucu uuacauaauu cagagugguu cacugccuu ccuacccucu    3180 cuaauggccc cuccauuuau uugacuaaag caucacacag uggcacuagc auuauaccaa    3240
gaguaugaga aauacagugc uuuauggcuc uaacauuacu gccuucagua ucaaggcugc    3300
cuggagaaag gauggcagcc ucagggcuuc cuuaugccu ccaccacaag agcuccuuga    3360
ugaaggucau cuuuuccccc uauccuguuc uuccccuccc cgcuccuaau gguacguggg    3420
uacccaggcu gguucuuggg cuaguagug gggaccaagu cauuaccuc ccaucaguu    3480 cuagcauagu aaacuacggu accaguguua gugggaagag cuggguuuuc cuaguauacc    3540
cacugcaucc uacuccuacc uggucaaccc gcugcuucca gguaugggac cugcuaagug    3600
uggaauuacc ugauaaggga gagggaaaua caaggagggc cucuggugu ccuggccuca    3660 gccagcugcc cacaagccau aaaccaauaa aacaagaaua cugagucagu uuuuaucug    3720 gguucucuuc auucccacug cacuuggugc ugcuuggcu gacugggaac accccauaac    3780
uacagagucu gacaggaaga cuggagacug uccacuucua gcucggaacu uacuguguaa    3840
auaaacuuuc agaacugcua ccaugaagug aaaaugccac auuuugcuuu auaauuucua    3900
cccauguugg gaaaaacugg cuuuuuccca gcccuuucca gggcauaaaa cucaaccccu    3960
ucgauagcaa gucccaucag ccauuauuu uuuuaaagaa aacuugcacu uguuuucuu    4020 uuuacaguua cuuccuuccu gccccaaaau uauaaacucu aaguguaaaa aaaagucuua    4080
acaacagcuu cuugcuugua aaaauaugua uuauacaucu guauuuuaa auucugcucc    4140 ugaaaaauga cugucccauu uccacucac ugcauuggg ccuucccca uggucugca    4200 ugucuuuuau cauugcaggc caguggacag agggagaagg gagaacaggg gucgccaaca    4260 cuugcuguugc uuucgacug auccugaaca agaaagagua acacgaggc gcucgcuccc    4320 augcacaacu cuccaaaaca cuuauccucc ugcaagagug ggcuuuccag ggucuuuacu    4380
gggaagcagu uaagccccu ccucaccccu uccuuuuuuc uuucuuuacu ccuuuggcuu    4440
caaaggauuu uggaaaagaa acaauaugcu uuacacucau uuucaauuuc uaaauuugca    4500
ggggauacug aaaauacgg caguggccu aaggcugcug uaaaguugag gggagaggaa    4560
aucuuaagau uacaagauaa aaaacgaauc cccaaacaa aaagaacaau agaacugguc    4620
uuccauuuug ccaccuuucc uguucaugac agcuacuaac cuggagacag uaacauuuca    4680
uuaaccaaag aaagugggguc accgaccuc ugaagagcug aguacucagg ccacuccaau    4740
cacccuacaa gaugccaagg agucccagg aaguccagcu ccuuaaacug acgcuaguca    4800
auaaaccugg gcaagugagg caagagaaau gaggaagaau ccaucuguga ggugacaggc    4860
aaggaugaaa gacaaagaag gaaagaagua ucaaaggcag aaaggagauc auuuaguugg    4920
gucugaaagg aaaagucuuu gcuauccgac auguacugcu aguaccugua agcauuuag    4980 gucccagaau ggaaaaaaaa aucagcuauu gguauauaa uaaugccuu ucccuggagu    5040 caguuuuuu aaaagcuuaa cucuuaguuu uuacuuguuu aauucaaaa agaagggag    5100 cugaggccau ucccuguagg aguaaagaua aaaggauagg aaaagauuca aagcucuaau    5160
agagucacag cuuucccagg uauaaaaccu aaaauuaaga aguacaauaa gcagaggugg    5220
aaaaugaucu aguccugau agcuacccac agagcaagug auuuauaaau uugaaaucca    5280
aacuacuuuc uuaauaucac uuggucucc auuuucccca ggacaggaaa uaugccccc    5340 ccuaacuuuc uugcuucaaa aauuaaaauc cagcaucccc agaucauucu acaaguaauu    5400
```

| | |
|---|---|
| uugcacagac aucuccucac cccagugccu gucuggagcu cacccaaggu caccaaacaa | 5460 |
| cuugguugug aaccaacugc cuuaaccuuc uggggagggg ggauuagcua gacuaggaga | 5520 |
| ccagaaguga augggaaagg gugaggacuu cacaauguug gccgucaga gcuugauuag | 5580 |
| aagccaagac aguggcagca aaggaagacu uggcccagga aaaaccugug gguugugcua | 5640 |
| auuucugucc agaaaauagg guggacagaa gcuugugggg uacauggagg aauugggacc | 5700 |
| ugguuauguu guuauucucg gacugugaau uuugguugaug uaaaacagaa uauucuguaa | 5760 |
| accuaauguc uguauaaaua augagcguua acacaguaaa auauucaaua agaagucaaa | 5820 |
| cuacuagggu ua | 5832 |

<210> SEQ ID NO 19
<211> LENGTH: 5757
<212> TYPE: RNA
<213> ORGANISM: Homo sapiens
<220> FEATURE:
<221> NAME/KEY: misc_feature
<222> LOCATION: (1)..(5757)
<223> OTHER INFORMATION: LOCUS      BACE                  5757 bp
       mRNA    linear     P
       RI 05-NOV-2002 DEFINITION  Homo sapiens beta-site APP-cleaving
       enzyme (BACE), tr anscript variant b, mRNA. ACCESSION
       NM_138972; VERSION       NM_138972.1  GI:21040365
<300> PUBLICATION INFORMATION:
<308> DATABASE ACCESSION NUMBER: NM_138972
<309> DATABASE ENTRY DATE: 2002-11-05
<313> RELEVANT RESIDUES IN SEQ ID NO: (1)..(5757)

<400> SEQUENCE: 19

| | |
|---|---|
| uccccagccc gcccgggagc ugcgagccgc gagcuggauu augguggccu gagcagccaa | 60 |
| cgcagccgca ggagcccgga gcccuugccc cugcccgcgc cgccgcccgc cgggggggacc | 120 |
| agggaagccg ccaccggccc gccaugcccg ccccucccag ccccgccggg agcccgcgcc | 180 |
| cgcugcccag gcuggccgcc gccgugccga guagcgggc uccggauccc agccucuccc | 240 |
| cugcucccgu gcucugcgga ucuccccuga ccgcucucca cagcccggac ccggggggcug | 300 |
| gcccagggcc cugcaggccc uggcguccug augcccccaa gcucccucuc cugagaagcc | 360 |
| accagcacca cccagacuug ggggcaggcg ccagggacgg acgugggcca gugcgagccc | 420 |
| agagggcccg aaggccgggg cccaccaugg cccaagcccu gcccuggcuc cugcugugga | 480 |
| ugggcgcggg agugcugccu gccacggca cccagcacgg cauccggcug ccccugcgca | 540 |
| gcggccuggg gggcgccccc cuggggcugc ggcugccccg ggagaccgac gaagagcccg | 600 |
| aggagcccgg ccggagggggc agcuuugugg agauggugga caaccugagg ggcaagucgg | 660 |
| ggcagggcua cuacguggag augaccgugg gcagccccccc gcagacgcuc aacauccugg | 720 |
| uggauacagg cagcaguaac uuugcaguggg ugcugccccc ccaccccuuc cugcaucgcu | 780 |
| acuaccagag gcagcugucc agcacauacc gggaccuccg gaagggugug uaugugcccu | 840 |
| acacccaggg caaguggggaa ggggagcugg gcaccgaccu gguaagcauc cccauggcc | 900 |
| ccaacgucac ugugcgugcc aacauugcug ccaucacuga aucagacaag uucuucauca | 960 |
| acggcuccaa cugggaaggc auccgggggcu uggccuaugc ugagauugcc aggcuuugug | 1020 |
| gugcuggcuu ccccccucaac cagucugaag ugcuggccuc ugucggaggg agcaugauca | 1080 |
| uuggagguau cgaccacucg cuguacacag gcagucucug guauacaccc aucccggcgg | 1140 |
| agugguauua ugaggucauc auugugcggg uggagaucaa uggacaggau cugaaaaugg | 1200 |
| acugcaagga guacaacuau gacaagagca uuuggacag uggcaccacc aaccuucguu | 1260 |
| ugcccaagaa aguguuugaa gcugcagcuca aauccaucaa ggcagccucc uccacggaga | 1320 |

| | |
|---|---|
| aguucccuga ugguuucugg cuaggagagc agcuggugug cuggcaagca ggcaccaccc | 1380 |
| cuuggaacau uuucccaguc aucucacucu accuaauggg ugagguuacc aaccaguccu | 1440 |
| uccgcaucac cauccuuccg cagcaauacc ugcggccagu ggaagaugug gccacguccc | 1500 |
| aagacgacug uuacaaguuu gccaucucac agucauccac gggcacuguu augggagcug | 1560 |
| uuaucaugga gggcuucuac guugucuuug aucgggcccg aaaacgaauu ggcuuugcug | 1620 |
| ucagcgcuug ccaugugcac gaugaguuca ggacggcagc ggugcaaggc cuuuugucca | 1680 |
| ccuuggacau ggaagacugu ggcuacaaca uccacagac agaugagucaacccucauga | 1740 |
| ccauagccua ugcauggcu gccaucugcg cccucuucau gcugccacuc ugccucaugg | 1800 |
| ugugucagug gcgcugccuc cgcugccugc gccagcagca ugaugacuuu gcugaugaca | 1860 |
| ucucccugcu gaagugagga ggcccauggg cagaagauag agauuccccu ggaccacacc | 1920 |
| uccgugguuc acuuugguca caaguaggag acacagaugg caccugugge cagagcaccu | 1980 |
| caggacccuc cccacccacc aaaugccucu gccuugaugg agaaggaaaa ggcuggcaag | 2040 |
| guggguucca gggacuguac cuguaggaaa cagaaaagag aagaaagaag cacucugcug | 2100 |
| gcgggaauac ucuggucac cucaaauuua agcgggaaa uucugcugcu ugaaacuuca | 2160 |
| gcccugaacc uuuguccacc auuccuuuaa auucuccaac ccaaaguauu cuucuuuucu | 2220 |
| uaguuucaga aguacuggca ucacacgcag guuaccuugg cgugugucccugugguaccc | 2280 |
| uggcagagaa gagaccaagc uuguuucccu gcuggccaaa gucaguagga gaggaugcac | 2340 |
| aguuugcuau uugcuuuaga gacagggacu guauaaacaa gccaacauu ggugcaaaga | 2400 |
| uugccucuug aauuaaaaaa aaaaacuaga uugacuauuu auacaaaugg gggcggcugg | 2460 |
| aaagaggaga aggagaggga guacaaagac agggaauagu gggaucaaag cuaggaaagg | 2520 |
| cagaaacaca accacucacc aguccuaguu uuagaccuca ucccaagau agcaucccau | 2580 |
| cucagaagau ggguguuguu ucaauguuu ucuuuucgu gguugcagcc ugaccaaaag | 2640 |
| ugagaugga agggcuuauc uagccaaaga gcucuuuuuu agcucucuua aaugaagugc | 2700 |
| ccacuaagaa guuccacuua acacaugaau uucugccaua uuaauuucau ugucucuauc | 2760 |
| ugaaccaccc uuuauucuac auaugauagg cagcacugaa auauccuaac ccccuaagcu | 2820 |
| ccaggugccc ugugggagag caacuggacu auagcagggc ugggcucugu cuuccugguc | 2880 |
| auaggcucac ucuuucccc aaaucuuccu cuggagcuuu gcagccaagg ugcuaaaagg | 2940 |
| aauaggugg agaccucuuc uaucuaaucc uuaaaagcau aauguugaac auucauucaa | 3000 |
| cagcugaugc ccuauaaccc cugccuggau uucuuccuau uaggcauaa gaaguagcaa | 3060 |
| gaucuuuaca uaauucagag ugguuucacu gccuuccuac ccucucuaau ggccccucca | 3120 |
| uuuauuugac uaaagcauca cacaguggca cuagcauuau accaagagua ugagaaauac | 3180 |
| agugcuuuau ggcucuaaca uuacugccuu caguaucaag gcugccugga gaaggaugg | 3240 |
| cagccucagg gcuuccuuau guccuccacc acaagagcuc cuugaugaag gucaucuuuu | 3300 |
| ucccccuaucc uguucuuccc cuccccgcuc cuaauggua gugguaccc aggcugguuc | 3360 |
| uugggcuagg uaguggggac caaguucauu accucccuau caguucuagc auaguaaacu | 3420 |
| acgguaccag uguuaguggg aagagcuggg uuuuccuagu auacccacug cauccuacuc | 3480 |
| cuaccgguc aacccgcugc uuccagguau gggaccugcu aagguggaa uuaccugaua | 3540 |
| agggagaggg aaauacaagg agggccucug uguuccugg cccagccag cugcccacaa | 3600 |
| gccauaaacc aauaaaacaa gaauacgag ucaguuuuuu aucgggguuc ucuucauucc | 3660 |
| cacugcacuu ggugcugcuu uggcugacug ggaacacccc auaacuacag agucugacag | 3720 |

```
gaagacugga gacuguccac uucuagcucg gaacuuacug uguaaauaaa cuuucagaac   3780
ugcuaccaug aagugaaaau gccacauuuu gcuuuauaau uucuacccau guugggaaaa   3840
acuggcuuuu ucccagcccu uccagggcca uaaaacucaa ccccuucgau agcaagcccc   3900
aucagccuau uauuuuuuua aagaaaacuu gcacuuguuu ucuuuuuac aguuacuucc   3960 uuccugcccc aaaauuauaa acucuaagug uaaaaaaag ucuuaacaac agcuucuugc   4020
uuguaaaaau auguauuaua caucuguauu uuuaaauucu gcuccugaaa aaugacuguc   4080
ccauucucca cucacugcau uuggggccuu ucccauuggu cugcaugucu uuuaucauug   4140
caggccagug gacagaggga gaagggagaa caggggucgc caacacuugu guugcuuucu   4200
gacugauccu gaacaagaaa gaguaacacu gaggcgcucg cucccaugca caacucucca   4260
aaacacuuau ccuccugcaa gagugggcuu uccaggucu uuacgggaa gcaguuaagc    4320 cccccuccuca cccccuuccuu uuuucuuucu uuacuccuuu ggcuucaaag gauuugaa    4380 aagaaacaau augcuuuaca cucauuuuca auuucuaaau uugcagggga uacgaaaaa    4440 uacggcaggu ggccuaaggc ugcuguaaag uugaggggag aggaaaucuu aagauuacaa   4500
gauaaaaaac gaaucccccua aacaaaaaga acaauagaac uggucuucca uuuugccacc   4560 uuccuguuc augacagcua cuaaccugga gacaguaaca uuucauuaac caaagaaagu    4620 ggucaccug accucugaag agcugaguac ucaggccacu ccaaucaccc uacaagaugc    4680
caaggagguc ccaggaaguc cagcuccuua aacgacgcu agcaauaaa ccugggcaag    4740 ugaggcaaga gaaugagga agaauccauc ugugagguga caggcaagga ugaaagacaa    4800
agaaggaaaa gaguaucaaa ggcagaaagg agaucauuua guugggucug aaaggaaaag   4860
ucuuugcuau ccgacaugua cugcuaguac cuguaagcau uuuaggucc agaauggaaa    4920 aaaaaaucag cuauugguaa uauaauaaug uccuucccu ggagucaguu uuuuaaaaa     4980 guuaacucuu aguuuucuacu uguuuaaauc uaaaagagaa gggagcugag gccauuccu    5040 guaggaguaa agauaaaagg auaggaaaag auucaaagcu cuaauagagu cacagcuuc     5100 ccagguuaa aaccaaaau uaagaaguac aauaagcaga ggugaaaau gaucuaguuc     5160 cugauagcua cccacagagc aagugauuua uaaauugaa auccaaacua cuuucuuaau    5220
aucacuuugg ucuccauuu ucccaggaca ggaaauaugu ccccccuaa cuuucuugcu    5280 ucaaaauua aauccagca ucccaagauc auucuacaag uaauuuugca cagacaucuc    5340
cucaccccag ugccugucug gagcucaccc aaggucacca aacaacuugg uugugaacca    5400
acugccuuaa ccuucggggg aggggggauu agcuagacua ggagaccaga agugaauggg    5460
aaagggugag gacuucacaa uguuggccug ucagagcuug auuagaagcc aagacagugg    5520
cagcaaagga agacuuggcc caggaaaaac cugggguuug ugcuaauuuc ugccagaaa     5580 auagggugga cagaagcuug ugggguacau ggaggaauug ggaccugguu auguuguuau    5640
ucucggacug ugaauuuugg ugauguaaaa cagauauuc uguaaaccua augcucguau    5700
aaauaaugag cguuaacaca guaaauauu caauaagaag ucaaacuacu aggguua       5757

<210> SEQ ID NO 20
<211> LENGTH: 5700
<212> TYPE: RNA
<213> ORGANISM: Homo sapiens
<220> FEATURE:
<221> NAME/KEY: misc_feature
<222> LOCATION: (1)..(5700)
<223> OTHER INFORMATION: LOCUS       BACE                  5700 bp
      mRNA    linear    P
      RI 21-MAY-2002 DEFINITION  Homo sapiens beta-site APP-cleaving
      enzyme (BACE), tr anscript variant c, mRNA. ACCESSION
```

NM_138971; VERSION  NM_138971.1  GI:21040363
<300> PUBLICATION INFORMATION:
<308> DATABASE ACCESSION NUMBER: NM_138971.1
<309> DATABASE ENTRY DATE: 2002-05-21
<313> RELEVANT RESIDUES IN SEQ ID NO: (1)..(5700)

<400> SEQUENCE: 20

| | | | | | |
|---|---|---|---|---|---|
| uccccagccc | gcccgggagc | ugcgagccgc | gagcuggauu | augguggccu | gagcagccaa | 60 |
| cgcagccgca | ggagcccgga | gcccuugccc | cugcccgcgc | cgccgcccgc | cgggggggacc | 120 |
| agggaagccg | ccaccggccc | gccaugcccg | ccccucccag | ccccgccggg | agcccgcgcc | 180 |
| cgcugcccag | gcuggccgcc | gccgugccga | guagcgggc | uccggauccc | agccucuccc | 240 |
| cugcucccgu | gcucugcgga | ucuccccuga | ccgcucucca | cagcccggac | cgggggcug | 300 |
| gcccagggcc | cugcaggccc | uggcguccug | augcccccaa | gcucccucuc | cugagaagcc | 360 |
| accagcacca | cccagacuug | ggggcaggcg | ccagggacgg | acgugggcca | gugcgagccc | 420 |
| agagggcccg | aaggccgggg | cccaccaugg | cccaagcccu | gcccuggcuc | cugcugugga | 480 |
| ugggcgcggg | agugcugccu | gcccacggca | cccagcacgg | cauccggcug | ccccugcgca | 540 |
| gcggccuggg | gggcgccccc | cuggggcugc | ggcugcccg | ggagaccgac | gaagagcccg | 600 |
| aggagcccgg | ccggaggggc | agcuuugugg | agauggugga | caaccugagg | ggcaagucgg | 660 |
| ggcagggcua | cuacguggag | augaccgugg | gcagccccc | gcagacgcuc | aacauccugg | 720 |
| uggauacagg | cagcaguaac | uuugcagugg | gugcugcccc | ccaccccuuc | cugcaucgcu | 780 |
| acuaccagag | gcagcugucc | agcacauacc | gggaccuccg | gaagggugug | uaugugcccu | 840 |
| acacccaggg | caagugggaa | ggggagcugg | gcaccgaccu | gcugacgac | ucccuggagc | 900 |
| cuuucuuuga | cucucuggua | aagcagaccc | acguucccaa | ccucuucccc | cugcagcuuu | 960 |
| guggugcugg | cuuccccccuc | aaccagucug | aagugcuggc | cucugucgga | gggagcauga | 1020 |
| ucauuggagg | uaucgaccac | ucgcuguaca | caggcagucu | cugguauaca | cccauccggc | 1080 |
| gggaguggua | uuaugaagguc | aucauugcg | ggguggagau | caauggacag | gaucugaaaa | 1140 |
| uggacugcaa | ggaguacaac | uaugacaaga | gcauugugga | caguggcacc | accaaccuuc | 1200 |
| guuugcccaa | gaaaguguuu | gaagcugcag | ucaaauccau | caaggcagcc | uccuccacgg | 1260 |
| agaaguuccc | ugauguuuuc | uggcuaggag | agcagcuggu | gugcuggcaa | gcaggcacca | 1320 |
| ccccuuggaa | cauuuccca | gucaucucac | ucuaccuaau | gggugagguu | accaaccagu | 1380 |
| ccuuccgcau | caccauccuu | ccgcagcaau | accugcggcc | aguggaagau | guggccacgu | 1440 |
| cccaagacga | cuguuacaag | uuugccaucu | cacagucauc | cacgggcacu | guuauggggag | 1500 |
| cuguuaucau | ggagggcuuc | uacguugucu | uugaucgggc | ccgaaaacga | auuggcuuug | 1560 |
| cugucagcgc | uugccaugug | cacgaugagu | ucaggacggc | agcgguggaa | ggcccuuuug | 1620 |
| ucaccuugga | cauggaagac | uguggcuaca | cauuccaca | gacagaugag | ucaacccuca | 1680 |
| ugaccauagc | cuaugucaug | gcugccaucu | gcgcccucuu | caugcugcca | cucugcccuca | 1740 |
| uggugugca | guggcgcugc | cuccgcugcc | ugcgccagca | gcaugaugac | uuugcugaug | 1800 |
| acauucccccu | gcugaaguga | ggaggccccau | gggcagaaga | uagagauucc | ccuggaccac | 1860 |
| accuccgugg | uucacuuugg | ucacaaguag | gagacacaga | uggcaccugu | ggccagagca | 1920 |
| ccucaggacc | cucccacccc | accaaaugcc | ucugccuuga | uggagaagga | aaaggcuggc | 1980 |
| aaggugggu | ccagggacug | uaccuguagg | aaacagaaaa | gagaagaaag | aagcacucug | 2040 |
| cuggcgggaa | uacucuuggu | caccucaaau | uuaagucggg | aaauucugcu | gcuugaaacu | 2100 |
| ucagcccuga | accuuugucc | accauuccuu | uaaauucucc | aacccaaagu | auucuucuuu | 2160 |

```
ucuuaguuuc agaaguacug gcaucacacg cagguuaccu uggcgugugu cccuggggua    2220
cccuggcaga gaagagacca agcuuguuuc ccugcuggcc aaagucagua ggagaggaug    2280
cacaguuugc uauuugcuuu agagacaggg acuguauaaa caagccuaac auuggugcaa    2340
agauugccuu uugaauuaaa aaaaaaaacu agauugacua uuuauacaaa uggggggcggc    2400 uggaaagagg agaaggagag ggaguacaaa gacagggaau aguggggauca aagcuaggaa   2460 aggcagaaac acaaccacuc accagcccua guuuugacc ucaucuccaa gauagcaucc    2520
caucucagaa gaugggyguu guuucaaug uuucuuuuc ugugguugca gccugaccaa     2580
aagugagaug ggaagggcuu aucuagccaa agagcucuuu uuuagcucuc uuaaaugaag   2640
ugcccacuaa gaaguuccac uuaacacaug aauuucugcc auauuaauuu cauugucucu   2700
aucugaacca cccuuuauuc uacauaugau aggcagcacu gaaauauccu aacccccuaa   2760
gcuccaggug cccugugggga gagcaacugg acuauagcag ggcugggcuc ugucuuccug  2820
gucauaggcu cacucuuuccc cccaaaucuu ccucuggagc uuugcagcca aggugcuaaa  2880
aggaauaggu aggagaccuc uucuaucuaa uccuuaaaag cauaauguug aacauucauu   2940
caacagcuga ugcccuauaa ccccugccug gauuucuucc uauuaggcua uaagaaguag   3000
caagaucuuu acauaauuca gaguggguuuc acugccuucc uacccucucu aauggcccccu 3060 ccauuuauuu gacuaaagca ucacacagug gcacuagcau uauaccaaga guaugagaaa  3120
uacagugcuu uauggcucua acauuacugc cuucaguauc aaggcugccu ggagaaagga  3180
uggcagccuc agggcuuccu uauguccucc accacaagag cuccuugaug aaggucaucu  3240
uuucccccua uccuguucuu ccccucccg cuccuaaugg uacgugggua cccaggcugg   3300
uucuggggcu agguagguggg gaccaaguuc auuaccuccc uaucaguucu agcauaguaa  3360
acuacgguac caguguuagu gggaagagcu ggguuuuccu aguauaccca cugcauccua  3420
cuccuaccug gucaacccgc ugcuccagg uaugggaccu gcuaagugug gaauuaccug   3480
auaagggaga gggaaauaca aggagggccu cugguguucc uggccucagc cagcugccca  3540
caagccauaa accaauaaaa caagaauacu gagucaguuu uuuaucuggg uucucuucau  3600
ucccacugca cuuggugcug cuuuggcuga cugggaacac cccauaacua cagagucuga  3660
caggaagacu ggagacuguc cacuucuagc ucggaacuua cuguguaaau aaacuuucag   3720
aacugcuacc augaagugaa aaugccacau uuugcuuuau aauuucuacc caugutuggga  3780 aaaacuggcu uuuucccagc ccuuccagg gcauaaaacu caacccccuuc gauagcaagu  3840 cccaucagcc uauuauuuu uuaaagaaaa cuugcacuug uuuuucuuuu uacaguuacu   3900
uccuuccugc cccaaaauua uaaacucuaa guguaaaaaa aagucuuaac aacagcuucu   3960
ugcuuguaaa aauauguauu auacaucugu auuuuuaaau ucugcuccug aaaaaugacu   4020
gucccauucu ccacucacug cauuugggc cuucccauu ggucugcaug ucuuuuauca    4080
uugcaggcca guggacagag ggagaaggga gaacagggu cgccaacacu uguguugcuu   4140
ucugacugau ccugaacaag aaagaguaac acugaggcgc ucgcucccau gcacaacucu  4200
ccaaaacacu uauccuccug caagaguggg cuuccaggg ucuuuacugg gaagcaguua   4260 agccccccucc ucaccccuuc cuuuuucuu ucuuuacucc uuuggcuuca aaggauuuug   4320
gaaaagaaac aauaugcuuu acacucauuu ucaauuucua aauuugcagg ggauacugaa  4380
aaauacggca ggguggccuaa ggcugcugua aaguugaggg gagaggaaau cuuaagauua 4440
caagauaaaa aacgaauccc cuaaacaaaa agaacaauag aacuggucuu ccauuuugcc  4500
accuuuccug uucaugacag cuacuaaccu ggagacagua acauuucauu aaccaaagaa  4560
```

-continued

```
aguggguacac cugaccucug aagagcugag uacucaggcc acuccaauca cccuacaaga      4620
ugccaaggag gucccaggaa guccagcucc uuaaacugac gcuagucaau aaaccugggc      4680
aagugaggca agagaaauga ggaagaaucc aucgugagg ugacaggcaa ggaugaaaga       4740
caaagaagga aaagaguauc aaaggcagaa aggagaucau uaguugggu cugaaaggaa      4800 aagucuuugc uauccgacau guacugcuag uaccuguaag cauuuuaggu cccagaaugg      4860
aaaaaaaaau cagcuauugg uaauauaaua auguccuuuc ccuggaguca guuuuuuaa       4920 aaaguuaacu cuuaguuuuu acuuguuuaa uucuaaaaga gaagggagcu gaggccauuc      4980
ccuguaggag uaaagauaaa aggauaggaa aagauucaaa gcucuaauag agucacagcu      5040
uucccaggua uaaaaccuaa aauuaagaag uacaauaagc agagguggaa aaugaucuag      5100
uuccugauag cuacccacag agcaagugau uuauaaauuu gaaauccaaa cuacuuucuu      5160
aauaucacuu uggucuccau uuucccagg acaggaaaua uguccccccc uaacuuucuu      5220
gcuucaaaaa uuaaaaucca gcaucccaag aucauucuac aaguaauuuu gcacagacau      5280 cuccucacc cagugccugu cuggagcuca cccaagguca ccaaacaacu gguuguugaa      5340
ccaacugccu uaaccuucug ggggagggggg auuagcuaga cuaggagacc agaagugaau      5400
gggaaagggu gaggacuuca caauguuggc cugucagagc uugauuagaa gccaagacag      5460
uggcagcaaa ggaagacuug gcccaggaaa aaccuguggg uugugcuaau uucugccag      5520 aaaauagggu ggacagaagc uuguggggua cauggaggaa uuggggaccug guuauguugu      5580 uauucucgga cuguugaauuu uggugaugua aaacagaaua uucuguaaac cuaaugucug      5640 uauaauaau gagcguuaac acaguaaaau auucaauaag aagucaaaacu acuagggua     5700
```

<210> SEQ ID NO 21
<211> LENGTH: 5625
<212> TYPE: RNA
<213> ORGANISM: Homo sapiens
<220> FEATURE:
<221> NAME/KEY: misc_feature
<222> LOCATION: (1)..(5625)
<223> OTHER INFORMATION: LOCUS         BACE                 5625 bp
    mRNA    linear     P
    RI 05-NOV-2002 DEFINITION  Homo sapiens beta-site APP-cleaving
    enzyme (BACE), tr anscript variant d, mRNA. ACCESSION
    NM_138973; VERSION    NM_138973.1  GI:21040367
<300> PUBLICATION INFORMATION:
<308> DATABASE ACCESSION NUMBER: NM_138973
<309> DATABASE ENTRY DATE: 2002-11-05
<313> RELEVANT RESIDUES IN SEQ ID NO: (1)..(5625)

<400> SEQUENCE: 21

```
uccccagccc gcccgggagc ugcgagccgc gagcuggauu augguggccu gagcagccaa       60
cgcagccgca ggagcccgga gcccuugccc cugcccgcgc cgccgcccgc cgggggggacc     120 agggaagccg ccaccggccc gccaugcccg ccccucccag cccgccgggg agcccgcgcc     180
cgcugcccag gcuggccgcc gccgugccga guagcgggc uccggauccc agccucuccc     240
cugcucccgu gcucugcgga ucuccccuga ccgcucucca cagcccggac ccggggggcug    300 gcccagggcc cugcaggccc uggcguccug augcccccaa gcucccucuc cugagaagcc    360
accagcacca cccagacuug ggggcaggcg ccagggacgg acgugggcca gugcgagccc    420
agagggcccg aaggccgggg cccaccaugg cccaagcccu gcccuggcuc ugcuguggga   480
ugggcgcggg aguggcucgcc ugccacgcc ccccagcacgg caucggcug cccugcgca    540 gcggccuggg gggcgccccc cuggggcugc ggcugcccgg ggaagcccgac gaaagagcccg   600 aggagcccgg ccgggggggc agcuuuuguggg agauuguggu caaccugagg ggcaagucgg   660
```

-continued

| | | | | |
|---|---|---|---|---|
| ggcagggcua | cuacguggag | augaccgugg | gcagcccccc | gcagacgcuc | aacauccugg | 720 |
| uggauacagg | cagcaguaac | uuugcagugg | gugcugcccc | ccacccuuc | cugcaucgcu | 780 |
| acuaccagag | gcagcugucc | agcacauacc | gggaccuccg | gaagggugug | uaugugcccu | 840 |
| acacccaggg | caagugggaa | ggggagcugg | gcaccgaccu | gcuuguggu | gcuggcuucc | 900 |
| cccucaacca | gucugaagug | cuggccucug | ucggaggag | caugaucauu | ggagguaucg | 960 |
| accacucgcu | guacacaggc | agucucuggu | auacacccau | ccggcgggag | ugguauuaug | 1020 |
| aggucaucau | ugugcggug | gagaucaaug | gacaggaucu | gaaaauggac | ugcaaggagu | 1080 |
| acaacuauga | caagagcauu | guggacagug | gcaccaccaa | ccuucguuug | cccaagaaag | 1140 |
| uguuugaagc | ugcagucaaa | uccaucaagg | cagccuccuc | cacggagaag | uucccugaug | 1200 |
| guuucuggcu | aggagagcag | cuggugugcu | ggcaagcagg | caccaccccu | uggaacauuu | 1260 |
| ucccagucau | cucacucuac | cuaaugggug | agguuaccaa | ccagccuuc | cgcaucacca | 1320 |
| uccuuccgca | gcaauaccug | cggccagugg | aagaugugc | cacgucccaa | gacgacuguu | 1380 |
| acaaguuugc | caucucacag | ucauccacgg | gcacuguuau | gggagcuguu | aucauggagg | 1440 |
| gcuucuacgu | ugucuuugau | cgggcccgaa | aacgaauugg | cuuugcuguc | agcgcuugcc | 1500 |
| augugcacga | ugaguucagg | acggcagcgg | uggaaggccc | uuuugucacc | uuggacaugg | 1560 |
| aagacugugg | cuacaacauu | ccacagacag | augagucaac | ccucaugacc | auagccuaug | 1620 |
| ucauggcugc | caucugcgcc | cucuucaugc | ugccacucug | ccuaugguug | ugucaguggc | 1680 |
| gcugccuccg | cugccugcgc | cagcagcaug | augacuuugc | ugaugacauc | ucccugcuga | 1740 |
| agugaggagg | cccaugggca | gaagauagag | auuccccugg | accacaccuc | cgugguucac | 1800 |
| uuuggucaca | aguaggagac | acagauggca | ccuguggcca | gagcaccuca | ggacccucc | 1860 |
| caccaccaa | augccucugc | cuugauggag | aaggaaaagg | cuggcaaggu | ggguuccagg | 1920 |
| gacuguaccu | guaggaaaca | gaaaagagaa | gaaagaagca | cucugcuggc | gggaauacuc | 1980 |
| uuggucaccu | caaauuuaag | ucgggaaauu | cugcugcuug | aaacuucagc | ccugaaccuu | 2040 |
| uguccaccau | uccuuaaaau | ucccaacccc | aaaguauucu | ucuuuucuua | guuucagaag | 2100 |
| uacuggcauc | acacgcaggu | uaccuuggcg | ugugucccug | ugguacccug | gcagagaaga | 2160 |
| gaccaagcuu | guuucccugc | uggccaaagu | caguaggaga | ggaugcacag | uuugcuauuu | 2220 |
| gcuuuagaga | cagggacugu | auaaacaagc | cuaacauugg | ugcaaagauu | gcccucugaa | 2280 |
| uuaaaaaaa | aaacuagauu | gacuauuuau | acaaauggg | gcggcuggaa | agaggagaag | 2340 |
| gagggagu | acaaagacag | ggauaguggg | gaucaaagcu | aggaaaggca | gaaacacaac | 2400 |
| cacucaccag | uccuaguuuu | agaccucauc | uccaagauag | caucccaucu | cagaagaugg | 2460 |
| guguugu | caauguuuuc | uuuucugugg | uugcagccug | accaaaagug | agaugggaag | 2520 |
| ggcuuaucua | gccaaagagc | ucuuuuuag | cucucuuaaa | ugaagugccc | acuaagaagu | 2580 |
| uccacuuaac | acaugaauuu | cugccauauu | aauuucauug | ucucuaucug | aaccacccuu | 2640 |
| uauucuacau | augauaggca | gcacugaaau | uccuaaccc | ccuaagcucc | aggugcccug | 2700 |
| ugggagagca | acuggacuau | agcagggcug | ggcucugucu | uccuggucau | aggcucacuc | 2760 |
| uuuccccaa | aucuuccucu | ggagcuuugc | agccaaggug | cuaaaaggaa | uagguaggag | 2820 |
| accucuucua | ucuaauccuu | aaaagcauaa | uguugaacau | ucauucaaca | gcugaugccc | 2880 |
| uauaaccccu | gccuggauuu | cuuccuauua | ggcuauaaga | aguagcaaga | ucuuuacaua | 2940 |
| auucagagug | guuucacugc | cuuccuaccc | ucucuaaugg | ccccuccauu | uauuugacua | 3000 |
| aagcaucaca | caguggcacu | agcauuauac | caagaguaug | agaaauacag | ugcuuuaugg | 3060 |

```
cucuaacauu acugccuuca guaucaaggc ugccuggaga aaggauggca gccucagggc   3120
uuccuuaugu ccuccaccac aagagcuccu ugaugaaggu caucuuuuc cccuauccug    3180 uucuuccccu ccccgcuccu aauggacgu ggguacccag gcugguucuu gggcuaggua    3240 gugggggacca aguucauuac cucccuauca guucuagcau aguaaacuac gguaccagug   3300 uuaguggga gagcuggguu uccuaguau acccacugca uccuacuccu accggucaa      3360 cccgcugcuu ccagguaugg gaccugcuaa gguggaauu accgauaag ggagagggaa    3420 auacaaggag ggccucuggu guuccuggcc ucagccagcu gcccacaagc cauaaaccaa   3480
uaaaacaaga auacgaguc aguuuuuuau cugggucuc ucauccca cugcacuugg      3540 ugcugcuuug gcugacuggg aacaccccau aacuacagag ucugacagga gacuggaga    3600 cuguccacuu cuagcucgga acuuacugug uaaauaaacu ucagaacug cuaccaugaa   3660 gugaaaaugc cacauuuugc uuuauaauuu cucccaugu ugggaaaaac uggcuuuuuc   3720
ccagcccuuu ccagggcaua aaacucaacc ccuucgauag caagucccau cagccuauua   3780 uuuuuuaaa gaaaacuugc acuuguuuu cuuuuacag uuacuuccuu ccugcccaa     3840 aauuauaaac ucuaagugua aaaaaagc uuaacaacag cuucuugcuu guaaaauau    3900 guauuauaca ucuguauuuu uaaauucugc uccugaaaaa ugacugucc auucuccacu   3960 cacugcauuu ggggccuuuc ccauuggucu gcaugucuu uaucauugca ggccagugga   4020
cagagggaga agggagaaca ggggucgcca acacugugu ugcuuucuga cugauccuga  4080
acaagaaaga guaacacuga ggcgcucgcu cccaugcaca acucuccaaa acacuuaucc   4140
uccugcaaga gugggcuuuc cagggucuuu acugggaagc aguuaagccc ccuccucacc   4200
ccuuccuuuu uucuuucuuu acuccuuugg cuucaaagga uuuugaaaaa gaaacaauau   4260
gcuuuacacu cauuuucaau uucuaaauuu gcagggaua cugaaaaaua cggcaggugg   4320
ccuaaggcug cuguaaaguu gagggggagag gaaaucuuaa gauuacaaga uaaaaacga    4380 auccccuaaa caaaaagaac aauagaacug gucuuccauu uugccaccuu uccuguucau  4440
gacagcuacu aaccuggaga caguaacauu ucauuaacca agaaaaagugg gucaccugac  4500 cucugaagag cugaguacuc aggccacucc aaucacccua caagaugcca aggaggucccc  4560 aggaagucca gcuccuuaaa cugacgcuag ucaauaaacc ugggcaagug aggcaagaga   4620
aaugaggaag aauccaucug ugaggugaca ggcaaggaug aaagacaaag aaggaaaaga  4680
guaucaaagg cagaaaggag aucauuuagu ugggucugaa aggaaaaguc uuugcuaucc   4740
gacauguacu gcuaguaccu guaagcauuu uaggucccag aauggaaaaa aaaaucagcu  4800
auugguaaua uaauaaugucg cuuucccugg agucaguuuu uuuaaaaagu uaacucuuag  4860
uuuuuacuug uuuaauucua aaagagaagg gagcugaggc cauucccugu aggaguaaag   4920
auaaaaggau aggaaaagau ucaaagcucu aauagaguca cagcuuuccc agguauaaaa  4980
ccuaaaauua agaaguacaa uaagcagagg uggaaaauga ucuaguuccu gauagcuacc  5040
cacagagcaa gugauuuaua aauuugaaau ccaaacuacu ucuuaauau cacuuugguc   5100 uccauuuuuc ccaggacagg aaauaugccc ccccuaacu uucuugcuuc aaaaauuaaa   5160
auccagcauc ccaagaucau ucuacaagua auuuugcaca gacaucuccu caccccagug  5220
ccugucugga gcucacccaa ggucaccaaa caacuugguu gugaaccaac ugccuuaacc   5280 uucggggga ggggauuag cuagacuagg agaccagaag ugaaugggaa agggugagga    5340
cuucacaaug uuggccuguc agagcuugau uagaagccaa gacaguggca gcaaaggaag   5400
acuuggccca ggaaaaaccu gugggguugug cuaauuucug uccagaaaau agggugggaca  5460
```

```
gaagcuugug ggguacaugg aggaauuggg accugguuau guuguuauuc ucggacugug    5520
aauuuuggug auguaaaaca gaauauucug uaaaccuaau gucuguauaa auaaugagcg    5580
uuaacacagu aaaauauuca auaagaaguc aaacuacuag gguua                   5625
```

```
<210> SEQ ID NO 22
<211> LENGTH: 3880
<212> TYPE: RNA
<213> ORGANISM: Mus musculus
<220> FEATURE:
<221> NAME/KEY: misc_feature
<222> LOCATION: (1)..(3880)
<223> OTHER INFORMATION: LOCUS         Bace              3880 bp
      mRNA       linear     R
      OD 07-JAN-2002 DEFINITION  Mus musculus beta-site APP cleaving
      enzyme (Bace), mR NA. ACCESSION    NM_011792; VERSION
      NM_011792.2  GI:6857758
<300> PUBLICATION INFORMATION:
<308> DATABASE ACCESSION NUMBER: NM_011792
<309> DATABASE ENTRY DATE: 2002-01-07
<313> RELEVANT RESIDUES IN SEQ ID NO: (1)..(3880)

<400> SEQUENCE: 22
ccccagccug ccuaggugcu gggagccggg agcuggauua uggugggccug agcagccgac    60 gcagccgcag gagcugggag ucccucacgc ugcaaagucc gccuggaaga cccugaaagc   120
ugcaggcucc gauagccaug cccgccccuc ccagccccac aaggggcccg auccccccgc   180
ugaggcuggc ggucgccguc cagauuuagc uggguccccc ggaucgccau cguccucuuc   240
ucucgugcgc uacagauuuc uccugcccac ucuccaccgc cgggagcagg aacugaucga   300
aggggccugc agacucugca guccugaugc ccccgaggcc gcuccugga gagaagccac    360 caccacccag acuuaggggc aggcaagagg gacagucacc aaccggacca caaggcccgg   420
gcucacuaug gccccagcgc ugcacuggcu ccugcuaugg guggcucgg gaaugcugcc   480 ugcccaggga acccaucucg gcauccggcu gccccuucgc agcggccugg cagggccacc   540
ccugggccug aggcugcccc gggagaccga cgaggaaucg gaggagccug gccggagagg   600
cagcuuugug gagaugguggg acaaccuuag ggggaaaaguc cggccagggcu acuaugugga   660 gaugaccgua ggcagccccc cacagacgcu caacauccug guggacacgg gcaguaguaa   720
cuuugcagug ggggcugccc cacacccuuu ccugcaucgc uacuaccaga ggcagcuguc   780
cagcacauau cgagaccucc gaaagggugu guaugugccc uacacccagg caaguggga   840 gggggaacug ggcaccgacc uggugagcau cccucauggc cccaacguca cugugcgugc   900 caaacauugcu gccaucacug aaucggacaa guucuucauc aauggguucca acugggaggg   960 cauccuaggg cuggccuaug cugagauugc caggcccgac gacucuuugg agcccuucuu  1020 ugacuccucug gugaagcaga cccacauucc aaucaucuuu ucccugcagc ucuggggcgc  1080
uggcuucccc cucaaccaga ccgaggcacu ggccucggug ggaggggagca ugaucauugg  1140 ugguaucgac cacucgcuau acacgggcag ucucugguca cacccauccc ggcgggagug  1200
guauuaugaa gugaucauug uacgugugga aaucaauggu caagaucuca agauggacug  1260
caaggaguac aacuacgaca agagcauugu ggacaguggg accaccaacc uucgcuugcc  1320
caagaaagua uuugaagcug ccgucaaguc caucaaggca gccucuucga cggagaaguu  1380
cccggauggc uuuuggcuag gggagcagcu ggugugcugg caagcaggca cgacccccuug  1440 gaacauuuuc ccagucauuu cacuuuaccu caugggugaa gucaccaauc agucccuccg  1500
caucaccauc cuuccucagc aauaccuacg gccgguggag gacgugggcca cgucccaaga  1560 cgacuguuac aaguucgcug ucucacaguc auccacgggc acuguuaugg gagccgucau  1620
```

```
cauggaaggu uucuaugucg ucuucgaucg agcccgaaag cgaauuggcu uugcugucag    1680
cgcuugccau gugcacgaug aguucaggac ggcggcagug aagguccgu uuguuacggc     1740 agacauggaa gacuguggcu acaacauucc ccagacagau gagucaacac uuaugaccau    1800
agccuauguc auggcggcca ucugcgcccu cuucauguug ccacucugcc ucaugguaug    1860
ucaguggcgc ugccugcguu gccugcgcca ccagcacgau gacuuugcug augacaucuc    1920
ccugcucaag uaaggaggcc cgugggcaga ugauggagac gccccuggac cacaucuggg    1980
ugguucccuu uggucacaug aguuggagcu auggauggua ccugugccca gagcaccuca    2040
ggacccucac caaccugcca augcuucugg cgugacagaa cagagaaauc aggcaagcug    2100
gauuacaggg cuugcaccug uaggacacag agagggaag gaagcagcgu ucugguggca     2160
ggaauauccu uagacaccac aaacuugagu uggaaauuuu gcugcuugaa gcuucagccc    2220
ugacccucug cccagcaucc uuuagagucu ccaaccucga guauucuuuc ugccuucca    2280 gaaguacugg ugucauacuc aggcuacccg gcaugugucc cugugguacc cuggcagaga    2340
aagggccaau cuucauuucc ccugcuggcc aaagucagca gaagaaagug aaguuugcca    2400
guugcuuuag ugauagggac uugcagacuc aagccuacac ugguacaaag acugcgucuu    2460
gagauaaaca gaaccuaug cgaugcgaau guuuauacuc cuggggcag ucaagaugag      2520 gagacaggau aggauagaga caggaaggag augguagcaa aacugggaaa ggcagaacuc    2580
ugaucacuuu cuaguuccaa guuuagacuc aucuccaaga cagaagccca ucuggacuaa    2640
gagguaucau uccccaaugu gccguggguu guagucugaa cugaaaugaa augggggaaa    2700
aagggcuuau uagccaaaga gcucuuuuua acacucuuag aggaacagug cucaugagaa    2760
aagucccacu ggacagauga auccuaaucu uguuaauucu gucucucucu gcuucuucaa    2820
caugcuaagu ggcaccaaaa ugacccaacc ccaaggucuu aggugcccua ugggacaaca    2880
guuagaauau guagggcua gggauggucu cccagcaua gguucacucc aaccaaggug       2940
cuaaaaggaa cagacaggag aaguccuccu cucugaucca caaaggcaga gcccucaaga    3000
uucauccagc cagggguuagg gcugaugcau uugccucugc cuggauuuug uuuuuauuuu   3060
cuuucuuuuu gcccaagugg guacaaaacg auaagcucuu uauggaauac ugagugggu     3120 cauuccucuc uugcccucuc caauggcccc ucuauuuauc uggcuaagga aacaccacgc    3180
auuggcuagu auuaaacagc aacguaaga uagagggcuu ucuguucuau gucauugccu     3240
ucaguaucaa ggcugccugg agaaaggaug gcagccucag ggcuuccuua cuucuucuc     3300 cuuuccugac agagcagccu uucuguccug cucucgcgc cccucccaa uauaauccau      3360 ggguacccag gcugguucuu gggcuagguu gugggggcca cacucaccuc uucccugcca    3420
guucuaacac gacagacaug aagccagugu agugggaag agcuggguuu ucccaggaug     3480
accacugcau ccucuccugg uacgcucuac acugcuuuca ggcuggggac cugccaagug    3540
ugggacaguu gaugaggaag agacauuagc agggccucug gaguugcugg cccagccagc   3600
ugcccacaag ccauaaacca auaaauaag aauccugcgu cacaguuucc agcugggucc    3660
ucuuccuugc cccgcacug gugcugcucu ggcugaguag gaauacaccc acagacugcc     3720
aggaagaugg agacuguccg cuuccggcuc agaacuacag uguaauuaag cuuccaggau    3780
cacuaccaug aaaacgccgc auucugcuuu aucauuucua cccauguugg gaaaaacugg    3840
cuuuuucccc auuucuuuac agggcaaaaa aaaaaaaaa                           3880
```

<210> SEQ ID NO 23
<211> LENGTH: 1096
<212> TYPE: RNA

```
<213> ORGANISM: Homo sapiens
<220> FEATURE:
<221> NAME/KEY: misc_feature
<222> LOCATION: (1)..(1096)
<223> OTHER INFORMATION: LOCUS       SNCA              1096 bp
      mRNA    linear    P
      RI 05-NOV-2002 DEFINITION  Homo sapiens synuclein, alpha (non A4
      component of am yloid precursor) (SNCA), transcript variant
      NACP112, mRNA. ACCESSION   NM_007308: VERSION    NM_007308.1
<300> PUBLICATION INFORMATION:
<308> DATABASE ACCESSION NUMBER: NM_007308
<309> DATABASE ENTRY DATE: 2002-12-05
<313> RELEVANT RESIDUES IN SEQ ID NO: (1)..(1096)

<400> SEQUENCE: 23
gaauucauua gccauggaug uauucaugaa aggacuuuca aaggccaagg agggaguugu     60
ggcugcugcu gagaaaacca aacagggugu ggcagaagca gcaggaaaga caaaagaggg    120
uguucucuau guaggcucca aaaccaagga gggaguggug caugguguga caacagugge    180 ugagaagacc aaagagcaag ugacaaaugu uggaggagca guggugacgg gugugacagc    240
aguagcccag aagacagugg agggagcagg gagcauugca gcagccacug gcuuugucaa    300
aaaggaccag uugggcaagg aagggusaua agacuacgaa ccugaagccu aagaaauauc    360 uuugcucucca guucuugag aucugcugac agauguucca uccuguacaa gugcucaguu    420
ccaaugugcc cagucaugac auuucucaaa guuuuuacag uguaucucga agucuuccau    480
cagcagugau ugaaguaucu guaccugccc ccacucagca uuucggugcu ucccuuucac    540
ugaagugaau acauugguagc agggucuuug ugugcguqgg auuuugugc uucaaucuac    600 gauguuaaaa caauuaaaaa acaccuaagu gacuaccacu uauuucuaaa uccucacuau    660
uuuuuuguug cuguuguuca gaaguuguua gugauuugcu aucauauauu auaagauuuu    720
uaggugucuu uuaaugauac ugucuaagaa uaaugacgua uugugaaauu uguuaauaua    780 uauaauaucuu aaaaauaugu gagcaugaaa cuaugcaccu auaaauacua aauaugaaau    840
uuuaccauuu ugcgaugugu uuuauucacu uguguuugua uauaaugqu gagaauuaaa    900 auaaaacguu aucucauugc aaaaauauuu uauuuuuauc ccaucucacu uuaauaauaa    960
aaaucaugcu uauaagcaac augaauuaag aacugacaca aaggacaaaa auauaaaguu    1020
auuaauagcc auuugaagaa ggaggaauuu uagaagaggu agagaaaaug gaacauuaac    1080
ccuacacucg gaauuc                                                   1096

<210> SEQ ID NO 24
<211> LENGTH: 21
<212> TYPE: DNA
<213> ORGANISM: Mus musculus
<220> FEATURE:
<221> NAME/KEY: misc_feature
<222> LOCATION: (0803)..(0803)
<223> OTHER INFORMATION: Starting position within mouse BACE1 cDNA
      (Genbank Accession NM_011792) and corresponding human sequences.
      DNA sequence corresponding to the therapeutic siRNA starting at
      base 0803. The two 5' nucleotides AA are optional in MB0803.

<400> SEQUENCE: 24
aagggtgtgt atgtgccta c                                                21

<210> SEQ ID NO 25
<211> LENGTH: 21
<212> TYPE: DNA
<213> ORGANISM: Mus Musculus
<220> FEATURE:
<221> NAME/KEY: misc_feature
<222> LOCATION: (1663)..(1663)
<223> OTHER INFORMATION: Starting position within mouse BACE1 cDNA
```

```
        (Genbank Accession NM_011792) and corresponding human sequences.
        DNA sequence corresponding to the therapeutic siRNA starting at
        base 1663. The two 5' nucleotides AA are optional in MB1663.

<400> SEQUENCE: 25
aattggcttt gctgtcagcg c                                              21

<210> SEQ ID NO 26
<211> LENGTH: 21
<212> TYPE: DNA
<213> ORGANISM: Mus Musculus
<220> FEATURE:
<221> NAME/KEY: misc_feature
<222> LOCATION: (1749)..(1749)
<223> OTHER INFORMATION: Starting position within mouse BACE1 cDNA
        (Genbank Accession NM_011792) and corresponding human sequences.
        DNA sequence corresponding to the therapeutic siRNA starting at
        base 1749. The two 5' nucleotides AA are optional in MB1749.

<400> SEQUENCE: 26
aagactgtgg ctacaacatt c                                              21

<210> SEQ ID NO 27
<211> LENGTH: 21
<212> TYPE: DNA
<213> ORGANISM: Mus Musculus
<220> FEATURE:
<221> NAME/KEY: misc_feature
<222> LOCATION: (3249)..(3249)
<223> OTHER INFORMATION: Starting position within mouse BACE1 cDNA
        (Genbank Accession NM_011792) and corresponding human sequences.
        DNA sequence corresponding to the therapeutic siRNA starting at
        base 3249.
<220> FEATURE:
<221> NAME/KEY: misc_feature
<222> LOCATION: (3249)..(3249)
<223> OTHER INFORMATION: Starting position within mouse BACE1 cDNA
        (Genbank Accession NM_011792) and corresponding human sequences.
        DNA sequence corresponding to the therapeutic siRNA starting at
        base 3249.  The two 5' nucleotides AA are optional in MB3249.

<400> SEQUENCE: 27
aaggctgcct ggagaaagga t                                              21

<210> SEQ ID NO 28
<211> LENGTH: 21
<212> TYPE: DNA
<213> ORGANISM: Mus Musculus
<220> FEATURE:
<221> NAME/KEY: misc_feature
<222> LOCATION: (0916)..(0916)
<223> OTHER INFORMATION: Starting position within mouse BACE1 cDNA
        (Genbank Accession NM_011792) and corresponding human sequences.
        DNA sequence corresponding to the therapeutic siRNA starting at
        base 0916. The two 5' nucleotides CA are optional in DhMB0918.

<400> SEQUENCE: 28
cactgaatcg gacaagttct t                                              21

<210> SEQ ID NO 29
<211> LENGTH: 21
<212> TYPE: DNA
<213> ORGANISM: Mus Musculus
<220> FEATURE:
<221> NAME/KEY: misc_feature
<222> LOCATION: (1129)..(1129)
<223> OTHER INFORMATION: Starting position within mouse BACE1 cDNA
        (Genbank Accession NM_011792) and corresponding human sequences.
        DNA sequence corresponding to the therapeutic siRNA starting at
        base 1129. The two 5' nucleotides CA are optional in DhMB1131.

<400> SEQUENCE: 29
```
catgatcatt ggtggtatcg a                                              21

<210> SEQ ID NO 30
<211> LENGTH: 21
<212> TYPE: DNA
<213> ORGANISM: Mus Musculus
<220> FEATURE:
<221> NAME/KEY: misc_feature
<222> LOCATION: (1231)..(1231)
<223> OTHER INFORMATION: Starting position within mouse BACE1 cDNA
      (Genbank Accession NM_011792) and corresponding human sequences.
      DNA sequence corresponding to the therapeutic siRNA starting at
      base 1231.
<220> FEATURE:
<221> NAME/KEY: misc_feature
<222> LOCATION: (1231)..(1231)
<223> OTHER INFORMATION: Starting position within mouse BACE1 cDNA
      (Genbank Accession NM_011792) and corresponding human sequences.
      DNA sequence corresponding to the therapeutic siRNA starting at
      base 1231. The two 5' nucleotides AA are optional in DhMB1233.

<400> SEQUENCE: 30
aatcaatggt caagatctca a                                              21

<210> SEQ ID NO 31
<211> LENGTH: 21
<212> TYPE: DNA
<213> ORGANISM: Mus Musculus
<220> FEATURE:
<221> NAME/KEY: misc_feature
<222> LOCATION: (1507)..(1507)
<223> OTHER INFORMATION: Starting position within mouse BACE1 cDNA
      (Genbank Accession NM_011792) and corresponding human sequences.
      DNA sequence corresponding to the therapeutic siRNA starting at
      base 1507. The two 5' nucleotides CA are optional in DhMB1509.

<400> SEQUENCE: 31
catccttcct cagcaatacc t                                              21

<210> SEQ ID NO 32
<211> LENGTH: 21
<212> TYPE: DNA
<213> ORGANISM: Mus musculus
<220> FEATURE:
<221> NAME/KEY: misc_feature
<222> LOCATION: (0683)..(0683)
<223> OTHER INFORMATION: Starting position within mouse BACE1 cDNA
      (Genbank Accession NM_011792) and corresponding human sequences.
      DNA sequence corresponding to the therapeutic siRNA starting at
      base 0683. The two 5' nucleotides CA are optional in SEC0683.

<400> SEQUENCE: 32
cagacgctca acatcctggt g                                              21

<210> SEQ ID NO 33
<211> LENGTH: 21
<212> TYPE: DNA
<213> ORGANISM: Mus musculus
<220> FEATURE:
<221> NAME/KEY: misc_feature
<222> LOCATION: (1722)..(1722)
<223> OTHER INFORMATION: Starting position within mouse BACE1 cDNA
      (Genbank Accession NM_011792) and corresponding human sequences.
      DNA sequence corresponding to the therapeutic siRNA starting at
      base 1722. The two 5' nucleotides AA are optional in SEC1722.

<400> SEQUENCE: 33
aaggtccgtt tgttacggca g                                              21

<210> SEQ ID NO 34

```
<211> LENGTH: 21
<212> TYPE: DNA
<213> ORGANISM: Mus musculus
<220> FEATURE:
<221> NAME/KEY: misc_feature
<222> LOCATION: (2163)..(2163)
<223> OTHER INFORMATION: Starting position within mouse BACE1 cDNA
      (Genbank Accession NM_011792) and corresponding human sequences.
      DNA sequence corresponding to the therapeutic siRNA starting at
      base 2163. The two 5' nucleotides AA are optional in SEC2163.

<400> SEQUENCE: 34
aatatcctta gacaccacaa a                                              21

<210> SEQ ID NO 35
<211> LENGTH: 21
<212> TYPE: DNA
<213> ORGANISM: Mus musculus
<220> FEATURE:
<221> NAME/KEY: misc_feature
<222> LOCATION: (2466)..(2466)
<223> OTHER INFORMATION: Starting position within mouse BACE1 cDNA
      (Genbank Accession NM_011792) and corresponding human sequences.
      DNA sequence corresponding to the therapeutic siRNA starting at
      base 2466. The two 5' nucleotides AA are optional in SEC2466.

<400> SEQUENCE: 35
aaacaagaac ctatgcgatg c                                              21

<210> SEQ ID NO 36
<211> LENGTH: 21
<212> TYPE: DNA
<213> ORGANISM: Mus musculus
<220> FEATURE:
<221> NAME/KEY: misc_feature
<222> LOCATION: (2473)..(2473)
<223> OTHER INFORMATION: Starting position within mouse BACE1 cDNA
      (Genbank Accession NM_011792) and corresponding human sequences.
      DNA sequence corresponding to the therapeutic siRNA starting at
      base 2473. The two 5' nucleotides AA are optional in SEC2473.

<400> SEQUENCE: 36
aacctatgcg atgcgaatgt t                                              21

<210> SEQ ID NO 37
<211> LENGTH: 22
<212> TYPE: DNA
<213> ORGANISM: Mus musculus
<220> FEATURE:
<221> NAME/KEY: misc_feature
<223> OTHER INFORMATION: Oligonucleotide MB1749A to construct the DNA
      encoding for a hairpin loop of RNA corresponding to MB1749.

<400> SEQUENCE: 37
gaagactgtg gctacaacat tc                                             22

<210> SEQ ID NO 38
<211> LENGTH: 38
<212> TYPE: DNA
<213> ORGANISM: Mus musculus
<220> FEATURE:
<221> NAME/KEY: misc_feature
<223> OTHER INFORMATION: Oligonucleotide MB1749B to construct the DNA
      encoding for a hairpin loop of RNA corresponding to MB1749.

<400> SEQUENCE: 38
ttcaagagag aatgttgtag ccacagtctt cttttttg                            38

<210> SEQ ID NO 39
<211> LENGTH: 35
```

```
<212> TYPE: DNA
<213> ORGANISM: Mus musculus
<220> FEATURE:
<221> NAME/KEY: misc_feature
<223> OTHER INFORMATION: Oligonucleotide MB1749C to construct the DNA
      encoding for a hairpin loop of RNA corresponding to MB1749.

<400> SEQUENCE: 39
tctcttgaag aatgttgtag ccacagtctt cggcc                              35

<210> SEQ ID NO 40
<211> LENGTH: 33
<212> TYPE: DNA
<213> ORGANISM: Mus musculus
<220> FEATURE:
<221> NAME/KEY: misc_feature
<223> OTHER INFORMATION: Oligonucleotide MB1749D to construct the DNA
      encoding for a hairpin loop of RNA corresponding to MB1749.

<400> SEQUENCE: 40
aattcaaaaa agaagactgt ggctacaaca ttc                                33

<210> SEQ ID NO 41
<211> LENGTH: 21
<212> TYPE: DNA
<213> ORGANISM: Homo sapiens
<220> FEATURE:
<221> NAME/KEY: misc_feature
<222> LOCATION: (0188)..(0188)
<223> OTHER INFORMATION: Oligonucleotide MD0188 to construct the DNA
      encoding for siRNA starting at position 0188 within human
      Huntington cDNA(Genbank Accession NM_002111.3.  The first two 5'
      nucleotides AA are optional in MD0188

<400> SEQUENCE: 41
aagatggacg gccgctcagg t                                             21

<210> SEQ ID NO 42
<211> LENGTH: 21
<212> TYPE: DNA
<213> ORGANISM: Homo sapiens
<220> FEATURE:
<221> NAME/KEY: misc_feature
<222> LOCATION: (0358)..(0358)
<223> OTHER INFORMATION: Oligonucleotide MD0358 to construct the DNA
      encoding for siRNA starting at position 0358 within human
      Huntington cDNA(Genbank Accession NM_002111.3.  The first two 5'
      nucleotides AA are optional in MD0358,

<400> SEQUENCE: 42
aagtccttcc agcagcagca g                                             21

<210> SEQ ID NO 43
<211> LENGTH: 21
<212> TYPE: DNA
<213> ORGANISM: Homo sapiens
<220> FEATURE:
<221> NAME/KEY: misc_feature
<222> LOCATION: (0813)..(0813)
<223> OTHER INFORMATION: Oligonucleotide MD0813 to construct the DNA
      encoding for siRNA starting at position 0813 within human
      Huntington cDNA (Genbank Accession NM_002111.3.).  The first two
      5' nucleotides AA are optional in MD0813.

<400> SEQUENCE: 43
aaggttacag ctcgagctct a                                             21

<210> SEQ ID NO 44
<211> LENGTH: 21
<212> TYPE: DNA
```

```
<213> ORGANISM: Homo sapiens
<220> FEATURE:
<221> NAME/KEY: misc_feature
<222> LOCATION: (1066)..(1066)
<223> OTHER INFORMATION: Oligonucleotide M1066 to construct the DNA
      encoding for siRNA starting at position 1066 within human
      Huntington cDNA (Genbank Accession NM_002111.3.).  The two 5'
      nucleotides AA are optional in M1066.

<400> SEQUENCE: 44
aaggttttgt taaaggcctt c                                              21

<210> SEQ ID NO 45
<211> LENGTH: 21
<212> TYPE: DNA
<213> ORGANISM: Homo sapiens
<220> FEATURE:
<221> NAME/KEY: misc_feature
<222> LOCATION: (1639)..(1639)
<223> OTHER INFORMATION: Oligonucleotide M1639 to construct the DNA
      encoding for siRNA starting at position 1639 within human
      Huntington cDNA (Genbank Accession NM_002111.3.).  The two 5'
      nucleotides AA are optional in M1639.

<400> SEQUENCE: 45
aaaggcaaag tgctcttagg a                                              21

<210> SEQ ID NO 46
<211> LENGTH: 21
<212> TYPE: DNA
<213> ORGANISM: Homo sapiens
<220> FEATURE:
<221> NAME/KEY: misc_feature
<222> LOCATION: (2060)..(2060)
<223> OTHER INFORMATION: Oligonucleotide M2060 to construct the DNA
      encoding for siRNA starting at position 2060 within human
      Huntington cDNA (Genbank Accession NM_002111.3.).  The two 5'
      nucleotides AA are optional in M2060.

<400> SEQUENCE: 46
aaattgtgtt agacggtacc g                                              21

<210> SEQ ID NO 47
<211> LENGTH: 21
<212> TYPE: DNA
<213> ORGANISM: Homo sapiens
<220> FEATURE:
<221> NAME/KEY: misc_feature
<222> LOCATION: (2714)..(2714)
<223> OTHER INFORMATION: Oligonucleotide M2714 to construct the DNA
      encoding for siRNA starting at position 2714 within human
      Huntington cDNA (Genbank Accession NM_002111.3.).  The two 5'
      nucleotides CA are optional in M2714.

<400> SEQUENCE: 47
caggaaatac attttctttg g                                              21

<210> SEQ ID NO 48
<211> LENGTH: 846
<212> TYPE: DNA
<213> ORGANISM: Ovis aries

<400> SEQUENCE: 48
atggcgaccc tggaaaagct gatgaaggcc ttcgagtccc tcaagtcctt ccagcagcag     60
cagcagcagc agcagcagca gcagcagcaa cagccgccac cgccgccacc cggcccggct    120
gtggctgagg agccgctgca ccgaccaaag aaagagctct cagccaccaa gaaagaccgc    180
gtgaaccact gtctgacaat ctgtgaaaac atcgtcgcgc agtctctcag aaattctcca    240
```

```
gaatttcaga aacttctggg catcgctatg gaacttttc tgctgtgcag tgatgacgca    300
gagtcagatg tcaggatggt ggctgacgaa tgcctcaaca agtcataaa agctttgatg    360 gactctaatc ttccgaggtt gcagctagaa ctctacaagg aaattaaaaa gaacggcgcc    420
ccgcggagcc tgcgcgcggc cctctggagg ttcgccgagc tggctcacct ggtccggcct    480
cagaagtgca ggccgtacct ggtgaacctg ttgccctgcc tgacgcgcac aagcaagaga    540
cccgaggagt ccgtccagga gacgctggct gcagcgatcc ctaaaattat ggcttctttt    600
ggcaactttg cgaacgacaa tgagattaag gttctgttga aggctttcat cgcgaacctg    660
aagtccagtt ccccgactgt gcggcggacc gcggcgggct cagtggtcag catctgccag    720
cactccagga ggacgcagta cttttacagc tggctgctca gcgtgctcct aggtttgctg    780
gtccccgtgg aggaggagca ccccacccctg ctgatcctcg gcgtcctgct caccctgagg    840
tatctg                                                              846
```

<210> SEQ ID NO 49
<211> LENGTH: 21
<212> TYPE: DNA
<213> ORGANISM: Ovis aries
<220> FEATURE:
<221> NAME/KEY: misc_feature
<222> LOCATION: (205)..(205)
<223> OTHER INFORMATION: Oligonucleotide EB1 to construct the DNA
      encoding for siRNA starting at position 205 in sheep Huntington
      sequence and starting position 643 of the (partially) homologous
      sequence in the human Huntington gene (NM_00211.3). The two 5'
      nucleotides GA are optio

<400> SEQUENCE: 49
gaaaacatcg tcgcgcagtc t                                              21

<210> SEQ ID NO 50
<211> LENGTH: 21
<212> TYPE: DNA
<213> ORGANISM: Ovis aries
<220> FEATURE:
<221> NAME/KEY: misc_feature
<222> LOCATION: (328)..(328)
<223> OTHER INFORMATION: Oligonucleotide EB2 to construct the DNA
      encoding for siRNA starting at position 328 in sheep Huntington
      sequence and starting position 766 of the (partially) homologous
      sequence in the human Huntington gene (NM_00211.3). The two 5'
      nucleotides GA are optio

<400> SEQUENCE: 50
gaatgcctca acaaagtcat a                                              21

<210> SEQ ID NO 51
<211> LENGTH: 21
<212> TYPE: DNA
<213> ORGANISM: Ovis aries
<220> FEATURE:
<221> NAME/KEY: misc_feature
<222> LOCATION: (603)..(603)
<223> OTHER INFORMATION: Oligonucleotide EB3 to construct the DNA
      encoding for siRNA starting at position 603 in sheep Huntington
      sequence and starting position 1041 of the (partially) homologous
      sequence in the human Huntington gene (NM_00211.3). The two 5'
      nucleotides CA are opti

<400> SEQUENCE: 51
caactttgcg aacgacaatg a                                              21

<210> SEQ ID NO 52
<211> LENGTH: 21
<212> TYPE: DNA

```
<213> ORGANISM: Ovis aries
<220> FEATURE:
<221> NAME/KEY: misc_feature
<222> LOCATION: (628)..(628)
<223> OTHER INFORMATION: Oligonucleotide EB4 to construct the DNA
      encoding for siRNA starting at position 628 in sheep Huntington
      sequence and starting position 1066 of the (partially) homologous
      sequence in the human Huntington gene (NM_00211.3). The two 5'
      nucleotides AA are opti

<400> SEQUENCE: 52
aaggttctgt tgaaggcttt c                                              21

<210> SEQ ID NO 53
<211> LENGTH: 21
<212> TYPE: DNA
<213> ORGANISM: Ovis aries
<220> FEATURE:
<221> NAME/KEY: misc_feature
<223> OTHER INFORMATION: Oligonucleotide EB5 to construct the DNA
      encoding for siRNA starting at position 367 in sheep Huntington
      sequence and starting position 805 of the (partially) homologous
      sequence in the human Huntington gene (NM_00211.3). The two 5'
      nucleotides AA are optio

<400> SEQUENCE: 53
aatcttccga ggttgcagct a                                              21

<210> SEQ ID NO 54
<211> LENGTH: 1500
<212> TYPE: DNA
<213> ORGANISM: Homo sapiens

<400> SEQUENCE: 54
ttgctgtgtg aggcagaacc tgcgggggca ggggcgggct ggttccctgg ccagccattg      60
gcagagtccg caggctaggg ctgtcaatca tgctggccgg cgtggccccg cctccgccgg     120
cgcggccccg cctccgccgg cgcacgtctg ggacgcaagg cgccgtgggg gctgccggga     180
cgggtccaag atggacggcc gctcaggttc tgcttttacc tgcggcccag agccccattc     240
attgccccgt gctgagcgg cgccgcgagt cggcccgagg cctccgggga ctgccgtgcc     300
gggcgggaga ccgccatggc gaccctggaa aagctgatga aggccttcga gtccctcaag     360
tccttccagc agcagcagca gcagcagcag cagcagcagc agcagcagca gcagcagcag     420
cagcagcagc aacagccgcc accgccgccg ccgccgccgc cgcctcctca gcttcctcag     480
ccgccgccgc aggcacagcc gctgctgcct cagccgcagc cgcccccgcc gccgcccccg     540
ccgccacccg gcccggctgt ggctgaggag ccgctgcacc gaccaaagaa agaactttca     600
gctaccaaga agaccgtgt gaatcattgt ctgacaatat gtgaaaacat agtggcacag     660
tctgtcagaa attctccaga atttcagaaa cttctgggca tcgctatgga acttttctg     720 ctgtgcagtg atgacgcaga gtcagatgtc aggatggtgg ctgacgaatg cctcaacaaa     780
gttatcaaag ctttgatgga ttctaatctt ccaaggttac agctcgagct ctataaggaa     840
attaaaaaga atggtgcccc tcggagtttg cgtgctgccc tgtggaggtt tgctgagctg     900
gctcacctgg ttcggcctca gaaatgcagg ccttacctgg tgaaccttct gccgtgcctg     960
actcgaacaa gcaagagacc cgaagaatca gtccaggaga ccttggctgc agctgttccc    1020
aaaattatgg cttcttttgg caattttgca atgacaatg aaattaaggt tttgttaaag    1080
gccttcatag cgaacctgaa gtcaagctcc ccaccattc ggcggacagc ggctggatca    1140
gcagtgagca tctgccagca ctcaagaagg acacaatatt tctatagttg gctactaaat    1200
gtgctcttag gcttactcgt tcctgtcgag gatgaacact ccactctgct gattcttggc    1260
```

```
gtgctgctca ccctgaggta tttggtgccc ttgctgcagc agcaggtcaa ggacacaagc    1320
ctgaaaggca gcttcggagt gacaaggaaa gaaatggaag tctctccttc tgcagagcag    1380
cttgtccagg tttatgaact gacgttacat catacacagc accaagacca caatgttgtg    1440
accggagccc tggagctgtt gcagcagctc ttcagaacgc ctccacccga gcttctgcaa    1500

<210> SEQ ID NO 55
<211> LENGTH: 20
<212> TYPE: DNA
<213> ORGANISM: Homo sapiens

<400> SEQUENCE: 55
tggtgttcaa tgcttttccc                                                 20

<210> SEQ ID NO 56
<211> LENGTH: 20
<212> TYPE: DNA
<213> ORGANISM: Homo sapiens

<400> SEQUENCE: 56
gcgtcttgta gttcccgtca                                                 20

<210> SEQ ID NO 57
<211> LENGTH: 60
<212> TYPE: DNA
<213> ORGANISM: Homo sapiens

<400> SEQUENCE: 57
gaagactgtg gctacaacat tcttcaagag agaatgttgt agccacagtc ttcttttttg    60

<210> SEQ ID NO 58
<211> LENGTH: 68
<212> TYPE: DNA
<213> ORGANISM: Homo sapiens

<400> SEQUENCE: 58
aattcaaaaa agaagactgt ggctacaaca ttctctcttg aagaatgttg tagccacagt    60
cttcggcc                                                              68

<210> SEQ ID NO 59
<211> LENGTH: 22
<212> TYPE: DNA
<213> ORGANISM: Homo sapiens

<400> SEQUENCE: 59
tgacacagcc gctactacat tg                                              22

<210> SEQ ID NO 60
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 60
aagtagggca catacacacc ccctgtctc                                       29

<210> SEQ ID NO 61
<211> LENGTH: 29
<212> TYPE: DNA
<213> ORGANISM: Artificial Sequence
<220> FEATURE:
<223> OTHER INFORMATION: DNA Oligonucleotides for producing siRNA
```

```
<400> SEQUENCE: 61
aagggtgtgt atgtgcccta ccctgtctc                                    29

<210> SEQ ID NO 62
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 62
aagcgctgac agcaaagcca acctgtctc                                    29

<210> SEQ ID NO 63
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 63
aattggcttt gctgtcagcg ccctgtctc                                    29

<210> SEQ ID NO 64
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 64
aagaatgttg tagccacagt ccctgtctc                                    29

<210> SEQ ID NO 65
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 65
aagactgtgg ctacaacatt ccctgtctc                                    29

<210> SEQ ID NO 66
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 66
aaatcctttc tccaggcagc ccctgtctc                                    29

<210> SEQ ID NO 67
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 67
aaggctgcct ggagaaagga tcctgtctc                                    29

<210> SEQ ID NO 68
<211> LENGTH: 23
```

```
<212> TYPE: DNA
<213> ORGANISM: Artificial Sequence
<220> FEATURE:
<223> OTHER INFORMATION: siRNA strand

<400> SEQUENCE: 68
cugaaucgga caaguucuud tdt                                              23

<210> SEQ ID NO 69
<211> LENGTH: 23
<212> TYPE: DNA
<213> ORGANISM: Artificial Sequence
<220> FEATURE:
<223> OTHER INFORMATION: siRNA strand

<400> SEQUENCE: 69
aagaacuugu ccgauucagd tdt                                              23

<210> SEQ ID NO 70
<211> LENGTH: 23
<212> TYPE: DNA
<213> ORGANISM: Artificial Sequence
<220> FEATURE:
<223> OTHER INFORMATION: siRNA strand

<400> SEQUENCE: 70
ugaucauugg ugguaucgad tdt                                              23

<210> SEQ ID NO 71
<211> LENGTH: 23
<212> TYPE: DNA
<213> ORGANISM: Artificial Sequence
<220> FEATURE:
<223> OTHER INFORMATION: siRNA strand

<400> SEQUENCE: 71
ucgauaccac caaugaucad tdt                                              23

<210> SEQ ID NO 72
<211> LENGTH: 23
<212> TYPE: DNA
<213> ORGANISM: Artificial Sequence
<220> FEATURE:
<223> OTHER INFORMATION: siRNA strand

<400> SEQUENCE: 72
ucaaugguca agaucucaad tdt                                              23

<210> SEQ ID NO 73
<211> LENGTH: 23
<212> TYPE: DNA
<213> ORGANISM: Artificial Sequence
<220> FEATURE:
<223> OTHER INFORMATION: siRNA strand

<400> SEQUENCE: 73
uugagaucuu gaccauugad tdt                                              23

<210> SEQ ID NO 74
<211> LENGTH: 23
<212> TYPE: DNA
<213> ORGANISM: Artificial Sequence
<220> FEATURE:
<223> OTHER INFORMATION: siRNA strand

<400> SEQUENCE: 74
uccuuccuca gcaauaccud tdt                                              23
```

<210> SEQ ID NO 75
<211> LENGTH: 23
<212> TYPE: DNA
<213> ORGANISM: Artificial Sequence
<220> FEATURE:
<223> OTHER INFORMATION: siRNA strand

<400> SEQUENCE: 75
agguauugcu gaggaaggad tdt                                              23

<210> SEQ ID NO 76
<211> LENGTH: 55
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 76
ggtgaagctt gaccaggatg ttgagcgtct gccggtgttt cgtcctttcc acaag           55

<210> SEQ ID NO 77
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 77
cggcgaagct ttttccaaaa aacagacgct caacatcctg gtgaagcttg acca            54

<210> SEQ ID NO 78
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 78
cagctacaca aactgccgta acaaacggac ccggtgtttc gtcctttcca caag             54

<210> SEQ ID NO 79
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 79
cggcgaagct ttttccaaaa aaggtccgtt tgttacggca gctacacaaa ctgc             54

<210> SEQ ID NO 80
<211> LENGTH: 55
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 80
aaactacaca aatttgtggt gtctaaggat accggtgttt cgtcctttcc acaag            55

<210> SEQ ID NO 81

```
-continued

<211> LENGTH: 55
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 81
cggcgaagct tttttccaaa aaatatcctt agacaccaca aactacacaa atttg            55

<210> SEQ ID NO 82
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 82
tgcctacaca aagcatcgca taggttcttg tcggtgtttc gtcctttcca caag             54

<210> SEQ ID NO 83
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 83
cggcgaagct ttttccaaaa aaacaagaac ctatgcgatg cctacacaaa gcat             54

<210> SEQ ID NO 84
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 84
gttgaagctt gaacattcgc atcgcatagg ccggtgtttc gtcctttcca caag             54

<210> SEQ ID NO 85
<211> LENGTH: 53
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 85
cggcgaagct ttttccaaaa aacctatgcg atgcgaatgt tgaagcttga aca              53
```

DEVICES, SYSTEMS AND METHODS FOR IMPROVING MEMORY AND/OR COGNITIVE FUNCTION THROUGH BRAIN DELIVERY OF SIRNA

CROSS REFERENCE TO RELATED APPLICATIONS

This application is a Continuation of U.S. patent application Ser. No. 11/930,939, filed Oct. 31, 2007 and now U.S. Pat. No. 8,058,251, which is a Continuation-in-part of application Ser. No. 11/253,393 filed on Oct. 19, 2005 and now U.S. Pat. No. 7,618,948, which is a continuation-in-part of U.S. application Ser. No. 10/852,997, filed on May 25, 2004 and now U.S. Pat. No. 7,829,694, which is a continuation-in-part of U.S. application Ser. No. 10/721,693, filed on Nov. 25, 2003 and now U.S. Pat. No. 7,605,249, which claims priority from U.S. Provisional Patent Application No. 60/444,614, filed on Feb. 3, 2003, and U.S. Provisional Patent Application No. 60/429,387, filed on Nov. 26, 2002, which are incorporated herein by reference. U.S. application Ser. No. 11/253, 393 is also a continuation-in-part of U.S. application Ser. No. 11/157,608, filed on Jun. 21, 2005, and PCT Patent Application No. US05/022156, also filed on Jun. 21, 2005 which claim the benefit of U.S. Provisional Application Ser. No. 60/581,730, filed Jun. 21, 2004, and which are also incorporated herein by reference.

FIELD OF INVENTION

This invention relates to devices, systems, and methods for improving memory and/or cognitive function by brain delivery of small interfering RNA or vectors containing the DNA encoding for small interfering RNA.

BACKGROUND OF THE INVENTION

Memory, or the function of a living organism to store information and retrieve it at a later time in a functional form, comprises multiple processes and requires the function of many different brain areas. Human memory provides declarative recall, i.e., facts and events accessible to conscious recollection, and non-declarative recall, i.e., procedural memory of skills and operations not stored regarding time and place.

The processing of information to be added to memory occurs in several stages. A newly acquired experience initially is susceptible to various forms of disruption. With time, however, the new experience becomes resistant to disruption. This observation has been interpreted to indicate that a labile, working, short-term memory is "consolidated" into a more stable, long term memory. The initial phase of memory consolidation occurs in the first few minutes after we are exposed to a new idea or learning experience. The next phase occurs over a longer period of time, such as during sleep. If a learning experience has on-going meaning to us, the next week or so serves as a further period of memory consolidation. In effect, in this phase, the memory moves from short-term to long-term storage.

Various mechanisms have been proposed for the formation of long-term memory. A wide range of observations suggest an evolutionarily conserved molecular mechanism for the formation of long-term memory. These observations include increase in release of synaptic transmitter and number of synaptic receptors as well as decrease in Km of the receptors, synthesis of new memory factors either in the pre-synaptic or post-synaptic element, new synaptic connections, and increase in the active area in the pre-synaptic membrane. Synaptic plasticity, the change in the strength of neuronal connections in the brain, is thought to underlie long-term memory storage.

On the molecular level, a series of classic studies showed that inhibition of mRNA and protein synthesis during a critical time window could disrupt the formation of long-term memory. Initial learning and recall of previously stored information was not impaired by the transient blockage of protein synthesis. This led to a hypothesis that new gene expression is necessary for the conversion or consolidation of a short-term modification of the brain into a long-term memory.

Memory consolidation, or long-term memory, is also believed to play a crucial role in a variety of neurological and mental disorders, including mental retardation, Alzheimer's disease and depression. Indeed, loss or impairment of long-term memory is a significant feature of such diseases.

For several neurodegenerative diseases, such as Parkinson's disease, Alzheimer's disease, Huntington's disease, Spinocerebellar Ataxia Type 1, Type 2, and Type 3, and dentatorubral pallidoluysian atrophy (DRLPA), proteins involved in the overall pathogenic progression of the disease have been identified. There is currently no cure for these neurodegenerative diseases. These diseases are progressively debilitating and most are ultimately fatal.

Further problematic of these neurodegenerative diseases (especially Alzheimer's disease and Parkinson's disease) is that their prevalence continues to increase, thus creating a serious public health problem. Recent studies have pointed to alpha-synuclein (Parkinson's disease), beta-amyloid-cleaving enzyme 1 (BACE1 (including variants thereof, e.g. variants A, B, C, and D)) (Alzheimer's disease), huntingtin (Huntington's disease), and ataxin 1 (Spinocerebellar Ataxia Type 1) as major factors in the pathogenesis of each of these diseases, respectively.

The neurodegenerative process in Parkinson's disease and Alzheimer's disease is characterized by extensive loss of selected neuronal cell populations accompanied by synaptic injury and astrogliosis. Pathological hallmarks of Alzheimer's disease include formation of amyloid plaques, neurofibrillary tangles and neuropil thread formation. Although the mechanisms triggering cell dysfunction and death are unclear, the prevailing view is that neurodegeneration results from toxic effects subsequent to the accumulation of specific neuronal cell proteins, such as amyloid precursor protein (APP) (Alzheimer's disease—processed into beta-amyloid by BACE1 (including variants thereof, e.g. variants A, B, C, and D)).

Alzheimer's disease is a progressive degenerative disorder of the brain characterized by mental deterioration, memory loss, confusion, and disorientation. Among the cellular mechanisms contributing to this pathology are two types of fibrillar protein deposits in the brain: intracellular neurofibrillary tangles composed of polymerized tau protein, and abundant extracellular fibrils comprised largely of beta-amyloid. Beta-amyloid, also known as Abeta, arises from the proteolytic processing of the amyloid precursor protein (APP) at the beta- and gamma-secretase cleavage sites giving rise to the cellular toxicity and amyloid-forming capacity of the two major forms of Abeta (Abeta$_{40}$ and Abeta$_{42}$). Thus, preventing APP processing into plaque-producing forms of amyloid may critically influence the formation and progression of the disease making BACE1 (including variants thereof, e.g. variants A, B, C, and D) a clinical target for inhibiting or arresting this disease. Similar reports suggest presenilins are candidate targets for redirecting aberrant processing.

The design and use of small interfering RNA complementary to mRNA targets that produce particular proteins is a recent tool employed by molecular biologists to prevent translation of specific mRNAs. Various groups have been recently studying the effectiveness of siRNAs as biologically active agents for suppressing the expression of specific proteins involved in neurological disorders. Caplen, et al. (*Human Molecular Genetics*, 11(2): 175-184 (2002)) assessed a variety of different double stranded RNAs for their ability to inhibit cell expression of mRNA transcripts of the human androgen receptor gene containing different CAG repeats. Their work found gene-specific inhibition occurred with double stranded RNAs containing CAG repeats only when flanking sequences to the CAG repeats were present in the double stranded RNAs. They were also able to show that constructed double stranded RNAs were able to rescue caspase-3 activation induced by expression of a protein with an expanded polyglutamine region. Xia, Mao, et al. (*Nature Biotechnology*, 20: 1006-1010 (2002)) demonstrated the inhibition of polyglutamine (CAG) expression in engineered neural PC12 clonal cell lines that express a fused polyglutamine-fluorescent protein using constructed recombinant adenovirus expressing siRNAs targeting the mRNA encoding green fluorescent protein.

Other tools used by molecular biologists to interfere with protein expression prior to translation involve cleavage of the mRNA sequences using ribozymes against therapeutic targets for Alzheimer's disease (see WO01/16312A2) and Parkinson's disease (see WO99/50300A1 and WO01/60794A2). However, none of the above aforementioned patents disclose methods for the specifically localized delivery of small interfering RNA vectors to targeted cells of the brain in a manner capable of local treatment of neurodegenerative diseases. The above patents do not disclose use of delivery devices or any method of delivery or infusion of small interfering RNA vectors to the brain. For example, the above patents do not disclose or suggest a method of delivery or infusion of small interfering RNA vectors to the brain by an intracranial delivery device.

The delivery of biologically active agents to the brain is an important and challenging aspect of treating a variety of neurological disorders. For treatment of some neurological disorders, it is desirable to deliver a biologically active agent (e.g., a therapeutic agent) to the brain that will cause brain cells to express DNA, for example, a missing gene (i.e., gene therapy), and/or RNA, for example, a small interfering RNA (siRNA).

Some approaches to gene therapy for neurological disorders involve surgical delivery of non-viral or viral vectors directly into the brain tissue, which is generally necessary since non-viral and viral vectors normally do not cross the blood-brain barrier (BBB). These approaches are limited by difficulty in achieving sufficient distribution and diffusion of the vector into the targeted areas of the brain, and by the potential for viral vectors to produce an immune reaction in the patient. One approach for achieving enhanced diffusion of vectors into the brain tissue is to use the technique of "convection enhanced delivery," whereby the non-viral or viral vectors are administered at a low flow rate over a long period of time with a pump providing pressure and flow volume to enhance the distribution of the vector into the tissue. While convection enhanced delivery has been shown to yield delivery of molecules and virus particles to substantial three-dimensional regions of rodent and primate brains, scale-up of this delivery approach to the three-dimensional volume of the human brain remains a technical challenge. Effective treatment of certain neurological diseases (e.g., Alzheimer's disease) using a gene or protein delivery or suppression therapy will most likely require delivery of the biologically active agents to most of the human cerebrum. In other neurological disorders, such as Parkinson's disease and Huntington's disease, even though there are circumscribed regions of the brain anatomy that are especially affected by the disease process, for example, the substantia nigra or striatum (caudate and putamen) and result in cardinal symptoms of the diseases (e.g., dyskinesias, rigidity, etc.), patients will likely benefit further from treatment of broader regions of the brain, in which the disease process causes additional symptoms (e.g., depression and cognitive deficits).

An approach of using viral vectors to deliver genes or gene suppressing agents to the brain tissue using stereotactic neurosurgery including, for example, the use of adeno-associated virus (AAV) to deliver gene therapy to the subthalamic nucleus, has shown considerable promise. However, the usefulness of stereotactic neurosurgery to deliver a viral vector carrying a gene or protein suppression therapy can be limited by one or more of the following factors. Stereotactic neurosurgery always involves a low level of surgical risk including, for example, accidental perforation of a blood vessel, which can result in cerebral hemorrhage and death. Dispersion of a viral vector to large regions of brain tissue, even using convection enhanced delivery and optimal vectors, catheter designs, and surgical technique, is likely to be limited relative to what can be attained using the blood stream as the distribution system. Manufacturing of viral particles (e.g., capsid plus DNA payload) in sufficient quantities for therapeutic use, while feasible, is costly relative to production of DNA alone. Viral particles (i.e., the capsid proteins) might be immunogenic, causing adverse reactions in sensitized individuals. While the immune response to some viruses (e.g., AAV) when administered to the brain appears minimal, it remains a potential limitation particularly for repeated therapy administrations.

It would be advantageous to administer a biologically active agent by a route that is no more invasive than a simple intravenous injection. With this approach, a biologically active agent could be delivered through the BBB by targeting the biologically active agent to the brain via endogenous BBB transport systems. Expression of a DNA or RNA in the brain requires that the biologically active agent that is injected into the blood is transported not only across the BBB by, for example, receptor-mediated transcytosis (RMT), but also across the brain cell membrane (BCM) by, for example, receptor-mediated endocytosis (RME) into the target cell in the brain. In addition, using endogenous BBB transport systems to target biologically active agents non-invasively to the brain also requires the development of a suitable formulation of the biologically active agent that is stable in the bloodstream.

An effective method for delivering gene therapy to the entire primate brain using compositions that carry plasmid DNA or antisense RNA across the blood brain barrier and into brain cells was recently disclosed in U.S. Pat. No. 6,372,250 (Pardridge). The reported ability of this method to deliver plasmid DNA to the entire primate brain constitutes an impressive technical breakthrough. However, therapeutic use of the disclosed method may be limited by one or more of the factors listed herein below. Gene expression from a plasmid or RNA is generally temporary (e.g., limited to a period of days or weeks). Intravenous delivery of the disclosed compositions can result in unintended treatment of all bodily organs, potentially resulting in adverse side-effects. Finally, intravenous delivery can result in a loss of dosing as the dose intended for the brain is delivered to other parts of the body.

Further, the foregoing prior art does not disclose any technique for delivering or infusing into the brain small interfering RNA vectors which are then capable of reducing production of at least one protein involved in the loss of memory.

The prior art describes direct systemic delivery of ribozymes. This approach for treatment of memory loss or neurodegenerative disorders would appear neither possible nor desirable. First, interfering RNAs are distinctly different than ribozymes. Second, small RNA molecules delivered systemically will not persist in vivo long enough to reach the desired target, nor are they likely to cross the blood-brain barrier. Further, the approach taken by the prior art may be impractical because of the large quantity of small interfering RNA that might have to be administered by this method to achieve an effective quantity in the brain. Even when the blood-brain barrier is temporarily opened, the vast majority of oligonucleotide delivered via the bloodstream may be lost to other organ systems in the body, especially the liver.

U.S. Pat. Nos. 5,735,814 and 6,042,579 disclose the use of drug infusion for the treatment of Huntington's disease, but the drugs specifically identified in these patents pertain to agents capable of altering the level of excitation of neurons, and do not specifically identify agents intended to enter the cell and alter protein production within cells.

Thus, new compositions and methods for delivering to the brain biologically active agents for the treatment of memory loss and cognitive dysfunction are needed.

SUMMARY OF THE INVENTION

The present invention provides devices, systems, and methods for improving memory and/or cognitive function in a normal brain, or a brain affected by a neurodegenerative disorder, by brain delivery or infusion of small interfering RNA or vectors containing the DNA encoding for small interfering RNA.

A first objective of the described therapies of the present invention is to deliver specifically tailored small interfering RNA as therapeutic agents for enhancement of cognitive function and/or memory function of a subject. In certain embodiments, the subject method can be used to treat patients who have been diagnosed as having or being at risk of developing disorders in which diminished declarative memory is a symptom, e.g., as opposed to procedural memory. As a result, the methods of the present invention may be useful for preventing memory impairment. Contemplated causes of memory impairment include toxicant exposure, brain injury, age-associated memory impairment, mild cognitive impairment, epilepsy, mental retardation in children, and dementia resulting from a disease, such as in certain cases of Parkinson's disease, Alzheimer's disease, AIDS, head trauma, Huntington's disease, Pick's disease, Creutzfeldt-Jakob disease, post cardiac surgery, Downs Syndrome, Anterior Communicating Artery Syndrome, and other symptoms of stroke. In addition, the present invention may be useful in enhancing memory in normal individuals.

A second objective of the described therapies is to deliver specifically tailored small interfering RNA as therapeutic agents for treatment of Alzheimer's disease. Specifically tailored small interfering RNA for Alzheimer's disease target the mRNA for BACE1 (including variants thereof, e.g. variants A, B, C, and D) in order to reduce the amount of BACE1 (including variants thereof, e.g. variants A, B, C, and D) protein produced in neurological cells and thereby interfere with the production of beta-amyloid. In a related embodiment the present invention provides devices that specifically access the nucleus basalis of Meynart and the cerebral cortex for delivery of anti-BACE1 (including variants thereof, e.g. variants A, B, C, and D) small interfering RNA.

The present invention provides a method of treating memory loss in a subject caused by the presence of beta amyloid produced from amyloid precursor protein by beta amyloid cleaving enzyme type 1, or BACE1 in the brain.

The present invention also provides a delivery system for a small interfering RNA vector therapy for memory loss or cognitive dysfunction that permits targeted delivery of small interfering RNA or vectors containing DNA encoding for small interfering RNA (small interfering RNA vectors) to targeted sites in the brain for brief durations of time or over an extended period of care for the patient.

In one embodiment of the present invention, small interfering RNA vectors are infused into targeted sites of the brain wherein the small interfering RNA vectors are taken up by neurons and transported to the nucleus of targeted cells. The small interfering RNA vectors are then transcribed into RNA by the host cellular machinery to produce small interfering RNA that prevent production of the targeted protein involved in memory loss or cognitive dysfunction.

In one aspect, the present invention provides a medical system for delivering DNA encoding a biologically active agent across a blood-brain barrier.

In another aspect, the present invention provides methods of using neurosurgical devices to deliver therapeutic small interfering RNA vectors to selected regions of the brain. In particular, the present invention provides methods that use surgically implanted catheters for singular, repeated, or chronic delivery of small interfering RNA vectors to the brain. The small interfering RNA vectors introduced into the affected cells have the necessary DNA sequences for transcription of the required small interfering RNA by the cells, including a promoter sequence, the small interfering RNA sequence, and optionally flanking regions allowing defined ends of the therapeutic small interfering RNA to be produced, and optionally a polyadenylation signal sequence.

In one embodiment, the system includes: a neurovascular catheter having a distal end positioned in a blood vessel supplying a patient's brain; and a means for delivering to the catheter a composition including: an artificial adeno-associated virus (AAV) vector including DNA encoding a biologically active agent; and a component to deliver at least the DNA across the blood-brain barrier.

In another embodiment, the medical system includes a neurovascular catheter having a distal end positioned in a blood vessel supplying a patient's brain; and a means for delivering to the catheter a composition including a receptor-specific nanocontainer, wherein the receptor-specific nanocontainer includes: a nanoparticle or liposome having an exterior surface and an internal compartment; an artificial adeno-associated virus (AAV) vector located within the internal compartment of the liposome, wherein the AAV vector includes DNA encoding a biologically active agent; one or more blood-brain barrier and brain cell membrane targeting agents; and one or more conjugation agents wherein each targeting agent is connected to the exterior surface of the nanocontainer via at least one of the conjugation agents.

In another aspect, the present invention provides a method for delivering DNA across a blood-brain barrier for expression in the brain. The method includes administering to a patient a composition including: an artificial adeno-associated virus (AAV) vector including DNA encoding a biologically active agent; and a component to deliver at least the DNA across the blood-brain barrier.

In another aspect, the present invention provides a method for delivering DNA across a blood-brain barrier for expression in the brain. The method includes administering to a patient a composition including a receptor-specific nanocontainer, wherein the receptor-specific nanocontainer includes: a nanoparticle or liposome having an exterior surface and an internal compartment; an artificial adeno-associated virus (AAV) vector located within the internal compartment of the nanocontainer, wherein the AAV vector includes DNA encoding a biologically active agent; one or more blood-brain barrier and brain cell membrane targeting agents; and one or more conjugation agents wherein each targeting agent is connected to the exterior surface of the nanocontainer via at least one of the conjugation agents.

In another aspect, the present invention provide artificial AAV vectors for delivering DNA encoding a biologically active agent, and methods of making and using such vectors.

In one embodiment, the present invention provides an artificial AAV vector including, in 5-prime to 3-prime order: a 5-prime AAV-ITR; a single stranded DNA encoding a biologically active agent; an internal AAV-ITR; a reverse complement of the single stranded DNA encoding the biologically active agent: and a 3-prime AAV-ITR. Methods of making such vectors are also provided.

In another embodiment, the present invention provides an artificial adeno-associated virus (AAV) vector for delivery of a linear, double stranded DNA encoding a biologically active agent, the artificial AAV vector including the linear, double stranded DNA having AAV-ITRs at the 5-prime and 3-prime ends of each strand. Preferably, the artificial AAV vector has been thermally treated in at least one heating and cooling cycle.

The present invention can offer advantages over other methods of delivering biologically active agents including, for example, conventional enhanced delivery, stereotactic neurosurgical delivery of viral or non-viral vectors, and/or intravenous delivery of a composition for carrying plasmid DNA or RNA across the blood brain barrier.

The use of an artificial AAV vector to deliver a gene or a gene-suppressing agent to a patient's brain can have many advantages over the delivery of plasmid DNA, or the delivery of actual AAV virus particles. One possible advantage of delivering the DNA of an AAV vector to the brain, rather than a plasmid DNA, is that expression of AAV-delivered gene constructs in the primate brain is known to persist for at least 3 to 4 years, whereas expression of gene constructs from plasmids is temporary. The advantages of delivering the DNA of a synthetic AAV vector over delivery of AAV virus particles can be several. First, delivery of just the DNA can circumvent the delivery of AAV viral capsids to the patient's brain. Since it is the AAV viral capsid proteins that are most likely to trigger an immune response, dispensing with the need to deliver viral particles can avoid most of the risk of adverse immune reactions to the therapy. Further, delivery of the DNA can circumvent the need to produce complete AAV particles, a difficult manufacturing step that requires the use of specially engineered and cultured cells to make the AAV capsids and package the DNA into the virus capsids. Finally, delivery of DNA rather than AAV particles can circumvent the natural limitation on the length of the DNA that can be packaged inside AAV capsids, which is about 4,700 bases of DNA. Although this size limitation is not a problem for delivery of constructs for gene suppression (e.g., DNA coding for small, interfering RNA), it can be a limitation for delivery of missing genes, if the sequence for the missing gene is longer than 4,700 bases, which has been noted as a limitation on the use of AAV as a vector for gene therapy.

DETAILED DESCRIPTION OF THE PREFERRED EMBODIMENTS

Figure 1:
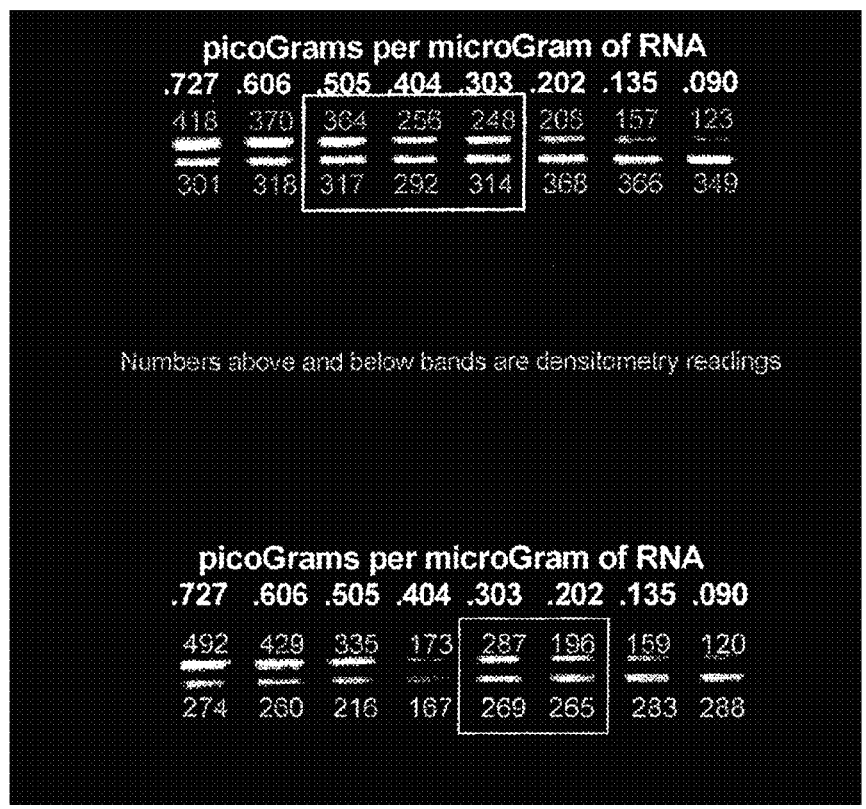
FIG. 1 shows the assay (using a quantitative RT-PCR method known to those practiced in the art) of the ataxin1 mRNA obtained from HEK293H cells that have been transfected with plasmid containing an anti-ataxin1 ribozyme (top lanes in FIG. 1) or with siRNA against ataxin1 (bottom lanes of FIG. 1).

The present invention solves two problems in the prior art at the same time: (1) the problem of how to improve impaired memory function caused by the production in neurons of a protein that has pathogenic properties and (2) the problem of delivery of therapeutic small interfering RNA to affected neurons.

In the following descriptions, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense.

All scientific and technical terms used in this application have meanings commonly used in the art unless otherwise specified. The definitions provided herein are to facilitate understanding of certain terms used frequently herein and are not meant to limit the scope of the present disclosure.

TERMINOLOGY

By "alpha-synuclein, BACE1 (including variants thereof, e.g. variants A, B, C, and D), huntingtin, ataxin-1, ataxin-3, and/or atrophin-1 proteins" is meant, a protein or a mutant protein derivative thereof, comprising the amino-acid sequence expressed and/or encoded by alpha-synuclein (Parkinson's disease), and beta-site APP-cleaving enzyme (BACE1 (including variants thereof, e.g. variants A, B, C, and D)) (Alzheimer's disease), huntingtin (Huntington's disease), and ataxin-1 (Spinocerebellar Ataxia Type 1), ataxin-3 (Spinocerebellar Ataxia Type 3 or Machado-Joseph's Disease), and/or dentatorubral-pallidoluysian atrophy (DRPLA) genes and/or the human genomic DNA respectively.

As used herein "cell" is used in its usual biological sense, and does not refer to an entire multicellular organism. The cell may be present in an organism which may be a human but is preferably of mammalian origin, e.g., such as humans, cows, sheep, apes, monkeys, swine, dogs, cats, and the like. However, several steps of producing small interfering RNA may require use of prokaryotic cells (e.g., bacterial cell) or eukaryotic cell (e.g., mammalian cell) and thereby are also included within the term "cell".

By "complementarity" it is meant that a molecule comprised of one or more nucleic acids (DNA or RNA) can form hydrogen bond(s) with another molecule comprised of one or more nucleic acids by either traditional Watson-Crick pairing or other non-traditional types.

By "equivalent" DNA to alpha-synuclein, BACE1 (including variants thereof, e.g. variants A, B, C, and D), huntingtin, ataxin-1, ataxin-3, and/or atrophin-1 it is meant to include those naturally occurring DNA molecules having homology (partial or complete) to DNA encoding for alpha-synuclein, BACE1 (including variants thereof, e.g. variants A, B, C, and D), huntingtin, ataxin-1, ataxin-3 and/or atrophin-1 proteins or encoding for proteins with similar function as alpha-synuclein, BACE1 (including variants thereof, e.g. variants A, B, C, and D), huntingtin, ataxin-1, ataxin-3 and/or atrophin-1 in various organisms, including human, rodent, primate, rabbit, pig, and microorganisms. The equivalent DNA sequence also includes regions such as the 5'-untranslated region, the 3'-untranslated region, introns, intron-exon junctions, small interfering RNA targeted site and the like, optionally incorporated into the DNA of infective viruses, such as adeno-associated virus (AAV).

The term "functional equivalent" refers to any derivative that is functionally similar to the reference sequence or protein. In particular the term "functional equivalent" includes derivatives in which the nucleotide bases(s) have been added, deleted, or replaced without a significant adverse effect on biological function.

As used herein, the term "biologically active" as used with "agent" or "siRNA" means that the agent or siRNA can modify a cell in any way including, for example, modifying the metabolism of the cell, the structure of the cell, the function of the cell, and/or permit the cell containing the agent or siRNA to be detected. Examples of biologically active agents and/or siRNAs include, for example, polynucleotides, polypeptides, and combinations thereof. A biologically active agent or siRNA may be therapeutic (i.e., able to treat or prevent a disease) or non-therapeutic (i.e., not directed to the treatment or prevention of a disease). Non-therapeutic biologically active compounds include detection or diagnostic agents including, for example, markers that can be used for detecting the presence of a particular cell, distinguishing cells, and/or detecting whether a targeting group is functioning to target a particular tissue. As used herein, the term "polynucleotide" or "nucleic acid molecule" refers to a polymeric form of nucleotides of any length, either ribonucleotides or deoxynucleotides, and includes both double- and single-stranded DNA and RNA, and combinations thereof. A polynucleotide may include nucleotide sequences having different functions including, for example, coding sequences and non-coding sequences such as regulatory sequences. Coding sequence, non-coding sequence, and regulatory sequence are defined below. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, or a fragment.

A "coding sequence" or a "coding region" is a polynucleotide that encodes a polypeptide and, when placed under the control of appropriate regulatory sequences, expresses the encoded polypeptide. The boundaries of a coding region are generally determined by a translational start codon at its 5-prime end and a translational stop codon at its 3-prime end. A regulatory sequence is a nucleotide sequence that regulates expression of a coding region to which it is operably linked. Nonlimiting examples of regulatory sequences include promoters, transcriptional initiation sites, translational start sites, translational stop sites, transcriptional terminators (including, for example, polyadenylation signals), and intervening sequences (introns). "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

By "gene" it is meant a region of DNA that controls the production of RNA. In context of producing functional small interfering RNA, this definition includes the necessary DNA sequence information encompassing the DNA sequences encoding the small interfering RNA, noncoding regulatory sequence and any included introns. The term "gene" is meant to include a polynucleotide that includes a coding sequence or coding region. The present definition does not exclude the possibility that additional genes encoding proteins may function in association or in tandem with the genes encoding small interfering RNA.

The term "vector" is commonly known in the art and defines a plasmid DNA, phage DNA, viral DNA and the like, which can serve as a DNA vehicle into which DNA of the present invention can be inserted, and from which RNA can be transcribed. The term "vectors" refers to any of these nucleic acid and/or viral-based techniques used to deliver a desired nucleic acid. Numerous types of vectors exist and are well known in the art.

The term "expression" defines the process by which a gene is transcribed into RNA (transcription); the RNA may be further processed into the mature small interfering RNA.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

"Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain −10 and −35 consensus sequences, which serve to initiate transcription.

By "homology" it is meant that the nucleotide sequence of two or more nucleic acid molecules is partially or completely identical.

By "highly conserved sequence region" it is meant that a nucleotide sequence of one or more regions in a target gene does not vary significantly from one generation to the other or from one biological system to the other.

By the term "inhibit" or "inhibitory" it is meant that the activity of the target genes or level of mRNAs or equivalent RNAs encoding target genes is reduced below that observed in the absence of the provided small interfering RNA. Preferably the inhibition is at least 10% less, 25% less, 50% less, or 75% less, 85% less, or 95% less than in the absence of the small interfering RNA.

By "inhibited expression" it is meant that the reduction of alpha-synuclein, BACE1 (including variants thereof, e.g. variants A, B, C, and D), huntingtin, ataxin-1, ataxin-3 and/or atrophin-1 mRNA levels and thus reduction in the level of the respective protein to relieve, to some extent, the symptoms of the disease or condition.

By "RNA" is meant ribonucleic acid, a molecule consisting of ribonucleotides connected via a phosphate-ribose (sugar) backbone. By "ribonucleotide" is meant guanine, cytosine, uracil, or adenine or some nucleotide with a hydroxyl group at the 2' position of a beta-D-ribo-furanose moiety. As is well known in the art, the genetic code uses thymidine as a base in DNA sequences and uracil in RNA. One skilled in the art knows how to replace thymidine with uracil in a written nucleic acid sequence to convert a written DNA sequence into a written RNA sequence, or vice versa.

By "patient" is meant an organism, which is a donor or recipient of explanted cells or the cells themselves. "Patient" also refers to an organism to which the nucleic acid molecules of the invention can be administered. Preferably, a patient is a mammal or mammalian cells, e.g., such as humans, cows, sheep, apes, monkeys, swine, dogs, cats, and the like, or cells of these animals used for transplantation. More preferably, a patient is a human or human cells.

The term "synuclein" may refer to alpha-synuclein (especially human or mouse) or beta-synuclein (especially human or mouse). The full nucleotide sequence encoding human alpha-synuclein is available under Accession No AF163864 (SEQ ID NO:7). Two variants of the human alpha-synuclein sequence are available under Accession No NM_000345 (SEQ ID NO:14) and Accession No NM_007308 (SEQ ID NO:23). The mouse alpha-synuclein is available under Accession No. AF163865 (SEQ ID NO:10).

The term "BACE1" may refer to beta-site amyloid precursor protein cleaving enzyme type 1 (especially human or mouse). Several variants of BACE1 have been sequenced, including variants A, B, C, and D. In some scientific literature, BACE1 is also known as ASP2 and Memapsin2. The full nucleotide sequences encoding human BACE1, and variants related thereto, are available under Accession No. NM_138971 (SEQ ID NO:20), Accession No. NM_138972 (SEQ ID NO:19), Accession No. NM_138973 (SEQ ID NO:21), and Accession No. NM_012104 (SEQ ID NO:18). The sequence for a mouse homolog is available under accession number NM_011792 (SEQ ID NO:22).

The term "huntingtin" may refer to the protein product encoded by the Huntington's Disease gene (IT-15) (especially human or mouse). The full nucleotide sequence encoding human IT-15 is available under Accession No AH003045 (SEQ ID NO:9). The mouse sequence is available under Accession No. U24233 (SEQ ID NO:12).

The term "ataxin-1" may refer to the protein product encoded by the Spinocerebellar Ataxia Type 1 gene (especially human or mouse). The full nucleotide sequence encoding human SCA1 is available under Accession No NM_000332 (SEQ ID NO:15). The mouse sca1 is available under Accession No. NM_009124 (SEQ ID NO:13).

The term "ataxin-3" may refer to the protein product encoded by the Spinocerebellar Ataxia Type 3 gene (especially human or mouse). The full nucleotide sequence encoding human SCA3 is available under Accession No NM_004993 (splice variant 1) (SEQ ID NO:16), and NM_030660 (splice variant 2) (SEQ ID NO:17).

The term "atrophin-1" may refer to the protein product encoded by the dentatorubral-pallidolysian atrophy (DRPLA) gene (especially human or mouse).

The term "modification" includes derivatives substantially similar to the reference sequence or protein.

By "nucleic acid molecule" as used herein is meant a molecule having nucleotides. The nucleic acid can be single, double, or multiple stranded and may comprise modified or unmodified nucleotides or non-nucleotides or various mixtures and combinations thereof. An example of a nucleic acid molecule according to the invention is a gene which encodes for a small interfering RNA, even though it does not necessarily have its more common meaning for encoding for the production of protein.

By "small interfering RNA" is meant a nucleic acid molecule which has complementarity in a substrate binding region to a specified gene target, and which acts to specifically guide enzymes in the host cell to cleave the target RNA. That is, the small interfering RNA by virtue of the specificity of its sequence and its homology to the RNA target, is able to cause cleavage of the RNA strand and thereby inactivate a target RNA molecule because it is no longer able to be transcribed. These complementary regions allow sufficient hybridization of the small interfering RNA to the target RNA and thus permit cleavage. One hundred percent complementarity often necessary for biological activity and therefore is preferred, but complementarity as low as 90% may also be useful in this invention. The specific small interfering RNA described in the present application are not meant to be limiting and those skilled in the art will recognize that all that is important in a small interfering RNA of this invention is that it have a specific substrate binding site which is complementary to one or more of the target nucleic acid regions.

Small interfering RNAs are double stranded RNA agents that have complementary to (i.e., able to base-pair with) a portion of the target RNA (generally messenger RNA). Generally, such complementarity is 100%, but can be less if desired, such as 91%, 92%, 93%, 94%, 95%, 96%, 97%, 98%, or 99%. For example, bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences.

The small interfering RNA sequence needs to be of sufficient length to bring the small interfering RNA and target RNA together through complementary base-pairing interactions. The small interfering RNA of the invention may be of varying lengths. The length of the small interfering RNA is preferably greater than or equal to ten nucleotides and of sufficient length to stably interact with the target RNA; specifically 15-30 nucleotides; more specifically any integer between 15 and 30 nucleotides, such as 15, 16, 17, 18, 19, 20, 21, 22, 23, 24, 25, 26, 27, 28, 29, and 30. By "sufficient length" is meant an oligonucleotide of greater than or equal to 15 nucleotides that is of a length great enough to provide the intended function under the expected condition. By "stably interact" is meant interaction of the small interfering RNA with target nucleic acid (e.g., by forming hydrogen bonds with complementary nucleotides in the target under physiological conditions).

A "reverse complement" of a DNA strand in a 5-prime to 3-prime direction is a DNA strand in the reverse order with the corresponding complementary bases according to Watson-Crick or other base pairing rules.

By "comprising" is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The present invention provides devices, systems and methods for improving memory and/or cognitive function through delivery of siRNA to a subject. In this aspect of the invention the method provides for improving memory function in a subject in need thereof, comprising administering to the subject a therapeutically effective dose of a composition that decreases the expression of a beta amyloid cleaving enzyme type 1, or BACE1, in a cell of the nervous system of the subject, wherein the composition comprises a small interfering RNA molecule specific for a BACE1 gene and wherein the small interfering RNA molecule specifically suppresses BACE1 gene expression in a cell of the nervous system of the subject.

Another aspect of the invention provides a method for improving memory function in a subject in need thereof, comprising modulating the expression or production of a beta amyloid cleaving enzyme type 1, or BACE1 protein in neurons by intracranial delivery of a small interfering RNA specific for a BACE1 gene that reduces said expression of production of said BACE1 protein, in a pharmaceutically acceptable carrier.

Another aspect of the present invention provides medical systems and methods for delivering DNA to a target site (e.g., to a cell or across the blood-brain barrier). The cell may be in vivo or ex vivo. As used herein, the term "ex vivo" refers to a cell that has been removed, for example, isolated, from the body of a subject. Ex vivo cells include, for example, primary cells (e.g., cells that have recently been removed from a subject and are capable of limited growth or maintenance in tissue culture medium), and cultured cells (e.g., cells that are capable of extended growth or maintenance in tissue culture medium). As used herein, the term "in vivo" refers to a cell that is within the body of a subject.

The medical systems include a neurovascular catheter having its distal end positioned in a blood vessel supplying a patient's brain. Optionally, the system further includes an implantable pump for delivery of the composition to the patient's blood stream. The medical system further includes a means for delivering to the catheter a composition as described herein. Methods of delivering such compositions to a cell or across the blood-brain barrier for expression in the brain are also described herein.

In brief, compositions disclosed and used in the present invention include an artificial adeno-associated virus (AAV) vector (single or double stranded vector; preferably a single stranded vector), including DNA encoding a biologically active agent; and a component (e.g., a receptor-specific liposome as described herein) that delivers at least the DNA across the blood-brain barrier. In some embodiments, the artificial AAV vector includes, in 5-prime to 3-prime order: a 5-prime AAV inverted terminal repeat (AAV-ITR); a single stranded DNA encoding the biologically active agent; and a 3-prime AAV-ITR. In other embodiments, the artificial AAV vector includes, in 5-prime to 3-prime order: a 5-prime AAV-ITR; a single stranded DNA encoding a biologically active agent; an internal AAV-ITR; a reverse complement of the single stranded DNA encoding the biologically active agent: and a 3-prime AAV-ITR. In still other embodiments, the artificial AAV vector includes a linear, double stranded DNA having AAV-ITRs at the 5-prime and 3-prime ends of each strand. Preferably, the artificial AAV vector does not include a coding sequence to encode a capsid, and thus, the preferred vectors are not encapsulated in a viral capsid structure. Methods of making artificial AAV vectors are also disclosed.

For embodiments in which the DNA encodes a small interfering RNA, the compositions can be useful for treating, among other things, various neurodegenerative disorders caused by a pathogenic protein. For embodiments in which the DNA encodes a protein, the compositions can be useful for treating, among other things, various neurological diseases caused by the absence of the protein.

In some embodiments, the compositions include a receptor-specific liposome and a pharmaceutically acceptable carrier for the receptor-specific liposome, wherein the receptor-specific liposome includes: a liposome having an exterior surface and an internal compartment; the artificial adeno-associated virus (AAV) vector located within the internal compartment of the liposome; one or more blood-brain barrier and brain cell membrane targeting agents; and one or more conjugation agents, wherein each targeting agent is connected to the exterior surface of the liposome via at least one of the conjugation agents.

In other embodiments, the compositions include a receptor-specific nanocontainer (i.e., a container having at least one dimension on the order of a few nanometers or less) and a pharmaceutically acceptable carrier for the receptor-specific nanocontainer, wherein the receptor-specific nanocontainer includes: a nanocontainer having an exterior surface and an internal compartment; an artificial adeno-associated virus (AAV) vector located within the internal compartment of the nanocontainer; one or more receptor specific targeting agents that target the receptor located on the cell; and one or more conjugation agents, wherein each targeting agent is connected to the exterior surface of the nanocontainer via at least one of the conjugation agents.

Another aspect of the invention provides a method of delivering a small interfering RNA to a location in the brain of a subject suffering from memory impairment comprising the steps of: a) surgically implanting an intracranial access delivery device; and b) infusing a small interfering RNA and/or a vector encoding said small interfering RNA at a predetermined site in the brain, wherein at least one attribute of memory function is improved.

Another aspect of the invention provides a method for improving memory function in a subject comprised of modulating the expression or production of a beta amyloid cleaving enzyme type 1, or BACE1 protein in neurons by intracranial delivery of a small interfering RNA from SEQ ID NOS: 24-40 that reduces said expression of production of said BACE1 protein, in a pharmaceutically acceptable carrier.

Another aspect of the invention provides a method of delivering a small interfering RNA to a location in the brain of a subject suffering from memory impairment comprising the steps of: a) surgically implanting an intracranial access delivery device; and b) infusing a small interfering RNA and/or a vector encoding said small interfering RNA containing one or more sequences coded from SEQ ID NOS: 24-40 at a predetermined site in the brain; wherein at least one attribute of said memory impairment is improved.

Another aspect of the invention provides a medical system for improving memory function in a subject comprising: a) an intracranial access device; b) a mapping means for locating a predetermined location in the brain; c) a deliverable amount of a small interfering RNA or vector encoding said small interfering RNA selected from one or more sequences coded from SEQ ID NOS: 24-40; and d) a delivery means for delivering said small interfering RNA or vector encoding said small interfering RNA to said location of the brain from said intracranial access device.

Medical Devices

The present invention also provides medical devices that include a neurovascular catheter and an optional implantable pump for delivery of the composition into a patient's blood stream. The distal, delivery end of the neurovascular catheter is positioned in a blood vessel supplying the brain. For acute use, the proximal end of the neurovascular catheter would remain outside the patient's body at the point of introduction (e.g., the femoral artery) and used by the physician to deliver the composition in a suitable fluid solution to the patient's brain. Although the delivery in this case is acute, the therapy may nevertheless be long-lasting as described herein below.

Alternatively, the proximal end of the neurovascular catheter can be attached to the optional implantable pump, and both the pump and catheter chronically implanted in the body. In the latter case, the pump provides a "catheter access port" through which the physician can transcutaneously make repeated bolus injections of the composition through the catheter into the blood vessel supplying the patient's brain. The pump provides a fluid reservoir used to supply heparinized saline, dilute tissue plasminogen activator (tPA), or a similar agent that is continuously pumped at a low rate through the neurovascular catheter in between uses of the catheter for bolus injections. The purpose is to prevent blood clots from forming at the distal end of the catheter, occluding the catheter lumen and posing a risk of embolic stroke to the patient.

Using the small interfering RNA vectors previously described, the present invention also provides devices, systems, and methods for delivery of small interfering RNA to target locations of the brain. The envisioned route of delivery is through the use of implanted, indwelling, intraparenchymal catheters that provide a means for injecting small volumes of fluid containing AAV or other vectors directly into local brain tissue. The proximal end of these catheters may be connected to an implanted, intracerebral access port surgically affixed to the patient's cranium, or to an implanted drug pump located in the patient's torso.

Figure 4:
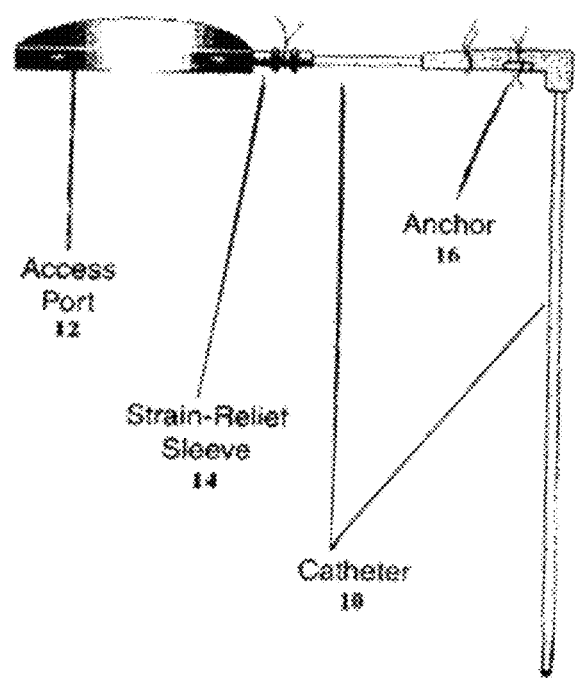
FIG. 4 illustrates an investigational device (by Medtronic, Inc. of Minneapolis, Minn. Model 8506), which can be implanted subcutaneously on the cranium, and provides an access port through which therapeutic agents may be delivered to the brain.
Figure 5:
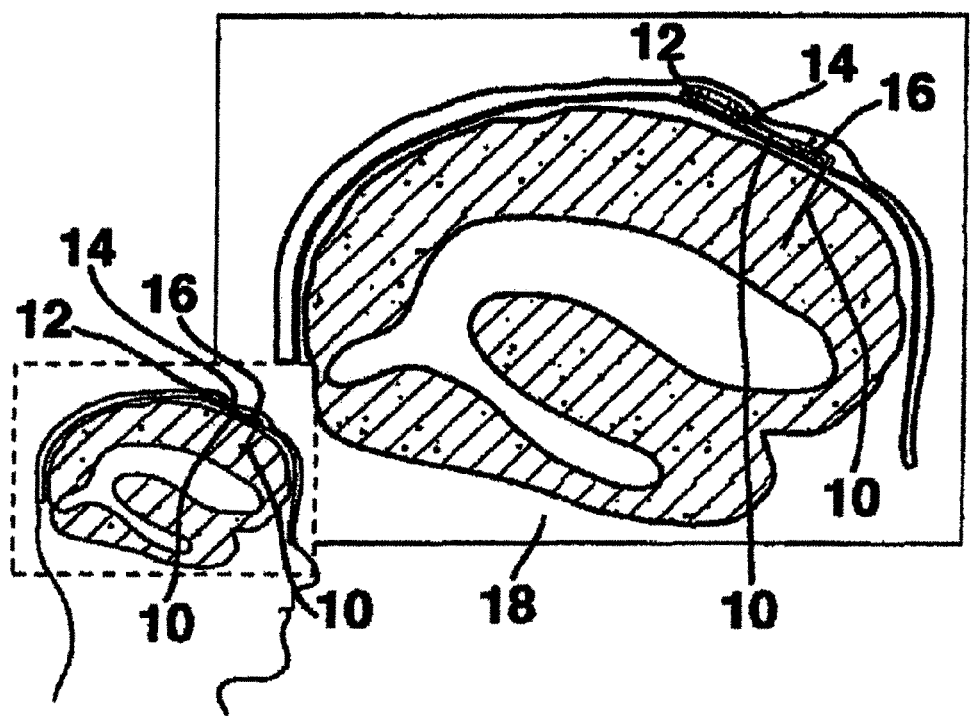
FIG. 5 illustrates a cranium of a patient with an investigational device (by Medtronic, Inc. of Minneapolis, Minn.—schematic of Model 8506), implanted subcutaneously on the cranium, and provides an access port through which therapeutic agents may be delivered to the brain.

Examples of the delivery devices within the scope of the present invention include the Model 8506 investigational device (by Medtronic, Inc. of Minneapolis, Minn.), which can be implanted subcutaneously on the cranium, and provides an access port through which therapeutic agents may be delivered to the brain. Delivery occurs through a stereotactically implanted polyurethane catheter. The Model 8506 is schematically depicted in FIGS. 4 and 5. Briefly, referring to FIG. 4, the device comprises a catheter 10. The catheter 10 is secured to the intracranial access port 12 which may optionally have strain relief 14. The catheter is also secured to the skull of the patient by anchor 16. FIG. 5 shows the device illustrated in FIG. 4 implanted into the patient, as shown by the saggital view of the patient's head 18. The intracranial access port 12 is implanted subcutaneously on the cranium of the patient. The catheter 10 extends through the relief strain 14 and is secured by the anchor 16 to the patient's skull. The distal tip of the catheter 10 is located in the predetermined location in the patient's brain. It is preferred to place some means for locating the distal end of the catheter 10 during the access and location process. This is preferably done by applying a marker, to the distal end of the catheter which is detected during the access and location process. If access and location is accomplished using some form of x-ray radiation, the marker is preferably radiopaque. Radiopaque marker renders at least a portion of distal tip opaque to x-rays, enabling the tip to be observed via fluoroscopy or via x-ray during access and location of catheter 10. In a preferred embodiment, radiopaque marker comprises tantalum powder dispersed in a matrix composed of a biocompatible adhesive, such as those discussed above. Other materials may also be suitable for radiopaque marker, such as barium or platinum materials. Alternately, the radiographic marker may be chosen of a material that has sufficient radiodensity for visualization during radiologic procedures, but in powdered form that is dispersed in the catheter tip at the time the distal tip of the catheter is molded. Alternatively, the marker may be composed of a material that is compatible to nuclear magnetic resonance imaging (MRI) to enable the distal tip of the catheter 10 to be detected during an MRI scan. Preferred material for such a marker is platinum, though barium, tantalum, and similar materials are also suitable. Regardless of whether radiography or MRI is being utilized, the goal of providing a radiographic marker is to enable the operator to accurately detect the precise location of the distal tip of the catheter to facilitate placement and later verification of the integrity and position of the distal tip of catheter 10. Two models of catheters that can function with the Model 8506 access port include the Model 8770 ventricular catheter by Medtronic, Inc., for delivery to the intracerebral ventricles, which is disclosed in U.S. Pat. No. 6,093,180, incorporated herein by reference, and the IPA1 catheter by Medtronic, Inc., for delivery to the brain tissue itself (i.e., intraparenchymal delivery), disclosed in U.S. Ser. Nos. 09/540,444 (U.S. Pat. No. 6,551,290) and 09/625,751 (U.S. Pat. No. 6,945,969), which are incorporated herein by reference. The latter catheter has multiple outlets on its distal end to deliver the therapeutic agent to multiple sites along the catheter path. In addition to the aforementioned device, the delivery of the small interfering RNA vectors in accordance with the present invention can be accomplished with a wide variety of devices, including but not limited to U.S. Pat. Nos. 5,735,814, 5,814,014, and 6,042,579, all of which are incorporated herein by reference. Using the teachings of the present invention and those of skill in the art will recognize that these and other devices and systems may be suitable for delivery of small interfering RNA vectors for the treatment of neurodegenerative diseases in accordance with the present invention.

In one preferred embodiment, the method further comprises the steps of implanting a pump outside the brain, the pump coupled to a proximal end of the catheter, and operating the pump to deliver the predetermined dosage of the at least one small interfering RNA or small interfering RNA vector through the discharge portion of the catheter. A further embodiment comprises the further step of periodically refreshing a supply of the at least one small interfering RNA or small interfering RNA vector to the pump outside said brain.

Thus, the present invention includes the delivery of small interfering RNA vectors using an implantable pump and catheter, like that taught in U.S. Pat. Nos. 5,735,814 and 6,042,579, and further using a sensor as part of the infusion system to regulate the amount of small interfering RNA vectors delivered to the brain, like that taught in U.S. Pat. No. 5,814,014. Other devices and systems can be used in accordance with the method of the present invention, for example, the devices and systems disclosed in U.S. Ser. Nos. 09/872,698 (filed Jun. 1, 2001) and 09/864,646 (filed May 23, 2001), which are incorporated herein by reference.

The design and use of small interfering RNA complementary to mRNA targets that produce particular proteins is a recent tool employed by molecular biologists to prevent translation of specific mRNAs. Other tools used by molecular biologists to interfere with protein expression prior to translation involve cleavage of the mRNA sequences using ribozymes against therapeutic targets for Alzheimer's disease (see, for example, PCT International Application Publication No. WO 01/16312 A2 (McSwiggen et al.)) and Parkinson's disease (see, for example, PCT International Application Publication Nos. WO 99/50300 A1 (Trojanowski et al.) and WO 01/60794 A2 (Eliezer)). PCT International Application Publication No. WO 2004/047872 A2 (Kaemmerer) and U.S. Patent Application Publication No. 2004/0220132 A1 (Kaemmerer) disclose devices, small interfering RNA, and methods for treating a neurodegenerative disorder including the steps of surgically implanting a catheter so that a discharge portion of the catheter lies adjacent to a predetermined infusion site in a brain, and discharging through the discharge portion of the catheter a predetermined dosage of at least one substance that inhibits production of at least one neurodegenerative protein. PCT International Application Publication No. WO 2004/047872 A2 (Kaemmerer) and U.S. Patent Application Publication No. 2004/0220132 A1 (Kaemmerer) further disclose small interfering RNA vectors, and methods for treating neurodegenerative disorders such as Alzheimer's disease, Parkinson's disease, Huntington's disease, Spinocerebellar Ataxia Type 1, Type 2, Type 3, and/or dentatorubral-pallidoluysian atrophy.

As previously indicated, the small interfering RNA (or siRNA) described herein, is a segment of double stranded RNA that is from 15 to 30 nucleotides in length. It is used to trigger a cellular reaction known as RNA interference. In RNA interference, double-stranded RNA is digested by an intracellular enzyme known as Dicer, producing siRNA duplexes. The siRNA duplexes bind to another intracellular enzyme complex which is thereby activated to target whatever mRNA molecules are homologous (or complementary) to the siRNA sequence. The activated enzyme complex cleaves the targeted mRNA, destroying it and preventing it from being used to direct the synthesis of its corresponding protein product.

Recent evidence suggests that RNA interference is an ancient, innate mechanism for not only defense against viral infection (many viruses introduce foreign RNA into cells) but also gene regulation at very fundamental levels. RNA interference has been found to occur in plants, insects, lower animals, and mammals, and has been found to be dramatically more effective than other gene silencing technologies, such as antisense or ribozymes. Used as a biotechnology, siRNA involves introducing into cells (or causing cells to produce) short, double-stranded molecules of RNA similar to those that would be produced by the Dicer enzyme from an invading double-stranded RNA virus. The artificially-triggered RNA interference process then continues from that point.

To deliver a small interfering RNA to a patient's brain, a preferred method will be to introduce the DNA encoding for the siRNA, rather than the siRNA molecules themselves, into the cells of the brain. The DNA sequence encoding for the particular therapeutic siRNA can be specified upon knowing (a) the sequence for a small and accessible portion of the target mRNA (available in public human genome databases), and (b) well-known scientific rules for how to specify DNA that will result in production of a corresponding RNA sequence when the DNA is transcribed by cells. The DNA sequence, once specified, can be constructed in the laboratory from synthetic molecules ordered from a laboratory supplier, and inserted using standard molecular biology methods into one of several alternative "vectors" for delivery of DNA to cells. Once delivered into the neurons of the patient's brain, those neurons will themselves produce the RNA that becomes the therapeutic siRNA, by transcribing the inserted DNA into RNA. The result will be that the cells themselves produce the siRNA that will silence the targeted gene. The result will be a reduction of the amount of the targeted protein produced by the cell.

Small Interfering RNA and Small Interfering RNA Vectors

In accordance with the present invention, small interfering RNA against specific mRNAs produced in the affected cells prevent the production of the disease related proteins in neurons. In accordance with the present invention is the use of specifically tailored vectors designed to deliver small interfering RNA to targeted cells. The success of the designed small interfering RNA is predicated on their successful delivery to the targeted cells of the brain to treat the neurodegenerative diseases.

Small interfering RNA have been shown to be capable of targeting specific mRNA molecules in human cells. Small interfering RNA vectors can be constructed to transfect human cells and produce small interfering RNA that cause the cleavage of the target RNA and thereby interrupt production of the encoded protein.

A small interfering RNA vector of the present invention will prevent production of the pathogenic protein by suppressing production of the neuropathogenic protein itself or by suppressing production of a protein involved in the production or processing of the neuropathogenic protein. Repeated administration of the therapeutic agent to the patient may be required to accomplish the change in a large enough number of neurons to improve the patient's quality of life. Within an individual neuron, however, the change is longstanding enough to provide a therapeutic benefit. The desperate situation of many patients suffering from neurodegenerative disorders, such as Alzheimer's disease, Parkinson's disease, Huntington's disease, or Spinocerebellar Ataxia Type 1 provides a strong likelihood that the benefit from the therapy will outweigh the risks of the therapy delivery and administration. While it may be possible to accomplish some reduction in the production of neuropathogenic proteins with other therapeutic agents and routes of administration, development of successful therapies involving direct in vivo transfection of neurons may provide the best approach based on delivery of small interfering RNA vectors to targeted cells.

The preferred vector for delivery of foreign DNA to neurons in the brain is adeno-associated virus (AAV), such as recombinant adeno-associated virus serotype 2 or recombinant adeno-associated virus serotype 5. Alternatively, other viral vectors, such as herpes simplex virus, may be used for delivery of foreign DNA to central nervous system neurons. It is also possible that non-viral vectors, such as plasmid DNA delivered alone or complexed with liposomal compounds or polyethyleneimine, may be used to deliver foreign DNA to neurons in the brain.

It is important to note that the anti-ataxin-1 small interfering RNA and the anti-BACE1 small interfering RNA illustrated here, as well as the other small interfering RNAs for treating neurodegenerative disorders, are just but some examples of the embodiment of the invention. Experimentation using neurosurgical methods with animals, known to those practiced in neuroscience, can be used to identify the candidate small interfering RNAs. The target site on the mRNA and the corresponding small interfering RNA identified by these empirical methods will be the one that will lead to the greatest therapeutic effect when administered to patients with the subject neurodegenerative disease.

In reference to the nucleic molecules of the present invention, the small interfering RNA are targeted to complementary sequences in the mRNA sequence coding for the production of the target protein, either within the actual protein coding sequence, or in the 5' untranslated region or the 3' untranslated region. After hybridization, the host enzymes guided by the siRNA are capable of cleavage of the mRNA sequence. Perfect or a very high degree of complementarity is needed for the small interfering RNA to be effective. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. However, it should be noted that single mismatches, or base-substitutions, within the siRNA sequence can substantially reduce the gene silencing activity of a small interfering RNA.

In preferred embodiments of the present invention, a small interfering RNA is 15 to 30 nucleotides in length. In particular embodiments, the nucleic acid molecule is 15, 16, 17, 18, 19, 20, 21, 22, 23, 24, 25, 26, 27, 28, 29, or 30 nucleotides in length. In preferred embodiments the length of the siRNA sequence can be between 19-30 base pairs, and more preferably between 21 and 25 base pairs, and more preferably between 21 and 23 base pairs.

In a preferred embodiment, the invention provides a method for producing a class of nucleic acid-based gene inhibiting agents that exhibit a high degree of specificity for the RNA of a desired target. For example, the small interfering RNA is preferably targeted to a highly conserved sequence region of target RNAs encoding BACE1 (including variants thereof, e.g. variants A, B, C, and D), RNA such that specific treatment of a disease or condition can be provided with either one or several nucleic acid molecules of the invention. Further, generally, interfering RNA sequences are selected by identifying regions in the target sequence that begin with a pair of adenine bases (AA) (see Examples). SiRNAs can be constructed in vitro or in vivo using appropriate transcription enzymes or expression vectors.

SiRNAs can be constructed in vitro using DNA oligonucleotides. These oligonucleotides can be constructed to include an 8 base sequence complementary to the 5' end of the T7 promoter primer included in the Silencer siRNA (Ambion Construction Kit 1620). Each gene specific oligonucleotide is annealed to a supplied T7 promoter primer, and a fill-in reaction with Klenow fragment generates a full-length DNA template for transcription into RNA. Two in vitro transcribed RNAs (one the antisense to the other) are generated by in vitro transcription reactions and then hybridized to each other to make double-stranded RNA. The double-stranded RNA product is treated with DNase (to remove the DNA transcription templates) and RNase (to polish the ends of the double-stranded RNA), and column purified to provide the siRNA that can be delivered and tested in cells.

Construction of siRNA vectors that express siRNAs within mammalian cells typically use an RNA polymerase III promoter to drive expression of a short hairpin RNA that mimics the structure of an siRNA. The insert that encodes this hairpin is designed to have two inverted repeats separated by a short spacer sequence. One inverted repeat is complementary to the mRNA to which the siRNA is targeted. A string of six consecutive thymidines added to the 3' end serves as a pol III transcription termination site. Once inside the cell, the vector constitutively expresses the hairpin RNA. The hairpin RNA is processed into an siRNA which induces silencing of the expression of the target gene, which is called RNA interference (RNAi).

In most siRNA expression vectors described to date, one of three different RNA polymerase III (pol III) promoters is used to drive the expression of a small hairpin siRNA (1-5). These promoters include the well-characterized human and mouse U6 promoters and the human H1 promoter. RNA pol III was chosen to drive siRNA expression because it expresses relatively large amounts of small RNAs in mammalian cells and it terminates transcription upon incorporating a string of 3-6 uridines.

The constructed nucleic acid molecules can be delivered exogenously to specific tissue or cellular targets as required. Alternatively, the nucleic acid molecules (e.g., small interfering RNA) can be expressed from DNA plasmid, DNA viral vectors, and/or RNA retroviral vectors that are delivered to specific cells.

The delivered small nuclear RNA sequences delivered to the targeted cells or tissues are nucleic acid-based inhibitors of BACE1 (including variants thereof, e.g. variants A, B, C, and D), that are useful for the prevention of the neurodegenerative diseases including Alzheimer's disease, memory loss or cognitive dysfunction, and any other diseases or conditions related to the level of BACE1 and/or beta-amyloid in a cell or tissue.

The nucleic acid-based inhibitors of the invention are added directly, or can be complexed with cationic lipids, packaged within liposomes, packaged within viral vectors, or otherwise delivered to target cells or tissues. The nucleic acid or nucleic acid complexes can be locally administered to relevant tissues ex vivo, or in vivo through injection, infusion pump or stent, with or without their incorporation in biopolymers. In preferred embodiments, the nucleic acid inhibitors comprise sequences which are a sufficient length and/or stably interact with their complementary substrate sequences identified in SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53. Examples of such small interfering RNA (siRNA) also are shown in SEQ ID NOS: 1, 2, 3, 4, for SEQ ID NOS: relating to siRNAs suppressing Ataxin1 mRNA (see also Examples 1-3). Examples of such small interfering RNA are shown in SEQ ID NOS: 24, 25, 26, 27, 28, 29, 30, 31, 32, 33, 34, 35, 36, 37, 38, 39, or 40 relating to suppressing BACE1 mRNA (see also all of Examples 4-6). Examples of such small interfering RNA are shown in SEQ ID NOS: 41, 42, 43, 44, 45, 46, 47, 48, 49, 50, 51, 52, and 53 relating to siRNAs suppressing Huntington mRNA.

In another aspect, the invention provides mammalian cells containing one or more nucleic acid molecules and/or expression vectors of this invention. The one or more nucleic acid molecules may independently be targeted to the same or different sites.

In another aspect of the invention, small interfering RNA molecules that interact with target RNA molecules and inhibit alpha-synuclein, BACE1 (including variants thereof, e.g. variants A, B, C, and D), huntingtin, ataxin-1, ataxin-3 and/or atrophin-1 RNA activity are expressed from transcription units inserted into DNA or RNA vectors. The recombinant vectors are preferably DNA plasmids or viral vectors. Small interfering RNA expressed from viral vectors could be constructed based on, but not limited to, the vector sequences of adeno-associated virus, retrovirus, or adenovirus. Preferably, the recombinant vectors capable of expressing the small interfering RNA are delivered as described above, and persist in target cells. Alternatively, viral vectors may be used that provide for transient expression of small interfering RNA. Such vectors might be repeatedly administered as necessary. Once expressed, the small interfering RNA bind to the target RNA and through use of the host machinery inhibit its expression and thereby its function. Delivery of small interfering RNA expressing vectors, or the small interfering RNA themselves, is by use of intracranial access devices.

The nucleic acid molecules of the instant invention, individually, or in combination or in conjunction with other drugs, can be used to treat diseases or conditions discussed above. For example, to treat a disease or condition associated with alpha-synuclein (Parkinson's Disease), and beta-site APP-cleaving enzyme (Alzheimer's Disease), huntingtin (Huntington's Disease), and Ataxin 1 (Spinocerebellar Ataxia), the patient may be treated, or other appropriate cells may be treated, as is evident to those skilled in the art, individually or in combination with one or more drugs under conditions suitable for the treatment.

In a further embodiment, the described small interfering RNA can be used in combination with other known treatments to treat conditions or diseases discussed above.

In another preferred embodiment, the invention provides nucleic acid-based inhibitors (e.g., small interfering RNA) and methods for their use to downregulate or inhibit the expression of RNA (e.g., alpha-synuclein, BACE1 (including variants thereof, e.g. variants A, B, C, and D), huntingtin, ataxin-1, ataxin-3 and/or atrophin-1) coding for proteins involved in the progression and/or maintenance of Parkinson's disease, Alzheimer's disease, Huntington's disease, Spinocerebellar Ataxia Type 1, Spinocerebellar Ataxia Type 3, and dentatorubral-pallidoluysian atrophy.

The present invention also provides nucleic acid molecules that can be expressed within cells from known eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; propulic et al., 1992, J Virol., 66, 1432-41; Weerasinghe et al., 1991, J Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45; all of these references are hereby incorporated herein, in their totalities, by reference). Those skilled in the art realize that any nucleic acid can be expressed in eukaryotic cells from the appropriate DNA/RNA vector. The activity of such nucleic acids can be augmented by their release from the primary transcript by ribozymes (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J Biol. Chem., 269, 25856; all of these references are hereby incorporated in their totality by reference herein).

In another aspect of the invention, RNA molecules of the present invention are preferably expressed from transcription units (see, for example, Couture et al., 1996, TIG., 12, 5-10) inserted into DNA or RNA vectors. The recombinant vectors are preferably DNA plasmids or viral vectors. Small interfering RNA expressing viral vectors could be constructed based on, but not limited to, adeno-associated virus, retrovirus, adenovirus, or alphavirus.

In one aspect, the invention features an expression vector comprising a nucleic acid sequence encoding at least one functional segment of the nucleic acid molecules of the instant invention. The nucleic acid sequence encoding the nucleic acid molecule of the instant invention is operably linked in a manner which allows expression of that nucleic acid molecule.

In another aspect the invention features an expression vector comprising: a) a transcription initiation region (e.g., eukaryotic pol I, II or III initiation region); b) a nucleic acid sequence encoding at least one of the nucleic acid agents of the instant invention; and c) a transcription termination region (e.g., eukaryotic pol I, II or III termination region); wherein said sequence is operably linked to said initiation region and said termination region, in a manner which allows expression and/or delivery of said nucleic acid molecule.

Transcription of the nucleic acid molecule sequences are driven from a promoter for eukaryotic RNA polymerase I (pol 1), RNA polymerase II (pol II), or RNA polymerase III (pol III) as is known and appreciated in the art. All of these references are incorporated by reference herein. Several investigators have demonstrated that RNA molecules can be expressed from such promoters can function in mammalian cells (e.g. Kashani-Sabet et al., 1992, Antisense Res. Dev., 2, 3-15; Ojwang et al., 1992, Proc. Natl. Acad Sci. USA, 89, 10802-6; Chen et al., 1992, Nucleic Acids Res., 20, 4581-9; Yu et al., 1993, Proc. Natl. Acad Sci. USA, 90, 6340-4; L'Huillier et al., 1992, EMBO J, 11, 4411-8; Lisziewicz et al., 1993, Proc. Natl. Acad. Sci. U.S. A, 90, 8000-4; Thompson et al., 1995, Nucleic Acids Res., 23, 2259; Sullenger & Cech, 1993, Science, 262, 1566). More specifically, transcription units such as the ones derived from genes encoding U6 small nuclear (snRNA), transfer RNA (tRNA) and adenovirus VA RNA are useful in generating high concentrations of desired RNA molecules such as small interfering RNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96118736; all of these publications are incorporated by reference herein). The above small interfering RNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

It should be noted that the exemplified methods for constructing the small interfering RNA to be used as the therapeutic agents in the invention (that is, in vitro transcription from DNA templates and assembly into double-stranded RNA, or cloning the DNA coding for a hairpin structure of RNA into an adeno-associated viral expression vector) are only two possible means for making the therapeutic small interfering RNA. Other larger scale, more efficient methods for manufacturing small interfering RNA may be used to produce the clinical grade and clinical quantities used for treating human patients, without altering the essence of the invention.

Those of skill in the art are familiar with the principles and procedures discussed in widely known and available sources as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990) both of which are incorporated herein by reference.

In a preferred embodiment of the present invention, the composition comprising the siRNA agent or precursors or derivatives thereof is formulated in accordance with standard procedure as a pharmaceutical composition adapted for delivered administration to human beings and other mammals. Typically, compositions for intravenous administration are solutions in sterile isotonic aqueous buffer.

Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

In yet another preferred embodiment, therapeutics containing small interfering RNA or precursors or derivatives thereof can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

The amount of the therapeutic of the present invention which will be effective in the treatment of a particular disorder or condition will depend on the nature of the disorder or condition, and can be determined by standard clinical techniques, well established in the administration of therapeutics. The precise dose to be employed in the formulation will also depend on the route of administration, and the seriousness of the disease or disorder, and should be decided according to the judgment of the practitioner and the patient's needs. Suitable dose ranges for intracranial administration are generally about $10^3$ to $10^{15}$ infectious units of viral vector per microliter delivered in 1 to 3000 microliters of single injection volume. Addition amounts of infections units of vector per micro liter would generally contain about $10^4$, $10^5$, $10^6$, $10^7$, $10^8$, $10^9$, $10^{10}$, $10^{11}$, $10^{12}$, $10^{13}$, $10^{14}$ infectious units of viral vector delivered in about 10, 50, 100, 200, 500, 1000, or 2000 microliters. Effective doses may be extrapolated from dose-responsive curves derived from in vitro or in vivo test systems.

For the small interfering RNA vector therapy for neurodegenerative disease of the present invention, multiple catheters having access ports can be implanted in a given patient for a complete therapy. In a preferred embodiment, there is one port and catheter system per cerebral or cerebellar hemisphere, and perhaps several. Once the implantations are performed by a neurosurgeon, the patient's neurologist can perform a course of therapy consisting of repeated bolus injections of small interfering RNA expression vectors over a period of weeks to months, along with monitoring for therapeutic effect over time. The devices can remain implanted for several months or years for a full course of therapy. After confirmation of therapeutic efficacy, the access ports might optionally be explanted, and the catheters can be sealed and abandoned, or explanted as well. The device material should not interfere with magnetic resonance imaging, and, of course, the small interfering RNA preparations must be compatible with the access port and catheter materials and any surface coatings.

The polymerase chain reaction (PCR) used in the construction of siRNA expression plasmids and/or viral vectors is carried out in accordance with known techniques. See, e.g., U.S. Pat. Nos. 4,683,195; 4,683,202; 4,800,159; and 4,965,188 (the disclosures of all three U.S. patent are incorporated herein by reference). In general, PCR involves a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophoresis, or using a detectable label in accordance with known techniques, and the like. For a review on PCR techniques (see PCR Protocols, A Guide to Methods and Amplifications, Michael et al. Eds, Acad. Press, 1990).

Artificial AAV Vector

An artificial AAV vector includes DNA encoding a biologically active agent, and can be used to deliver a gene or a gene-suppressing agent to a patient's neurons. Thus, the artificial AAV preferably includes a cassette to deliver a gene, or a cassette to deliver a gene-suppressing agent. For example, in the case of a gene therapy intended to supply a missing gene to the patient's brain, the expression cassette can include a promoter element, the coding sequence for the missing gene, and a polyadenylation signal sequence. For another example, in the case of a gene suppression therapy intended to suppress the expression of an endogenous gene in the patient's brain, the expression cassette can include a promoter element, the coding sequence for a small, interfering RNA (siRNA), and a termination sequence.

In one embodiment, the artificial AAV vector is a double stranded vector. The double stranded vector, which may include either type of expression cassette, includes a 5-prime copy of the inverted terminal repeat (AAV-ITR) from the adeno-associated virus genome, followed by an expression cassette for a gene or gene-suppressing agent (whose identity depends upon the neurological disorder to be treated), followed at the 3-prime end by a 3-prime copy of the AAV-ITR.

In another embodiment, the artificial AAV vector, which may include either type of expression cassette, is a single stranded vector. The single stranded vector includes a single stranded DNA segment including a 5-prime copy of the inverted terminal repeat (AAV-ITR) from the adeno-associated virus genome, followed by an expression cassette for a gene or gene-suppressing agent (whose identity depends upon the neurological disorder to be treated), followed at the 3-prime end by a 3-prime copy of the AAV-ITR. Optionally and preferably, the entire DNA sequence including either type of expression cassette is repeated in reverse complement order, so that the DNA sequence includes the 5-prime AAV-ITR, the expression cassette, an internal AAV-ITR, the reverse complement of the expression cassette, and the 3-prime AAV-ITR. The 3-prime AAV-ITR is the reverse complement of the 5-prime AAV-ITR (as illustrated, for example, in Example 1 herein), and either a 3-prime or 5-prime AAV-ITR can be used as the internal AAV-ITR. The resulting "self-complementary" artificial AAV vector is preferred because it may produce more effective transfection of neurons by the DNA. See, for example, Fu et al., *Molecular Therapy* 8:911-917 (2003).

Figure 3A:
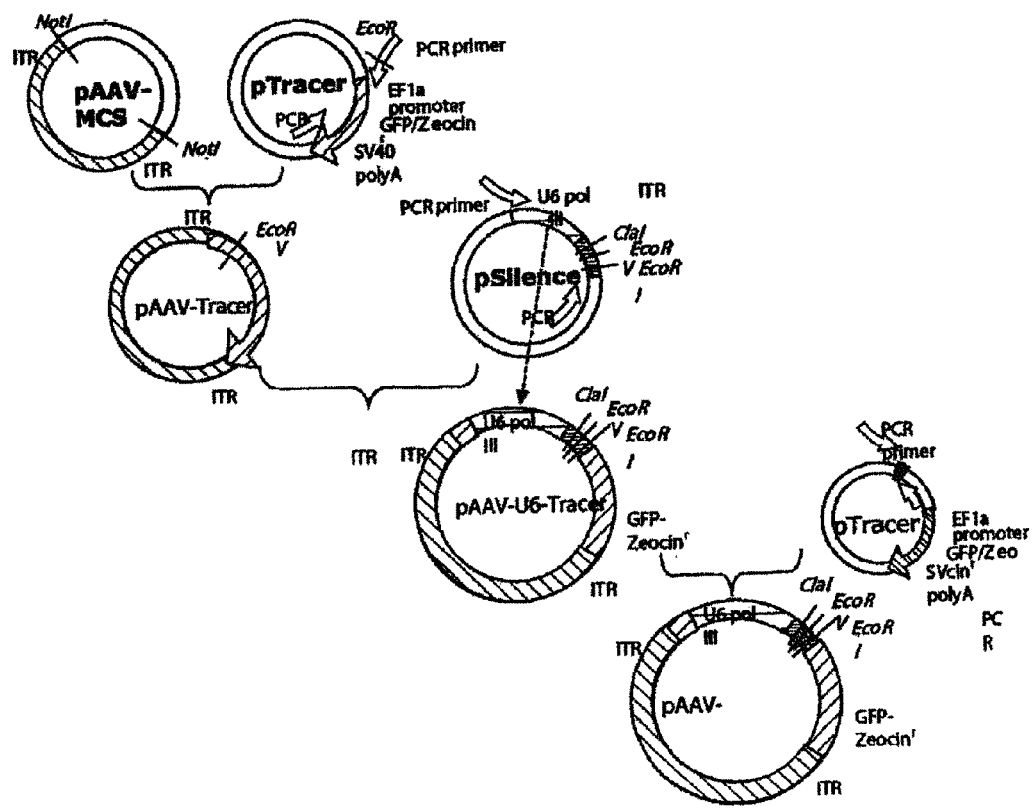
FIG. 3a shows the construction of the adeno-associated virus expression vector pAAV-siRNA as described in Example 3.
Figure 3B:
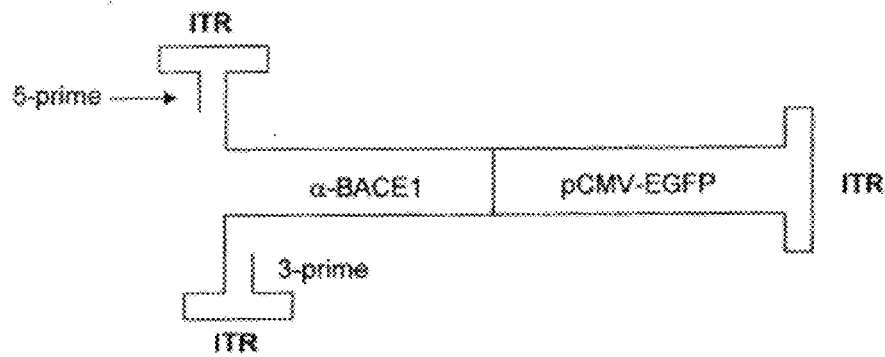
FIG. 3b is a schematic representation of one embodiment of a self-complementary artificial AAV vector for delivery of a single stranded DNA. The artificial AAV vector includes, in 5-prime to 3-prime order: a 5-prime AAV-ITR (ITR); a single stranded DNA ($\alpha$-BACE1/pCMV-EGFP); an internal AAV-ITR (ITR); a reverse complement of the single stranded DNA ($\alpha$-BACE1/pCMV-EGFP); and a 3-prime AAV-ITR (ITR).
Figure 3C:
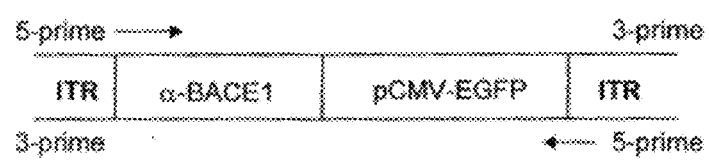
FIG. 3c is a schematic representation of one embodiment of an artificial AAV vector for delivery of a linear, double stranded DNA. The linear, double stranded DNA ($\alpha$-BACE1/pCMV-EGFP) has AAV-ITRs (ITR) at the 5-prime and 3-prime ends of each strand.

It will be appreciated by those skilled in the art that the embodiment of a double-stranded artificial AAV vector and the embodiment of a single-stranded self-complementary artificial AAV vector differ only in that the single stranded self-complementary vector has a single, single-stranded AAV-ITR joining the complementary strands of the expression cassette (covalently joining the 3-prime end of one strand to the 5-prime end of the complementary strand, as shown schematically in FIG. 3b) so that the entire artificial AAV vector is one single DNA strand "folded back" on itself with hydrogen bonds between the complementary strands of the expression cassette. In the case of the double stranded artificial AAV vector, there are double-stranded AAV-ITRs at the 5-prime end and the 3-prime end of the expression cassette with no covalent bond joining strands at either end (as illustrated schematically in FIG. 3c).

Figure 3D:
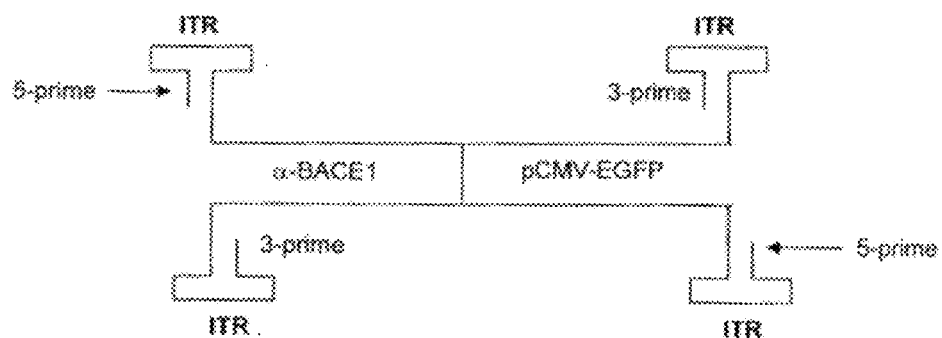
FIG. 3d is a schematic representation of one embodiment of an artificial AAV vector for delivery of a linear, double stranded DNA as illustrated in FIG. 3c that has been thermally treated in at least one heating and cooling cycle. The schematic representation illustrates a secondary structure of the ITRs in which the ITRs have folded so as to allow the self-complementary portions of each ITR to internally hybridize.

An exemplary method for preparing a double-stranded artificial AAV vector is disclosed. The method includes the steps of: assembling the 5-prime AAV-ITR, expression cassette, and 3-prime AAV-ITR in any suitable DNA plasmid using standard DNA cloning methods; liberating the 5-prime AAV-ITR, expression cassette, and 3-prime AAV-ITR from the plasmid by digesting the plasmid with a restriction enzyme that cuts the DNA at a site just 5-prime to the 5-prime AAV-ITR and just 3-prime to the 3-prime AAV-ITR; and purifying the linear DNA fragment consisting of the 5-prime AAV-ITR, expression cassette, and 3-prime AAV-ITR using standard methods. Optionally, the resulting linear double-stranded artificial AAV vector may be further processed by a thermal treatment step including, for example, heating the purified linear DNA fragment (e.g., heating to 65° C. or higher for 10 minutes or more), followed by cooling (e.g., allowing the DNA fragment to cool slowly to room temperature over a period of 10 minutes or more). These heating and cooling steps can allow the AAV ITRs to assume a secondary structure, conducive to long-term gene expression from this double-stranded artificial AAV vector, as illustrated schematically in FIG. 3d.

Exemplary methods for preparing a single-stranded DNA as described herein above are also disclosed. One method includes the steps of: assembling the 5-prime AAV-ITR, expression cassette, and 3-prime AAV-ITR in any suitable DNA plasmid using standard DNA cloning methods; generating a single-stranded RNA transcript of the desired single-stranded DNA from the DNA plasmid using standard in vitro transcription methods; generating single-stranded DNA from the RNA transcript by reverse transcription using standard reverse transcription reaction methods; removing the RNA transcript from the reaction products by digestion of the RNA using RNase enzyme; and purifying the resulting single-stranded DNA product from the reaction products by standard DNA purification methods, such as gel purification or column affinity methods.

Another method includes the steps of: assembling the 5-prime AAV-ITR, expression cassette, and 3-prime AAV-ITR in any suitable DNA plasmid using standard DNA cloning methods; linearizing the circular plasmid by digesting the plasmid with a restriction enzyme that cuts the DNA at a single, known location in the plasmid sequence just 5-prime to the 5-prime AAV-ITR; chemically conjugating an affinity tag (e.g., a biotin molecule) to the 5-prime ends of each strand of the linearized plasmid; cutting the DNA sequence with a restriction enzyme that cuts the DNA at a second single, known location in the plasmid sequence just 3-prime to the 3-prime AAV-ITR, such that the restriction digest results in two linear double-stranded DNA segments of different sizes; separating the populations of DNA molecules by size using any suitable size separation method (e.g., column filtration or gel electrophoresis) and recovering the desired double-stranded DNA; and melting the DNA to separate its two complementary strands into two single strands and passing the mixture through an affinity column for the tag (e.g., a streptavidin affinity column when a biotin molecule is used as the affinity tag) such that the strand which was tagged in step is captured on the column while the non-tagged single-strand flows through as the desired final product. This method can be advantageous for not involving any DNA or RNA polymerization steps that might introduce sequence errors in the final product.

In the case of a self-complementary AAV, the method includes the steps of: assembling the 5-prime AAV-ITR, expression cassette, internal AAV-ITR, reverse complement of the same expression cassette, and 3-prime AAV-ITR into any suitable DNA plasmid using standard DNA cloning methods; linearizing the circular plasmid by digesting the plasmid with restriction enzymes that cut out the desired DNA sequence (from the 5-prime AAV-ITR through the 3-prime AAV-ITR); recovering the desired DNA sequence from step 2 by size using any suitable size separation method; melting this double-stranded DNA to separate its two complementary strands into two single strands; and lowering the temperature (preferably slowly) of the melted DNA to allow the single strands to self-anneal into a hairpin form. All of the resulting single strands ("sense" or "anti-sense" strand) would be useful as the final product, since either strand would contain a copy of the desired expression cassette in a 5-prime to 3-prime orientation.

Compositions

For embodiments in which the composition is delivered across the blood-brain barrier, the composition includes, for example, a liposome as described, for example, in U.S. Pat. No. 6,372,250 (Pardridge), and a pharmaceutically acceptable carrier. Preferably the liposome is a receptor-specific liposome, wherein the receptor-specific liposome includes: a liposome having an exterior surface and an internal compartment; an artificial adeno-associated virus (AAV) vector located within the internal compartment of the liposome; one or more blood-brain barrier and brain cell membrane targeting agents; and one or more conjugation agents (e.g., polyethylene glycol (PEG) strands), wherein each targeting agent is connected to the exterior surface of the liposome via at least one of the conjugation agents. Receptor-specific liposomes including an artificial adeno-associated virus (AAV) vector located within the internal compartment of the liposome can be prepared by the general methods described in U.S. Pat. No. 6,372,250 (Pardridge), except that the artificial adeno-associated virus (AAV) vector is used instead of the plasmid DNA.

Liposomes as described herein can deliver biologically active agents across the blood-brain barrier, followed by expression in the brain. Liposomes and nanoparticles are exemplary forms of nanocontainers that are commonly used for encapsulation of drugs. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol, along with a small amount (1%) of cationic lipid, such as didodecyldimethylammonium bromide (DDAB) to stabilize the DNA within the liposome.

Although the invention has been described using liposomes as the preferred nanocontainer, it will be recognized by those skilled in the art that other nanocontainers may be used. For example, the liposome can be replaced with a nanoparticle or any other molecular nanocontainer with a diameter <200 nm that can encapsulate the DNA and protect the nucleic acid from nucleases while the formulation is still in the blood or in transit from the blood to the intracellular compartment of the target cell. Also, instead of using conjugation agents such as PEG strands, one or more other polymeric substances, such as sphingomylein, can be attached to the surface of the liposome or nanocontainer and serve the dual purpose of providing a scaffold for conjugation of the "transportable peptide" and for delaying the removal of the formulation from blood and optimizing the plasma pharmacokinetics. Further, the present invention contemplates delivery of DNA to any group of cells or organs which have specific target receptors. The liposomes may be used to deliver DNA to organs, such as liver, lung and spleen.

The liposomes may be combined with any suitable pharmaceutical carrier for intravenous administration. Intravenous administration of the composition is the preferred route since it is the least invasive. Other routes of administration are possible, if desired. Suitable pharmaceutically acceptable carriers include saline, Tris buffer, phosphate buffer, or any other aqueous solution. An appropriate dosage can be established by procedures well known to those of ordinary skill in the art.

Those of skill in the art are familiar with the principles and procedures discussed in widely known and available sources as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990).

In a preferred embodiment of the present invention, the compositions or precursors or derivatives thereof are formulated in accordance with standard procedure as a pharmaceutical composition adapted for delivered administration to human beings and other mammals. Typically, compositions for intravenous administration are solutions in sterile isotonic aqueous buffer.

Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a composition of the present invention including encapsulation in liposomes, microparticles, microcapsules and the like.

In yet another preferred embodiment, compositions can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

The amount of a composition of the present invention which will be effective in the treatment of a particular disorder or condition will depend on the nature of the disorder or condition, and can be determined by standard clinical techniques, well established in the administration of compositions. The precise dose to be employed in the formulation will also depend on the route of administration, and the seriousness of the disease or disorder, and should be decided according to the judgment of the practitioner and the patient's needs. Suitable dose ranges for intracranial administration are generally about $10^3$ to $10^{15}$ infectious units of viral vector per microliter delivered in 1 to 3000 microliters of single injection volume. Addition amounts of infections units of vector per micro liter would generally contain about $10^4$, $10^5$, $10^6$, $10^7$, $10^8$, $10^9$, $10^{10}$, $10^{11}$, $10^{12}$, $10^{13}$, $10^{14}$ infectious units of viral vector delivered in about 10, 50, 100, 200, 500, 1000, or 2000 microliters. Appropriate dosage may be extrapolated from dose-responsive curves derived from in vitro or in vivo test systems.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor. Laboratories) and Ausubel et al. (1994, Current Protocols in Molecular Biology, Wiley, New York).

To summarize, the present invention provides methods to deliver small interfering RNA vectors to the human central nervous system, and thus treat memory loss in normal human brains and neurodegenerative diseases by reducing the production of a pathogenic protein within neurons.

The present invention is illustrated by the following examples. It is to be understood that the particular examples, materials, amounts, and procedures are to be interpreted broadly in accordance with the scope and spirit of the invention as set forth herein.

EXAMPLES

Example 1

Construction of a Small Interfering RNA Targeting Human Ataxin1 mRNA

As an example of the embodiments of the invention, a small interfering RNA that targets the mRNA for human ataxin1 was made. This small interfering RNA reduces the amount of mRNA for human ataxin1 in human cells, in cell cultures. As a therapy for Spinocerebellar Ataxia Type 1 (SCA1), this same small interfering RNA or a similar small interfering RNA will be delivered to the cells of the cerebellum in the patient's brain, using implanted access ports and catheters. The result will be a reduction in the amount of ataxin1 protein in these cells, thereby slowing or arresting the progression of the patient's SCA1 disease.

The small interfering RNA against human ataxin1 was been constructed from the nucleotide sequence for human ataxin1. The sequence from human ataxin 1 was retrieved from the publicly-accessible nucleotide database provided by NCBI, retrievable as NCBI accession number NM_000332 (SEQ ID NO:15). A portion of the human mRNA sequence for ataxin1 was identified as a potential site for small interfering RNA cleavage and also predicted to be single-stranded by MFOLD analysis. In accession NM_000332 (SEQ ID NO:15), three pairs of anti-ataxin1 siRNA targets were constructed:

```
1. Anti-ataxin1 siRNA targeting the mRNA
sequence at sites numbered 945 through 965:
                                        SEQ ID NO: 1
5' - AACCAAGAGCGGAGCAACGAA - 3'
                                        SEQ ID NO: 2
3' - GGTTCTCGCCTCGTTGCTTAA - 5'

2. Anti-ataxin1 siRNA targeting the mRNA
sequence at sites numbered 1671 - through 1691:
                                        SEQ ID NO: 3
5' - AACCAAGAGCGGAGCAACGAA - 3'
                                        SEQ ID NO: 4
3' - GGTTCTCGCCTCGTTGCTTAA - 5'

3. Anti-ataxin1 siRNA targeting the mRNA
sequence at sites numbered 2750 - through 2770:
                                        SEQ ID NO: 5
5' - AACCAGTACGTCCACATTTCC - 3'
                                        SEQ ID NO: 6
3' - GGTCATGCAGGTGTAAAGGAA - 5'
```

A series of six deoxyoligonucleotide fragments were designed, ordered and purchased from the MWG Biotech, Inc., custom oligonucleotide synthesis service to provide the six fragments making up the three target sites. Additionally, these oligonucletides were constructed to include an 8 base sequence complementary to the 5' end of the T7 promoter primer included in an siRNA construction kit (Ambion, Inc. catalog number 1620). Each specific oligonucleotide was annealed to the supplied T7 promoter primer, and filled-in with Klenow fragment to generate a full-length DNA template for transcription into RNA. Two in vitro transcribed RNAs (one the antisense to the other) were generated by in vitro transcription reactions then hybridized to each other to make double-stranded RNA. The double-stranded RNA product was treated with DNase (to remove the DNA transcription templates) and RNase (to polish the ends of the double-stranded RNA), and column purified to provide the three siRNAs that were delivered and tested in cells.

Example 2

Delivery of a Small Interfering RNA Targeting Human Ataxin1 mRNA

The constructed siRNA molecules 1-3 described in Example 1 were transfected into HEK293 cells. The RNA produced by the transfected cells was harvested and assayed to measure the amount of human ataxin1 mRNA.

FIG. 1 shows the results of a quantitative reverse-transcriptase polymerase chain reaction (qRT-PCR) assay for the amount of ataxin1 messenger RNA (mRNA) per microgram of total RNA from cultures of HEK293H cells. Four cell populations were assayed. The first were 293H cells that had been transiently transfected with siRNA against GAPDH, a "housekeeping gene" with no known relationship to ataxin1 mRNA expression. (The siRNA against GAPDH was supplied as a standard control by Ambion, Inc., in their commercially-available kit for making and testing siRNA). The second were 293H cells that had been transiently transfected with siRNA against ataxin1 mRNA at location 1671 in the ataxin1 mRNA sequence. The third were 293H cells transiently transfected with a plasmid containing a ribozyme against ataxin1 mRNA (which cleaves ataxin1 mRNA at position 1364 in the ataxin1 mRNA sequence). The fourth were 293H cells transiently transfected with siRNA against ataxin1 mRNA at location 0945. All cell populations were harvested concurrently for total cellular RNA, at a time point 48 hours after transfection.

On the gels pictured, the amplified DNA products of the RT-PCR reaction were separated by molecular size, using gel electrophoresis, and are visible as bands of varying intensity. Each cell population described was assayed using a series of parallel reactions, shown as a set of lanes at the top or bottom of each gel. Each set of lanes contains two bands per lane. The top band is the DNA product amplified from a known quantity of DNA added to the reaction to compete with the endogenous cDNA reverse transcribed from the cellular mRNA. If the bands in a given lane are of the same intensity, then the amount of cellular mRNA in the original cell sample can be inferred to be equivalent to the amount of known quantity of DNA added to the reaction tube. From left to right across the lanes, the amount of known DNA standard added was decreased, in the picogram amounts shown. The assay is interpreted by looking for the set of lanes for which the intensity of the bands "crosses over" from being brightest for the DNA standard, to being brightest for the cellular product below it, indicating that the amount of DNA standard is now lower than the amount of cellular mRNA.

On the gel shown in FIG. 1, the top set of lanes is from the cells transfected with the ribozyme against ataxin1 mRNA. The comparison of the bands from this cellular sample to the bands from the DNA standards indicates that the amount of ataxin1 mRNA in these cells is between 0.505 and 0.303 picograms per microgram of total cellular RNA. The bottom set of lanes is from the cells transfected with siRNA against ataxin1 at position 0945. Analysis of these lanes indicates that the amount of ataxin1 mRNA in these cells is between 0.303 and 0.202 picograms per microgram of total cellular RNA.

Figure 2:
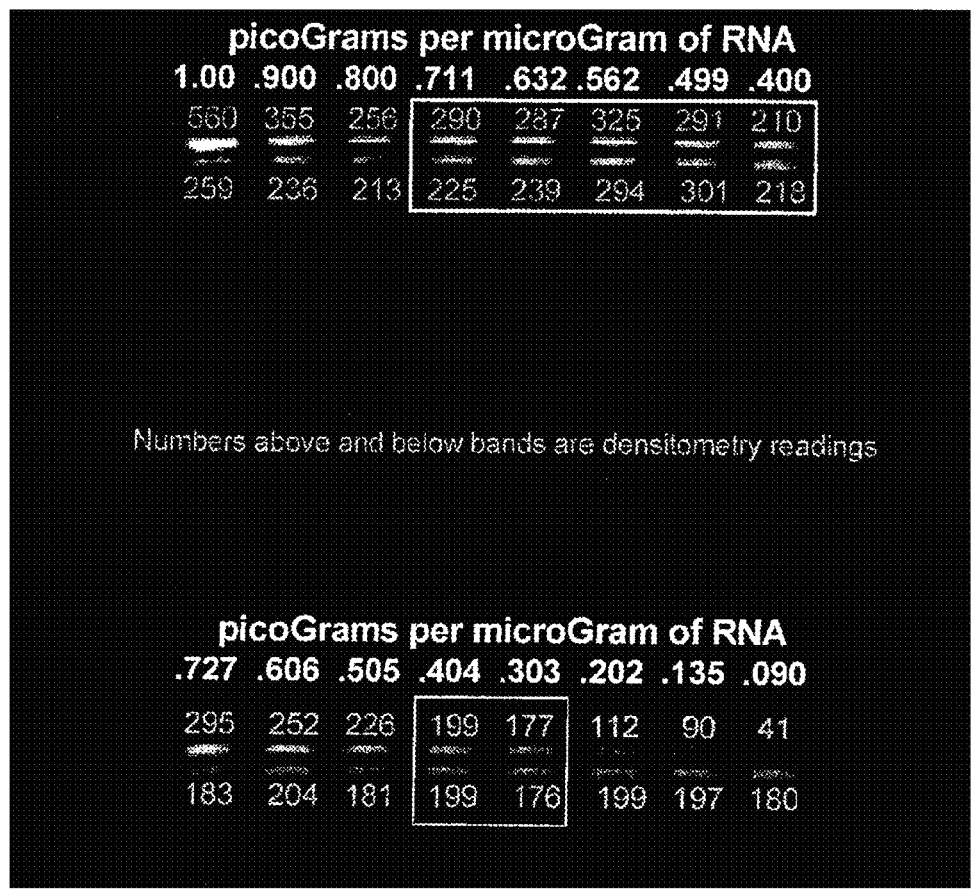
FIG. 2 shows the assay (using the same quantitative RT-PCR method known to those practiced in the art) of the ataxin-1 mRNA obtained from HEK293H cells that have been transfected with anti-ataxin-1 small interfering RNA (bottom lanes) compared to the mRNA obtained from HEK293H cells that have been transfected with a control siRNA that targets the mRNA for glyceraldehyde-3-phosphate dehydrogenase (GAPDH)

On the gel shown in FIG. 2, the top set of lanes is from the cells transfected with a control siRNA against GAPDH. Analysis of these lanes indicates that the amount of ataxin1 mRNA in these cells is between 0.711 and 0.400 picograms per microgram of total cellular RNA. Finally, the bottom set of lanes is from cells transfected with another siRNA against ataxin1, at position 1671. These lanes indicate that the amount of ataxin1 mRNA in these cells is between 0.404 and 0.303 picograms per microgram of total cellular RNA.

In summary, the results of this particular analysis were:

| Treatment | Amount of ataxin1 mRNA (picograms per microgram total cellular RNA) | | |
|---|---|---|---|
| | Lower bound | Upper bound | Midpoint Estimate |
| Control (GAPDH) | 0.400 | 0.711 | 0.555 |
| Ribozyme (A1364A) | 0.303 | 0.505 | 0.404 |
| siRNA (AT1671) SEQ ID Nos: 3 and 4 | 0.303 | 0.404 | 0.353 |
| siRNA (AT0945) SEQ ID Nos: 1 and 2 | 0.202 | 0.303 | 0.252 |

These data indicate that both the AT1671 and AT0945 siRNA against ataxin1 were effective at reducing the amount of ataxin1 mRNA in these cells within 48 hours after transfection, and that the siRNA were more effective at the reduction of ataxin1 mRNA than was this anti-ataxin1 ribozyme.

It should be noted that the exemplified method for constructing the small interfering RNA to be used as the therapeutic agents in the invention (that is, assembly from oligonucleotides using in vitro transcription and hybridization) is only one possible means for making the therapeutic small interfering RNA. Other larger scale, more efficient methods for manufacturing small interfering RNA may be used to produce the clinical grade and clinical quantities used for treating human patients, without altering the essence of the invention or departing from the spirit and scope of this invention, as set forth in the appended claims.

Example 3

Construction of Small, Interfering RNA Viral Vectors

A selectable reporter plasmid, pAAV-U6-Tracer for cloning siRNA was constructed. (See FIG. 3). The plasmid pAAV-U6-Tracer was constructed to contain the inverted terminal repeats (ITR) of adeno-associated virus, flanking the U6 RNA polymerase III promoter from pSilencer (Ambion), and the EF1a promoter, green fluorescence protein, Zeocin" resistance, and SV40 poly A from pTracer (Invitrogen). The gene segments are cloned as shown in FIG. 3. Oligonucleotides for expressing siRNA are cloned into the multiple cloning region just downstream in the 3' direction from the U6 RNA polymerase III promoter.

HEK293 Cells are cotransfected with pAAV-siRNA, pHelper, and pAAV-RC to make viral producer cells, where the pAAV-RC and pHelper plasmids are part of the three plasmid AAV production system Avigen, Inc.). The producer 293 cells are grown in culture and are used to isolate recombinant viruses which is used to transfect cells for assessment of treatment effect, such as: HeLa Cells, DAOY cells, and SK-N-SH cells.

Example 4

Treatment of Memory Dysfunction Using RNA Interference Targeting Beta-Amyloid Cleaving Enzyme Type 1 (BACE1)

One aspect of the invention provides a therapy for Alzheimer's disease. Another aspect of the invention provides a therapy for memory dysfunction. The latter therapy has been tested in normal, aged mice. This therapy uses a viral vector that encodes for a siRNA sequence that, upon uptake by a neuronal cell, reduces the amount of mRNA for beta-amyloid cleaving enzyme type 1 (BACE1) produced in that neuronal cell. Reducing the amount of BACE1 mRNA in cells results in a reduction of the amount of the enzyme produced, and subsequently the amount of beta-amyloid fragments cleaved from the amyloid-precursor protein (APP) by the BACE1 enzyme. Reduction in the amount of beta-amyloid fragments in the brain is the biological mechanism by which memory dysfunction is treated by this therapy.

The overall steps involved in this work include (1) in vitro screening of candidate anti-BACE1 siRNA sequences for efficacy, (2) construction of a viral vector for in vivo delivery of DNA encoding for the anti-BACE1 siRNA to the mammalian brain, (3) neurosurgical administration of the vector to the mice, (4) testing of the behavior of the mice to assess the effect of the treatment, and (5) examination of the brain tissue of the mice to assess the effect of the treatment. Steps 1 and 2 are described in this Example in detail below, and steps 3, 4, and 5 are described in Example 5.

(1) Screening of Anti-BACE1 siRNA Sequences for In Vitro Efficacy

Identification of candidate anti-BACE1 siRNA sequences: In order to identify an siRNA sequence that is effective at reducing the expression of BACE1 mRNA in neuronal cells, analysis of the human and mouse cDNA sequences for the BACE1 gene available in the Genbank database (National Center for Biotechnology Information, accession numbers NM_012104, NM_138971, NM_138972, and NM_138973 for human, and NM_011792 for mouse) was performed. The analysis consisted of identifying sections of the cDNA sequence beginning with two successive adenine nucleotides (AA) or with a cytosine and adenine (CA), and comprising those two nucleotides plus the nineteen successive nucleotides. These candidate sequences were tested for possible partial matches to other sequences in other genes, using the BLAST software program provided by the National Center for Biotechnology Information website and sequences with a high amount of partial matching to other genes (e.g., a match of more than 15 out of the 19 successive nucleotides following the AA or CA nucleotides) were eliminated from further consideration. Candidate sequences with an extreme percentage of guanine or cytosine (G or C) nucleotides in the sequence (e.g., greater than 65% or less than 35% of the 19 successive nucleotides were G or C rather than A or T) were also eliminated from consideration. From the remaining candidates, the following were selected for laboratory screening:

Anti-BACE1 siRNA Candidates and Corresponding In Vitro Suppression of BACE1 Expression

| Seq. ID No | Item | Name | Starting position within mouse BACE1 cDNA (Genbank Accession NM_011792) | DNA sequence corresponding to the therapeutic siRNA | Method for production of siRNA for in vitro screening | Mean %* | SD | N trials |
| --- | --- | --- | --- | --- | --- | --- | --- | --- |
| 24 | 1 | MB0803 | 0803 | AAGGGTGTGTATGTGCCCTAC | in vitro transcription | 57.0 | 1.4 | 2 |
| 25 | 2 | MB1663 | 1663 | AATTGGCTTTGCTGTCAGCGC | in vitro transcription | 42.0 | 24.0 | 2 |
| 26 | 3 | MB1749 | 1749 | AAGACTGTGGCTACAACATTC | in vitro transcription | 96.5 | 0.7 | 2 |
| 27 | 4 | MB3249 | 3249 | AAGGCTGCCTGGAGAAAGGAT | in vitro transcription | 0.0 | 11.3 | 2 |
| 28 | 5 | DhMB0918 | 0916 | CaCTGAATCGGACAAGTTCTT | chemical synthesis | 78.7 | 24.8 | 3 |
| 29 | 6 | DhMB1131 | 1129 | CaTGATCATTGGTGGTATCGA | chemical synthesis | 85.0 | 10.4 | 3 |
| 30 | 7 | DhMB1233 | 1231 | AaTCAATGGTCAAGATCTCAA | chemical synthesis | 81.7 | 13.7 | 3 |
| 31 | 8 | DhMB1509 | 1507 | CaTCCTTCCTCAGCAATACCT | chemical synthesis | 57.3 | 39.3 | 3 |
| 32 | 9 | SEC0683 | 0683 | CAGACGCTCAACATCCTGGTG | expression cassette | 54.3 | 19.0 | 4 |
| 33 | 10 | SEC1722 | 1722 | AAGGTCCGTTTGTTACGGCAG | expression cassette | 50.3 | 31.6 | 4 |
| 34 | 11 | SEC2163 | 2163 | AATATCCTTAGACACCACAAA | expression cassette | 47.5 | 19.2 | 4 |
| 35 | 12 | SEC2466 | 2466 | AAACAAGAACCTATGCGATGC | expression cassette | 41.5 | 33.3 | 4 |
| 36 | 13 | SEC2473 | 2473 | AACCTATGCGATGCGAATGTT | expression cassette | 61.0 | 18.6 | 4 |

*Percent suppression of co-transfected BACE1 in Neuro2a cell cultures.

The set screened in the laboratory were selected to include candidates from a wide range of positions within the cDNA of the mouse BACE1 sequence. For purposes of testing this therapy in mice, it was essential that the siRNA sequence be effective at suppressing the native mouse BACE1 enzyme in the mice. Therefore, priority was given to candidate siRNA sequences corresponding to mouse cDNA regardless of the amount of homology to human BACE1 cDNA. However, some of the candidate siRNA sequences correspond 100% to human as well as mouse BACE1 cDNA. For example, MB1749, targets a regions of BACE1 mRNA that is 100% identical across the human and mouse species, and thus constitutes a therapy component that is applicable to humans as well as mice.

Production of siRNA candidates for in vitro testing: Double-stranded RNA corresponding to the MB0803, MB1663, MB1749, or MB3249 siRNA candidates were made by in vitro transcription from custom DNA oligonucleotides and other reagents using the Ambion Silencer™ siRNA Construction Kit (Ambion, Inc., Austin, Tex.; catalog number 1620) following the procedure recommended by the manufacturer. The custom DNA oligonucleotides used to produce our specific siRNA were as follows. The siRNA target sequences are listed in capital letters, while other oligonucleotides for use in the in vitro transcription method are listed in lower case letters.

DNA expression cassettes were made from which cells transcribe RNA that forms a hairpin corresponding to the SEC0683, SEC1722, SEC2163, SEC2466, or SEC2473 siRNA candidates by polymerase chain reaction, using custom DNA oligonucleotides plus reagents from the Ambion Silencer™ Express siRNA Expression Cassette Kit (Ambion, Inc., Austin, Tex.; catalog number 1682) following the procedure recommended by the manufacturer. The custom DNA oligonucleotides used to produce specific siRNA expression cassettes were as follows. The siRNA target sequences are listed in capital letters, while other oligonucleotides needed for use in the expression cassette method are listed in lower case letters.

| SEQ ID: Sense | siRNA | siRNA Sense oligonucleotide (DNA) | Antisense oligonucleotide (DNA) | SEQ ID antisense |
|---|---|---|---|---|
| 60 | MB0803 | aaGTAGGGCACATACACACCCcctgtctc | AAGGGTGTGTATGTGCCCTACcctgtctc | 61 |
| 62 | MB1663 | aaGCGCTGACAGCAAAGCCAAcctgtctc | AATTGGCTTTGCTGTCAGCGCcctgtctc | 63 |
| 64 | MB1749 | aaGAATGTTGTAGCCACAGTCcctgtctc | AAGACTGTGGCTACAACATTCcctgtctc | 65 |
| 66 | MB3249 | aaATCCTTTCTCCAGGCAGCCcctgtctc | AAGGCTGCCTGGAGAAAGGATcctgtctc | 67 |

Chemically synthesized double-stranded RNA corresponding to the DhMB0918, DhMB1131, DhMB1233, and DhMB1509 siRNA candidates were ordered from Dharmacon, Inc. (Lafayette, Colo.). The sequences specified for the supplier to produce were as follows:

| SEQ ID: (to Sense Oligonucl. | siRNA | Sense oligonucleotide (DNA) | Antisense oligonucleotide (DNA) | SEQ ID antisense |
|---|---|---|---|---|
| 68 | DhMB0918 | CUGAAUCGGACAAGUUCUUdTdT | AAGAACUUGUCCGAUUCAGdTdT | 69 |
| 70 | DhMB1131 | UGAUCAUUGGUGGUAUCGAdTdT | UCGAUACCACCAAUGAUCAdTdT | 71 |
| 72 | DhMB1233 | UCAAUGGUCAAGAUCUCAAdTdT | UUGAGAUCUUGACCAUUGAdTdT | 73 |
| 74 | DhMB1509 | UCCUUCCUCAGCAAUACCUdTdT | AGGUAUUGCUGAGGAAGGAdTdT | 75 |

| siRNA | strand | oligonucleotide (DNA) | SEQ ID: |
|---|---|---|---|
| SEC0683 | sense | ggtgaagcttgACCAGGATGTTGAGCGTCTGccggtgtttcgtcctttccacaag | 76 |
| | antisense | cggcgaagcttttccaaaaaaCAGACGCTCAACATCCTGGTGaagcttgacca | 77 |
| SEC1722 | sense | cagctacacaaaCTGCCGTAACAAACGGACCcggtgtttcgtcctttccacaag | 78 |
| | antisense | cggcgaagcttttccaaaaAAGGTCCGTTTGTTACGGCAGctacacaaactgc | 79 |
| SEC2163 | sense | aaactacacaaaTTTGTGGTGTCTAAGGATAccggtgtttcgtcctttccacaag | 80 |
| | antisense | cggcgaagcttttccaaaaAATATCCTTAGACACCACAAActacacaaatttg | 81 |
| SEC2466 | sense | tgcctacacaaaGCATCGCATAGGTTCTTGTcggtgtttcgtcctttccacaag | 82 |
| | antisense | cggcgaagcttttccaaaaAAACAAGAACCTATGCGATGCctacacaaagcat | 83 |
| SEC2473 | sense | gttgaagcttgAACATTCGCATCGCATAGGccggtgtttcgtcctttccacaag | 84 |
| | antisense | cggcgaagcttttccaaaaAACCTATGCGATGCGAATGTTgaagcttgaaca | 85 |

Figure 6:
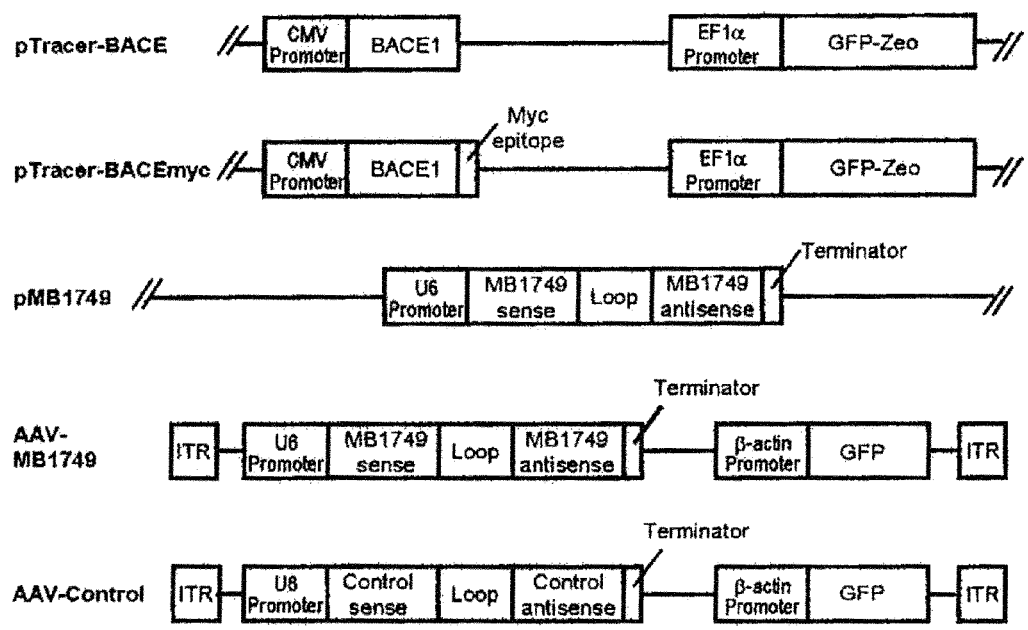
FIG. 6 illustrates diagrams of plasmids used. Plasmids pTracerBACE and pTracer-BACEmyc were used to screen for effective anti-BACE1 siRNA as described. Plasmid pMB1749 encoding for MB1749 as a shRNA was constructed as an intermediate step in the production of the viruses administered to mice as described, AAV-MB1749 and AAV-Control.

In vitro application of the siRNA candidates to neuronal cell cultures: To assess the effectiveness of each anti-BACE1 siRNA candidate in suppressing BACE1 mRNA in vitro, mouse neuronal cells of the Neuro2a cell line (American Type Culture Collection, catalog number CCL-131) were cultured using the standard cell culture conditions for these cells. Upon reaching 50-70% confluence, the cells were co-transfected with one of the siRNA candidates, and with a plasmid containing the cDNA for mouse BACE and for green fluorescent protein (GFP). This plasmid, called pTracerBace1, was constructed for this purpose by cloning the full length open reading frame of murine BACE1 cDNA (Open Biosystems, Huntsville Ala., IMAGE mouse cDNA clone 6831622) into the pTracer™-CMV2 plasmid (Invitrogen, Carlsbad Calif., #V885-20) downstream of the CMV promoter. The plasmid contains a second eukaryotic expression cassette encoding a fusion gene of green fluorescent protein and the Zeocin resistance marker (GFPzeo) whose expression is directed by the EF1α constitutive promoter (FIG. 6).

The cell transfection procedure and reagents used to conduct the in vitro testing varied as appropriate for the form (RNA or DNA) in which the siRNA candidate was applied. For transfection of cells with plasmid plus siRNA candidates produced by in vitro transcription (MB0803, MB1663, MB1749, MB3249) or by direct chemical synthesis (DhMB0918, DhMB1131, DhMB1233, DhMB1509), first a mixture of pTracerBace1 plasmid in Transit-Neural transfection reagent (Mirus, Inc. Madison, Wis.; catalog number 2144) was formed following the manufacturer's recommended procedures. Then, Transit-TKO transfection reagent (Mirus, Inc., catalog number 2154) was added dropwise to the Transit-Neural mixture, and incubated at room temperature for 10 minutes. Next, the siRNA was added to the mixture, incubated to allow the siRNA to form complexes with the Transit-TKO, then finally added dropwise to the cells. In all cases, the amount of pTracerBace1 plasmid per cell culture well was 1 microgram per well (of a six-well culture plate) across the various conditions, and the final concentration of siRNA per cell culture well is 25 nanoMolar.

For transfection of cells with plasmid plus siRNA candidates in the form of DNA (Silencer Expression Cassettes SEC0683, SEC1722, SEC2163, SEC2466, SEC2473) the method was similar, but SiPort-XP1 transfection reagent (Ambion, Inc., Austin, Tex.; catalog number 4506) was used for transfection of the cells with the double-stranded DNA PCR products constituting the expression cassettes. In these cases, SiPort-XP1 reagent was added dropwise to Opti-MEMO reduced-serum medium (Invitrogen, Carlsbad, Calif.; catalog number 22600), vortexed, and incubated at room temperature for 15 minutes following the procedure recommended by Ambion, Inc. Then, pTracerBace1 plasmid was added to one aliquot of the SiPort-XP1 mixture, and siRNA expression cassette DNA was added to a separate aliquot of SiPort-XP1 mixture. Each aliquot was incubated at room temperature for 15 minutes to allow the DNA molecules to complex with the SiPort-XP1 reagent, then the two mixtures were combined and added dropwise to cells. The amount of pTracerBace1 plasmid per cell culture well was 1 migrogram per well across the various conditions, and the amount of siRNA expression cassette DNA added per well was 500 nanograms per well.

Assay of the effect of siRNA candidates on BACE1 mRNA levels in cells: To determine the effect of siRNA candidate on BACE1 mRNA levels in cells, the cells were harvested 48 to 72 hours after transfection with the siRNA and pTracerBace1 plasmid, and total cellular RNA was recovered from the cell lysate using the Qiagen RNeasy Mini Kit (Qiagen, Inc., Valencia, Calif.; catalog number 74106). The RNA was treated with DNase during this isolation, to eliminate genomic and plasmid DNA from the samples. The RNA samples were reverse transcribed to cDNA using the StrataScript First Strand cDNA Synthesis Kit (Stratagene, Inc., La Jolla, Calif.; catalog number 200420) following the manufacturer's protocol, and using oligo-dT to prime the cDNA synthesis. Parallel samples included in the same protocol, but omitting the inclusion of the reverse transcriptase enzyme, were used to verify the lack of genomic or plasmid DNA carryover to the PCR analysis.

The cDNA samples obtained from the reverse transcription reactions were then used to conduct real-time quantitative PCR analysis of relative amounts of BACE1 cDNA, GAPDH cDNA, and GFP cDNA in the samples. The assays for the various cDNA species were conducted in parallel on aliquots of the same sample, divided just before the addition of the pertinent PCR primers and fluorescent substrates for the PCR reactions. All reactions were performed in parallel in a Rotor-Gene 3000 real-time PCR machine (Corbett Research, Inc., Sydney, Australia) using TaqMan Universal PCR Mix without Amperase UNG (Applied Biosystems Foster City, Calif.; catalog number 4324018) as the polymerase and nucleotide reagent. The PCR assay for mouse BACE1 was performed using the BACE1 Assay on Demand (Applied Biosystems; catalog number Mm00478664_m1). The assay for rodent GAPDH was the TaqMan® Rodent Gapdh Control Reagents (Applied Biosystems; catalog number 4308313). The assay for GFP (introduced into transfected cells by the pTracer-Bace1 plasmid) was the QuantiTect SYBR Green (Qiagen; catalog number 204143) and the following custom PCR primers: forward: 5'-TGGTGTTCAATGCTTTTCCC-3'

(SEQ ID NO: 55) and reverse: 5'-GCGTCTTGTAGTTC-CCGTCA-3' (SEQ ID NO: 56), produce an expected PCR product size of 128 basepairs.

To quantify the relative amounts of mRNA in various cell samples, a series of dilutions of cDNA from a sample of cells that was transfected with pTracerBace1 but not treated with any siRNA candidate was used to generate a standard curve relating PCR cycle threshold to cDNA quantity, ranging from 1 to 100 nanograms of mRNA per microliter of sample. Based on the standard curve for each mRNA target (BACE1, GAPDH, or GFP), the nanograms per microliter of mRNA of each gene product was obtained for each cell sample. Finally, the amount of BACE1 mRNA in the cell sample was normalized to the amount of GFP mRNA in the same sample. From these normalized amounts of BACE1 mRNA, the percentage reduction in BACE1 mRNA resulting from a given siRNA treatment relative to the untreated cells was calculated.

The cell transfections and quantitative real-time RT-PCR assays for BACE1 mRNA levels relative to GFP mRNA levels in transfected Neuro2a cells were repeated independently by at least two persons. The resulting percentage of BACE1 mRNA suppression for each siRNA candidate, averaged over the independent assays, was determined.

Figure 7:
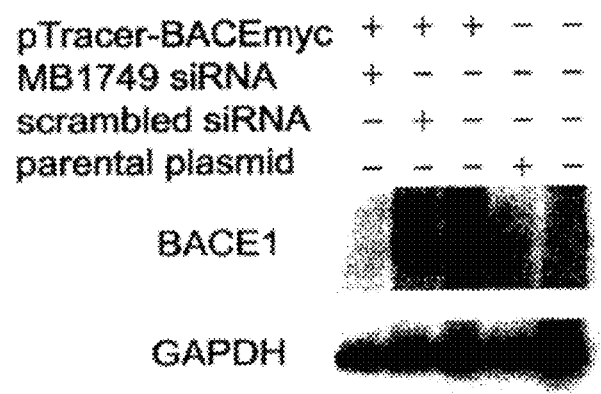
FIG. 7 illustrates western blot analysis of protein extracts from HEK293 cells transfected with a plasmid encoding a myc-tagged BACE1 or the parental myc-epitope plasmid, and optionally co-transfected with MB1749 or a scrambled control siRNA. Immunoblotting for the myc epitope shows suppression of BACE1 expression in cells co-transfected with MB1749 (leftmost lane). Re-blotting for GAPDH shows equivalent amounts of protein was loaded in each lane.

To further confirm the effectiveness of MB1749 at suppressing BACE1 expression, MB1749 siRNA or a scrambled control siRNA was co-transfected into HEK293 cells along with a variant of pTracer-BACE1 plasmid to which a myc epitope tag had been added at the carboxyl end of the BACE1 protein expression cassette (FIG. 6). A western blot of protein harvested from these cells 48 hours later showed substantial suppression of the myc-tagged BACE1 protein in cells transfected with the MB1749 siRNA compared to cells co-transfected with the scrambled siRNA or transfected with the pTracer-BACE1-myc plasmid alone (FIG. 7).

(2) Development of an AAV Vector Encoding for Anti-BACE1 siRNA:

To administer the MB1749 anti-BACE1 siRNA therapy to mice, an adeno-associated viral (AAV) vector containing DNA encoding for the MB1749 siRNA was chosen. AAV is known to transduce neuronal cells in vivo in the rodent brain following surgical injection into the brain tissue, and produce long-lasting expression of the delivered DNA within transduced neuronal cells. The expression of the MB1749 siRNA within transduced cells was driven by the mouse U6 RNA polymerase III promoter, provided by the pSilencer™ 1.0-U6 plasmid available from Ambion, Inc. (catalog number 7207). DNA was genetically engineered which encodes for a hairpin loop of RNA (consisting of the sequence for MB1749, a loop sequence, and the reverse complement of MB1749) (FIG. 6) into pSilencer™ between the ApaI and EcoRI restriction sites, using the following method.

Construction of the siRNA expression cassette using oligonucleotide condensation: In order to construct the DNA encoding for a hairpin loop of RNA corresponding to MB1749, the following four oligonucleotides were obtained from a synthesizing service:

| Oligo name | SEQ ID NO: | DNA sequence |
| --- | --- | --- |
| MB1749A | SEQ ID NO: 37 | 5'- <u>GAAGACTGTGGCTACAACATTC</u> -3' |
| MB1749B | SEQ ID NO: 38 | 5'- TTCAAGAGA<u>GAATGTTGTAGCCACAGTCTTC</u>TTTTTTG -3' |
| MB1749C | SEQ ID NO: 39 | 5'- TCTCTTGAAGAATGTTGTAGCCACAGTCTTCGGCC -3' |
| MB1749D | SEQ ID NO: 40 | 5'- AATTCAAAAAAG<u>AAGACTGTGGCTACAACATTC</u> -3' |

In the above table, the portions of the oligonucleotide sequences that correspond to the effective siRNA sequence against BACE1 are underlined. Note that the reverse complement for oligonucleotide A is found within the sequence for oligonucleotide C, and all but the first four bases of oligonucleotide D is the reverse complement of the 3' end of oligonucleotide B. Thus, A and C are largely complementary to one another, and B and D are largely complementary to one another.

To construct the double-stranded DNA insert to be cloned into pSilencer™ 1.0-U6 to make pMB1749 plasmid, the four oligonucleotides were suspended in water to a concentration of micromolar, then their ends were phosphorylated using T4 Polynucleotide Kinase enzyme. Next, in one tube, oligo MB1749A was mixed with oligo MB1749C, and in another tube, oligo MB1749B was mixed with oligo MB1749D. The mixtures were heated to 65° C. for 5 minutes then allowed to cool slowly to room temperature, to cause these complementary oligonucleotides to anneal into double-stranded form, with single-stranded overhangs. Next, a three-component ligation reaction was conducted by mixing oligosA/C and oligos B/D with pSilencer™ 1.0-U6 that had been linearized with ApaI and EcoRI restriction enzyme digestion, using standard molecular biology methods. The resulting ligation products were cloned into bacteria, and colonies screened to identify the desired plasmid product, which consists of the following construct inserted between the ApaI and EcoRI restrictions sites in pSilencer™ 1.0-U6 (SEQ ID NOs: 57 and 58, respectively):

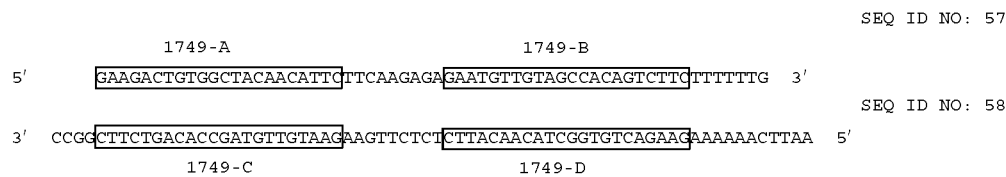

This strategy of assembling four oligonucleotides, rather than a single sense and antisense pair, was used to efficiently clone the DNA coding for the MB1749 hairpin siRNA. Use of single sense and antisense strands (such as can be obtained by concatenating the sequence for MB1749A with MB1749B, making one longer sense strand oligonucleotide, and contatenating MB1749C and MB1749D, making one longer antisense strand) results in molecular strands that tend to form intramolecular hairpins, preventing annealing into a double-stranded DNA, and ligation into the plasmid.

Verification of BACE1 mRNA expression by the MB1749 plasmid: In order to verify that the pMB1749 plasmid, coding for a hairpin loop of RNA corresponding to MB1749, does in fact produce an siRNA that reduces the amount of BACE1 mRNA in cells, mouse Neuro2a neuronal cells were co-transfected with pTracerBace1 plasmid and pMB1749 plasmid, using the SiPort-XP1 transfection reagent as described above. After 48 hours, the total cellular RNA was harvested from these cells, and used to conduct a reverse transcription quantitative real-time PCR assay, as described above. The results showed 94% suppression in BACE1 mRNA compared to cells not treated with pMB1749. A second plasmid (pControl) containing a scrambled sequence (shRNA corresponding to 5'-TGACACAGCCGCTACTACATTG-3', SEQ ID NO: 59) was constructed as a control, and confirmed not to suppress BACE1 mRNA expression in vitro.

Verification of BACE1 mRNA expression by the MB1749 viral vector: To obtain a supply of the viral vector for administration to the brains of mice in vivo, the pMB1749 plasmid was provided to GeneDetect, Ltd. (Auckland, New Zealand) for transfer of the U6 promoter, the MB1749 construct, and the RNA polymerase III termination sequence (consisting of 6 thymines in succession) into their plasmid containing AAV inverted terminal repeats and a green fluorescent protein reporter gene expressed from a chicken beta-actin enhancer and CMV promoter. The MB1749 expression cassette (U6 promoter, MB1749 construct, and termination sequence) was inserted following the 5' inverted terminal repeat for AAV, and before the GFP expression cassette. The resulting AAV plasmid was then used by GeneDetect to produce AAV-anti-BACE1-MB1749. GeneDetect was also provided with another plasmid containing a scrambled sequence for MB1749, which can be verified in vitro not to be active at suppressing BACE1 mRNA expression and not homologous to any known gene in Genbank, for production of AAV-control vector. AAV-MB1749 viral particles with a chimeric AAV1/2 capsid were produced from this plasmid using an adenovirus-free method, and were provided at a titer of 1.2-1.4×10$^{12}$ genomic particles per milliliter. Similarly, AAV-Control vector was made from the pControl plasmid, and provided at a titer of 3.8-4.1×10$^{12}$ genomic particles per milliliter.

To verify in vitro that the resulting AAV-anti-BACE1-MB1749 vector, when used to infect cells, results in suppression of BACE1 mRNA, and the AAV-control vector does not, HEK293 cells were infected with AAV-MB1749 or AAV-Control, then 24 hours later transfected with pTracerBACE1. Infection of cells by the AAV was confirmed by observation of GFP expression. In two separate cell cultures, AAV-MB1749 resulted in a 72.8% and 57.6% (average, 65.2%) reduction in BACE1 mRNA 72 hours post-viral transduction, while AAV-control vector had no significant effect (16.2% and <0% reduction in two separate cultures).

Example 5

AAV-Mediated BACE1 Gene Silencing in the Hippocampus Improves Contextual Fear Conditioning in Aging Mice The effect of reducing BACE1 levels in the hippocampus of aging, wildtype mice was determined following AAV-mediated siRNA delivery using the AAV vectors produced as described in Example 4. In this regard, behavioral freezing following contextual fear conditioning was used as an indicator of hippocampal function, as the acquisition and maintenance of a freezing response to a context previously paired with an unconditioned stimulus (foot shock) is dependent upon hippocampal function. Lesions of the dorsal hippocampus prevent the acquisition of contextual conditioning (Phillips, R. G. and LeDoux, J. E., Learn Mem., May-June (1994) 34-44) and post-training lesions attenuate contextual freezing (McNish, K. A., al., J. Neurosci., 17 (1997) 9353-9360).

It has been shown that single injections of AAV-mediated shRNA can result in persistent silencing of targeted gene expression in transduced regions of the rodent brain in vivo (Xia, H. et al., Nature Medicine, 10 (2004) 816-820). While reactive astrocytes have been shown to express BACE1 (Hartlage-Rubsamen, M., et al., Glia, 41 (2003) 169-179), the vast preponderance of BACE1 activity in the brain is in neurons (Zhao, J., et al., J. Biol. Chem., 271 (1996) 31407-31411). Accordingly, an AAV vector (with chimeric serotype 1/2) that preferentially transduces neurons almost to the exclusion of glia was used (Burger, C., et al., Mol. Ther., 10 (2004) 302-317). Overall steps in this work include (1) in vitro screening of candidate anti-BACE1 siRNA sequences for efficacy, and (2) construction of a viral vector for in vivo delivery of DNA encoding for the anti-BACE1 siRNA to the mammalian brain, as described in Example 4, and (3) neurosurgical administration of the vector to the mice, (4) testing of the behavior of the mice to assess the effect of the treatment, and (5) examination of the brain tissue of the mice to assess the effect of the treatment.

Step 3) Neurosurgical administration of the vector to the mice: Pilot injections (to confirm stereotactic coordinates): To verify correct anatomical targeting of the mouse hippocampus in this age and strain of mouse, and to verify expression from the AAV vector, three nine-month old wildtype C57BL/6 female mice were injected with 5 microliters of a standard AAV vector (at a concentration of approximately 2.3×10$^{12}$ viral particles per milliliter) containing the GFP reporter gene (rAVE-GFP 1/2, GeneDetect, Auckland, New Zealand). The injections were at the following stereotactic coordinates, expressed in millimeters from bregma, with the incisor bar at −5 mm: AP −2.70, ML ±3.00, DV −2.25. (The details of the neurosurgical procedure used to perform the injections are further described below).

Thirteen days post-surgery, these mice were euthanized and transcardially perfused with saline followed by 4% paraformaldehyde to flush and fix their organ tissues. The brains were cut into 30 micron thick sections along the parasagittal planes, with serial sections collected from throughout the entire left and right hemispheres. These sections were numbered sequentially with the lower numbers assigned to the lateral edge of the hemisphere, and higher numbers to the more medial sections of the hemisphere. Approximate targeting of the AAV vector to the hippocampus of the mice using this method was confirmed by visual confirmation of green fluorescent protein expression in the hippocampus of these mice by fluorescence microscopy, and the stereotactic coordinates for use in the main study were refined to −2.3 mm AP, +/−2.0 mm ML, and 1.6 mm DV below dura.

Neurosurgical method: The details of the neurosurgical method for use in delivery of the therapy of the present invention to mice are as follows. After the induction of surgical anesthesia using isofluorene inhalation, the mouse is placed in the stereotaxic frame and its head is immobilized using the ear bars, incisor bar and anesthesia mask associated with the apparatus (MyNeuroLab, St. Louis, Mo.; Benchmark™ Digital Stereotaxic). The patency of the mouse's airway is verified. The fur on the head is clipped, and betadyne is used to sanitize the scalp. After the depth of the mouse's anesthesia is verified (i.e., unresponsive to tail and paw pinch), a midline incision 1.0 to 1.5 cm in length is made in the skin over the skull in the saggital plane. The skin is manually retracted and membranous tissue covering the skull is scraped away with a sterile #11 scalpel blade. A Hamilton syringe (Hamilton Company, Reno, Nev.; Model 88011) is placed in the syringe holder of the stereotaxic frame, and the tip of the syringe needle is moved to the bregma point on the mouse's skull; (the intersection of the rostral, medial-lateral bone suture and the midline suture, identifiable by visual inspection). The needle is then positioned to the following stereotaxic coordinates on the left side of the skull: AP=−2.30 mm, ML=−2.00 mm. The corresponding point on the skull is noted visually through the surgical microscope. A dental drill with a sterile burr bit is used to erode a burr hole at this site through the skull bone. The syringe needle is again positioned at the bregma point, then moved to AP=−2.30 mm, ML=+2.00 mm on the right hemisphere of the skull. The site is noted visually, and a burr hole made at this site.

Once the burr holes are made, a Hamilton syringe is loaded with 5 microliters of AAV vector (AAV-antiBACE1-MB1749 or AAV-control at 1.3 to $3.9 \times 10^{12}$ genomic particles per milliliter), positioned from bregma to AP −2.30, ML −2.00, then lowered until the tip of the needle pierces the dura membrane covering the brain. Next, the needle is lowered to 1.25 mm below dura and left in place for 2 minutes. Then, the 5.0 microliters of AAV solution is injected into the hippocampus via the Hamilton syringe at the rate of 0.333 microliters per minute using an automated syringe pump. At the conclusion of the 15-minute injection, the needle is left in place for 2 minutes. Finally, the needle is slowly withdrawn from the brain at the rate of about 1 mm per minute. Once the needle tip is clear of the dura, the injection to this site is complete. Injection to the site in the right hemisphere proceeds in the same manner. Following completion of both injections, the incision in the skin over the skull is approximated using forceps and the skin is closed with silk sutures. The skin is swabbed with alcohol and the mouse is removed from the stereotaxic device and placed in a clean recovery cage. Sterile saline (0.5 mL) is injected subcutaneously at a site on the back to aid in hydration, and diazepam (1-2 mg/kg) is administered to prevent the occurrence of seizures during recovery. Upon complete recovery from anesthesia, the animal is returned to standard housing.

Eleven-month old female C57B6/SJL wildtype mice were obtained from the University of Minnesota (nine mice, courtesy of Karen Hsiao-Ashe) and from Taconic Farms (six mice, Germantown, N.Y.). Mice were housed two or three mice per cage in a 12-hour light/dark cycle temperature-controlled environment with food and water available ad lib. At 12 months of age, each mouse received a single, bilateral injection of either AAV-MB1749 or AAV-Control into the hippocampus at (from bregma) −2.3 mm AP, +/−2.0 mm ML, and 1.6 mm DV below dura, while under anesthesia by isofluorene inhalation. A digital stereotactic headframe was used for precise targeting. At each injection site, 5 microliters of AAV vector was infused via Hamilton syringe and syringe pump at a rate of 0.333 microliters per minute. Following each 15-minute infusion, the syringe was left in place for an additional two minutes for pressure equalization and then removed from the brain over a period of two minutes. Upon recovery from anesthesia, the mouse was returned to its normal housing. Mice were randomly assigned to receive either the AAV-MB1749 or AAV-Control vector, with nearly equal numbers of mice from each supplier assigned to each experimental group.

Step 4) Testing of the behavior of the mice to assess the effect of the treatment: The contextual fear conditioning procedure is a well-established method in the published research literature, and it has been determined that this method provides a measurement for hippocampus-dependent brain functioning. The procedure is a behavioral test that is performed over two successive days. On the first day, the mouse receives training to associate a cage context and auditory cue with a mild electric foot shock. On the second day, the mouse is placed in the same cage context as the first day, but no shocks are administered; rather, the amount of movement (or conversely, behavioral "freezing") of the mouse is observed and quantified by instrumentation. The mouse is returned to its home cage for an hour, then placed in a novel apparatus and again its amount of movement (or "freezing") is quantified.

At 15, 16, 18, and 19 months of age, each mouse was tested using a two-day contextual fear conditioning protocol similar to that described by Dineley, et al., (J. Biol. Chem., 277 (2005) 22768-22780). On the first day ("training"), the mouse was placed in the fear conditioning apparatus (Coulbourn Instruments, Allentown Pa. #H10-11M-TC), and allowed to freely explore the chamber for 3 minutes. Next, repetitions of the following stimulus regimen were presented: an auditory cue (80 dB white noise) and visual cue (lighting of a white bulb positioned in the chamber wall) were presented for 20 seconds. During the final two seconds of the 20-second period, a 0.20 millivolt (0.5 mAmp) foot shock was administered to the mouse through the floor grid of the chamber. A 40-second interval elapsed before the next cue presentation. At 15 months of age, five repetitions of this regimen were presented; at 16, 18, and 19 months of age, two repetitions were presented. On the second day of each two-day protocol, 24 hours after "training," the mouse was placed in the fear conditioning apparatus and its behavior was videotaped for five minutes. No cues or foot shocks were presented during this "test" period. One hour later, the light bulb and speaker were removed from the apparatus, and the apparatus was altered to have different wall appearance (color pattern versus bare metal), a different floor (smooth plastic versus wire grid), and a different scent (citrus versus no scent). The mouse was placed in this "novel" environment, and its behavior was videotaped for three minutes.

Contextual fear conditioning (a hippocampus-dependent function) was assessed by comparing motor "freezing" by the mice in the "test" compared to the "novel" environment. (Cued fear learning was not assessed). Freezing behavior was scored automatically by machine using the FreezeFrame™ video system (Actimetrics, Wilmette Ill.). This system computes frame-by-frame differences in the video image (at four frames per second), and is capable of detecting movements as small as 1 mm. Freezing "bouts" exceeding 1.0 second were scored as behavioral freezing; the amount of behavioral freezing per "training" period (prior to the first cue/shock presentation), per "test" period (five minute observation) and per "novel" period (three minute observation) were expressed as percent of total time spent freezing. The data for the mice receiving the AAV-MB1749 vector (n=7) and the mice receiving the AAV-Control vector (n=8) are shown in the table below. Contextual fear conditioning for each mouse was measured as the difference between the percent of time spent freezing in the "test" environment versus the "novel" environment, on the same measurement day. A repeated measures ANOVA of these difference scores shows significantly greater contextual fear conditioning in mice receiving the AAV-MB1749 vector (F (1.11)=8.57, p<0.015), and a marginally significant increase in contextual fear conditioning across both groups of mice over months (F (3.33)=2.35, p<0.09). The profile of difference scores across months did not differ by AAV treatment group (p=0.997 for F-test of interaction effect).

Percent Behavioral Freezing in Contextual Fear Conditioning Assay

| Context | Age (mos) | AAV-MB1749 | AAV-Control | p* |
| --- | --- | --- | --- | --- |
| Day 1: Training | 15 | 1.1% | 0.6% | ns |
| | 16 | 49.8 | 42.9 | ns |
| | 18 | 72.1 | 47.6 | 0.061 |
| | 19 | 66.8 | 52.8 | ns |
| Day 2: Test | 15 | 48.9 | 24.2 | 0.043 |
| | 16 | 61.8 | 36.1 | 0.062 |
| | 18 | 74.9 | 44.4 | 0.019 |
| | 19 | 60.1 | 45.2 | ns |
| Day 2: Novel context | 15 | 2.3 | 4.1 | ns |
| | 16 | 12.4 | 9.0 | ns |
| | 18 | 10.6 | 3.4 | ns |
| | 19 | 7.2 | 15.0 | ns |
| Difference (Test-Novel) | 15 | 46.6 | 20.2 | 0.016 |
| | 16 | 49.3 | 27.0 | 0.053 |
| | 18 | 64.3 | 41.0 | 0.059 |
| | 19 | 52.9 | 30.2 | 0.093 |

*p values for t-tests comparing treatment groups

Further analyses of these data on a month-by-month basis indicate that the mice receiving AAV-MB1749 exhibited more freezing than the mice receiving AAV-Control in the "test" period at ages 15, 16, and 18 months, while there was no difference among the two groups of mice in the amount of freezing exhibited in the "novel" environment at any age (see Table immediately above). In addition, there is marginally significant evidence (p=0.0613) that the mice receiving AAV-MB1749 had better long-term recall of the context in which they had received the foot shocks, in that they exhibited more freezing (72.1%) than control mice (47.6%) during the "training" period at age 18 months (prior to the first presentation of the cues and shock at that age) though they had not been exposed to the apparatus for two months. The mice receiving the AAV-Control vector did not display this enhanced long-term recall. These data are consistent with the interpretation that mice receiving hippocampal injections of the AAV-MB1749 vector at twelve months of age displayed better hippocampal-dependent learning and recall at 15 months of age, with the enhancement persisting for at least three more months (through 18 months of age).

Figure 8:
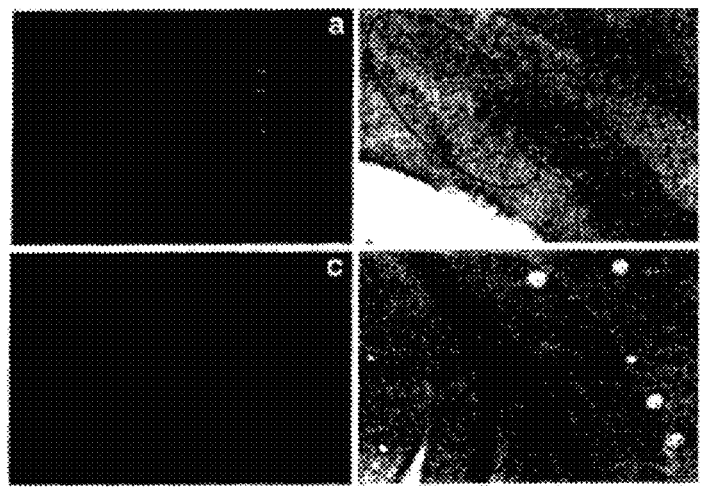
FIG. 8 illustrates fluorescence microscopy (left) and brightfield images (right, both 20× objective) showing GFP expression and BACE1 immunostaining respectively in example brain sections from a mouse treated with AAV-MB1749 (a,b) and a mouse treated with AAV-Control (c,d). The circled regions in the photographs designate regions of viral transduction (based on GFP expression). Levels of BACE1 immunoreactivity were reduced ($p<0.002$) in virally transduced regions in mice receiving AAV-MB1749.

5) Examination of the brain tissue of the mice to assess the effect of the treatment: To verify that the administration of AAV-MB1749 to the mice resulted in suppression of BACE1 protein expression, the brains of the mice were harvested at termination when the mice were 19.5 months old, and analyzed by immunohistochemistry. One mouse that received AAV-Control was found dead in its cage at 18.5 months of age—efforts to preserve its brain for histological analysis were unsuccessful. A blinded pathologist's examination of this mouse found a lymphosarcoma of the mesenteric lymph node, a common finding in SJL mice over 12 months of age (Katz, J. D. and Bonavida, B., Bioessays, 11 (1998) 181-185). Mice were euthanized by Nembutal overdose, then transcardially perfused with 50 mL of wash solution (137 mM NaCl, 20 mM dextrose, 23 mM sucrose, 2 mM anhydrous $CaCl_2$, and 1.6 mM anhydrous sodium cacodylate), followed by 100 mL of fixation solution (117 mM sucrose and 67 mM sodium cacodylate in 4% paraformaldehyde, pH 7.3). Brains were stored in 1.6 mM sodium cacodylate solution (pH 7.0) at 4 degrees C. until processing. All brains were then mounted in a single MultiBrain™ block (Neuroscience Associates [NSA], Knoxville Tenn.) and sectioned coronally (35 µM sections). Every fourth section throughout the hippocampus was stained for BACE1 by NSA using a polyclonal rabbit anti-BACE1 antibody (Calbiochem, San Diego Calif., #195111, 1:2000 dilution), visualized using peroxidase-conjugated secondary antibody (Vectastain™ ABC Method, Vector Laboratories #PK-6101). Adjacent sections were used to identify regions of AAV transduction, by means of fluorescence microscopy for GFP protein expression. The extent of transduction of mouse brains by the AAV-MB1749 or AAV-Control vector did not differ across treatment groups or hemispheres, with GFP-expressing cells detectable in an average of 3.5 coronal sections (spanning 490 microns rostrocaudally). Example images of hippocampal regions transduced by the AAV vectors and BACE1 immunostaining of these regions are shown in FIG. 8.

To quantify the level of expression of BACE1 in the mouse brains, scans of the brain sections immunostained for BACE1 were digitized as 24-bit color images at a resolution of 2400 pixels per inch with an Epson 4870 scanner. These images were overlaid with fluorescence microscopy images of adjacent, corresponding brain sections to identify regions that expressed GFP from the AAV transgene. Regions of pixels encompassing GFP-expressing cells in the neuronal layers of the hippocampus were identified for each hemisphere of each mouse brain section in a series of seven slides spanning 875 microns of the rostral-caudal extent of the hippocampus surrounding the AAV injection sites. The staining intensity for BACE1 in each hemisphere of each section was measured by averaging the pixel intensity value of pixels in these regions (min 3, max 16, average 10 regions per measurement). For each hemisphere and tissue section, a comparable intensity measurement was made for non-GFP expressing cells in adjacent areas of the hippocampus. Although the staining variability across sections and mice was minimal (due to the MultiBrain™ method of processing), the staining intensity of non-GFP-expressing cells was subtracted pairwise from the staining intensity of GFP-expressing cells to control for background staining levels. An ANOVA of these difference scores showed that the amount of BACE1 protein expressed by GFP-positive cells in the hippocampus of mice receiving AAV-MB1749 injections was significantly reduced compared to mice receiving AAV-Control injections (F (1.45) =10.88, p=0.0019). When expressed as a percentage of background intensity, the pixel intensity of BACE1 stained GFP-positive cells in mice treated with AAV-MB1749 was 12.7%±2.1% fainter than the background staining (versus 4.5%±2.1% [mean±se] fainter in mice treated with AAV-Control). These results indicate that hippocampal injections of AAV-MB1749 resulted in reduced expression of BACE1 enzyme in the treated mice, consistent with persistent expression of the anti-BACE1 shRNA transgene.

Reduction in Abeta in AAV-MB1749 treated mice resulting from the action of the anti-BACE1 shRNA transgene was investigated by staining sections from all mouse brains for soluble Abeta and amyloid deposits. However, in these wildtype mice, levels of soluble Abeta were below detection limits throughout the brain in both treatment groups, and no amyloid deposits were detectable. Nevertheless, because BACE1 activity is required for the production of Abeta from APP (Cai, H., et al., Nat. Neurosci., 4 (2001) 233-234; Luo, Y., et al., Neurobiol. Dis., 14 (2003) 81-88), and because increased expression of beta-secretase in mouse brain results in increase steady-state levels of beta amyloid (Bodendorf, U., et al., J. Neurochem., 80 (2002) 799-806), our results showing reduced BACE1 expression in the AAV-MB1749 treated mice suggest that Abeta production and steady-state levels of Abeta in the hippocampal regions of these mice also were reduced.

In this experiment, whether or not reduced Abeta could be measured, the possibility would remain that the enhanced fear conditioning observed in the AAV-MB1749 treated mice was due to a direct effect of reduced BACE1 expression or reduction in some other product of BACE1 activity (Kitazume, S., et al., J. Biol. Chem., 280 (2005) 8589-8595) rather than an effect mediated by reduced Abeta production. It has been shown that BACE1 knock-out mice have an "anxious" behavioral phenotype that includes reduced exploratory behavior and timidity (Harrison, S. M., et al., Mol. Cell Neurosci., 24 (2003) 646-655). However, the fear conditioning effect observed in the AAV-MB1749 treated mice was contextual, and not a reflection of an overall increase in fearful behavior. No differences were seen between these mice and control mice in behavior in the apparatus at the start of training (prior to the first shock presentation) or at any time in the "novel" context (see table immediately above). Thus, these results are more consistent with a local effect on hippocampal functioning than with a more general effect of BACE1 reduction.

Because soluble Abeta can be synaptotoxic (Mucke, L., et al., J. Neurosci., 20 (2000) 4050-4058) and intracerebroventricular administration of oligomeric forms of beta amyloid into normal rats is sufficient to produce cognitive impairment (Cleary, J. P., et al., Nat. Neurosci., 8 (2005) 79-84), these results support a beneficial effect of Abeta reduction in the hippocampus on hippocampal-dependent functioning, however it is possible that the beneficial effect of BACE1 suppression was due to some other mechanism. Notably, the effect did not require treatment of the animals at a young age, but was obtained in older adult animals. In addition, the beneficial effect was obtained in normal, aging animals, and was not dependent upon an over-expression of APP. These findings support the significance of BACE1 as a treatment target not only for Alzheimer's disease, but also for other mild cognitive impairments associated with aging.

Example 6

AAV-Mediated BACE1 Gene Silencing in the Hippocampus as a Treatment for Alzheimer's Disease in a Transgenic Mouse Model of Alzheimer's Disease The present invention can be validated for treatment of Alzheimer's disease by surgically injecting an AAV vector encoding for the MB1749 siRNA targeting murine BACE1 into the hippocampus of 12 month-old female Tg2576 mice, then assessing the mice for effects of the therapy at ages 15 months and beyond.

The Tg2576 mouse is an accepted animal model of Alzheimer's disease that overexpresses the human transgene for APP (Hsiao et al, 1996). The Tg2576 transgenic mouse line develops amyloid plaques containing beta-amyloid beginning at about 10 to 12 months of age (Gau et al, 2002). The plaques are particularly frequent in the cerebral cortex and hippocampus. They are readily detectable 15 months of age, and become more severe at 19 months of age and beyond (Kawarabayashi et al, 2001). Aged female Tg2576 mice deposit significantly more beta-amyloid in the brain than do aged male Tg2576 mice (Callahan et al, 2001). By 19 months of age, the Tg2576 mice exhibit behavioral and cognitive deficits on measures of balance, agility, and spatial memory (King and Arandash, 2002).

Experimental design for In Vivo Testing in Tg2576 Transgenic Mice Several heterozygous transgenic and age-matched wildtype controls from Tg2576 litters (obtained from Taconic Farms, Inc.) are injected with either AAV-anti-BACE1-MB1749 or AAV-control at 12 months of age using the above procedure. Half of the mice receive bilateral injections of AAV-antiBACE1-MB1749, and the other half receive bilateral injections of AAV-control, in a 2×2 design:

| Number of mice Genotype: | Treatment Administered AAV-anti-BACE1-MB1749 | AAV-control |
|---|---|---|
| Tg2576 heterozygote | N | N |
| Wildtype | N | N |

* N equals the number of mice used in the experiment.

Overall steps in this work will include (1) in vitro screening of candidate anti-BACE1 siRNA sequences for efficacy, and (2) construction of a viral vector for in vivo delivery of DNA encoding for the anti-BACE1 siRNA to the mammalian brain, as described in Example 4, and (3) neurosurgical administration of the vector to the mice as described in Example 5, (4) testing of the behavior of the mice to assess the effect of the treatment as described in Example 5, and (5) examination of the brain tissue of the mice to assess the effect of the treatment as described below.

Step 5) Histological analysis of the effects of anti-BACE1 siRNA treatment in the Tg2576 mouse brain tissue: Once the mice that have been treated with AAV-anti-Bace1-MB1749 or AAV-control have attained the age of 19 months, they will be euthanized and their brain tissue examined to determine the effect of the treatment on level of BACE1 protein in the treated regions of the hippocampus, and the effect of the treatment on the extent of beta-amyloid plaque formation in those regions. The treated regions will be identifiable based on the expression of green fluorescent protein in the neuronal cells. The level of BACE1 protein will be identifiable based on immunohistochemical staining using standard methods, with an anti-Bace1 primary antibody, and a peroxidase-conjugated secondary antibody for visualization.

In the treated animals (heterozygous Tg2576 or wildtype mice receiving AAV-anti-BACE1-MB1749), it is expected that the amount of BACE1 protein will be reduced in the regions expressing the GFP reporter gene, and that also in these regions in the heterozygous Tg2576 mice, there will be fewer beta-amyloid plaques.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference. Further, the hard copy of the sequence listing submitted herewith and the corresponding computer readable form are both incorporated herein by reference in their entireties.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

I claim:

1. A method for improving memory or cognitive function in a subject diagnosed as having a disorder in which a diminished declarative memory is a symptom, comprising intracranially administering to the subject a therapeutically effective dose of a composition that decreases the expression of a beta amyloid cleaving enzyme type 1, or BACE1, in a cell of the nervous system of the subject, wherein the composition comprises a shRNA or a siRNA or a vector encoding said siRNA or said shRNA, wherein further said shRNA or said siRNA comprises a double-stranded portion 21 to 30 nucleotides long and wherein one strand of said double-stranded portion comprises 21 contiguous nucleotides encoded by SEQ ID NO: 26, 30, or 28, and wherein at least one attribute of said memory or cognitive function is improved.

2. The method of claim 1 wherein the composition is delivered to the subject by intracranial delivery through an intracranial access device.

3. The method of claim 2, further comprising the step of: implanting a pump outside the brain, the pump coupled to the proximal end of an intracranial catheter.

4. The method of claim 3 comprising operating the pump to deliver a predetermined dosage of the said shRNA or said siRNA or said vector encoding said siRNA or said shRNA from the pump through a discharge portion of the said intracranial catheter.

5. The method of claim 3 further comprising the step of periodically refreshing the pump with said composition.

6. The method of claim 3 wherein the pump is an infusion pump.

7. The method of claim 6 wherein the infusion pump is an electromechanical pump.

8. The method of claim 6 wherein the infusion pump is an osmotic pump.

9. The method of claim 1, wherein said composition is delivered to the nucleus basalis of Meynert or the cerebral cortex or the hippocampus.

10. The method of claim 1, wherein the composition comprises the vector encoding said siRNA or said shRNA.

11. The method of claim 10, wherein the vector is selected from the group consisting of adeno-associated virus, adenovirus, herpes simplex virus, lentivirus and a DNA plasmid.

12. A method of delivering a small interfering RNA across a blood-brain barrier for expression in the brain of a subject diagnosed as having or being at risk of developing disorders in which diminished declarative memory is a symptom comprising administering to a blood vessel directly supplying blood to the brain of the subject a composition comprising a liposome having an exterior surface and an internal compartment containing an artificial adeno-associated virus (AAV) encoding a shRNA comprising a double-stranded portion between 21 and 30 nucleotides long, wherein one strand of said double-stranded portion is encoded by SEQ ID NO: 26, 30, or 28.

13. The method of claim 12, wherein the artificial AAV vector is for delivery of a single stranded DNA encoding the shRNA, the artificial AAV vector comprising the single stranded DNA having AAV-ITRs at the 5-prime and 3-prime ends.

14. The method of claim 12, wherein the artificial AAV vector is for delivery of a single stranded DNA encoding the shRNA, the artificial AAV vector comprising, in 5-prime to 3-prime order: a 5-prime AAV-ITR; the single stranded DNA; an internal AAV-ITR; a reverse complement of the single stranded DNA; and a 3-prime AAV-ITR.

15. The method of claim 12, wherein the artificial AAV vector is for delivery of a linear, double stranded DNA encoding said shRNA, the artificial AAV vector comprising the linear, double stranded DNA having AAV-ITRs at the 5-prime and 3-prime ends of each strand, or wherein the artificial AAV vector is for delivery of a single stranded DNA encoding said shRNA, the artificial AAV vector comprising, in 5-prime to 3-prime order: a 5-prime AAV-ITR; DNA encoding one strand of said shRNA; an internal AAV-ITR; DNA encoding the other strand of said shRNA; and a 3-prime AAV-ITR.

16. The method of claim 12, wherein the composition is administered intra-arterially.

17. The method of claim 12, wherein the liposome comprises an exterior surface defining a sphere having a diameter of at most 200 nanometers.

18. The method of claim 12, wherein the liposome comprises one or more blood-brain barrier and brain cell membrane targeting agents and wherein at least 5 and at most 1000 blood-brain barrier or brain cell membrane targeting agents are conjugated to an exterior surface of the liposome.

19. The method of claim 18, wherein at least 25 and at most 40 blood-brain barrier or brain cell membrane targeting agents are conjugated to the surface of the liposome.

20. The method of claim 12, wherein the exterior surface of the liposome further comprises one or more conjugation agents selected from the group consisting of polyethylene glycol, sphingomyelin, biotin, streptavidin, organic polymers, and combinations thereof.

21. The method of claim 20, wherein the molecular weight of the conjugation agent is at least 1000 Daltons and at most 50,000 Daltons.

22. The method of claim 12, wherein the artificial AAV vector has been thermally treated in at least one heating and cooling cycle.

23. A medical system for delivering a small interfering RNA into a pre-determined location in a brain of a patient comprising: an intracranial access device selected from the group consisting of an intracranial catheter and an intracranial access port; a deliverable amount of a siRNA or a shRNA or a vector encoding said siRNA or said shRNA wherein said siRNA or said shRNA comprises a double-stranded portion between 21 and 30 nucleotides long, wherein one strand comprises 21 contiguous nucleotides encoded by SEQ ID NO: 26, 30, or 28; and a delivery means for delivering said small interfering RNA or vector encoding said small interfering RNA to said location of the brain from said intracranial access device.

24. The medical system of claim 23, wherein said delivery means is selected from the group consisting of an infusion pump, an electromechanical pump, and an osmotic pump.

25. The medical system of claim 23, wherein the predetermined location is the nucleus basalis of Meynert or the cerebral cortex or the hippocampus.

26. The medical system of claim 23, wherein the delivery means is injection from an external syringe into an intracranial access port.

* * * * *